US011849633B2

(12) United States Patent
Uno

(10) Patent No.: US 11,849,633 B2
(45) Date of Patent: Dec. 19, 2023

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., Ltd., Yongin-si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 453 days.

(21) Appl. No.: 16/944,770

(22) Filed: Jul. 31, 2020

(65) Prior Publication Data

US 2021/0126198 A1 Apr. 29, 2021

(30) Foreign Application Priority Data

Oct. 23, 2019 (KR) ........................ 10-2019-0132166
Jun. 11, 2020 (KR) ........................ 10-2020-0071056

(51) Int. Cl.

| | |
|---|---|
| ***C07D 491/048*** | (2006.01) |
| ***H10K 85/60*** | (2023.01) |
| ***C07D 495/04*** | (2006.01) |
| *H10K 50/15* | (2023.01) |

(52) U.S. Cl.

CPC ....... *H10K 85/636* (2023.02); *C07D 491/048* (2013.01); *C07D 495/04* (2013.01); *H10K 85/633* (2023.02); *H10K 50/15* (2023.02); *H10K 85/657* (2023.02); *H10K 85/6574* (2023.02); *H10K 85/6576* (2023.02)

(58) Field of Classification Search

CPC .......................... C07D 491/048; C07D 495/04
See application file for complete search history.

(56) References Cited

U.S. PATENT DOCUMENTS

| | | | |
|---|---|---|---|
| 2018/0226579 A1 | 8/2018 | Kim et al. | |
| 2022/0153758 A1* | 5/2022 | Kim | C09K 11/06 |
| 2022/0310934 A1* | 9/2022 | Uno | H10K 85/6576 |

FOREIGN PATENT DOCUMENTS

| | | |
|---|---|---|
| KR | 10-2015-0042386 A | 4/2015 |
| KR | 10-2015-0058625 A | 5/2015 |
| KR | 10-2015-0066618 A | 6/2015 |
| KR | 10-2015-0073233 A | 7/2015 |
| KR | 10-2015-0124924 A | 11/2015 |
| KR | 10-1609027 B1 | 4/2016 |
| KR | 10-2018-0063708 A | 6/2018 |
| KR | 10-2018-0090931 A | 8/2018 |
| KR | 10-2019-0011463 A | 2/2019 |
| KR | 10-2019-0013208 A | 2/2019 |
| KR | 10-2019-0093740 * | 8/2019 |
| WO | WO 2014/104797 A1 | 7/2014 |
| WO | WO-2014104797 A1 * | 7/2014 |
| WO | WO 2014/196805 A1 | 12/2014 |
| WO | WO-2019027163 A1 * | 2/2019 |
| WO | WO-2021020929 A1 * | 2/2021 |
| WO | WO-2021206305 A1 * | 10/2021 |

OTHER PUBLICATIONS

CAS/CAPLUS Abstract and Indexed Compounds, K. So et al., WO 2019/027163 (Feb. 7, 2019) (Year: 2019).*
European Search Opinion, App. No. 20202765.2 (dated Feb. 24, 2021) (Year: 2021).*
International Union of Pure and Applied Chemistry, Compendium of Chemical Terminology (IUPAC), Gold Book, p. 73 of 1622 (2012) (Year: 2012).*

* cited by examiner

*Primary Examiner* — Alexander R Pagano
(74) *Attorney, Agent, or Firm* — Lewis Roca Rothgerber Christie LLP

(57) ABSTRACT

An organic electroluminescence device includes a first electrode, a hole transport region disposed on the first electrode, an emission layer disposed on the hole transport region, an electron transport region disposed on the emission layer, and a second electrode disposed on the electron transport region, wherein the hole transport region includes a monoamine compound represented by Formula 1, thereby providing high emission efficiency:

[Formula 1]

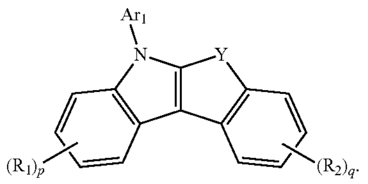

23 Claims, 2 Drawing Sheets

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

This application claims priority to and the benefit of Korean Patent Application No. 10-2019-0132166, filed on Oct. 23, 2019, and Korean Patent Application No. 10-2020-0071056, filed on Jun. 11, 2020 the entire content of which is hereby incorporated by reference.

BACKGROUND

1. Field

One or more aspects of embodiments of the present disclosure relate to an organic electroluminescence device and a monoamine compound for an organic electroluminescence device.

2. Description of the Related Art

Organic electroluminescence display devices are being actively conducted as image display devices. An organic electroluminescence display device is different from a liquid crystal display device and is a so-called a self-luminescent display device, in which holes and electrons respectively injected from a first electrode and a second electrode recombine in an emission layer, and a light-emitting organic compound in the emission layer emits light to attain display.

In the application of an organic electroluminescence device to a display device, a decrease in driving voltage, and increase in emission efficiency and lifespan of the organic electroluminescence device are desired or suitable, and materials for an organic electroluminescence device stably attaining such requirements are being continuously developed.

SUMMARY

One or more aspects of embodiments of the present disclosure are directed toward an organic electroluminescence device and a monoamine compound for an organic electroluminescence device, and for example, an organic electroluminescence device having high efficiency and a monoamine compound included in a hole transport region of an organic electroluminescence device.

One or more example embodiments of the present disclosure provide an organic electroluminescence device including a first electrode, a hole transport region provided on the first electrode, an emission layer provided on the hole transport region, an electron transport region provided on the emission layer, and a second electrode provided on the electron transport region, wherein the hole transport region includes a monoamine compound represented by Formula 1:

[Formula 1]

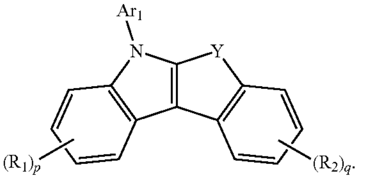

In Formula 1, Y may be O or S, "p" and "q" may each independently be an integer of 0 to 4, $Ar_1$ may be a substituted or unsubstituted aryl group of 6 to 30 carbon atoms for forming a ring, a substituted or unsubstituted heteroaryl group of 2 to 30 carbon atoms for forming a ring, or represented by Formula 2, $R_1$ and $R_2$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or represented by Formula 2, where one (e.g., only one) among $Ar_1$, $R_1$, and $R_2$ is represented by Formula 2:

[Formula 2]

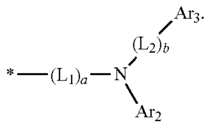

In Formula 2, $Ar_2$ may be a substituted or unsubstituted aryl group of 6 to 30 carbon atoms for forming a ring or a substituted or unsubstituted heteroaryl group of 2 to 30 carbon atoms for forming a ring, $Ar_3$ may be a substituted or unsubstituted heteroaryl group of 2 to 30 carbon atoms for forming a ring, $L_1$, and $L_2$ may each independently be a direct linkage, a substituted or unsubstituted arylene group of 6 to 30 carbon atoms for forming a ring or a substituted or unsubstituted heteroarylene group of 2 to 30 carbon atoms for forming a ring, and "a", and "b" may each independently be an integer of 0 to 3.

In an embodiment, $Ar_3$ may be represented by Formula 3:

[Formula 3]

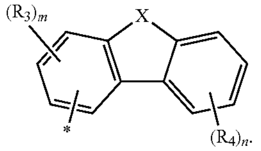

In Formula 3, X is O or S, $R_3$ and $R_4$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or combined with an adjacent group to form a ring, "m" may be an integer of 0 to 3, and "n" may be an integer of 0 to 4.

In an embodiment, Formula 1 may be represented by any one among Formula 4 to Formula 6:

[Formula 4]

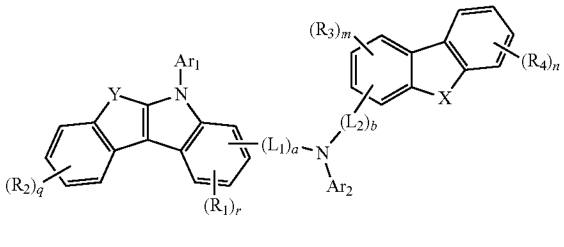

-continued

[Formula 5]

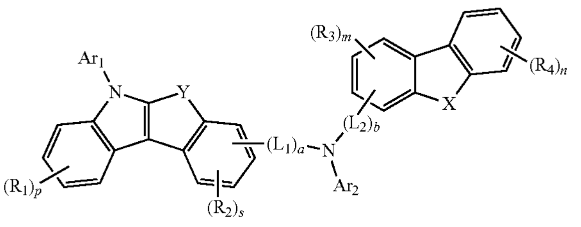

[Formula 6]

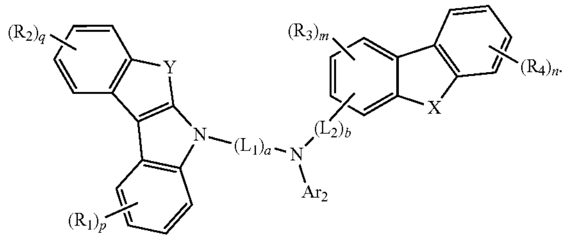

In Formula 4 to Formula 6, $Ar_1$ may be a substituted or unsubstituted aryl group of 6 to 30 carbon atoms for forming a ring, or a substituted or unsubstituted heteroaryl group of 2 to 30 carbon atoms for forming a ring, $R_1$ and $R_2$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "r" and "s" may each independently be an integer of 0 to 3, and X, Y, $Ar_2$, $L_1$, $L_2$, "a", "b", $R_3$, $R_4$, "m", "n", "p" and "q" may each independently be the same as defined in Formula 1 to Formula 3.

In an embodiment, Formula 4 may be represented by any one among Formula 4-1 to Formula 4-4:

[Formula 4-1]

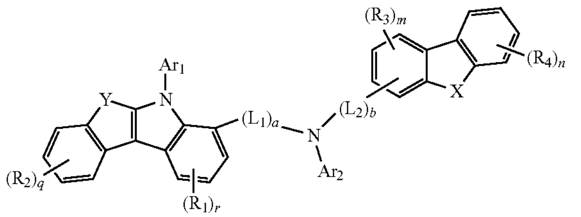

[Formula 4-2]

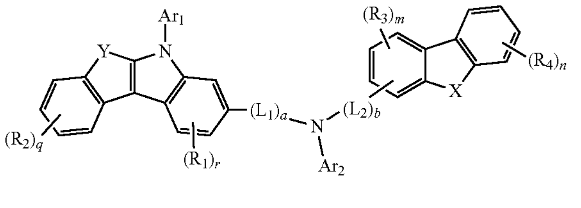

-continued

[Formula 4-3]

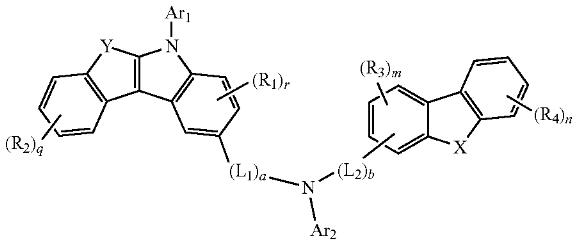

[Formula 4-4]

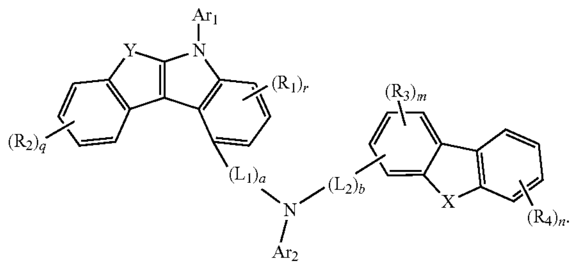

In Formula 4-1 to Formula 4-4, X, Y, $Ar_1$, $Ar_2$, $L_1$, $L_2$, $R_1$ to $R_4$, "a", "b", "m", "n", "q" and "r" may each independently be the same as defined in Formula 4.

In an embodiment, Formula 5 may be represented by any one among Formula 5-1 to Formula 5-4:

[Formula 5-1]

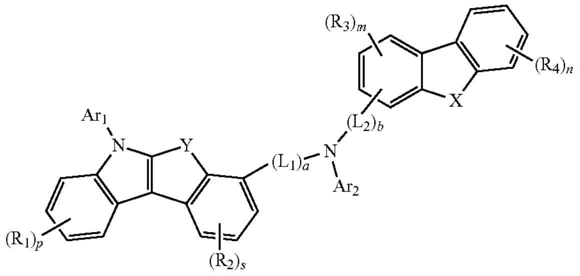

[Formula 5-2]

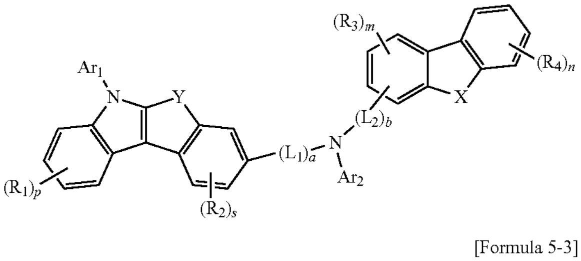

[Formula 5-3]

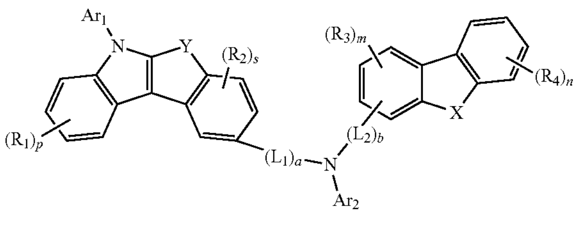

-continued

[Formula 5-4]

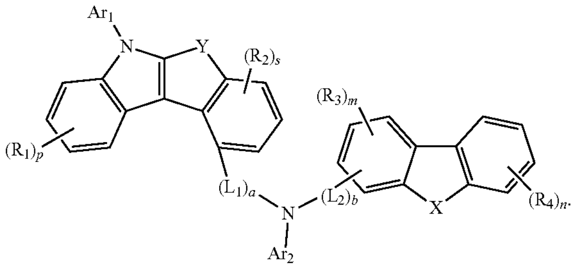

In Formula 5-1 to Formula 5-4, X, Y, $Ar_1$, $Ar_2$, $L_1$, $L_2$, $R_1$ to $R_4$, "a", "b", "m", "n", "p" and "s" may each independently be the same as defined in Formula 5.

In an embodiment, $L_1$, and $L_2$ may each independently be a direct linkage, a substituted or unsubstituted phenylene group, a substituted or unsubstituted biphenylene group, or a substituted or unsubstituted naphthylene group.

In an embodiment, "a" may be 1, and $L_1$ may be represented by any one among L-1 to L-4:

L-1

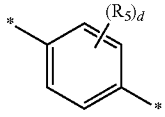

L-2

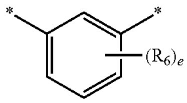

L-3

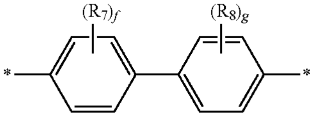

L-4

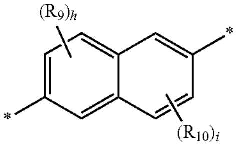

In L-1 to L-4, $R_5$ to $R_{10}$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "d" to "g" may each independently be an integer of 0 to 4, and "h" and "i" may each independently be an integer of 0 to 3.

In an embodiment, $R_1$, and $R_2$ may each independently be a hydrogen atom, a deuterium atom, a halogen atom, or a substituted or unsubstituted alkyl group of 1 to 10 carbon atoms.

In an embodiment, $Ar_1$ may be a substituted or unsubstituted phenyl group, a substituted or unsubstituted biphenyl group, a substituted or unsubstituted triphenyl group, a substituted or unsubstituted dibenzofuran group, or a substituted or unsubstituted dibenzothiophene group.

In an embodiment, the hole transport region may include a hole injection layer disposed on the first electrode; and a hole transport layer disposed on the hole injection layer, and the hole transport layer may include the monoamine compound represented by Formula 1.

In an embodiment, the hole transport region may further include an electron blocking layer disposed on the hole transport layer.

In an embodiment, the monoamine compound represented by Formula 1 may be at least one selected from the compounds represented in Compound Group 1 to Compound Group 3.

One or more example embodiments of the present disclosure provide a monoamine compound represented by Formula 1.

BRIEF DESCRIPTION OF THE DRAWINGS

The accompanying drawings are included to provide a further understanding of the present disclosure and are incorporated in and constitute a part of this specification. The drawings illustrate example embodiments of the present disclosure, and together with the description, serve to explain principles of the present disclosure. In the drawings.

DETAILED DESCRIPTION

Figure 1:
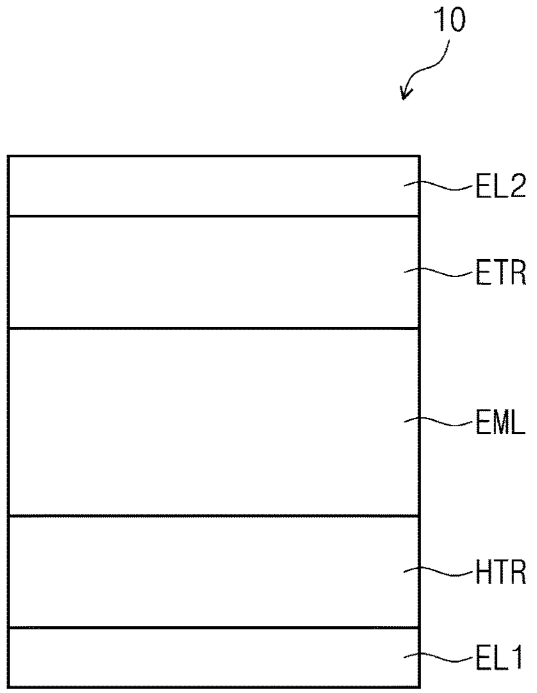
FIG. 1 is a schematic cross-sectional view of an organic electroluminescence device according to an embodiment of the present disclosure.

The present disclosure may have various modifications and may be embodied in different forms, and example embodiments will be explained in detail with reference to the accompany drawings. The present disclosure may, however, be embodied in different forms and should not be construed as being limited to the embodiments set forth herein. Rather, all modifications, equivalents, and substitutions in the spirit and technical scope of the present disclosure should be included.

It will be understood that when an element (or region, layer, part, etc.) is referred to as being "on", "connected to" or "coupled to" another element, it can be directly on, connected or coupled to the other element, or a third intervening element may be present.

Like reference numerals refer to like elements throughout, and duplicative descriptions thereof may not be provided. In addition, the thicknesses, ratios, and dimensions of constituent elements in the drawings may be exaggerated for effective explanation of technical contents.

The term "and/or" includes any and all combinations of one or more of the associated listed items. As used herein, the singular forms "a," "an," and "the" are intended to include the plural forms as well, unless the context clearly indicates otherwise. Further, expressions such as "at least one of", "one of", and "selected from", when preceding a list of elements, modify the entire list of elements and do not modify the individual elements of the list.

It will be understood that, although the terms first, second, etc. may be used herein to describe various elements, the elements should not be limited by these terms. These terms are only used to distinguish one element from another element. Thus, a first element could be alternatively termed a second element without departing from the teachings of the present disclosure. Similarly, a second element could be alternatively termed a first element. As used herein, the singular forms are intended to include the plural forms as well, unless the context clearly indicates otherwise.

In addition, the terms "below", "beneath", "on", and "above" are used for explaining the relation of elements shown in the drawings. The terms are relative concept and are explained based on the direction shown in the drawing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be further understood that the terms "includes," "including," "comprises," and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

Hereinafter, the organic electroluminescence device according to an embodiment of the present disclosure will be explained with reference to attached drawings.

FIGS. 1 to 4 are cross-sectional views schematically showing organic electroluminescence devices according to example embodiments of the present disclosure. Referring to FIGS. 1 to 4, in an organic electroluminescence device 10 according to an embodiment, a first electrode EL1 and a second electrode EL2 are oppositely disposed, and between the first electrode EL1 and the second electrode EL2, an emission layer EML may be disposed.

In some embodiments, the organic electroluminescence device 10 of an embodiment may further include a plurality of functional layers between the first electrode EL1 and the second electrode EL2 in addition to the emission layer EML. The plurality of the functional layers may include a hole transport region HTR and an electron transport region ETR. For example, the organic electroluminescence device 10 of an embodiment may include a first electrode EL1, a hole transport region HTR, an emission layer EML, an electron transport region ETR, and a second electrode, stacked one by one. In some embodiments, the organic electroluminescence device 10 of an embodiment may include a capping layer CPL disposed on the second electrode EL2.

The organic electroluminescence device 10 of an embodiment may include a monoamine compound of an embodiment, which will be explained later, in the emission layer EML disposed between the first electrode EL1 and the second electrode EL2. However, an embodiment of the present disclosure is not limited thereto, and in some embodiments the organic electroluminescence device 10 may include the compound in the hole transport region HTR or the electron transport region ETR, which may be included among the functional layers disposed between the first electrode EL1 and the second electrode EL2, in addition to the emission layer EML, or may in some embodiments include the compound in a capping layer CPL disposed on the second electrode EL2.

Figure 2:
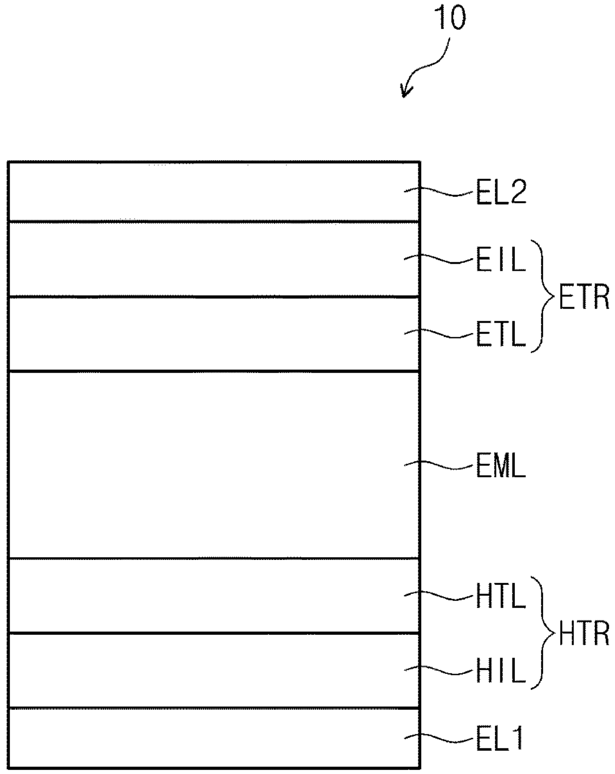
FIG. 2 is a schematic cross-sectional view of an organic electroluminescence device according to an embodiment of the present disclosure.
Figure 3:
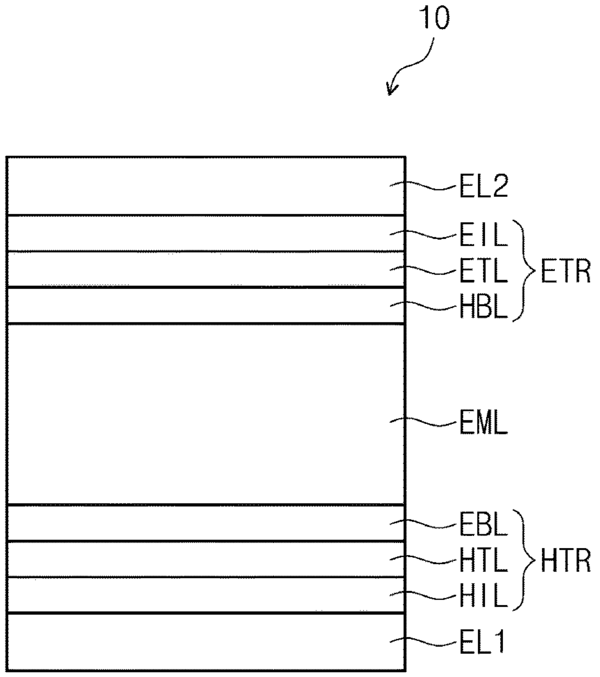
FIG. 3 is a schematic cross-sectional view of an organic electroluminescence device according to an embodiment of the present disclosure.
Figure 4:
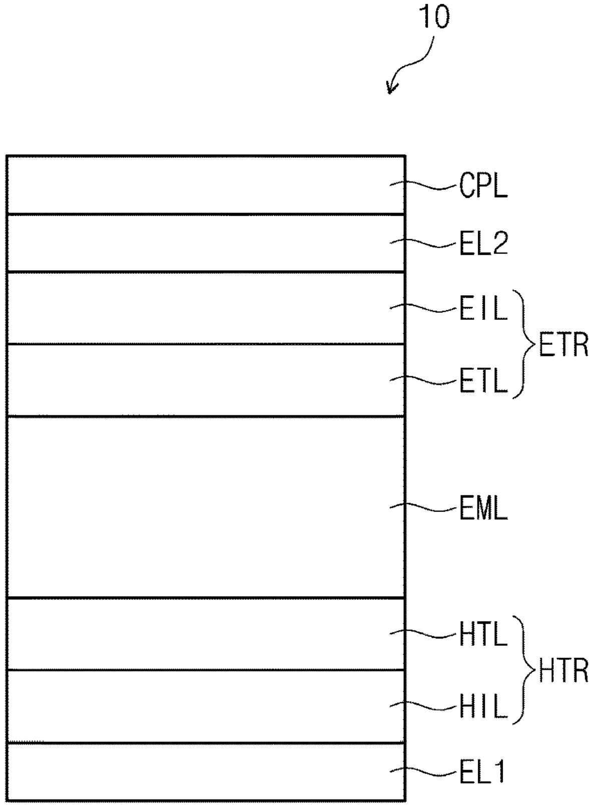
FIG. 4 is a schematic cross-sectional view of an organic electroluminescence device according to an embodiment of the present disclosure.

FIG. 2 shows the cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. FIG. 3 shows the cross-sectional view of an organic electroluminescence device 10 of an embodiment, wherein the hole transport region HTR includes the hole injection layer HIL, the hole transport layer HTL, and an electron blocking layer EBL, and the electron transport region ETR includes the electron injection layer EIL, the electron transport layer ETL, and a hole blocking layer HBL. FIG. 4 shows the cross-sectional view of an organic electroluminescence device 10 of an embodiment including a capping layer CPL disposed on the second electrode EL2.

The first electrode EL1 has conductivity. The first electrode EL1 may be formed using a metal alloy or a conductive compound. The first electrode EL1 may be a pixel electrode or an anode. The first electrode EL1 may be a transmissive electrode, a transflective electrode, or a reflective electrode. When the first electrode EL1 is a transmissive electrode, the first electrode EL1 may be formed using a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure including a plurality of layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, embodiments of the present disclosure are not limited thereto. The thickness of the first electrode EL1 may be about 1,000 Å to about 10,000 Å, for example, about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer, being a hole injection layer HIL or a hole transport layer HTL, or may have a structure of a single layer formed using a hole injection material and a hole transport material (e.g., together). In some embodiments, the hole transport region HTR may have a structure of a single layer formed using a plurality of different materials, or a multi-layer structure stacked on the first electrode EL1 of, for example, hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR of the organic electroluminescence device 10 of an embodiment includes the monoamine compound according to an embodiment.

In the description, the term "substituted or unsubstituted" corresponds to a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be unsubstituted, or further substituted. For example, a biphenyl group may be interpreted as an aryl group or a phenyl group substituted with a phenyl group.

In the description, non-limiting examples of the halogen atom may include a fluorine atom, a chlorine atom, a bromine atom, and an iodine atom.

In the description, the term "alkyl" may refer to a linear, branched or cyclic alkyl group. The carbon number of the alkyl may be 1 to 50, 1 to 30, 1 to 20, 1 to 10, or 1 to 6. Non-limiting examples of the alkyl include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the term "alkenyl group" refers to a hydrocarbon group including one or more carbon-carbon double bonds in the middle of or at the terminal of an alkyl group including 2 or more carbon atoms. The alkenyl group may be a linear chain or a branched chain alkenyl group. The carbon number is not specifically limited and may be 2 to 30, 2 to 20, or 2 to 10. Non-limiting examples of the alkenyl group include a vinyl group, a 1-butenyl group, a 1-pentenyl group, a 1,3-butadienyl aryl group, a styrenyl group, a styrylvinyl group, etc.

In the description, the term "alkynyl group" refers to a hydrocarbon group including one or more carbon-carbon triple bonds in the middle of or at the terminal of an alkyl group including 2 or more carbon atoms. The alkynyl group may be a linear chain or a branched chain alkynyl group. The carbon number is not specifically limited and may be 2 to 30, 2 to 20, or 2 to 10. Non-limiting examples of the alkynyl group include an ethynyl group, a propynyl group, etc.

In the description, the term "hydrocarbon ring group" refers to an optional functional group or substituent derived from an aliphatic hydrocarbon ring, or an optional functional group or substituent derived from an aromatic hydrocarbon ring. The carbon number for forming a ring of the hydrocarbon ring group may be 5 to 60, 5 to 30, or 5 to 20.

In the description, the term "aryl group" refers to a functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Non-limiting examples of the aryl group include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc.

In the description, the fluorenyl group may be substituted, and two substituents may be combined with each other to form a spiro structure. Non-limiting examples of the substituted fluorenyl group are as follows. However, embodiments of the present disclosure are not limited thereto.

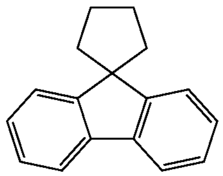
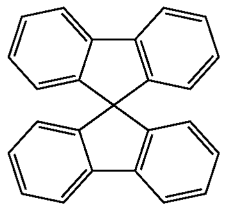
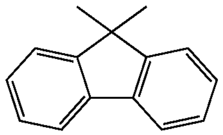
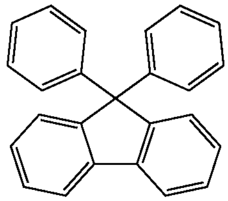
.

In the description, the term "heterocyclic group" refers to an optional functional group or substituent derived from a ring including one or more among boron (B), oxygen (O), nitrogen (N), phosphorus (P), silicon (Si), and sulfur (S) as heteroatoms. The heterocyclic group includes an aliphatic heterocyclic group and an aromatic heterocyclic group. The aromatic heterocyclic group may be a heteroaryl group. The aliphatic heterocycle and the aromatic heterocycle may each independently be monocyclic or polycyclic.

In the description, the term "heterocyclic group" may include one or more among B, O, N, P, Si and S as heteroatoms. When the heterocyclic group includes two or more heteroatoms, the two or more heteroatoms may be the same or different. The heterocyclic group may be a monocyclic heterocyclic group or a polycyclic heterocyclic group, and in some embodiments may be a heteroaryl group. The carbon number for forming a ring of the heteroaryl group may be 2 to 30, 2 to 20, or 2 to 10.

In the description, the aliphatic heterocyclic group may include one or more among B, O, N, P, Si and S as heteroatoms. The carbon number for forming a ring of the aliphatic heterocyclic group may be 2 to 30, 2 to 20, or 2 to 10. Non-limiting examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc.

In the description, the heteroaryl group may include one or more among B, O, N, P, Si and S as heteroatoms. If the heteroaryl group includes two or more heteroatoms, the two or more heteroatoms may be the same or different. The heteroaryl group may be a monocyclic heteroaryl group or a polycyclic heteroaryl group. The carbon number for forming a ring of the heteroaryl group may be 2 to 30, 2 to 20, or 2 to 10. Non-limiting examples of the heteroaryl group include thiophenyl group, furanyl group, pyrrolyl group, imidazolyl group, triazolyl group, pyridinyl group, bipyridinyl group, pyrimidinyl group, triazinyl group, triazolyl group, acridyl group, pyridazinyl group, pyrazinyl group, quinolinyl group, quinazolinyl group, quinoxalinyl group, phenoxazinyl group, phthalazinyl group, pyrido pyrimidinyl group, pyrido pyrazinyl group, pyrazino pyrazinyl group, isoquinolinyl group, indolyl group, carbazolyl group, N-arylcarbazolyl group, N-heteroarylcarbazolyl group, N-alkylcarbazolyl group, benzoxazolyl group, benzimidazolyl group, benzothiazolyl group, benzocarbazolyl group, benzothiophenyl group, dibenzothiophenyl group, thienothiophenyl group, benzofuranyl group, phenanthrolinyl group, thiazolyl group, isoxazolyl group, oxazolyl group, oxadiazolyl group, thiadiazolyl group, phenothiazinyl group, dibenzosilolyl group, dibenzofuranyl group, etc.

In the description, the carbon number of the amine group is not specifically limited, but may be 1 to 30. The amine group may include an alkyl amine group, an aryl amine group, or a heteroaryl amine group. Non-limiting examples of the amine group include a methylamine group, a dimethylamine group, a phenylamine group, a diphenylamine group, a naphthylamine group, a 9-methyl-anthracenylamine group, a triphenylamine group, etc.

In the description, the term "arylene group" may refer to a group substantially similar to the aryl group, except that the arylene group is a divalent group.

In the description, the term "heteroarylene group" may refer to a group substantially similar to the heteroaryl group, except that the heteroarylene group is a divalent group.

In the description, " —•" refers to a connected position.

The monoamine compound according to an embodiment of the present disclosure may be represented by Formula 1:

[Formula 1]

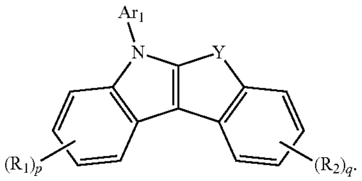

In Formula 1, Y may be O or S.

In Formula 1, "p" and "q" may each independently be an integer of 0 to 4. When "p" is 2 or more, a plurality of $R_1$ groups may be the same or different, and when "q" is 2 or more, a plurality of $R_2$ groups may be the same or different.

In Formula 1, $Ar_1$ may be a substituted or unsubstituted aryl group of 6 to 30 carbon atoms for forming a ring, a substituted or unsubstituted heteroaryl group of 2 to 30 carbon atoms for forming a ring, or represented by Formula 2 below.

In Formula 1, $R_1$ and $R_2$ may each be independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or represented by Formula 2.

In Formula 1, only one among $Ar_1$, $R_1$, and $R_2$ is represented by Formula 2:

[Formula 2]

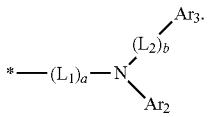

In Formula 2, $L_1$, and $L_2$ may each independently be a direct linkage, a substituted or unsubstituted arylene group of 6 to 30 carbon atoms for forming a ring, or a substituted or unsubstituted heteroarylene group of 2 to 30 carbon atoms for forming a ring.

In Formula 2, $Ar_2$ may be a substituted or unsubstituted aryl group of 6 to 30 carbon atoms for forming a ring or a substituted or unsubstituted heteroaryl group of 2 to 30 carbon atoms for forming a ring.

In Formula 2, $Ar_3$ may be a substituted or unsubstituted heteroaryl group of 2 to 30 carbon atoms for forming a ring.

In Formula 2, "a" and "b" may each independently be an integer of 0 to 3. When "a" is 2 or more, a plurality of $L_1$ groups may be the same or different, and when "b" is 2 or more, a plurality of $L_2$ groups are the same or different.

In Formula 2, " —•" refers to a connected position with Formula 1.

In an embodiment, $Ar_3$ of Formula 2 may be a polycyclic heteroaryl group in which at least two rings are condensed, or a polycyclic heteroaryl group in which at least three rings are condensed.

In an embodiment, $Ar_3$ of Formula 2 may be represented by Formula 3:

[Formula 3]

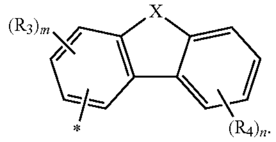

In Formula 3, X may be O or S.

In Formula 3, $R_3$ and $R_4$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or combined with an adjacent group to form a ring.

In Formula 3, "m" may be an integer of 0 to 3. When "m" is an integer of 2 or more, a plurality of $R_3$ groups may be the same or different.

In Formula 3, "n" may be an integer of 0 to 4. When "n" is 2 or more, a plurality of $R_4$ groups may be the same or different.

In Formula 3" —•" refers to a connected position with $L_2$.

In an embodiment, "p" of Formula 1 may be 1 or more, and $R_1$ may be represented by Formula 2. $Ar_3$ may be represented by Formula 3. In this case, Formula 1 may be represented by Formula 4:

[Formula 4]

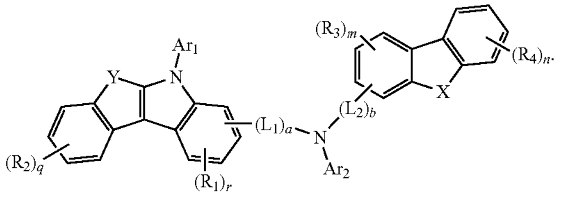

In Formula 4, $Ar_1$ may be a substituted or unsubstituted aryl group of 6 to 30 carbon atoms for forming a ring, or a substituted or unsubstituted heteroaryl group of 2 to 30 carbon atoms for forming a ring.

In Formula 4, $R_1$ and $R_2$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 4, "r" may be an integer of 0 to 3. When "r" is 2 or more, a plurality of $R_1$ groups may be the same or different.

In Formula 4, X, Y, $Ar_2$, $L_1$, $L_2$, "a", "b", $R_3$, $R_4$, "m", "n" and "q" may each independently be the same as defined in Formula 1 to Formula 3.

In an embodiment, "q" of Formula 1 may be 1 or more, and $R_2$ may be represented by Formula 2. $Ar_3$ may be represented by Formula 3. In this case, Formula 1 may be represented by Formula 5:

[Formula 5]

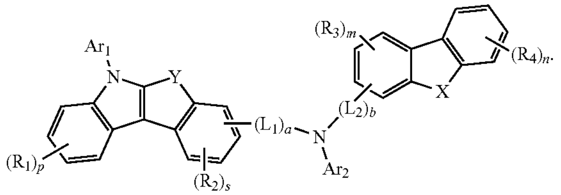

In Formula 5, $Ar_1$ may be a substituted or unsubstituted aryl group of 6 to 30 carbon atoms, or a substituted or unsubstituted heteroaryl group of 2 to 30 carbon atoms for forming a ring.

In Formula 5, $R_1$ and $R_2$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 5, "s" may be an integer of 0 to 3. When "s" is 2 or more, a plurality of $R_2$ groups may be the same or different.

In Formula 5, X, Y, $Ar_2$, $L_1$, $L_2$, "a", "b", $R_3$, $R_4$, "m", "n" and "p" may each independently be the same as defined in Formula 1 to Formula 3.

In an embodiment, $Ar_1$ of Formula 1 may be represented by Formula 2. $Ar_3$ may be represented by Formula 3. In this case, Formula 1 may be represented by Formula 6:

[Formula 6]

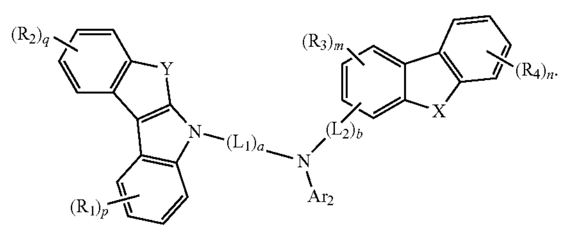

In Formula 6, $R_1$ and $R_2$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 6, X, Y, $Ar_2$, $L_1$, $L_2$, "a", "b", $R_3$, $R_4$, "m", "n", "p" and "q" may each independently be the same as defined in Formula 1 to Formula 3.

In an embodiment, Formula 4 may be represented by any one among Formula 4-1 to Formula 4-4:

[Formula 4-1]

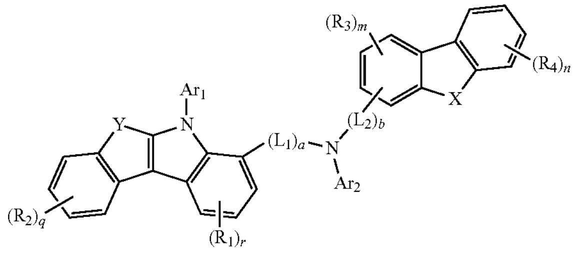

[Formula 4-2]

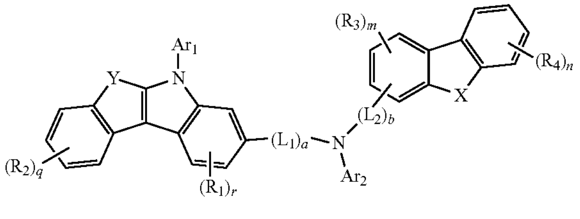

[Formula 4-3]

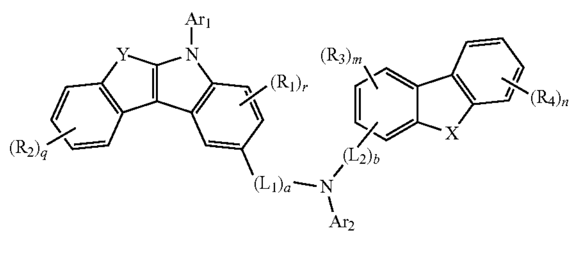

-continued

[Formula 4-4]

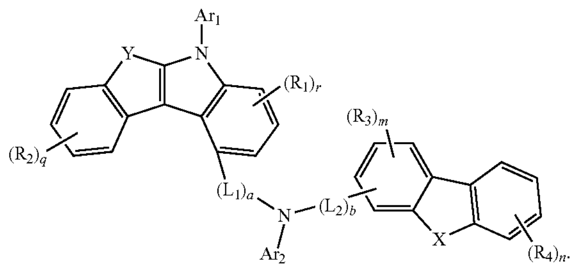

In Formula 4-1 to Formula 4-4, X, Y, $Ar_1$, $Ar_2$, $L_1$, $L_2$, $R_1$ to $R_4$, "a", "b", "m", "n", "q" and "r" may each independently be the same as defined in Formula 4.

In an embodiment, Formula 5 may be represented by any one among Formula 5-1 to Formula 5-4:

[Formula 5-1]

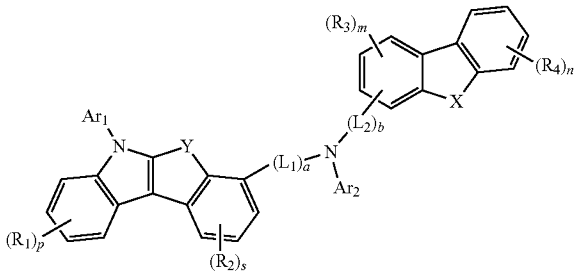

[Formula 5-2]

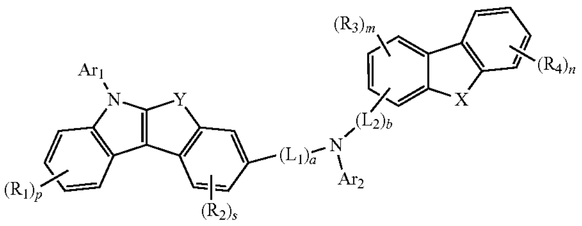

[Formula 5-3]

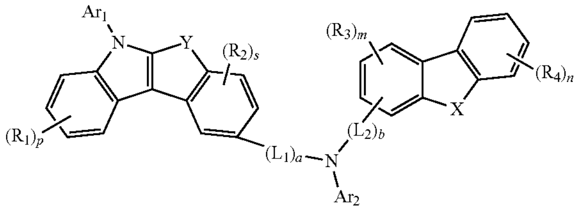

[Formula 5-4]

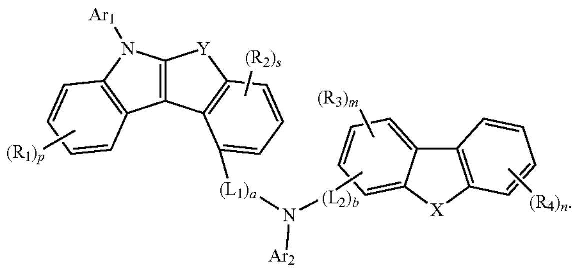

In Formula 5-1 to Formula 5-4, X, Y, $Ar_1$, $Ar_2$, $L_1$, $L_2$, $R_1$ to $R_4$, "a", "b", "m", "n", "p" and "s" may each independently be the same as defined in Formula 5.

In an embodiment, $L_1$, and $L_2$ of Formula 2, and Formula 4 to Formula 6 may each independently be a direct linkage, a substituted or unsubstituted phenylene group, a substituted or unsubstituted biphenylene group, or a substituted or unsubstituted naphthylene group.

In an embodiment, "a" of Formula 2, Formula 4 to Formula 6, Formula 4-1 to Formula 4-4, and Formula 5-1 to Formula 5-4 may be 1, and Li may be represented by any one among L-1 to L-4:

L-1

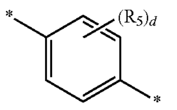

L-2

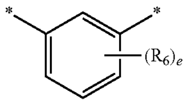

L-3

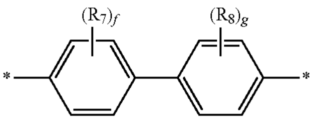

L-4

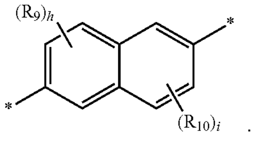

In L-1 to L-4, $R_5$ to $R_{10}$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In L-1 to L-3, "d" to "g" may each independently be an integer of 0 to 4. When "d" is 2 or more, a plurality of $R_5$ groups may be the same or different, when "e" is 2 or more, a plurality of $R_6$ groups may be the same or different, when "f" is 2 or more, a plurality of $R_7$ groups may be the same or different, and when "g" is 2 or more, a plurality of $R_8$ groups may be the same or different.

In L-4, "h" and "i" may each independently be an integer of 0 to 3. When "h" is 2 or more, a plurality of $R_9$ groups may be the same or different, and when "i" is 2 or more, a plurality of $R_{10}$ groups may be the same or different.

In an embodiment, $R_1$, and $R_2$ of Formula 1, Formula 4 to Formula 6, Formula 4-1 to Formula 4-4, and Formula 5-1 to Formula 5-4, may each independently be a hydrogen atom, a deuterium atom, a halogen atom or a substituted or unsubstituted alkyl group of 1 to 10 carbon atoms.

In an embodiment, $Ar_1$ of Formula 1, Formula 4, Formula 5, Formula 4-1 to Formula 4-4, and Formula 5-1 to Formula 5-4 may be a substituted or unsubstituted phenyl group, a substituted or unsubstituted biphenyl group, a substituted or unsubstituted triphenyl group, a substituted or unsubstituted dibenzofuran group, or a substituted or unsubstituted dibenzothiophene group.

The monoamine compound represented by Formula 1 according to an embodiment of the present disclosure may be any one selected among the compounds represented in Compound Groups 1 to 3:

[Compound Group 1]
A1
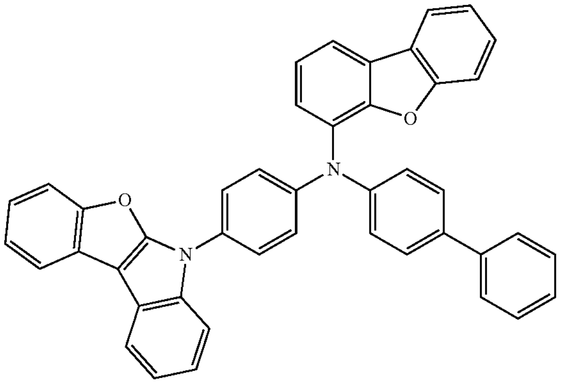
A2
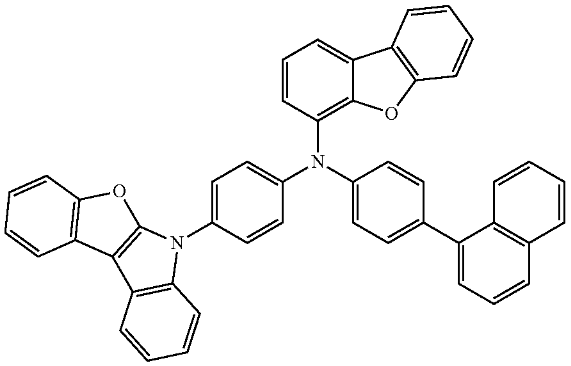
A3
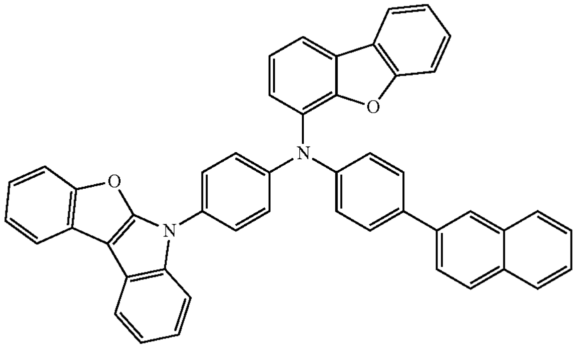
A4
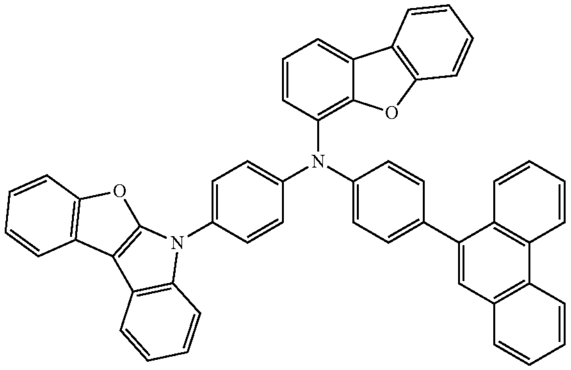
-continued
A5
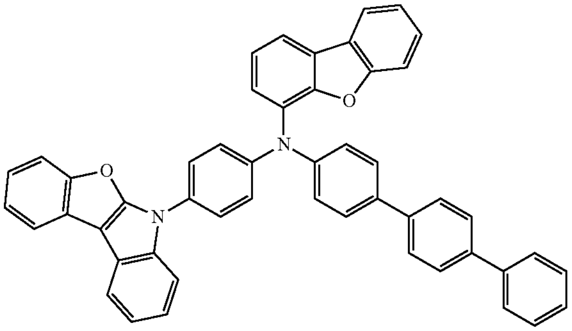
A6
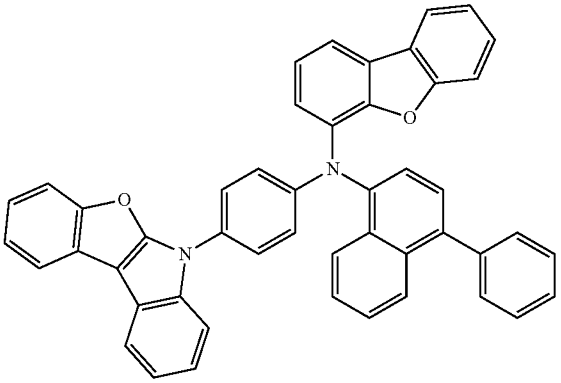
A7
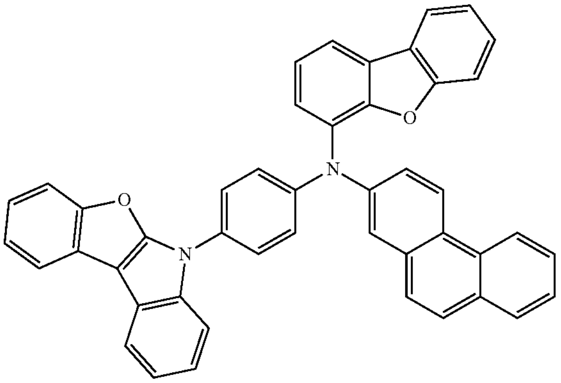
A8
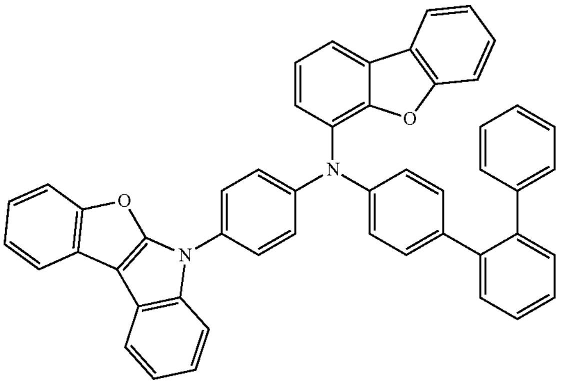

-continued
A9
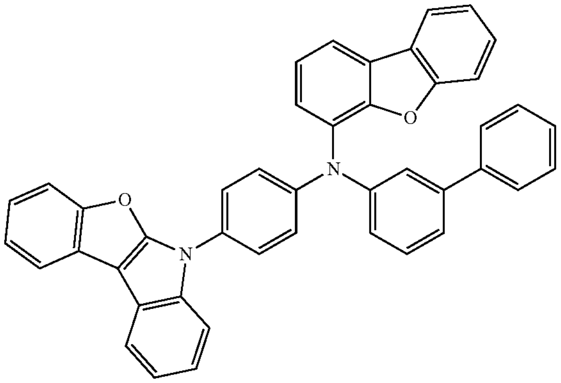
A10
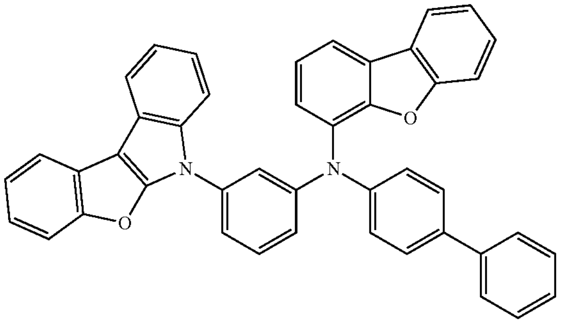
A11
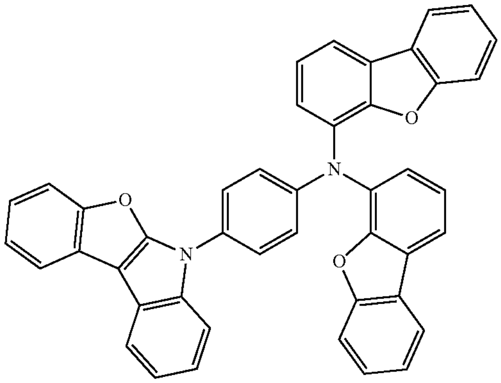
A12
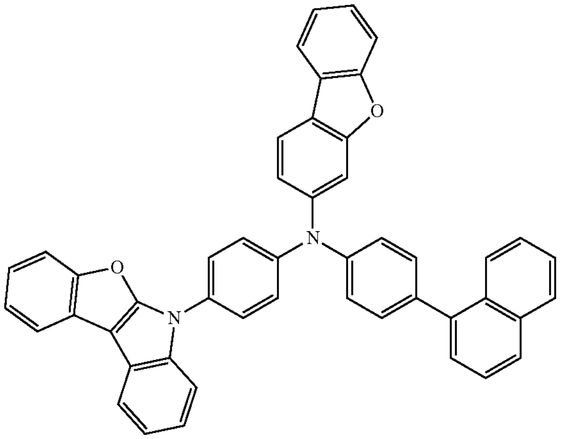
-continued
A13
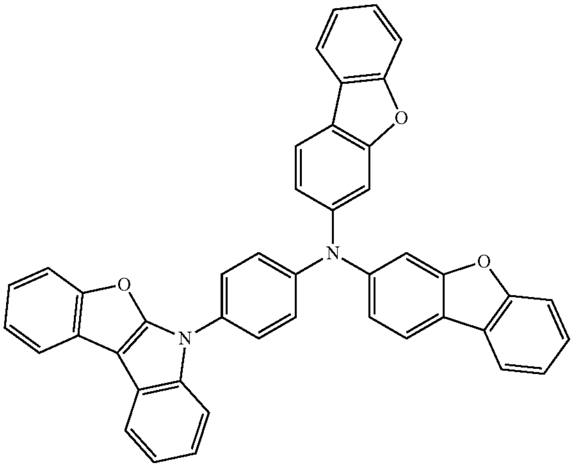
A14
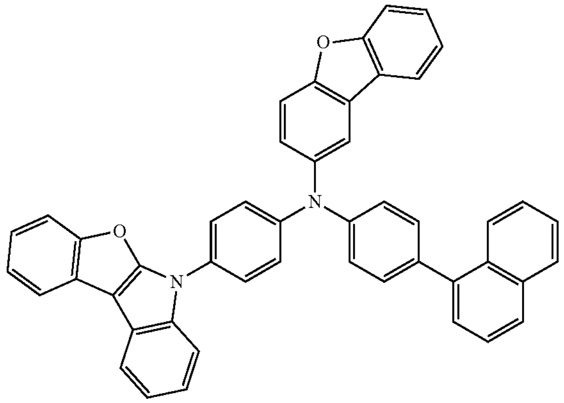
A15
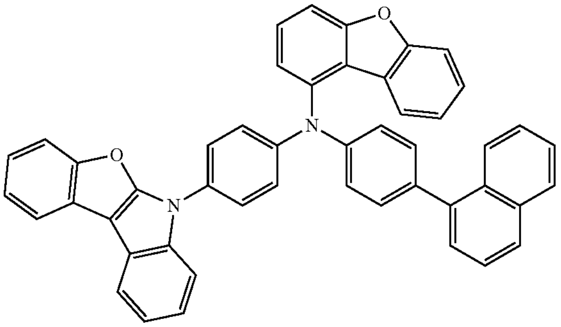

-continued
A16
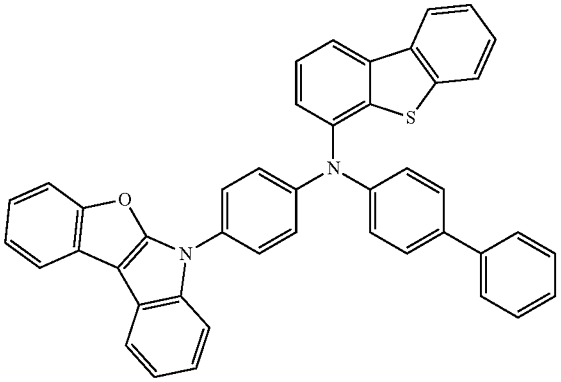
A17
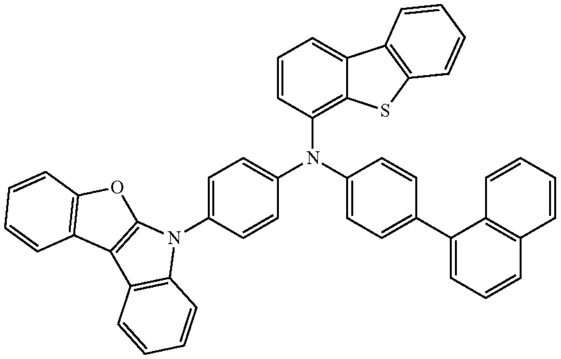
A18
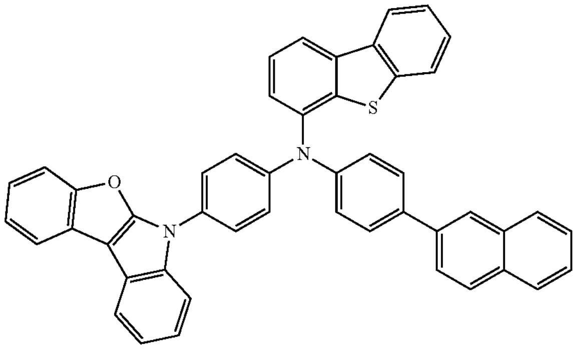
A19
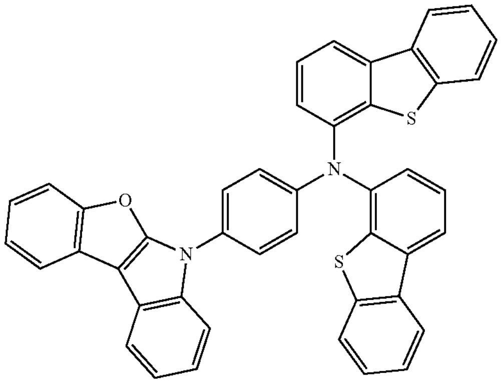
-continued
A20
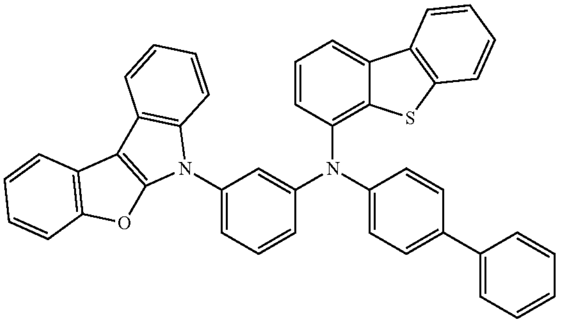
A21
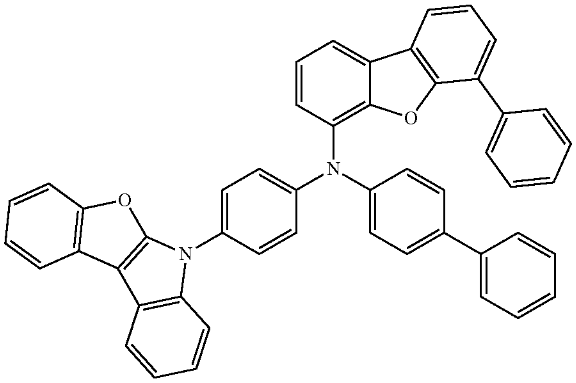
A22
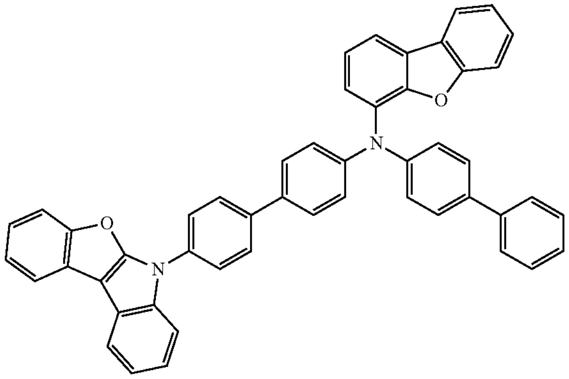
A23
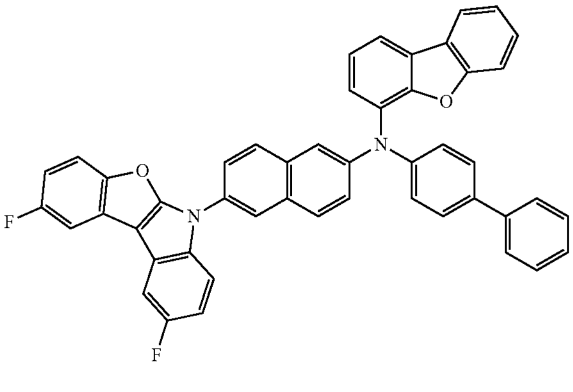

-continued
A24
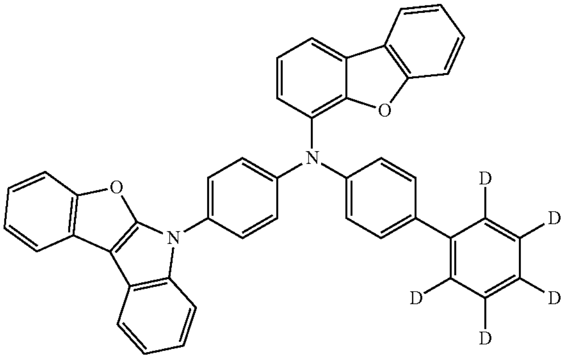
A25
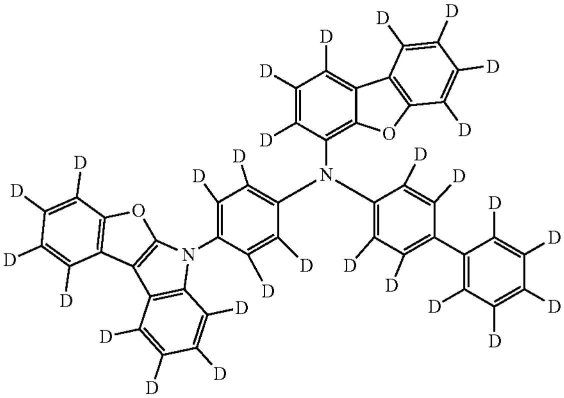
A26
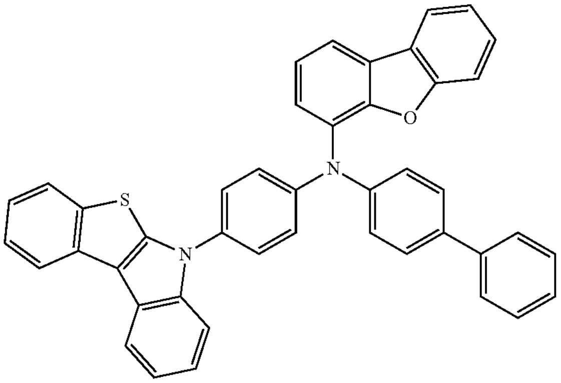
A27
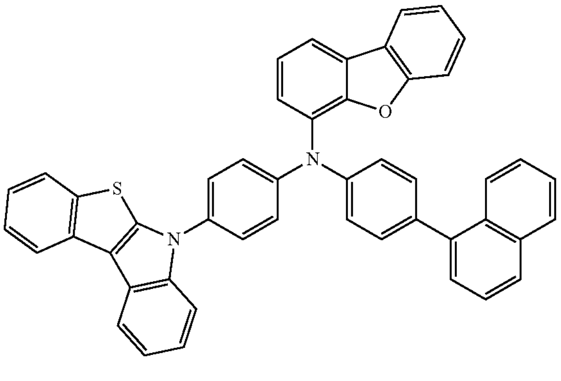
-continued
A28
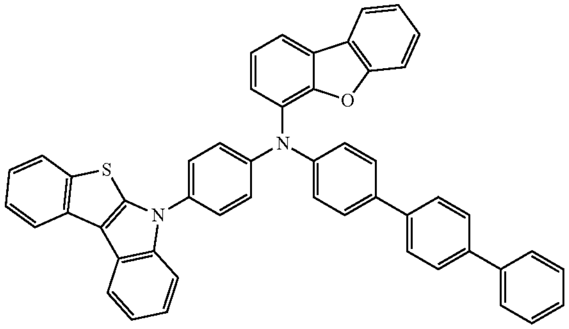
A29
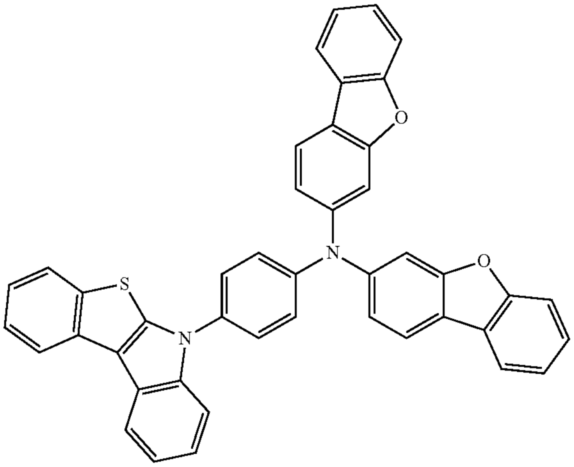
A30
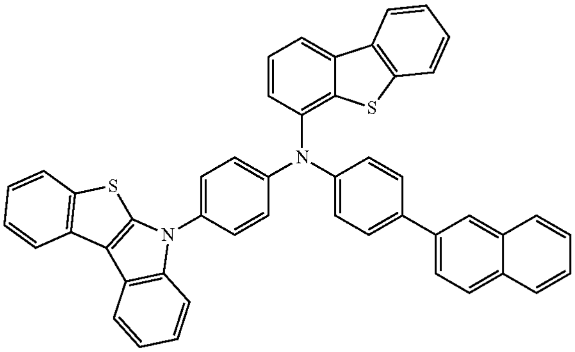

-continued
A31
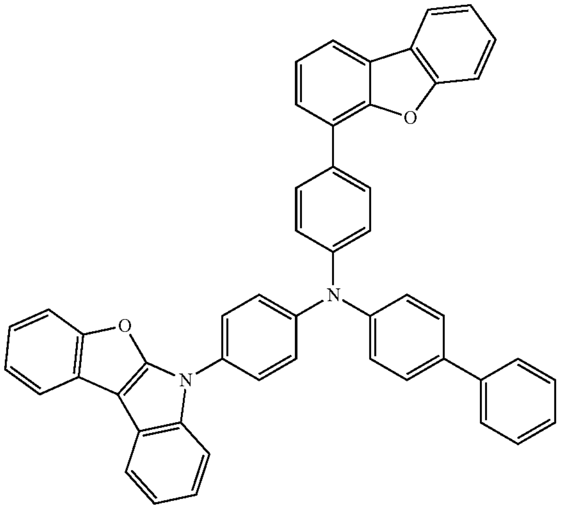
A32
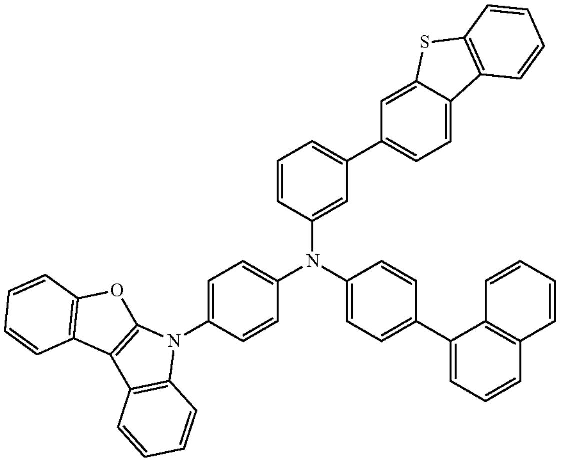
A33
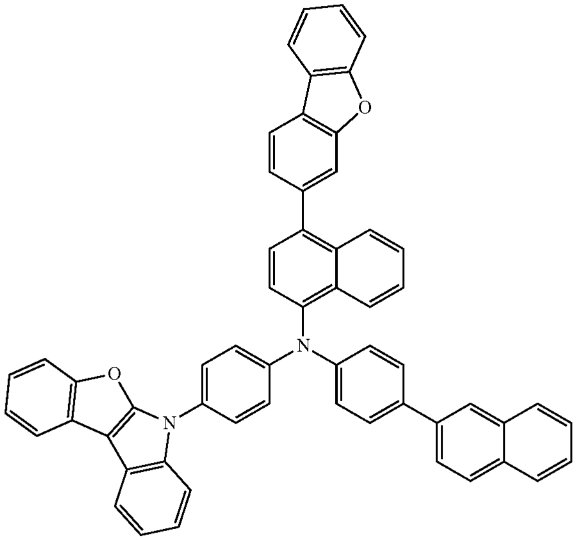
-continued
A34
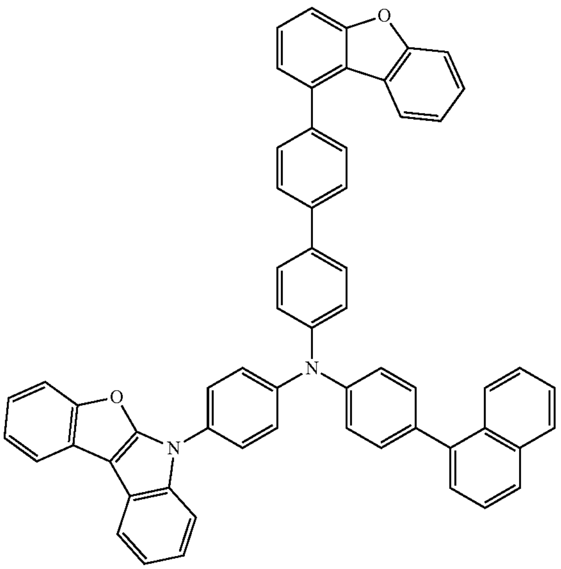
A34
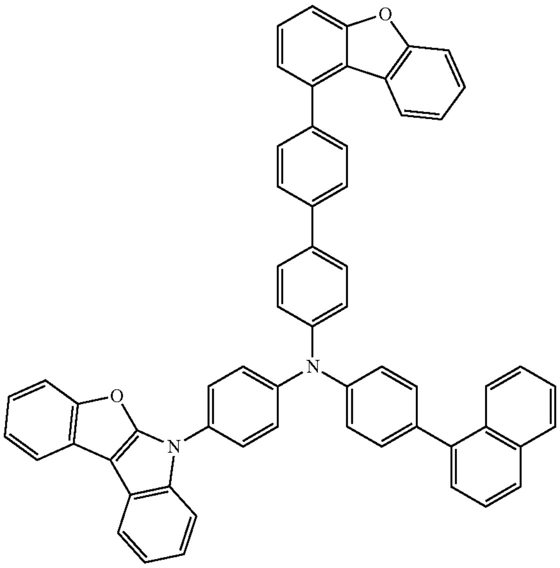
A35
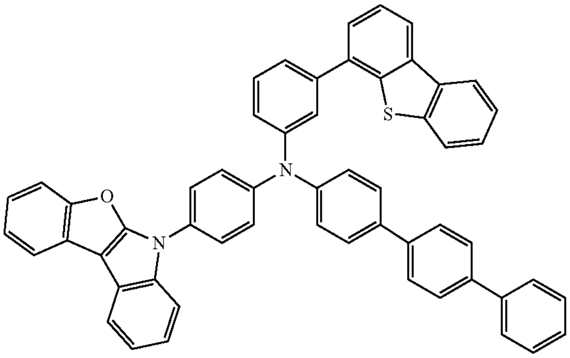

-continued
A36
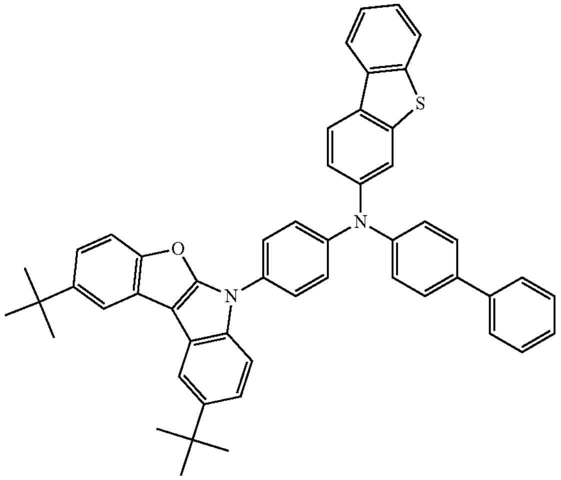
A37
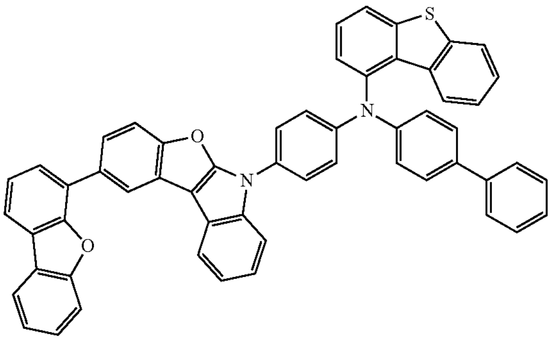
A38
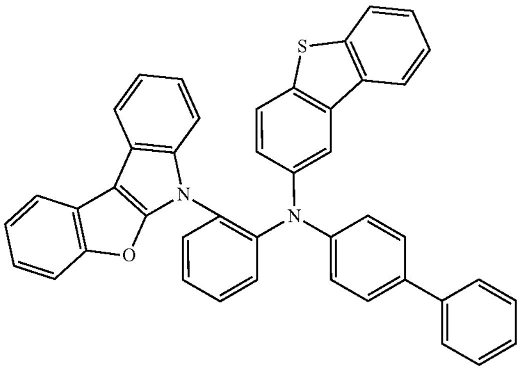
-continued
A39
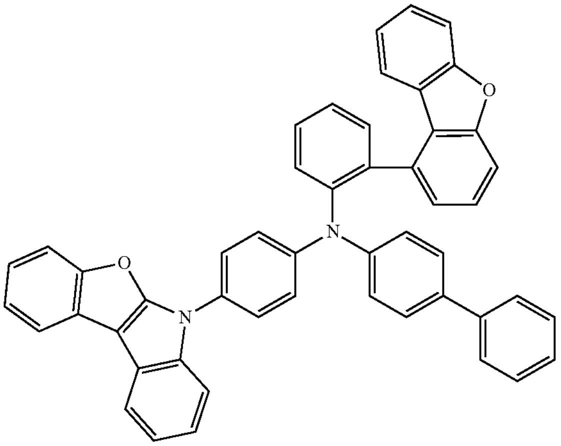
A40
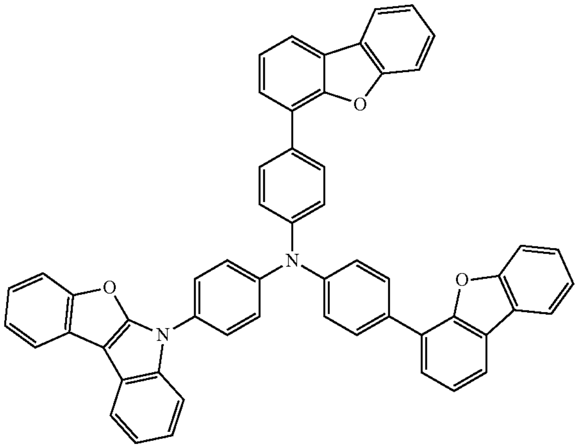
A41
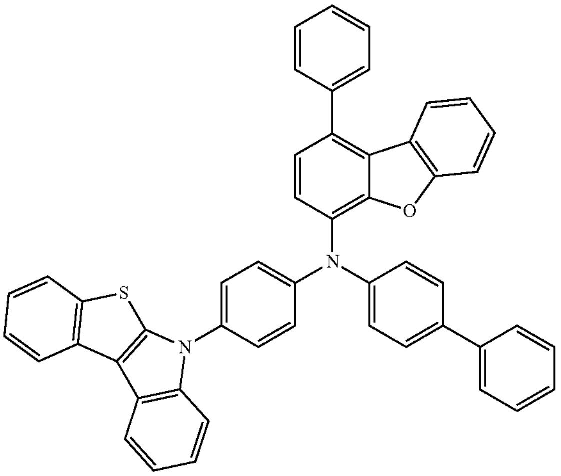

-continued
A42
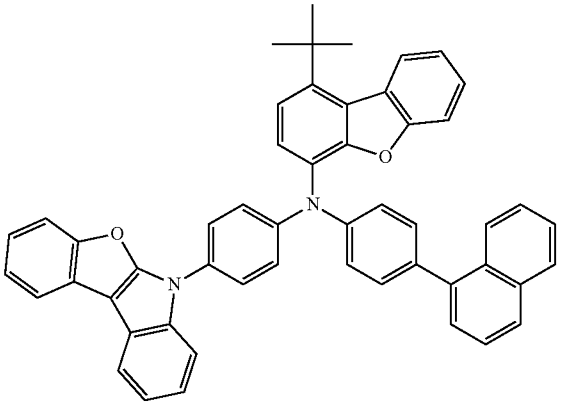
A43
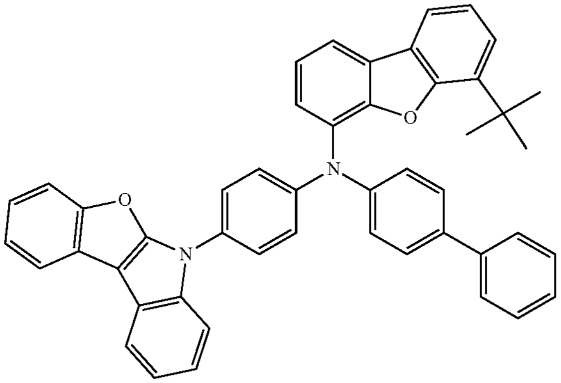
A44
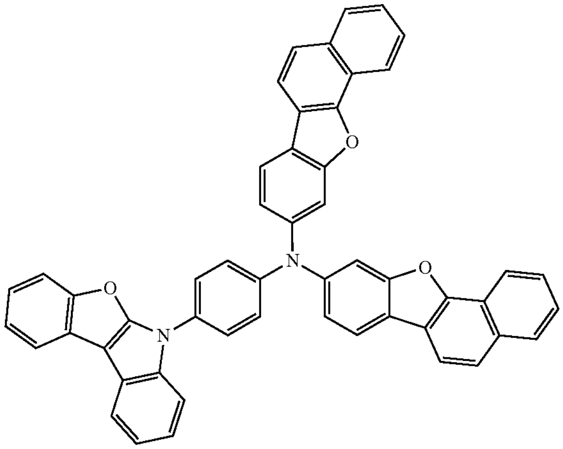
-continued
A45
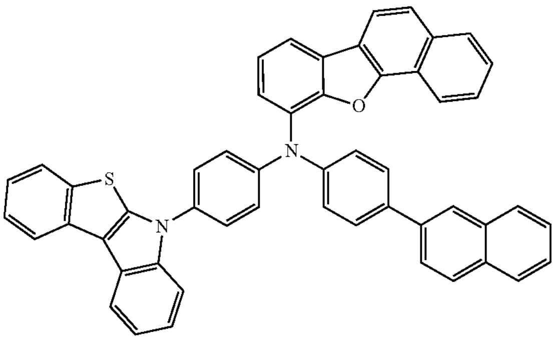
.
[Compound Group 2]
B1
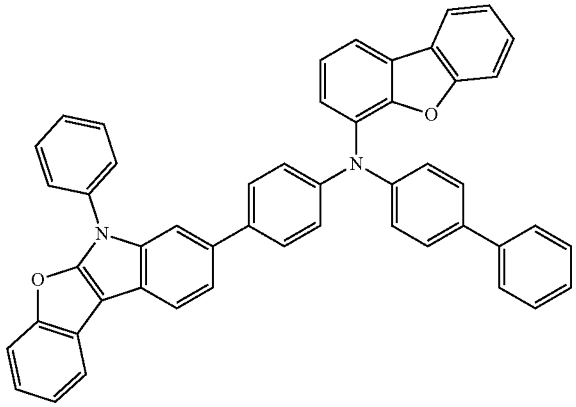
B2
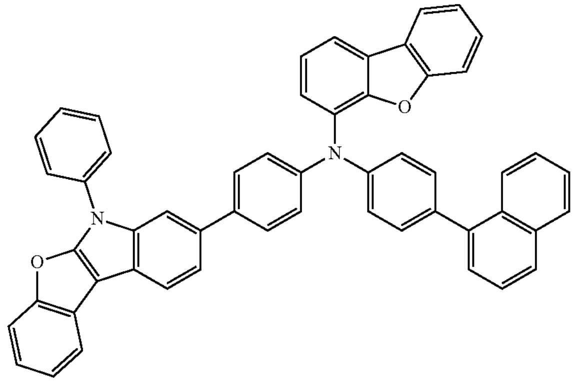
B3
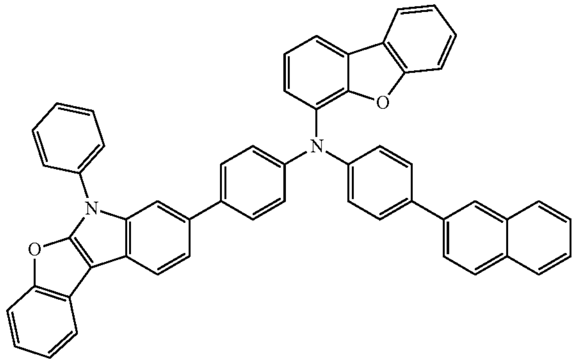

-continued
B4
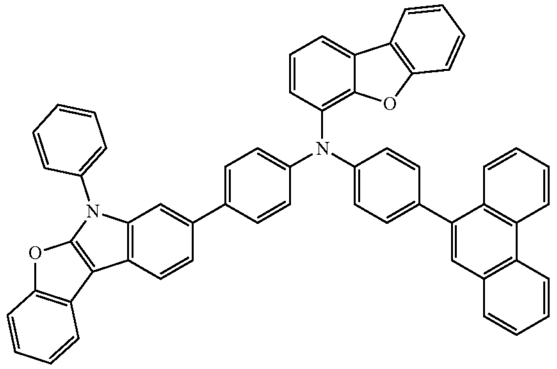
B5
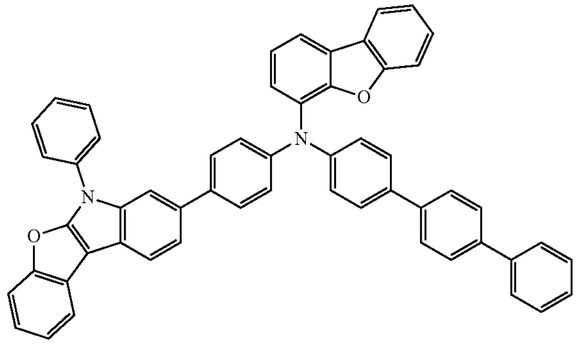
B6
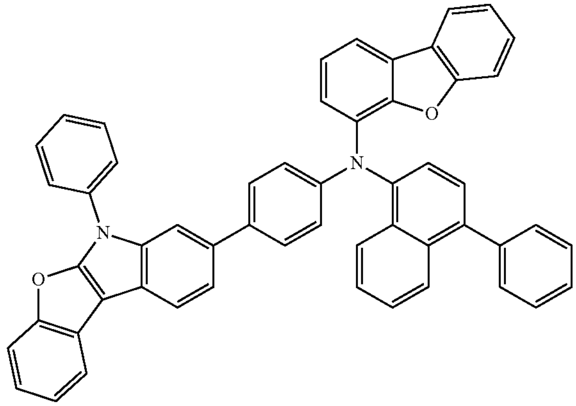
B7
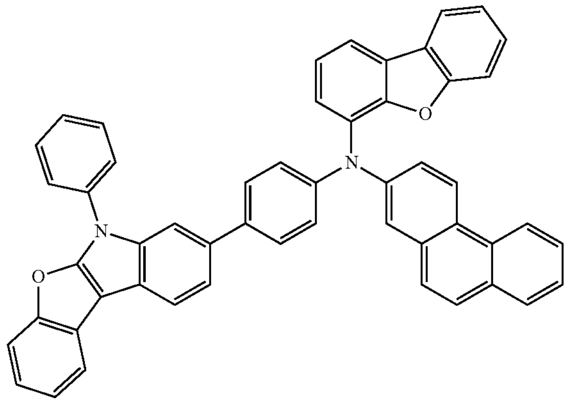
-continued
B8
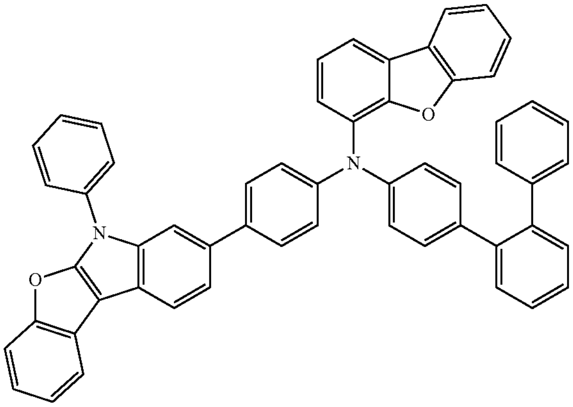
B9
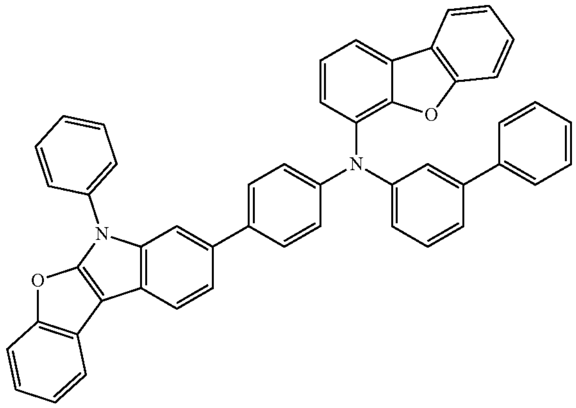
B10
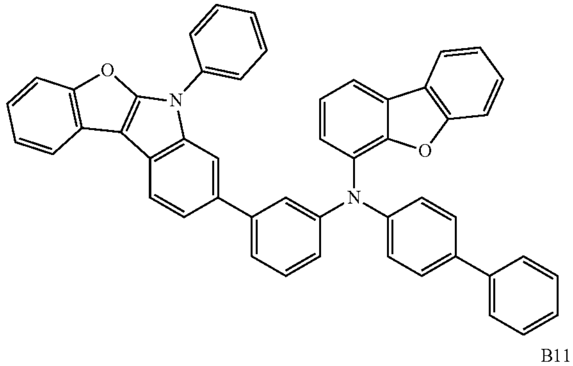
B11
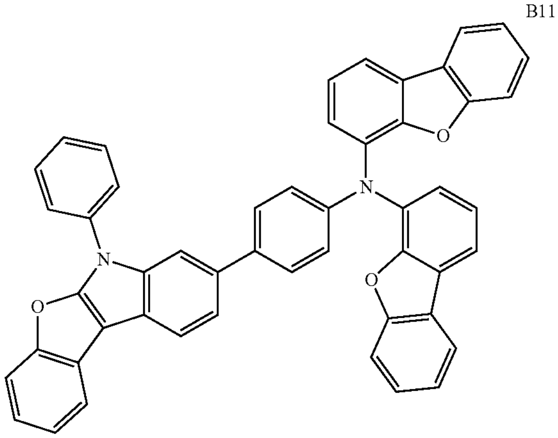

-continued
B12
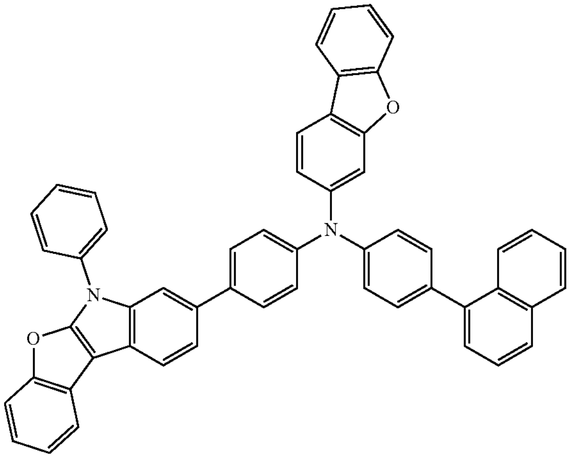
B13
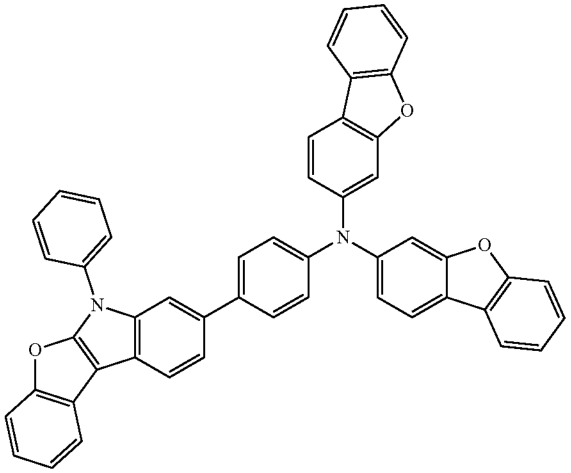
B14
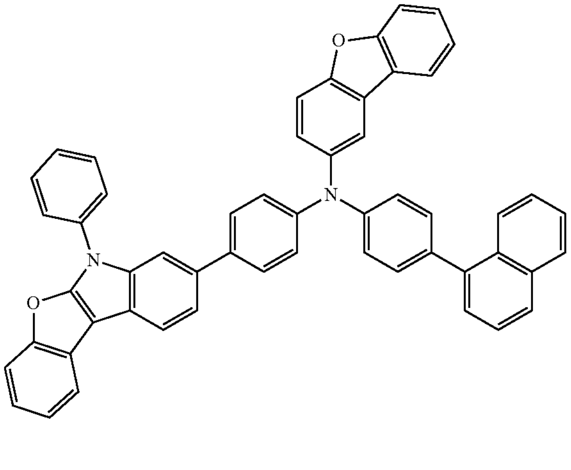
-continued
B15
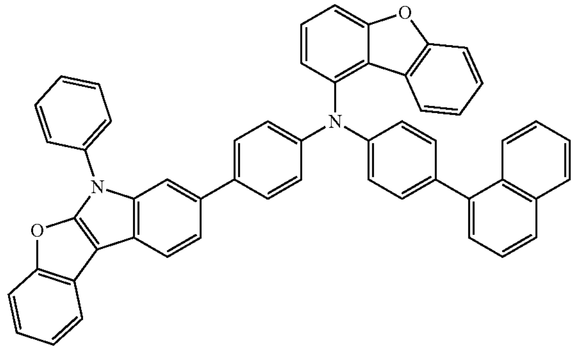
B16
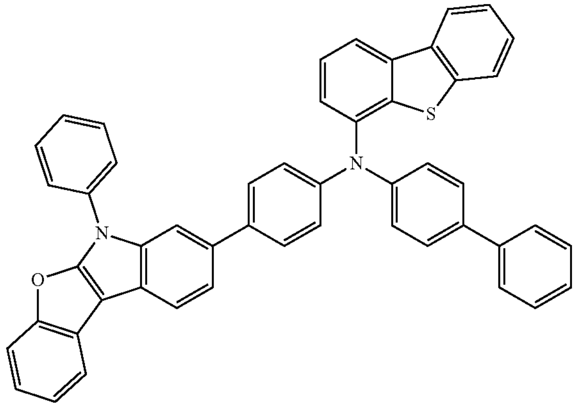
B17
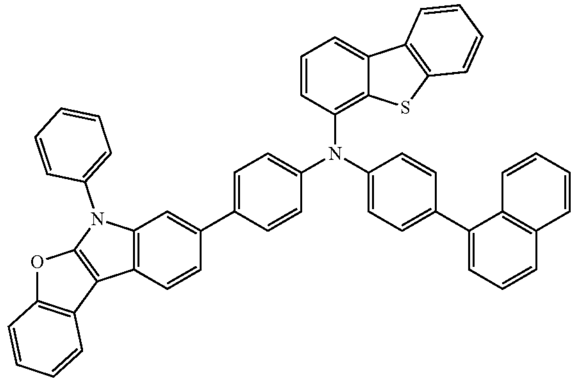
B18
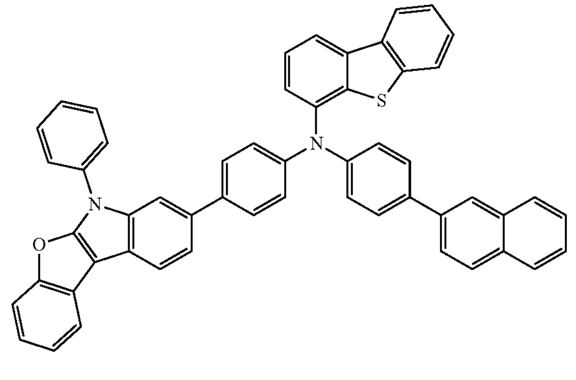

-continued
B19
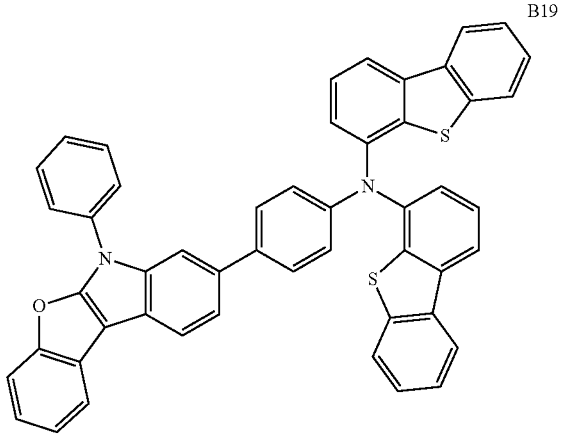
B20
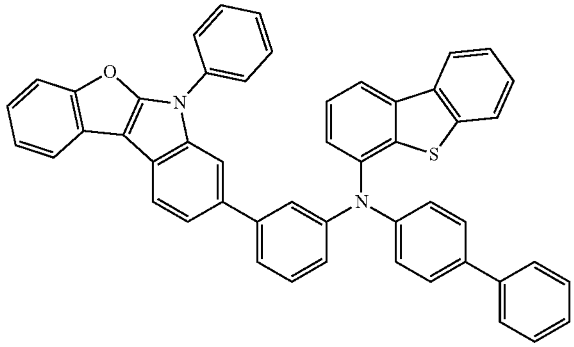
B21
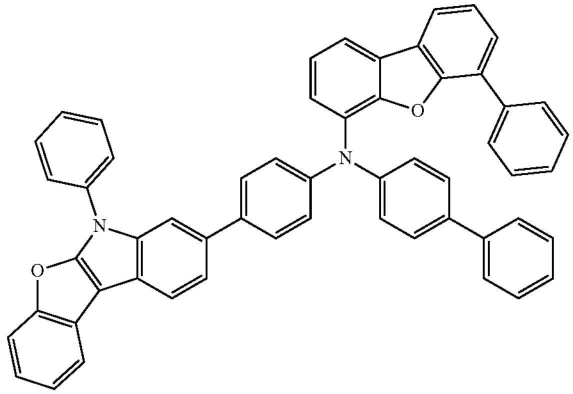
B22
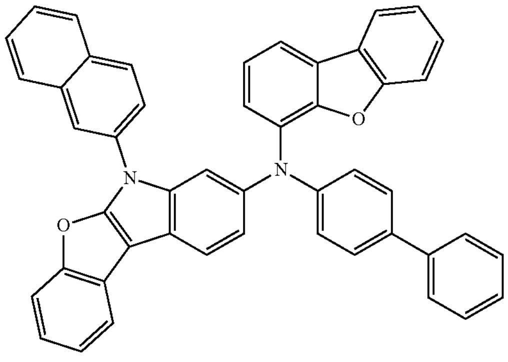
-continued
B23
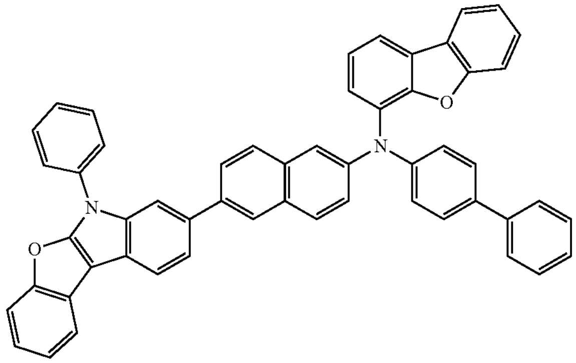
B24
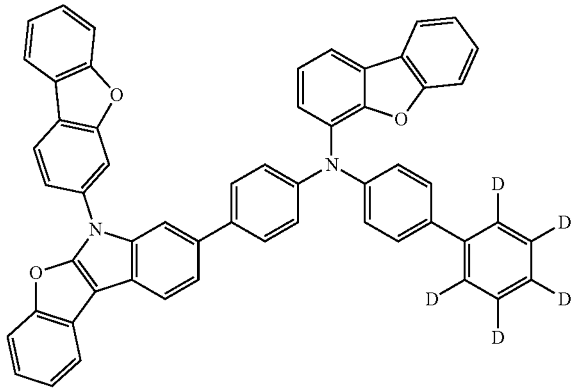
B25
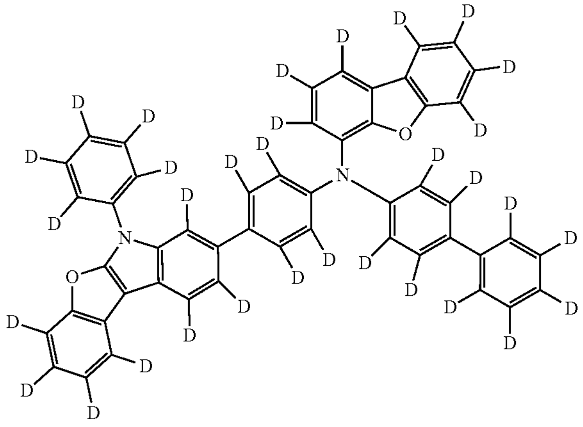

-continued
B26
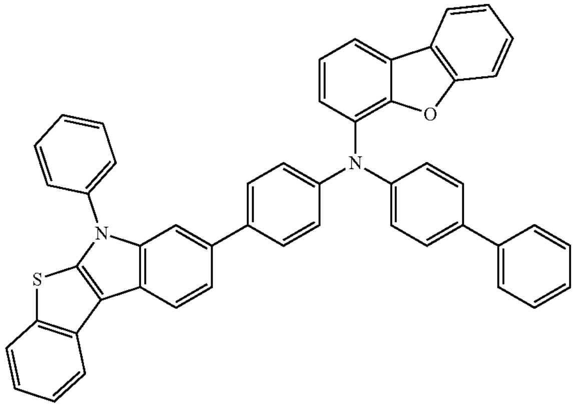
B27
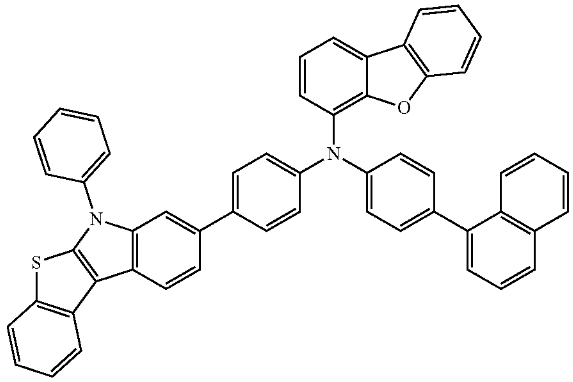
B28
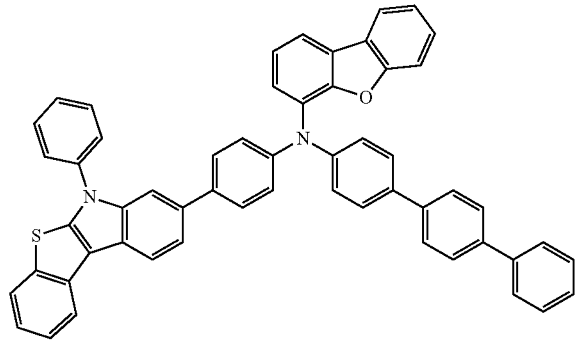
-continued
B29
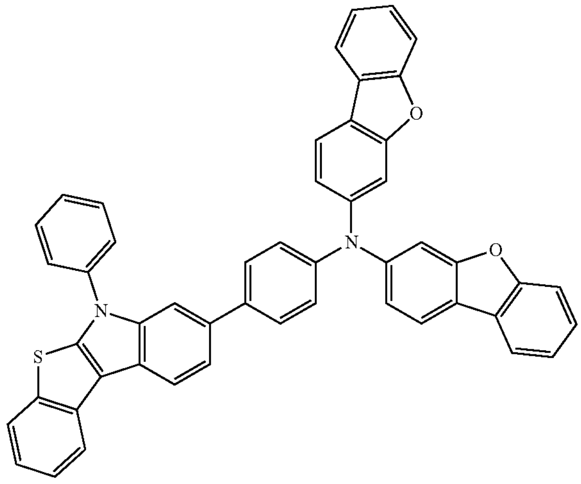
B30
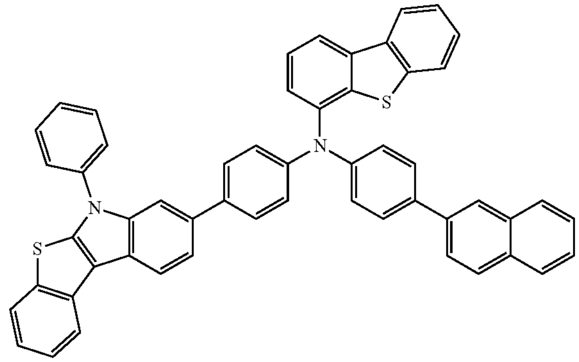
B31
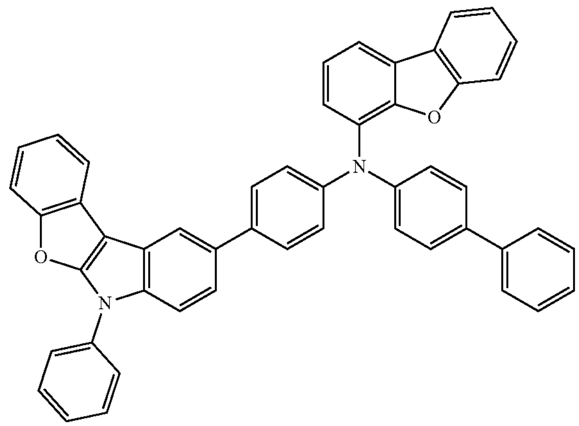

-continued
B32
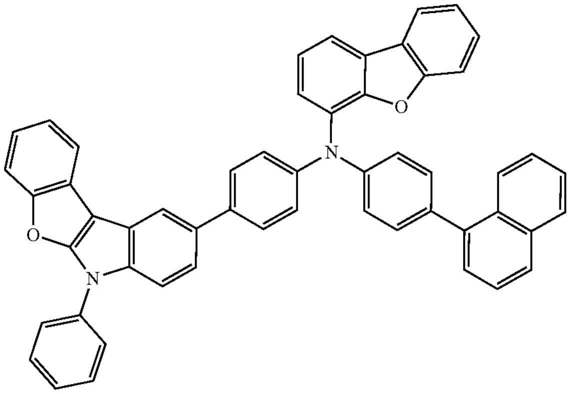
B33
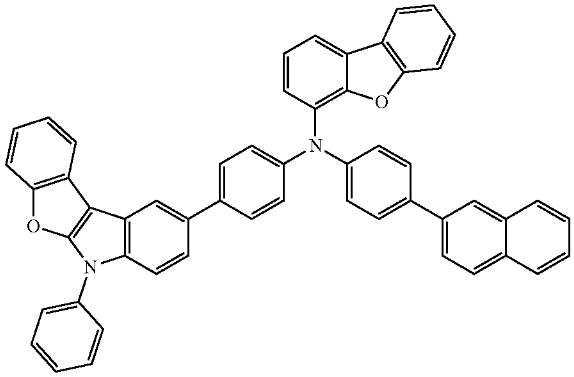
B34
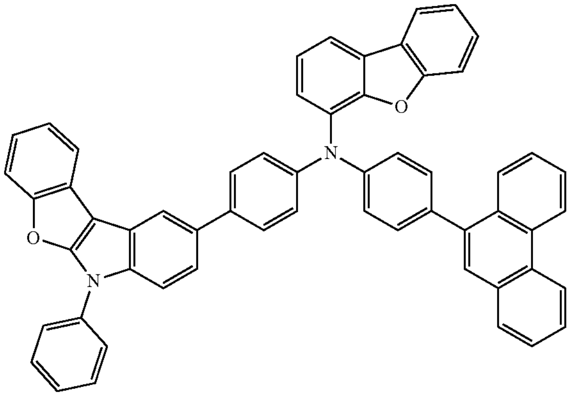
B35
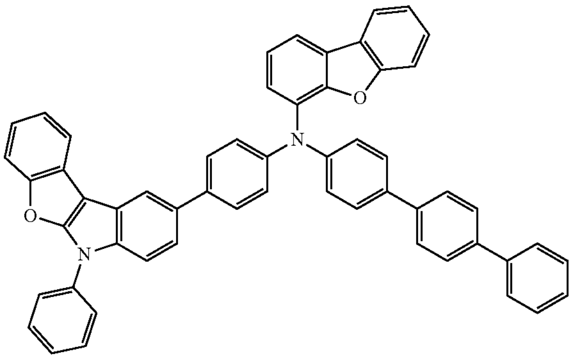
-continued
B36
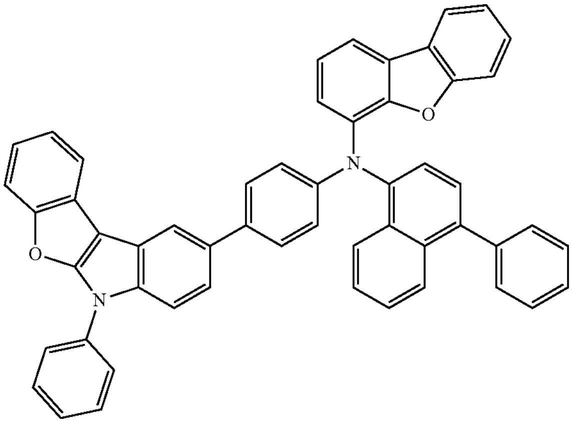
B37
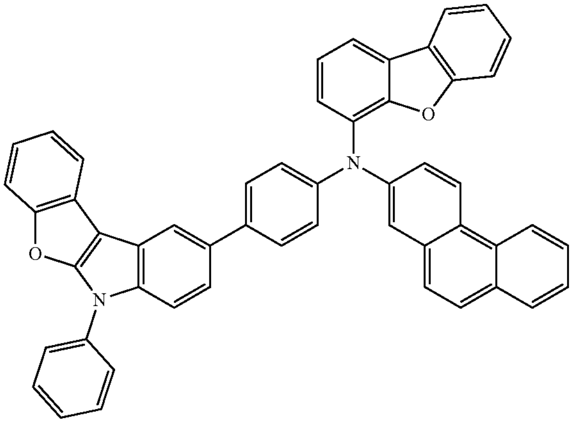
B38
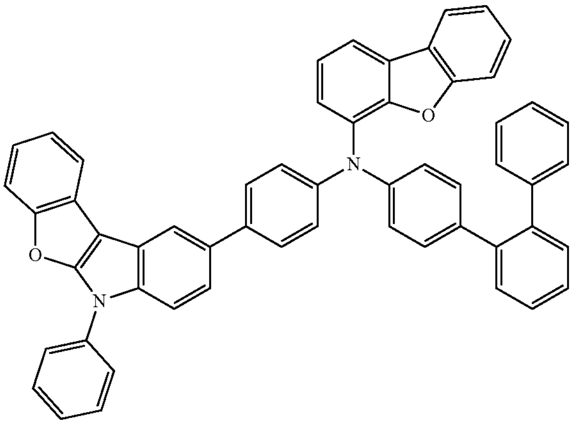

-continued
B39
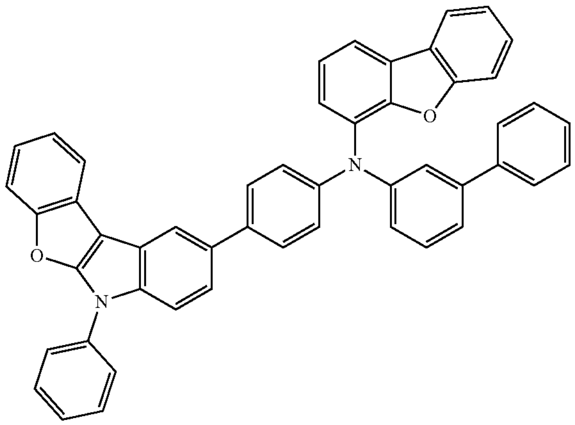
B40
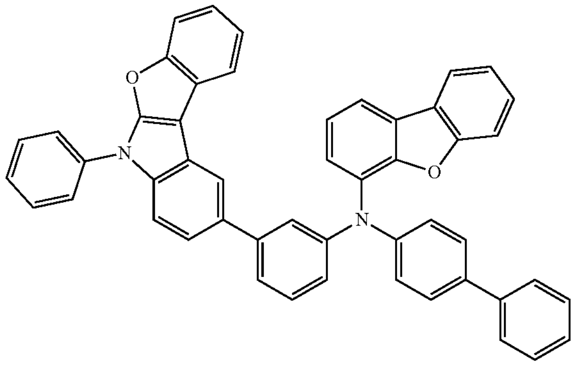
B41
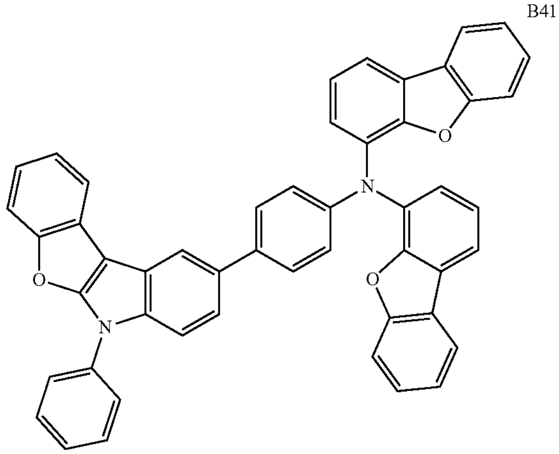
-continued
B42
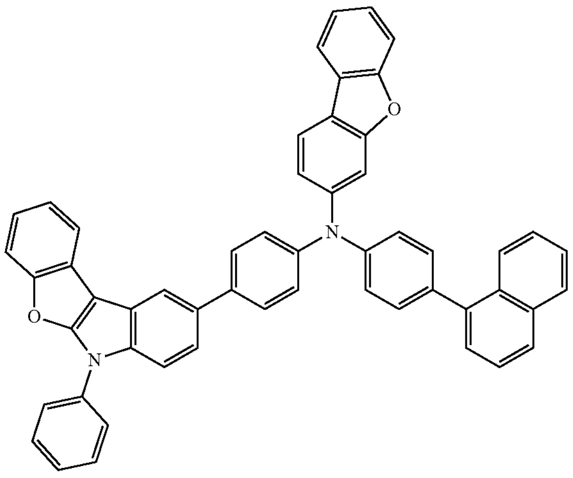
B43
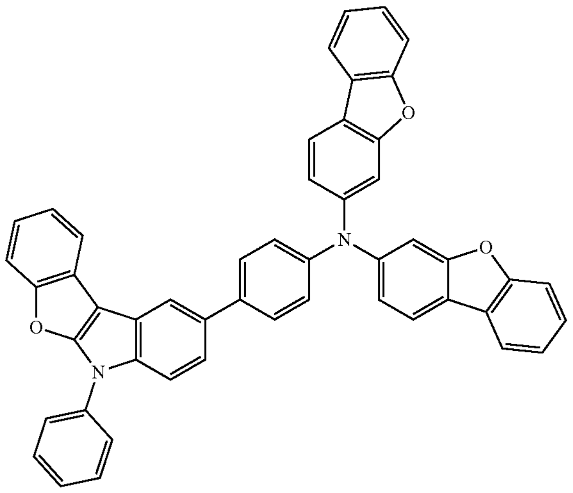
B44
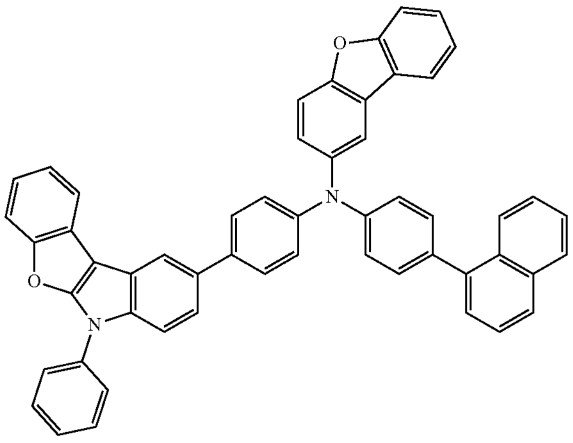

-continued
B45
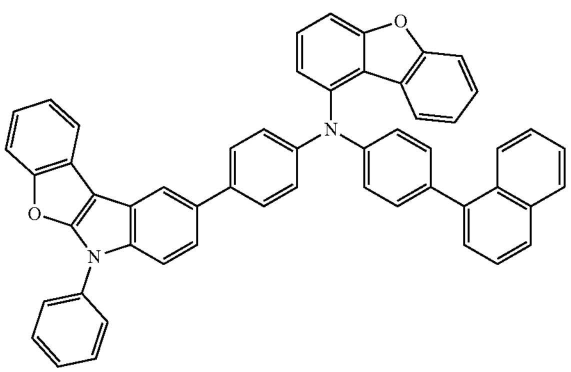
B46
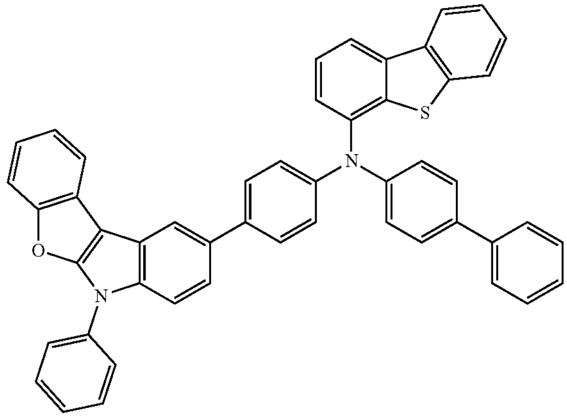
B47
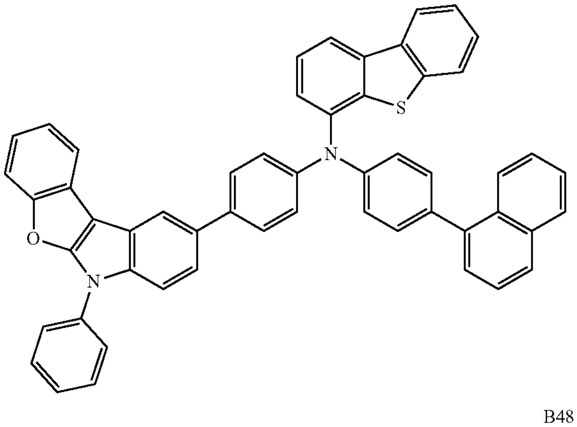
B48
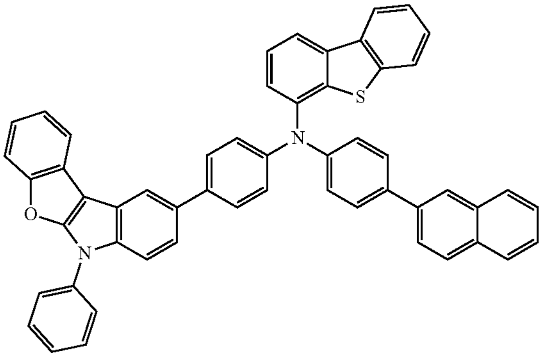
-continued
B49
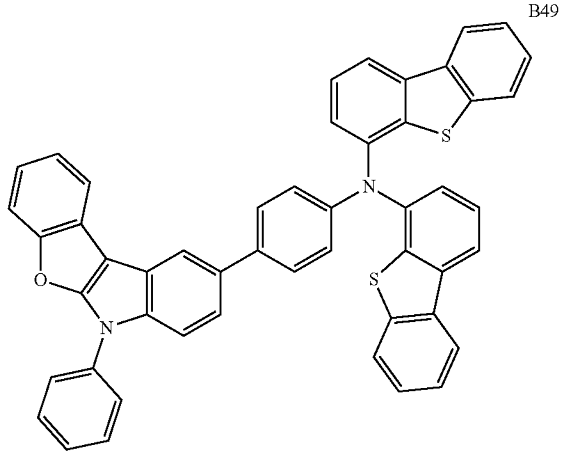
B50
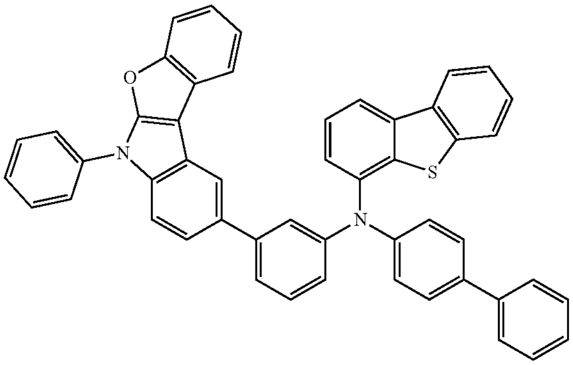
B51
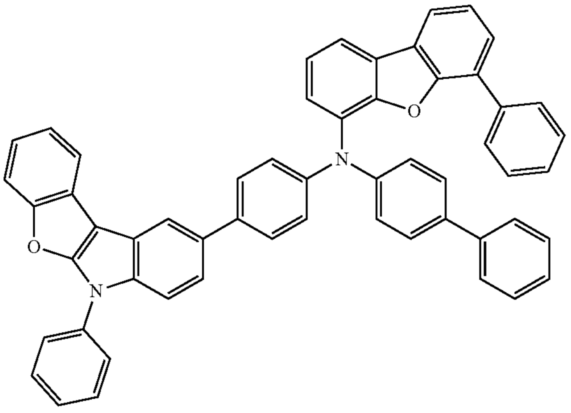

-continued
B52
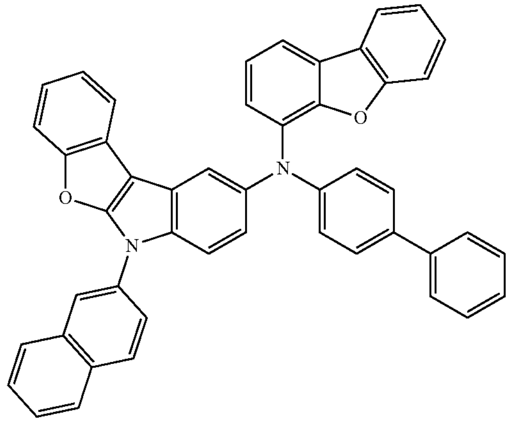
B53
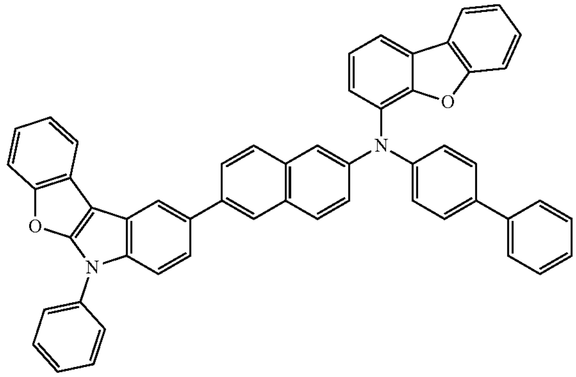
B54
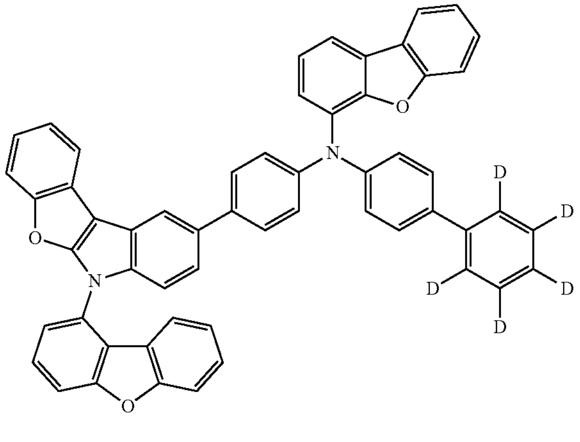
-continued
B55
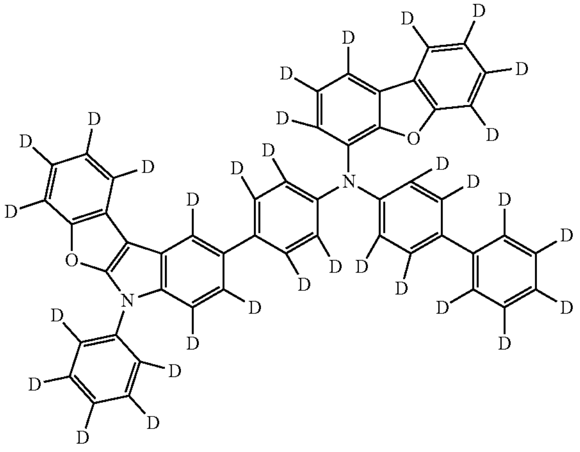
B56
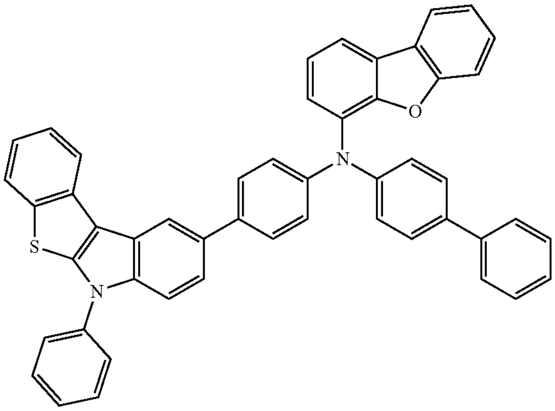
B57
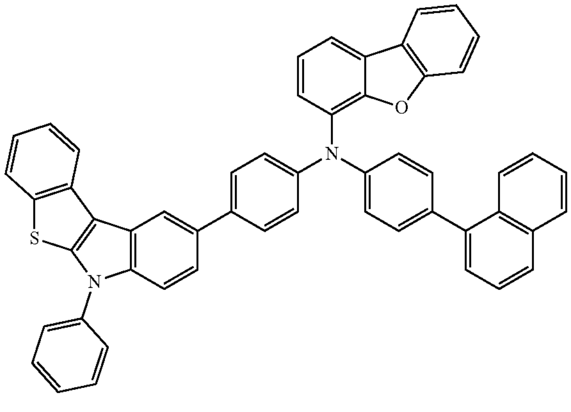

-continued
B58
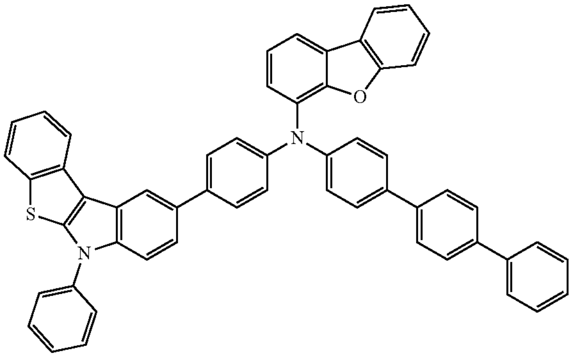
B59
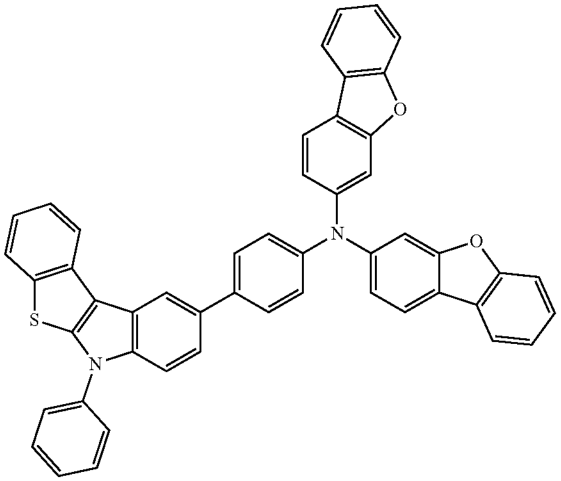
B60
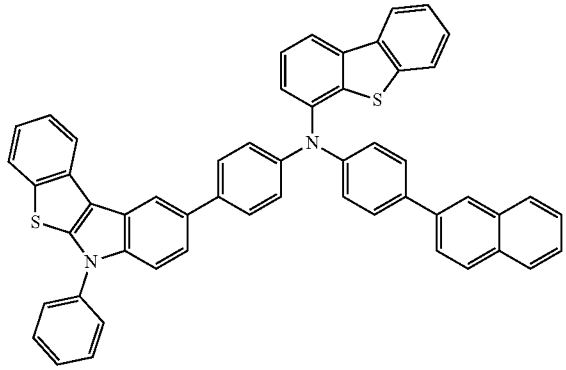
B61
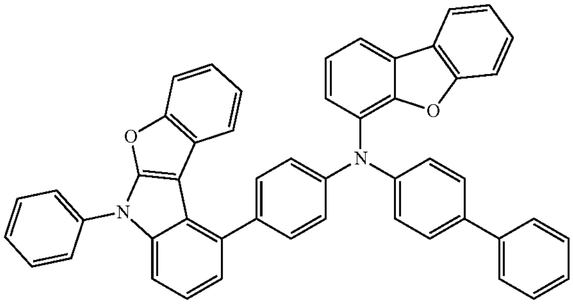
-continued
B62
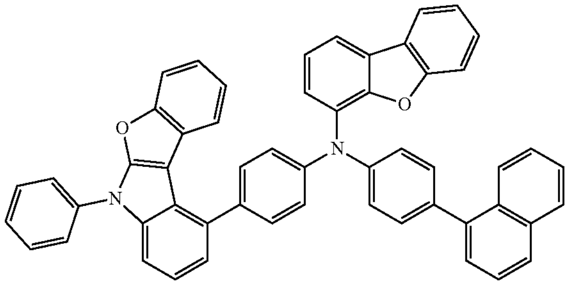
B63
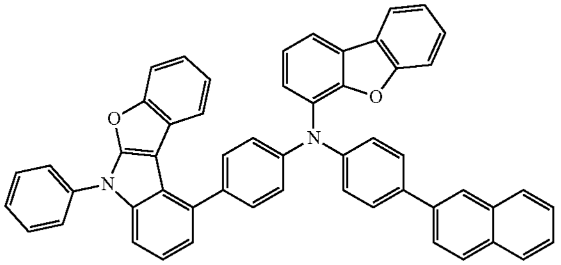
B64
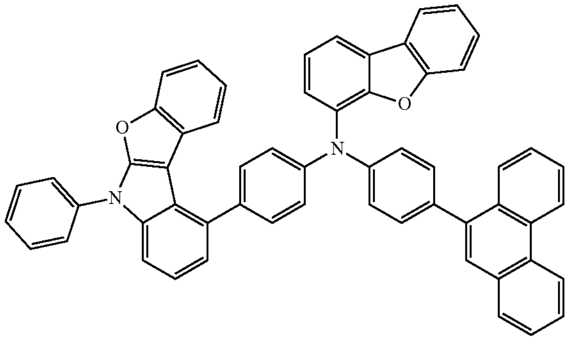
B65
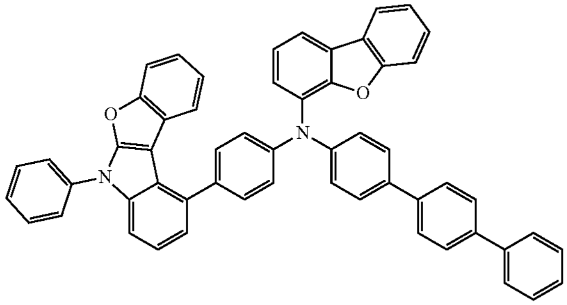
B66
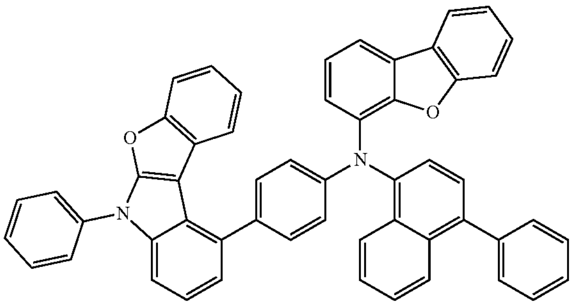

-continued
B67
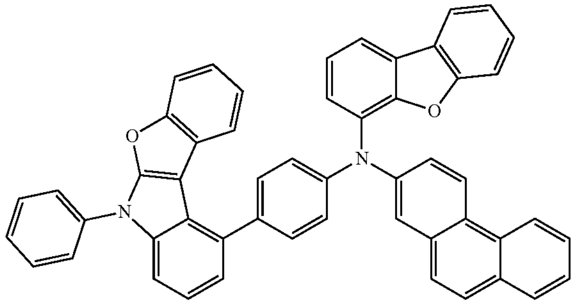
B68
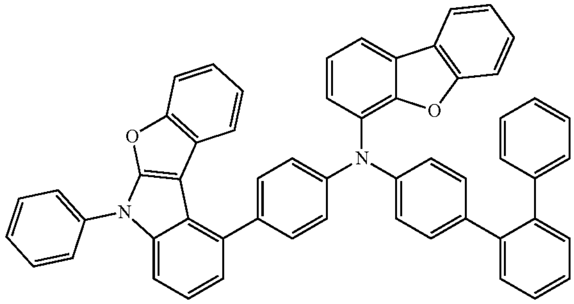
B69
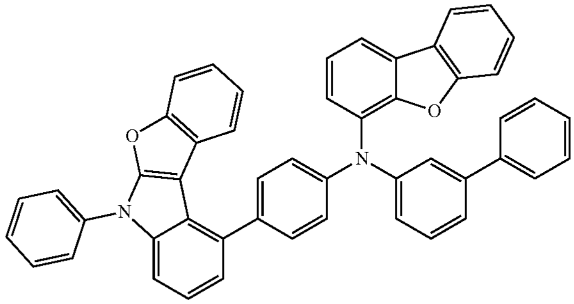
B70
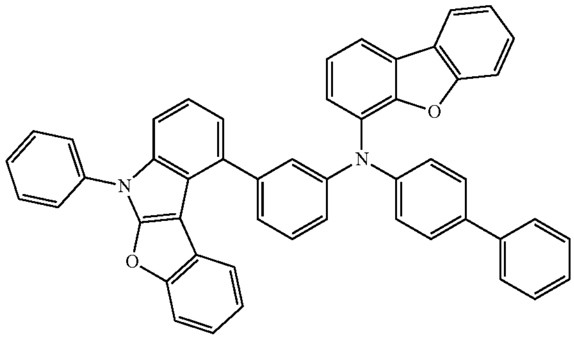
-continued
B71
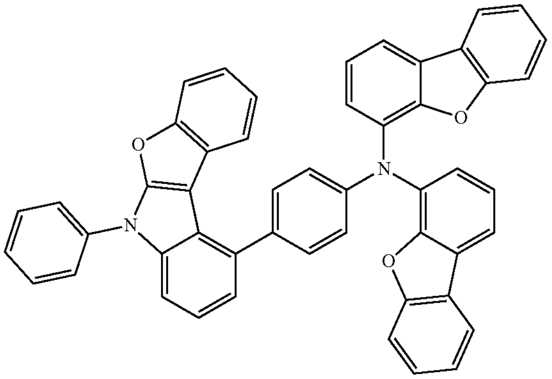
B72
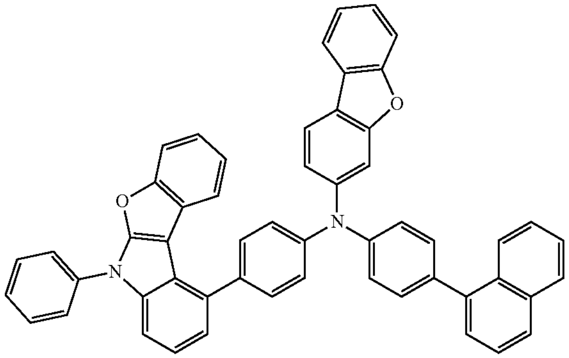
B73
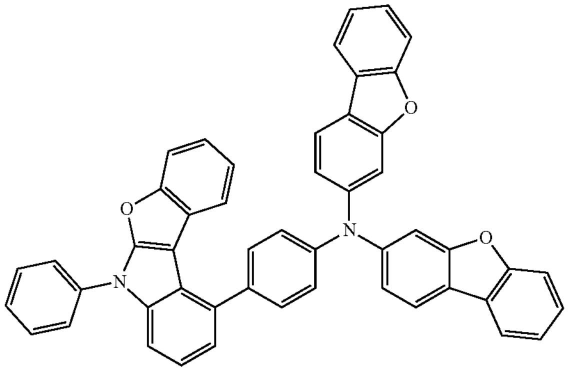
B74
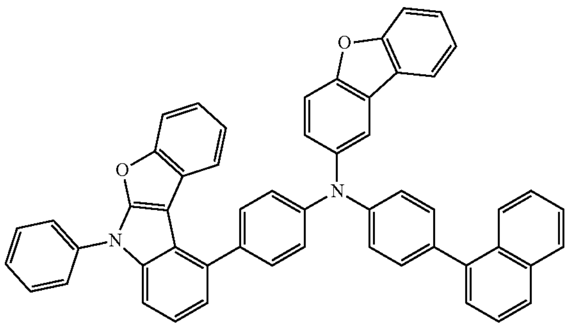

-continued
B75
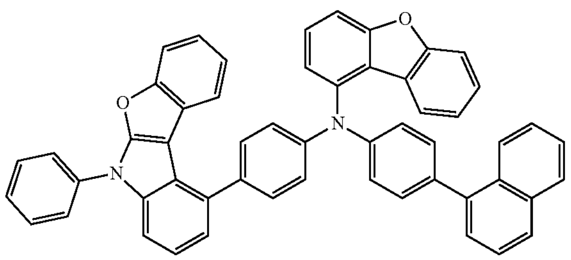
B76
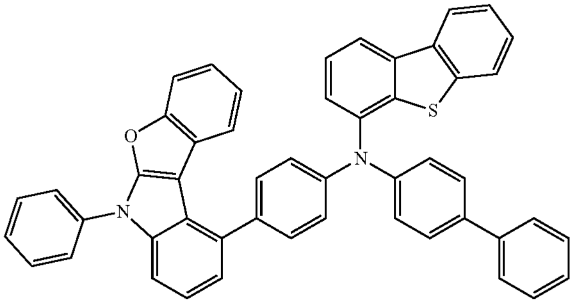
B77
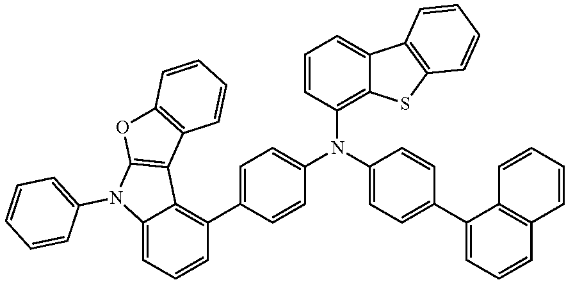
B78
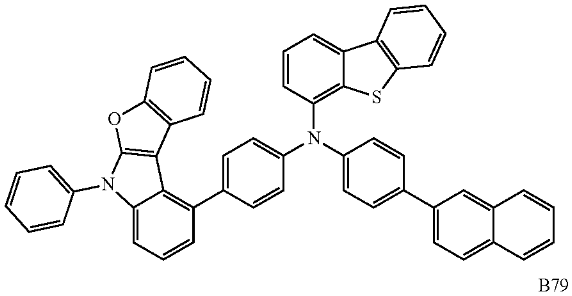
B79
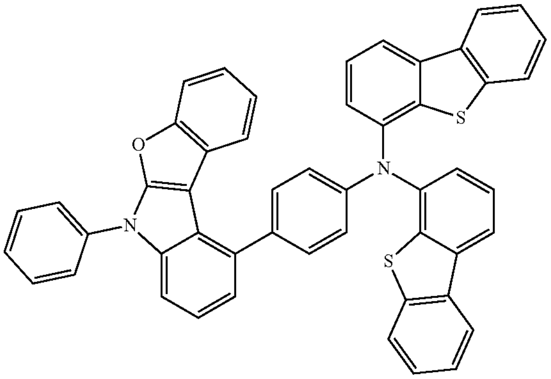
-continued
B80
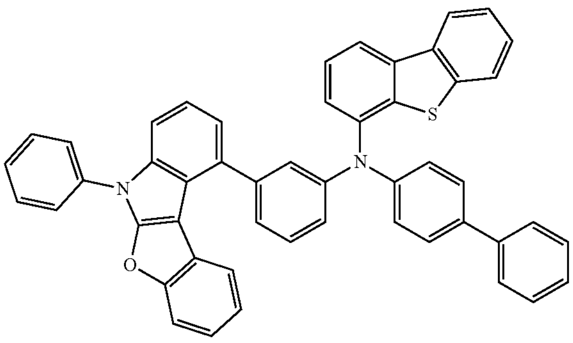
B81
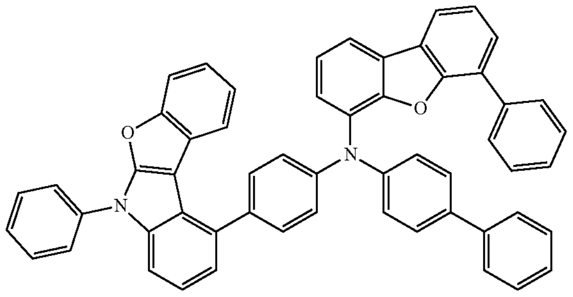
B82
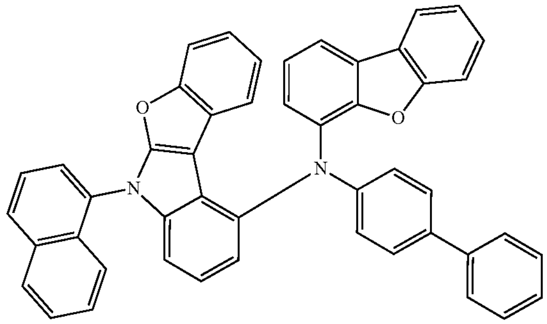
B83
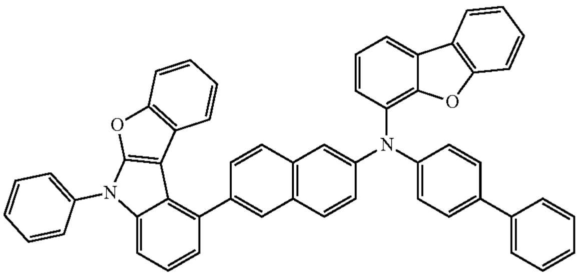
B84
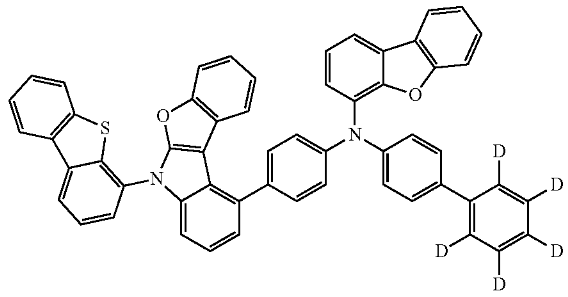

-continued
B85
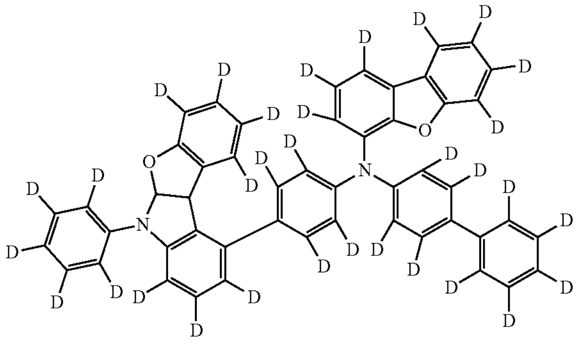
B86
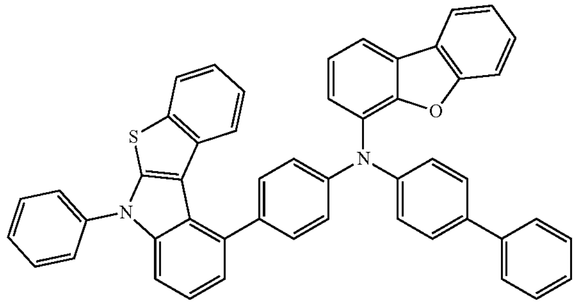
B87
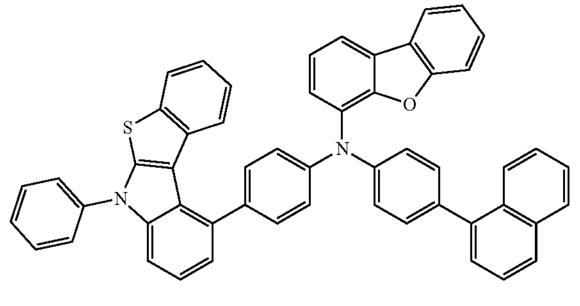
B88
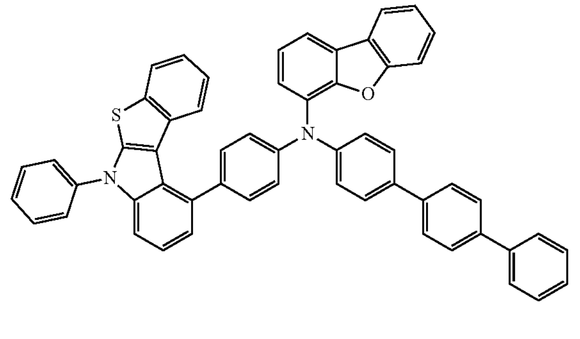
-continued
B89
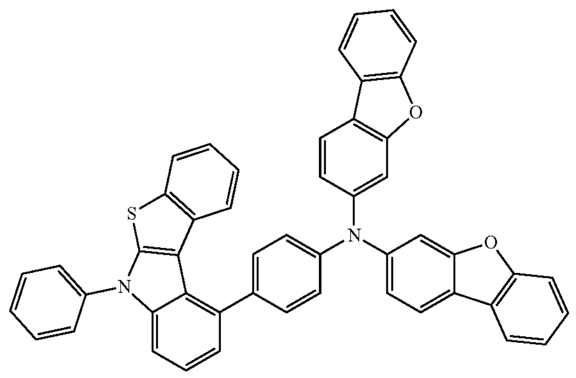
B90
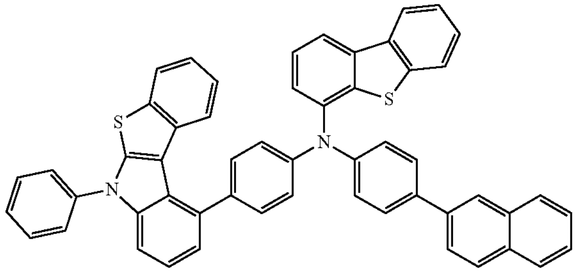
B91
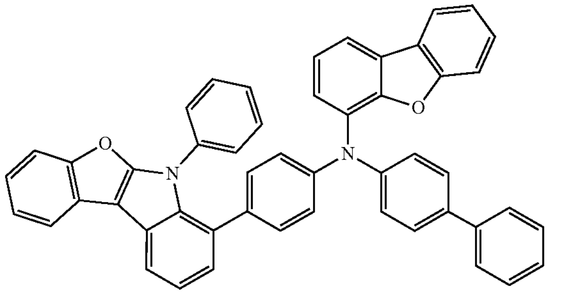
B92
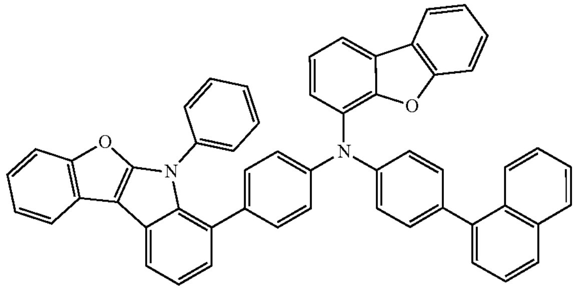
B93
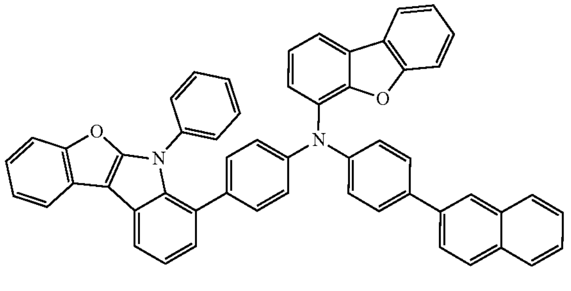

-continued
B94
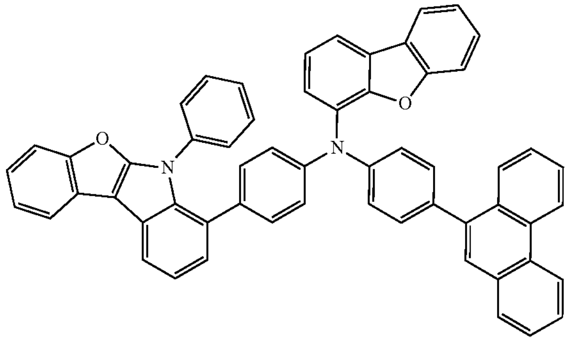
B95
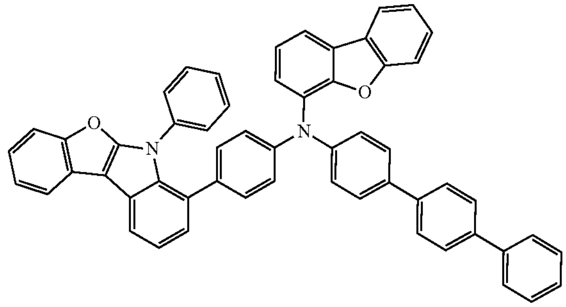
B96
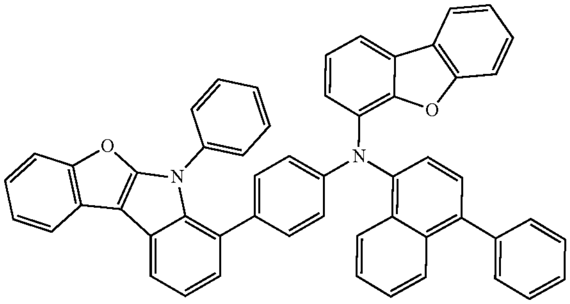
B97
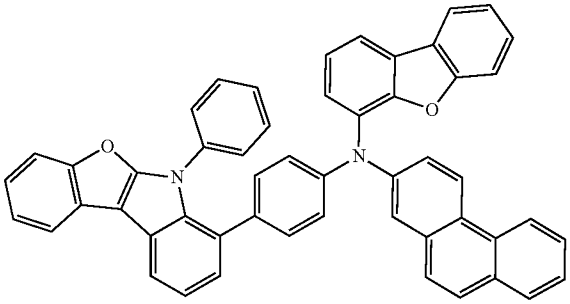
-continued
B98
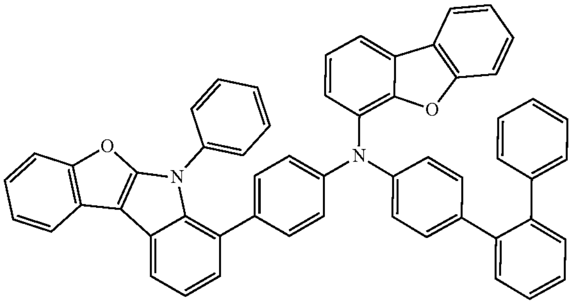
B99
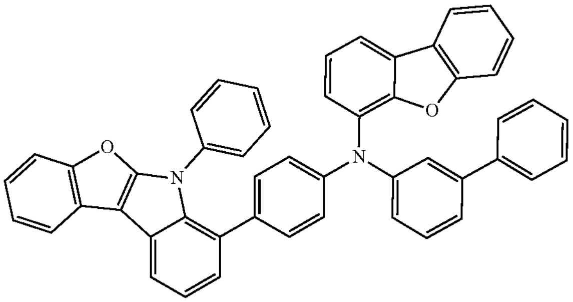
B100
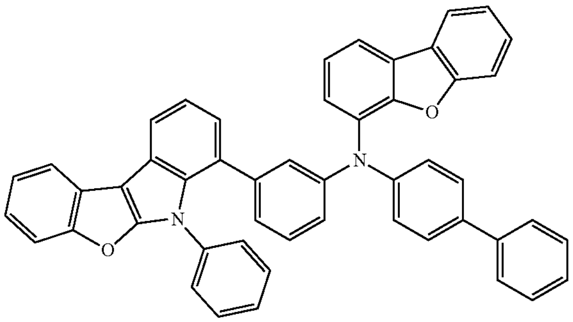
B101
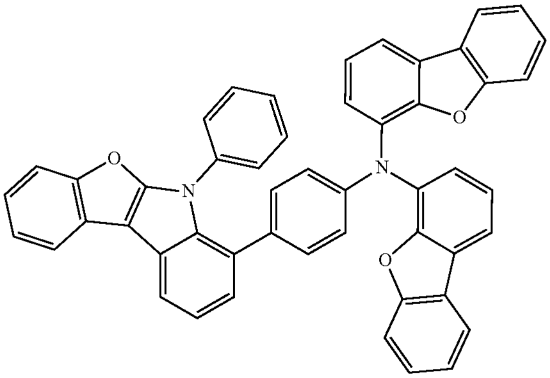

-continued
B102
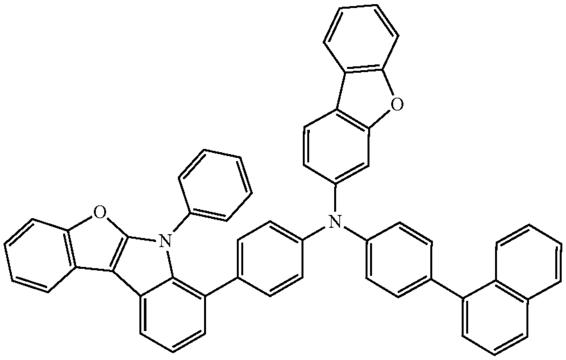
B103
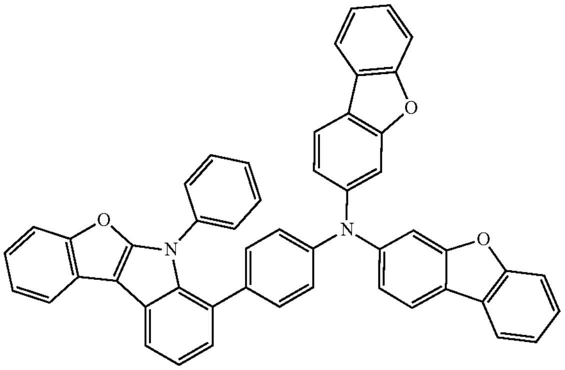
B104
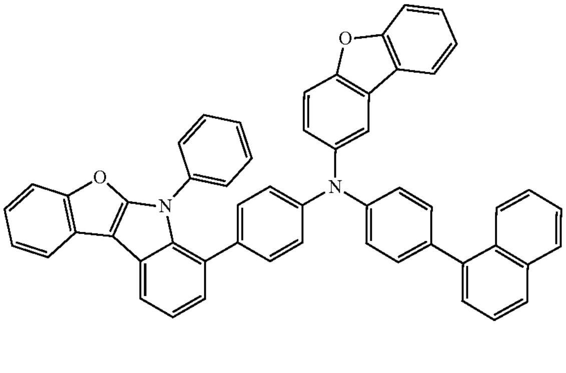
B105
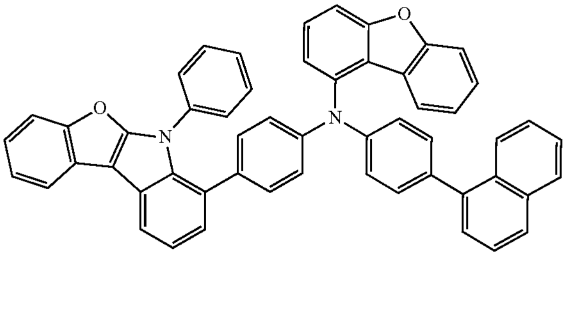
-continued
B106
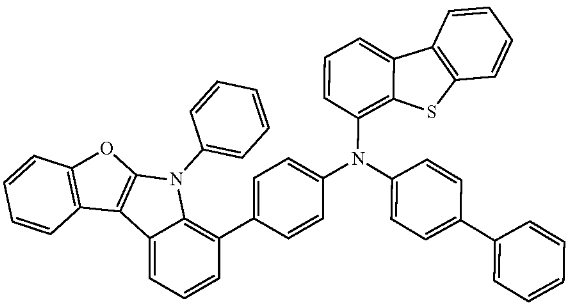
B107
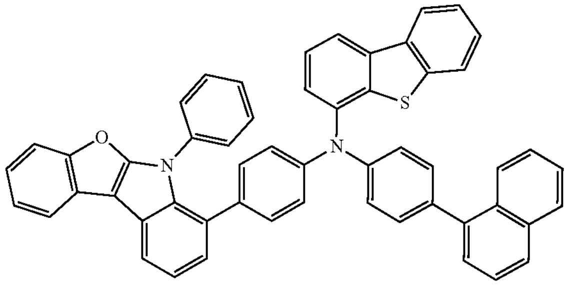
B108
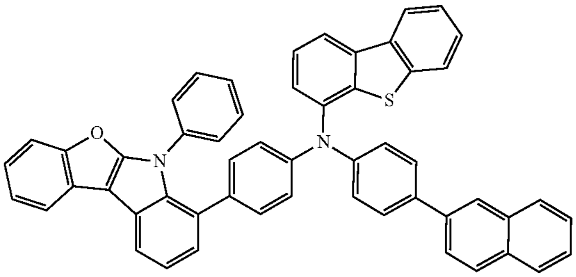
B109
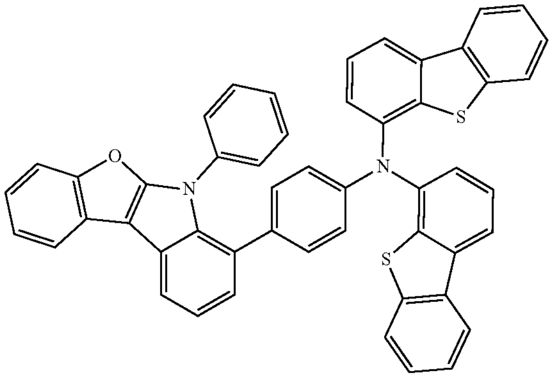

-continued
B110
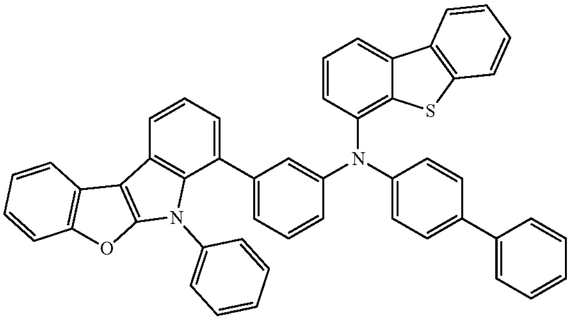
B111
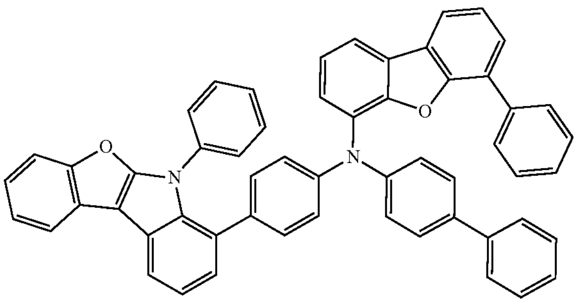
B112
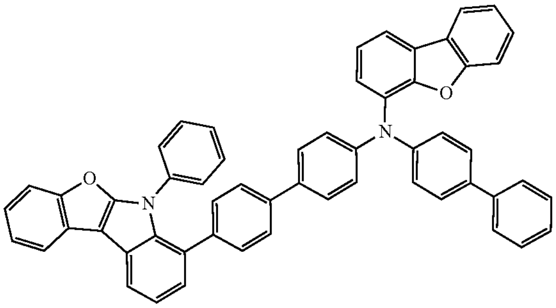
B113
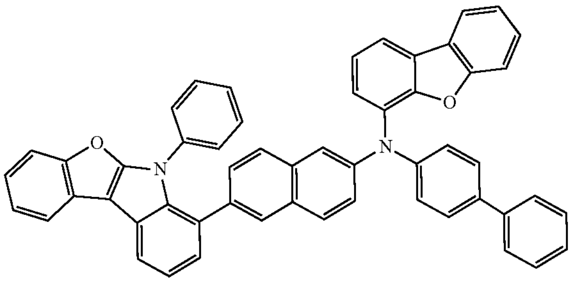
-continued
B114
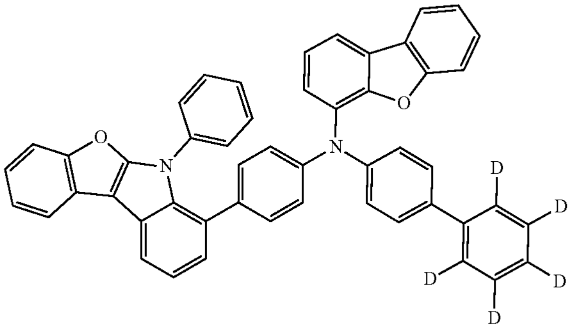
B115
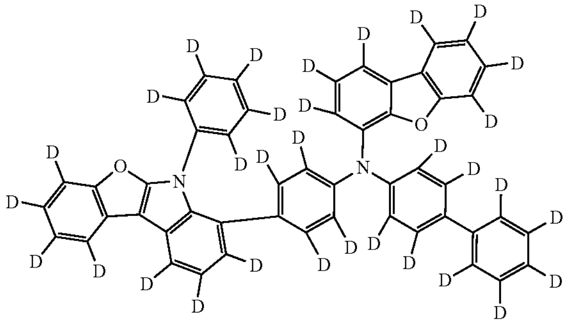
B116
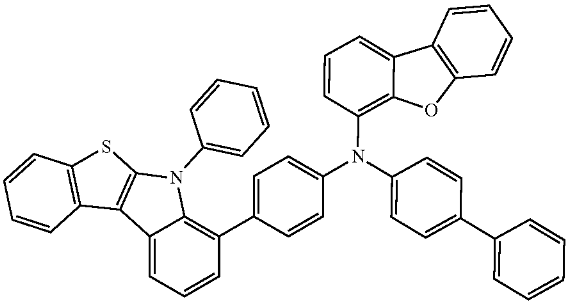
B117
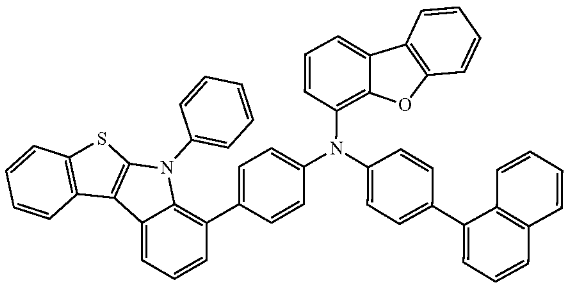

-continued
B118
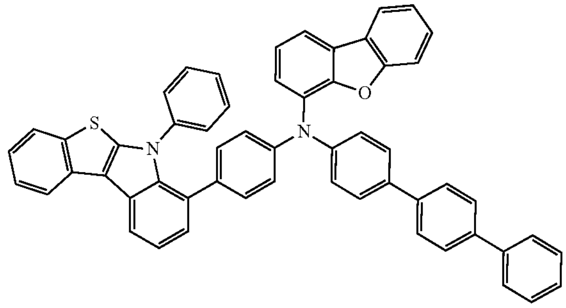
B119
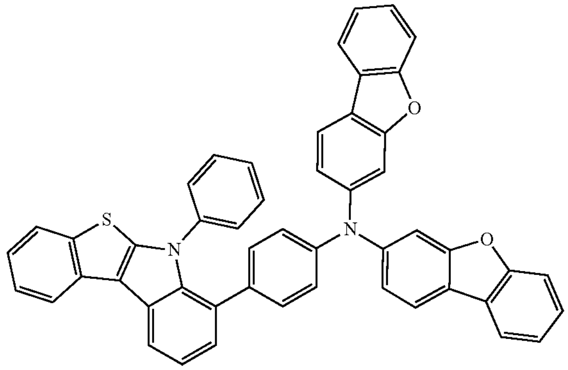
B120
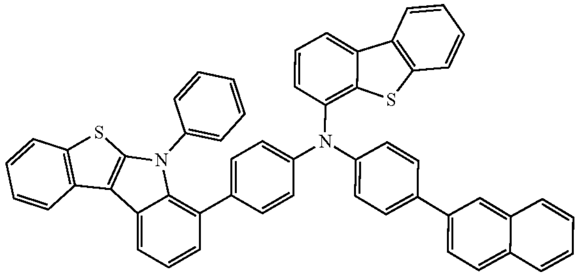
B121
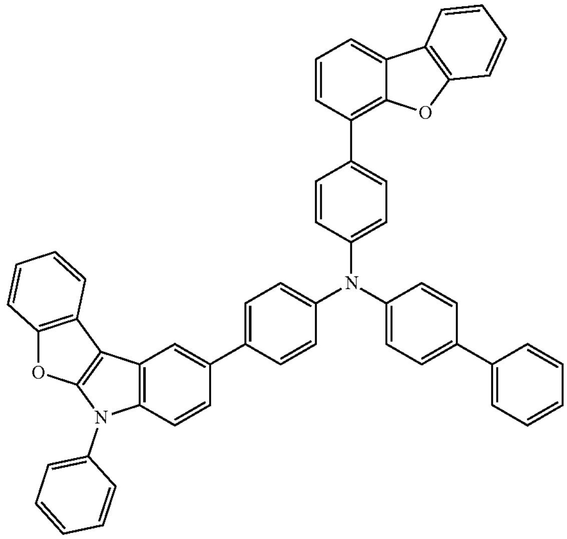
-continued
B122
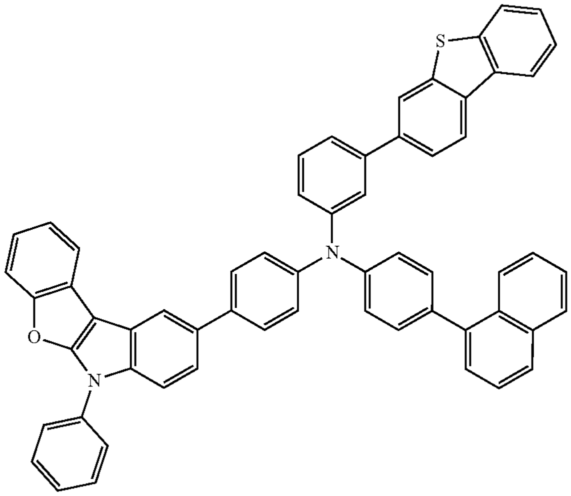
B123
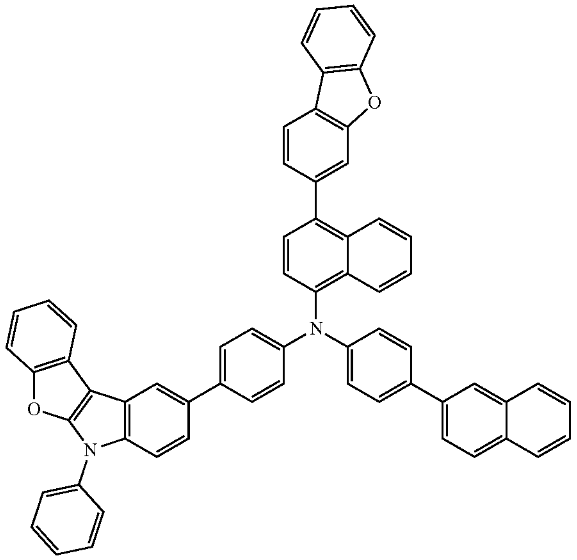

-continued
B124
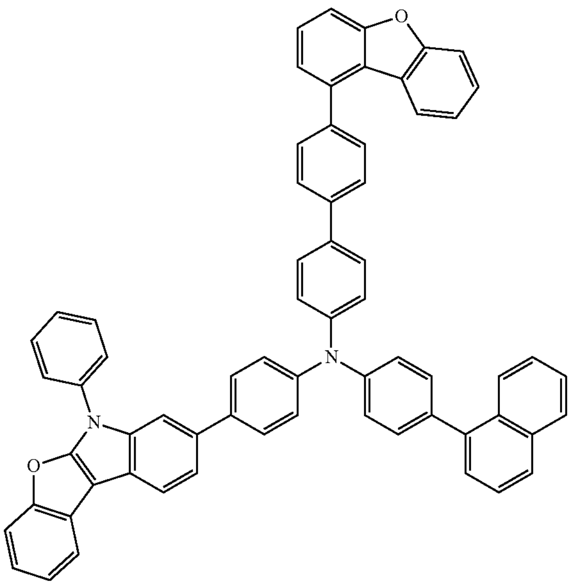
B125
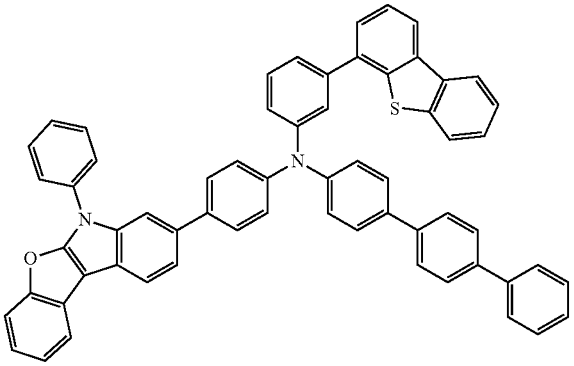
B126
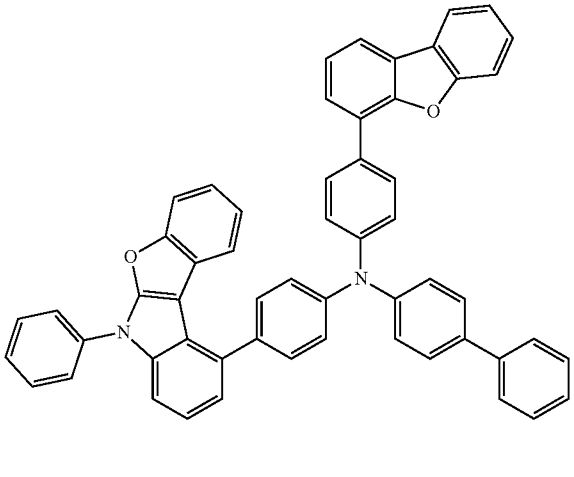
-continued
B127
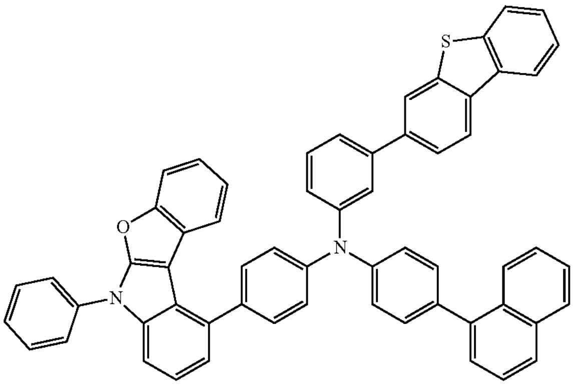
B128
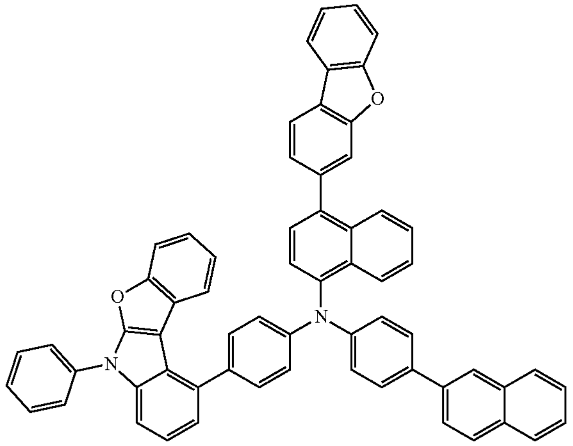
B129
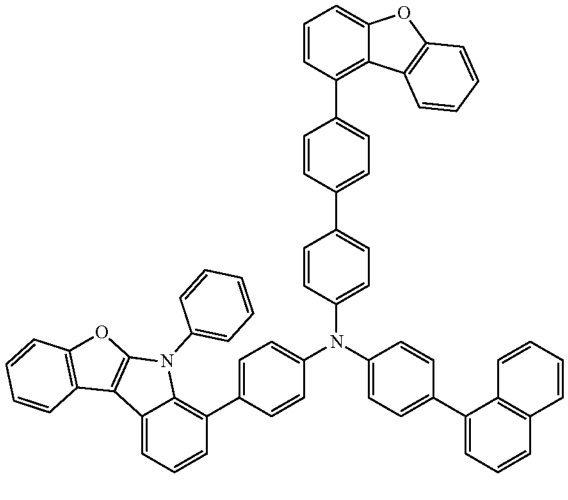

-continued
B130
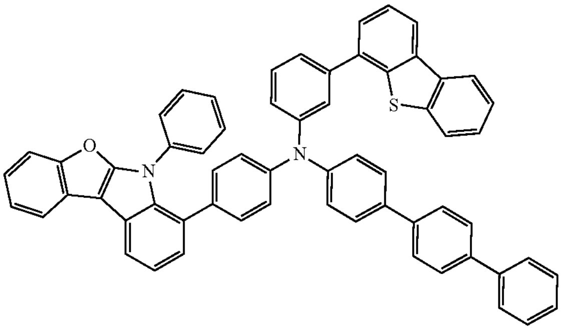
B131
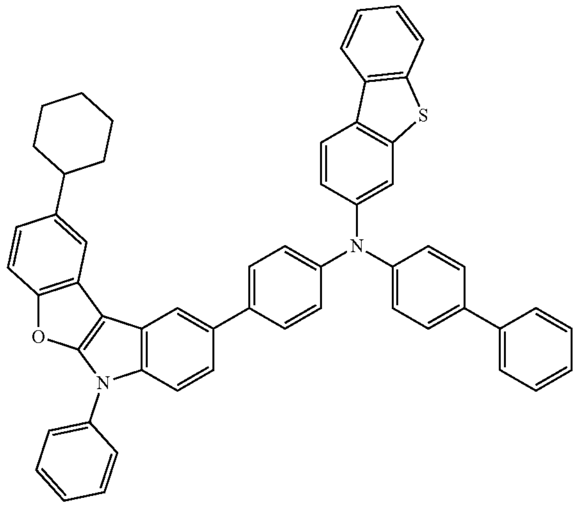
B132
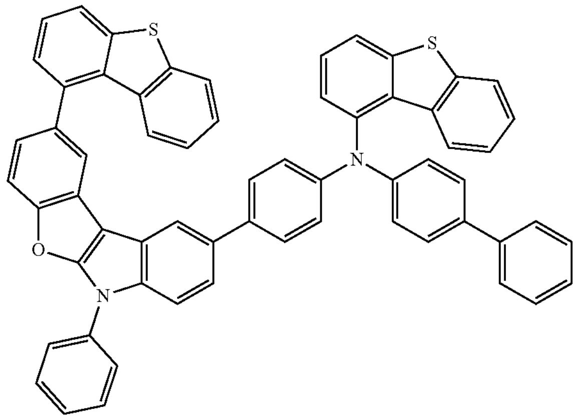
-continued
B133
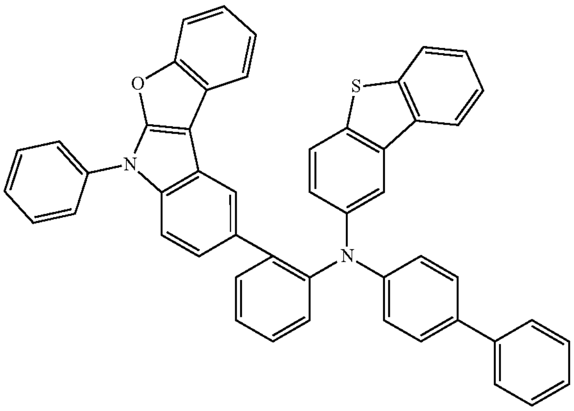
B134
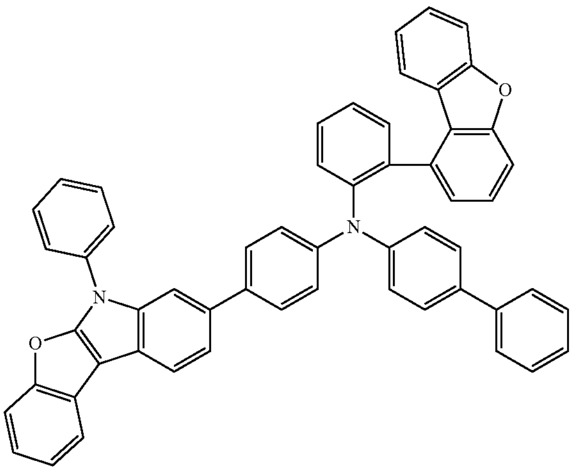
B135
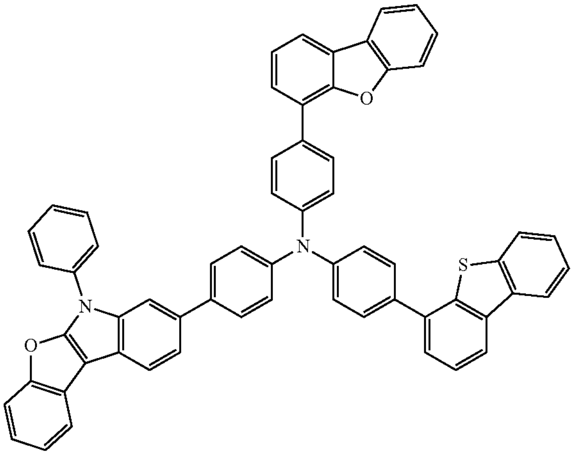

-continued
B136
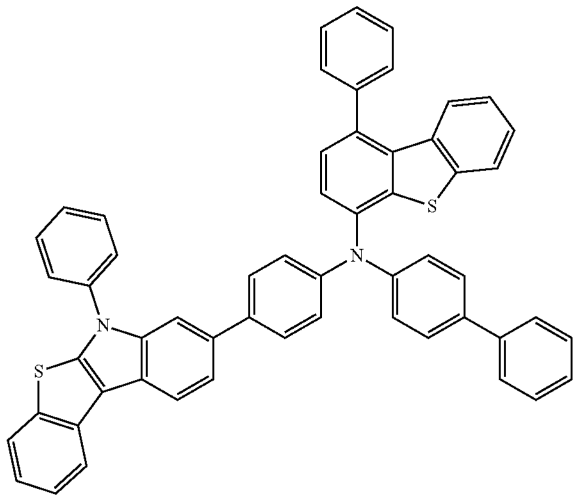
B137
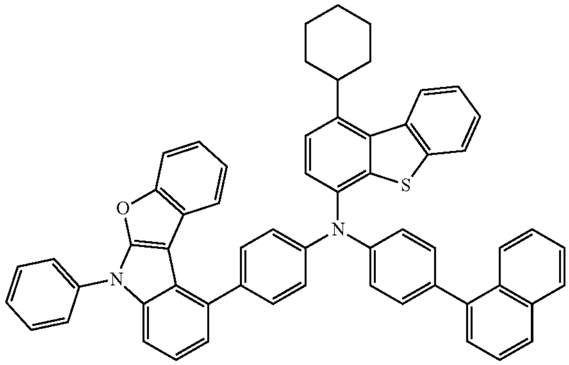
B138
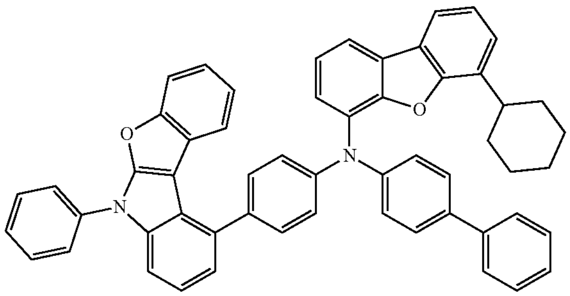
B139
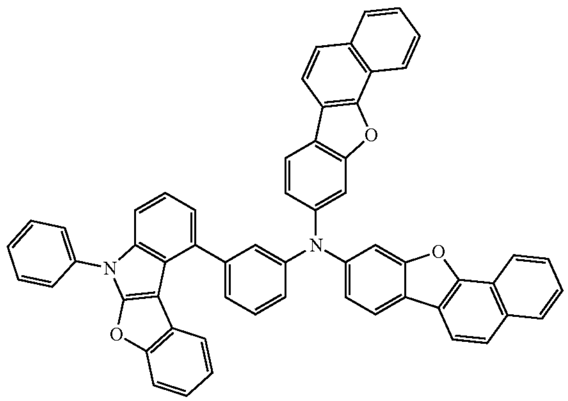
-continued
B140
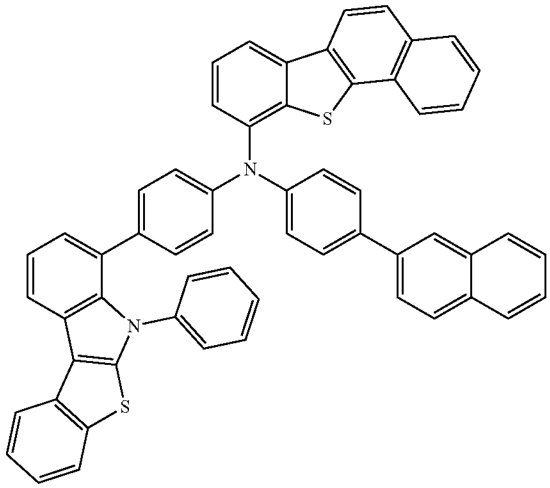
.
[Compound Group 3]
C1
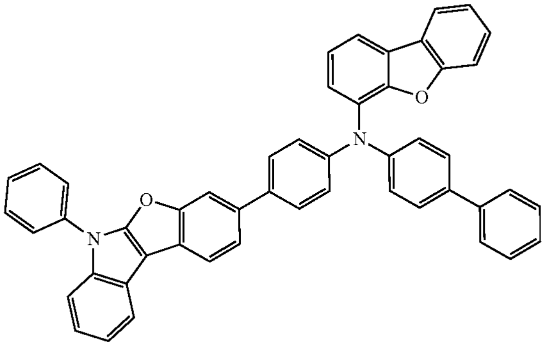
C2
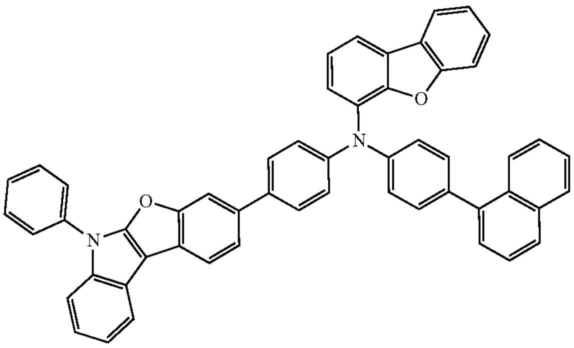

-continued
C3
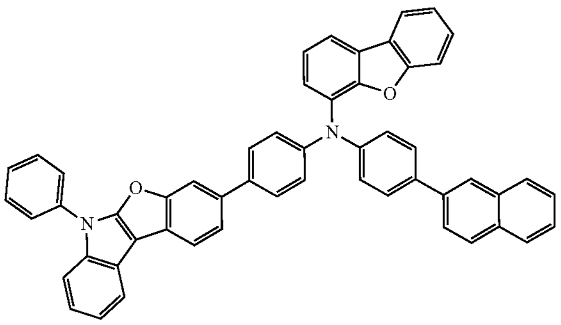
C4
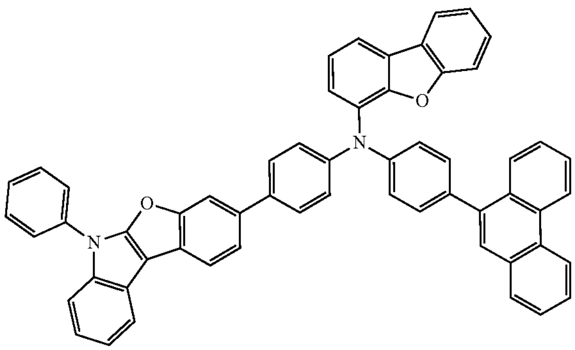
C5
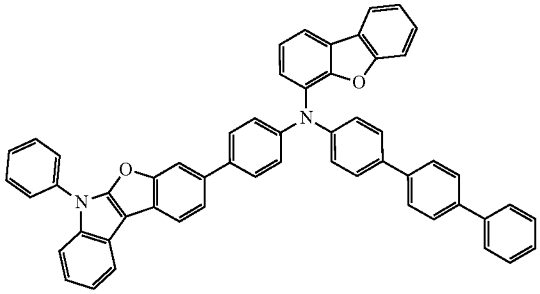
C6
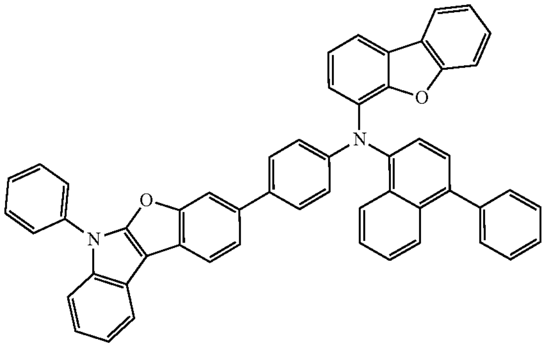
-continued
C7
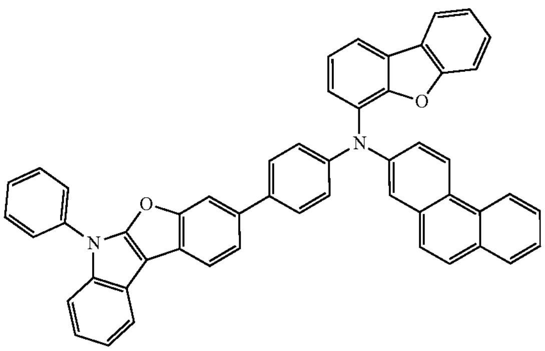
C8
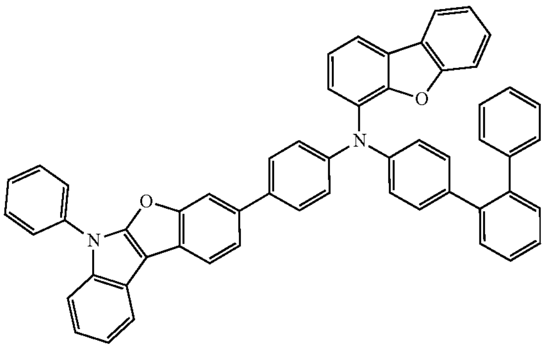
C9
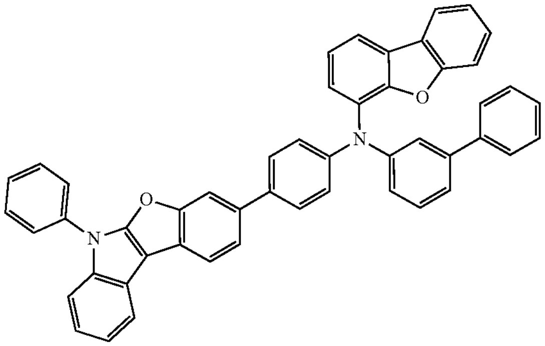
C10
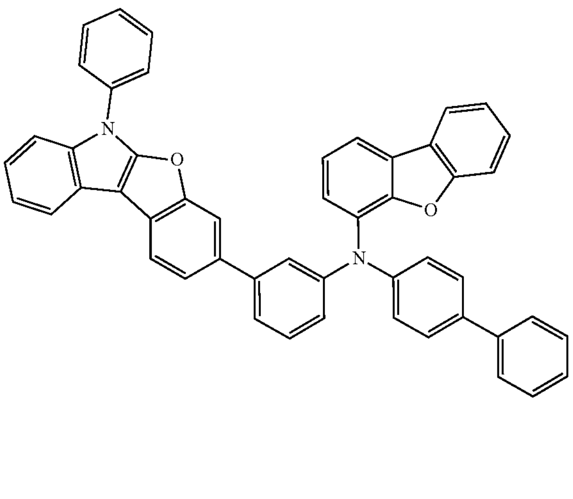

-continued
C11
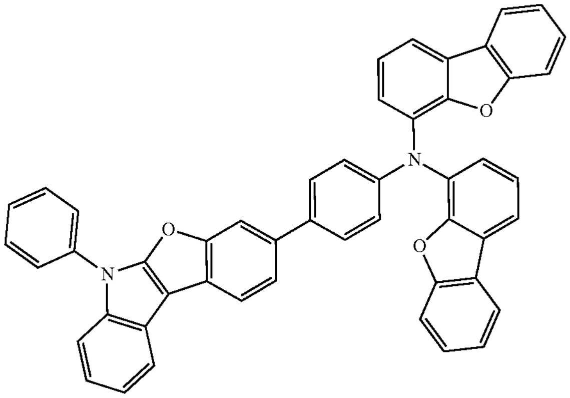
C12
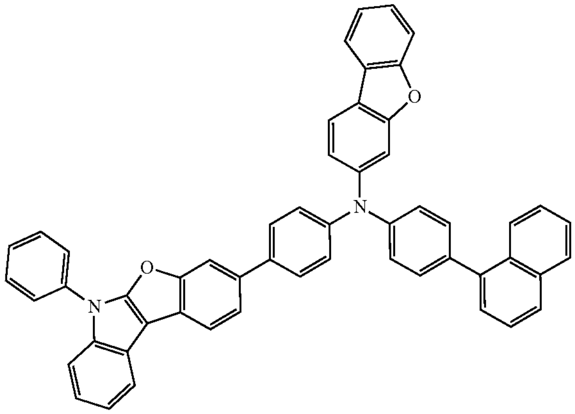
C13
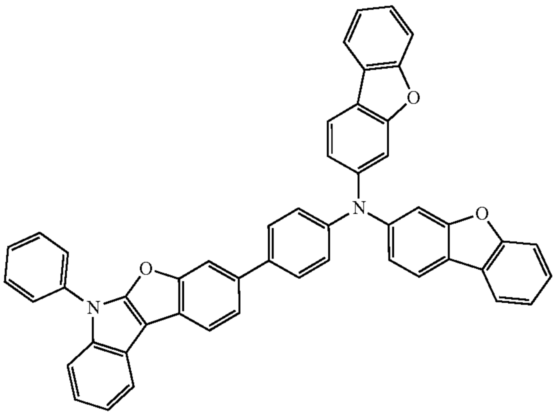
-continued
C14
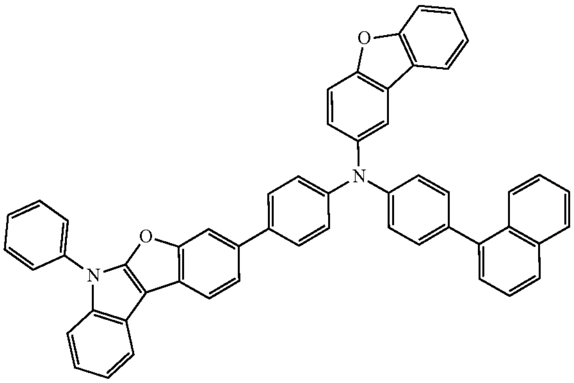
C15
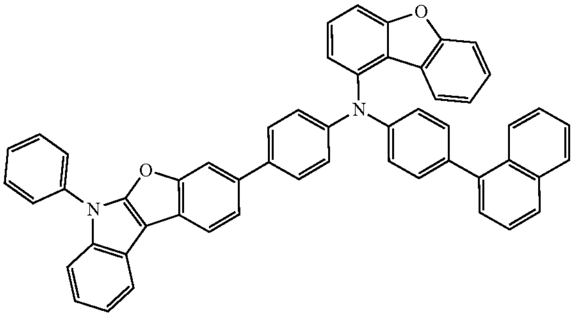
C16
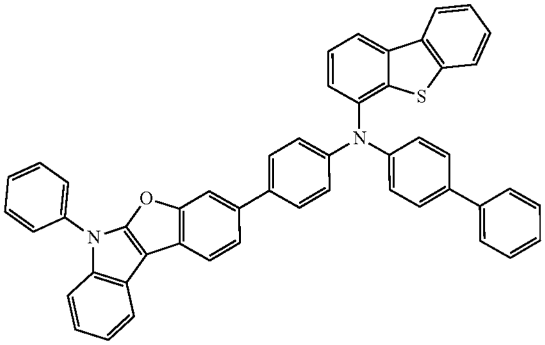
C17
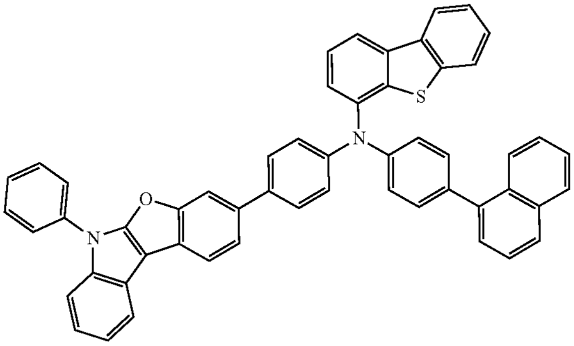

-continued
C18
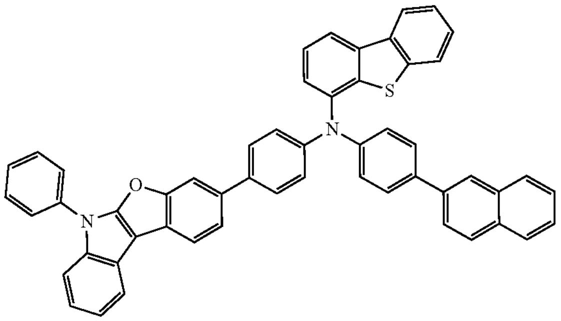
C19
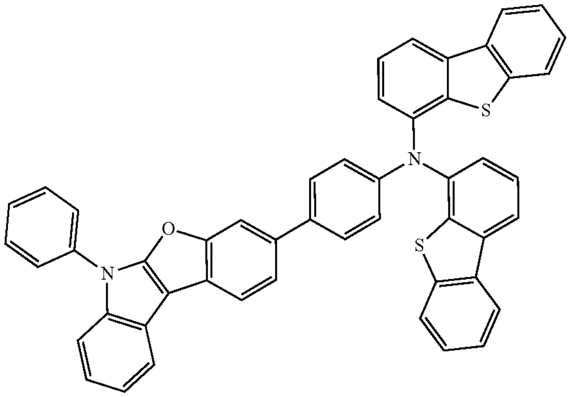
C20
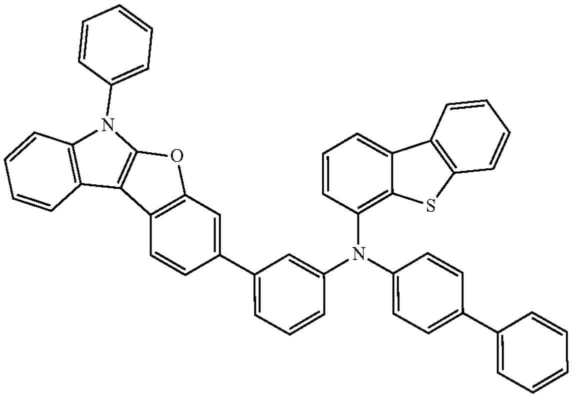
C21
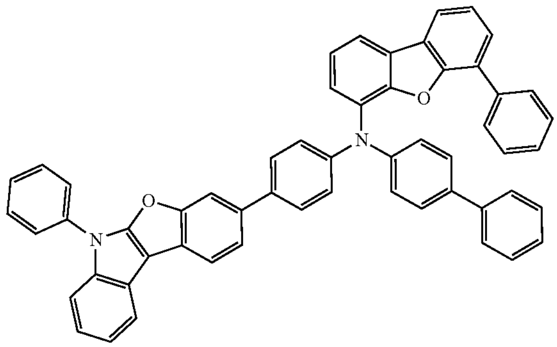
-continued
C22
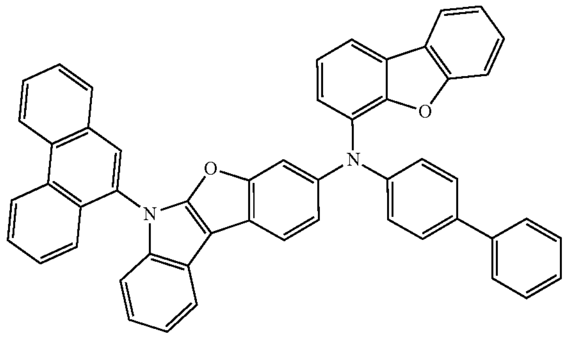
C23
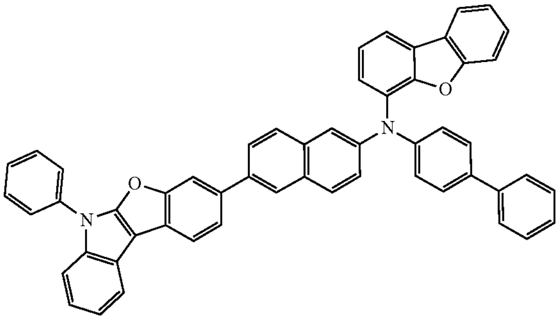
C24
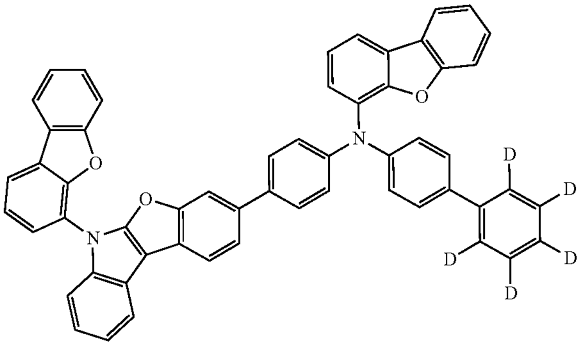
C25
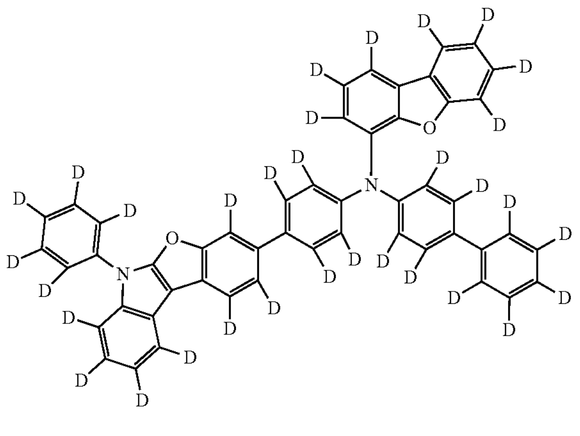

-continued
C26
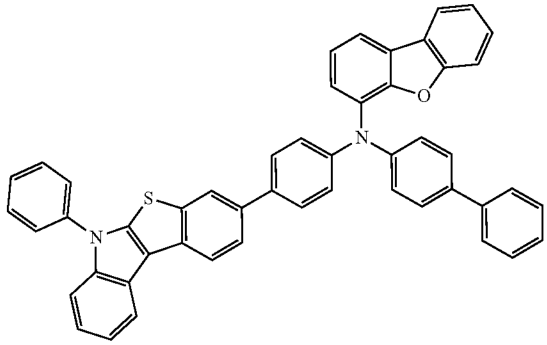
C27
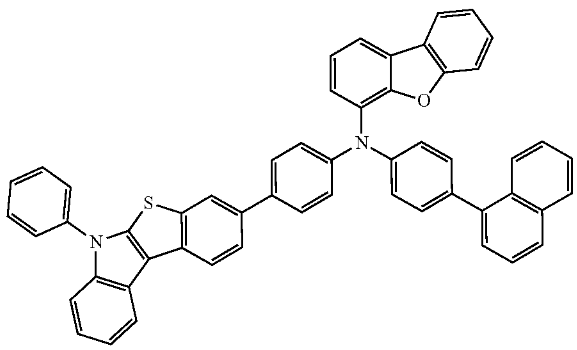
C28
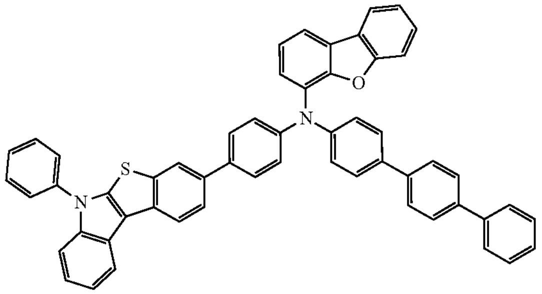
C29
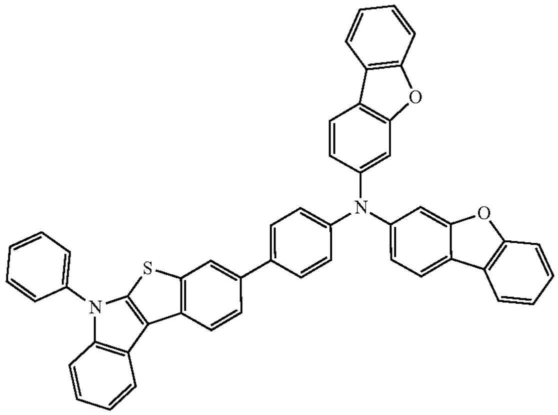
-continued
C30
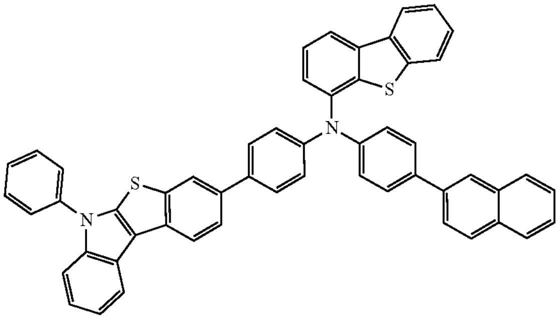
C31
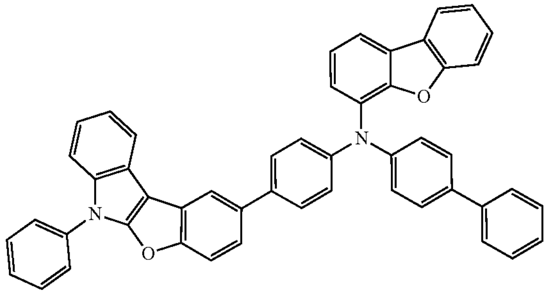
C32
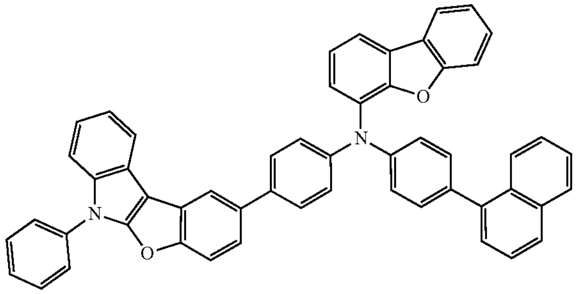
C33
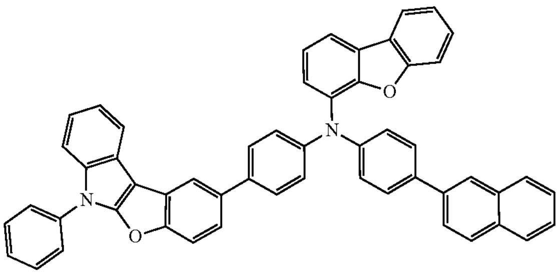
C34
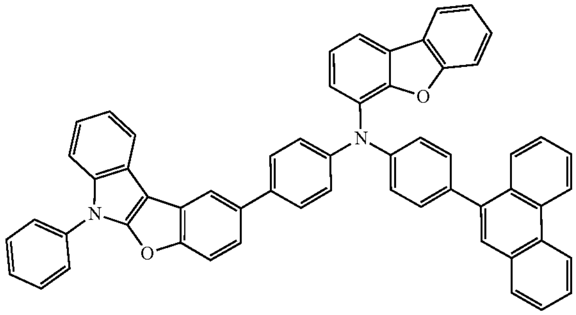

-continued
C35
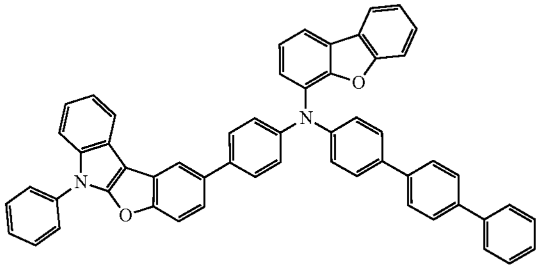
C36
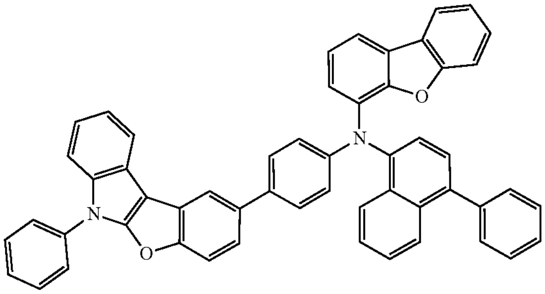
C37
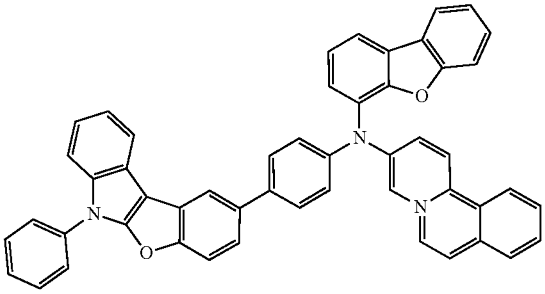
C38
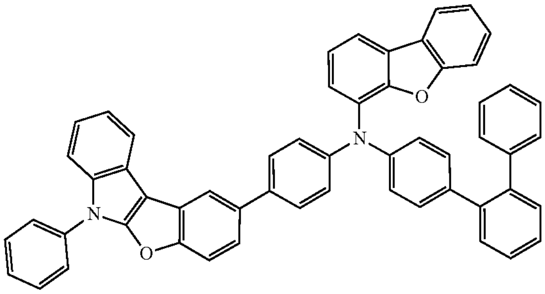
C39
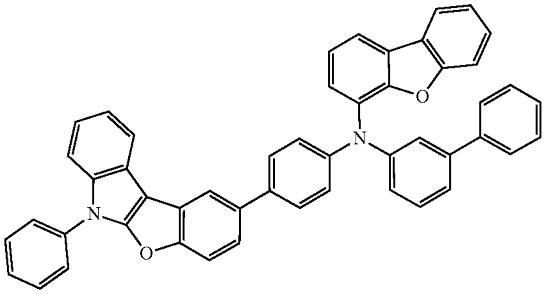
-continued
C40
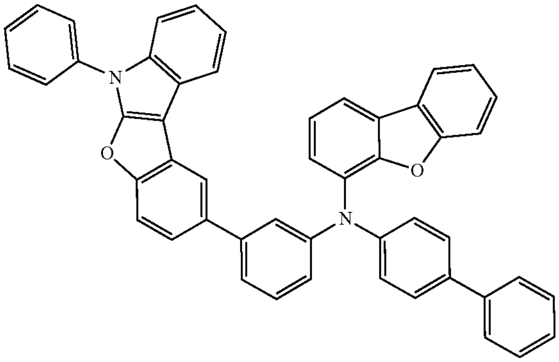
C41
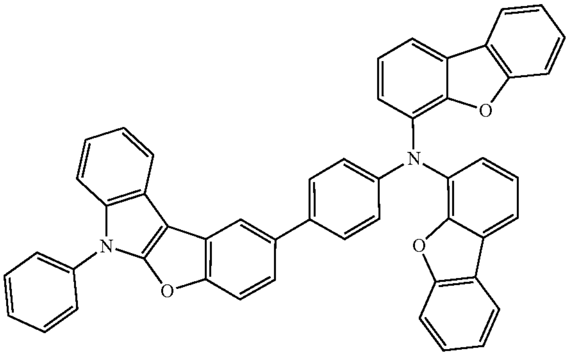
C42
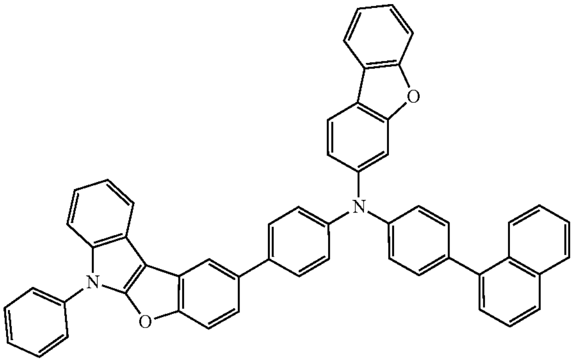
C43
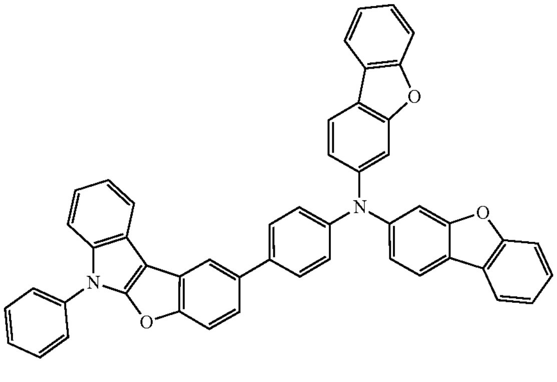

-continued
C44
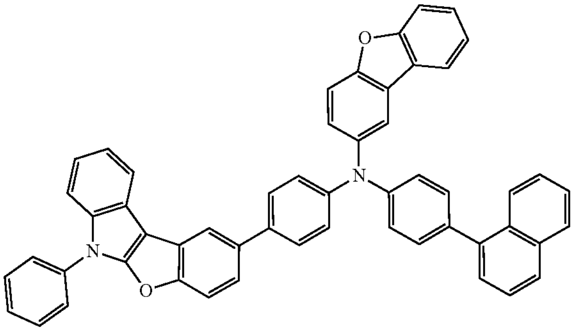
C45
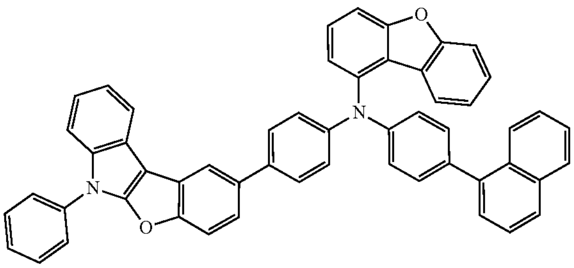
C46
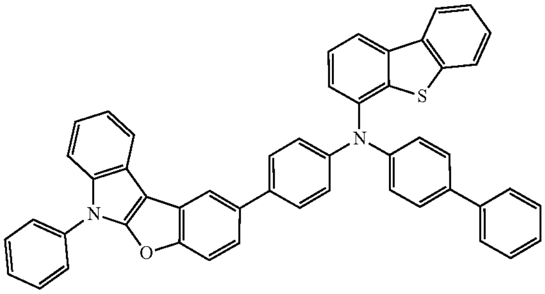
C47
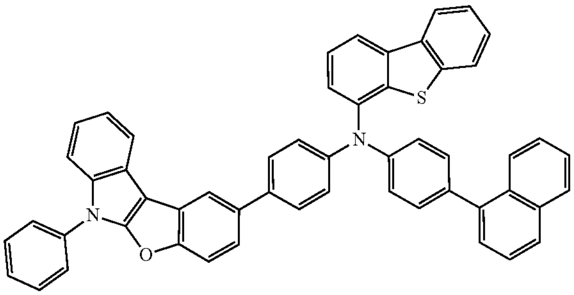
C48
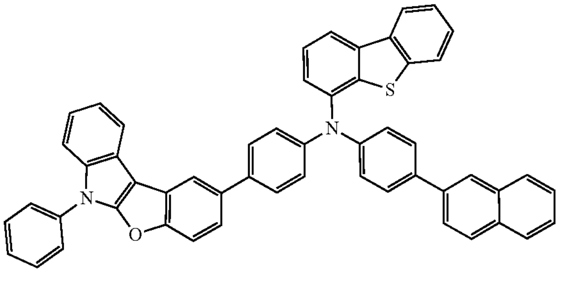
-continued
C49
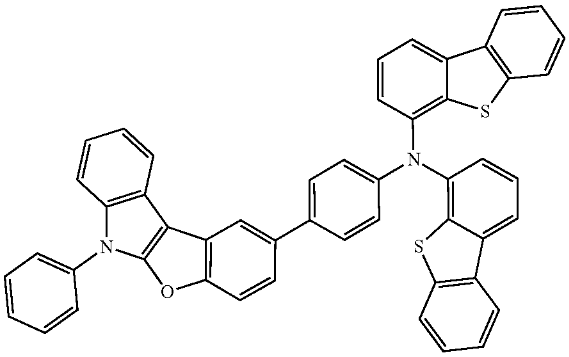
C50
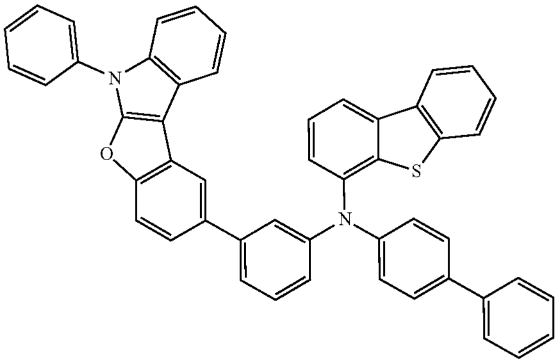
C51
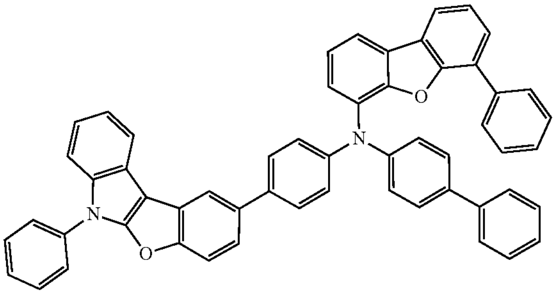
C52
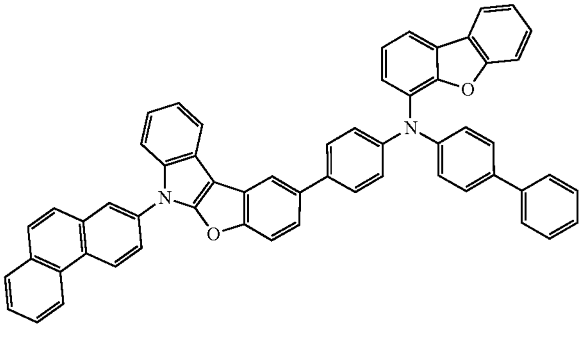

-continued
C53
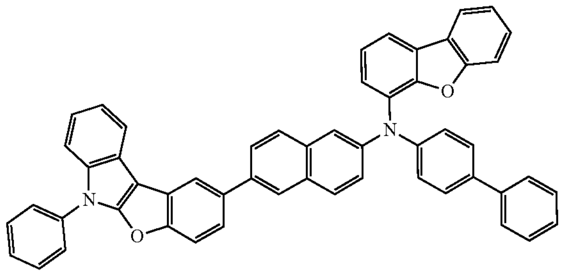
C54
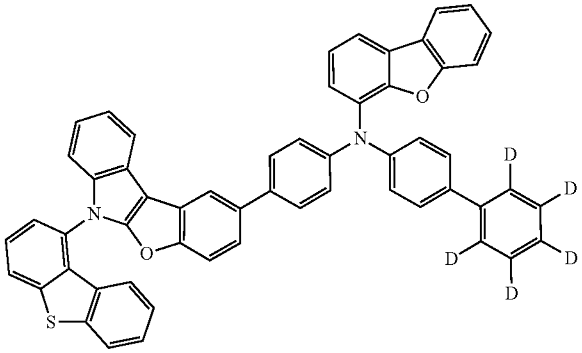
C55
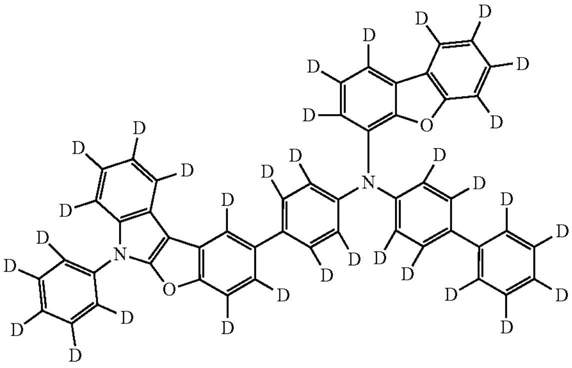
C56
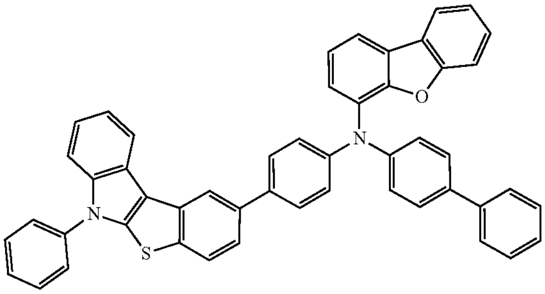
-continued
C57
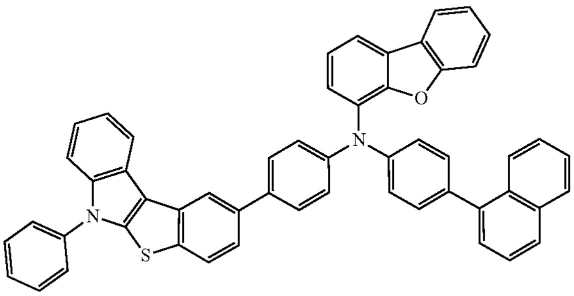
C58
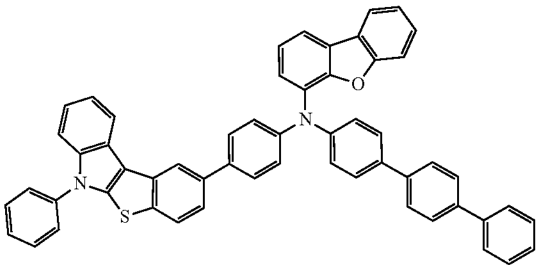
C59
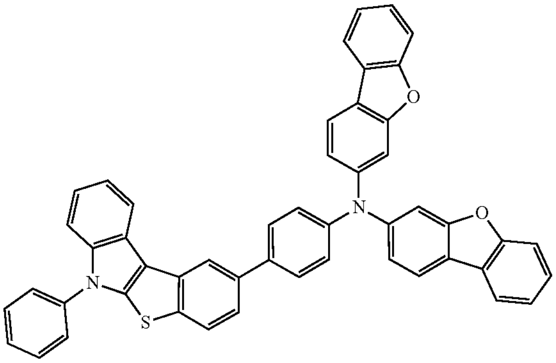
C60
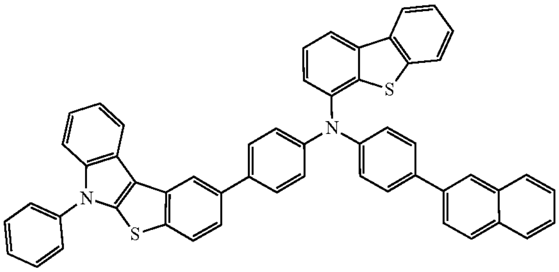
C61
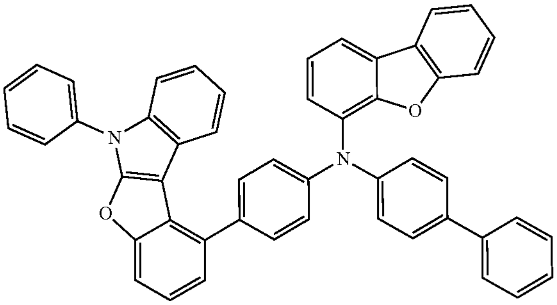

-continued
C62
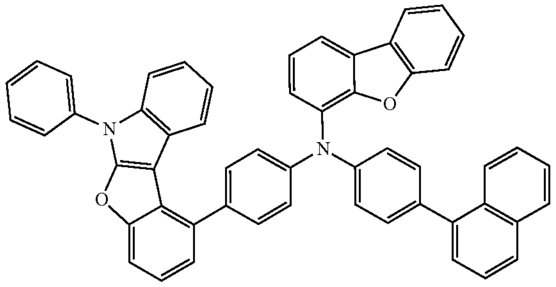
C63
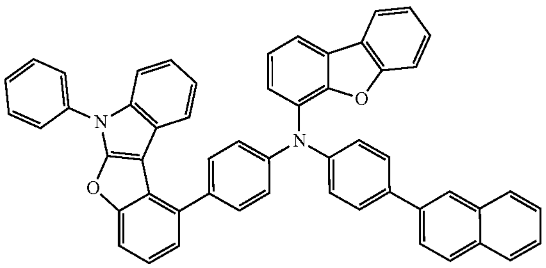
C64
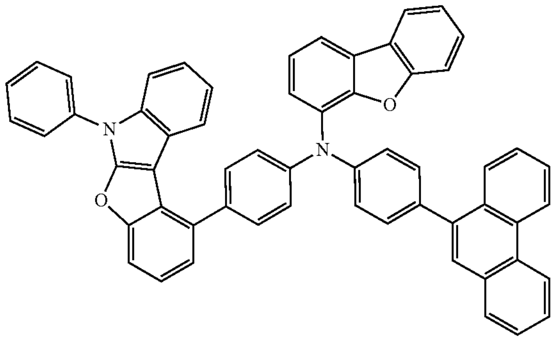
C65
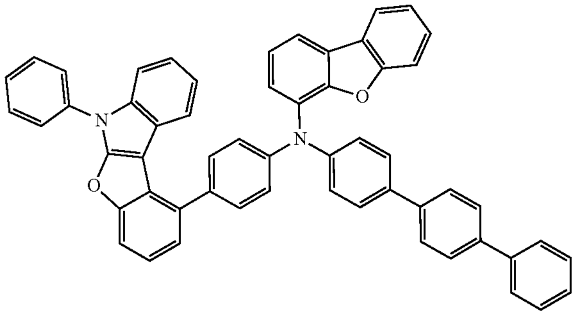
C66
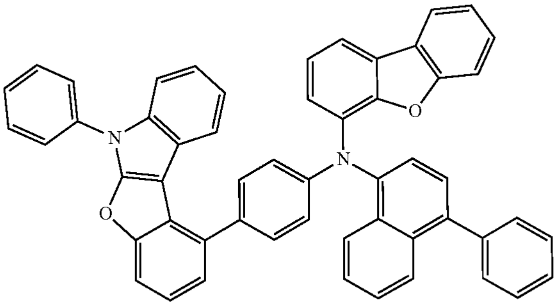
-continued
C67
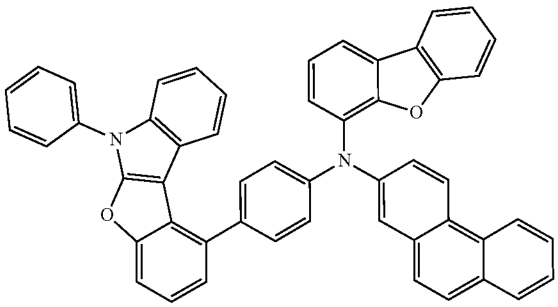
C68
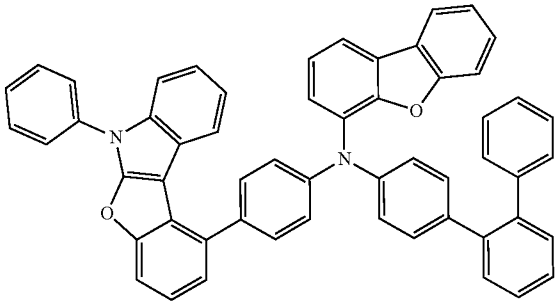
C69
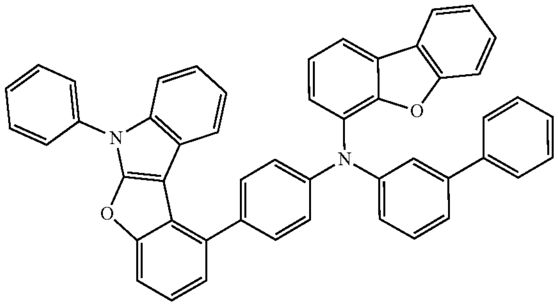
C70
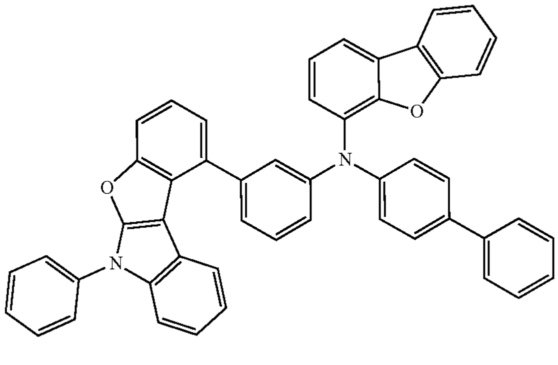

-continued
C71
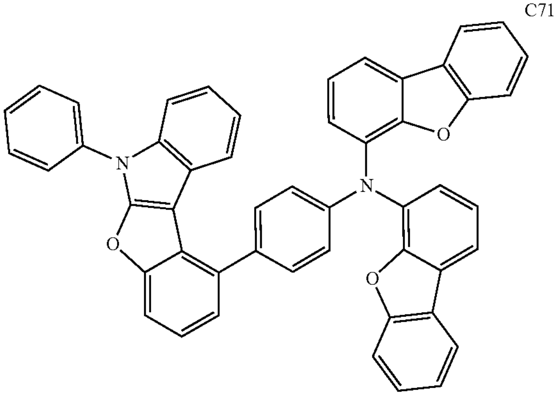
C72
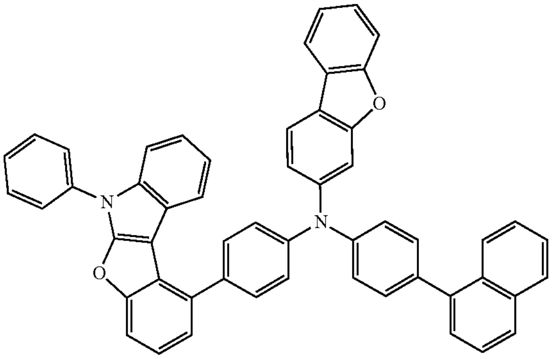
C73
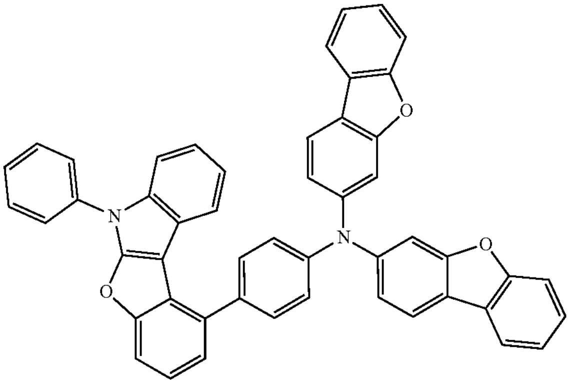
C74
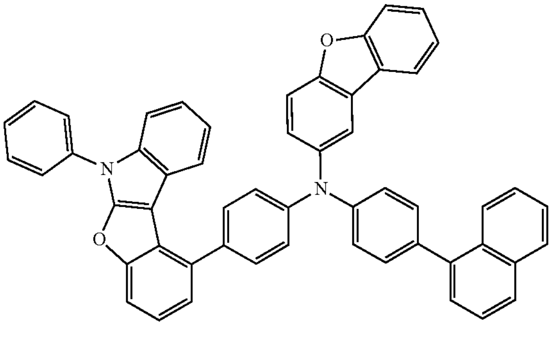
-continued
C75
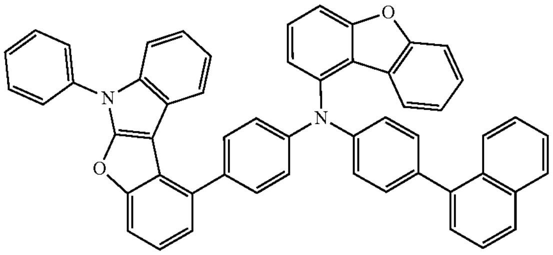
C76
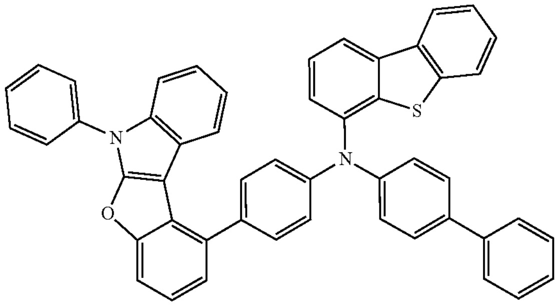
C77
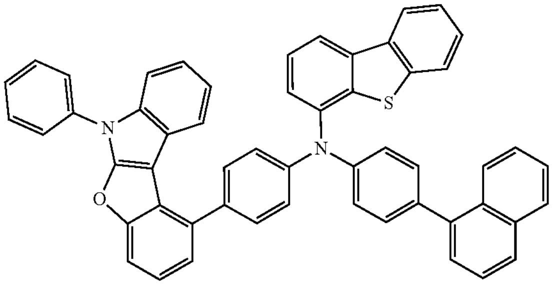
C78
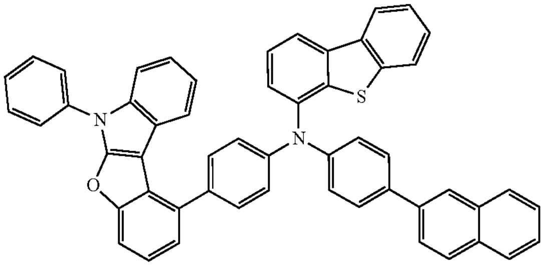
C79
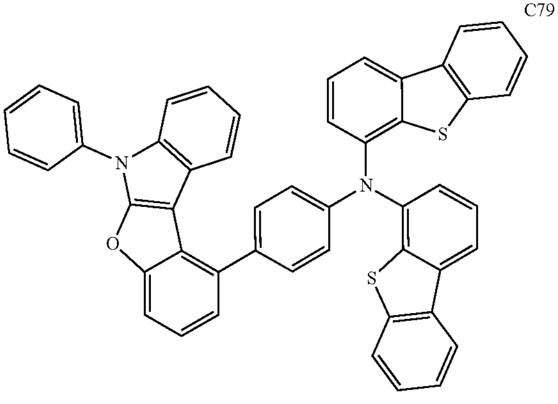

-continued
C80
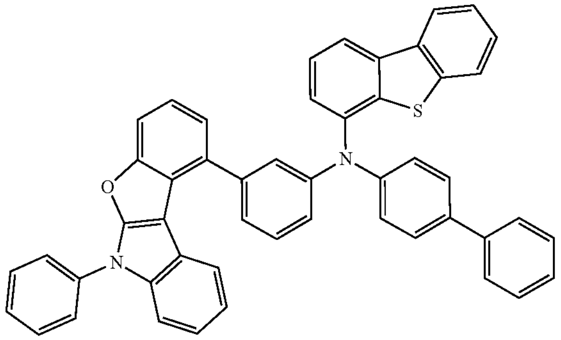
C81
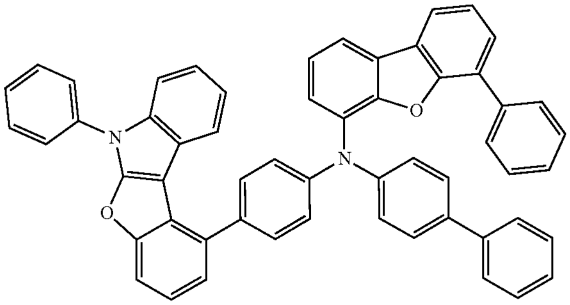
C82
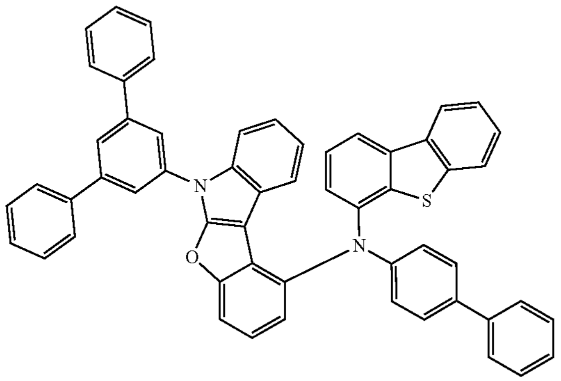
C83
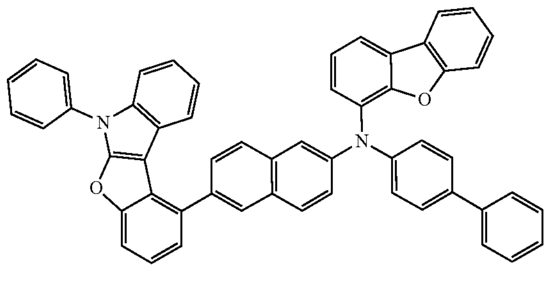
-continued
C84
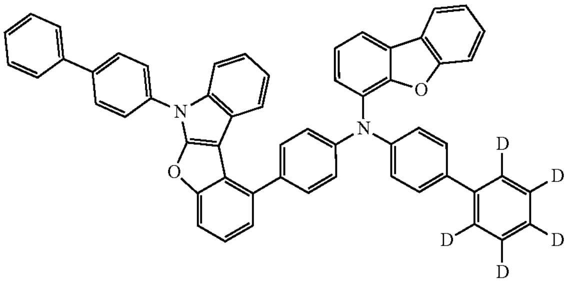
C85
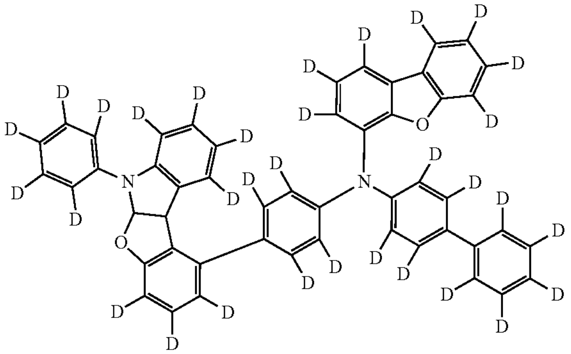
C86
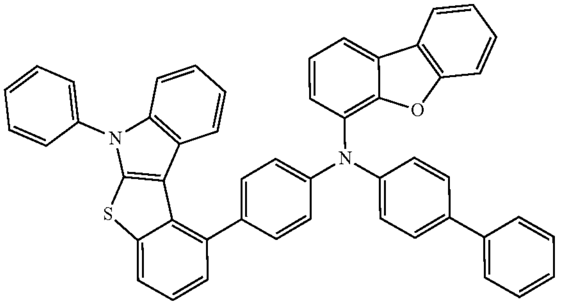
C87
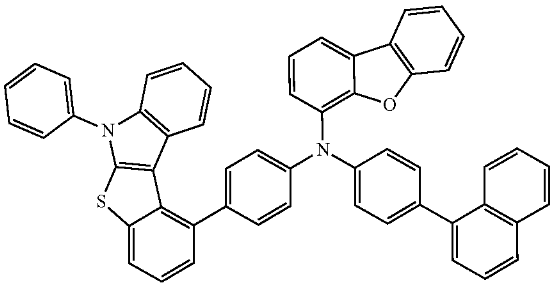

-continued
C88
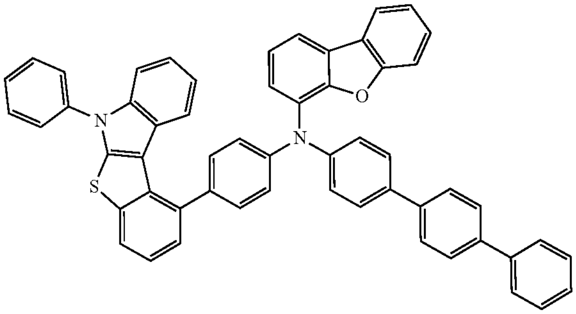
C89
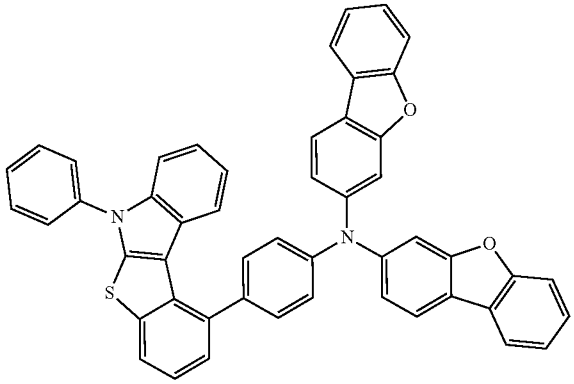
C90
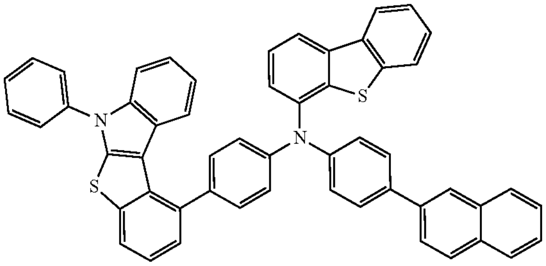
C91
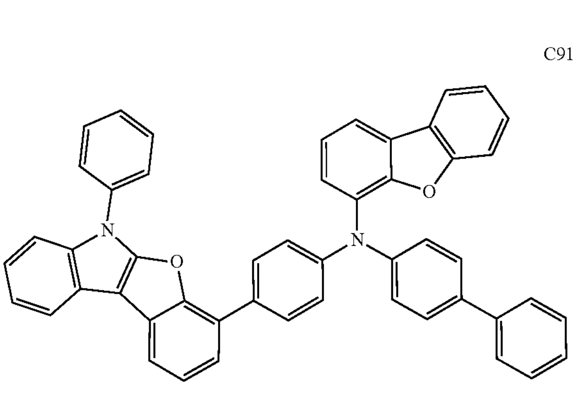
-continued
C92
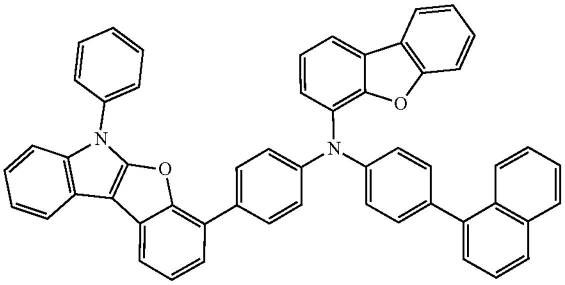
C93
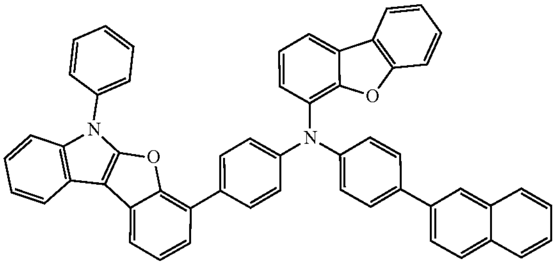
C94
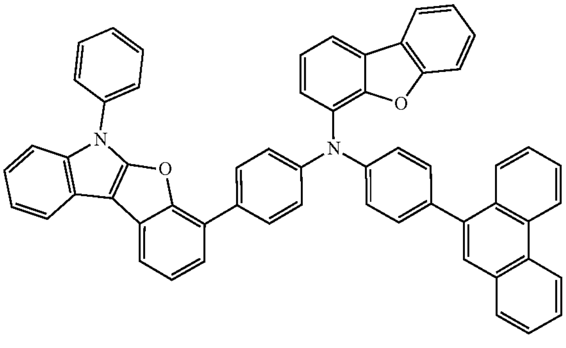
C95
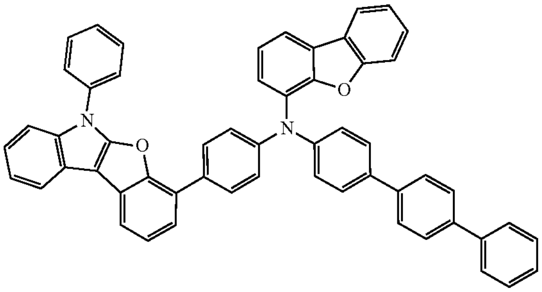
C96
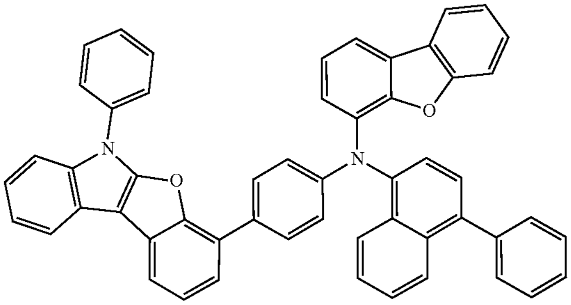

-continued
C97
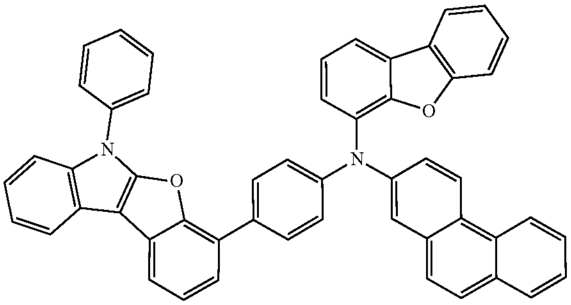
C98
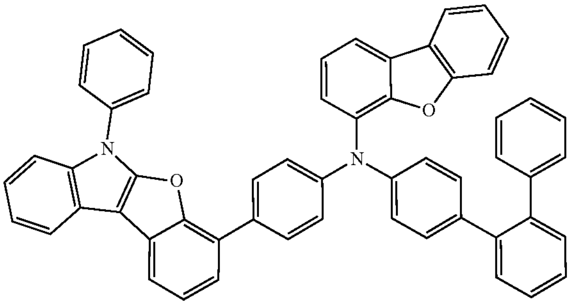
C99
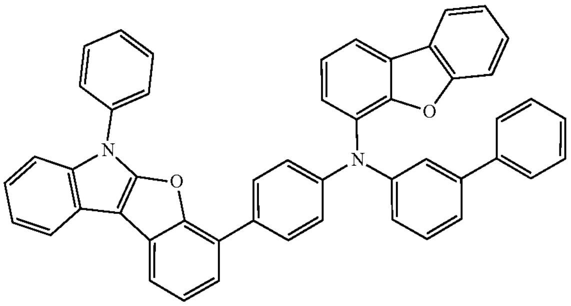
C100
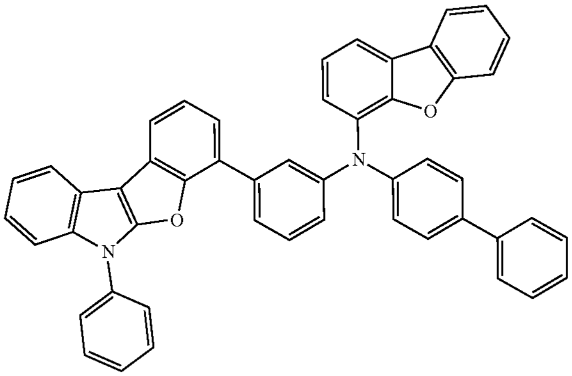
-continued
C101
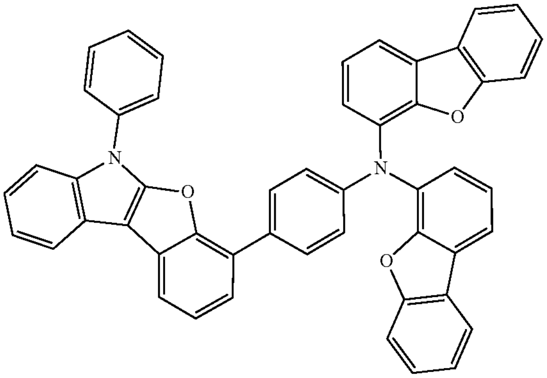
C102
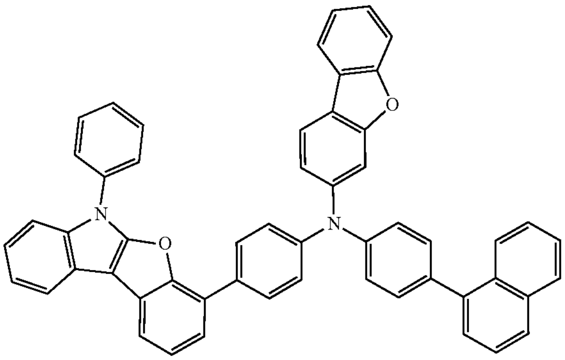
C103
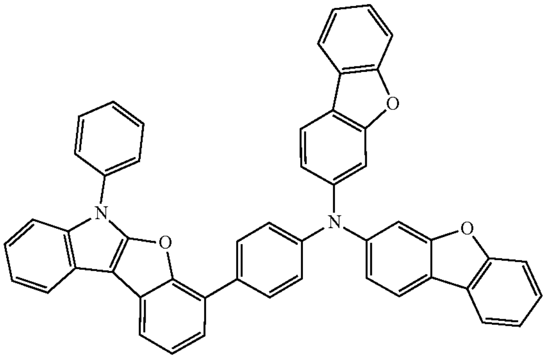
C104
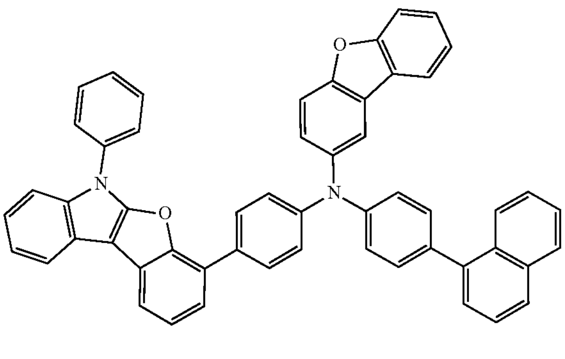

-continued
C105
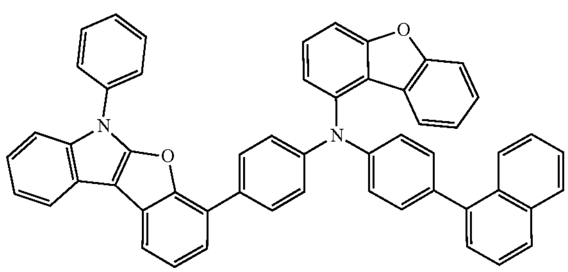
C106
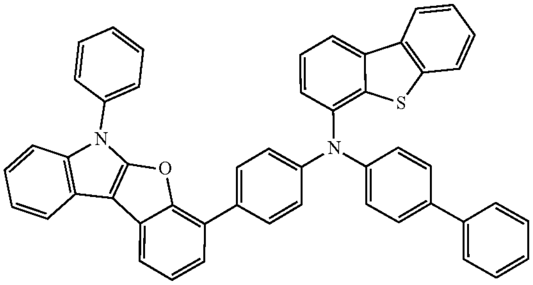
C107
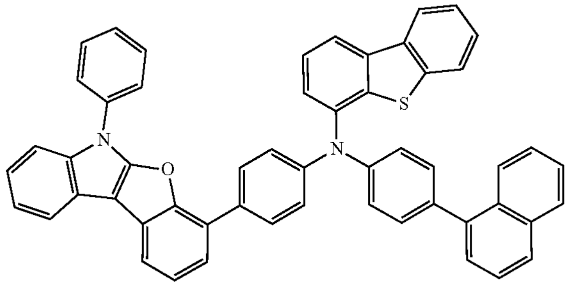
C108
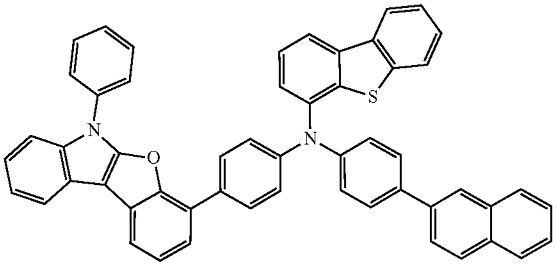
C109
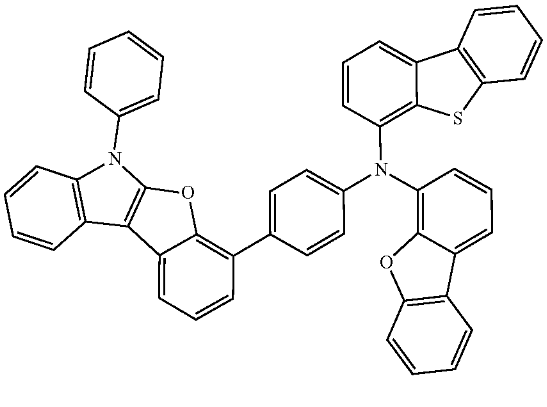
-continued
C110
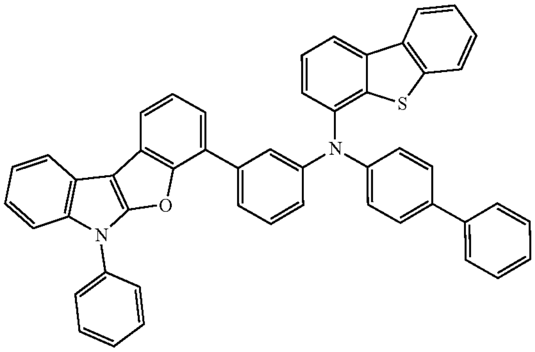
C111
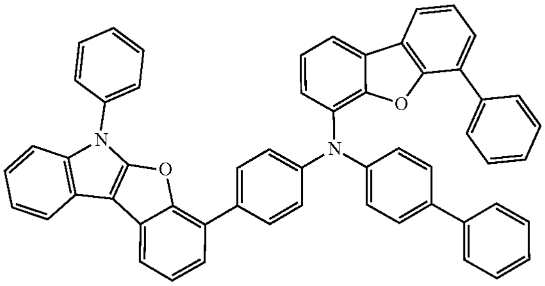
C112
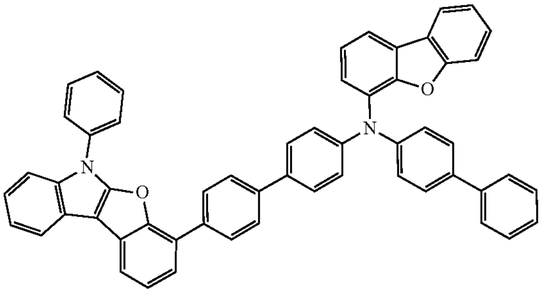
C113
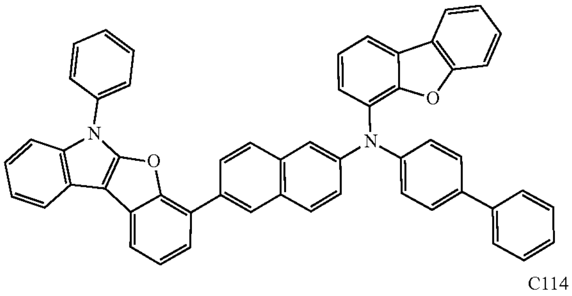
C114
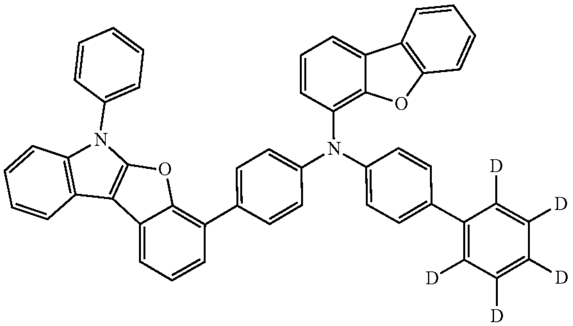

-continued
C115
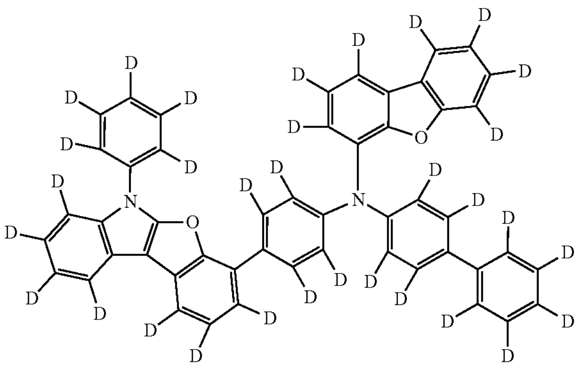
C116
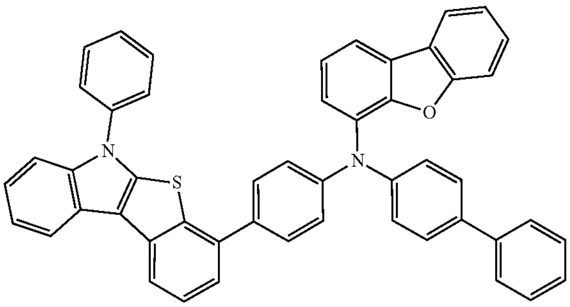
C117
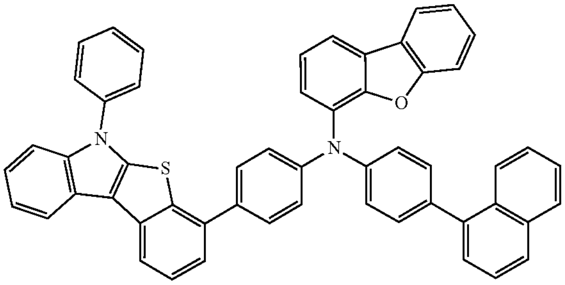
C118
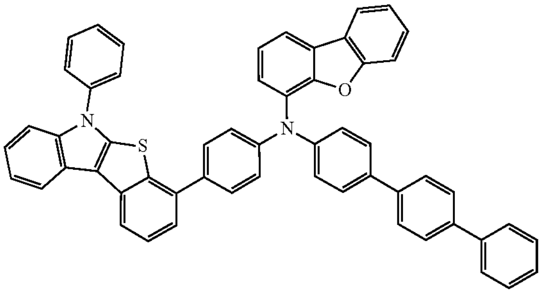
-continued
C119
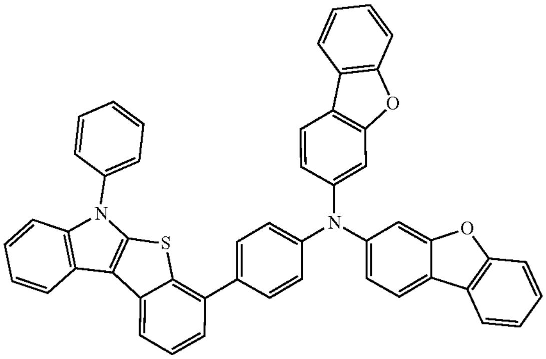
C120
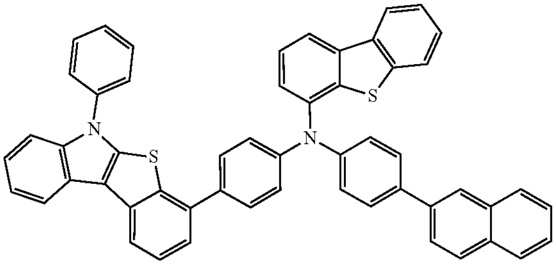
C121
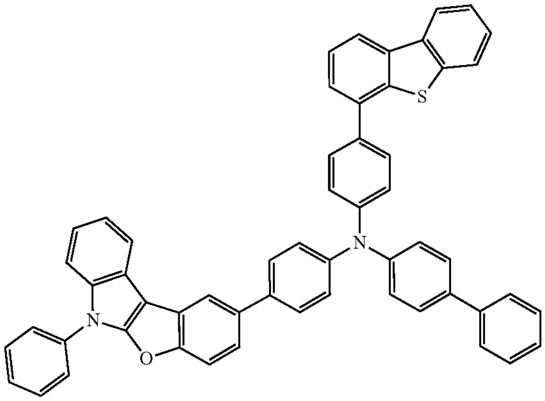
C122
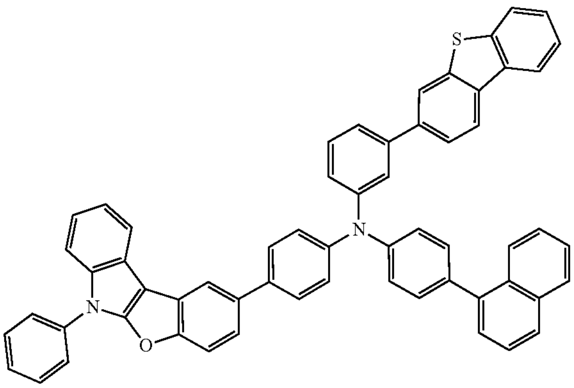

-continued
C123
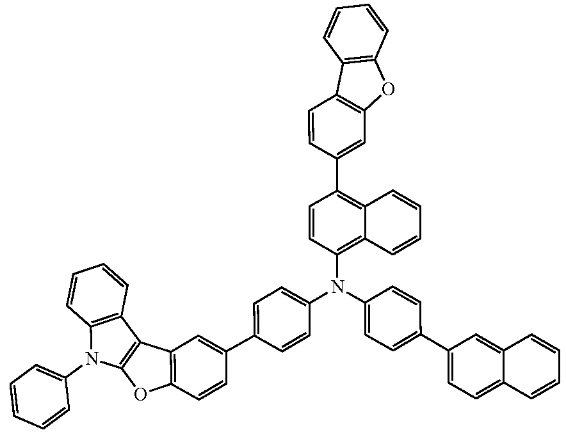
C124
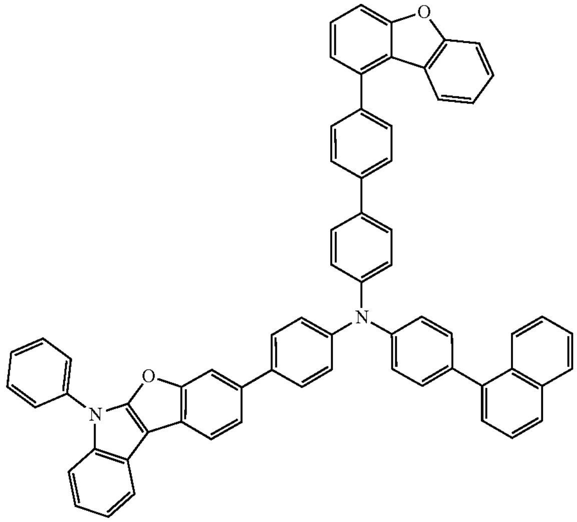
C125
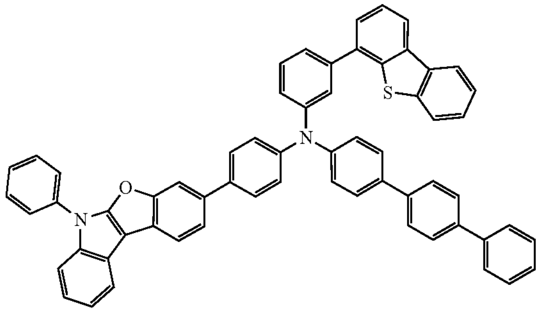
-continued
C126
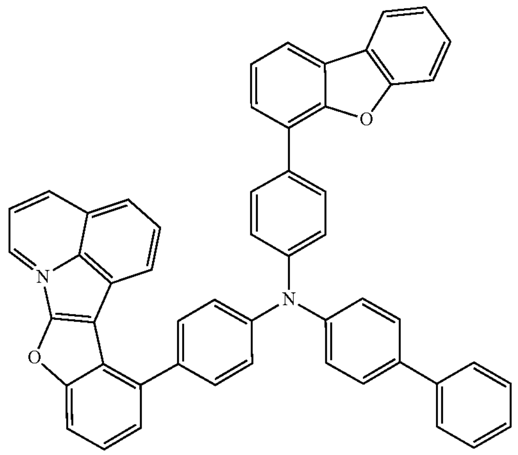
C127
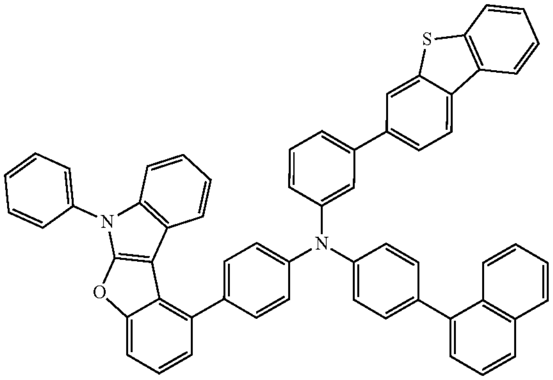
C128
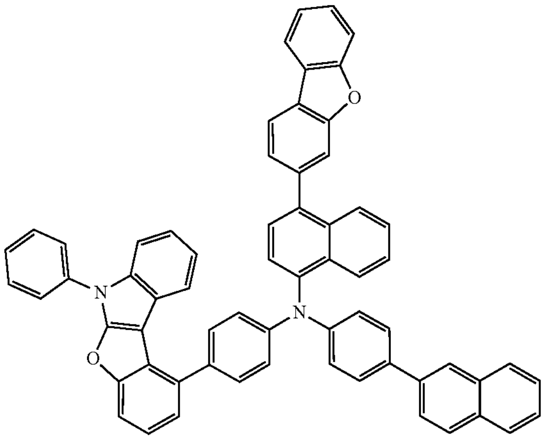

-continued
C129
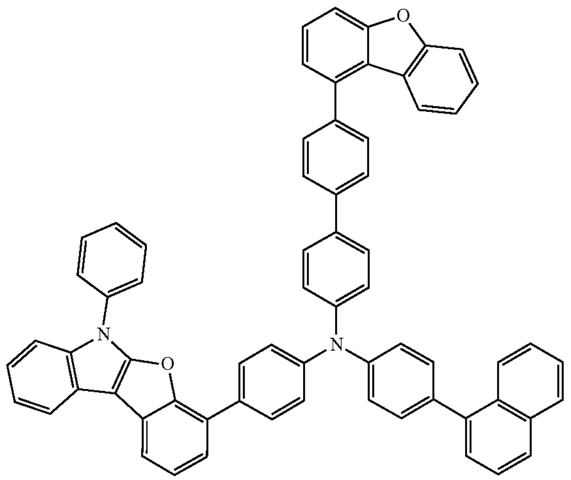
C130
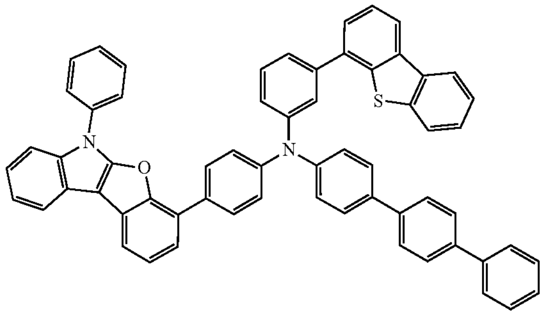
C131
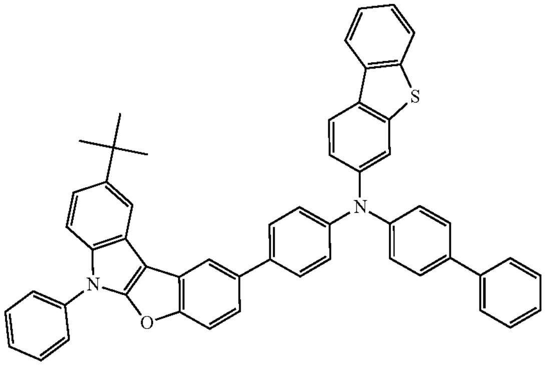
C132
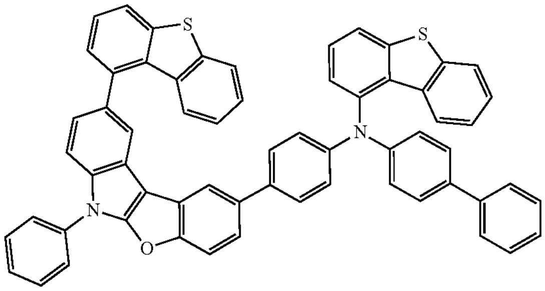
-continued
C133
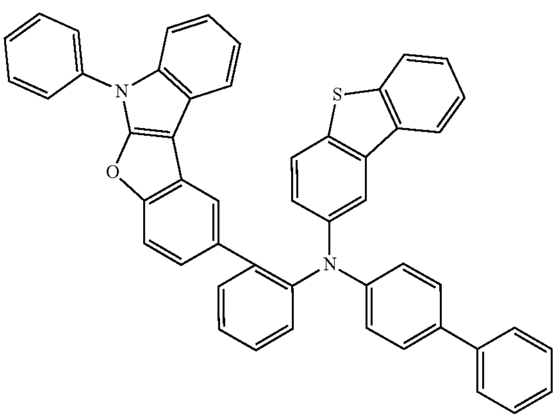
C134
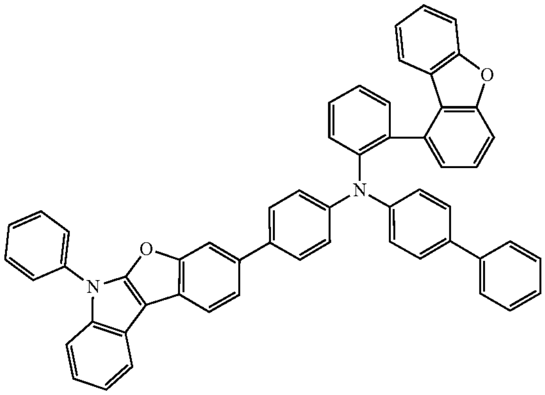
C135
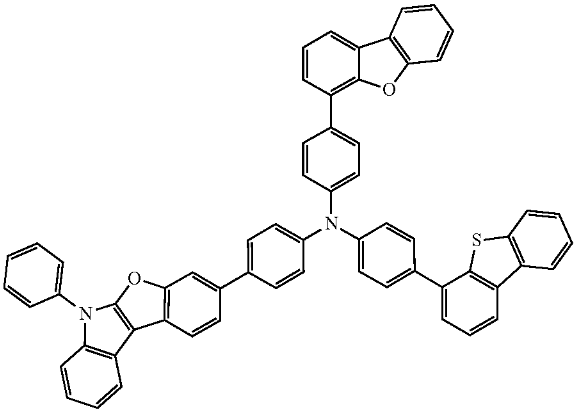

-continued

C136

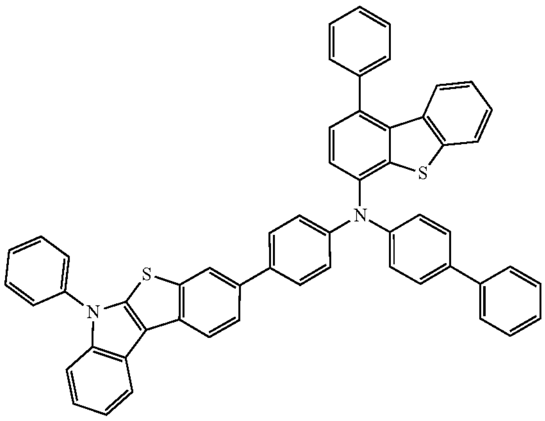

C137

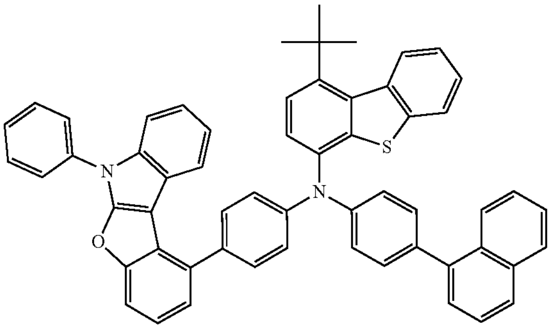

C138

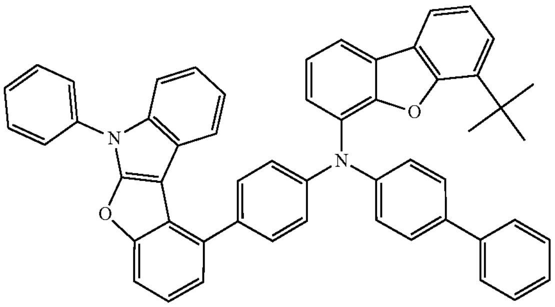

C139

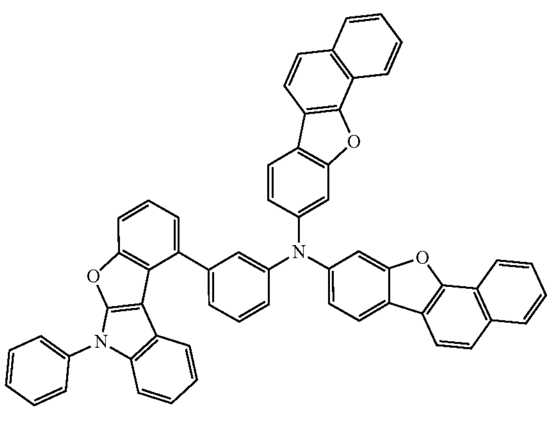

-continued

C140

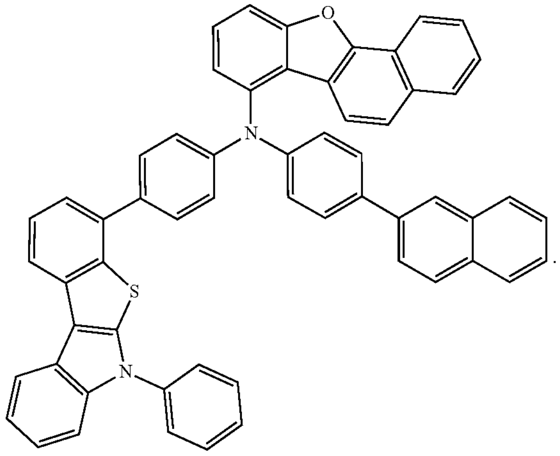

Referring to FIG. 1 to FIG. 3 again, an organic electroluminescence device according to an embodiment of the present disclosure will be explained.

As described above, the hole transport region HTR may include the above-described monoamine compound according to an embodiment of the present disclosure. For example, the hole transport region HTR may include the monoamine compound represented by Formula 1.

When the hole transport region HTR has a multilayer structure having a plurality of layers, any one layer among the plurality of layers may include the monoamine compound represented by Formula 1. For example, the hole transport region HTR may include a hole injection layer HIL disposed on a first electrode EL1, and a hole transport layer HTL disposed on the hole injection layer HIL, and the hole transport layer HTL may include the monoamine compound represented by Formula 1. However, embodiments of the present disclosure are not limited thereto. For example, the hole injection layer HIL may include the monoamine compound represented by Formula 1.

The hole transport region HTR may include one kind or two or more kinds of monoamine compounds represented by Formula 1. For example, the hole transport region HTR may include at least one selected from the compounds represented in the above-described Compound Groups 1 to 3.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole transport region may further include the materials below in each layer.

The hole injection layer HIL may include, for example, a phthalocyanine compound (such as copper phthalocyanine), N,N'-diphenyl-N,N'-bis-[4-(phenyl-m-tolyl-amino)-phenyl]-phenyl-4,4'-diamine (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrene sulfonate) (PANI/PSS), N,N'-di(1-naphthalene-1-yl)-N,N'-diphenylbenzidine (NPD), triphenylamine-containing polyether ketone (TPAPEK), 4-isopropyl-4'-methyldiphenyliodonium [tetrakis(pentafluorophenyl)borate], and/or dipyrazino[2,3-f:2',3'-h]quinoxaline-2,3,6,7,10,11-hexacarbonitrile (HAT-CN).

The hole transport layer HTL may include any suitable material available in the art. For example, the hole transport layer HTL may include carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl) triphenylamine (TCTA)), N,N'-di(1-naphthalene-1-yl)-N,N'-diphenyl-benzidine (NPD), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), etc.

The electron blocking layer EBL may include carbazole derivatives (such as N-phenyl carbazole and/or polyvinyl carbazole), fluorene based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), mCP, etc.

The thickness of the hole transport region HTR may be about 50 Å to about 15,000 Å, for example, about 100 Å to about 5,000 Å. The thickness of the hole injection region HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without a substantial increase in driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be a quinone derivative, metal oxide, or cyano group-containing compound, without limitation. Non-limiting examples of the p-dopant include quinone derivatives (such as tetracyanoquinodimethane (TCNQ) and/or 2,3,5,6-tetrafluoro-7,7',8,8'-tetracyanoquinodimethane (F4-TCNQ)), and metal oxides (such as tungsten oxide and/or molybdenum oxide).

As described above, the hole transport region HTR may further include at least one of a hole buffer layer or an electron blocking layer EBL. The hole buffer layer may compensate for an optical resonance distance depending on the wavelength of light emitted from the emission layer EML, and may increase light emission efficiency. The material included in the hole transport region HTR may be also be included in the hole buffer layer. The electron blocking layer EBL may prevent or reduce electron injection from the electron transport region ETR to the hole transport region HTR.

The emission layer EML is provided on the hole transport region HTR. The emission layer EML may have a thickness of, for example, about 100 Å to about 1,000 Å or about 100 Å to about 600 Å. The emission layer EML may be a single layer formed using a single material, a single layer formed using a plurality of different materials, or a multilayer structure including a plurality of layers formed using a plurality of different materials.

The emission layer EML may include any suitable material, for example, selected from fluoranthene derivatives, pyrene derivatives, arylacetylene derivatives, anthracene derivatives, fluorene derivatives, perylene derivatives, chrysene derivatives, etc., without specific limitation. In some embodiments, pyrene derivatives, perylene derivatives, and anthracene derivatives may be used. For example, an anthracene derivative represented by Formula 10 may be used as the host material of the emission layer EML.

[Formula 10]

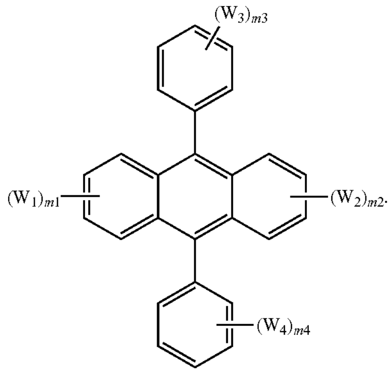

In Formula 10, $W_1$ to $W_4$ may each independently be a hydrogen atom, a deuterium atom, a halogen atom, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, or may be combined with an adjacent group to form a ring. m1 and m2 may each independently be an integer of 0 to 4, and m3 and m4 may each independently be an integer of 0 to 5.

When m1 is 1, $W_1$ may not be a hydrogen atom, when m2 is 1, $W_2$ may not be a hydrogen atom, when m3 is 1, $W_3$ may not be a hydrogen atom, and when m4 is 1, $W_4$ may not be a hydrogen atom.

When m1 is 2 or more, a plurality of $W_1$ groups may be the same or different, when m2 is 2 or more, a plurality of $W_2$ groups may be the same or different, when m3 is 2 or more, a plurality of $W_3$ groups may be the same or different, and when m4 is 2 or more, a plurality of $W_4$ groups may be the same or different.

The compound represented by Formula 10 may include, for example, the compounds represented by the structures below. However, the compound represented by Formula 10 is not limited thereto:

-continued
a-1
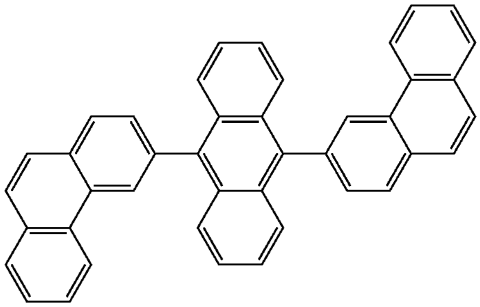
a-2
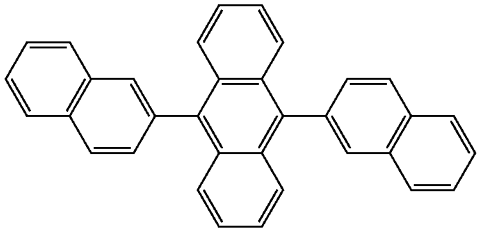
a-3
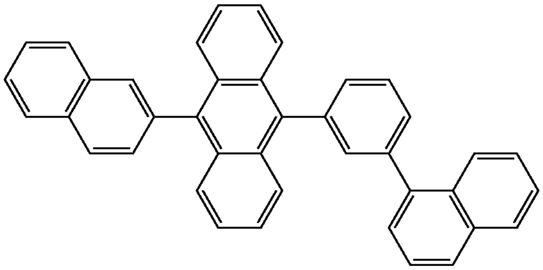
a-4
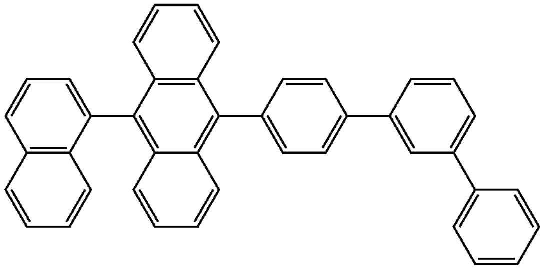
a-5
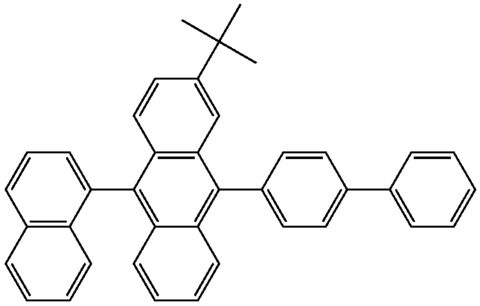
a-6
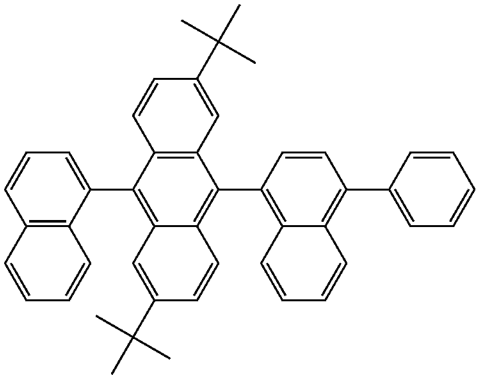
a-7
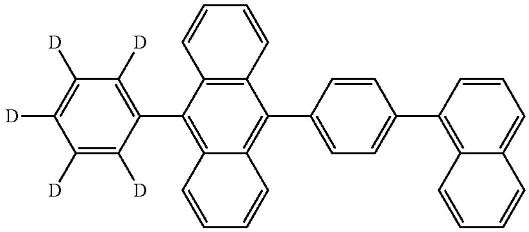
a-8
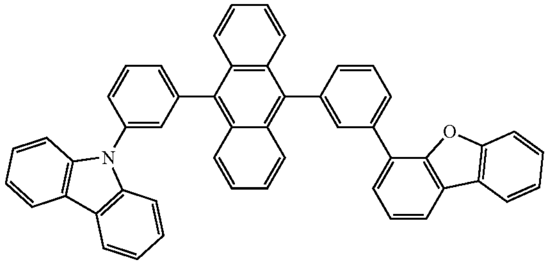
a-9
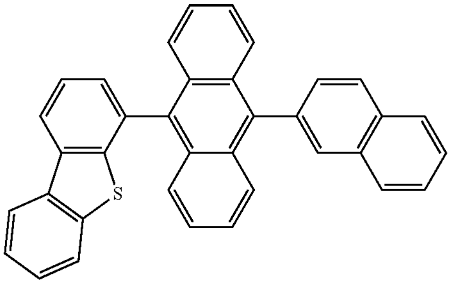
a-10
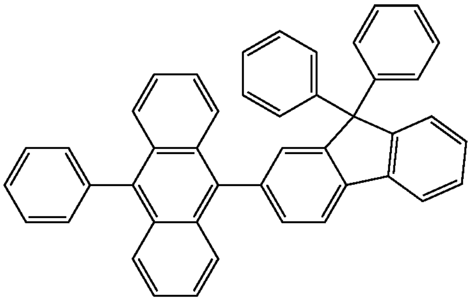

-continued a-11

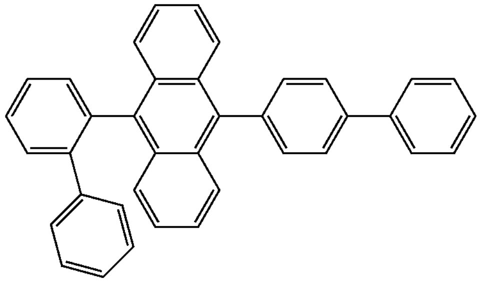

a-12

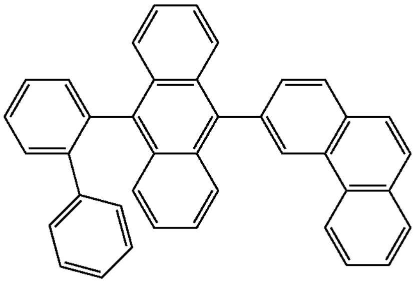

a-13

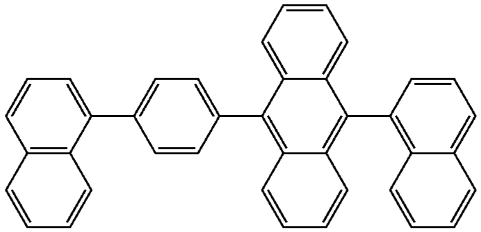

a-14

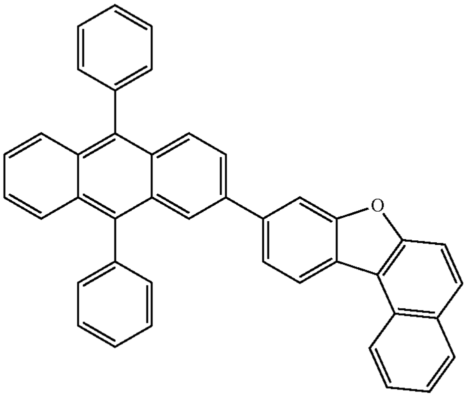

-continued a-15

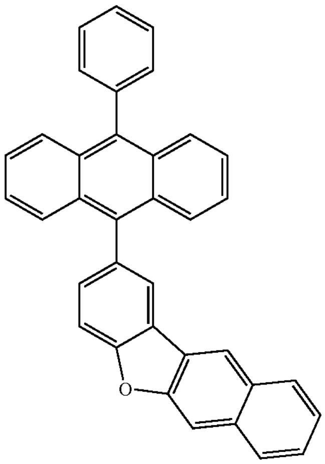

a-16

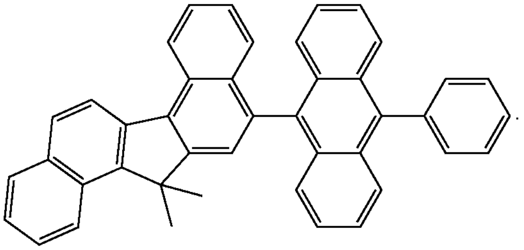

The emission layer EML may include any suitable dopant material. For example, the dopant may be or include at least one among styryl derivatives (for example, 1,4-bis[2-(3-N-ethylcarbazolyl)vinyl]benzene (BCzVB), 4-(di-p-tolylamino)-4"-[(di-p-tolylamino)styryl]stilbene (DPAVB), and/or N-(4-((E)-2-(6-((E)-4-(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBPe)), pyrene and derivatives thereof (for example, 1,1-dipyrene, 1,4-dipyrenylbenzene, 1,4-bis(N,N-diphenylamino)pyrene), 1,6-bis(N,N-diphenylamino)pyrene, 2,5,8,11-tetra-t-butylamino)pyrene (TBP), and 1,3,5-tris(1-phenyl-1H-benzo[d]imidazole-2-yl) benzene (TPBi), etc.

The emission layer EML may include a host material. For example, the emission layer may include as a host material, tris(8-hydroxyquinolino)aluminum ($Alq_3$), bis[2-(diphenylphosphino)phenyl] ether oxide (DPEPO), 4,4'-bis(carbazolyl-9-yl)biphenyl) (CBP), 1,3-bis(N-carbazol-9-yl)benzene (mCP), 2,8-bis(diphenylphosphoryl)dibenzo[b,d]furan (PPF), 4,4',4"-tris(carbazol-9-yl)-triphenylamine (TCTA), poly(N-vinylcarbazole) (PVK), 9,10-di(naphthalene-2-yl) anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis (naphthalen-2-yl)anthracene (MADN), hexaphenyl cyclotriphosphazene (CP1), 1,4-bis(triphenylsilyl)benzene (UGH-2), hexaphenylcyclotrisiloxane ($DPSiO_3$), octaphenylcyclotetrasiloxane ($DPSiO_4$), 2,8-bis(diphenylphosphoryl)dibenzofuran (PPF), and 1,3,5-tris(1-phenyl-1H-benzo [d]imidazole-2-yl)benzene (TPBi), etc. However, embodiments of the present disclosure are not limited thereto.

When the emission layer EML is to emit red light, the emission layer EML may further include, for example, a fluorescence material including tris(dibenzoylmethanato) phenanthroline europium (PBD:Eu(DBM)$_3$(Phen)) and/or perylene. When the emission layer EML is to emit red light, the dopant included in the emission layer EML may be selected from, for example, a metal complex or organometallic complex (such as bis(1-phenylisoquinoline)acetylacetonate iridium (PIQIr(acac)), bis(1-phenylquinoline)acetylacetonate iridium (PQIr(acac)), tris(1-phenylquinoline) iridium (PQr) and/or octaethylporphyrin platinum (PtOEP)), rubrene and derivatives thereof, and 4-dicyanomethylene-2-(p-dimethylaminostyryl)-6-methyl-4H-pyrane (DCM) and derivatives thereof.

In case where the emission layer EML is to emit green light, the emission layer EML may further include, for example, a fluorescence material including tris(8-hydroxyquinolino)aluminum (Alq$_3$). In case where the emission layer EML is to emit green light, the dopant included in the emission layer EML may be selected from, for example, a metal complex or organometallic complex (such as fac-tris (2-phenylpyridine)iridium (Ir(ppy)$_3$)), and coumarin and derivatives thereof.

When the emission layer EML is to emit blue light, the emission layer EML may further include a fluorescence material including any one selected from the group consisting of spiro-DPVBi, spiro-6P, distyryl-benzene (DSB), distyryl-arylene (DSA), a polyfluorene (PFO)-based polymer, and a poly(p-phenylene vinylene (PPV)-based polymer. When the emission layer EML is to emit blue light, the dopant included in the emission layer EML may be selected from a metal complex or an organometallic complex (such as (4,6-F2ppy)$_2$Irpic), and perylene and derivatives thereof.

The electron transport region ETR is provided on the emission layer EML. The electron transport region ETR may include at least one of a hole blocking layer HBL, an electron transport layer ETL, or an electron injection layer EIL, but embodiments of the present disclosure are not limited thereto.

The electron transport region ETR may be a single layer formed using a single material, a single layer formed using a plurality of different materials, or a multilayer structure having a plurality of layers formed using a plurality of different materials.

For example, the electron transport region ETR may have a single layer structure including an electron injection layer EIL or an electron transport layer ETL, or a single layer structure formed using an electron injection material and an electron transport material (e.g., together). In some embodiments, the electron transport region ETR may have a single layer structure having a plurality of different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, about 100 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include an anthracene-based compound. The electron transport region may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate (Bebq$_2$), 9,10-di(naphthalene-2-yl)anthracene (ADN), or a mixture thereof, without limitation. The thickness of the electron transport layer ETL may be from about 100 Å to about 1,000 Å and may be, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include, a metal halide such as LiF, NaCl, CsF, RbCl and RbI, a lanthanide metal (such as ytterbium (Yb), a metal oxide (such as $Li_2O$ and BaO), or lithium quinolate (LiQ). However, embodiments of the present disclosure are not limited thereto. The electron injection layer EIL may be formed using a mixture material of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, and/or metal stearates. The thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, embodiments of the present disclosure are not limited thereto.

The second electrode EL2 is provided on the electron transport region ETR. The second electrode EL2 may be a common electrode or a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials, and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, a capping layer (CPL) may be further disposed on the second electrode EL2 of the organic electroluminescence device 10 of an embodiment. The capping layer (CPL) may include, for example, α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol-[[sol-]]9-yl) triphenylamine (TCTA)), etc.

In the organic electroluminescence device 10, according to the application of voltages to the first electrode EL1 and the second electrode EL2, respectively, holes injected from the first electrode EL1 may move through the hole transport region HTR to the emission layer EML, and electrons injected from the second electrode EL2 may move through the electron transport region ETR to the emission layer EML. Electrons and holes recombine in the emission layer EML to produce excitons, and light is emitted via transition of the excitons from an excited state to the ground state.

When the organic electroluminescence device 10 is atop emission type (device), the first electrode EL1 may be a reflective electrode, and the second electrode EL2 may be a transmissive or transflective electrode. When the organic electroluminescence device 10 is a bottom emission type (device), the first electrode EL1 may be a transmissive or transflective electrode, and the second electrode EL2 may be a reflective electrode.

The organic electroluminescence device 10 according to an embodiment of the present disclosure may characteristically include the monoamine compound represented by Formula 1, and accordingly, high efficiency and long life may be achieved. Furthermore, the driving voltage may be decreased.

Hereinafter, the present disclosure will be explained in more detail by referring to embodiments and comparative embodiments. The following embodiments are only illustrations to assist the understanding of the present disclosure, and the scope of the present disclosure is not limited thereto.

SYNTHETIC EXAMPLES

The monoamine compound according to an embodiment of the present disclosure may be synthesized by, for example, the methods below. However, synthetic methods of the monoamine compound according to an embodiment of the present disclosure are not limited thereto.

1. Synthesis of Compound A2

(Synthesis of Intermediate IM-1)

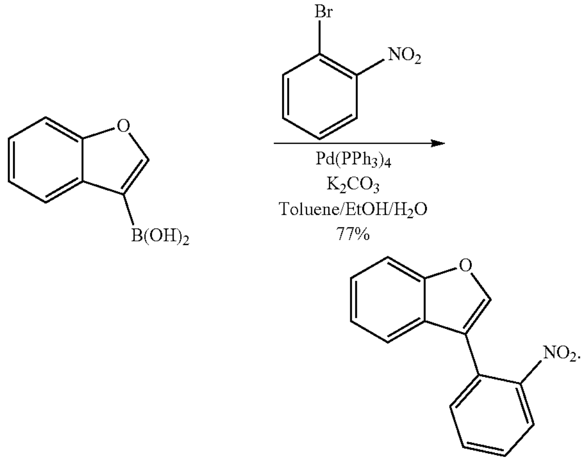

IM-1

Under an Ar atmosphere, to a 2,000 mL, three-neck flask, 30.00 g (185.2 mmol) of benzofuran-3-ylboronic acid, 41.16 g (1.1 eq, 203.8 mmol) of 1-bromo-2-nitrobenzene, 76.81 g (3.0 eq, 555.7 mmol) of $K_2CO_3$, 10.70 g (0.05 eq, 9.3 mmol) of $Pd(PPh_3)_4$, and 1,297 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-1 (34.12 g, yield 77%).

By the FAB-MS measurement, amass number, m/z=239 was observed as a molecular ion peak, and Intermediate IM-1 was identified.

(Synthesis of Intermediate IM-2)

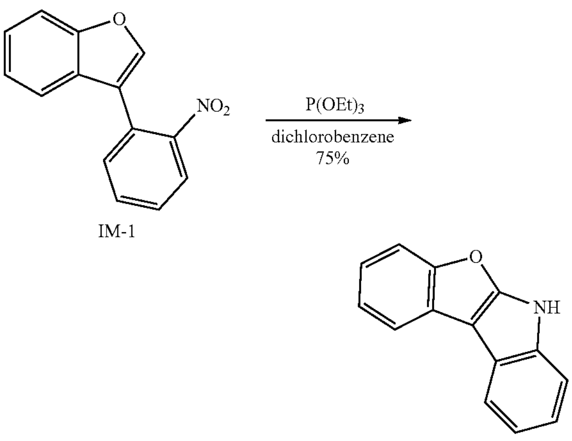

IM-1

IM-2

Under an Ar atmosphere, to a 500 mL, three-neck flask, 30.00 g (125.4 mmol) of IM-1, 250 mL of o-dichlorobenzene, and 83.35 g (4 eq, 501.6 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-2 (19.49 g, yield 75%).

By the FAB-MS measurement, a mass number, m/z=207 was observed as a molecular ion peak, and Intermediate IM-2 was identified.

(Synthesis of Intermediate IM-3)

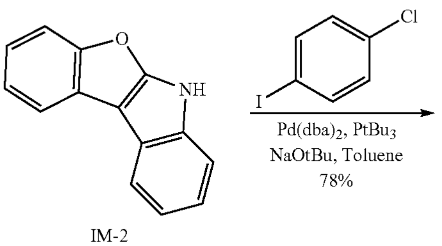

IM-2

-continued

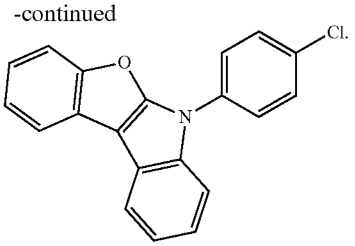

IM-3

Under an Ar atmosphere, to a 500 mL, three-neck flask, 15.00 g (72.4 mmol) of IM-2, 1.25 g (0.03 eq, 2.2 mmol) of $Pd(dba)_2$, 6.96 g (1.0 eq, 72.4 mmol) of NaOtBu, 362 mL of toluene, 18.99 g (1.1 eq, 79.6 mmol) of 1-chloro-4-iodobenzene, and 7.46 g (0.1 eq, 7.3 mmol) of $tBu_3P$ were added in order, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-3 (17.94 g, yield 78%).

By the FAB-MS measurement, a mass number, m/z=317 was observed as a molecular ion peak, and Intermediate IM-3 was identified.

(Synthesis of Intermediate IM-4)

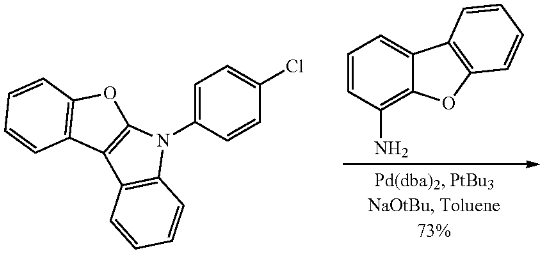

IM-3

-continued

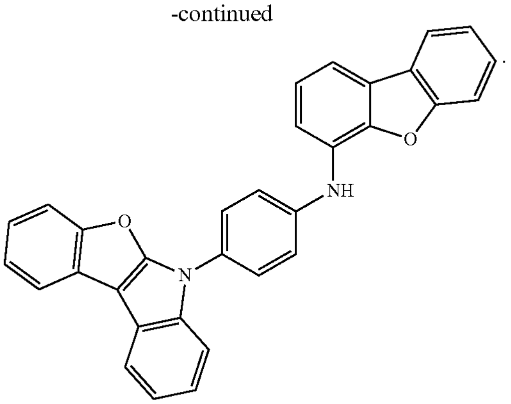

IM-4

Under an Ar atmosphere, to a 500 mL, three-neck flask, 15.00 g (47.2 mmol) of IM-3, 0.81 g (0.03 eq, 1.4 mmol) of $Pd(dba)_2$, 4.54 g (1.0 eq, 47.2 mmol) of NaOtBu, 236 mL of toluene, 9.51 g (1.1 eq, 51.9 mmol) of 4-aminodibenzofuran, and 0.96 g (0.1 eq, 4.7 mmol) of $tBu_3P$ were added in order, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-4 (16.01 g, yield 73%).

By the FAB-MS measurement, amass number, m/z=464 was observed as a molecular ion peak, and Intermediate IM-4 was identified.

(Synthesis of Compound A2)

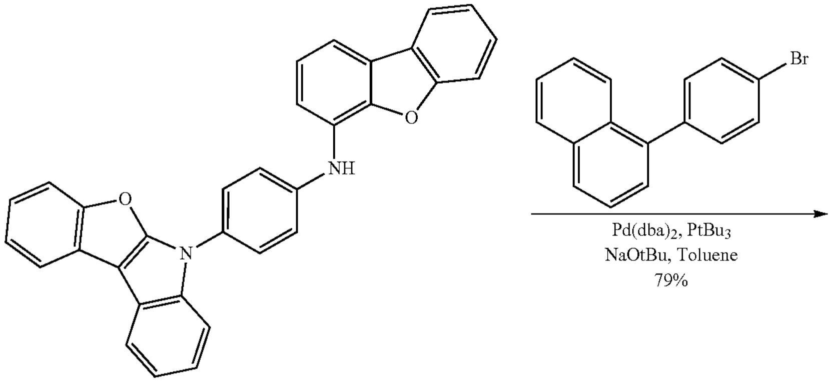

IM-4

-continued

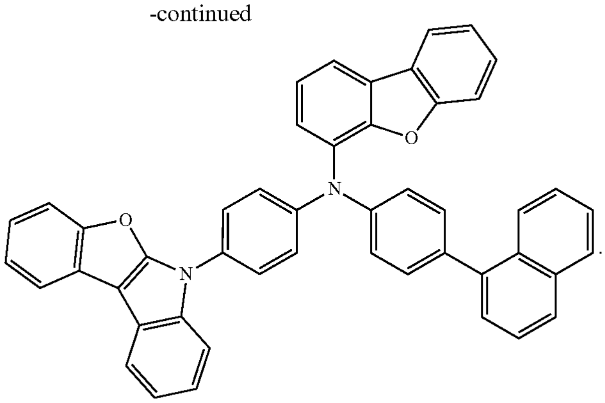

A2

Under an Ar atmosphere, to a 200 mL, three-neck flask, 10.00 g (21.5 mmol) of IM-4, 0.37 g (0.03 eq, 0.6 mmol) of $Pd(dba)_2$, 4.14 g (2.0 eq, 43.1 mmol) of NaOtBu, 107 mL of toluene, 6.71 g (1.1 eq, 23.7 mmol) of 1-(4-bromophenyl) naphthalene, and 0.44 g (0.1 eq, 2.2 mmol) of $tBu_3P$ were added in order, followed by heating, refluxing, and stirring. After air cooling to room temperature, water was added to the reaction solution, and an organic layer was separately taken. Toluene was added to an aqueous layer, and organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound A2 (11.34 g, yield 79%) as a solid.

By the FAB-MS measurement, amass number, m/z=666 was observed as a molecular ion peak, and Compound A2 was identified.

2. Synthesis of Compound A20

(Synthesis of Intermediate IM-5)

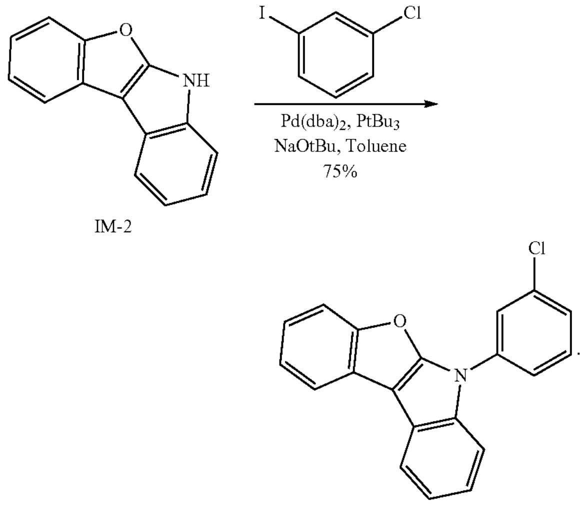

IM-2

IM-5

Under an Ar atmosphere, to a 500 mL, three-neck flask, 15.00 g (72.4 mmol) of IM-2, 1.25 g (0.03 eq, 2.2 mmol) of $Pd(dba)_2$, 6.96 g (1.0 eq, 72.4 mmol) of NaOtBu, 362 mL of toluene, 18.99 g (1.1 eq, 79.6 mmol) of 1-chloro-3-iodobenzene, and 7.46 g (0.1 eq, 7.3 mmol) of $tBu_3P$ were added in order, followed by heating, refluxing and stirring. After air cooling to room temperature, water was added to the reaction solution, and an organic layer was separately taken. Toluene was added to an aqueous layer, and organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-5 (17.25 g, yield 75%).

By the FAB-MS measurement, a mass number, m/z=317 was observed as a molecular ion peak, and Intermediate IM-5 was identified.

(Synthesis of Intermediate IM-6)

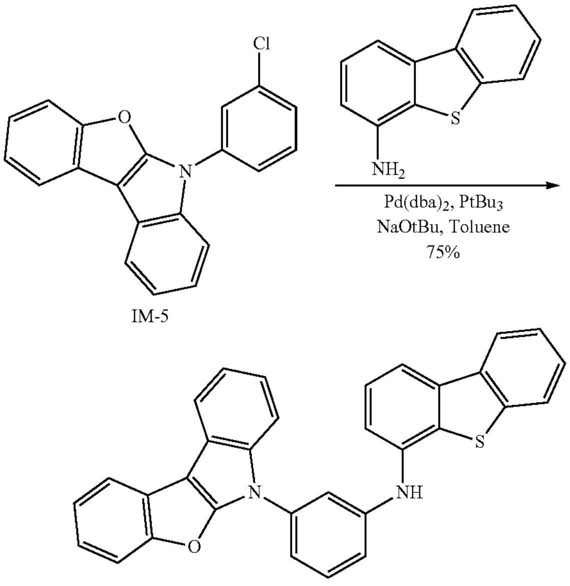

IM-5

IM-6

Under an Ar atmosphere, to a 500 mL, three-neck flask, 15.00 g (47.2 mmol) of IM-5, 0.81 g (0.03 eq, 1.4 mmol) of $Pd(dba)_2$, 4.54 g (1.0 eq, 47.2 mmol) of NaOtBu, 236 mL of toluene, 10.35 g (1.1 eq, 51.9 mmol) of 4-aminodibenzothiophene, and 0.96 g (0.1 eq, 4.7 mmol) of $tBu_3P$ were added in order, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-6 (17.01 g, yield 75%).

By the FAB-MS measurement, amass number, m/z=480 was observed as a molecular ion peak, and Intermediate IM-6 was identified.

(Synthesis of Compound A20)

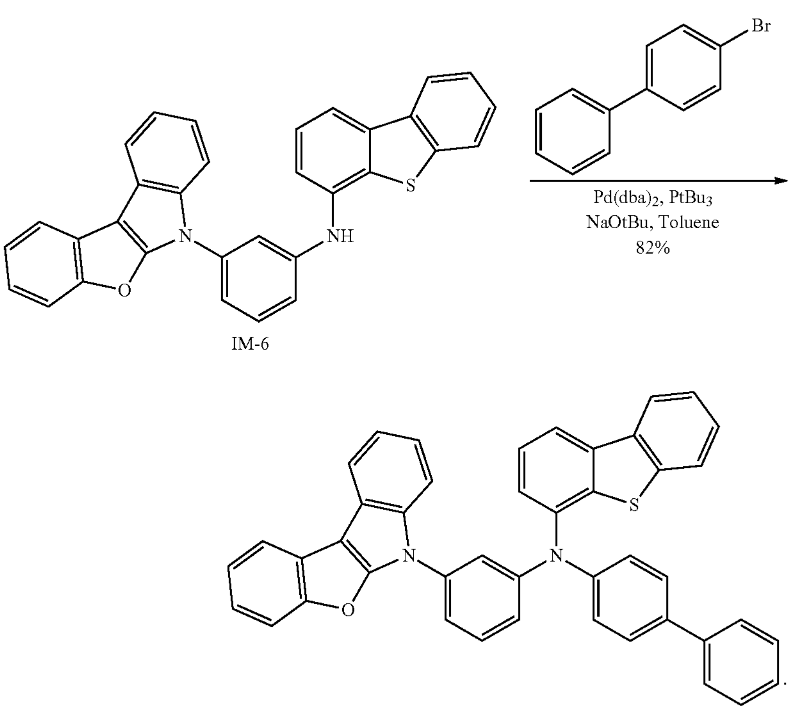

IM-6

A20

Under an Ar atmosphere, to a 200 mL, three-neck flask, 10.00 g (20.8 mmol) of IM-6, 0.36 g (0.03 eq, 0.6 mmol) of $Pd(dba)_2$, 4.00 g (2.0 eq, 41.6 mmol) of NaOtBu, 104 mL of toluene, 5.34 g (1.1 eq, 22.9 mmol) of 4-bromobiphenyl, and 0.42 g (0.1 eq, 2.1 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound A20 (10.80 g, yield 82%) as a solid.

By the FAB-MS measurement, amass number, m/z=632 was observed as a molecular ion peak, and Compound A20 was identified.

3. Synthesis of Compound B13

(Synthesis of Intermediate IM-7)

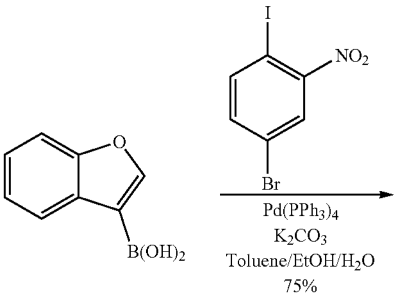

-continued

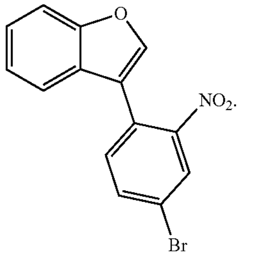

IM-7

Under an Ar atmosphere, to a 2,000 mL, three-neck flask, 30.00 g (185.2 mmol) of benzofuran-3-ylboronic acid, 66.82 g (1.1 eq, 203.8 mmol) of 4-bromo-1-iodo-2-nitrobenzene, 76.81 g (3.0 eq, 555.7 mmol) of $K_2CO_3$, 10.70 g (0.05 eq, 9.3 mmol) of $Pd(PPh_3)_4$, and 1,297 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-7 (44.20 g, yield 75%).

By the FAB-MS measurement, amass number, m/z=318 was observed as a molecular ion peak, and Intermediate IM-7 was identified.

(Synthesis of Intermediate IM-8)

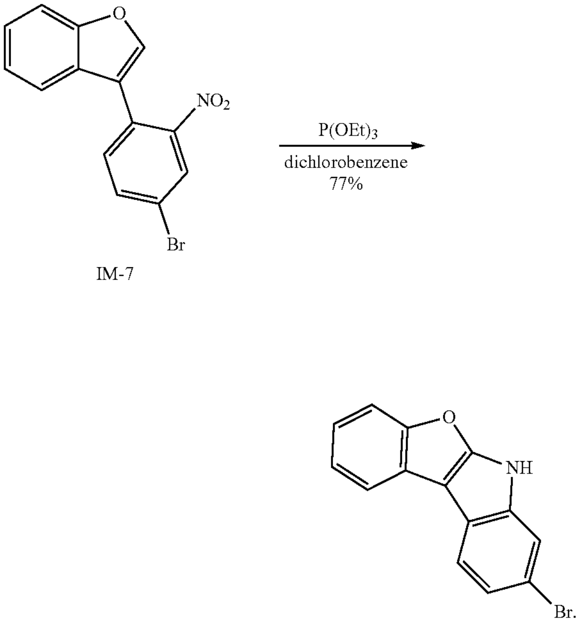

IM-7

IM-8

Under an Ar atmosphere, to a 500 mL, three-neck flask, 30.00 g (94.3 mmol) of IM-7, 188 ml of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-8 (20.78 g, yield 77%).

By the FAB-MS measurement, amass number, m/z=286 was observed as a molecular ion peak, and Intermediate IM-8 was identified.

(Synthesis of Intermediate IM-9)

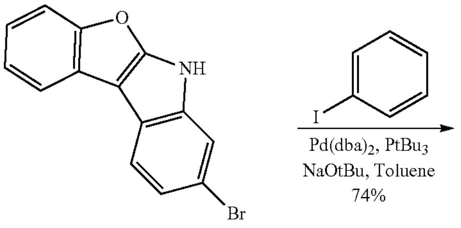

IM-8

-continued

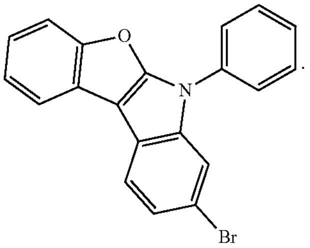

IM-9

Under an Ar atmosphere, to a 500 mL, three-neck flask, 18.00 g (62.9 mmol) of IM-8, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-9 (16.86 g, yield 74%).

By the FAB-MS measurement, amass number, m/z=362 was observed as a molecular ion peak, and Intermediate IM-9 was identified.

(Synthesis of Intermediate IM-10)

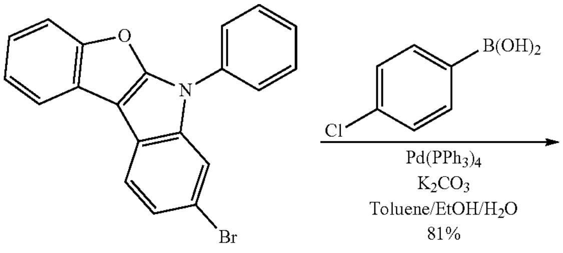

IM-9

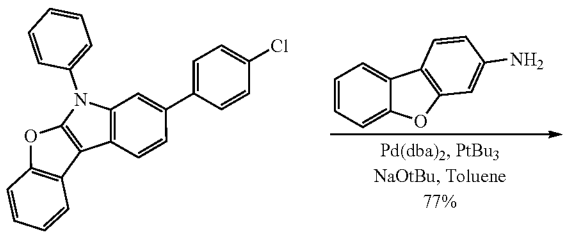

IM-46

-continued

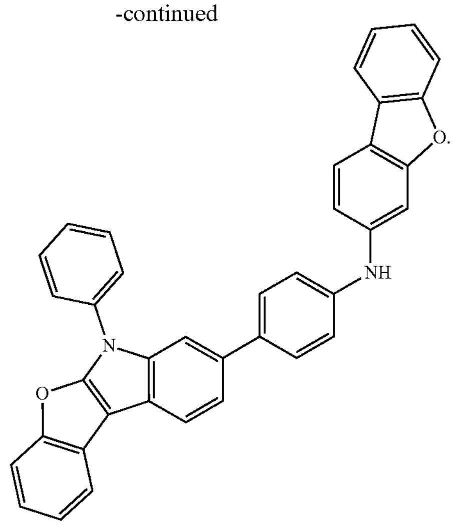

IM-10

Under an Ar atmosphere, 15.00 g (41.4 mmol) of IM-9, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-46 (13.21 g, yield 81%).

By the FAB-MS measurement, a mass number, m/z=393 was observed as a molecular ion peak, and Intermediate IM-46 was identified.

Under an Ar atmosphere, 15.00 g (38.1 mmol) of IM-46, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 3-aminodibenzofuran, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separated. Toluene was added to an aqueous layer, and additional organic layers were extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-10 (15.85 g, yield 77%).

By the FAB-MS measurement, amass number, m/z=540 was observed as a molecular ion peak, and Intermediate IM-10 was identified.

(Synthesis of Compound B13)

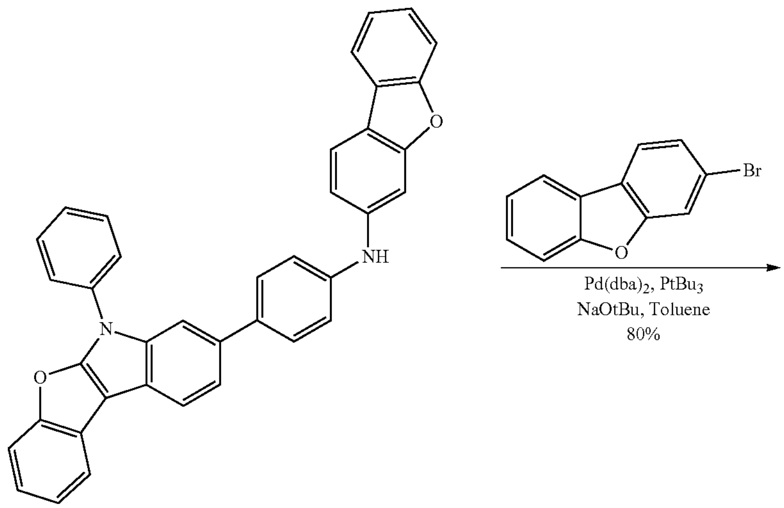

IM-10

-continued

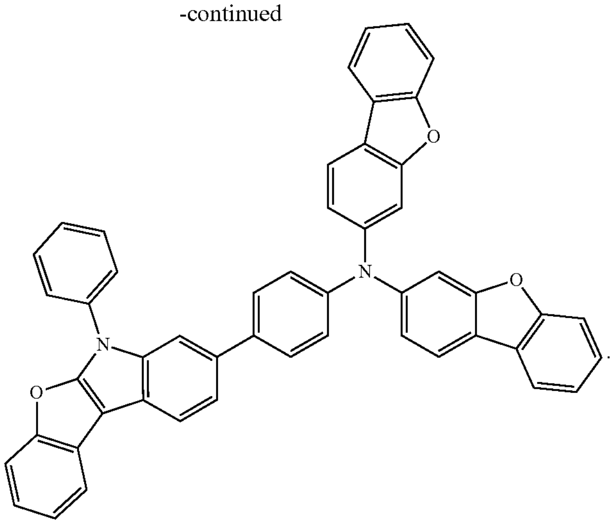

B13

Under an Ar atmosphere, to a 200 mL, three-neck flask, 10.00 g (18.5 mmol) of IM-10, 0.32 g (0.03 eq, 0.6 mmol) of $Pd(dba)_2$, 3.56 g (2.0 eq, 37.0 mmol) of NaOtBu, 92 mL of toluene, 5.03 g (1.1 eq, 20.3 mmol) of 3-bromodibenzofuran, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound B13 (10.46 g, yield 80%) as a solid.

By the FAB-MS measurement, amass number, m/z=706 was observed as a molecular ion peak, and Compound B13 was identified.

4. Synthesis of Compound B18

(Synthesis of Intermediate IM-11)

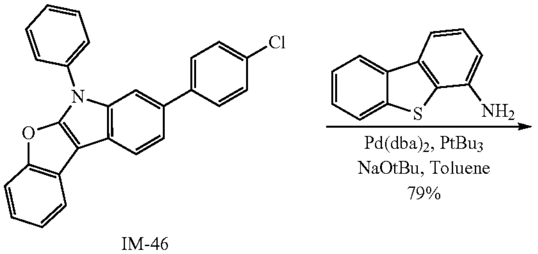

IM-46

-continued

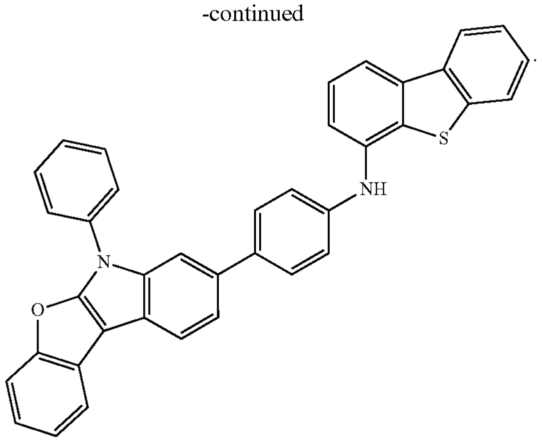

IM-11

Under an Ar atmosphere, 15.00 g (38.1 mmol) of IM-46, 0.66 g (0.03 eq, 1.1 mmol) of $Pd(dba)_2$, 3.66 g (1.0 eq, 38.0 mmol) of NaOtBu, 190 mL of toluene, 8.35 g (1.1 eq, 41.9 mmol) of 4-aminodibenzothiophene, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and additional organic layers were extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-11 (16.75 g, yield 79%).

By the FAB-MS measurement, amass number, m/z=556 was observed as a molecular ion peak, and Intermediate IM-11 was identified.

(Synthesis of Compound B18)

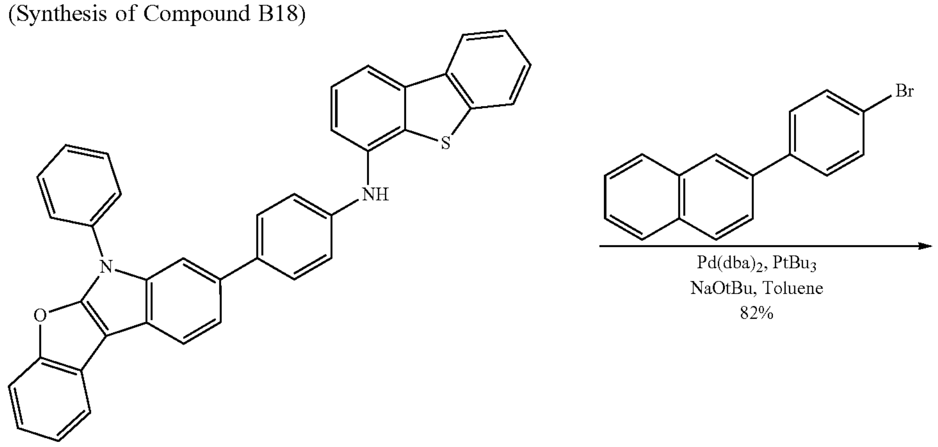

IM-11

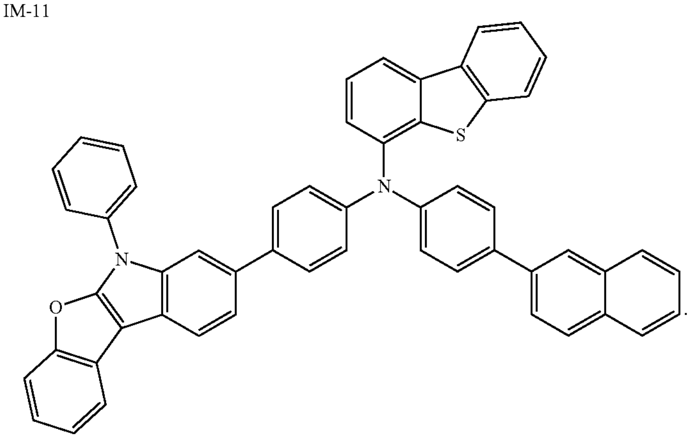

B18

Under an Ar atmosphere, to a 200 mL, three-neck flask, 10.00 g (18.0 mmol) of IM-11, 0.31 g (0.03 eq, 0.5 mmol) of $Pd(dba)_2$, 3.45 g (2.0 eq, 35.9 mmol) of NaOtBu, 90 mL of toluene, 5.96 g (1.1 eq, 19.8 mmol) of 2-(4-bromophenyl) naphthalene, and 0.36 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound B18 (11.18 g, yield 82%) as a solid.

By the FAB-MS measurement, a mass number, m/z=758 was observed as a molecular ion peak, and Compound B18 was identified.

5. Synthesis of Compound B36

(Synthesis of Intermediate IM-12)

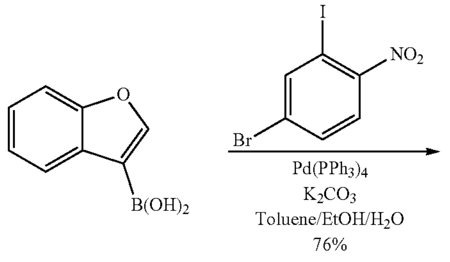

-continued

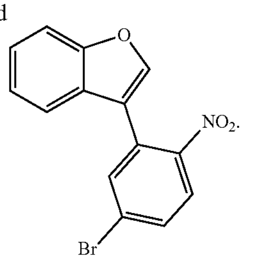

IM-12

Under an Ar atmosphere, to a 2,000 mL, three-neck flask, 30.00 g (185.2 mmol) of benzofuran-3-ylboronic acid, 66.82 g (1.1 eq, 203.8 mmol) of 4-bromo-2-iodo-1-nitrobenzene, 76.81 g (3.0 eq, 555.7 mmol) of $K_2CO_3$, 10.70 g (0.05 eq, 9.3 mmol) of $Pd(PPh_3)_4$, and 1,297 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-12 (44.79 g, yield 76%).

By the FAB-MS measurement, a mass number, m/z=318 was observed as a molecular ion peak, and Intermediate IM-12 was identified.

(Synthesis of Intermediate IM-13)

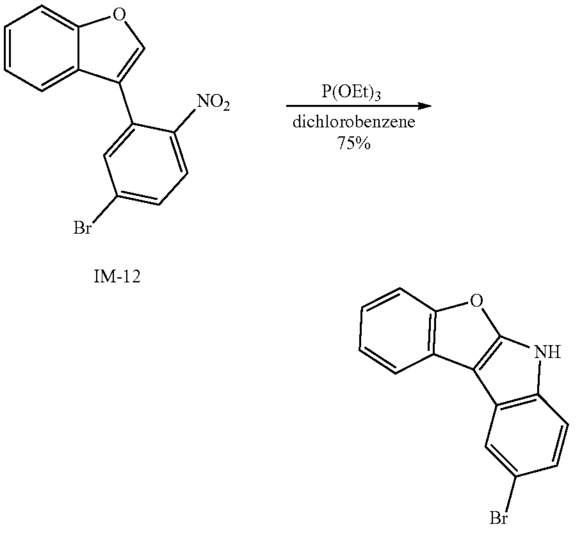

IM-12

IM-13

Under an Ar atmosphere, to a 500 mL, three-neck flask, 30.00 g (94.3 mmol) of IM-12, 188 mL of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-13 (20.24 g, yield 75%).

By the FAB-MS measurement, amass number, m/z=286 was observed as a molecular ion peak, and Intermediate IM-13 was identified.

(Synthesis of Intermediate IM-14)

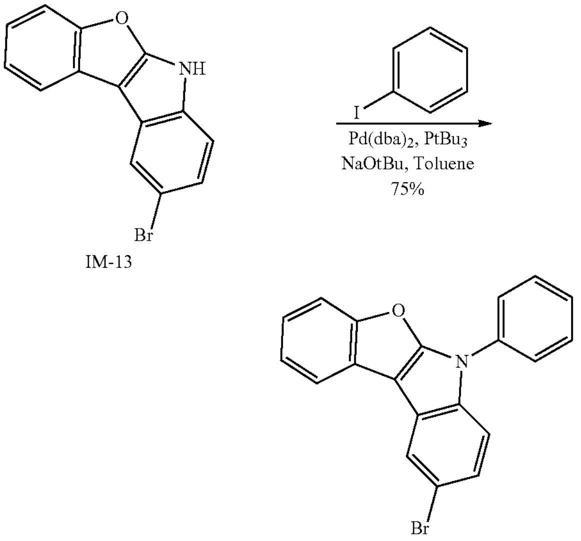

IM-13

IM-14

Under an Ar atmosphere, to a 500 mL, three-neck flask, 18.00 g (62.9 mmol) of IM-13, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-14 (17.09 g, yield 75%).

By the FAB-MS measurement, amass number, m/z=362 was observed as a molecular ion peak, and Intermediate IM-14 was identified.

(Synthesis of Intermediate IM-15)

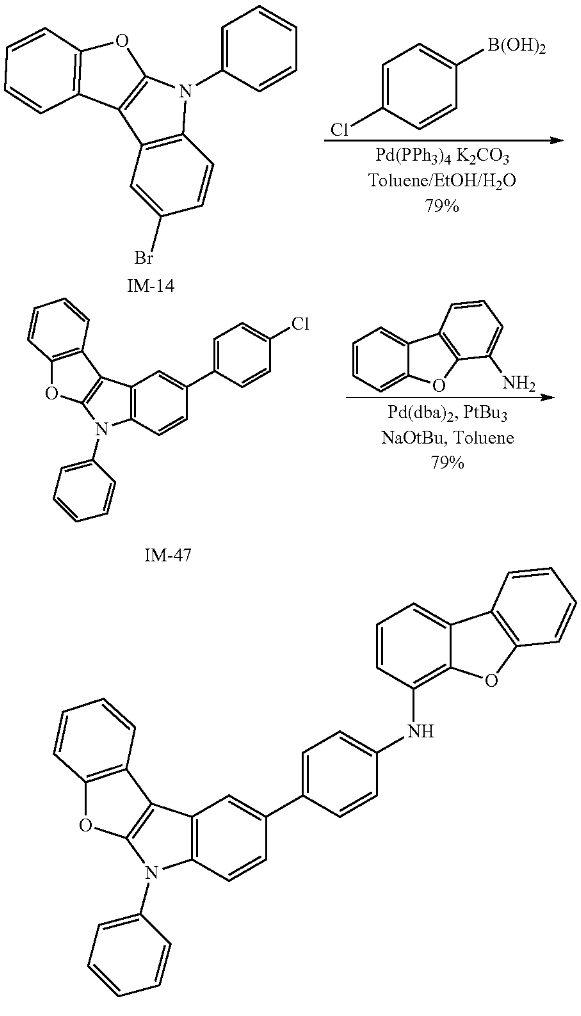

IM-14

IM-47

IM-15

Under an Ar atmosphere, 15.00 g (41.4 mmol) of IM-14, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mLI of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-47 (12.89 g, yield 79%).

By the FAB-MS measurement, a mass number, m/z=393 was observed as a molecular ion peak, and Intermediate IM-47 was identified.

Under an Ar atmosphere, 15.00 g (38.1 mmol) of IM-47, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 4-aminodibenzofuran and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and additional organic layers were extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-15 (16.27 g, yield 79%).

By the FAB-MS measurement, amass number, m/z=540 was observed as a molecular ion peak, and Intermediate IM-15 was identified.

(Synthesis of Compound B36)

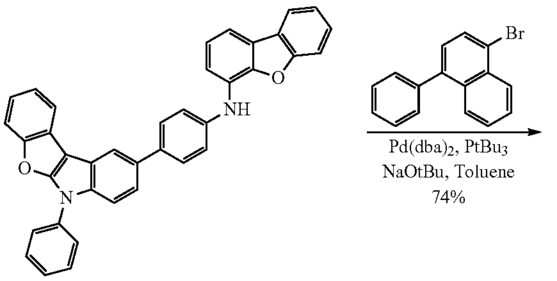

IM-15

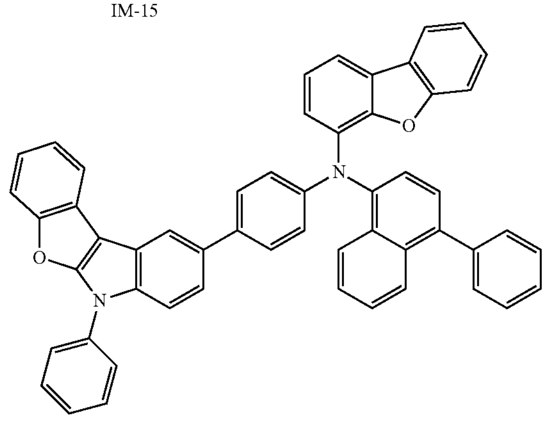

B36

Under an Ar atmosphere, to a 200 mL, three-neck flask, 10.00 g (18.5 mmol) of IM-15, 0.32 g (0.03 eq, 0.6 mmol) of $Pd(dba)_2$, 3.56 g (2.0 eq, 37.0 mmol) of NaOtBu, 92 mL of toluene, 5.76 g (1.1 eq, 20.3 mmol) of 1-bromo-4-phenylnaphthalene and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound B36 (10.46 g, yield 74%) as a solid.

By the FAB-MS measurement, a mass number, m/z=742 was observed as a molecular ion peak, and Compound B36 was identified.

6. Synthesis of Compound B49

(Synthesis of Intermediate IM-16)

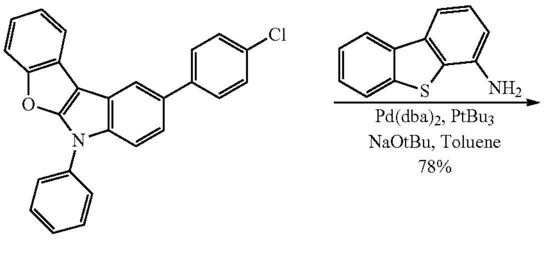

IM-47

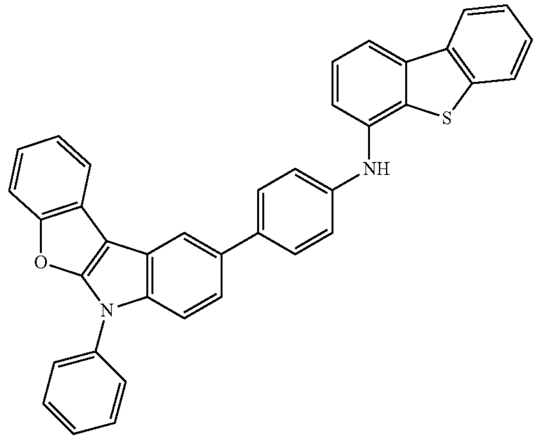

IM-16

Under an Ar atmosphere, 15.00 g (38.1 mmol) of IM-47, 0.66 g (0.03 eq, 1.1 mmol) of $Pd(dba)_2$, 3.66 g (1.0 eq, 38.0 mmol) of NaOtBu, 190 mL of toluene, 8.35 g (1.1 eq, 41.9 mmol) of 4-aminodibenzothiophene, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and additional organic layers were extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-16 (16.54 g, yield 78%).

By the FAB-MS measurement, amass number, m/z=556 was observed as a molecular ion peak, and Intermediate IM-16 was identified.

(Synthesis of Compound B49)

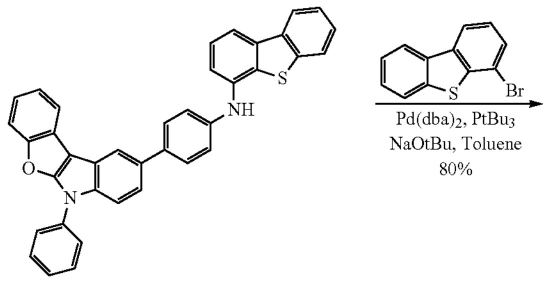

IM-16

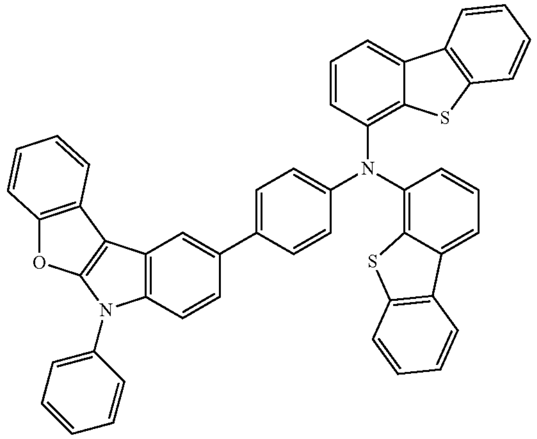

B49

Under an Ar atmosphere, to a 200 mL, three-neck flask, 10.00 g (18.0 mmol) of IM-16, 0.31 g (0.03 eq, 0.5 mmol) of $Pd(dba)_2$, 3.45 g (2.0 eq, 35.9 mmol) of NaOtBu, 90 mL of toluene, 5.20 g (1.1 eq, 19.8 mmol) of 4-bromodibenzothiophene, and 0.36 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. $MgSO_4$ was separated by filtering, and an organic layer was concentrated. The crude product thus obtained was separated by silica gel column chromatography (using a mixture solvent of hexane and toluene as an eluent) to obtain Compound B49 (10.62 g, yield 80%) as a solid.

By the FAB-MS measurement, amass number, m/z=738 was observed as a molecular ion peak, and Compound B49 was identified.

7. Synthesis of Compound B72

(Synthesis of Intermediate IM-17)

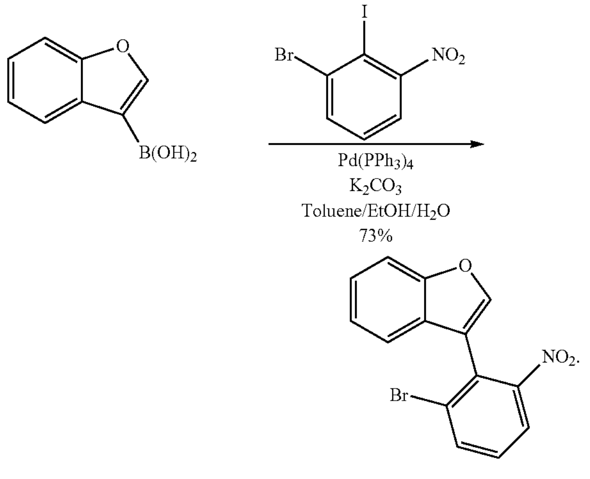

IM-17

Under an Ar atmosphere, to a 2,000 mL, three-neck flask, 30.00 g (185.2 mmol) of benzofuran-3-ylboronic acid, 66.82 g (1.1 eq, 203.8 mmol) of 1-bromo-2-iodo-3-nitrobenzene, 76.81 g (3.0 eq, 555.7 mmol) of $K_2CO_3$, 10.70 g (0.05 eq, 9.3 mmol) of $Pd(PPh_3)_4$, and 1,297 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-17 (43.02 g, yield 73%).

By the FAB-MS measurement, a mass number, m/z=318 was observed as a molecular ion peak, and Intermediate IM-17 was identified.

(Synthesis of Intermediate IM-18)

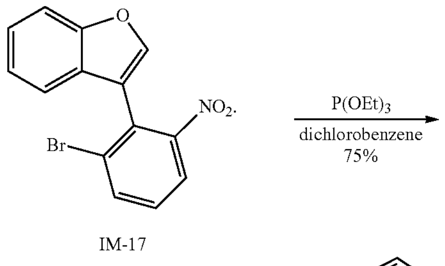

IM-17

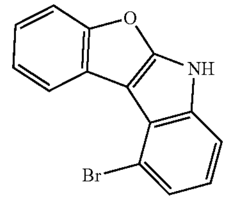

IM-18

Under an Ar atmosphere, to a 500 mL, three-neck flask, 30.00 g (94.3 mmol) of IM-18, 188 mL of o-dichlorobenzene, and 62.68 g (4 eq, 377.2 mmol) of $P(OEt)_3$ were added in order, followed by heating and stirring at about 160° C.

After air cooling to room temperature, the reaction solvent was removed by distillation. The crude product thus obtained was separated by silica gel column chromatography (using a mixture solvent of hexane and toluene as an eluent) to obtain Intermediate IM-18 (20.51 g, yield 76%).

By the FAB-MS measurement, amass number, m/z=286 was observed as a molecular ion peak, and Intermediate IM-18 was identified.

(Synthesis of Intermediate IM-19)

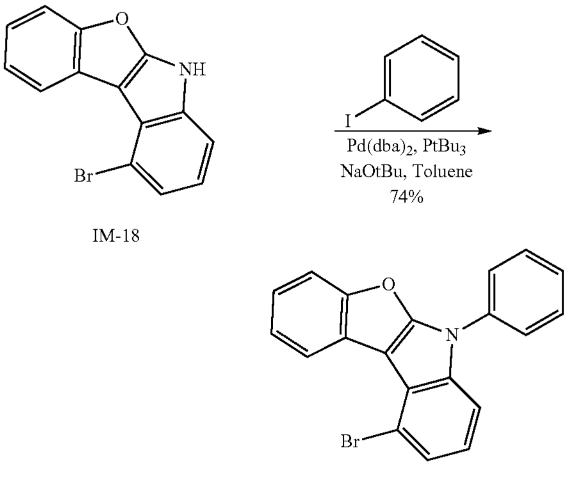

IM-18

IM-19

Under an Ar atmosphere, to a 500 mL, three-neck flask, 18.00 g (62.9 mmol) of IM-18, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-19 (16.86 g, yield 74%).

By the FAB-MS measurement, a mass number, m/z=362 was observed as a molecular ion peak, and Intermediate IM-19 was identified.

(Synthesis of Intermediate IM-20)

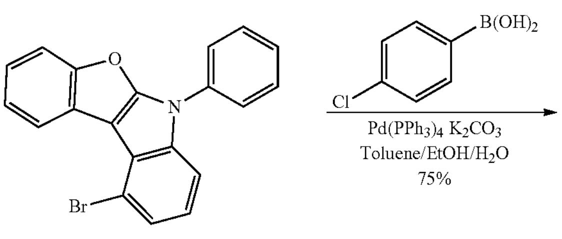

IM-19

-continued

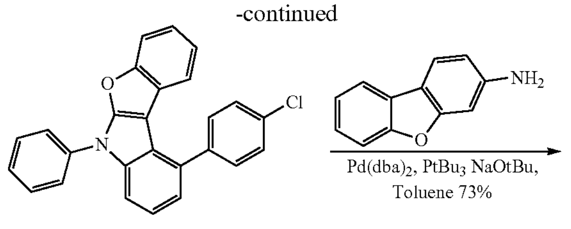

IM-48

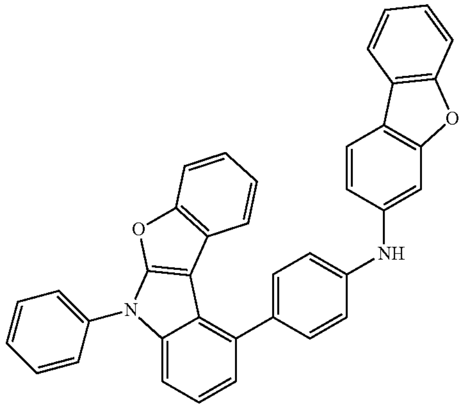

IM-20

Under an Ar atmosphere, 15.00 g (41.4 mmol) of IM-19, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-48 (12.23 g, yield 75%).

By the FAB-MS measurement, a mass number, m/z=393 was observed as a molecular ion peak, and Intermediate IM-48 was identified.

Under an Ar atmosphere, 15.00 g (38.1 mmol) of IM-48, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 3-aminodibenzofuran, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-20 (15.03 g, yield 73%).

By the FAB-MS measurement, a mass number, m/z=540 was observed as a molecular ion peak, and Intermediate IM-20 was identified.

(Synthesis of Compound B72)

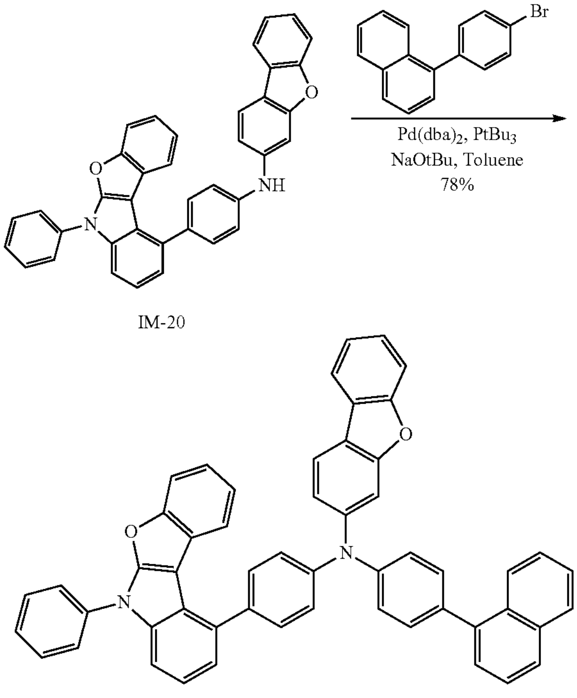

IM-20

B72

Under an Ar atmosphere, to a 200 mL, three-neck flask, 10.00 g (18.5 mmol) of IM-20, 0.32 g (0.03 eq, 0.6 mmol) of $Pd(dba)_2$, 3.56 g (2.0 eq, 37.0 mmol) of NaOtBu, 92 mL of toluene, 5.76 g (1.1 eq, 20.3 mmol) of 1-(4-bromopheny) naphthalene, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound B72 (10.72 g, yield 78%) as a solid.

By the FAB-MS measurement, a mass number, m/z=742 was observed as a molecular ion peak, and Compound B72 was identified.

8. Synthesis of Compound B105

(Synthesis of Intermediate IM-21)

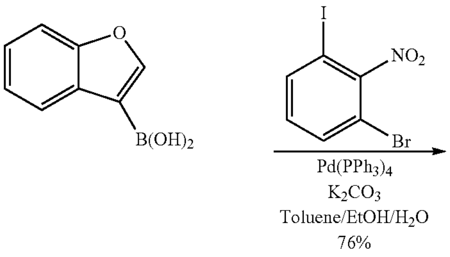

-continued

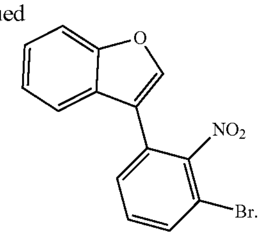

IM-21

Under an Ar atmosphere, to a 2,000 mL, three-neck flask, 30.00 g (185.2 mmol) of benzofuran-3-ylboronic acid, 66.82 g (1.1 eq, 203.8 mmol) of 1-bromo-3-iodo-2-nitrobenzene, 76.81 g (3.0 eq, 555.7 mmol) of $K_2CO_3$, 10.70 g (0.05 eq, 9.3 mmol) of $Pd(PPh_3)_4$, and 1,297 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-21 (44.79 g, yield 76%).

By the FAB-MS measurement, a mass number, m/z=318 was observed as a molecular ion peak, and Intermediate IM-21 was identified.

(Synthesis of Intermediate IM-22)

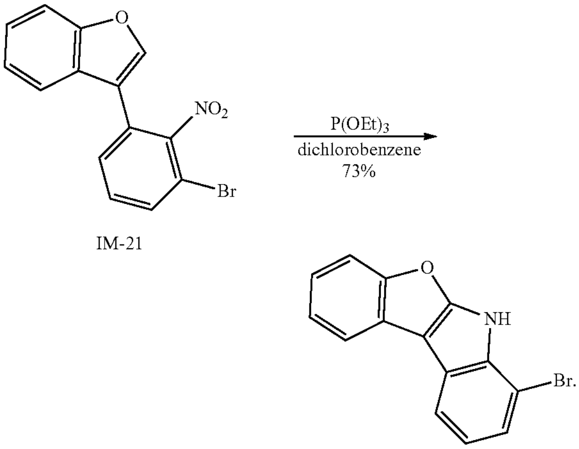

IM-21

IM-22

Under an Ar atmosphere, to a 500 mL, three-neck flask, 30.00 g (94.3 mmol) of IM-21, 188 mL of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-22 (19.70 g, yield 73%).

By the FAB-MS measurement, amass number, m/z=286 was observed as a molecular ion peak, and Intermediate IM-22 was identified.

(Synthesis of Intermediate IM-23)

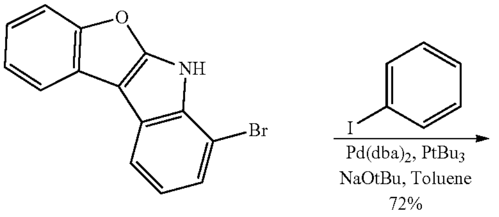

IM-22

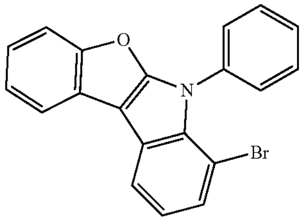

IM-23

Under an Ar atmosphere, to a 500 mL, three-neck flask, 18.00 g (62.9 mmol) of IM-22, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-23 (16.41 g, yield 72%).

By the FAB-MS measurement, a mass number, m/z=362 was observed as a molecular ion peak, and Intermediate IM-23 was identified.

(Synthesis of Intermediate IM-24)

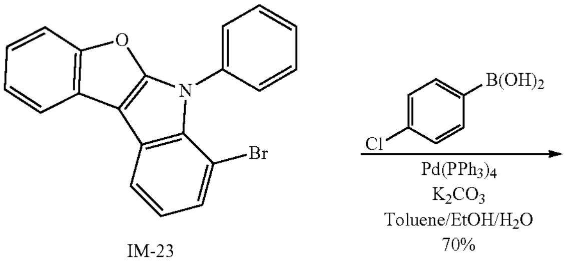

IM-23

-continued

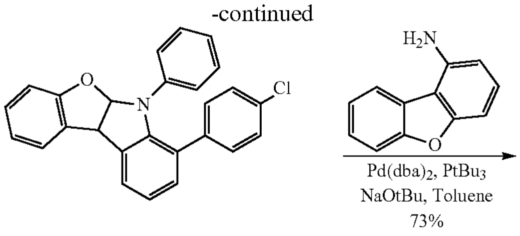

IM-49

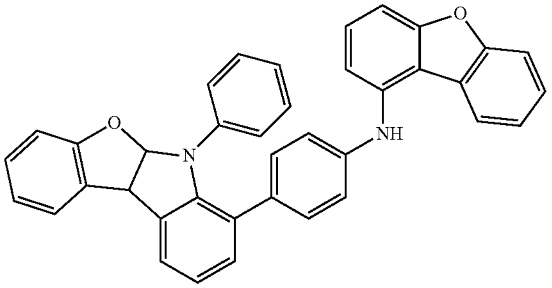

IM-24

Under an Ar atmosphere, 15.00 g (41.4 mmol) of IM-23, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-49 (11.49 g, yield 70%).

By the FAB-MS measurement, a mass number, m/z=393 was observed as a molecular ion peak, and Intermediate IM-49 was identified.

Under an Ar atmosphere, 15.00 g (38.1 mmol) of IM-49, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 1-aminodibenzofuran and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-24 (15.03 g, yield 73%).

By the FAB-MS measurement, a mass number, m/z=540 was observed as a molecular ion peak, and Intermediate IM-24 was identified.

(Synthesis of Compound B105)

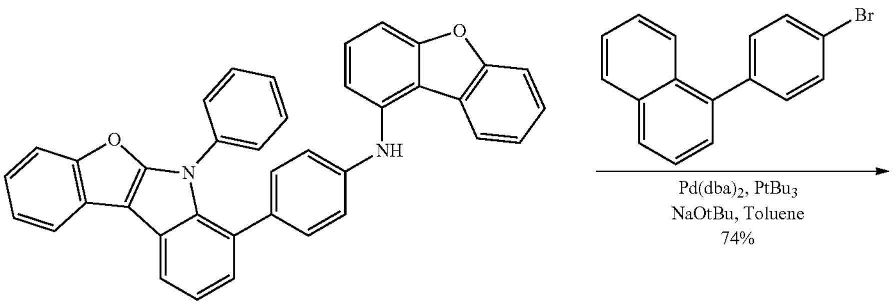

IM-24

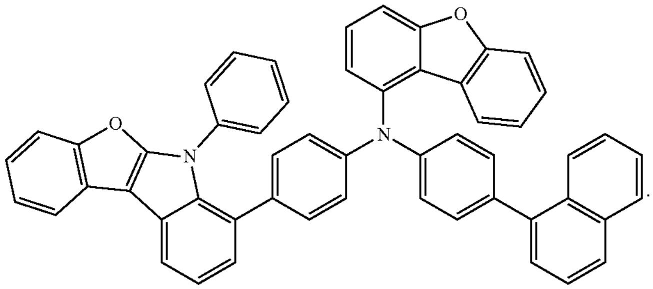

B105

Under an Ar atmosphere, to a 200 mL, three-neck flask, 10.00 g (18.5 mmol) of IM-24, 0.32 g (0.03 eq, 0.6 mmol) of $Pd(dba)_2$, 3.56 g (2.0 eq, 37.0 mmol) of NaOtBu, 92 mL of toluene, 5.76 g (1.1 eq, 20.3 mmol) of 1-(4-bromophenyl) naphthalene, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound B105 (10.17 g, yield 74%) as a solid.

By the FAB-MS measurement, a mass number, m/z=742 was observed as a molecular ion peak, and Compound B105 was identified.

9. Synthesis of Compound C4

(Synthesis of Intermediate IM-25)

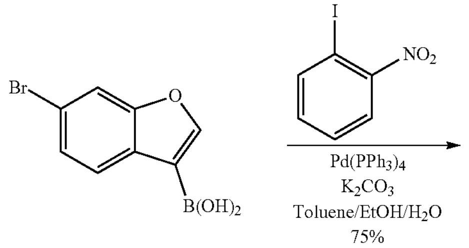

-continued

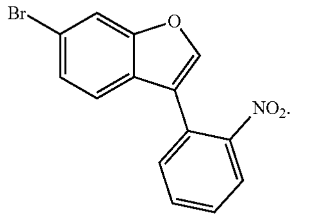

IM-25

Under an Ar atmosphere, to a 2,000 mL, three-neck flask, 35.00 g (145.3 mmol) of (6-bromobenzofuran-3-yl)boronic acid, 39.80 g (1.1 eq, 159.9 mmol) of 1-iodo-2-nitrobenzene, 60.25 g (3.0 eq, 436.0 mmol) of $K_2CO_3$, 8.40 g (0.05 eq, 7.3 mmol) of $Pd(PPh_3)_4$, and 1,017 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-25 (34.67 g, yield 75%).

By the FAB-MS measurement, a mass number, m/z=318 was observed as a molecular ion peak, and Intermediate IM-25 was identified.

(Synthesis of Intermediate IM-26)

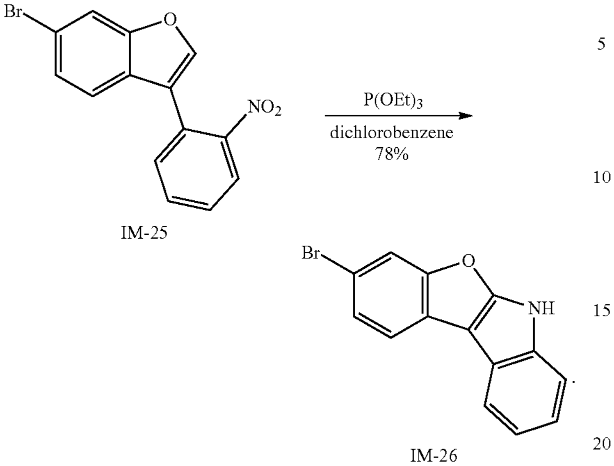

IM-25

IM-26

Under an Ar atmosphere, to a 500 mL, three-neck flask, 30.00 g (94.3 mmol) of IM-25, 188 mL of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-26 (21.05 g, yield 78%).

By the FAB-MS measurement, a mass number, m/z=286 was observed as a molecular ion peak, and Intermediate IM-26 was identified.

(Synthesis of Intermediate IM-27)

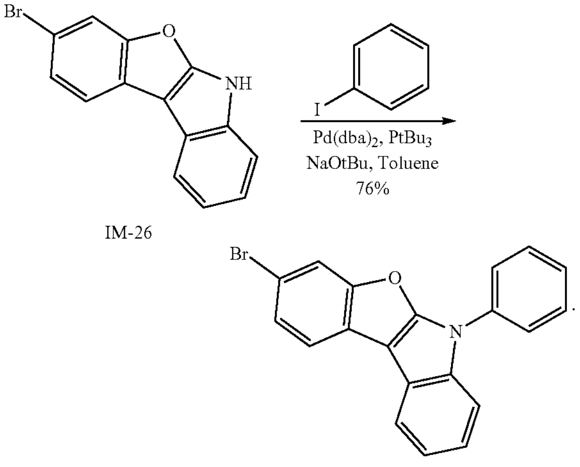

IM-26

IM-27

Under an Ar atmosphere, to a 500 mL, three-neck flask, 18.00 g (62.9 mmol) of IM-26, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-27 (17.32 g, yield 76%).

By the FAB-MS measurement, a mass number, m/z=362 was observed as a molecular ion peak, and Intermediate IM-27 was identified.

(Synthesis of Intermediate IM-28)

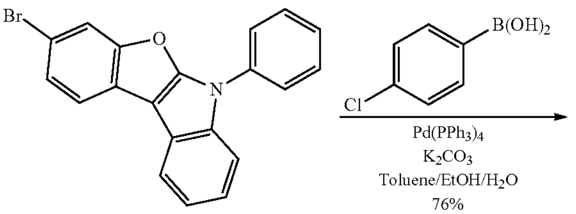

IM-27

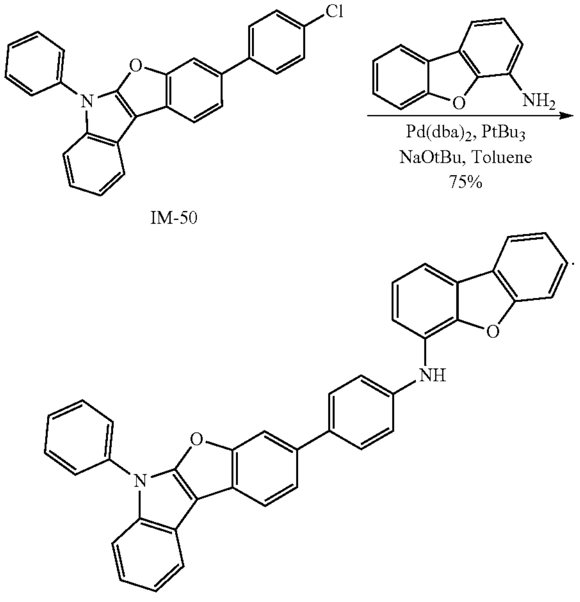

IM-50

IM-28

Under an Ar atmosphere, 15.00 g (41.4 mmol) of IM-27, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-50 (12.40 g, yield 76%). By the FAB-MS measurement, a mass number, m/z=393 was observed as a molecular ion peak, and Intermediate IM-50 was identified.

Under an Ar atmosphere, 15.00 g (38.1 mmol) of IM-50, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 4-aminodibenzofuran, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-28 (15.44 g, yield 75%).

By the FAB-MS measurement, a mass number, m/z=540 was observed as a molecular ion peak, and Intermediate IM-28 was identified.

(Synthesis of Compound C4)

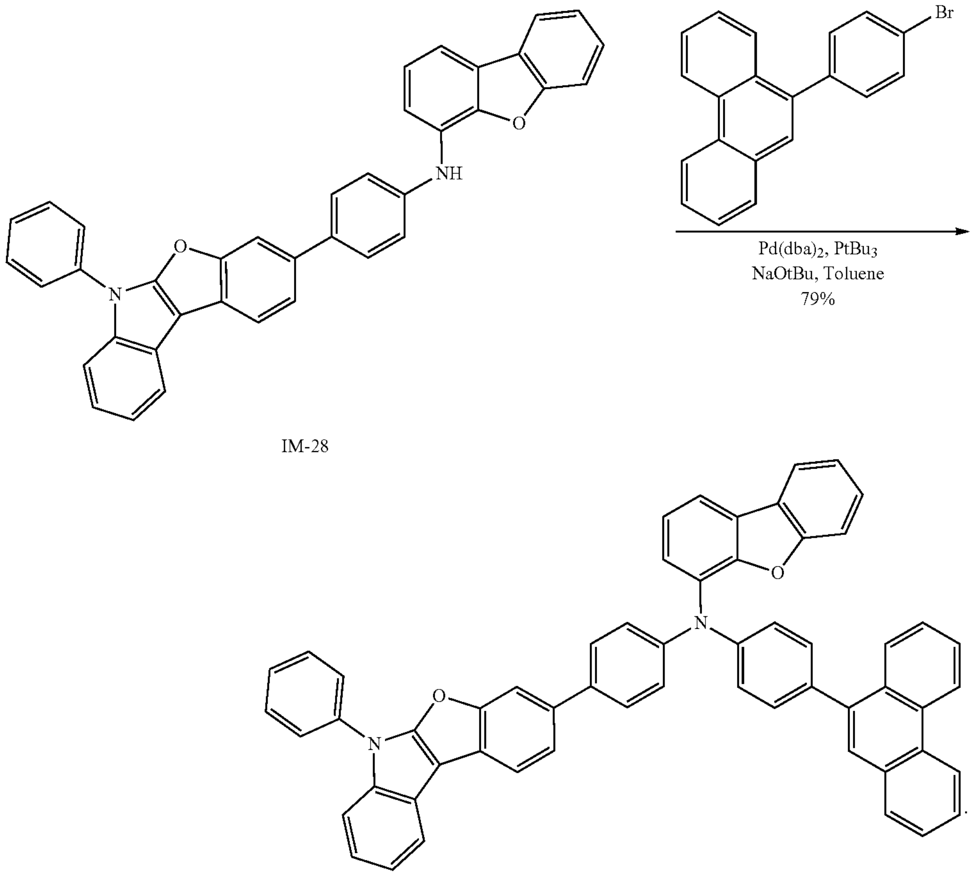

IM-28

C4

Under an Ar atmosphere, to a 200 mL, three-neck flask, 10.00 g (18.5 mmol) of IM-28, 0.32 g (0.03 eq, 0.6 mmol) of $Pd(dba)_2$, 3.56 g (2.0 eq, 37.0 mmol) of NaOtBu, 92 mL of toluene, 6.78 g (1.1 eq, 20.3 mmol) of 9-(4-bromophenyl) phenanthrene, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C4 (11.59 g, yield 79%) as a solid.

By the FAB-MS measurement, a mass number, m/z=792 was observed as a molecular ion peak, and Compound C4 was identified.

10. Synthesis of Compound C11

(Synthesis of Compound C11)

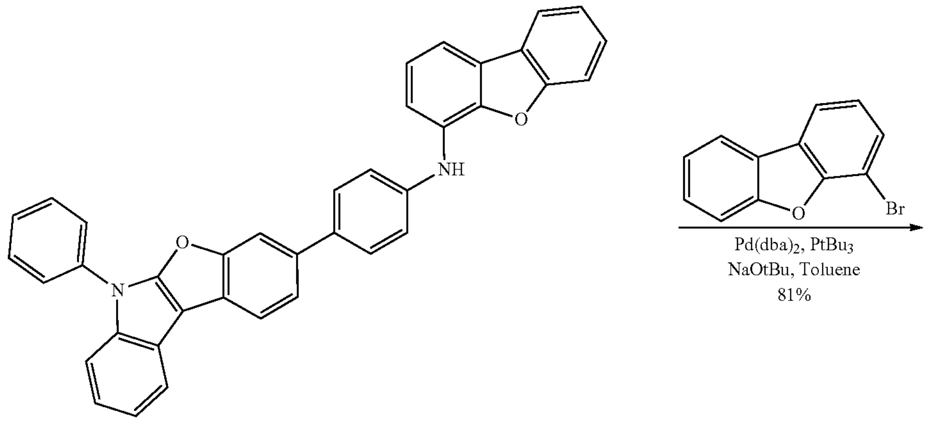

IM-28

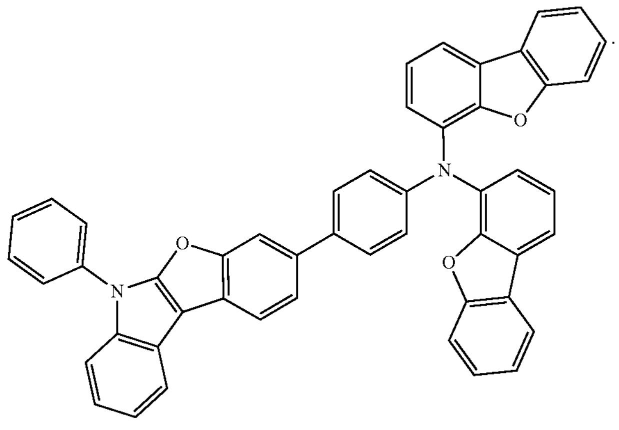

C11

Under an Ar atmosphere, to a 200 mL, three-neck flask, 10.00 g (18.5 mmol) of IM-28, 0.32 g (0.03 eq, 0.6 mmol) of $Pd(dba)_2$, 3.56 g (2.0 eq, 37.0 mmol) of NaOtBu, 92 mL of toluene, 5.03 g (1.1 eq, 20.3 mmol) of 4-bromodibenzofuran, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C11 (10.59 g, yield 81%) as a solid.

By the FAB-MS measurement, a mass number, m/z=706 was observed as a molecular ion peak, and Compound C11 was identified.

11. Synthesis of Compound C44

(Synthesis of Intermediate IM-29)

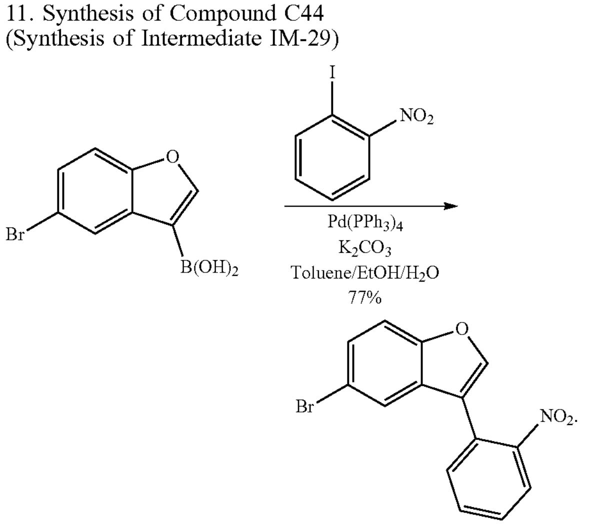

IM-29

Under an Ar atmosphere, to a 2,000 mL, three-neck flask, 35.00 g (145.3 mmol) of (5-bromobenzofuran-3-yl)boronic acid, 39.80 g (1.1 eq, 159.9 mmol) of 1-iodo-2-nitrobenzene, 60.25 g (3.0 eq, 436.0 mmol) of $K_2CO_3$, 8.40 g (0.05 eq, 7.3 mmol) of $Pd(PPh_3)_4$, and 1,017 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-29 (35.60 g, yield 77%).

By the FAB-MS measurement, a mass number, m/z=318 was observed as a molecular ion peak, and Intermediate IM-29 was identified.

(Synthesis of Intermediate IM-30)

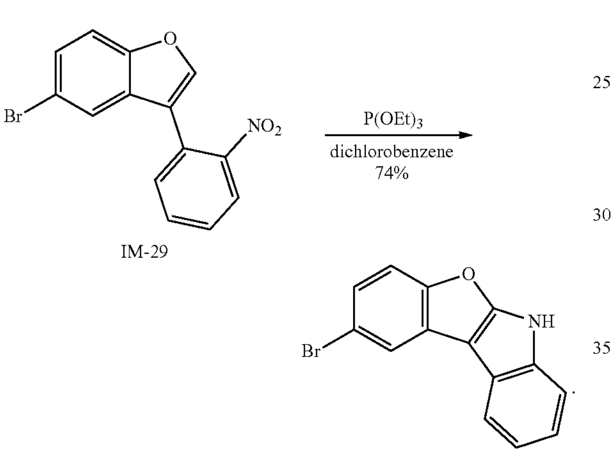

IM-29

IM-30

Under an Ar atmosphere, to a 500 mL, three-neck flask, 30.00 g (94.3 mmol) of IM-29, 188 mL of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-30 (19.97 g, yield 74%).

By the FAB-MS measurement, a mass number, m/z=286 was observed as a molecular ion peak, and Intermediate IM-30 was identified.

(Synthesis of Intermediate IM-31)

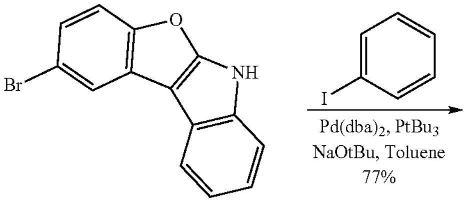

IM-30

-continued

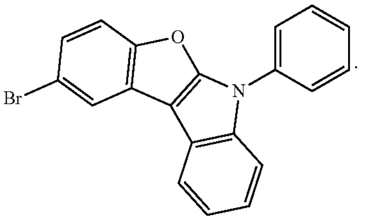

IM-31

Under an Ar atmosphere, to a 500 mL, three-neck flask, 18.00 g (62.9 mmol) of IM-30, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-31 (17.55 g, yield 77%).

By the FAB-MS measurement, a mass number, m/z=362 was observed as a molecular ion peak, and Intermediate IM-31 was identified.

(Synthesis of Intermediate IM-32)

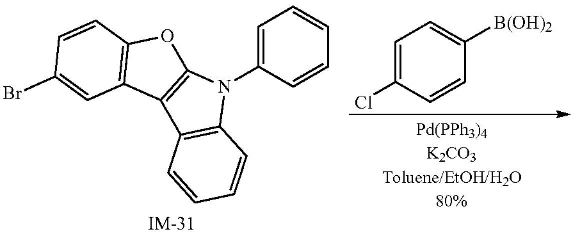

IM-31

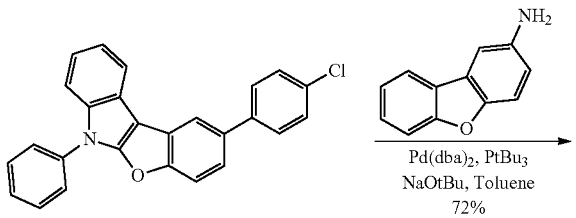

IM-51

-continued

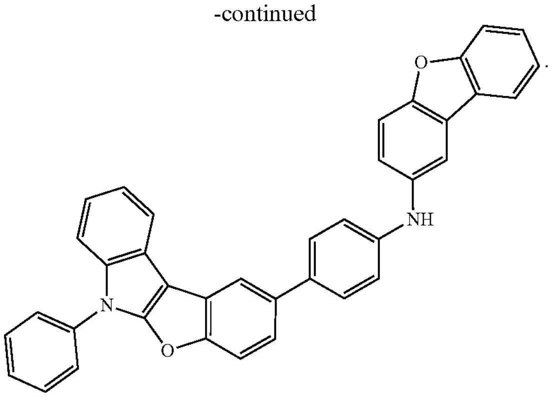

IM-32

Under an Ar atmosphere, 15.00 g (41.4 mmol) of IM-31, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-51 (13.05 g, yield 80%).

By the FAB-MS measurement, a mass number, m/z=393 was observed as a molecular ion peak, and Intermediate IM-51 was identified.

Under an Ar atmosphere, 15.00 g (38.1 mmol) of IM-51, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 2-aminodibenzofuran, and 0.77 g (0.1 eq, 3.8 mmol) of $tBu_3P$ were added in order to a 500 ml, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-32 (14.82 g, yield 72%).

By the FAB-MS measurement, a mass number, m/z=540 was observed as a molecular ion peak, and Intermediate IM-32 was identified.

(Synthesis of Compound C44)

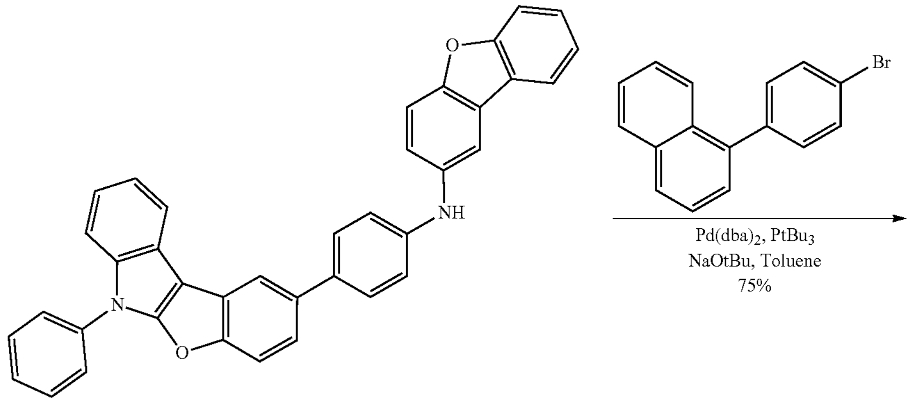

IM-32

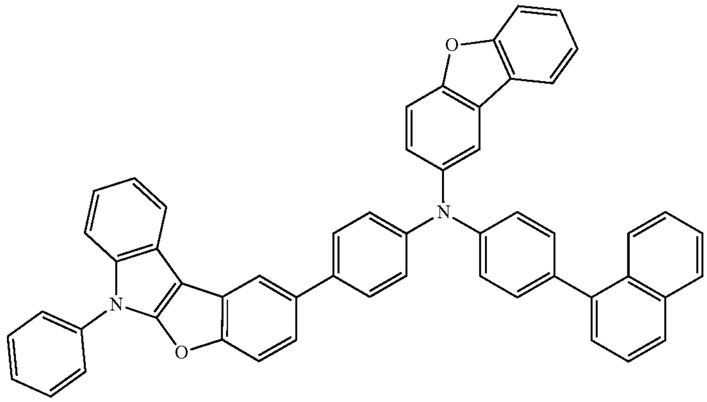

C44

Under an Ar atmosphere, to a 200 mL, three-neck flask, 10.00 g (18.5 mmol) of IM-32, 0.32 g (0.03 eq, 0.6 mmol) of $Pd(dba)_2$, 3.56 g (2.0 eq, 37.0 mmol) of NaOtBu, 92 mL of toluene, 5.76 g (1.1 eq, 20.3 mmol) of 1-(4-bromophenyl) naphthalene, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C44 (10.31 g, yield 75%) as a solid.

By the FAB-MS measurement, a mass number, m/z=742 was observed as a molecular ion peak, and Compound C44 was identified.

12. Synthesis of Compound C46

(Synthesis of Intermediate IM-33)

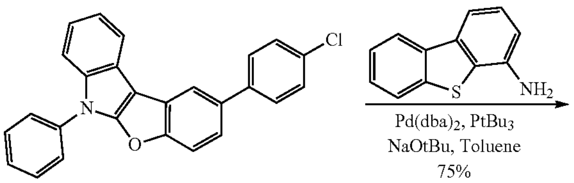

IM-51

-continued

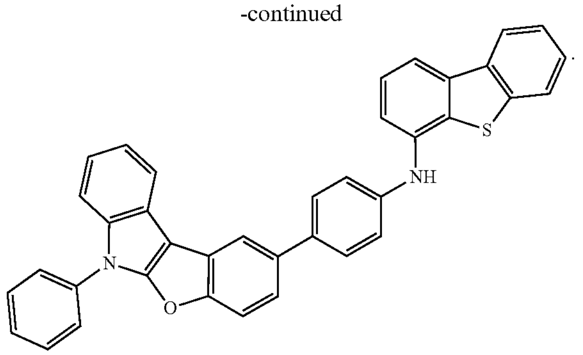

IM-33

Under an Ar atmosphere, 15.00 g (38.1 mmol) of IM-51, 0.66 g (0.03 eq, 1.1 mmol) of $Pd(dba)_2$, 3.66 g (1.0 eq, 38.0 mmol) of NaOtBu, 190 mL of toluene, 8.35 g (1.1 eq, 41.9 mmol) of 4-aminodibenzothiophene, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-33 (15.90 g, yield 75%).

By the FAB-MS measurement, a mass number, m/z=556 was observed as a molecular ion peak, and Intermediate IM-33 was identified.

(Synthesis of Compound C46)

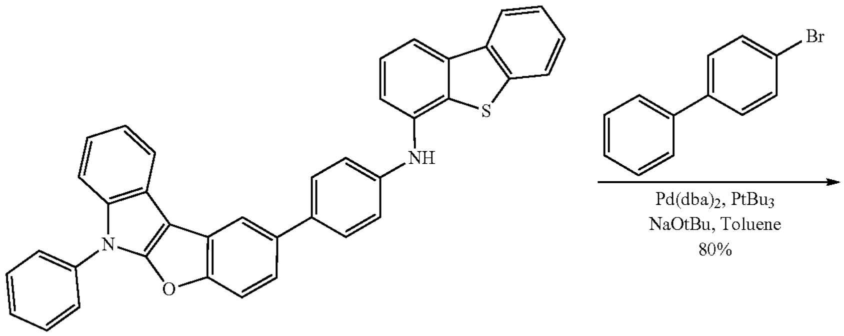

IM-33

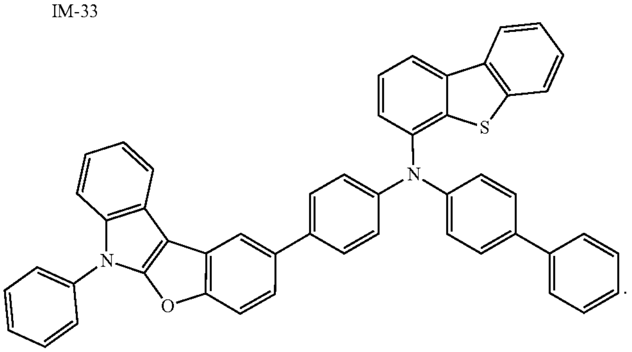

C46

Under an Ar atmosphere, to a 200 mL, three-neck flask, 10.00 g (18.0 mmol) of IM-33, 0.31 g (0.03 eq, 0.5 mmol) of $Pd(dba)_2$, 3.45 g (2.0 eq, 35.9 mmol) of NaOtBu, 90 mL of toluene, 4.61 g (1.1 eq, 19.8 mmol) of 4-bromobiphenyl, and 0.36 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C46 (10.19 g, yield 80%) as a solid.

By the FAB-MS measurement, a mass number, m/z=708 was observed as a molecular ion peak, and Compound C46 was identified.

13. Synthesis of Compound C65

(Synthesis of Intermediate IM-34)

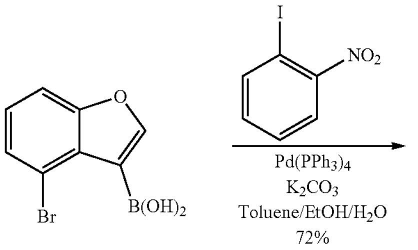

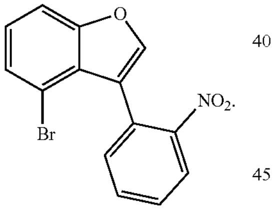

IM-34

Under an Ar atmosphere, to a 2,000 mL, three-neck flask, 35.00 g (145.3 mmol) of (4-bromobenzofuran-3-yl)boronic acid, 39.80 g (1.1 eq, 159.9 mmol) of 1-iodo-2-nitrobenzene, 60.25 g (3.0 eq, 436.0 mmol) of $K_2CO_3$, 8.40 g (0.05 eq, 7.3 mmol) of $Pd(PPh_3)_4$, and 1,017 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-34 (33.29 g, yield 72%).

By the FAB-MS measurement, a mass number, m/z=318 was observed as a molecular ion peak, and Intermediate IM-34 was identified.

(Synthesis of Intermediate IM-35)

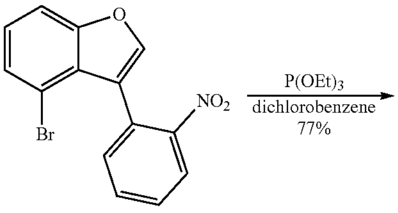

IM-34

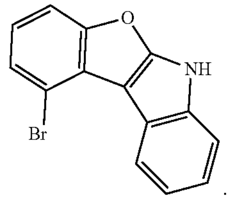

IM-35

Under an Ar atmosphere, to a 500 mL, three-neck flask, 30.00 g (94.3 mmol) of IM-34, 188 mL of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-35 (20.78 g, yield 77%).

By the FAB-MS measurement, a mass number, m/z=286 was observed as a molecular ion peak, and Intermediate IM-35 was identified.

(Synthesis of Intermediate IM-36)

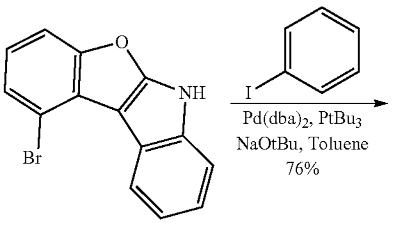

IM-35

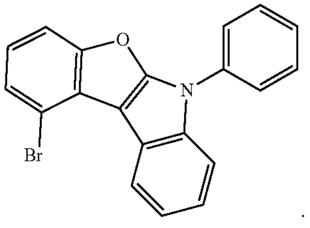

IM-36

Under an Ar atmosphere, to a 500 mL, three-neck flask, 18.00 g (62.9 mmol) of IM-35, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-36 (17.32 g, yield 76%).

By the FAB-MS measurement, a mass number, m/z=362 was observed as a molecular ion peak, and Intermediate IM-36 was identified.

(Synthesis of Intermediate IM-37)

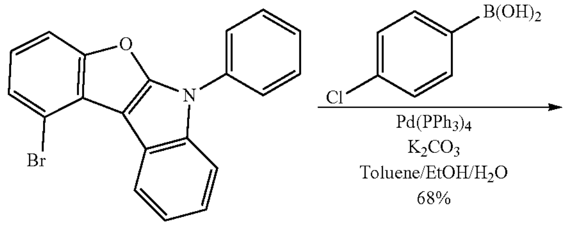

IM-36

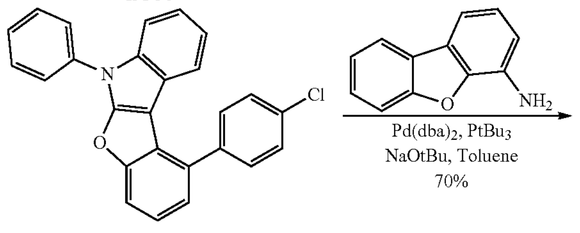

IM-52

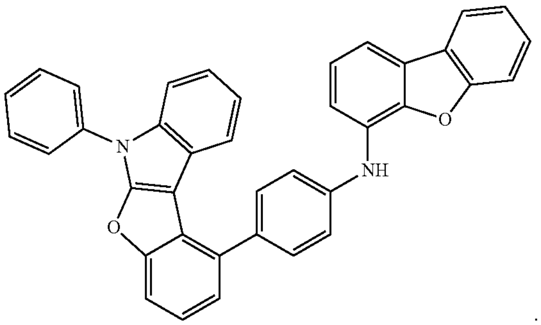

IM-37

Under an Ar atmosphere, 15.00 g (41.4 mmol) of IM-36, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-52 (11.09 g, yield 68%).

By the FAB-MS measurement, a mass number, m/z=393 was observed as a molecular ion peak, and Intermediate IM-52 was identified.

Under an Ar atmosphere, 15.00 g (38.1 mmol) of IM-52, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 4-aminodibenzofuran, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-37 (14.41 g, yield 70%).

By the FAB-MS measurement, a mass number, m/z=540 was observed as a molecular ion peak, and Intermediate IM-37 was identified.

(Synthesis of Compound C65)

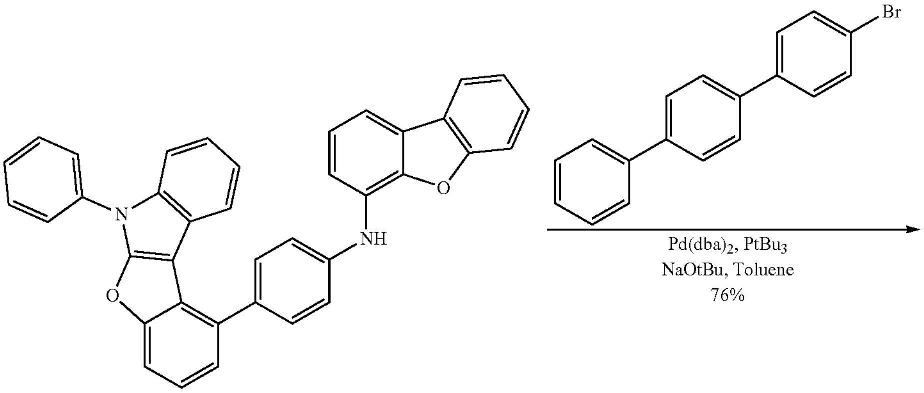

IM-37

-continued

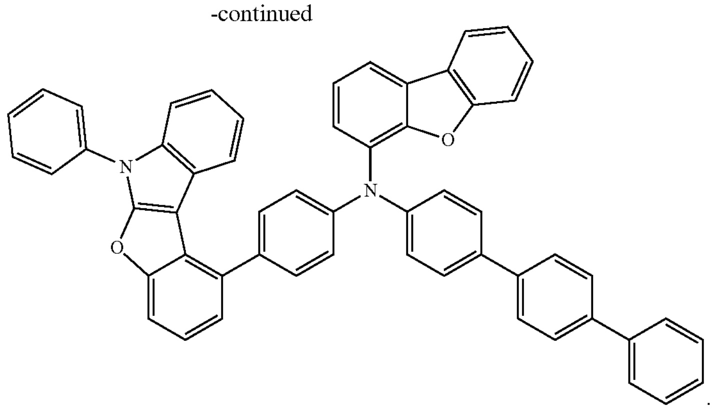

C65

Under an Ar atmosphere, to a 200 mL, three-neck flask, 10.00 g (18.5 mmol) of IM-37, 0.32 g (0.03 eq, 0.6 mmol) of $Pd(dba)_2$, 3.56 g (2.0 eq, 37.0 mmol) of NaOtBu, 92 mL of toluene, 6.29 g (1.1 eq, 20.3 mmol) of 4-bromo-terphenyl, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C65 (10.81 g, yield 76%) as a solid.

By the FAB-MS measurement, a mass number, m/z=768 was observed as a molecular ion peak, and Compound C65 was identified.

14. Synthesis of Compound C99

(Synthesis of Intermediate IM-38)

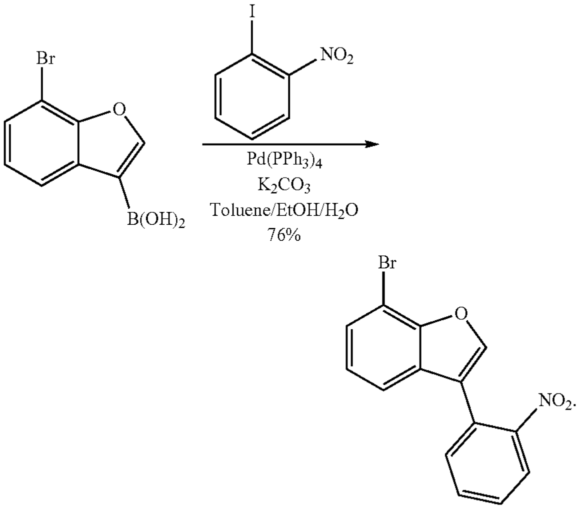

IM-38

Under an Ar atmosphere, to a 2,000 mL, three-neck flask, 35.00 g (145.3 mmol) of (7-bromobenzofuran-3-yl)boronic acid, 39.80 g (1.1 eq, 159.9 mmol) of 1-iodo-2-nitrobenzene, 60.25 g (3.0 eq, 436.0 mmol) of $K_2CO_3$, 8.40 g (0.05 eq, 7.3 mmol) of $Pd(PPh_3)_4$, and 1,017 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-38 (35.13 g, yield 76%).

By the FAB-MS measurement, a mass number, m/z=318 was observed as a molecular ion peak, and Intermediate IM-38 was identified.

(Synthesis of Intermediate IM-39)

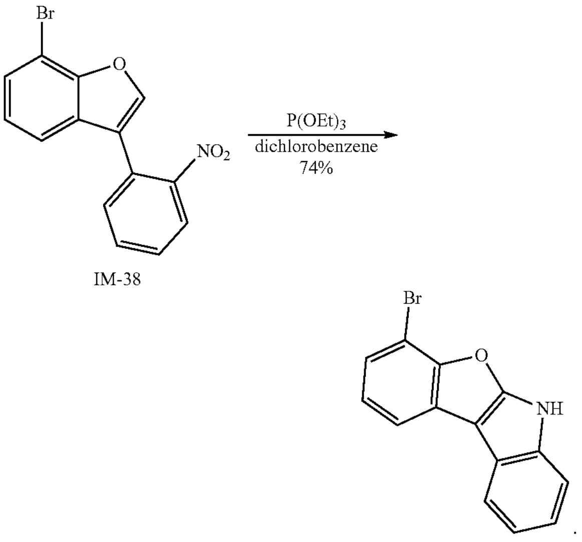

IM-38

IM-39

Under an Ar atmosphere, to a 500 mL, three-neck flask, 30.00 g (94.3 mmol) of IM-38, 188 mL of o-dichlorobenzene, and 62.68 g (4 eq, 377.2 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-39 (19.97 g, yield 74%).

By the FAB-MS measurement, a mass number, m/z=286 was observed as a molecular ion peak, and Intermediate IM-39 was identified.

(Synthesis of Intermediate IM-40)

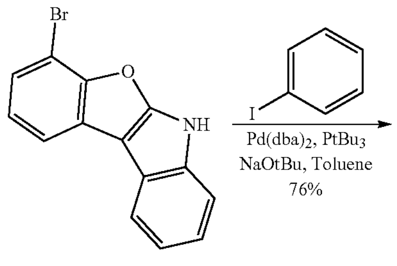

IM-39

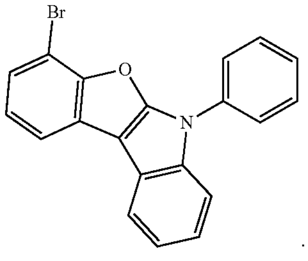

IM-40

Under an Ar atmosphere, to a 500 mL, three-neck flask, 18.00 g (62.9 mmol) of IM-39, 1.09 g (0.03 eq, 1.9 mmol) of $Pd(dba)_2$, 6.05 g (1.0 eq, 62.9 mmol) of NaOtBu, 314 mL of toluene, 14.12 g (1.1 eq, 69.2 mmol) of iodobenzene, and 1.27 g (0.1 eq, 6.3 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-40 (17.32 g, yield 76%).

By the FAB-MS measurement, a mass number, m/z=362 was observed as a molecular ion peak, and Intermediate IM-40 was identified.

(Synthesis of Intermediate IM-41)

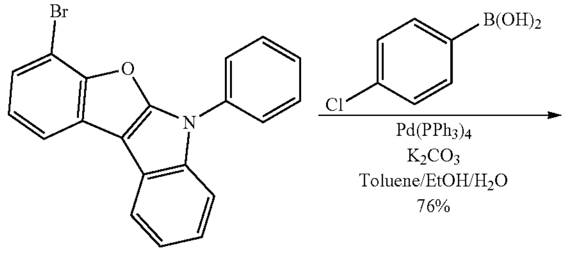

IM-40

-continued

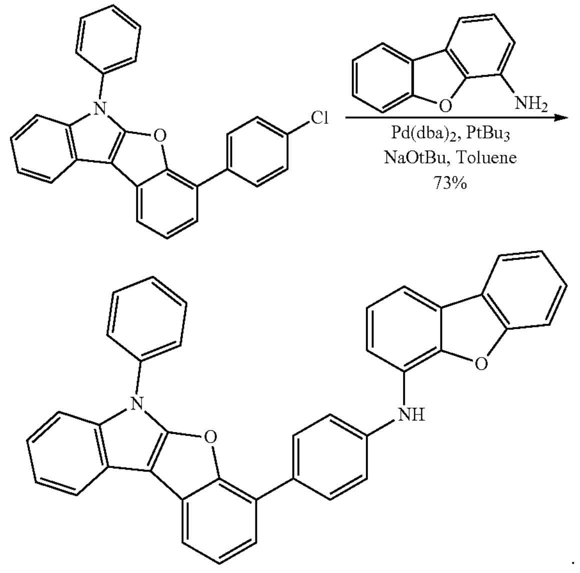

IM-41

Under an Ar atmosphere, 15.00 g (41.4 mmol) of IM-40, 7.12 g (1.1 eq, 45.6 mmol) of 4-chlorophenylboronic acid, 17.17 g (3.0 eq, 124.2 mmol) of $K_2CO_3$, 2.39 g (0.05 eq, 2.1 mmol) of $Pd(PPh_3)_4$, and 290 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-53 (12.40 g, yield 76%).

By the FAB-MS measurement, a mass number, m/z=393 was observed as a molecular ion peak, and Intermediate IM-53 was identified.

Under an Ar atmosphere, 15.00 g (38.1 mmol) of IM-53, 0.66 g (0.03 eq, 1.1 mmol) of $Pd(dba)_2$, 3.66 g (1.0 eq, 38.0 mmol) of NaOtBu, 190 mL of toluene, 7.68 g (1.1 eq, 41.9 mmol) of 4-aminodibenzofuran, and 0.77 g (0.1 eq, 3.8 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-41 (15.03 g, yield 73%).

By the FAB-MS measurement, a mass number, m/z=540 was observed as a molecular ion peak, and Intermediate IM-41 was identified.

(Synthesis of Compound C99)

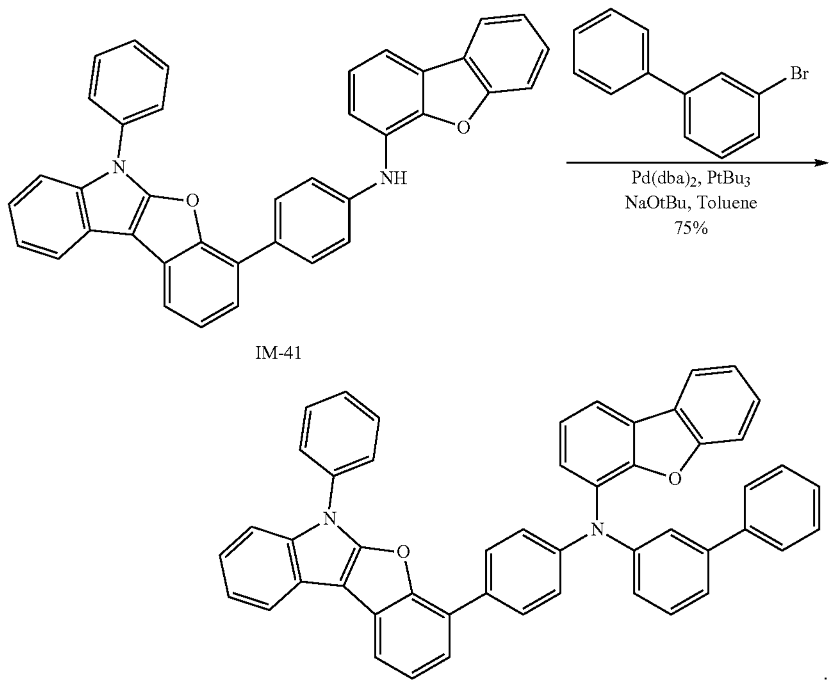

IM-41

C99

Under an Ar atmosphere, to a 200 mL, three-neck flask, 10.00 g (18.5 mmol) of IM-41, 0.32 g (0.03 eq, 0.6 mmol) of $Pd(dba)_2$, 3.56 g (2.0 eq, 37.0 mmol) of NaOtBu, 92 mL of toluene, 4.74 g (1.1 eq, 20.3 mmol) of 3-bromo-biphenyl, and 0.37 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C99 (9.61 g, yield 75%) as a solid.

By the FAB-MS measurement, a mass number, m/z=692 was observed as a molecular ion peak, and Compound C99 was identified.

15. Synthesis of Compound C119

(Synthesis of Intermediate IM-42)

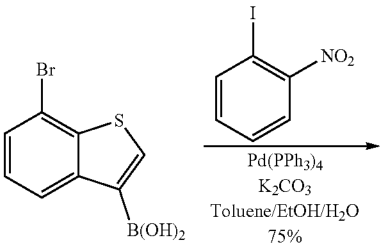

-continued

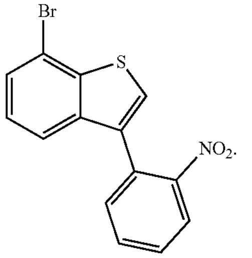

IM-42

Under an Ar atmosphere, to a 2,000 mL, three-neck flask, 35.00 g (136.2 mmol) of (7-bromobenzofuran-3-yl)boronic acid, 37.32 g (1.1 eq, 149.9 mmol) of 1-iodo-2-nitrobenzene, 56.48 g (3.0 eq, 408.7 mmol) of $K_2CO_3$, 7.87 g (0.05 eq, 6.8 mmol) of $Pd(PPh_3)_4$, and 954 mL of a mixture solution of toluene/EtOH/$H_2O$ (4/2/1) were added in order, followed by heating and stirring at about 80° C. After air cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-42 (34.15 g, yield 75%).

By the FAB-MS measurement, a mass number, m/z=334 was observed as a molecular ion peak, and Intermediate IM-42 was identified.

(Synthesis of Intermediate IM-43)

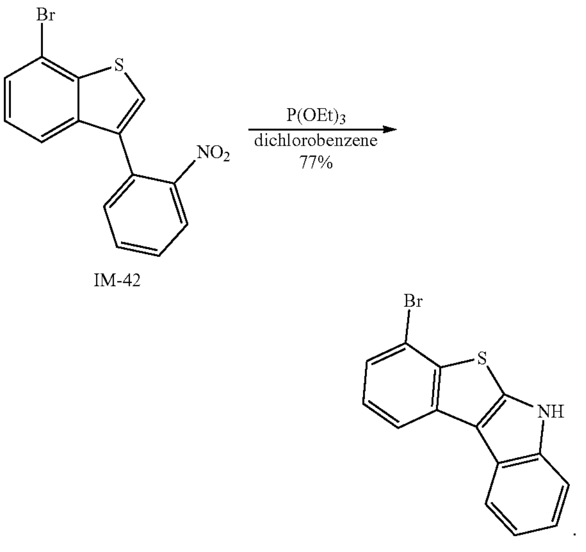

IM-42

IM-43

Under an Ar atmosphere, to a 500 mL, three-neck flask, 30.00 g (89.8 mmol) of IM-42, 180 mL of o-dichlorobenzene, and 59.66 g (4 eq, 359.1 mmol) of $P(OEt)_3$ were added in order, followed by heating and stirring at about 160° C. After air cooling to room temperature, the reaction solvent was removed by distillation. The crude product thus obtained was separated by silica gel column chromatography (using a mixture solvent of hexane and toluene as an eluent) to obtain Intermediate IM-43 (20.89 g, yield 77%).

By the FAB-MS measurement, a mass number, m/z=302 was observed as a molecular ion peak, and Intermediate IM-43 was identified.

(Synthesis of Intermediate IM-44)

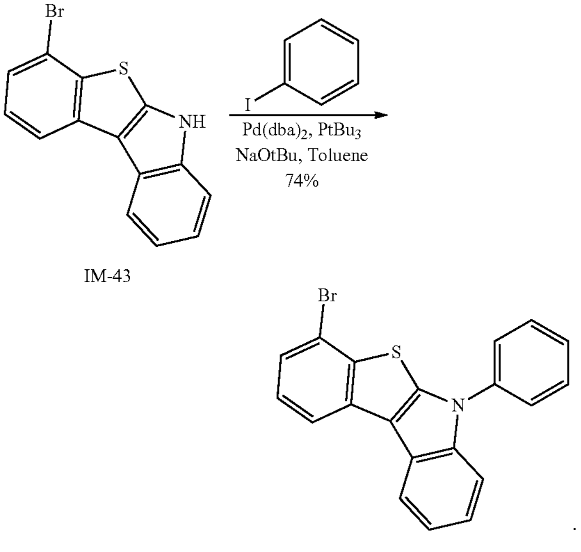

IM-43

IM-44

Under an Ar atmosphere, to a 500 mL, three-neck flask, 18.00 g (59.6 mmol) of IM-43, 1.03 g (0.03 eq, 1.8 mmol) of $Pd(dba)_2$, 5.72 g (1.0 eq, 59.6 mmol) of NaOtBu, 298 mL of toluene, 13.37 g (1.1 eq, 65.5 mmol) of iodobenzene, and 1.21 g (0.1 eq, 6.0 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-44 (16.67 g, yield 74%).

By the FAB-MS measurement, a mass number, m/z=378 was observed as a molecular ion peak, and Intermediate IM-44 was identified.

(Synthesis of Intermediate IM-45)

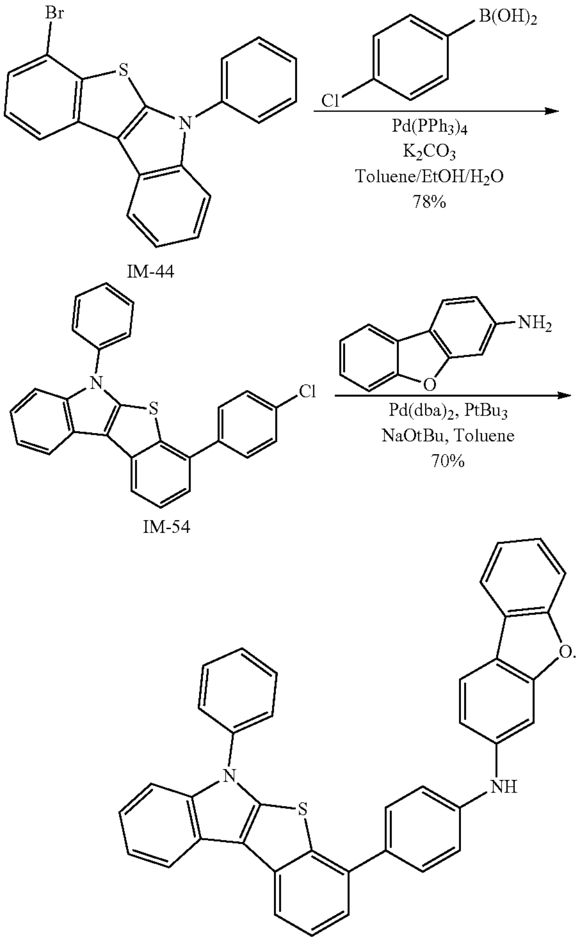

IM-44

IM-54

IM-45

Under an Ar atmosphere, 15.00 g (39.7 mmol) of IM-44, 6.82 g (1.1 eq, 43.6 mmol) of 4-chlorophenylboronic acid, 16.44 g (3.0 eq, 119.0 mmol) of $K_2CO_3$, 2.29 g (0.05 eq, 2.0 mmol) of $Pd(PPh_3)_4$, and 278 mL of a mixture solution of toluene/EtOH/$H_2O$ (4/2/1) were added in order to a 500 mL, three-neck flask, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-54 (12.68 g, yield 78%).

By the FAB-MS measurement, a mass number, m/z=409 was observed as a molecular ion peak, and Intermediate IM-54 was identified.

Under an Ar atmosphere, 15.00 g (36.6 mmol) of IM-54, 0.63 g (0.03 eq, 1.1 mmol) of $Pd(dba)_2$, 3.52 g (1.0 eq, 36.6 mmol) of NaOtBu, 183 mL of toluene, 7.37 g (1.1 eq, 40.3 mmol) of 3-aminodibenzofuran, and 0.74 g (0.1 eq, 3.7 mmol) of $tBu_3P$ were added in order to a 500 mL, three-neck flask, followed by heating, refluxing and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM-45 (14.26 g, yield 70%).

By the FAB-MS measurement, a mass number, m/z=556 was observed as a molecular ion peak, and Intermediate IM-45 was identified.

(Synthesis of Compound C119)

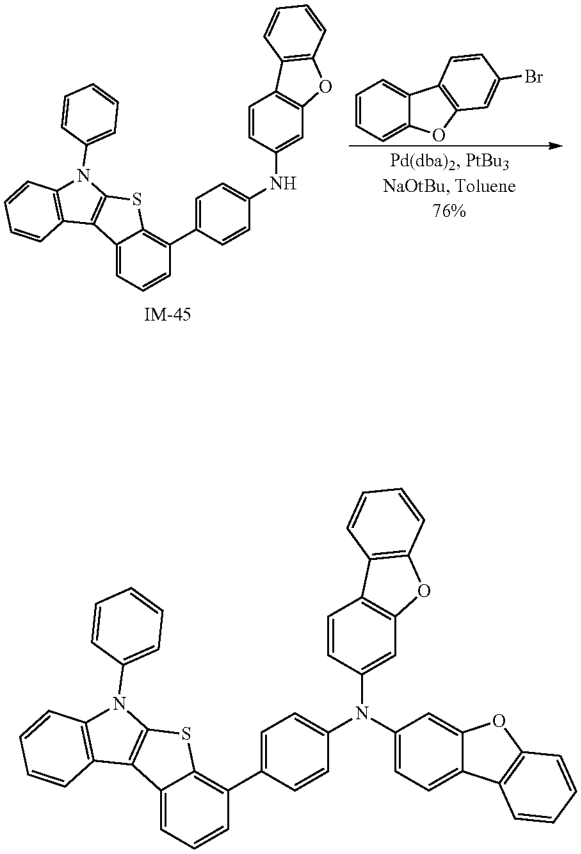

IM-45

C119

Under an Ar atmosphere, to a 200 mL, three-neck flask, 10.00 g (18.0 mmol) of IM-45, 0.31 g (0.03 eq, 0.5 mmol) of $Pd(dba)_2$, 3.45 g (2.0 eq, 35.9 mmol) of NaOtBu, 90 mL of toluene, 4.88 g (1.1 eq, 19.8 mmol) of 3-bromodibenzofuran, and 0.36 g (0.1 eq, 1.8 mmol) of $tBu_3P$ were added in order, followed by heating, refluxing, and stirring. After air cooling to room temperature, water was added to the reaction solution, and an organic layer was separately taken. Toluene was added to an aqueous layer, and the organic layers were additionally extracted. The organic layers were collected, washed with a saline solution, and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Compound C119 (9.87 g, yield 76%) as a solid.

By the FAB-MS measurement, a mass number, m/z=722 was observed as a molecular ion peak, and Compound C119 was identified.

DEVICE MANUFACTURING EXAMPLE

Organic electroluminescence devices were manufactured using the Example Compounds and Comparative Compounds below as materials for a hole transport region.

Example Compound

A2

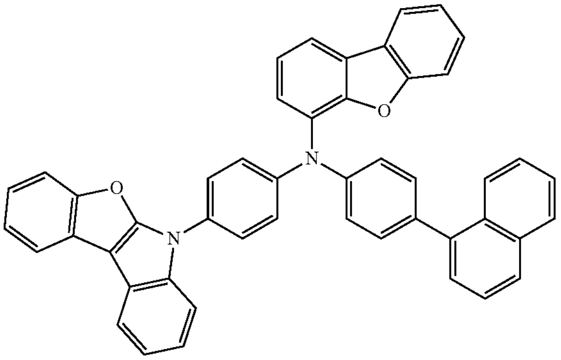

A20

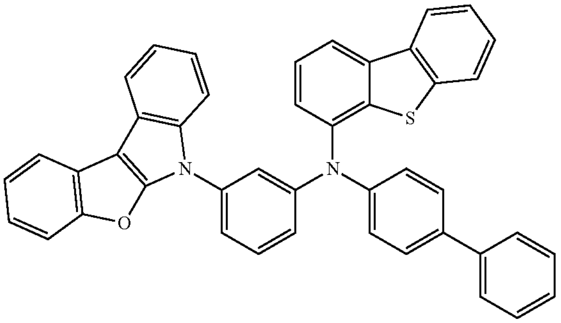

-continued
B13
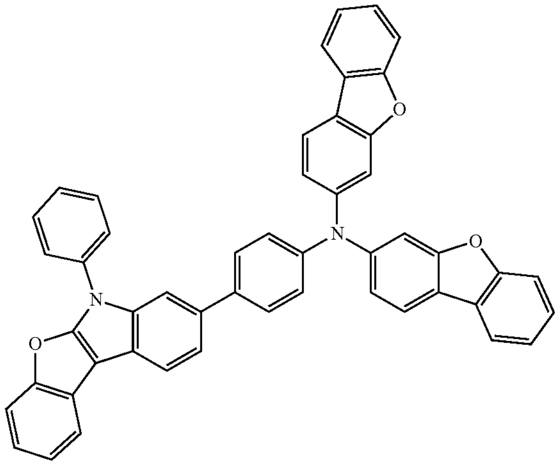
B18
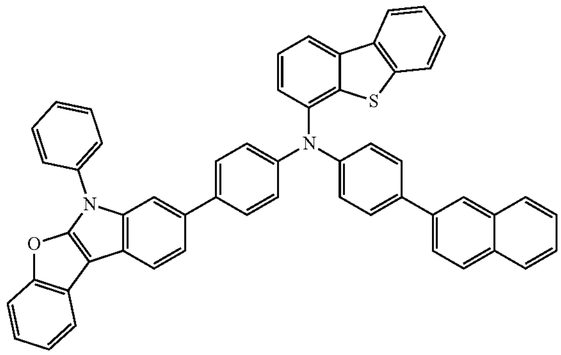
B36
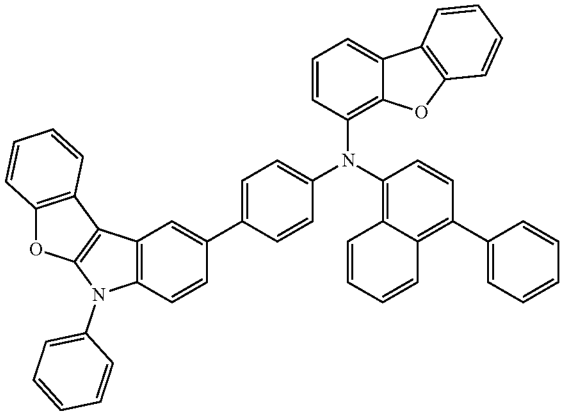
-continued
B49
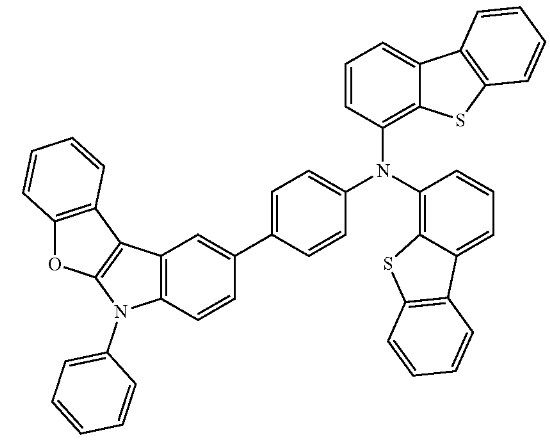
B72
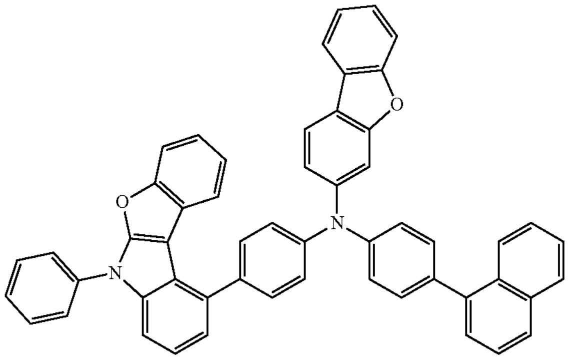
B105
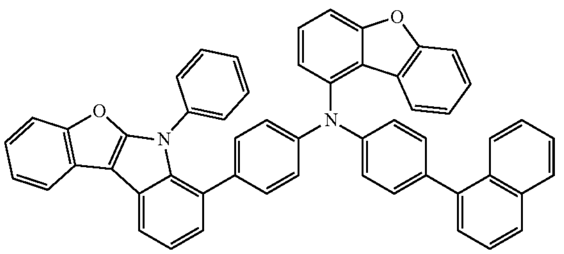
C4
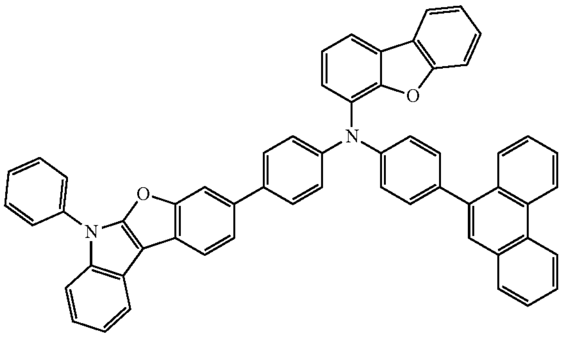

-continued
C11
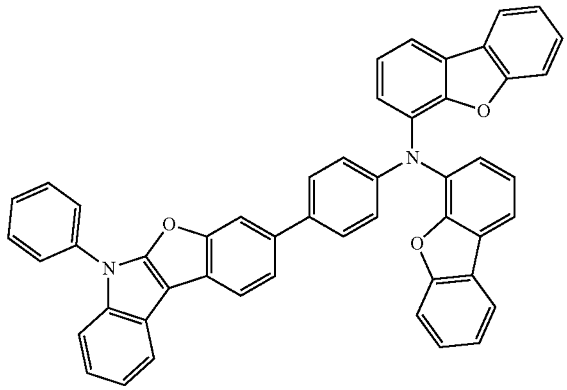
C44
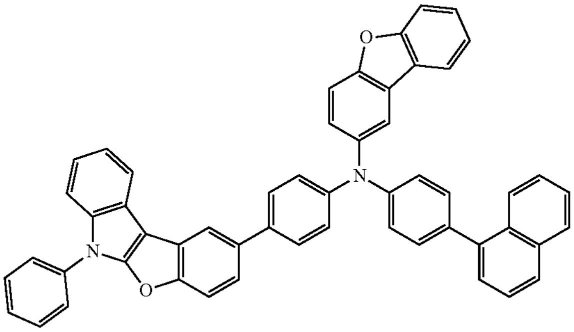
C46
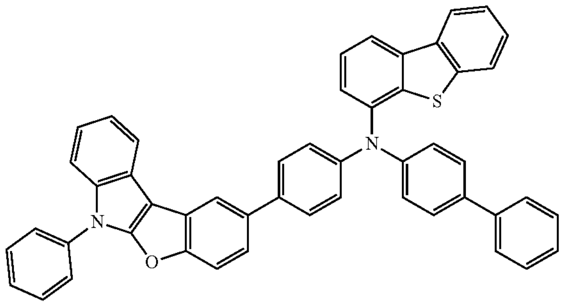
C65
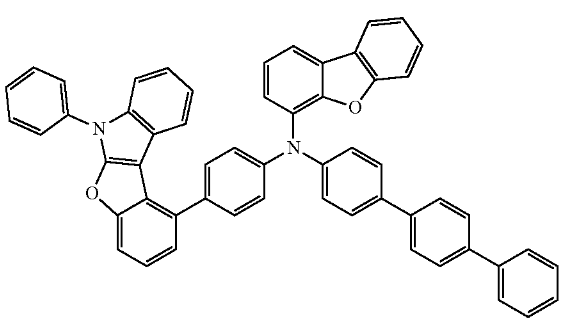
-continued
C99
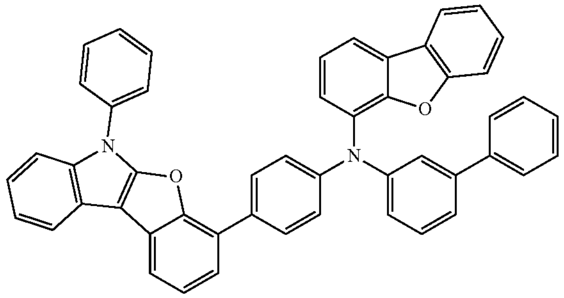
C119
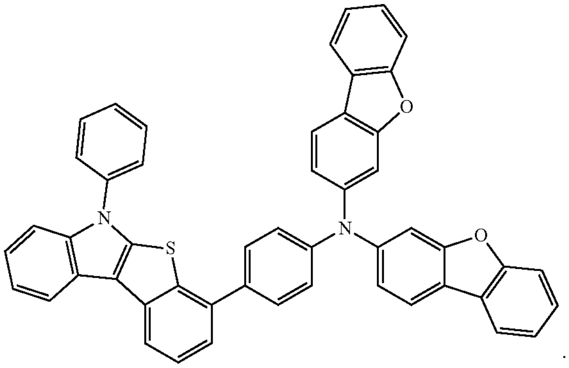
.
Comparative Compound
R1
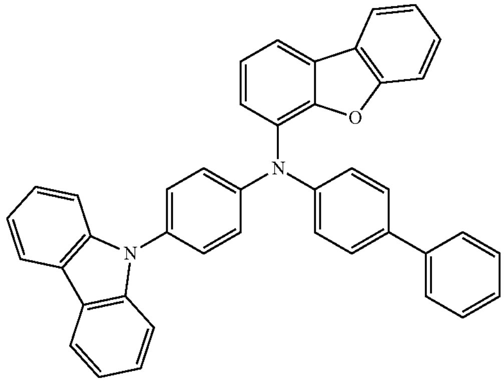
R2
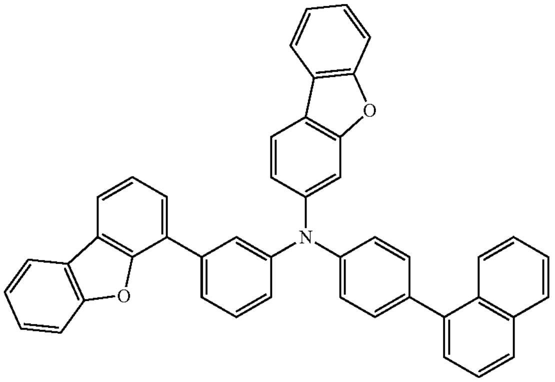

-continued

R3

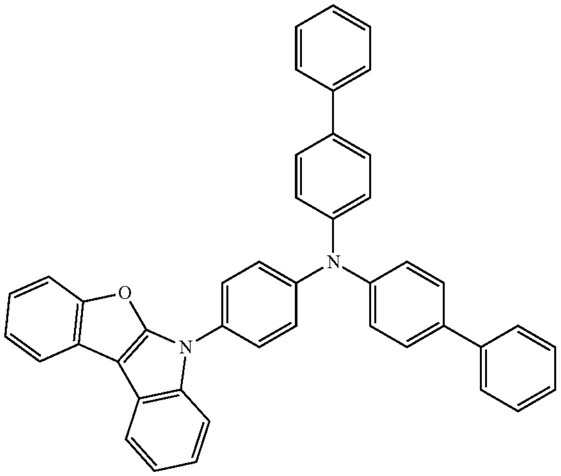

R4

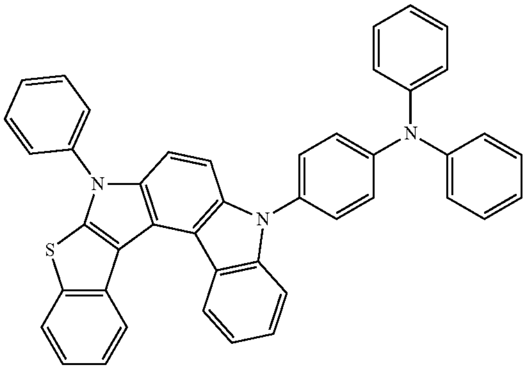

R5

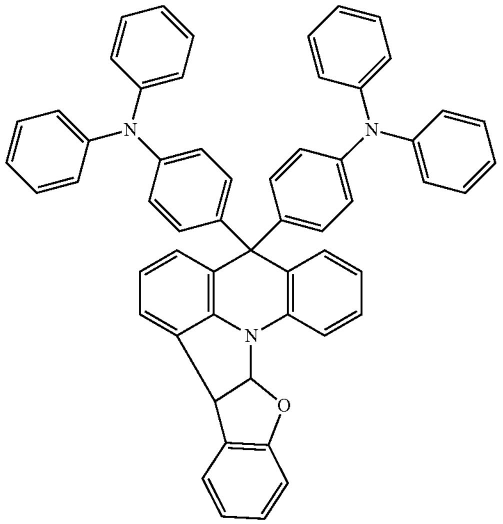

-continued

R6

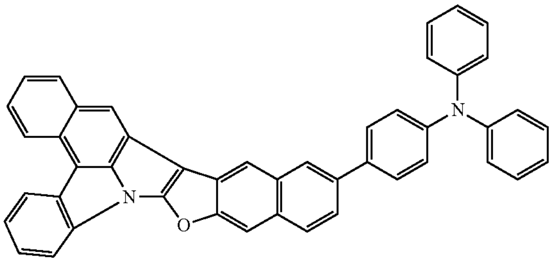

R7

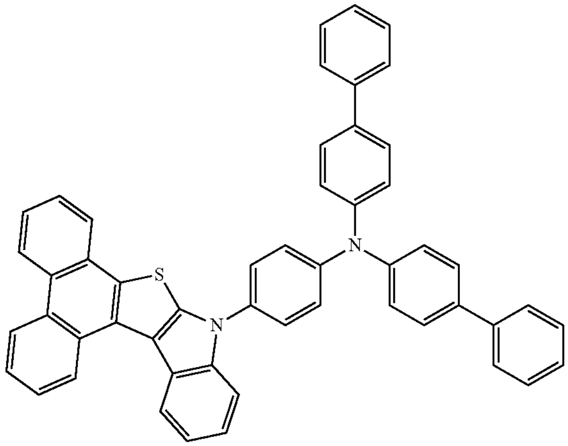

R8

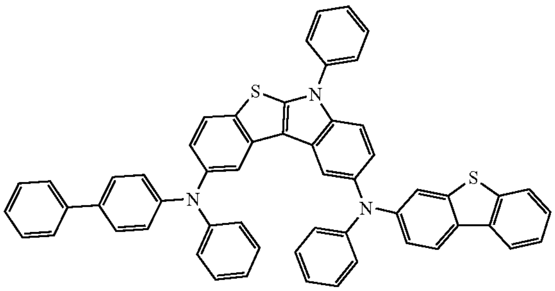

.

The organic electroluminescence devices of the Examples and Comparative Examples were manufactured using the below method. On a glass substrate, ITO with a thickness of about 150 nm was patterned and washed with ultra-pure water, and treated with UV-ozone for about 10 minutes to form a first electrode. Then, 2-TNATA was deposited to a thickness of about 60 nm, and the Example Compound or Comparative Compound was deposited to a thickness of about 30 nm to form a hole transport layer. Then, an emission layer was formed using ADN doped with 3% TBP to a thickness of about 25 nm, and a layer was formed using $Alq_3$ to a thickness of about 25 nm and a layer was formed using LiF to a thickness of about 1 nm to form an electron transport region. Then, a second electrode was formed using aluminum (Al) to a thickness of about 100 nm. All layers were formed by a vacuum deposition method.

The emission efficiency of the organic electroluminescence devices according to Examples 1 to 15 and Comparative Examples 1 to 8 are shown in Table 1 below. The emission efficiency was measured at a current density of about 10 mA/$cm^2$.

TABLE 1

| | Hole transport layer | Voltage (V) | Emission efficiency (%) | Lifespan LT50 (h) |
|---|---|---|---|---|
| Example 1 | Example Compound A2 | 5.5 | 7.7 | 1900 |
| Example 2 | Example Compound A20 | 5.6 | 7.8 | 1950 |
| Example 3 | Example Compound B13 | 5.4 | 7.4 | 2100 |
| Example 4 | Example Compound B18 | 5.5 | 7.5 | 2050 |
| Example 5 | Example Compound B36 | 5.6 | 7.5 | 1950 |
| Example 6 | Example Compound B49 | 5.6 | 7.6 | 2000 |
| Example 7 | Example Compound B72 | 5.5 | 7.7 | 1950 |
| Example 8 | Example Compound B105 | 5.5 | 7.7 | 2000 |
| Example 9 | Example Compound C4 | 5.4 | 7.6 | 2050 |
| Example 10 | Example Compound C11 | 5.5 | 7.7 | 2000 |
| Example 11 | Example Compound C44 | 5.6 | 7.6 | 2100 |
| Example 12 | Example Compound C46 | 5.4 | 7.5 | 2150 |
| Example 13 | Example Compound C65 | 5.5 | 7.4 | 2150 |
| Example 14 | Example Compound C99 | 5.6 | 7.7 | 1950 |
| Example 15 | Example Compound C119 | 5.5 | 7.6 | 2100 |
| Comparative Example 1 | Comparative Compound R1 | 6.2 | 6.0 | 1700 |
| Comparative Example 2 | Comparative Compound R2 | 6.1 | 6.1 | 1600 |
| Comparative Example 3 | Comparative Compound R3 | 6.0 | 6.4 | 1550 |
| Comparative Example 4 | Comparative Compound R4 | 6.1 | 6.1 | 1600 |
| Comparative Example 5 | Comparative Compound R5 | 6.2 | 5.8 | 1500 |
| Comparative Example 6 | Comparative Compound R6 | 5.5 | 6.0 | 1550 |
| Comparative Example 7 | Comparative Compound R7 | 6.3 | 6.1 | 1600 |
| Comparative Example 8 | Comparative Compound R8 | 6.4 | 5.9 | 1550 |

Referring to Table 1, it could be confirmed that Examples 1 to 15 achieved a lower voltage, longer life, and higher efficiency at the same time when compared with Comparative Examples 1 to 8.

The monoamine compound according to an embodiment of the present disclosure is used in a hole transport region to contribute to the decrease in driving voltage, and the increase of the efficiency and life of the organic electroluminescence device. The amine compound according to an embodiment of the present disclosure essentially includes two heteroaryl groups, i.e., the heteroaryl group represented by Formula 1 and $Ar_3$, so as to achieve heat resistance and charge tolerance with even further increased life. For example, the heteroatoms of the two heteroaryl groups may improve the hole transport properties of the whole molecule, such that the recombination probability of holes and electrons in an emission layer may be improved, and high emission efficiency may be achieved.

In Examples 1 and 2, Formula 2 is combined with the nitrogen atom of Formula 1, and the emission efficiency was specifically improved. Without being bound by the correctness of any explanation or theory, it is thought that when electron-rich nitrogen atoms are combined to each other via a linker, hole transport properties may be improved, the recombination probability of holes and electrons in an emission layer may be improved, and emission efficiency may be improved.

In Examples 3 to 15, Formula 2 is bonded to either terminal ring of Formula 1, and emission life was improved. Without being bound by the correctness of any explanation or theory, it is thought that the HOMO orbital of Formula 2 is widely enlarged to (e.g., delocalized over) the ring of Formula 1, such that the stability of a radical state may be improved.

Comparative Example 1 and Comparative Example 2 correspond to an amine compound including carbazole and/or dibenzofuran, and it is thought that as the number of heteroatoms included in a polycyclic condensed ring is decreased, hole transport properties are reduced, and accordingly, the emission efficiency is specifically reduced when compared with the Examples.

Comparative Example 3 has a structure similar to Formula 1 as in the present disclosure, but only one heteroaryl group is included. Accordingly, it is thought that heat resistance and charge tolerance are degraded, and both device efficiency and life are degraded (e.g., simultaneously) when compared with the Examples.

Comparative Example 4 corresponds to an amine compound having a polycyclic condensed ring obtained by additionally condensing indole to the structure of Formula 1, and the carrier balance of the amine was collapsed, thereby degrading both device efficiency and life (e.g., simultaneously) when compared with the Examples.

Comparative Example 5 corresponds to an amine having a polycyclic condensed ring obtained by additionally condensing acridine to the structure of Formula 1, and both device efficiency and life were degraded (e.g., simultaneously) when compared with the Examples. Without being bound by the correctness of any explanation or theory, it is thought that a $sp^3$ hybrid carbon atom moiety included in a molecule is unstable, and decomposition occurs during deposition.

Comparative Example 6 and Comparative Example 7 correspond to an amine having a polycyclic condensed ring obtained by additionally condensing an aryl ring to the structure of Formula 1, and both device efficiency and life were degraded (e.g., simultaneously) when compared with the Examples. Without being bound by the correctness of any explanation or theory, it is thought that as the planarity of a molecule is increased, stacking between molecules is increased, and the deposition temperature of a material is increased and layer forming properties are degraded.

Comparative Example 8 includes a similar structure as Formula 1, but is a diamine compound. Accordingly, carrier balance was collapsed, and both device efficiency and life were degraded (e.g., simultaneously) when compared with the Examples.

The monoamine compound according to an embodiment of the present disclosure is used in a hole transport region and contributes to the decrease of the driving voltage and the increase of the efficiency and life of an organic electroluminescence device.

The organic electroluminescence device according to an embodiment of the present disclosure has excellent efficiency.

The monoamine compound according to an embodiment of the present disclosure may be used as a material for a hole transport region of an organic electroluminescence device and by using thereof, the efficiency of the organic electroluminescence device may be improved.

As used herein, the terms “substantially”, “about”, and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of “1.0 to 10.0” is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments, but various changes and modifications can be made by one ordinary skilled in the art within the spirit and scope of the present disclosure as set forth in the following claims and equivalents thereof.

What is claimed is:

1. An organic electroluminescence device, comprising:

a first electrode;

a hole transport region on the first electrode;

an emission layer on the hole transport region;

an electron transport region on the emission layer; and a second electrode on the electron transport region;

wherein the hole transport region comprises a monoamine compound represented by Formula 1:

[Formula 1]

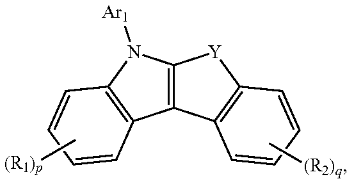

wherein in Formula 1,

Y is O or S, p and q are each independently an integer of 0 to 4, $Ar_1$ is a substituted or unsubstituted aryl group of 6 to 30 carbon atoms for forming a ring, a substituted or unsubstituted heteroaryl group of 2 to 30 carbon atoms for forming a ring, or represented by Formula 2, $R_1$ and $R_2$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or represented by Formula 2, where only one of $Ar_1$, $R_1$, and $R_2$ is represented by Formula 2:

[Formula 2]

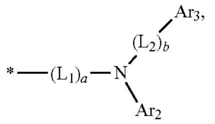

and wherein in Formula 2, $Ar_2$ is a substituted or unsubstituted aryl group of 6 to 30 carbon atoms for forming a ring or a substituted or unsubstituted heteroaryl group of 2 to 30 carbon atoms for forming a ring, $Ar_3$ is a substituted or unsubstituted heteroaryl group of 2 to 30 carbon atoms for forming a ring, $L_1$, and $L_2$ are each independently a direct linkage, a substituted or unsubstituted arylene group of 6 to 30 carbon atoms for forming a ring or a substituted or unsubstituted heteroarylene group of 2 to 30 carbon atoms for forming a ring, and a, and b are each independently an integer of 0 to 3, and wherein when $R_2$ is a substituted aryl group of 6 to 30 carbon atoms for forming a ring, a substituent of the substituted aryl group is selected from the group consisting of a deuterium atom, a halogen atom, a cyano group, a nitro group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group.

2. The organic electroluminescence device of claim 1, wherein Ara is represented by Formula 3:

[Formula 3]

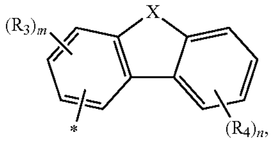

and wherein in Formula 3,

X is O or S, $R_3$ and $R_4$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or combined with an adjacent group to form a ring, m is an integer of 0 to 3, and n is an integer of 0 to 4.

3. The organic electroluminescence device of claim 2, wherein Formula 1 is represented by any one of Formula 4 to Formula 6:

[Formula 4]

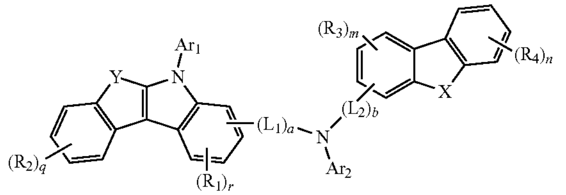

[Formula 5]

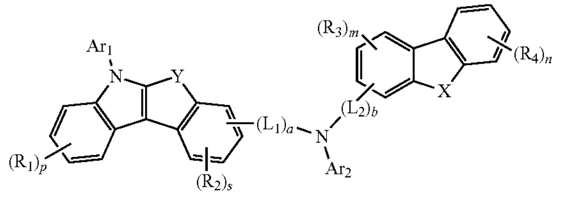

[Formula 6]

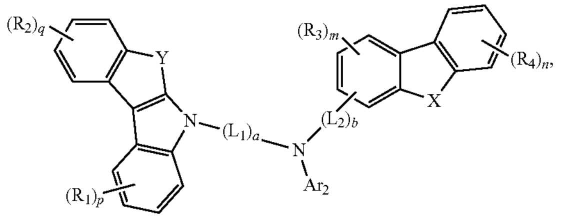

and wherein in Formula 4 to Formula 6, $Ar_1$ is a substituted or unsubstituted aryl group of 6 to 30 carbon atoms for forming a ring, or a substituted or unsubstituted heteroaryl group of 2 to 30 carbon atoms for forming a ring, $R_1$ and $R_2$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, r and s are each independently an integer of 0 to 3, and X, Y, $Ar_2$, $L_1$, $L_2$, a, b, $R_3$, $R_4$, m, n, p and q are each independently the same as defined in Formula 1 to Formula 3, and wherein when $R_2$ is a substituted aryl group of 6 to 30 carbon atoms for forming a ring, a substituent of the substituted aryl group is selected from the group consisting of a deuterium atom, a halogen atom, a cyano group, a nitro group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group.

4. The organic electroluminescence device of claim 3, wherein Formula 4 is represented by any one of Formula 4-1 to Formula 4-4:

[Formula 4-1]

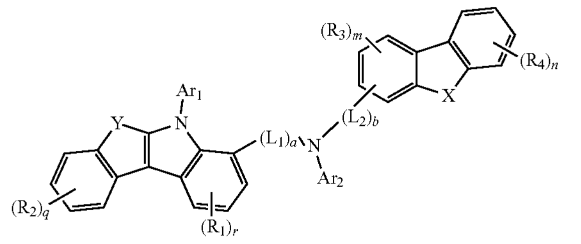

[Formula 4-2]

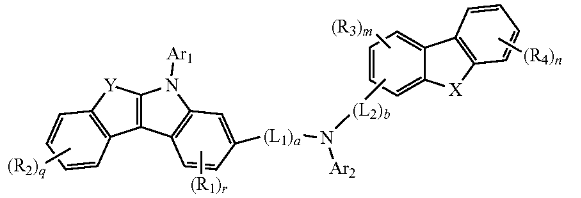

[Formula 4-3]

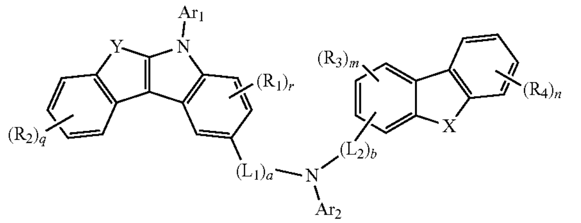

[Formula 4-4]

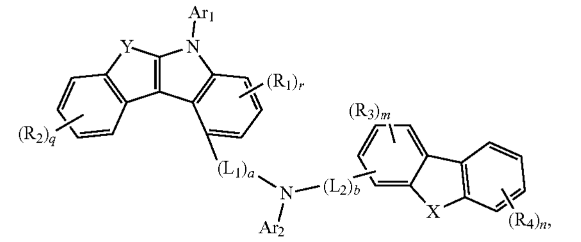

and wherein in Formula 4-1 to Formula 4-4,

X, Y, $Ar_1$, $Ar_2$, $L_1$, $L_2$, $R_1$ to $R_4$, a, b, m, n, q and r are each independently the same as defined in Formula 4.

5. The organic electroluminescence device of claim 3, wherein Formula 5 is represented by any one of Formula 5-1 to Formula 5-4:

[Formula 5-1]

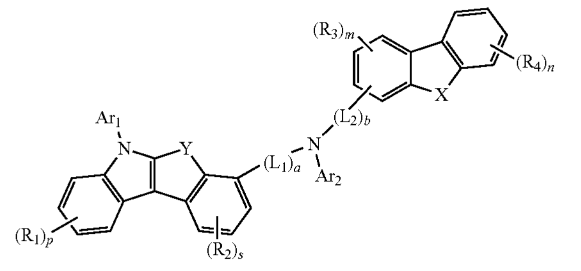

-continued

[Formula 5-2]

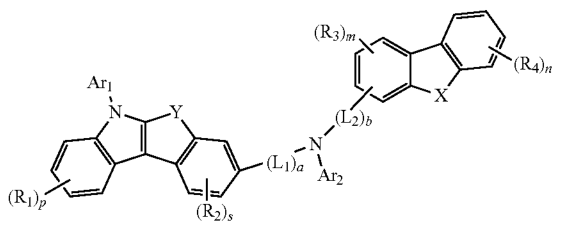

[Formula 5-3]

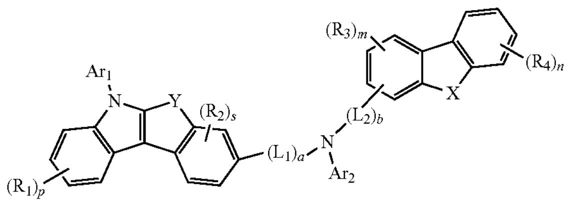

[Formula 5-4]

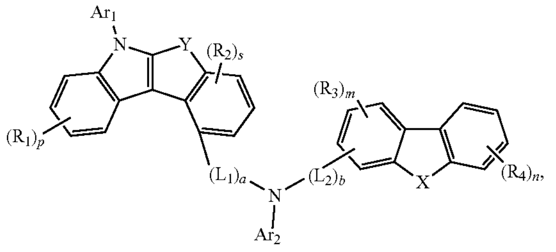

and wherein in Formula 5-1 to Formula 5-4,

X, Y, $Ar_1$, $Ar_2$, $L_1$, $L_2$, $R_1$ to $R_4$, a, b, m, n, p and s are each independently the same as defined in Formula 5.

6. The organic electroluminescence device of claim 1, wherein $L_1$, and $L_2$ are each independently a direct linkage, a substituted or unsubstituted phenylene group, a substituted or unsubstituted biphenylene group, or a substituted or unsubstituted naphthylene group.

7. An organic electroluminescence device, comprising:

a first electrode;

a hole transport region on the first electrode;

an emission layer on the hole transport region;

an electron transport region on the emission layer; and a second electrode on the electron transport region;

wherein the hole transport region comprises a monoamine compound represented by Formula 1:

[Formula 1]

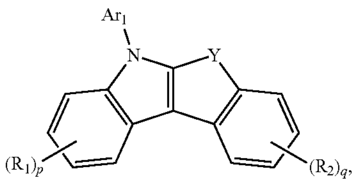

wherein in Formula 1,

Y is O or S, p and q are each independently an integer of 0 to 4, $Ar_1$ is a substituted or unsubstituted aryl group of 6 to 30 carbon atoms for forming a ring, a substituted or unsubstituted heteroaryl group of 2 to 30 carbon atoms for forming a ring, or represented by Formula 2, $R_1$ and $R_2$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or represented by Formula 2, where only one of $Ar_1$, $R_1$, and $R_2$ is represented by Formula 2:

[Formula 2]

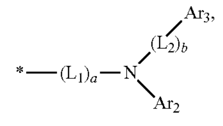

and wherein in Formula 2, $Ar_2$ is a substituted or unsubstituted aryl group of 6 to 30 carbon atoms for forming a ring or a substituted or unsubstituted heteroaryl group of 2 to 30 carbon atoms for forming a ring, $Ar_3$ is a substituted or unsubstituted heteroaryl group of 2 to 30 carbon atoms for forming a ring, $L_1$, and $L_2$ are each independently a direct linkage, a substituted or unsubstituted arylene group of 6 to 30 carbon atoms for forming a ring or a substituted or unsubstituted heteroarylene group of 2 to 30 carbon atoms for forming a ring, and b is an integer of 0 to 3, wherein a is 1, and $L_1$ is represented by any one of L-1 to L-4:

L-1

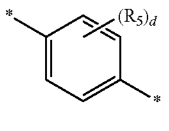

L-2

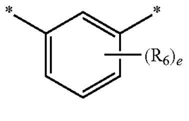

L-3

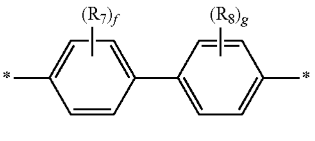

L-4

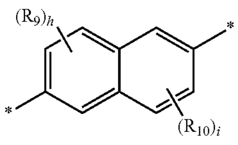

, wherein in L-1 to L-4, $R_5$ to $R_{10}$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, d to g are each independently an integer of 0 to 4, and h and i are each independently an integer of 0 to 3.

8. The organic electroluminescence device of claim 1, wherein and $R_2$ are each independently a hydrogen atom, a deuterium atom, a halogen atom, or a substituted or unsubstituted alkyl group of 1 to 10 carbon atoms.

9. The organic electroluminescence device of claim 1, wherein An is a substituted or unsubstituted phenyl group, a substituted or unsubstituted biphenyl group, a substituted or unsubstituted triphenyl group, a substituted or unsubstituted dibenzofuran group, or a substituted or unsubstituted dibenzothiophene group.

10. The organic electroluminescence device of claim 1, wherein the hole transport region comprises:

a hole injection layer on the first electrode; and a hole transport layer on the hole injection layer, and the hole transport layer comprises the monoamine compound represented by Formula 1.

11. The organic electroluminescence device of claim 10, wherein the hole transport region further comprises an electron blocking layer on the hole transport layer.

12. The organic electroluminescence device of claim 1, wherein the monoamine compound represented by Formula 1 is at least one compound represented in Compound Group 1:

[Compound Group 1]

A1

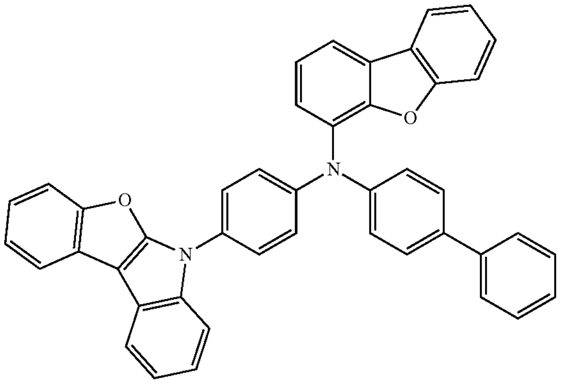

A2

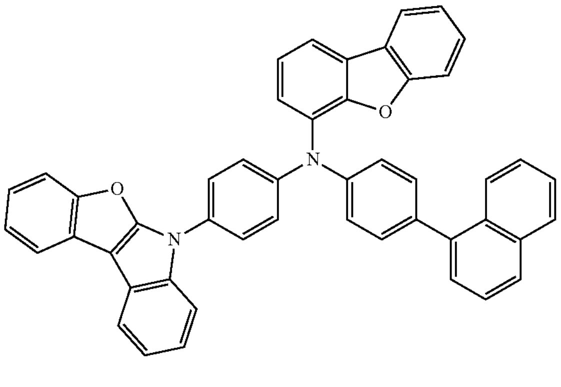

-continued

A3

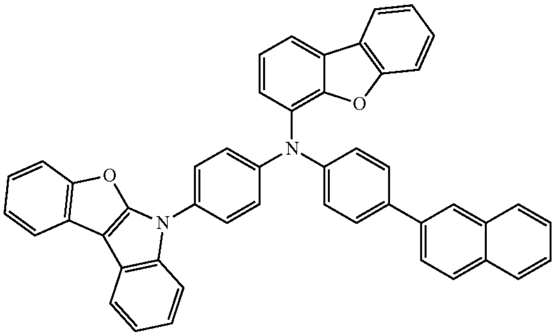

A4

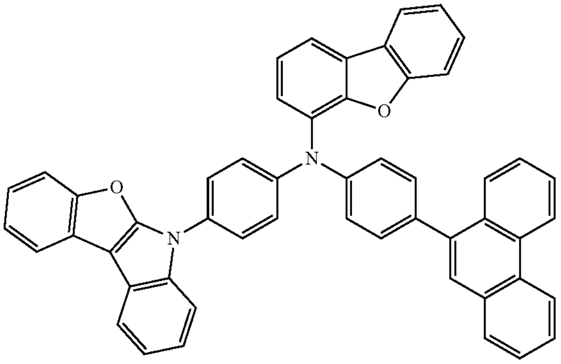

A5

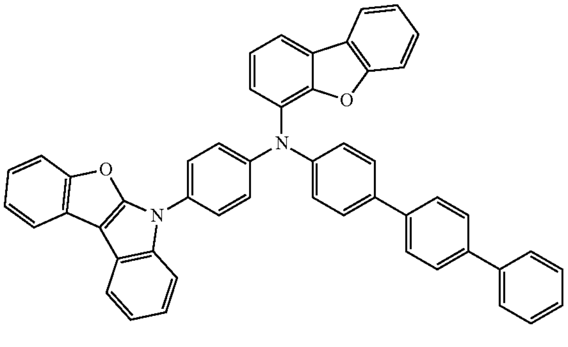

A6

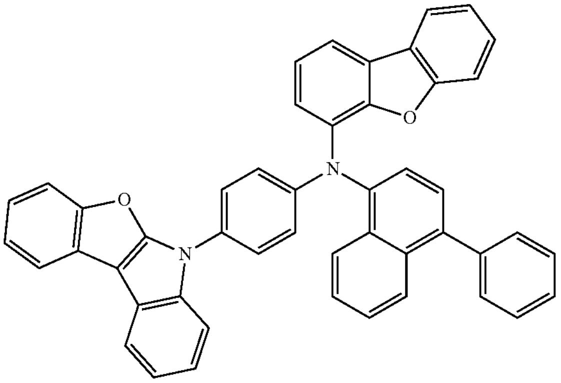

-continued
A7
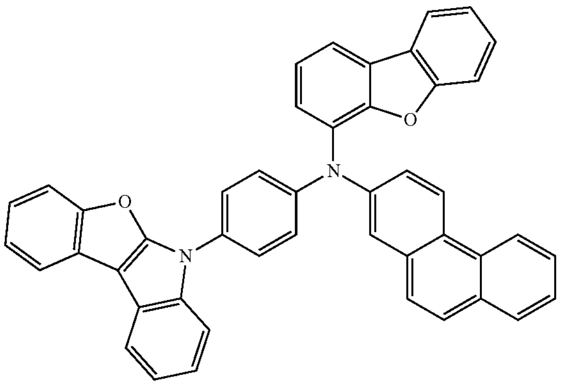
A8
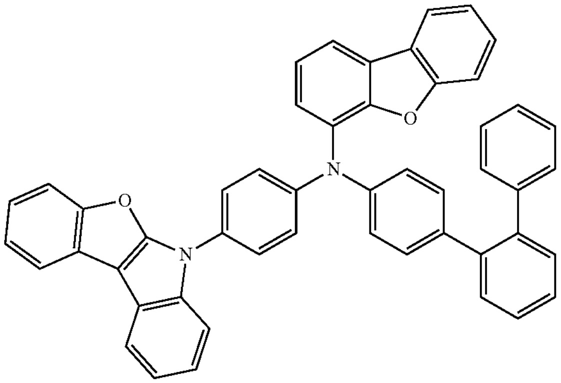
A9
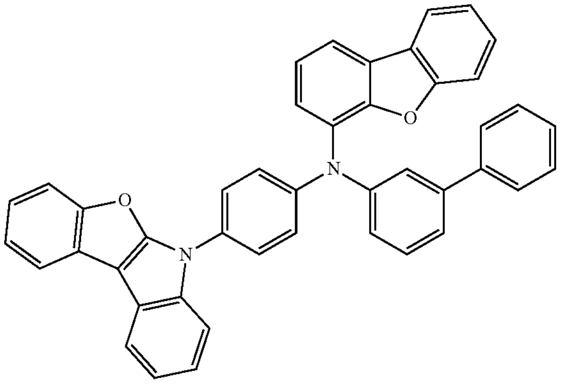
A10
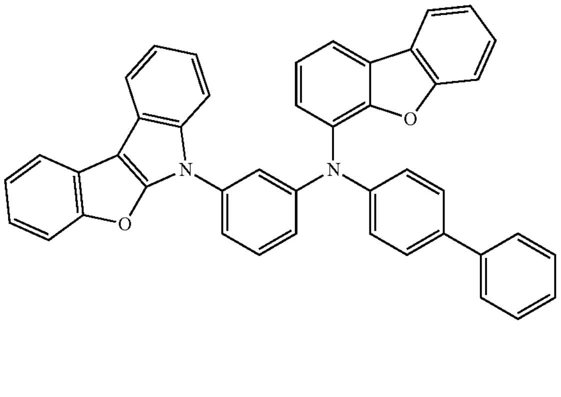
-continued
A11
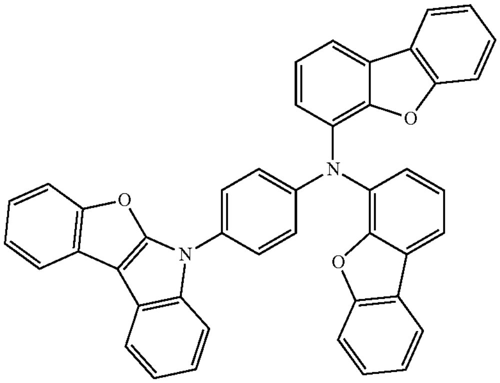
A12
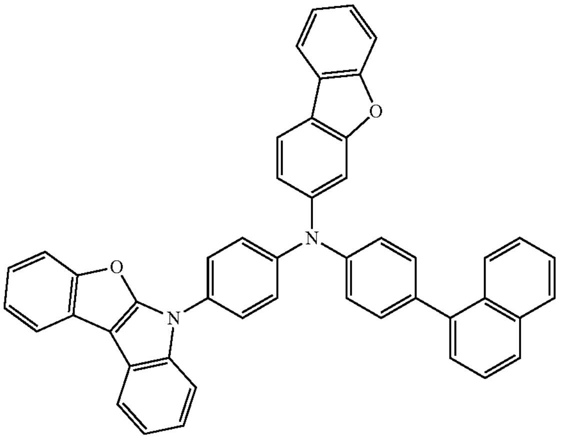
A13
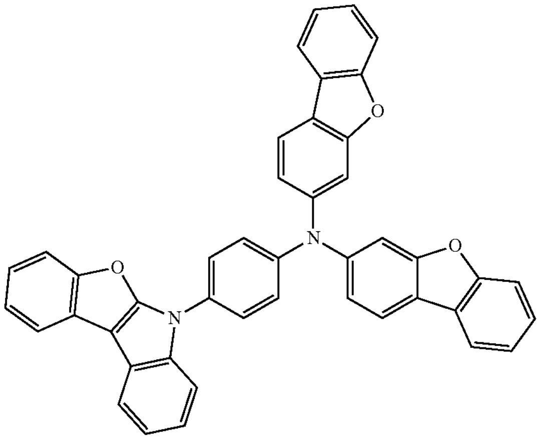

-continued
A14
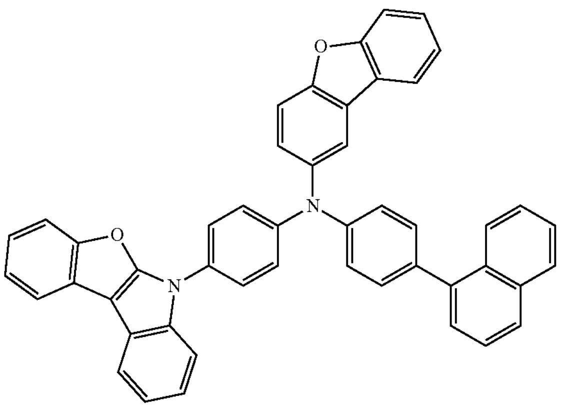
A15
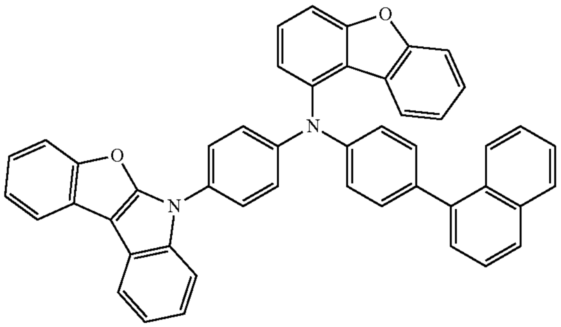
A16
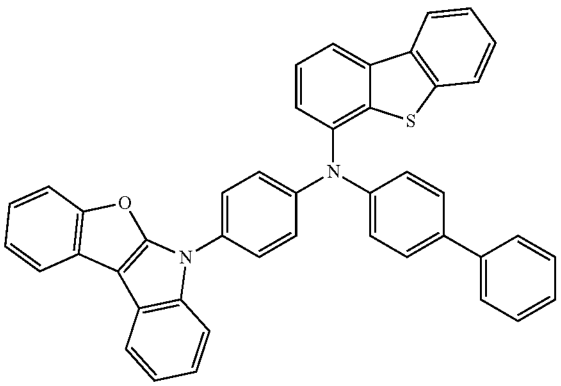
A17
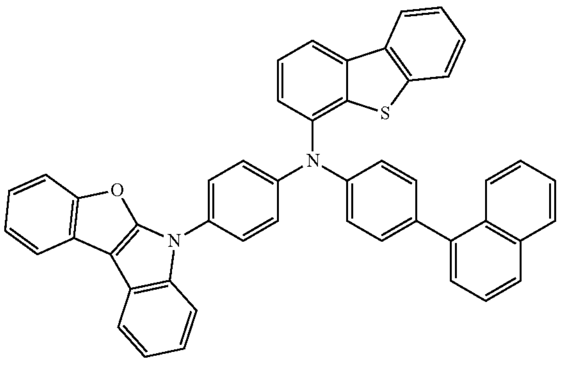
-continued
A18
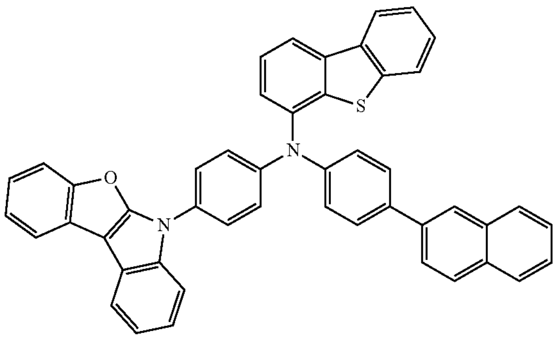
A19
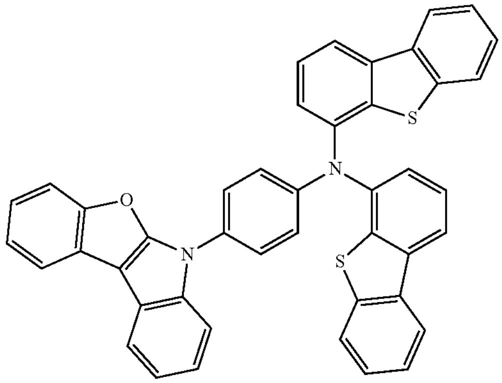
A20
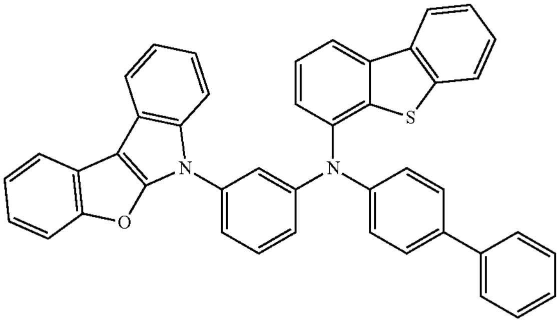
A21
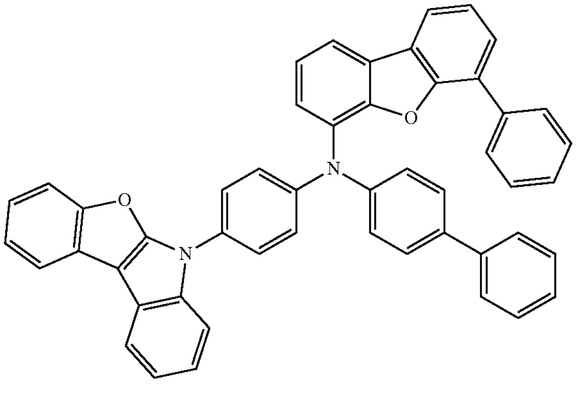

-continued
A22
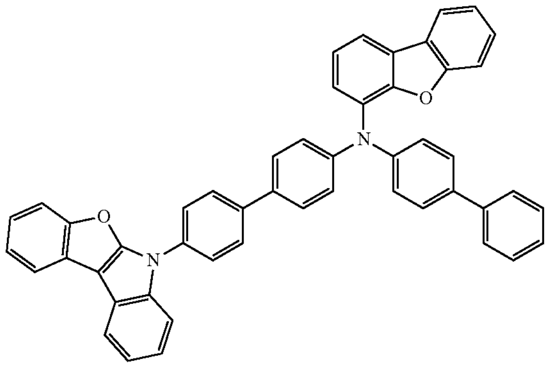
A23
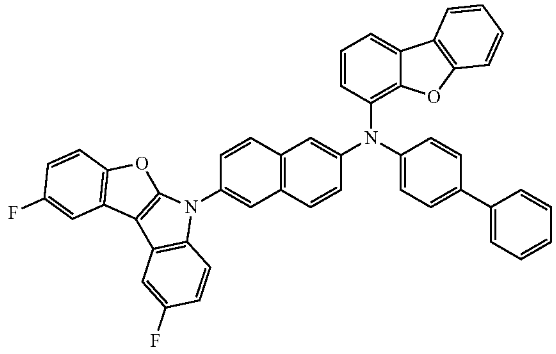
A24
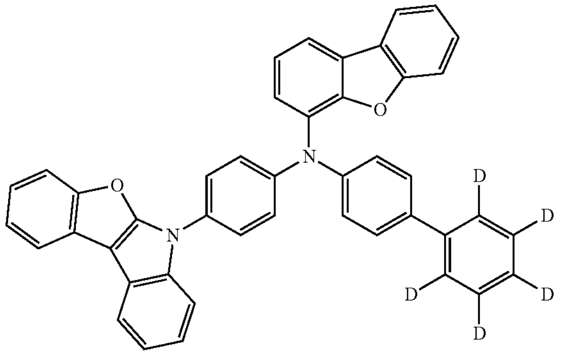
A25
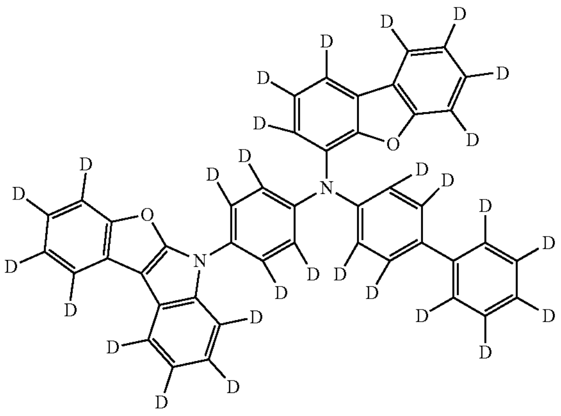
-continued
A26
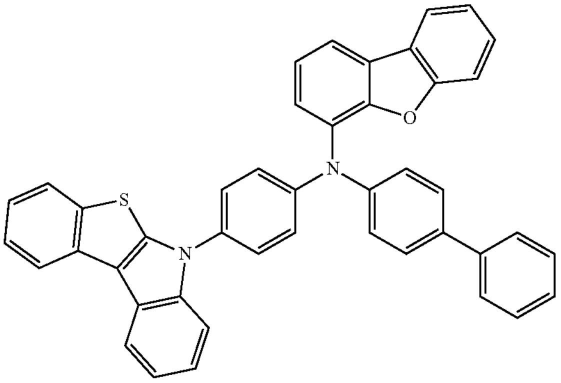
A27
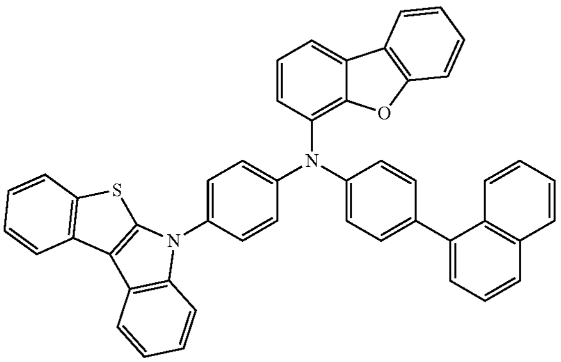
A28
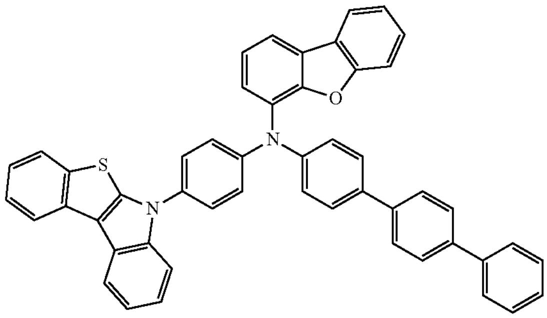
A29
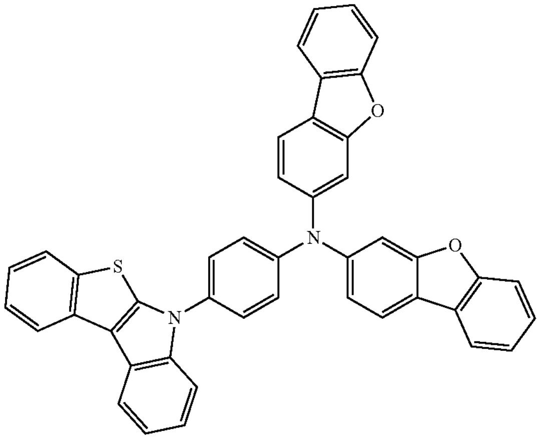

-continued
A30
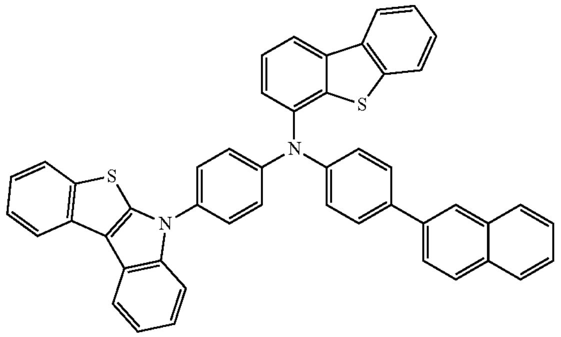
A31
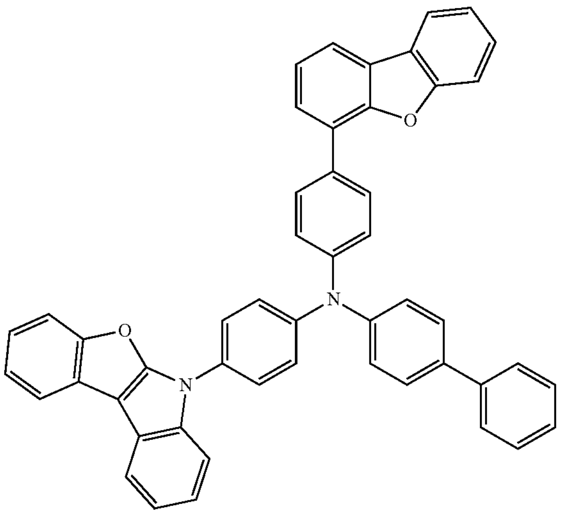
A32
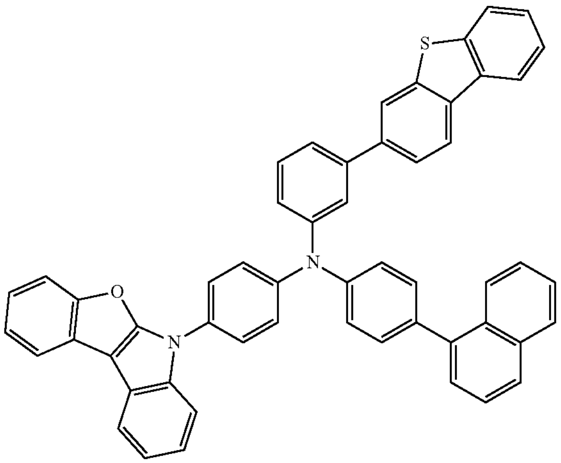
-continued
A33
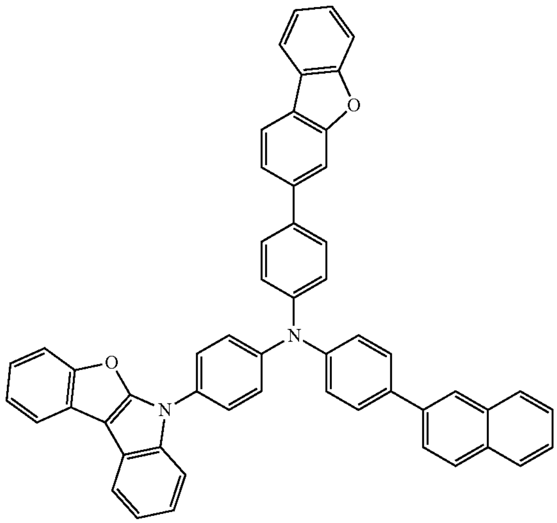
A34
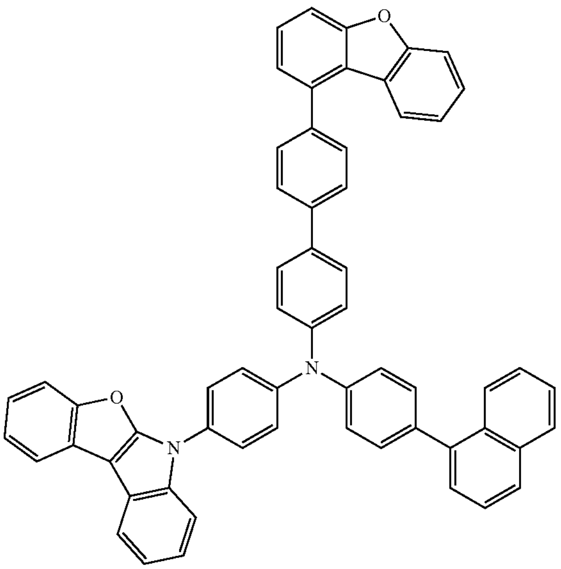
A35
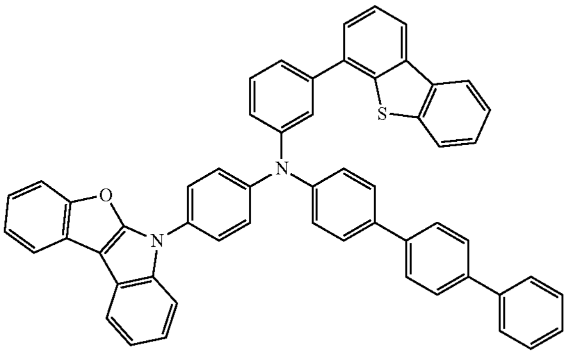

-continued
A36
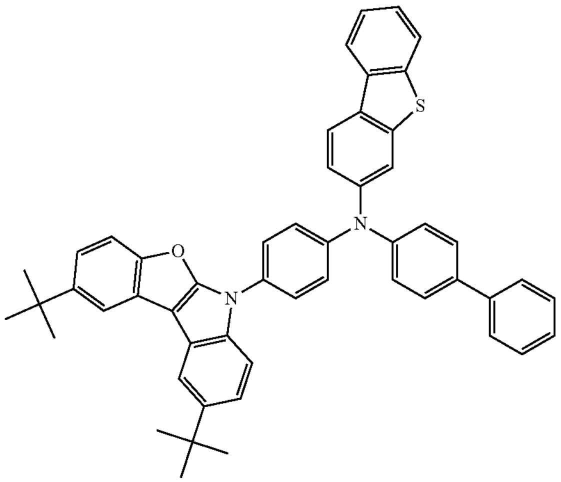
A37
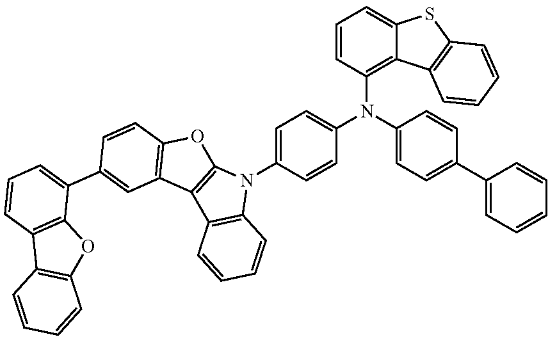
A38
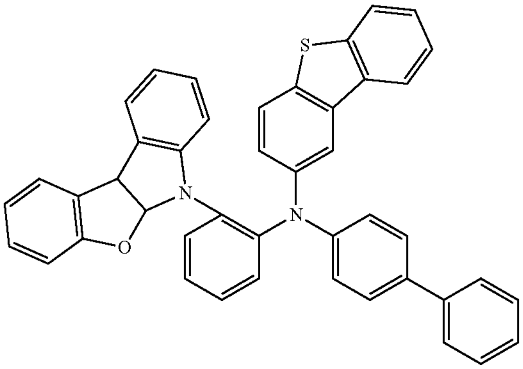
-continued
A39
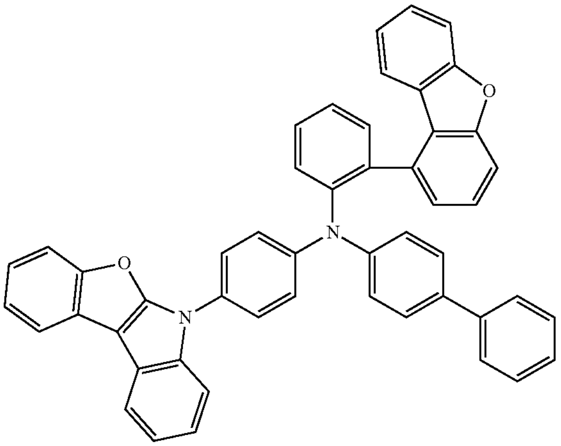
A40
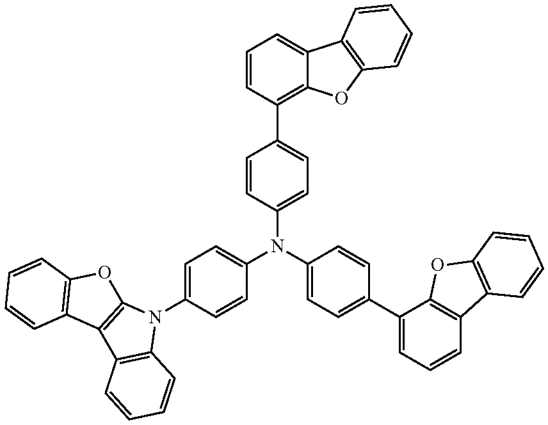
A41
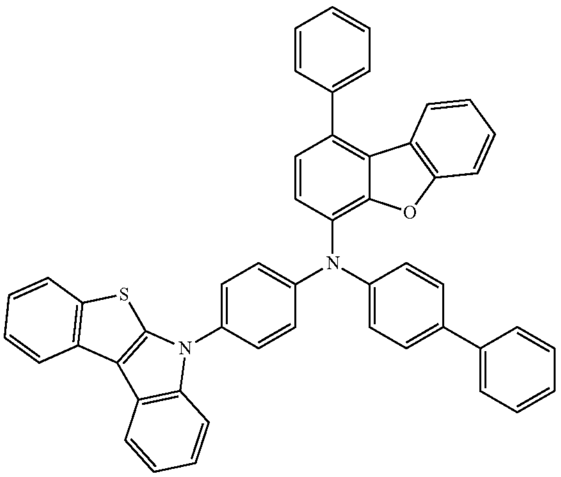

-continued
A42
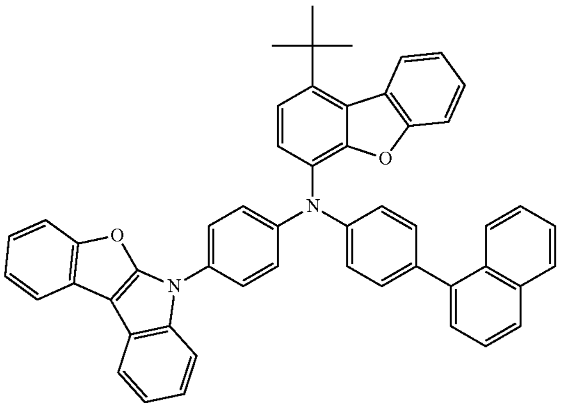
A43
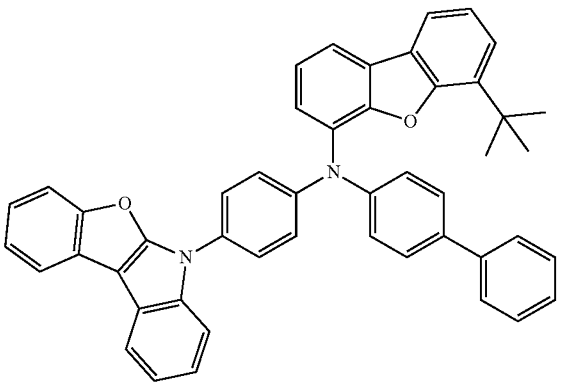
A44
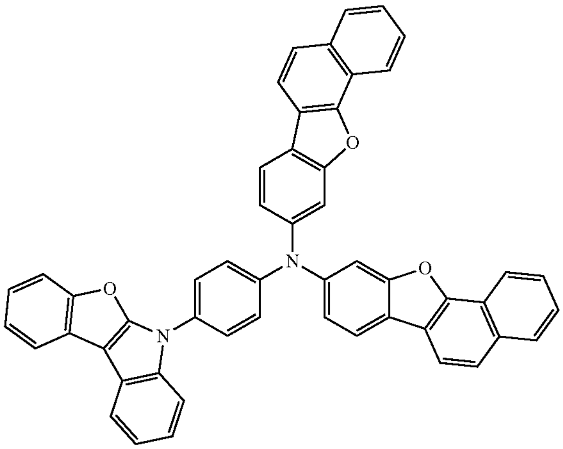
-continued
A45
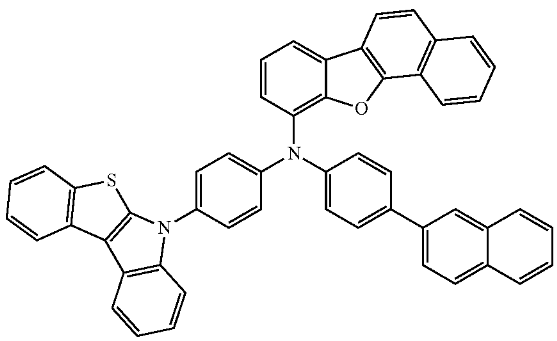
.
13. The organic electroluminescence device of claim 1, wherein the monoamine compound represented by Formula 1 is at least one compound represented in Compound Group 2:
[Compound Group 2]
B1
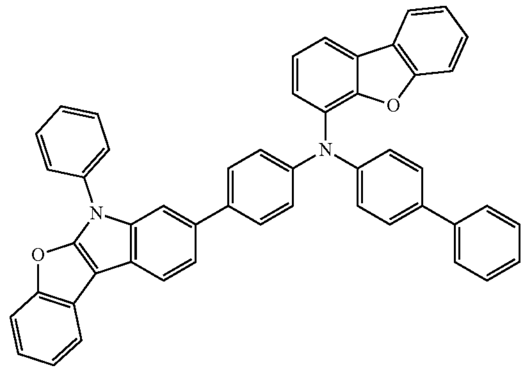
B2
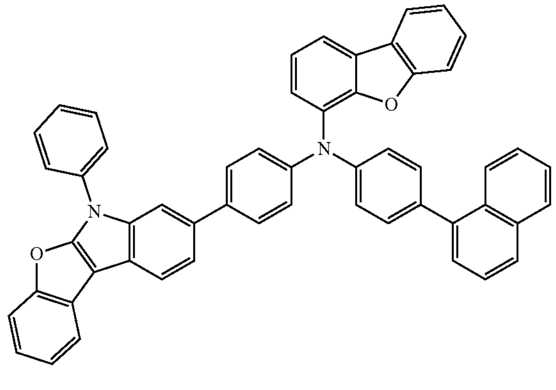

-continued
B3
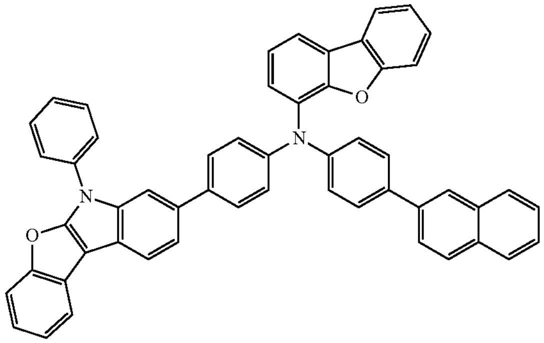
B4
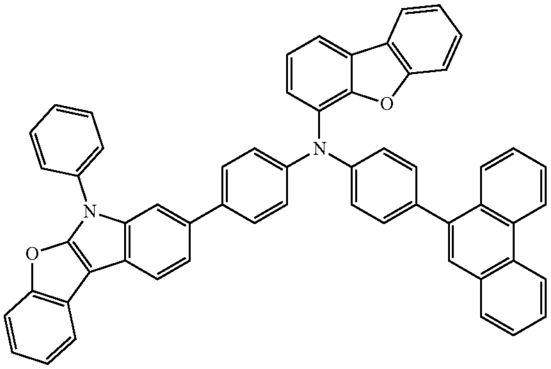
B5
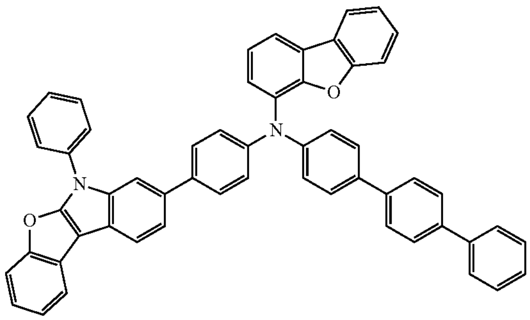
B6
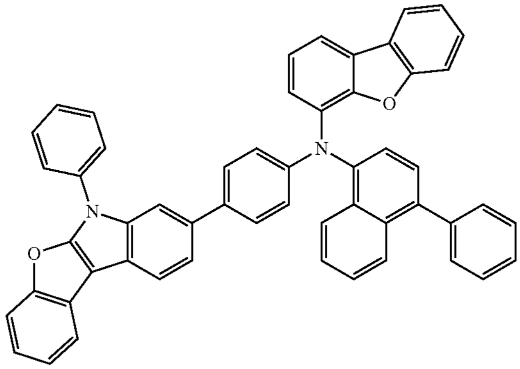
-continued
B7
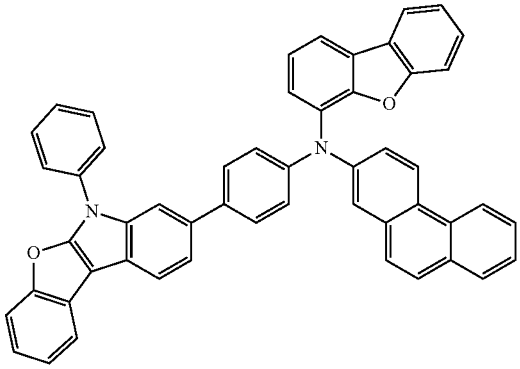
B8
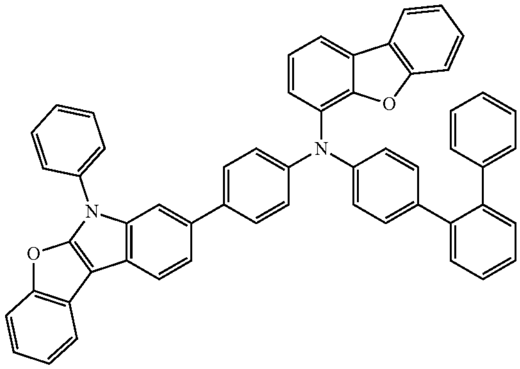
B9
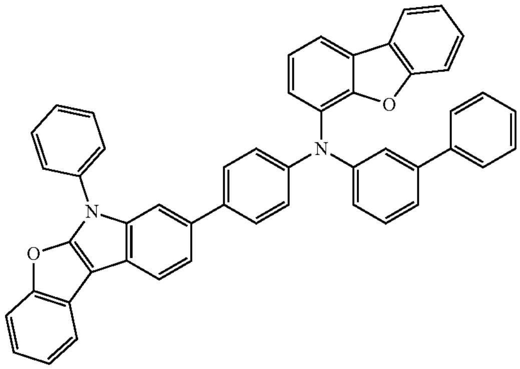
B10
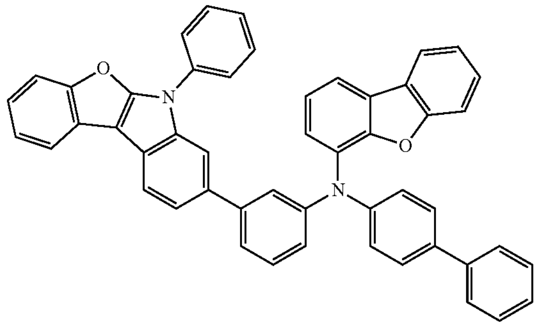

-continued
B11
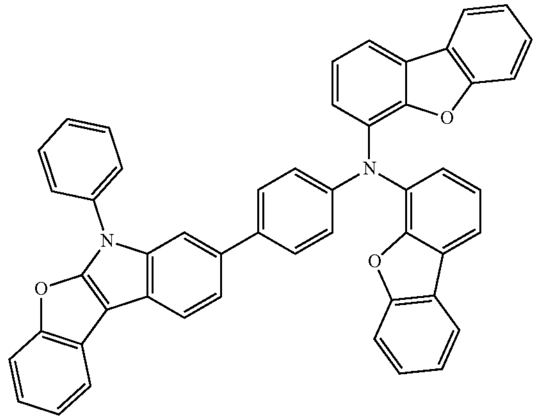
B12
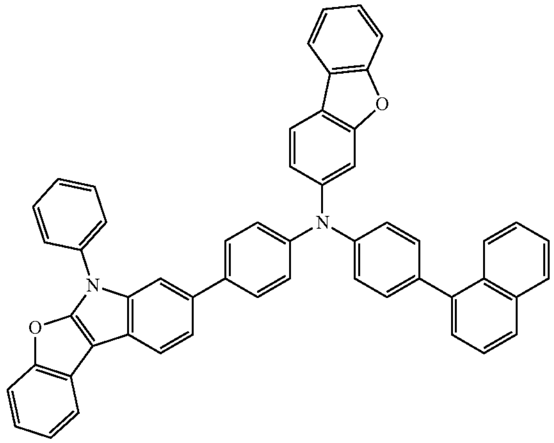
B13
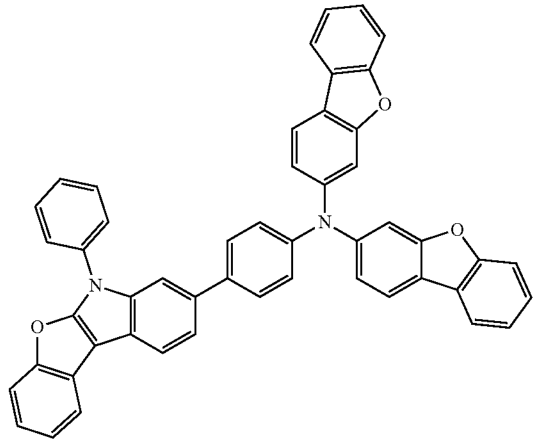
-continued
B14
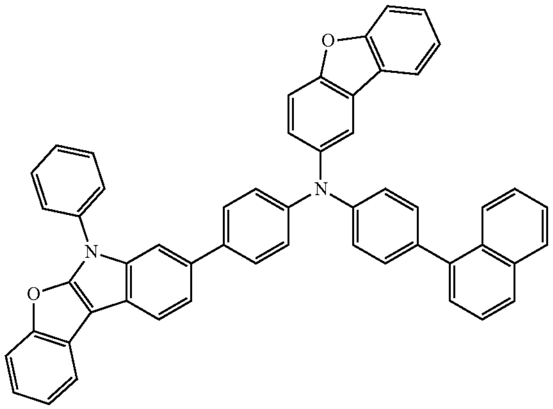
B15
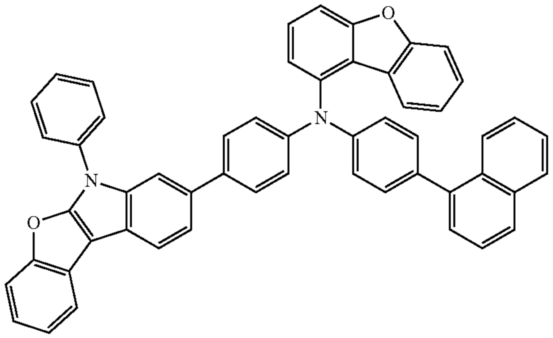
B16
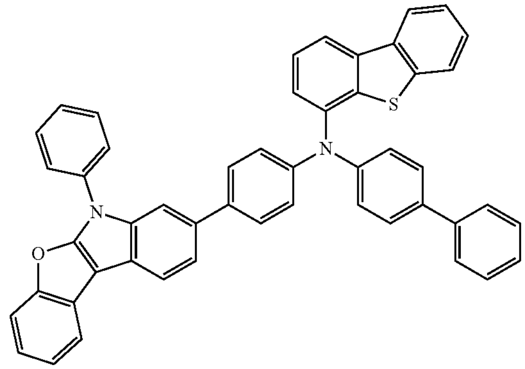
B17
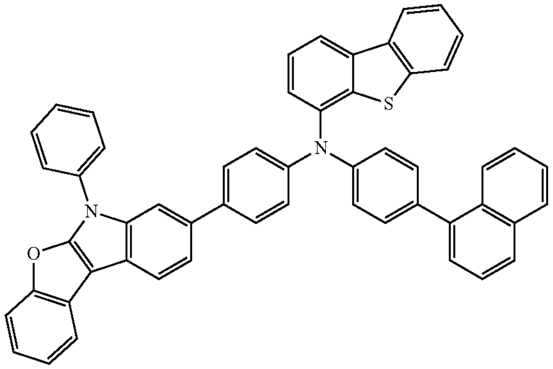

-continued
B18
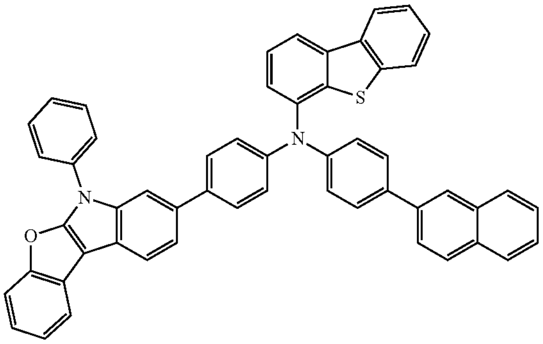
B19
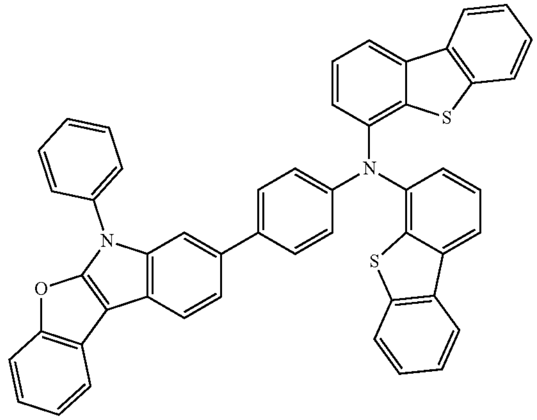
B20
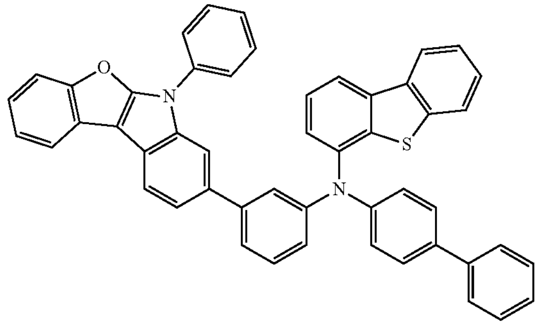
B21
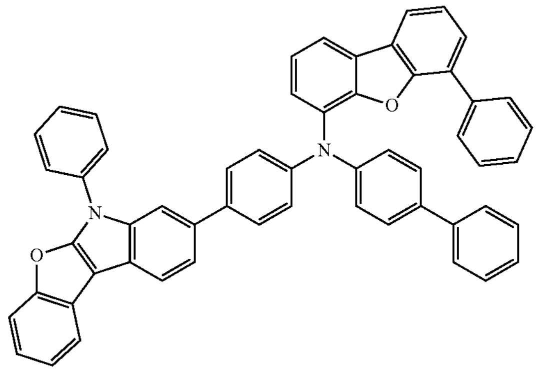
-continued
B22
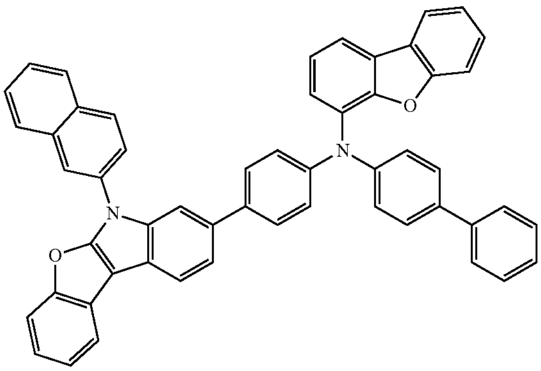
B23
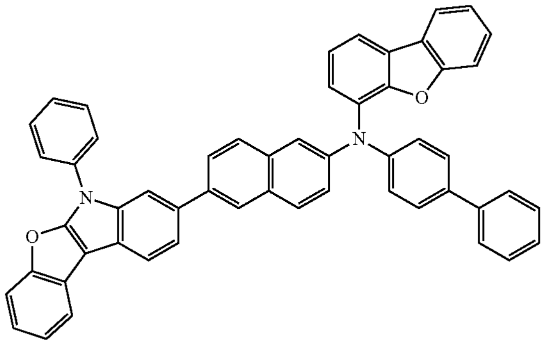
B24
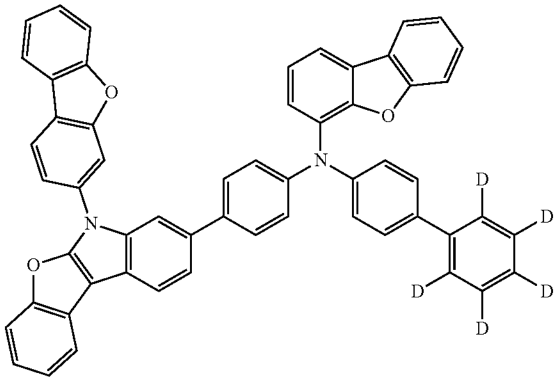
B25
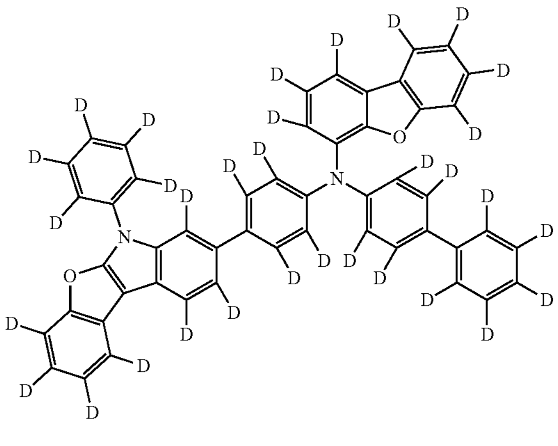

-continued
B26
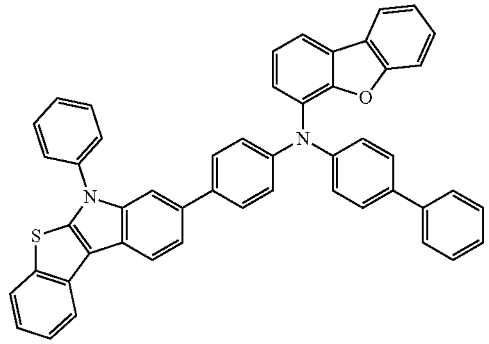
B27
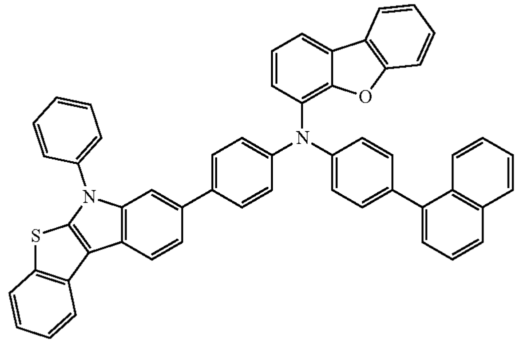
B28
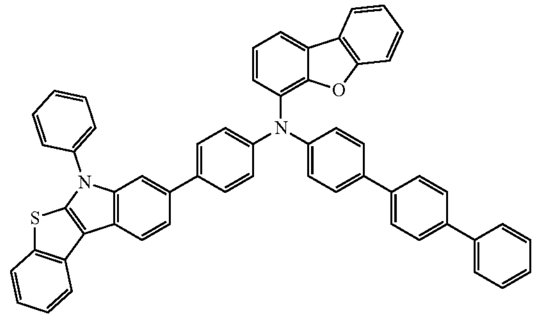
B29
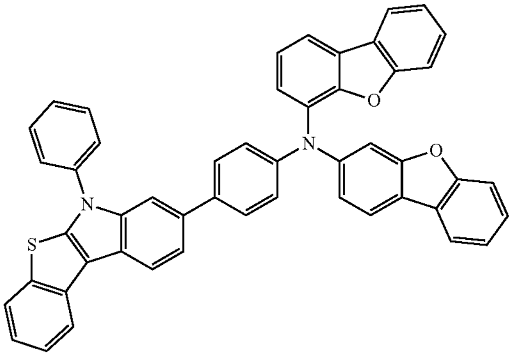
-continued
B30
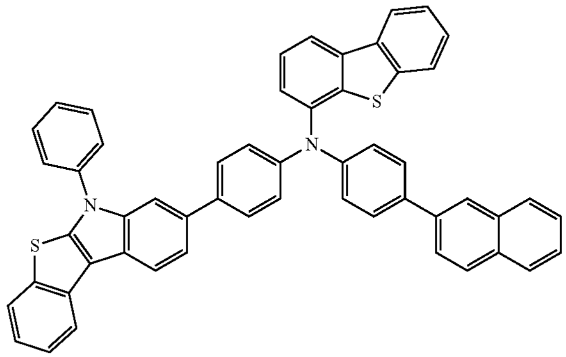
B31
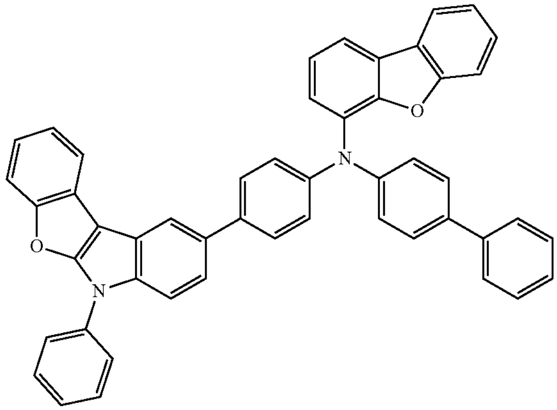
B32
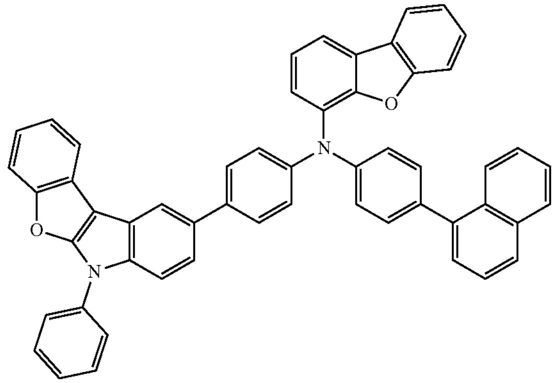
B33
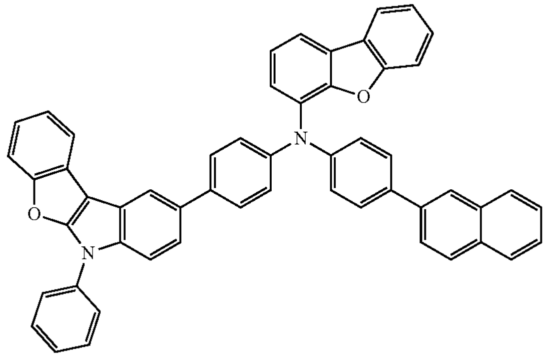

-continued
B34
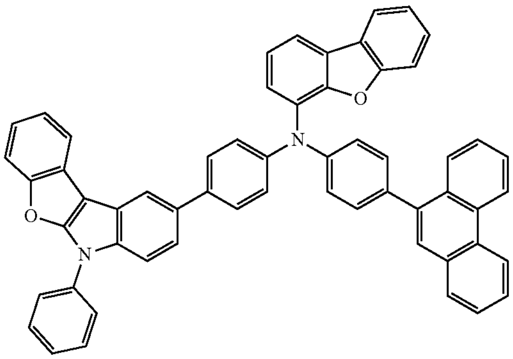
B35
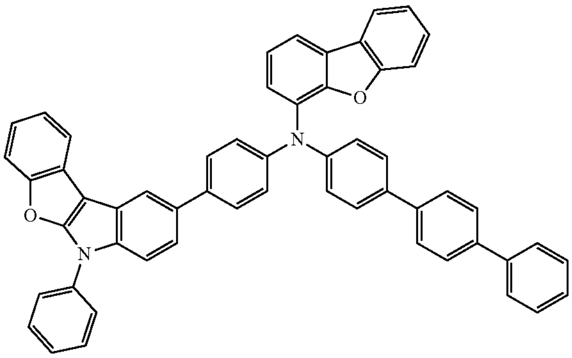
B36
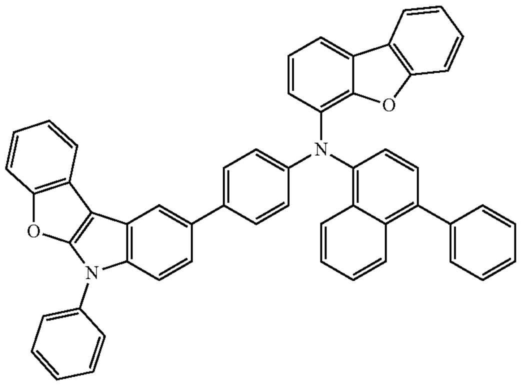
B37
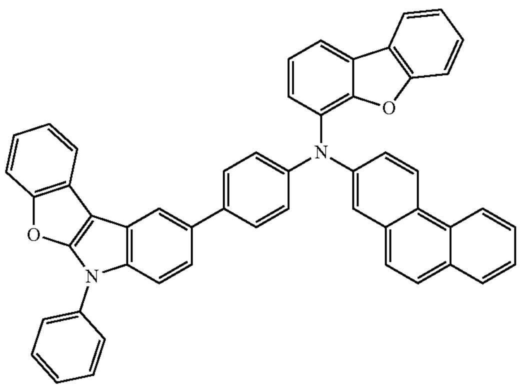
-continued
B38
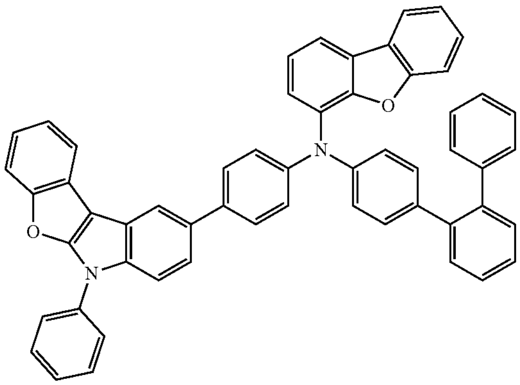
B39
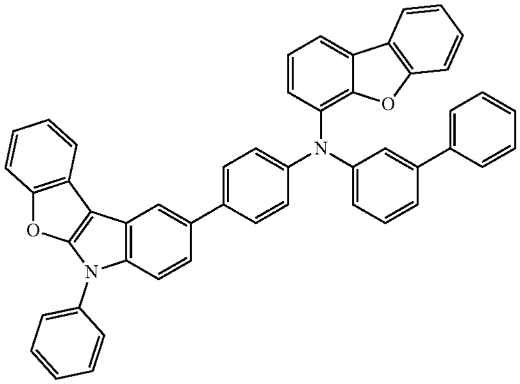
B40
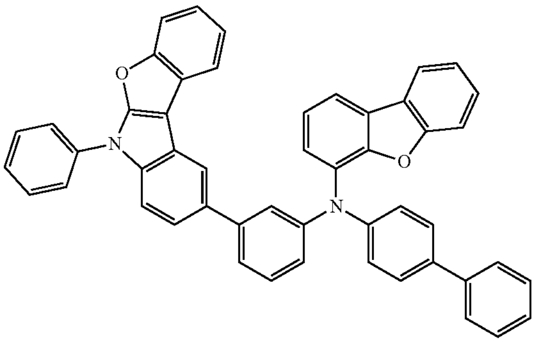
B41
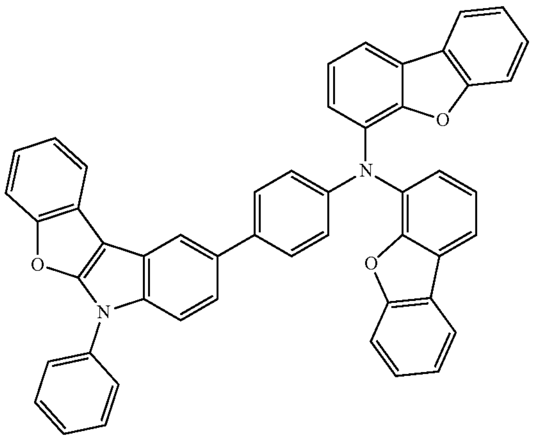

-continued
B42
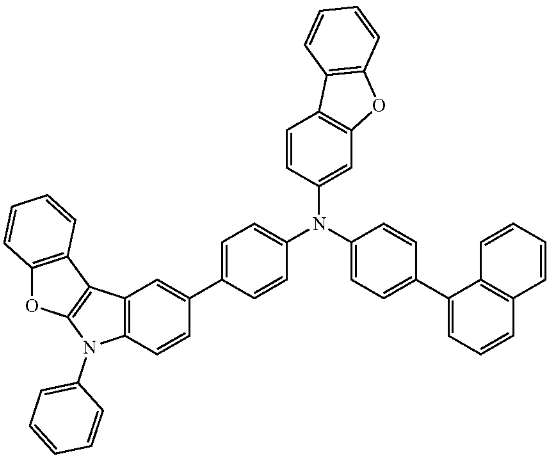
B43
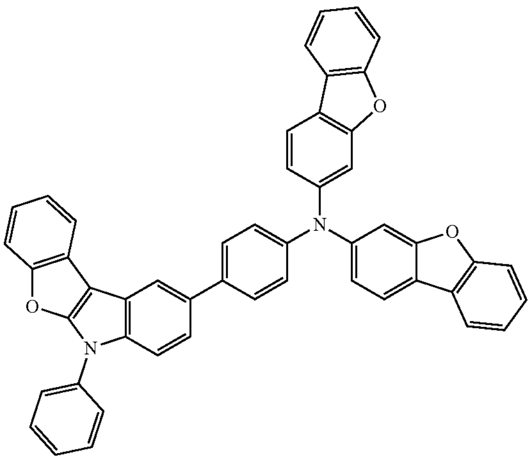
B44
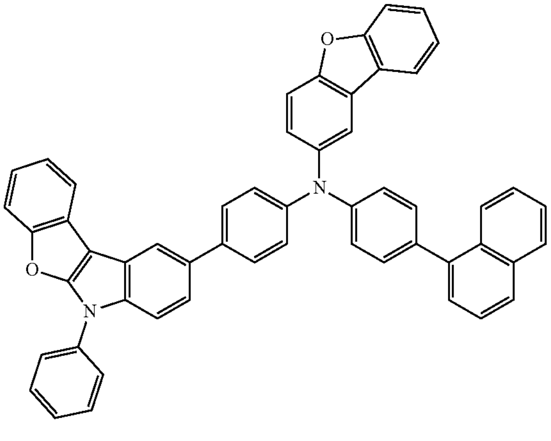
-continued
B45
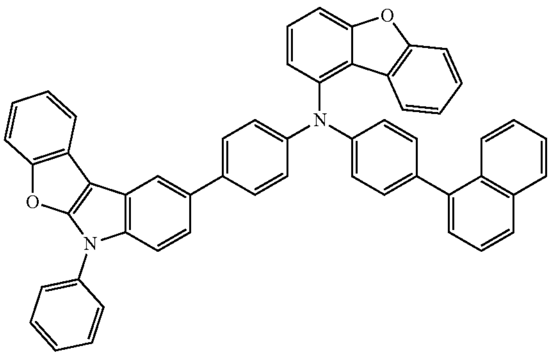
B46
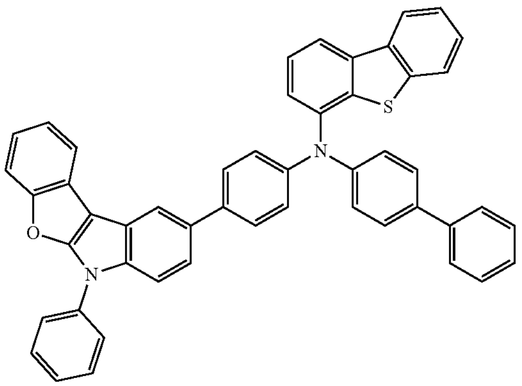
B47
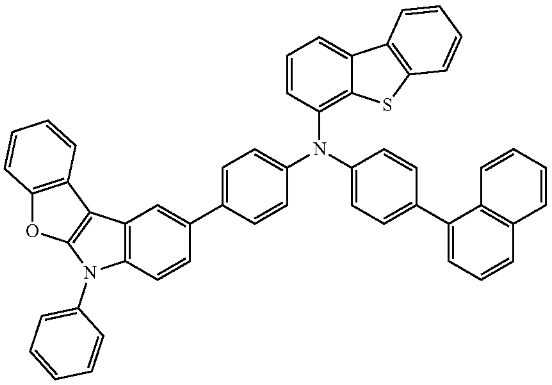
B48
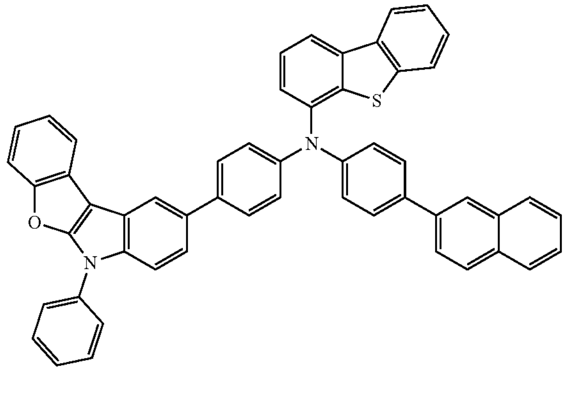

-continued
B49
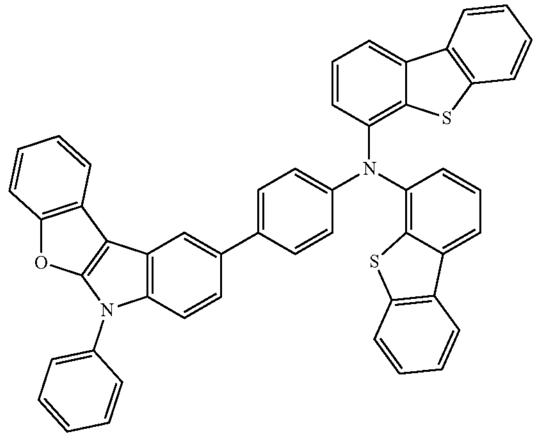
B50
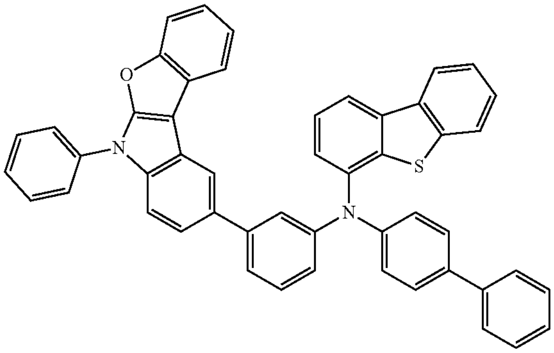
B51
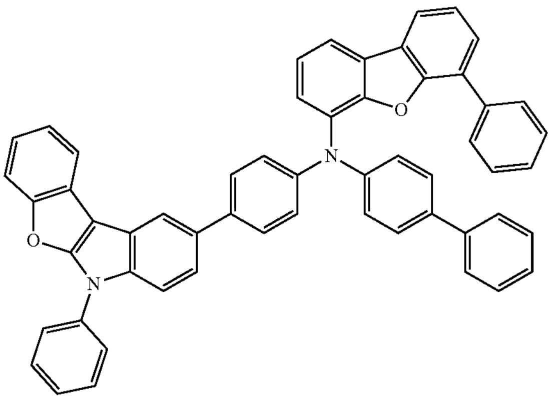
-continued
B52
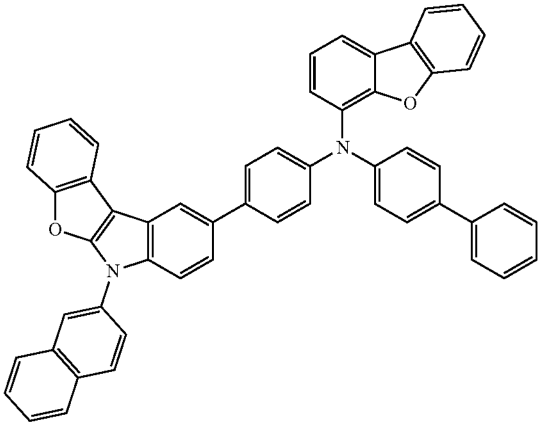
B53
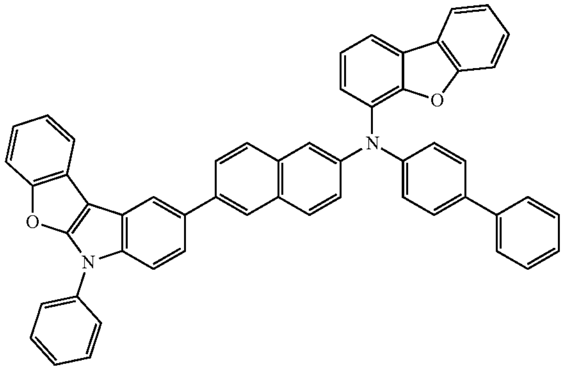
B54
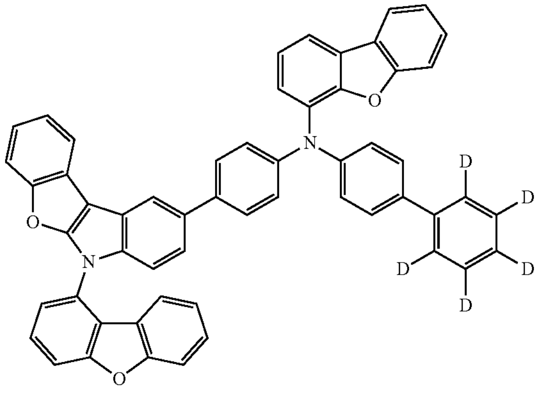

-continued
B55
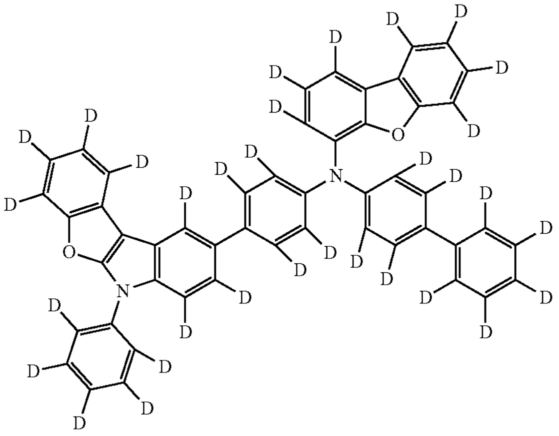
B56
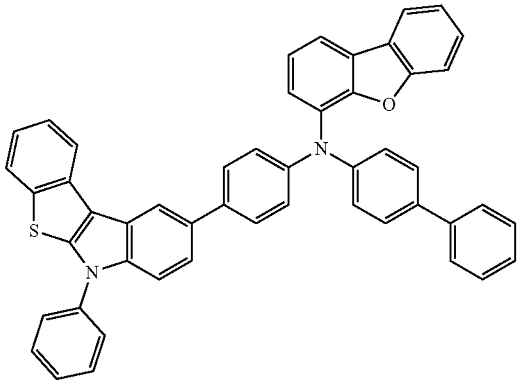
B57
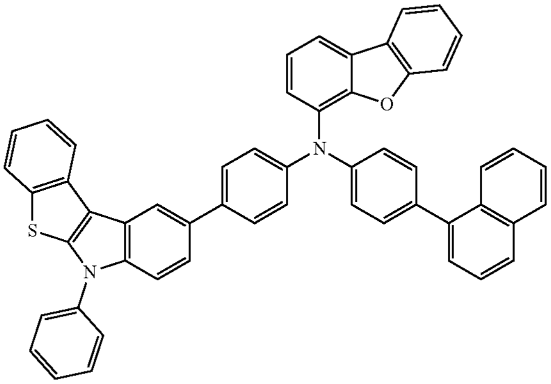
B58
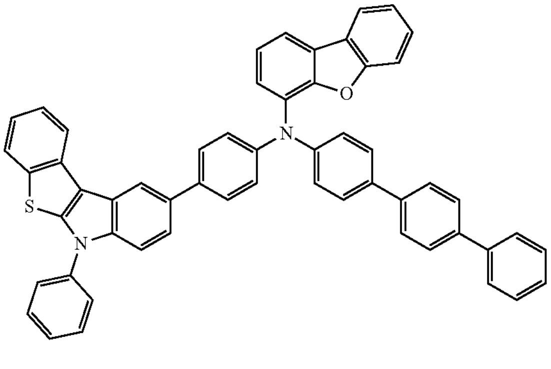
-continued
B59
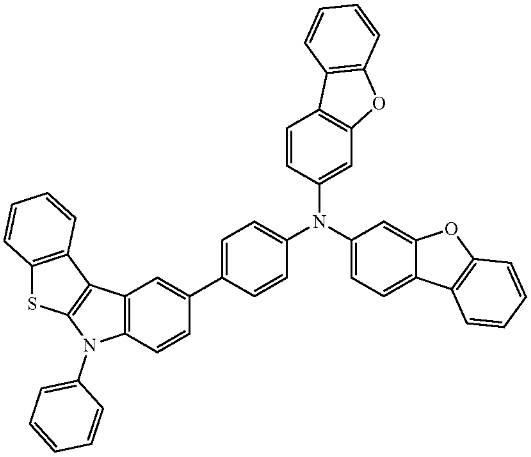
B60
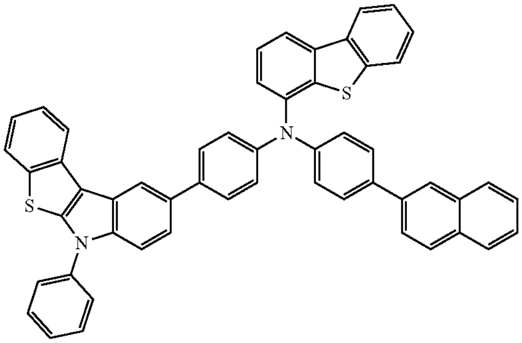
B61
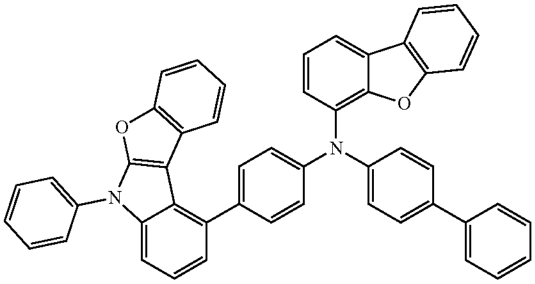
B62
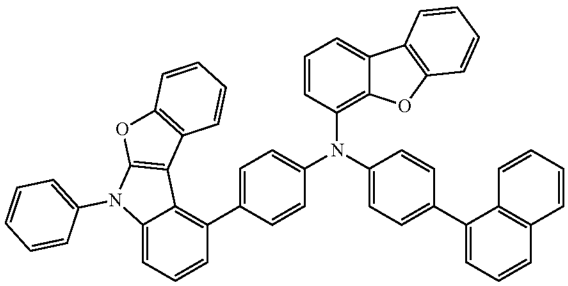

-continued
B63
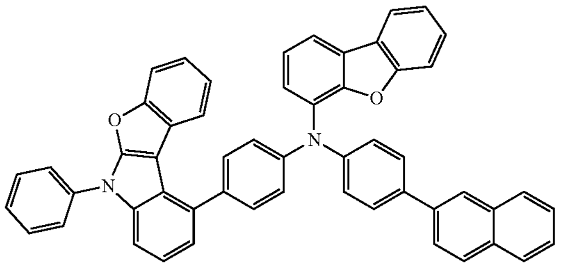
B64
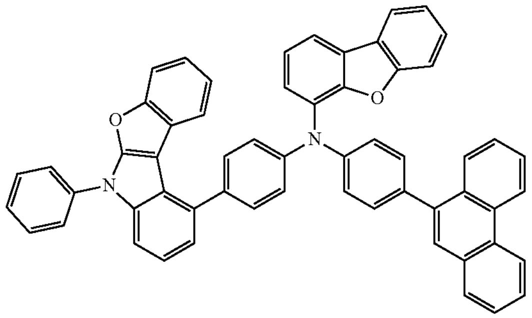
B65
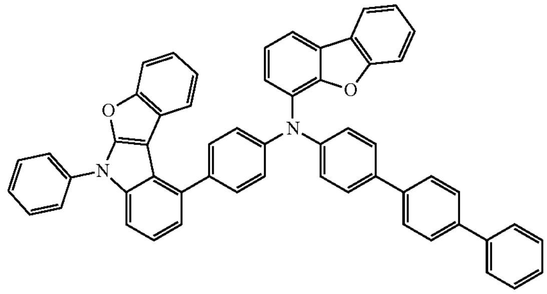
B66
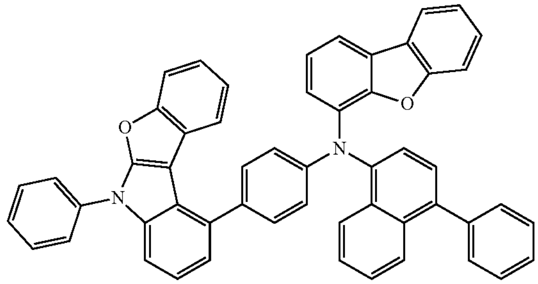
B67
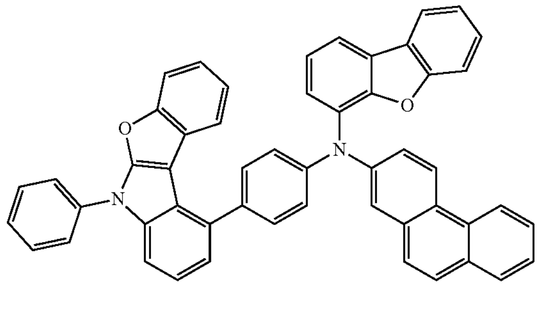
-continued
B68
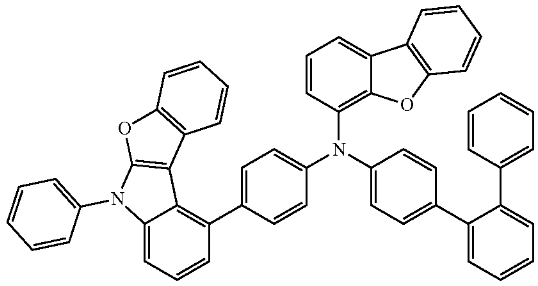
B69
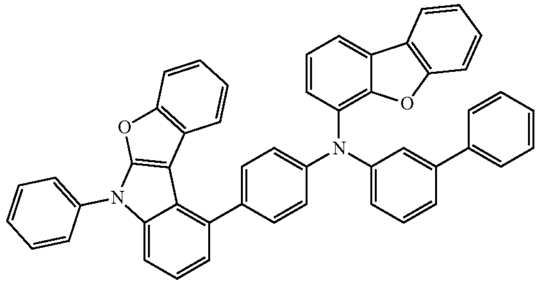
B70
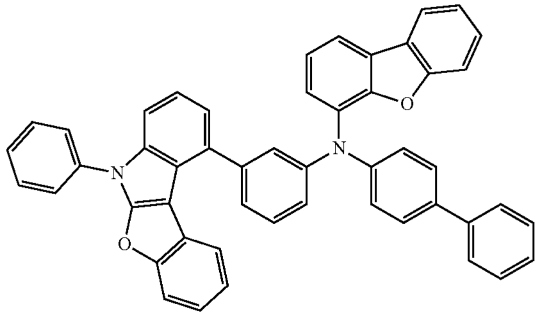
B71
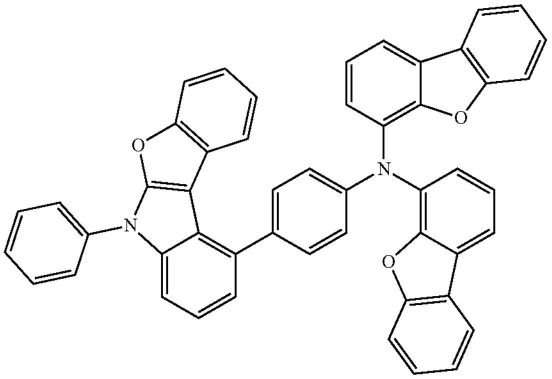

-continued
B72
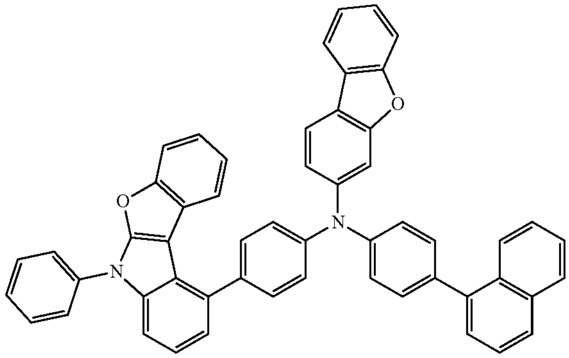
B73
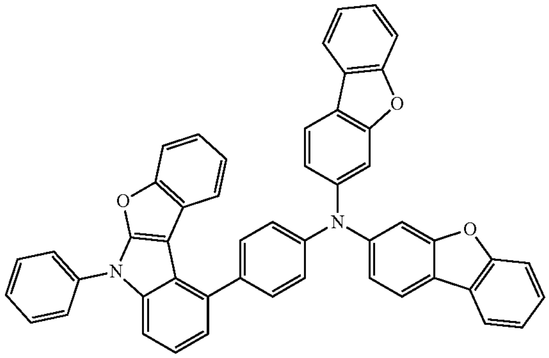
B74
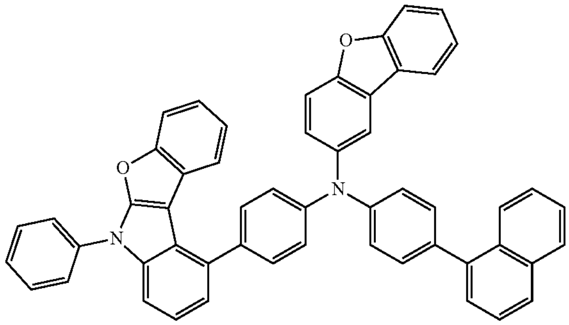
B75
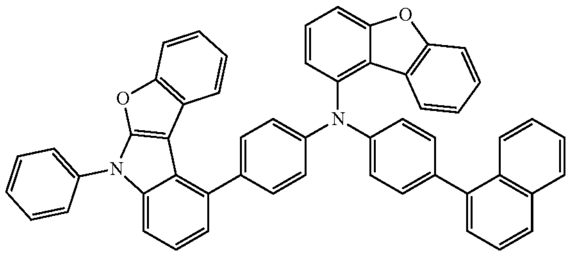
-continued
B76
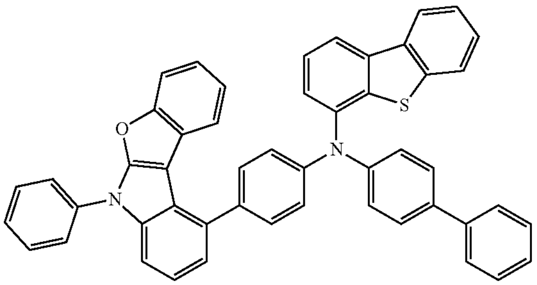
B77
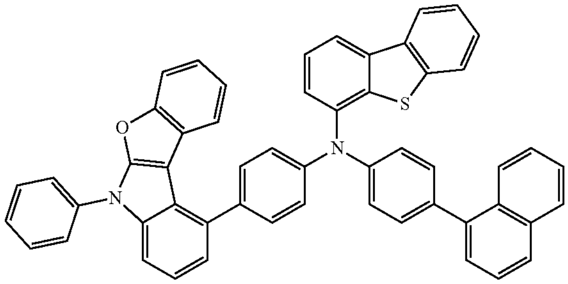
B78
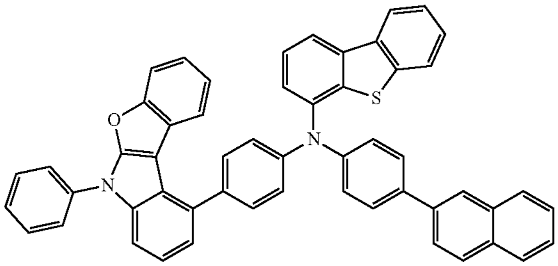
B79
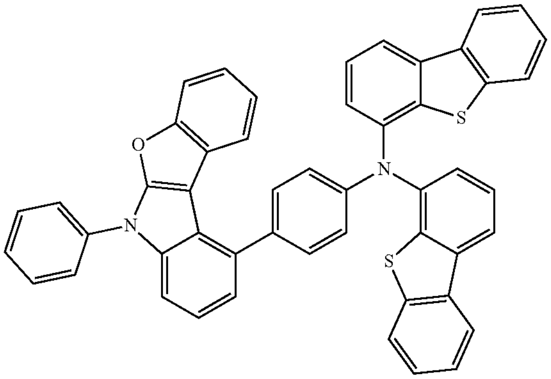
B80
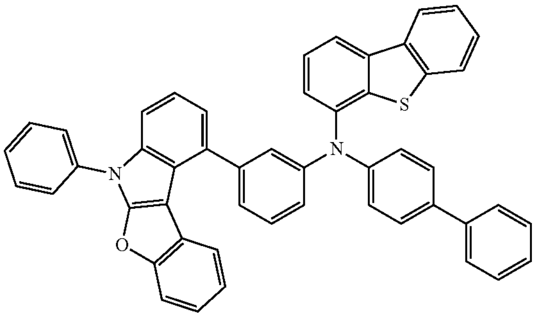

-continued
B81
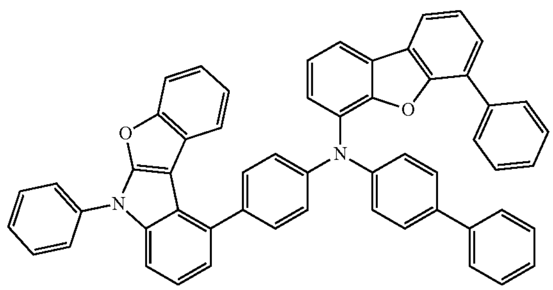
B82
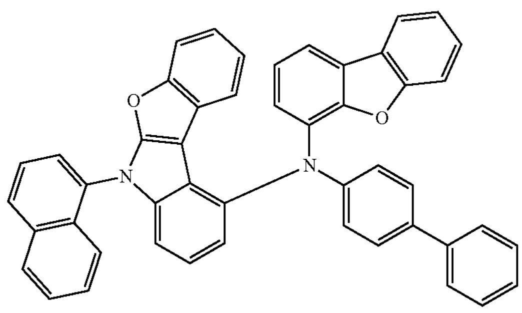
B83
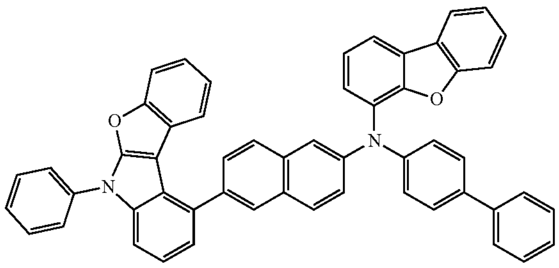
B84
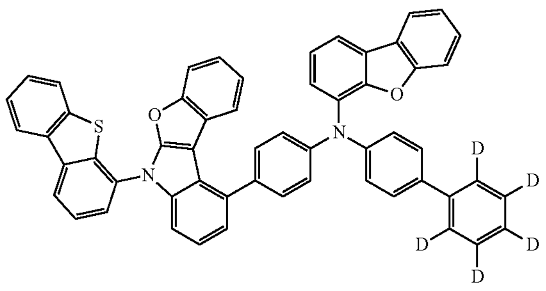
B85
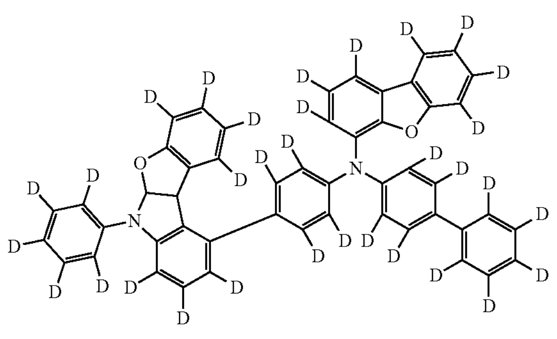
-continued
B86
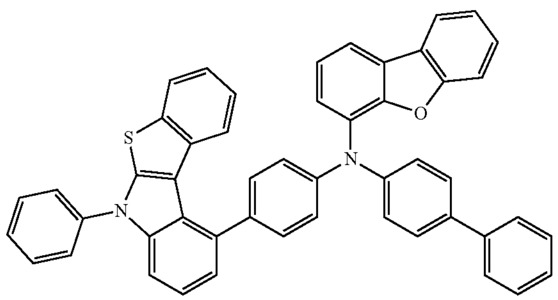
B87
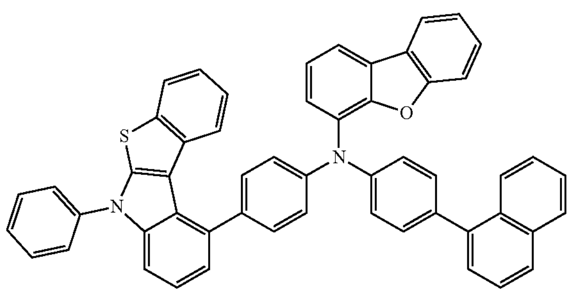
B88
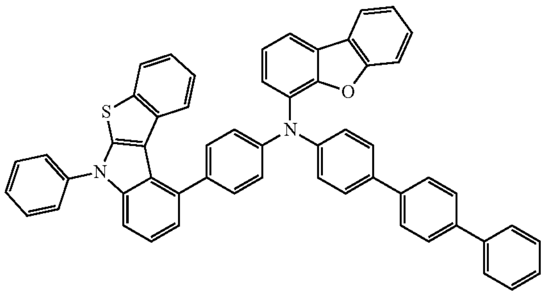
B89
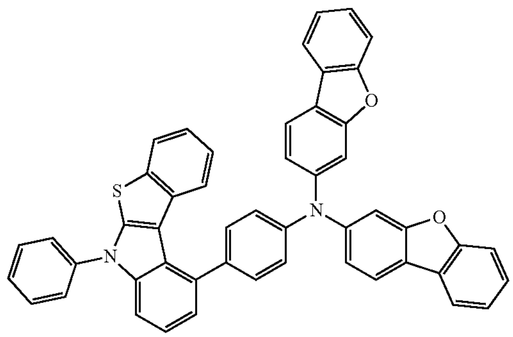
B90
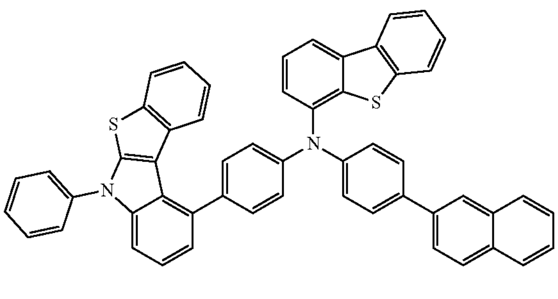

-continued
B91
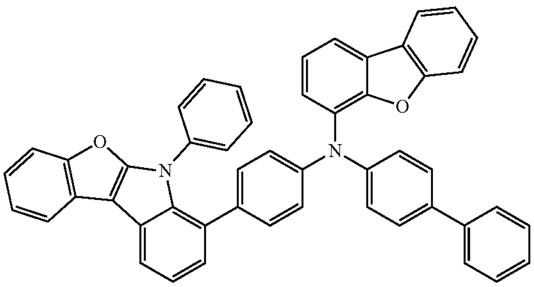
B92
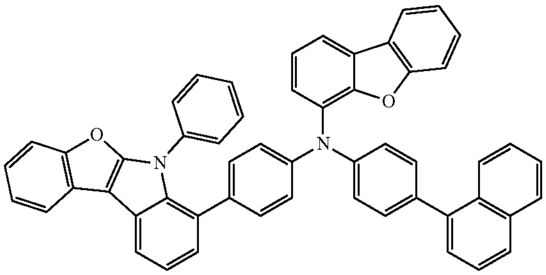
B93
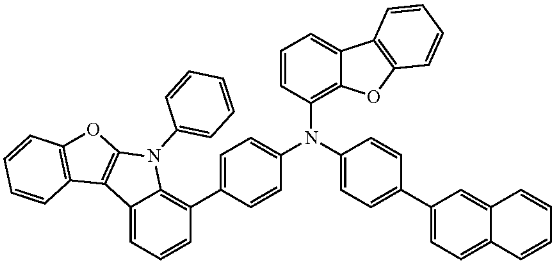
B94
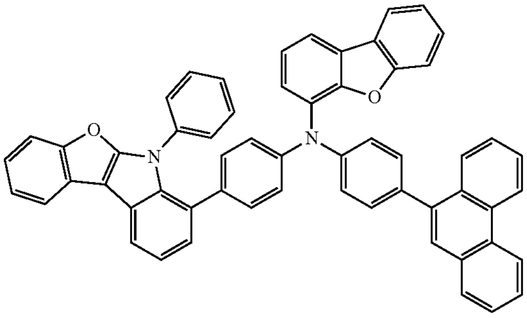
B95
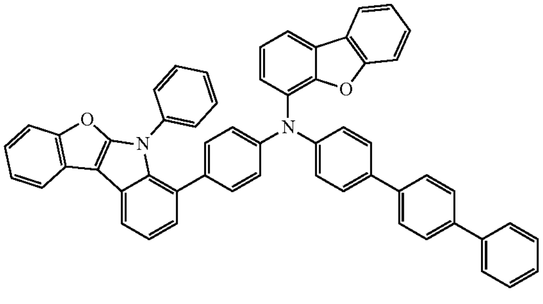
-continued
B96
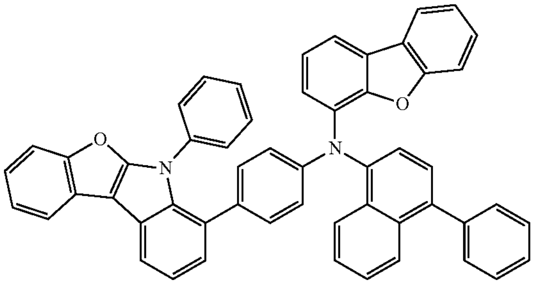
B97
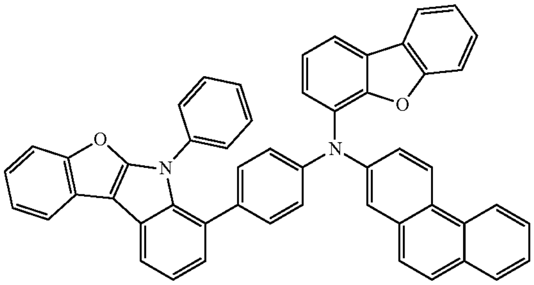
B98
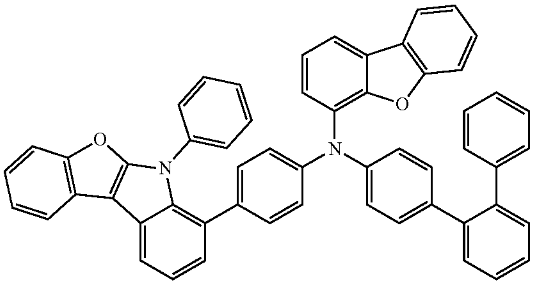
B99
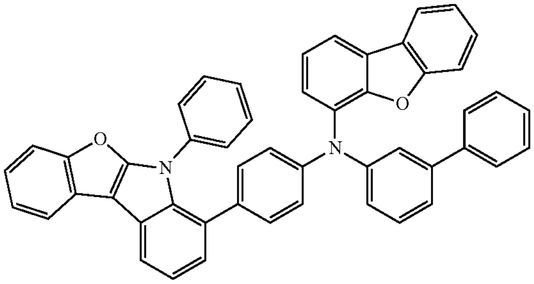
B100
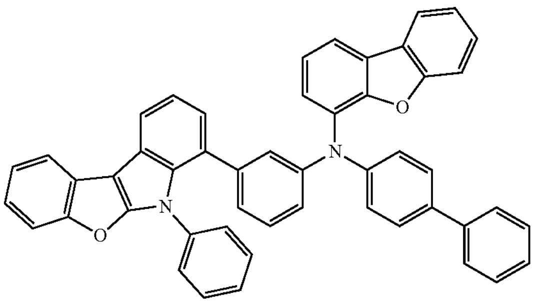

-continued
B101
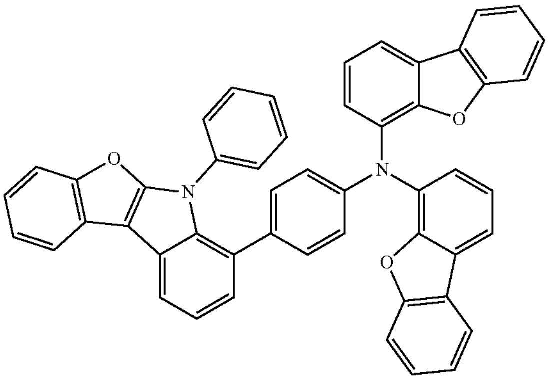
B102
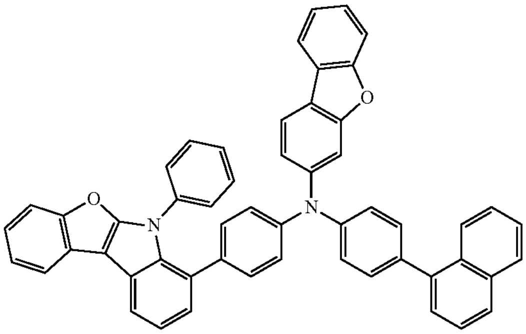
B103
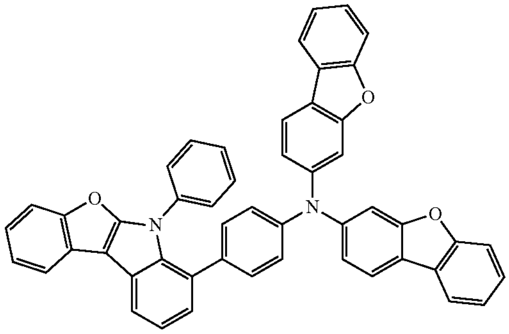
B104
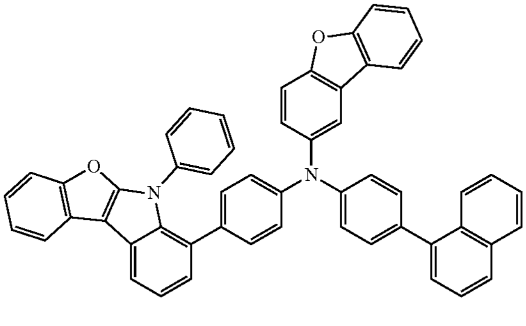
-continued
B105
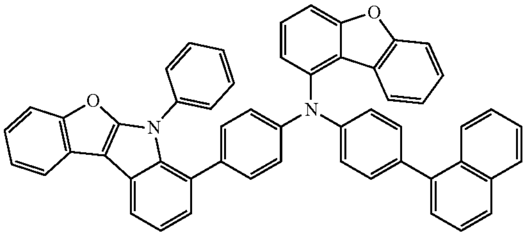
B106
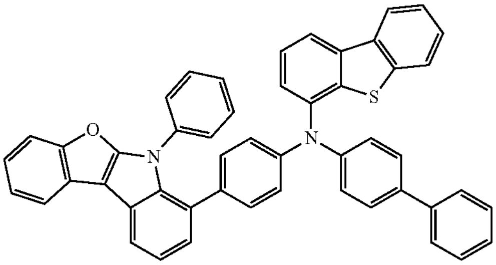
B107
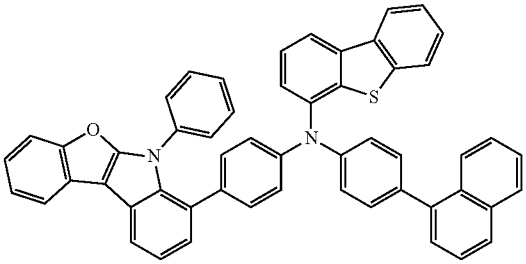
B108
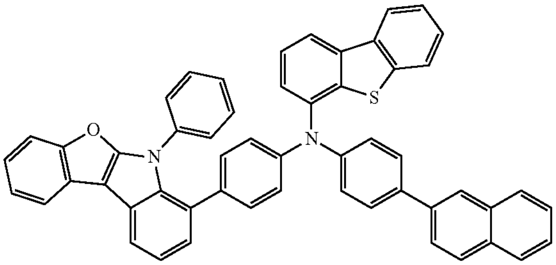
B109
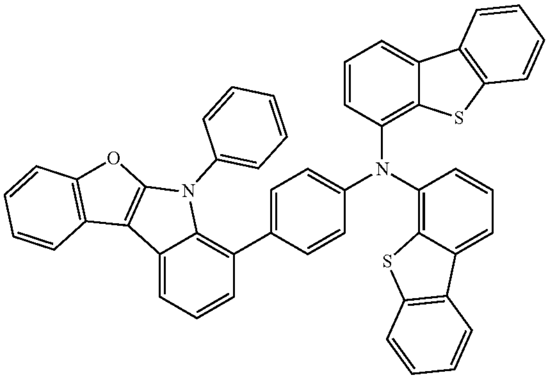

-continued
B110
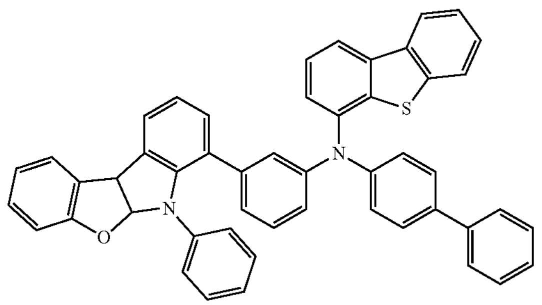
B111
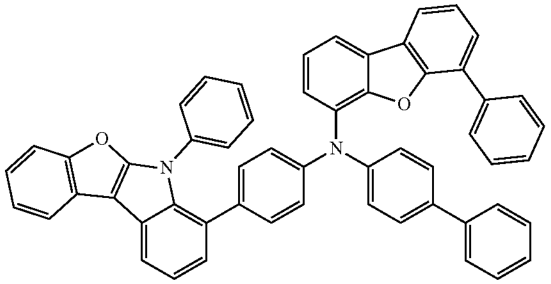
B112
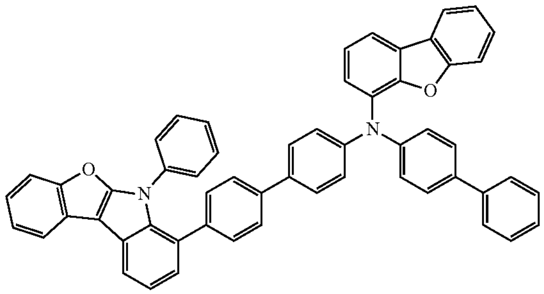
B113
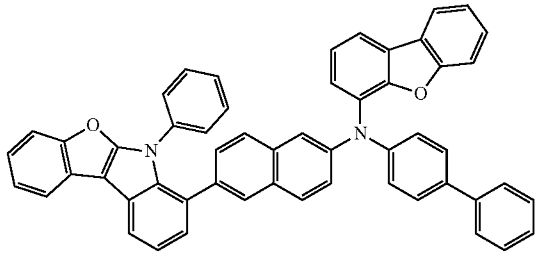
B114
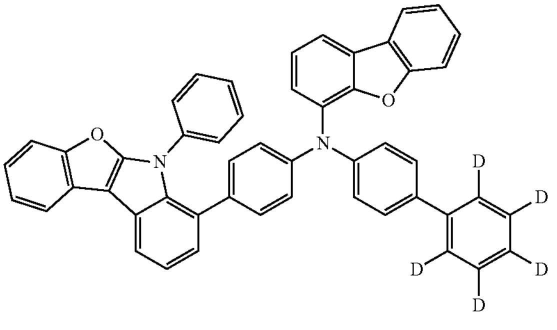
-continued
B115
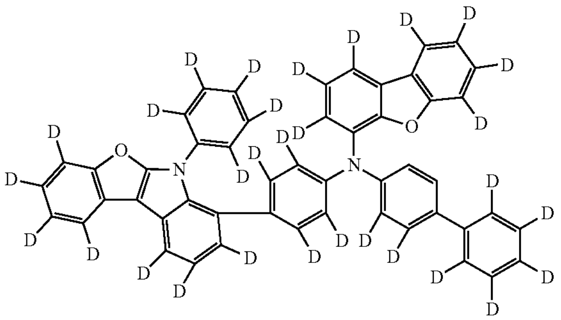
B116
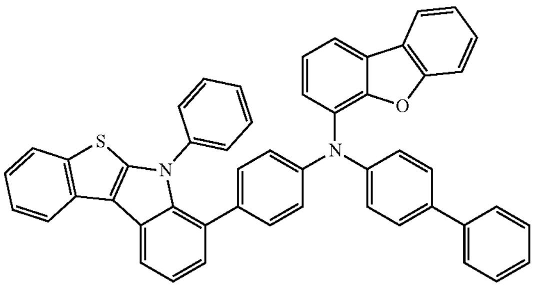
B117
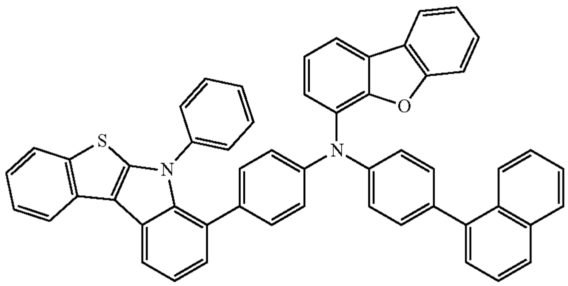
B118
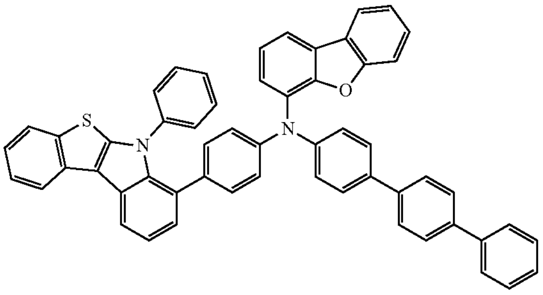

-continued
B119
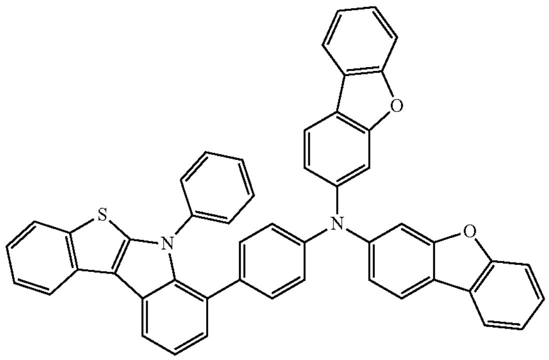
B120
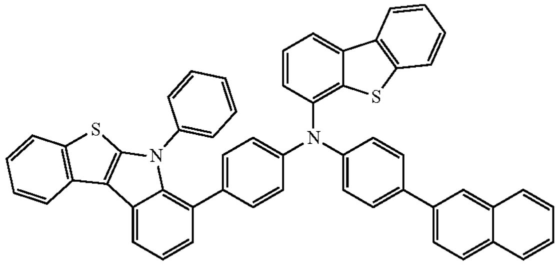
B121
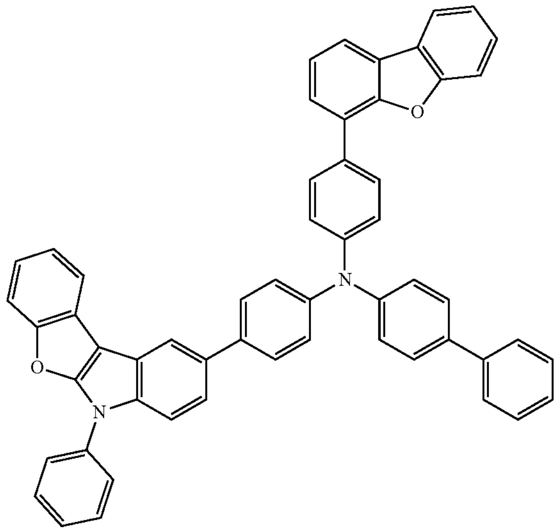
-continued
B122
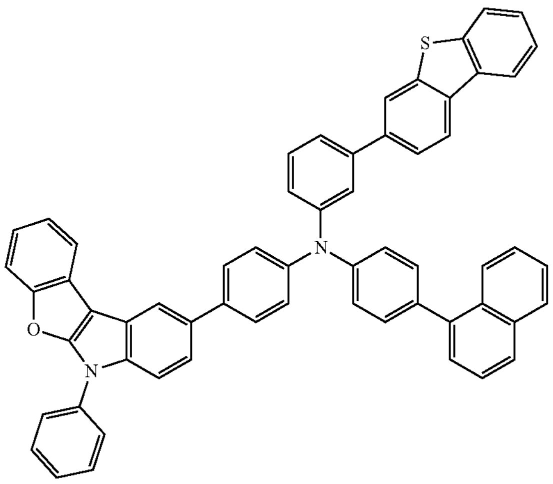
B123
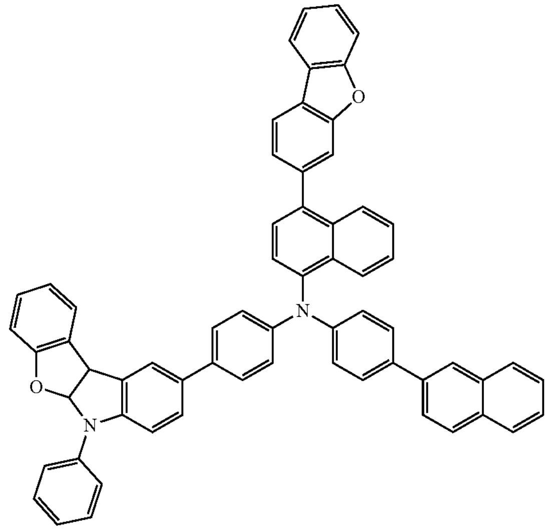
B124
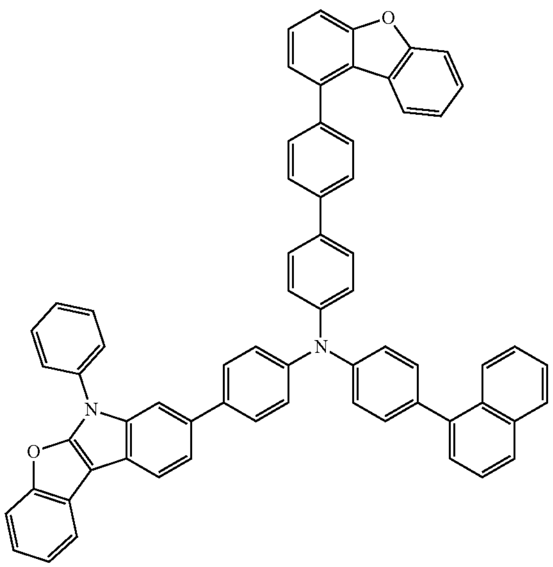

-continued
B125
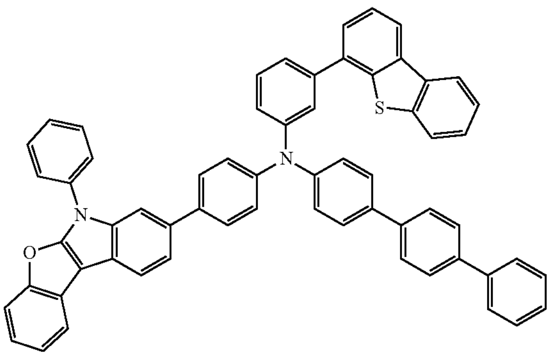
B126
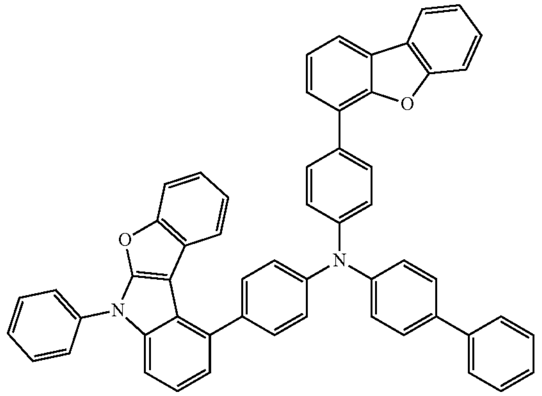
B127
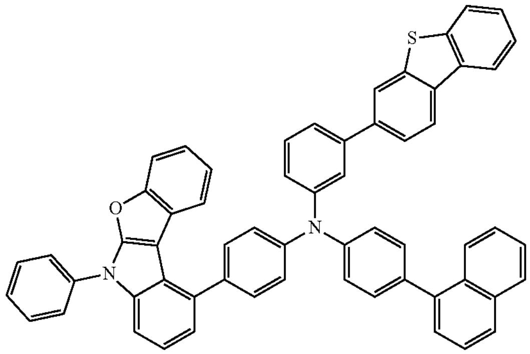
B128
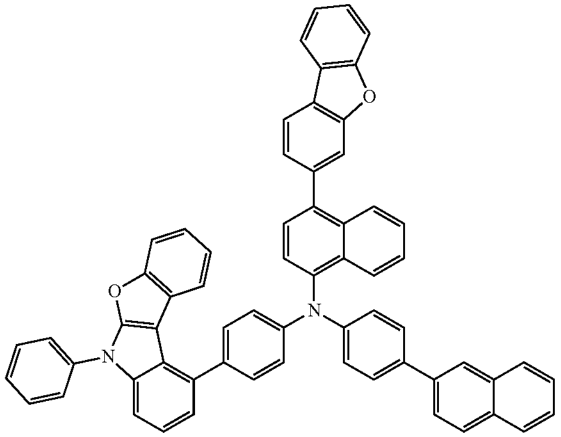
-continued
B129
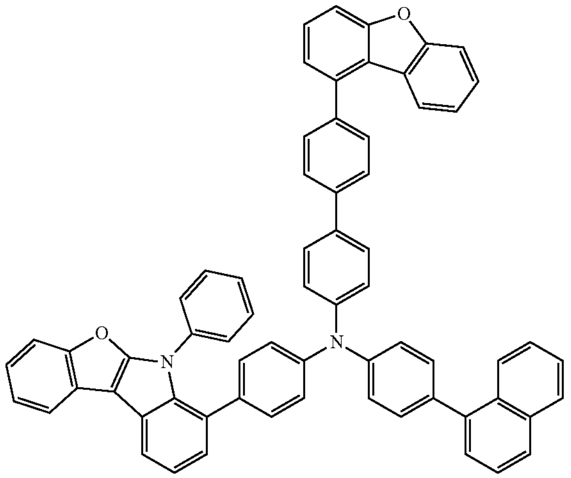
B130
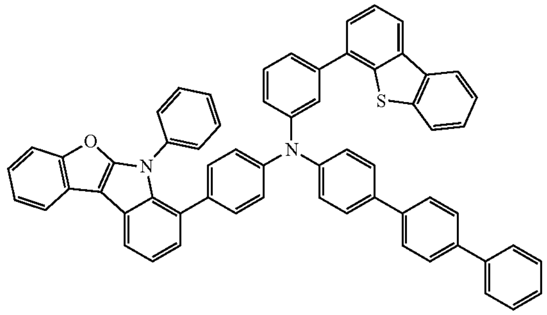
B131
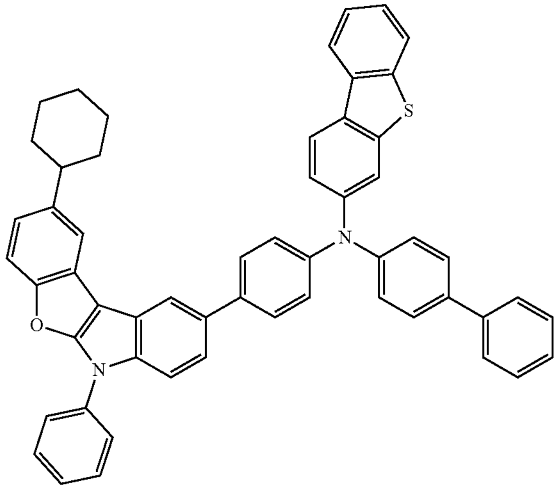

-continued
B132
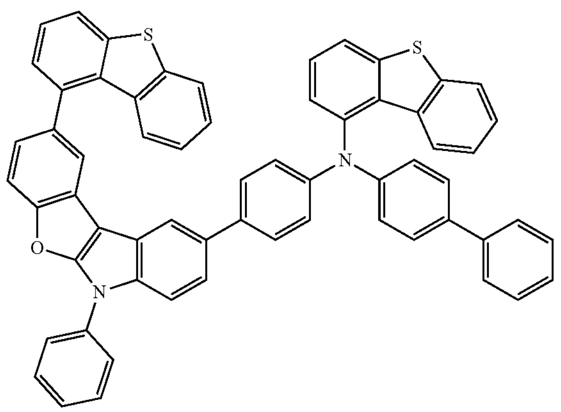
B133
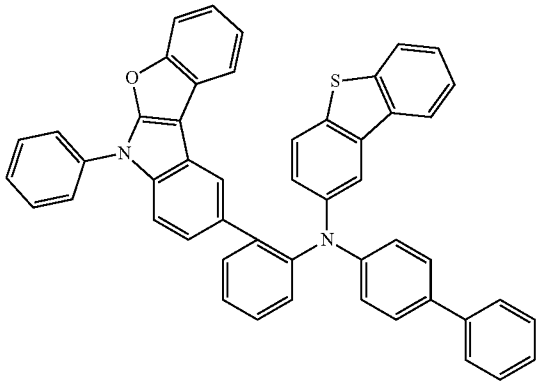
B134
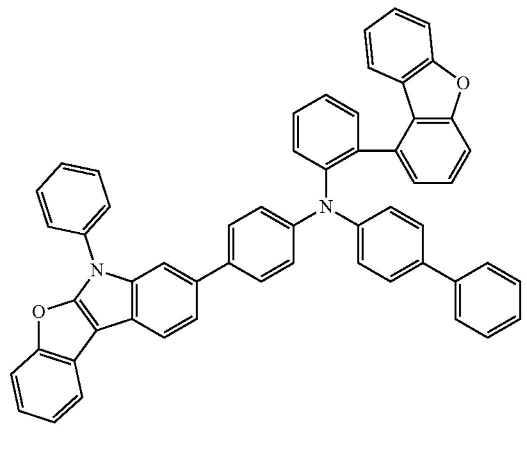
-continued
B135
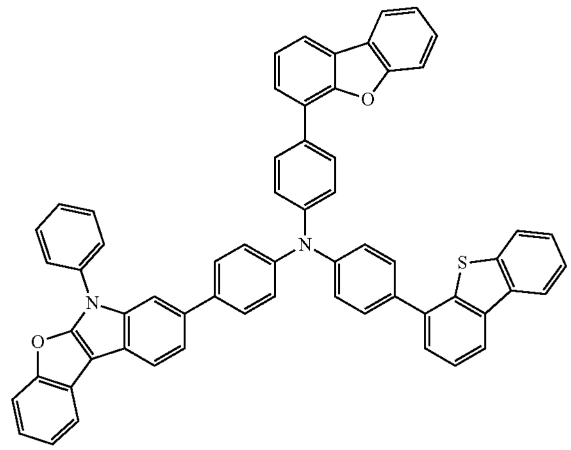
B136
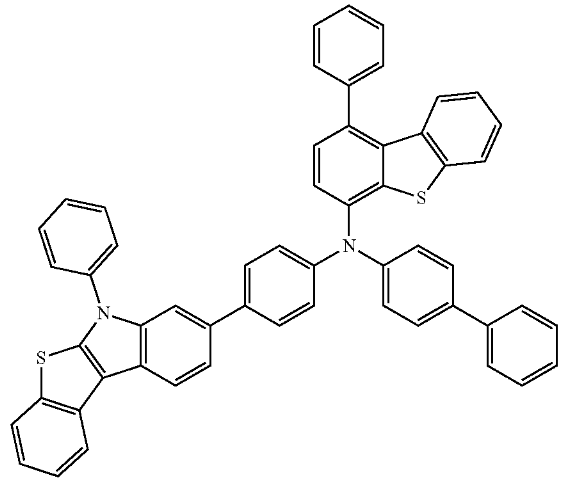
B137
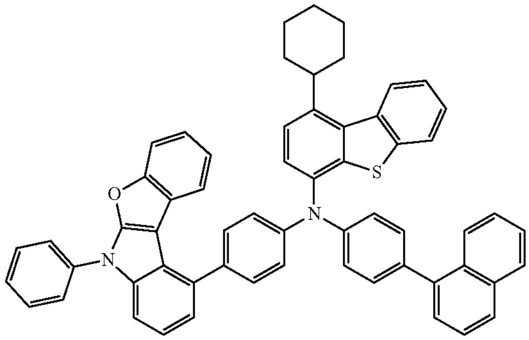
B138
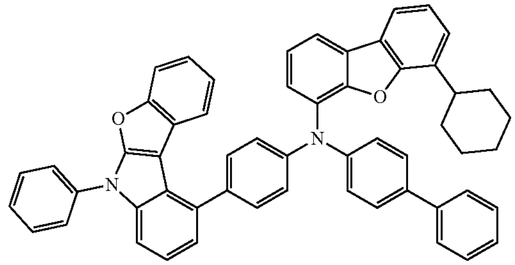

-continued
B139
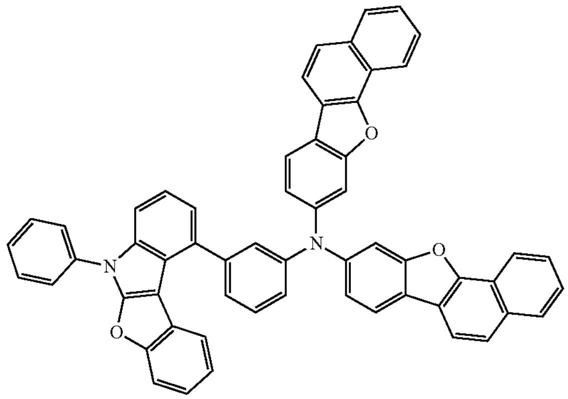
-continued
B140
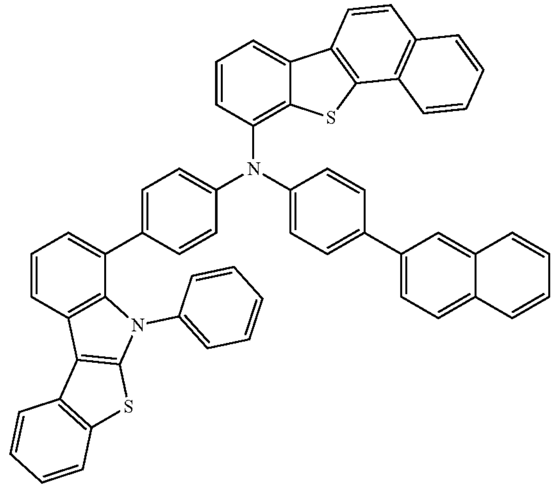
.
14. The organic electroluminescence device of claim 1, wherein the monoamine compound represented by Formula 1 is at least one compound represented in Compound Group 3:
[Compound Group 3]
C1
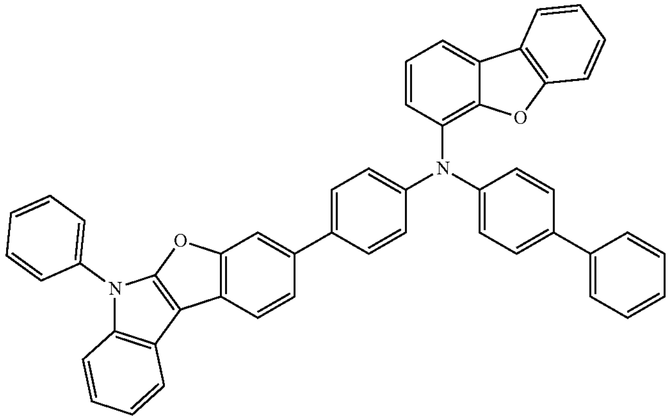
C2
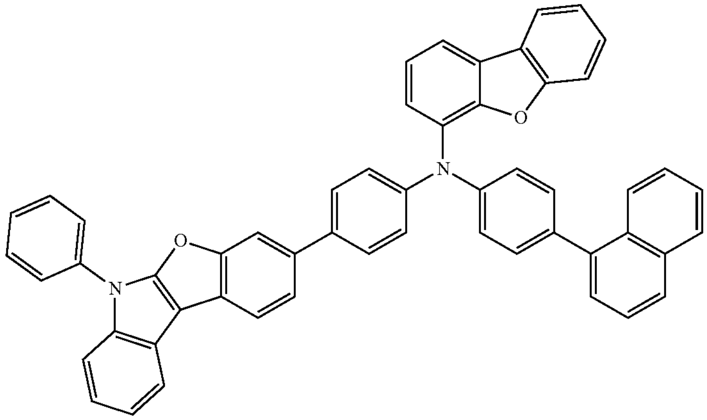

-continued
C3
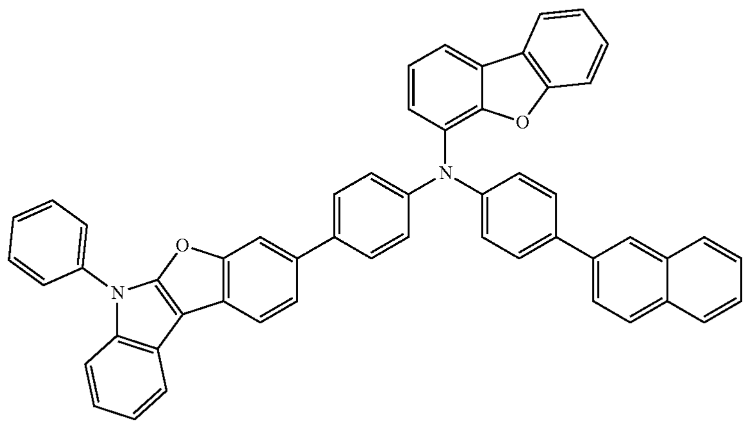
C4
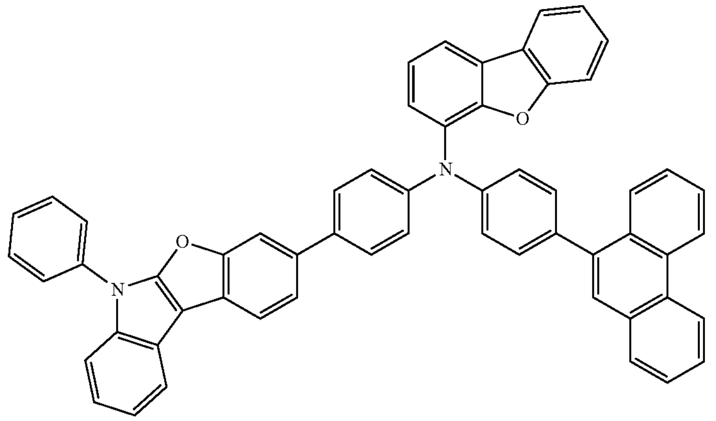
C5
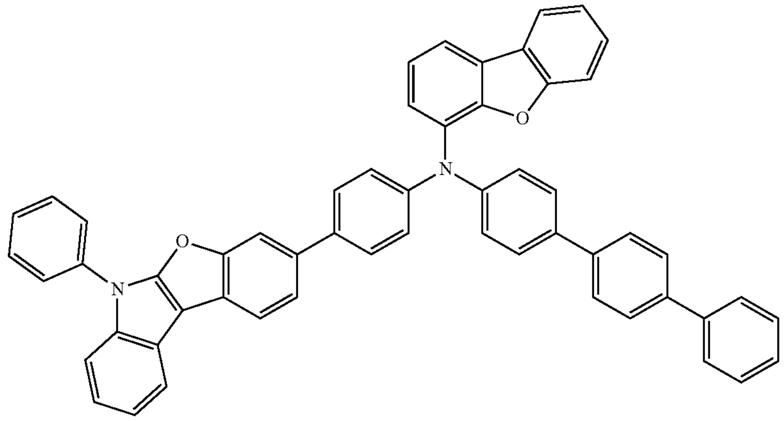

-continued
C6
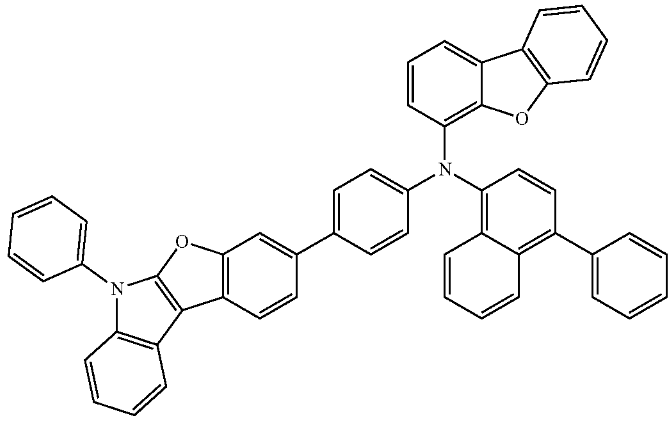
C7
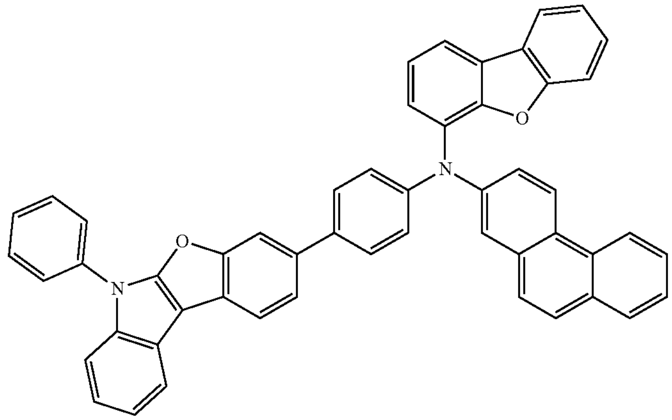
C8
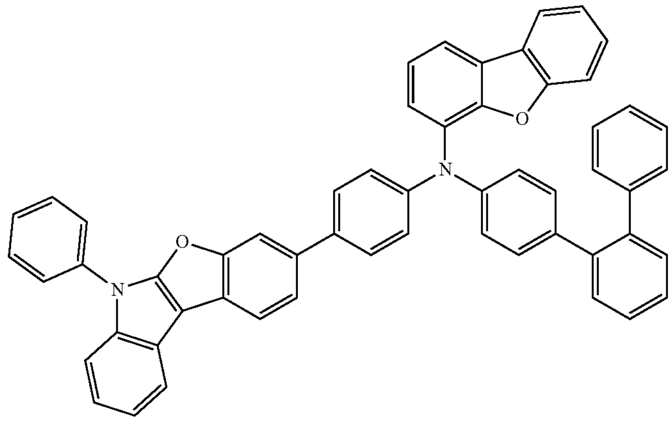

-continued
C9
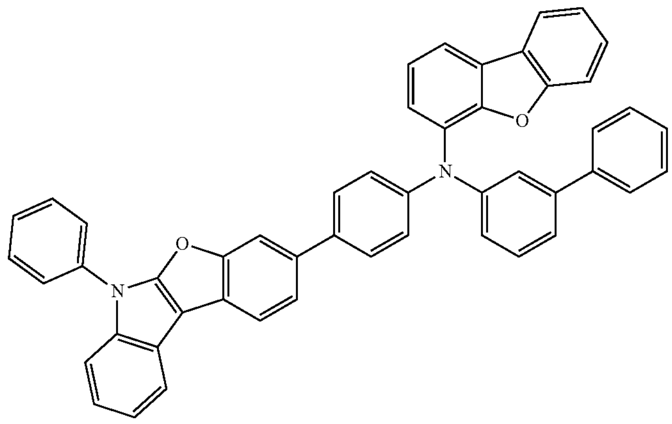
C10
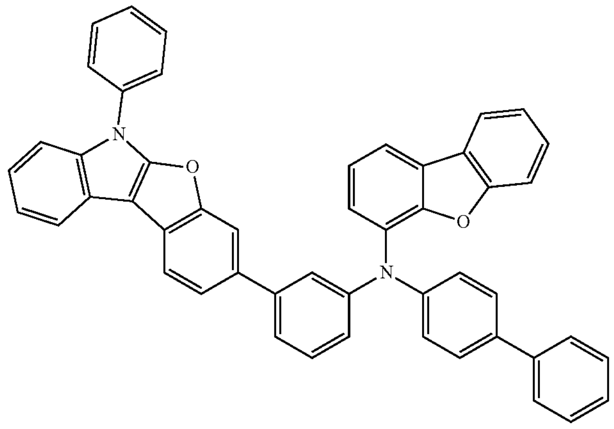
C11
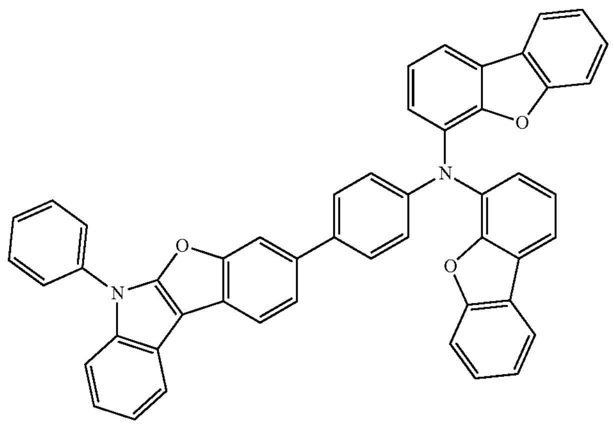

-continued
C12
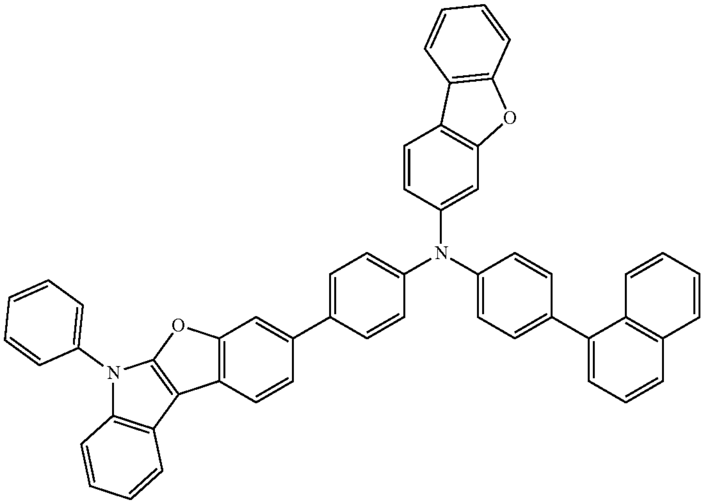
C13
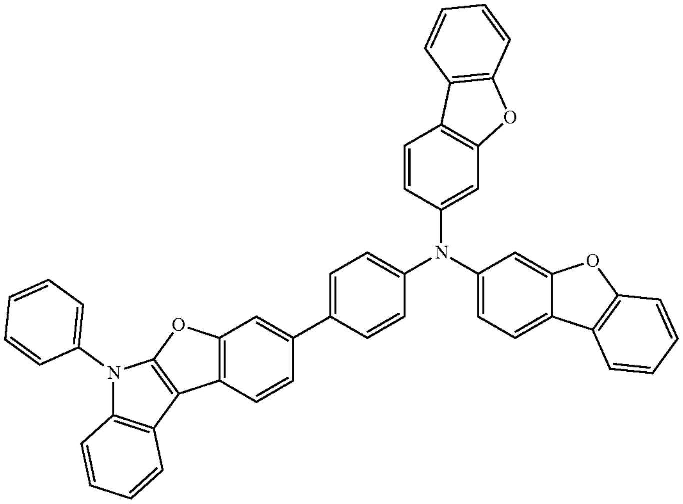
C14
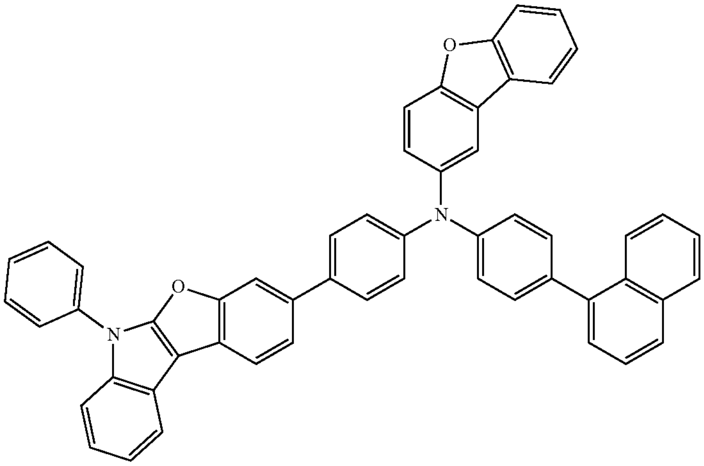

-continued
C15
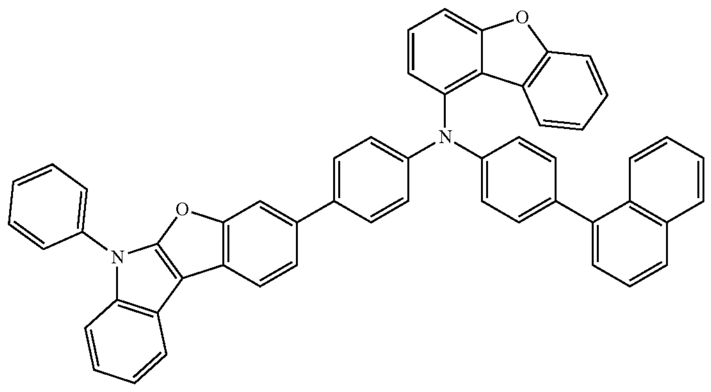
C16
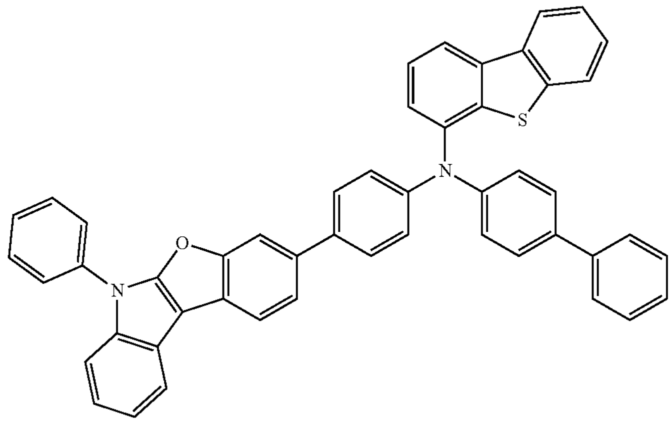
C17
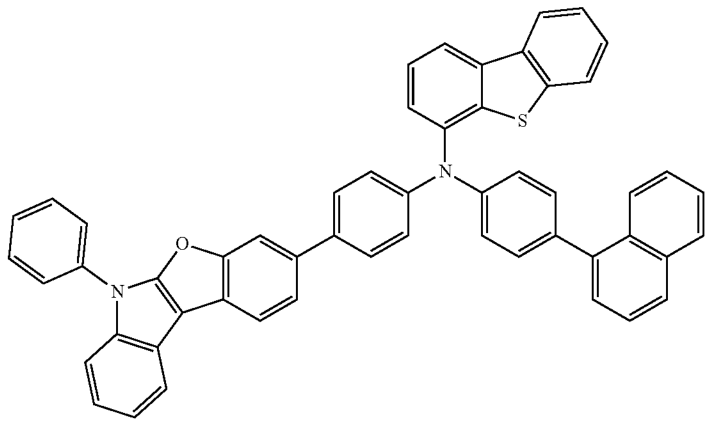

-continued
C18
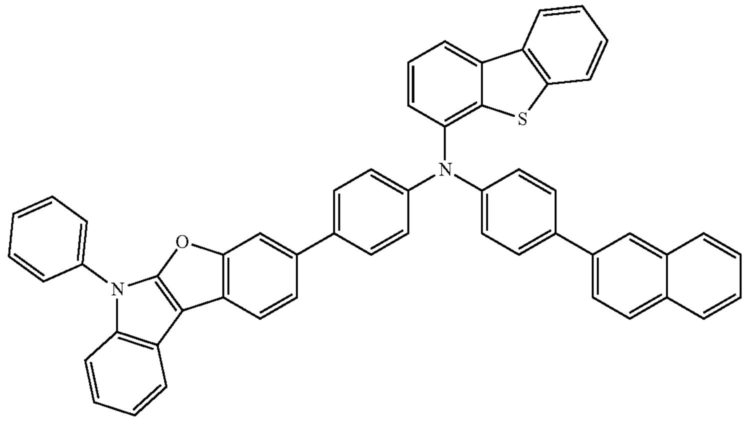
C19
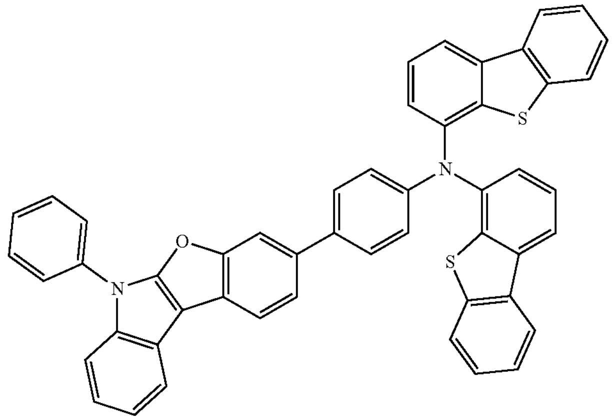
C20
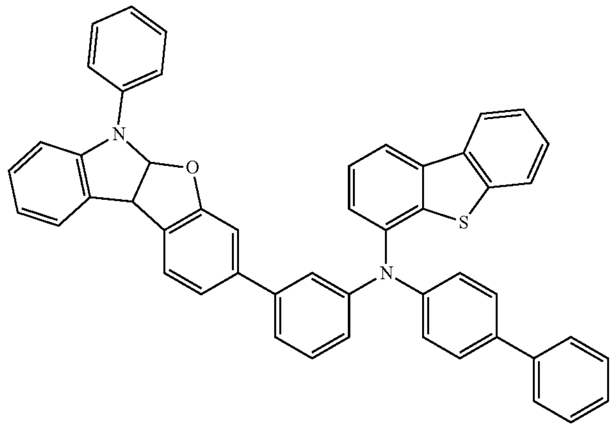

-continued
C21
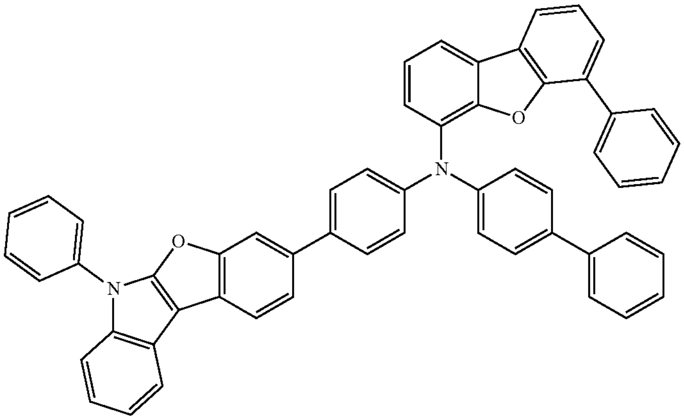
C22
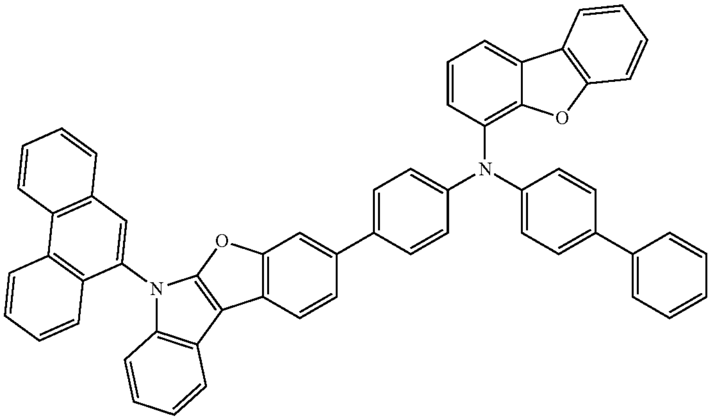
C23
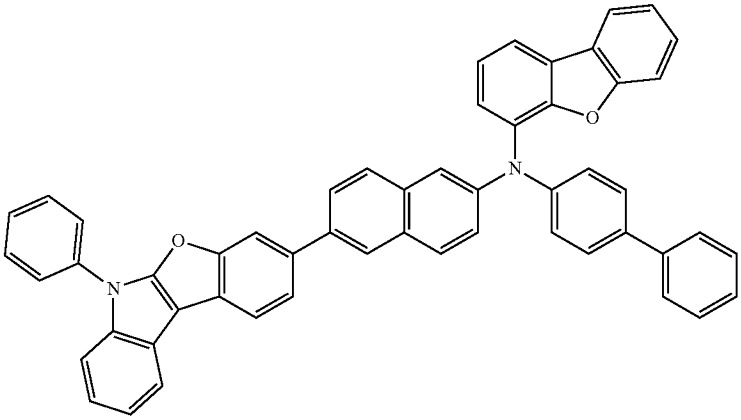

-continued
C24
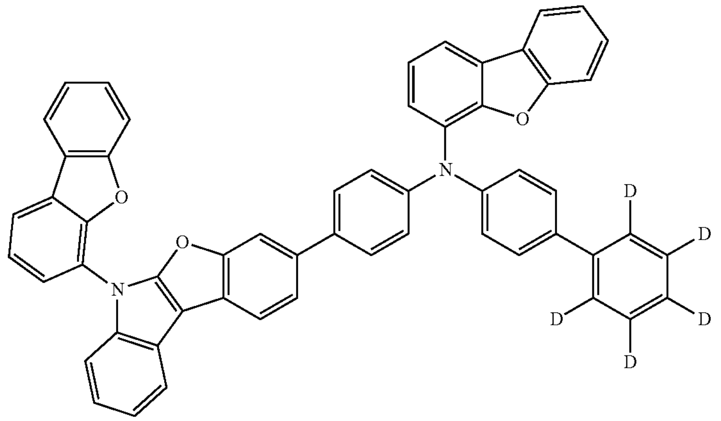
C25
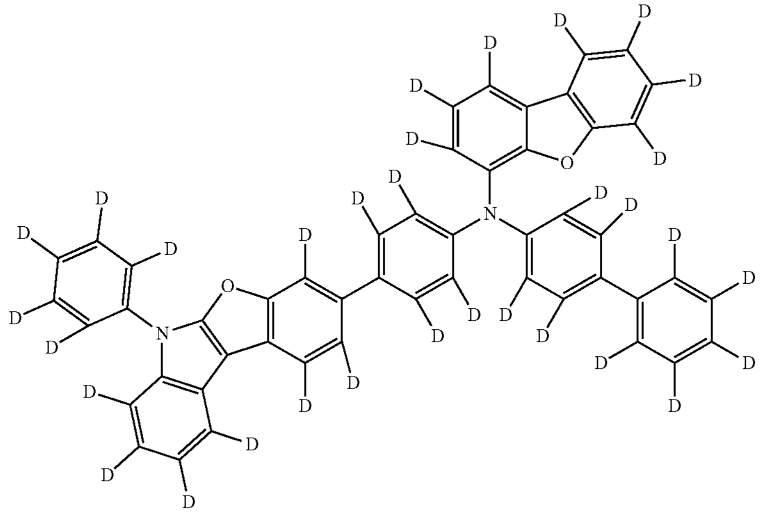
C26
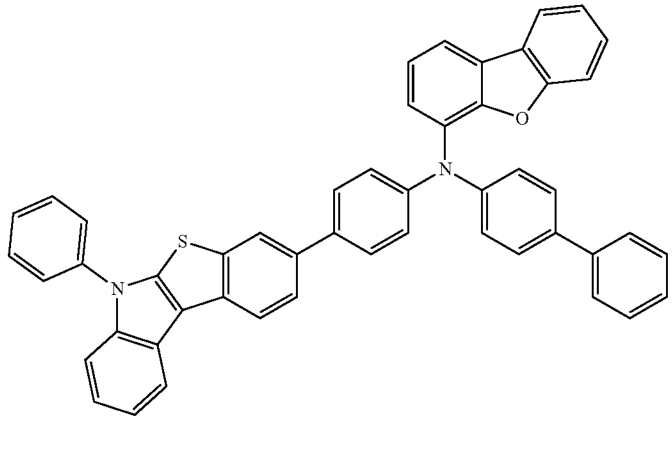

-continued
C27
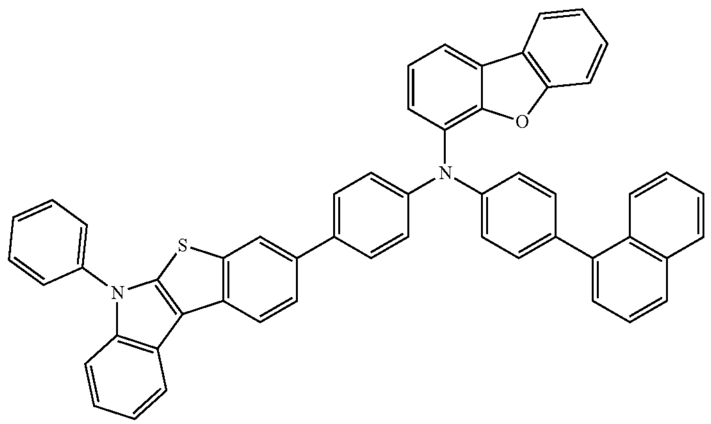
C28
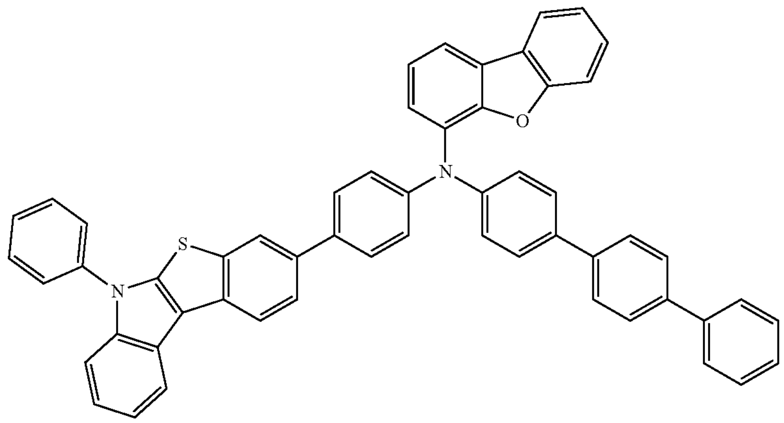
C29
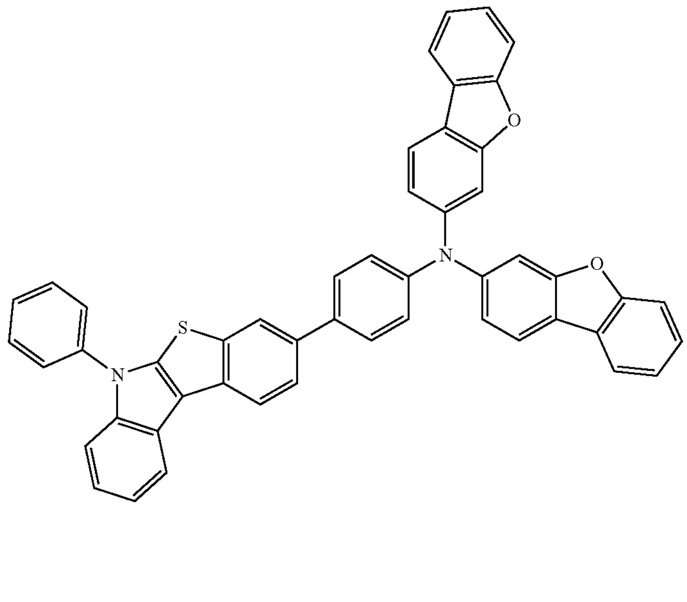

-continued
C30
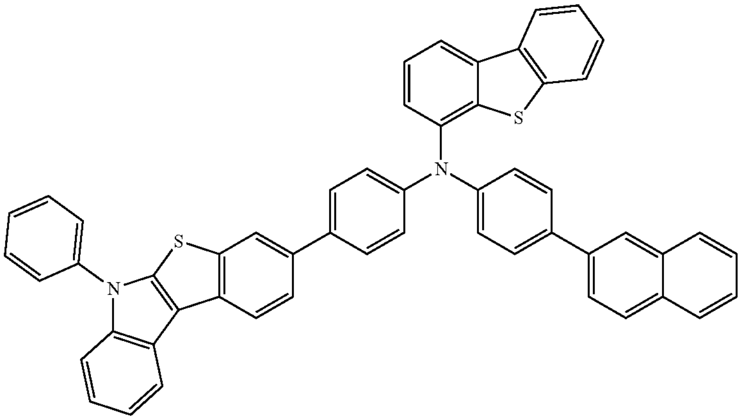
C31
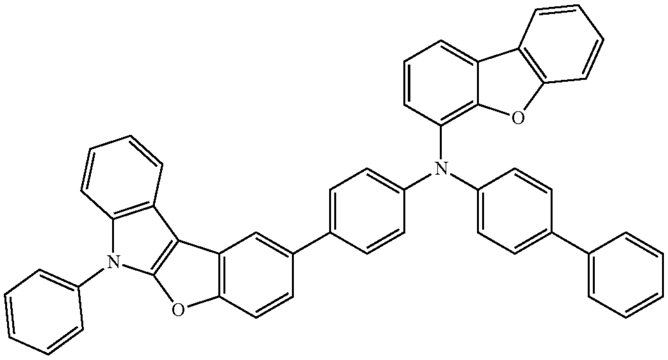
C32
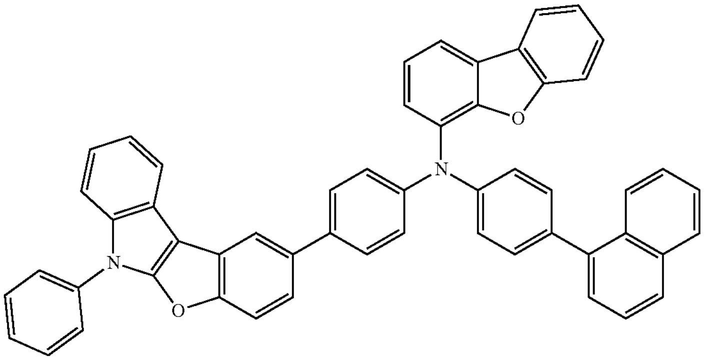
C33
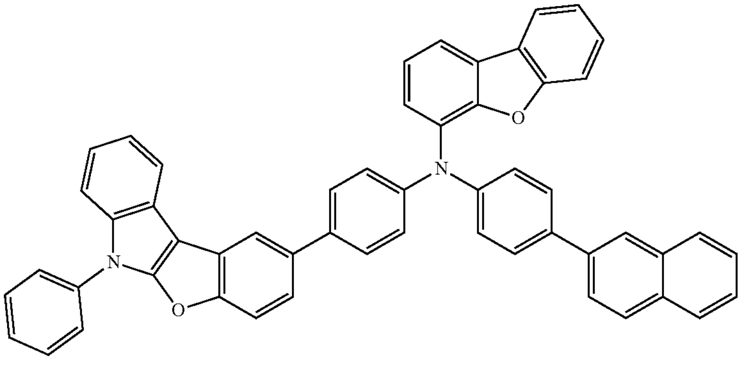

-continued
C34
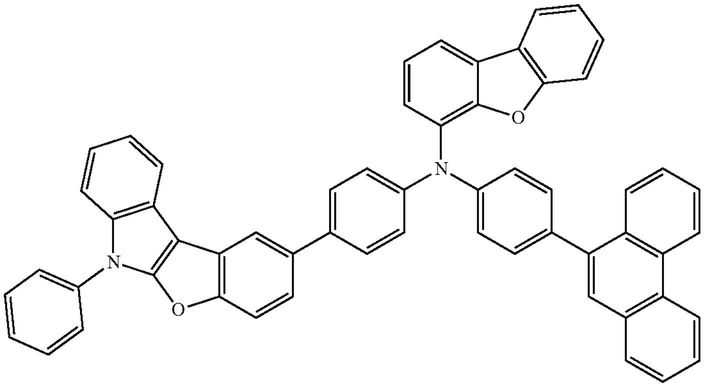
C35
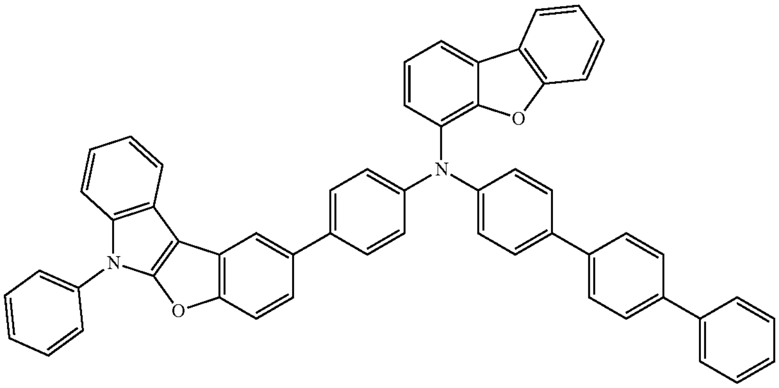
C36
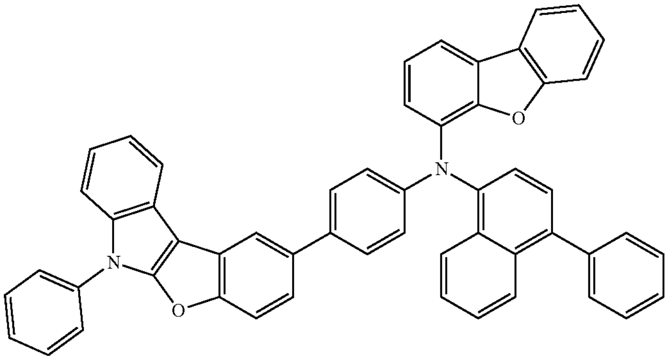
C37
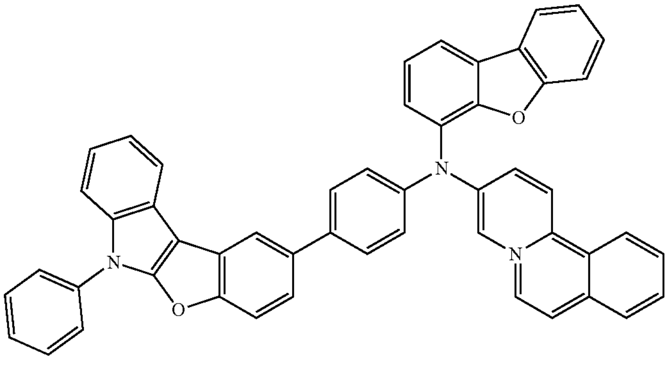

-continued
C38
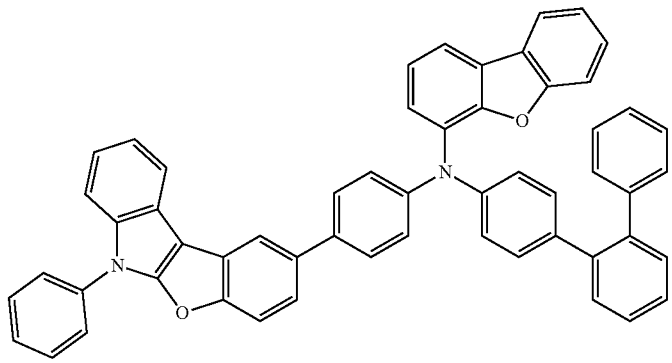
C39
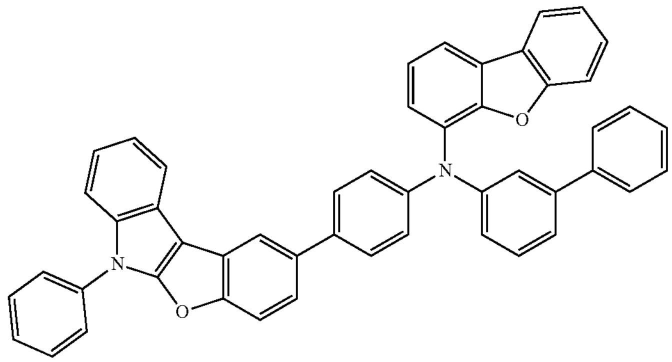
C40
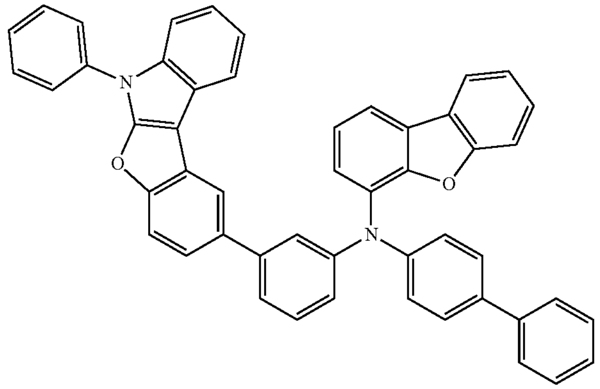
C41
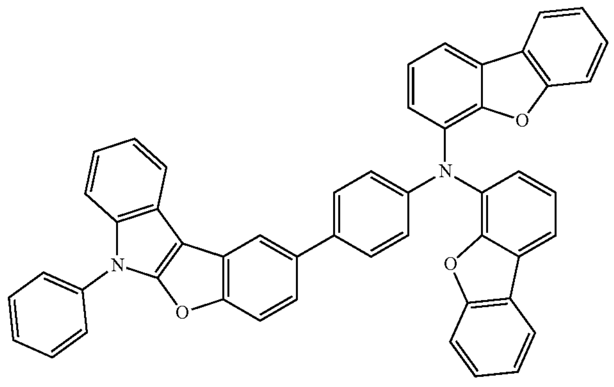

-continued
C42
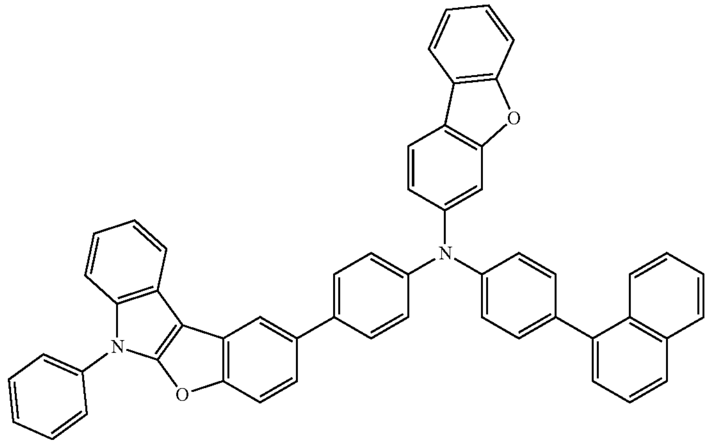
C43
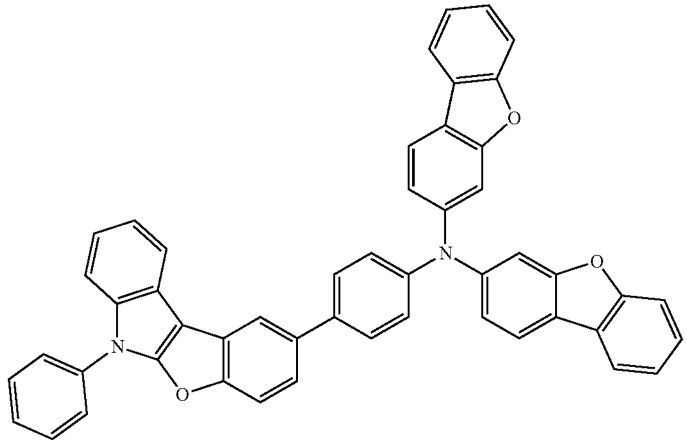
C44
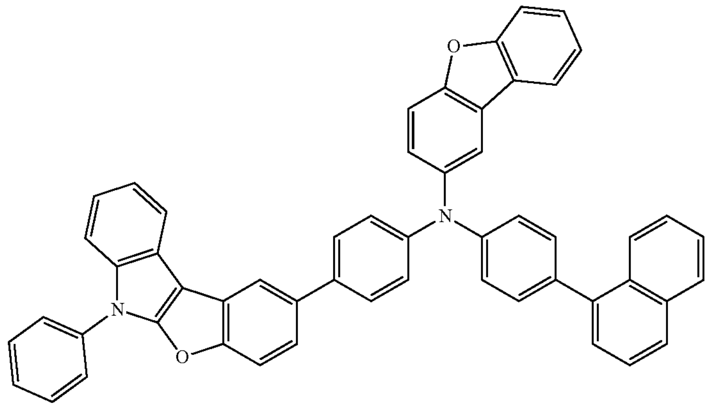
C45
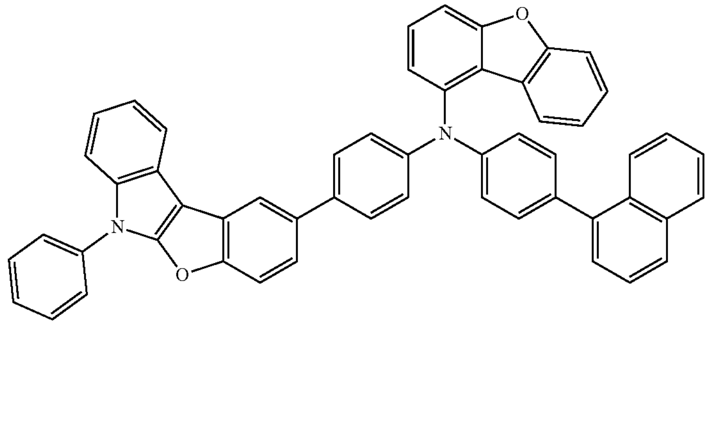

-continued
C46
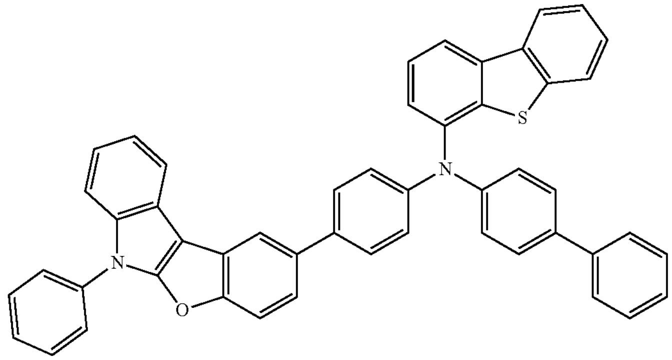
C47
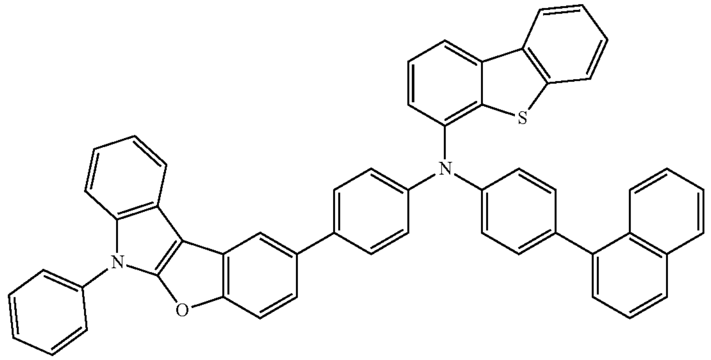
C48
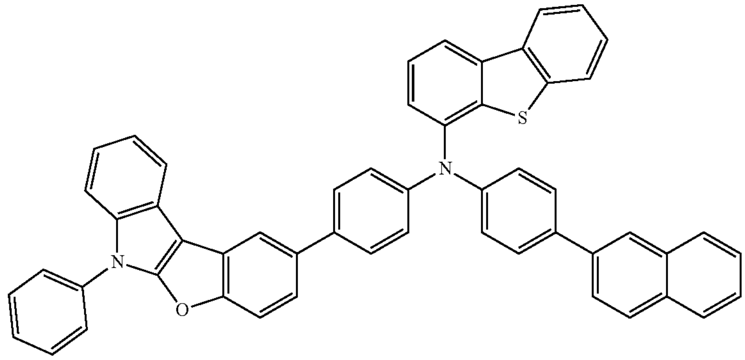
C49
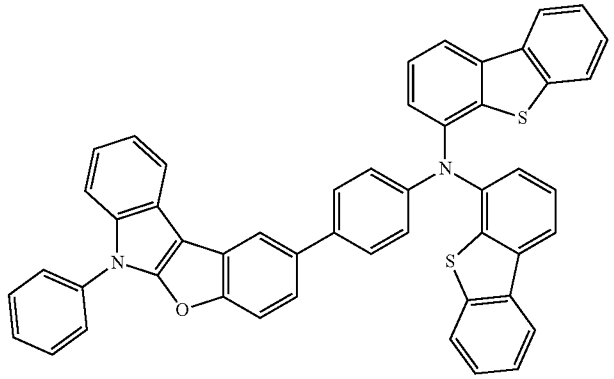

-continued
C50
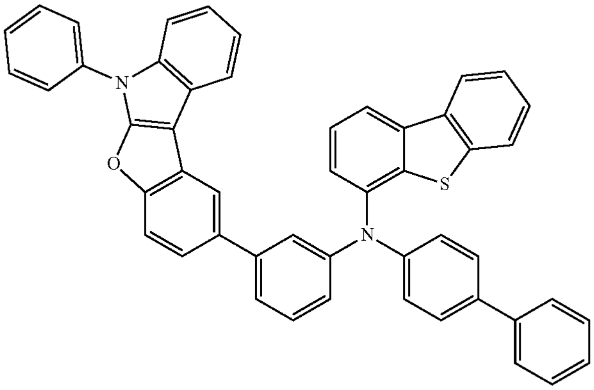
C51
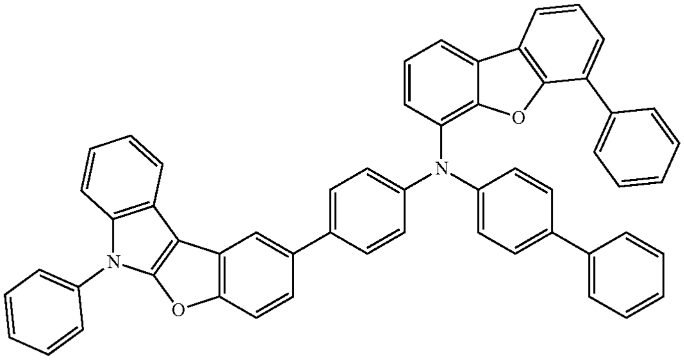
C52
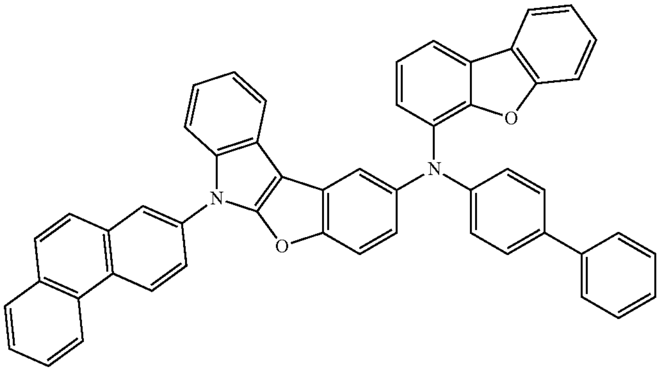
C53
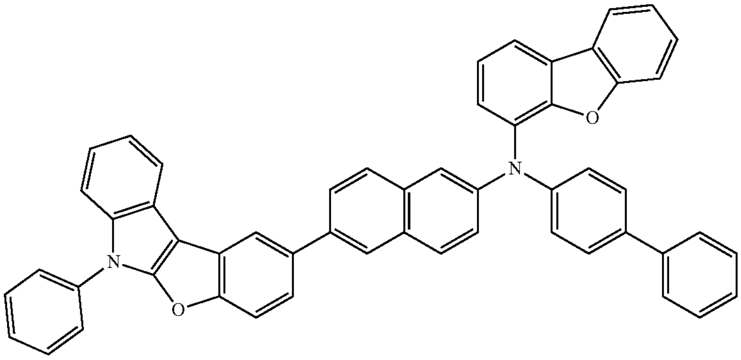

-continued
C54
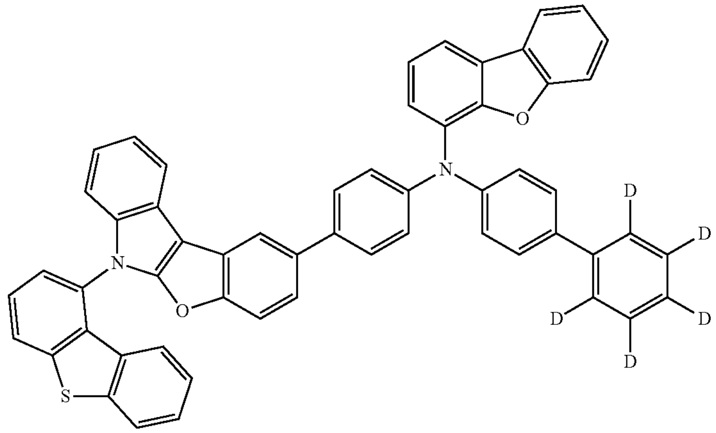
C55
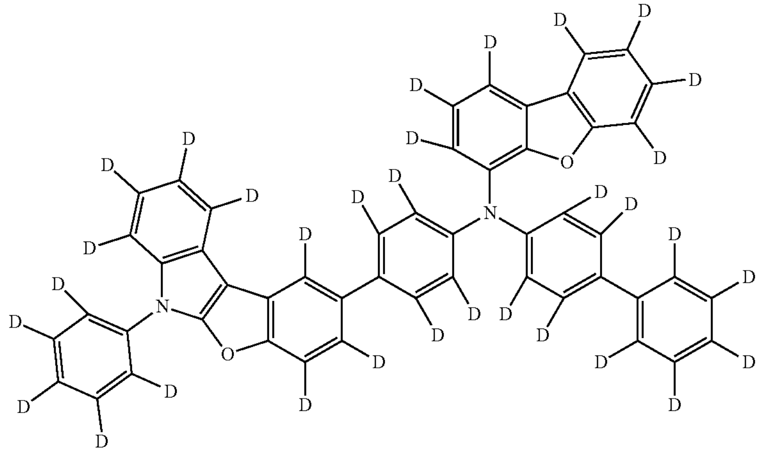
C56
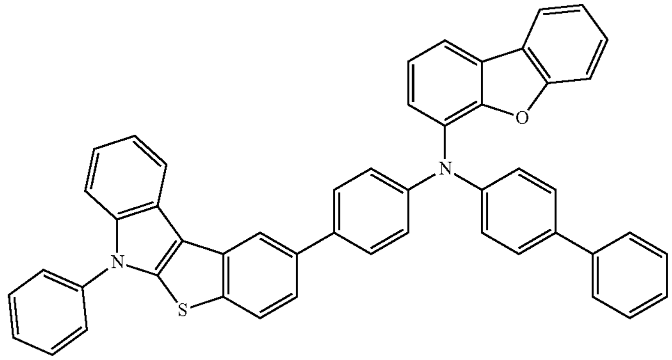
C57
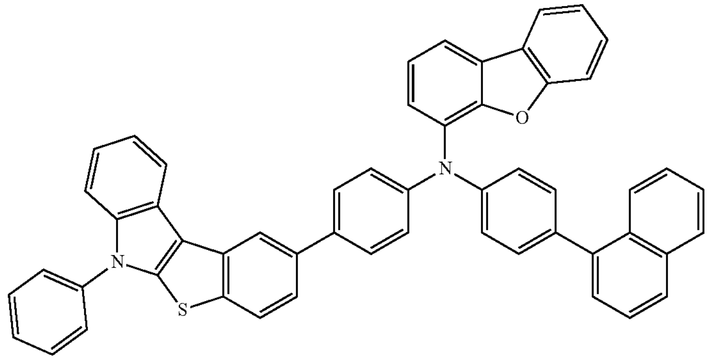

-continued
C58
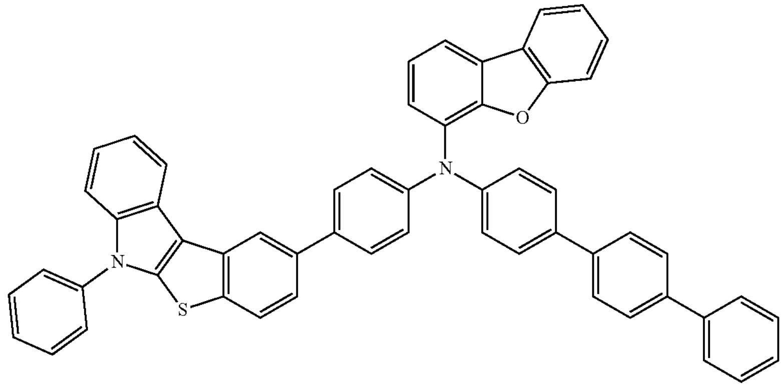
C59
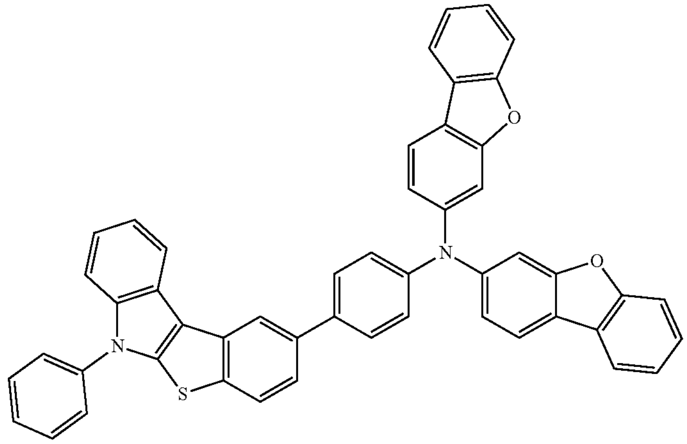
C60
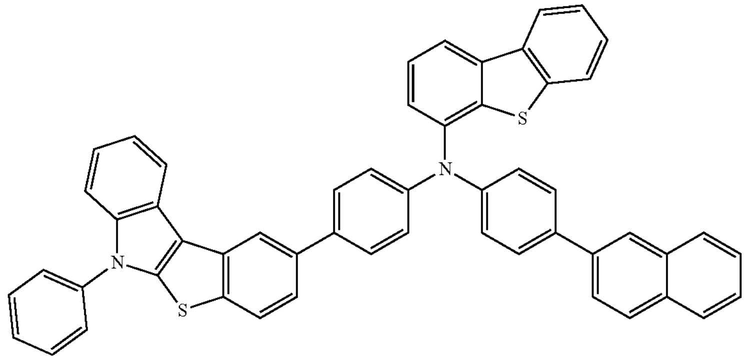
C61
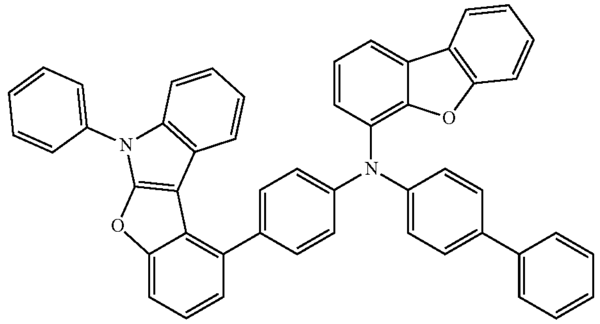

-continued
C62
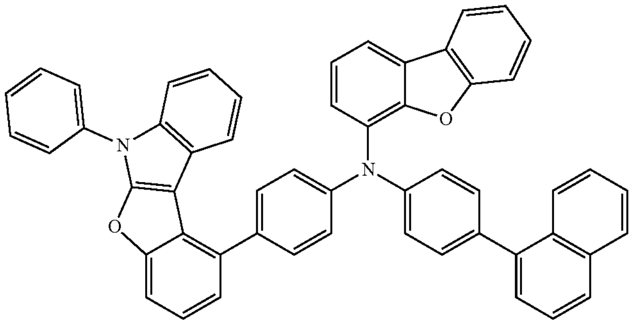
C63
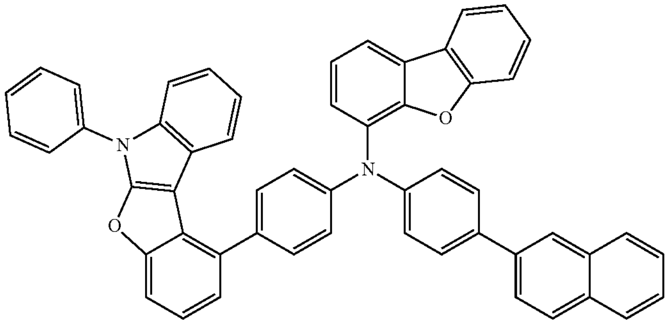
C64
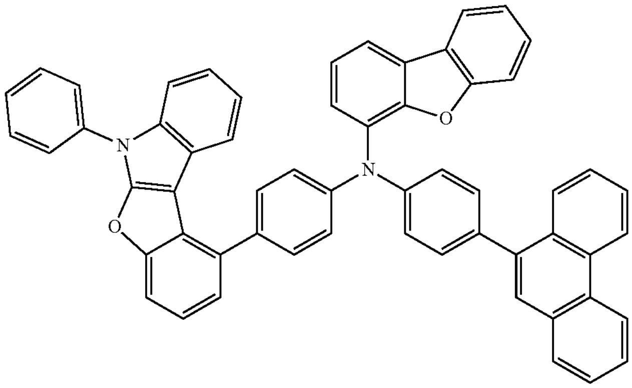
C65
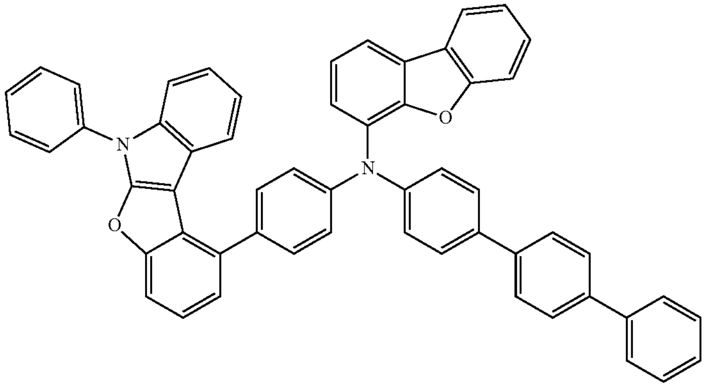

-continued
C66
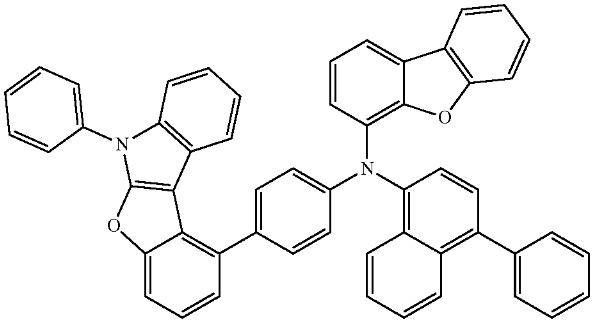
C67
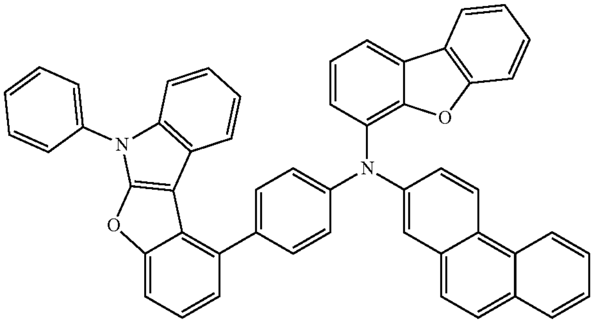
C68
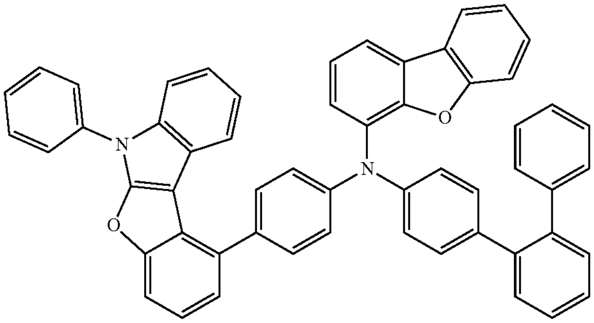
C69
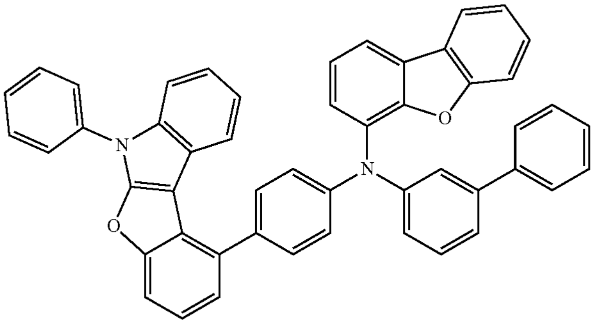

-continued
C70
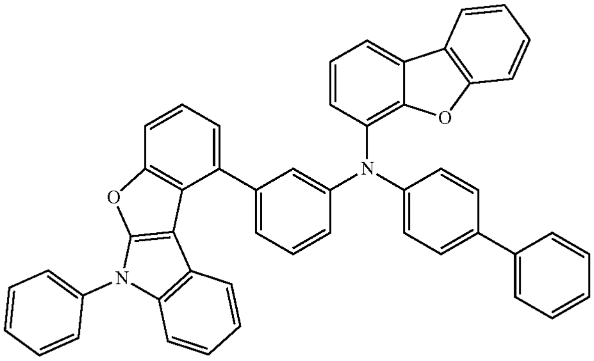
C71
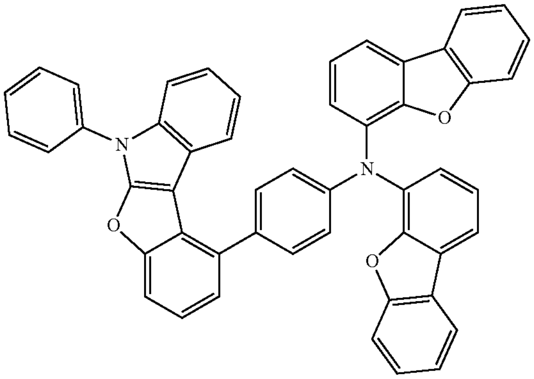
C72
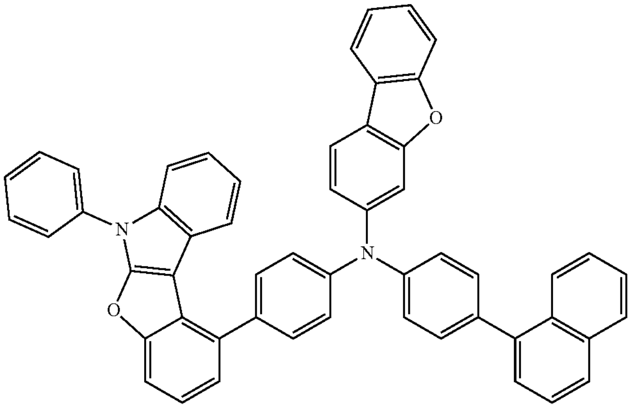
C73
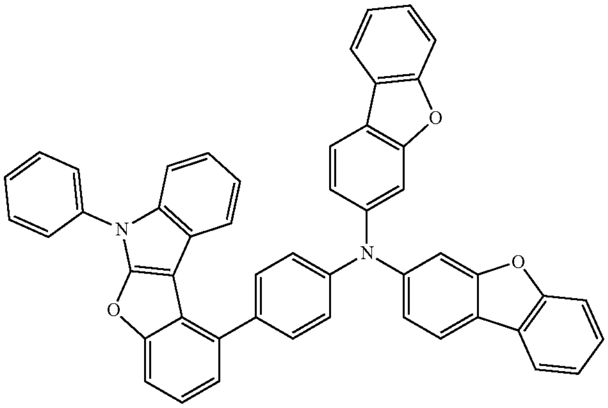

-continued
C74
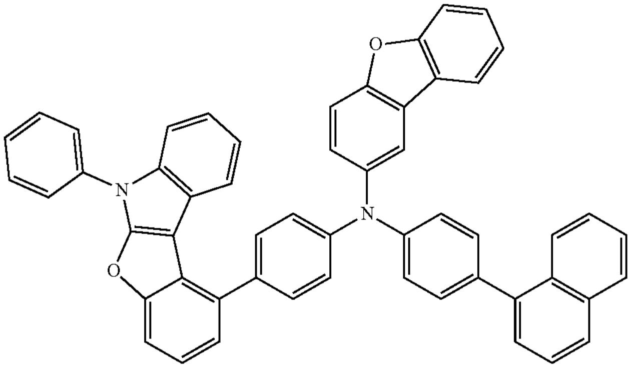
C75
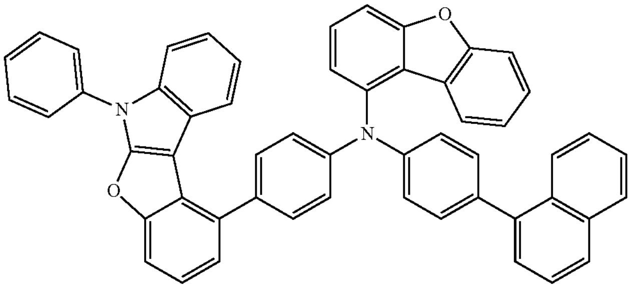
C76
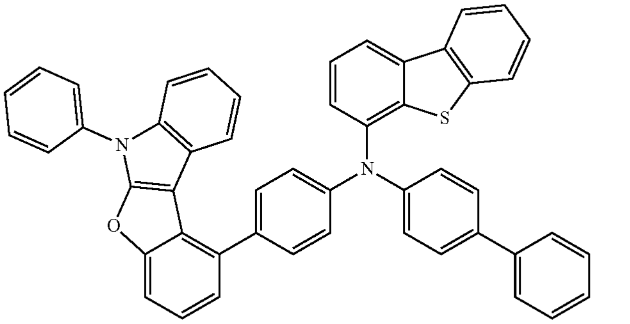
C77
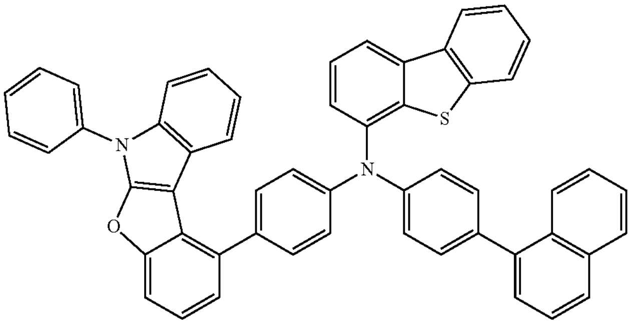
C78
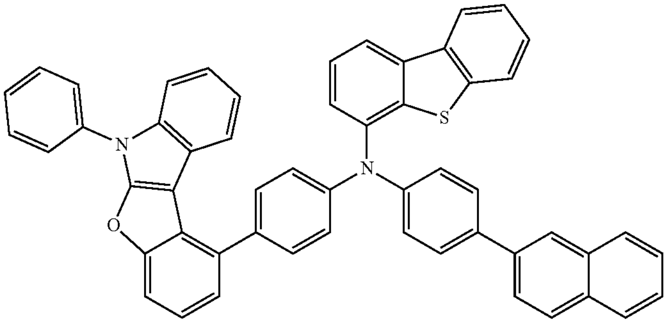

-continued
C79
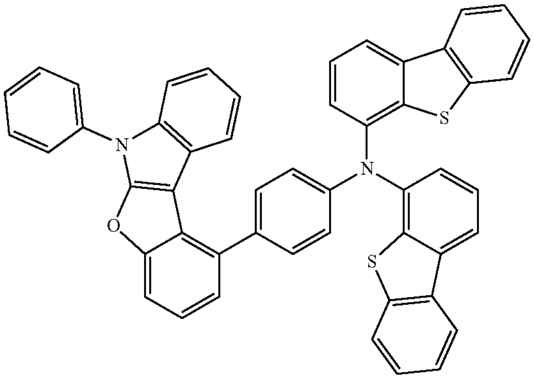
C80
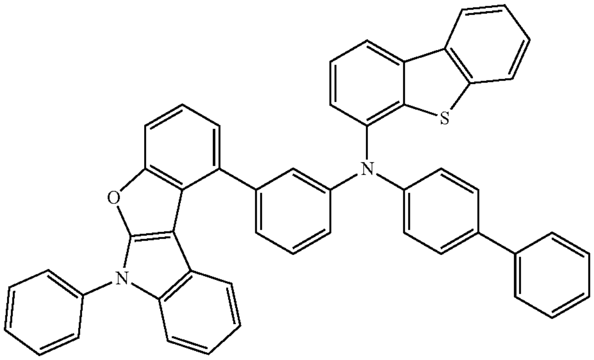
C81
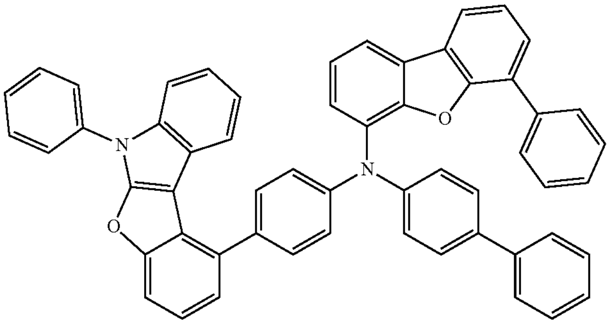
C82
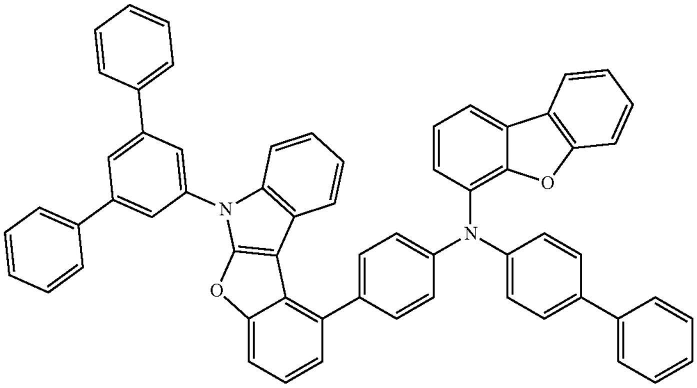

-continued
C83
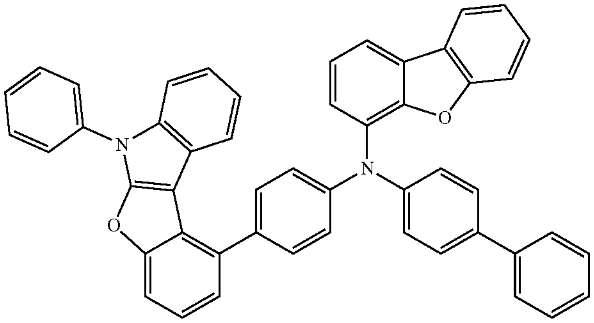
C84
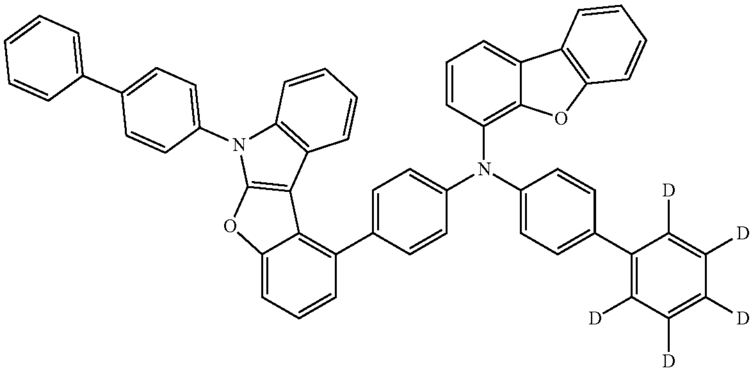
C85
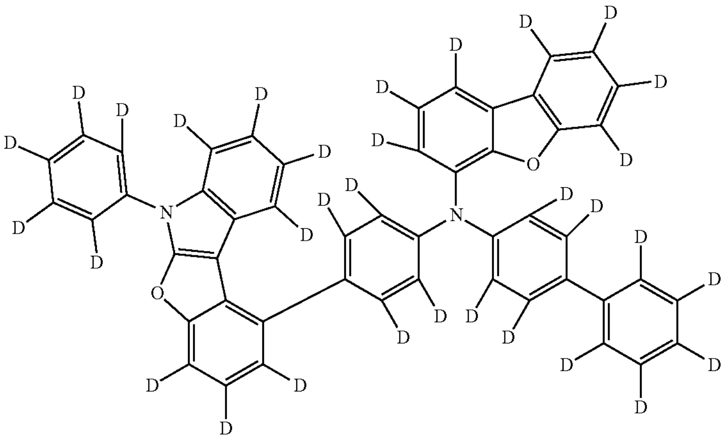
C86
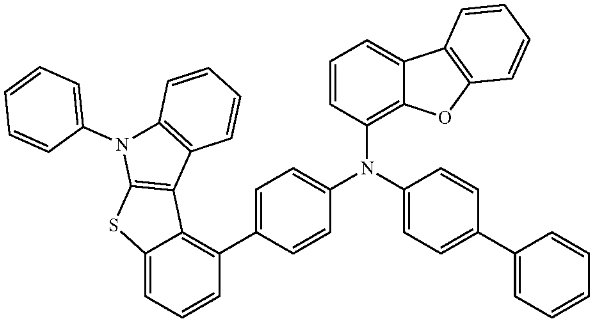

-continued
C87
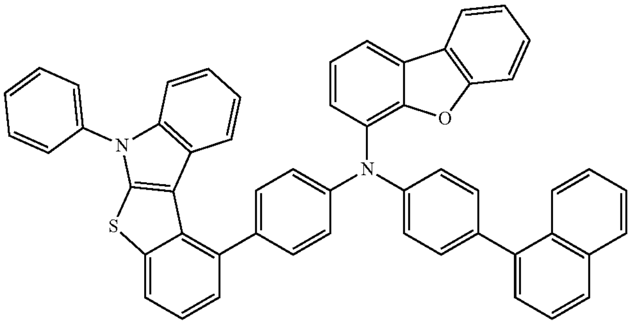
C88
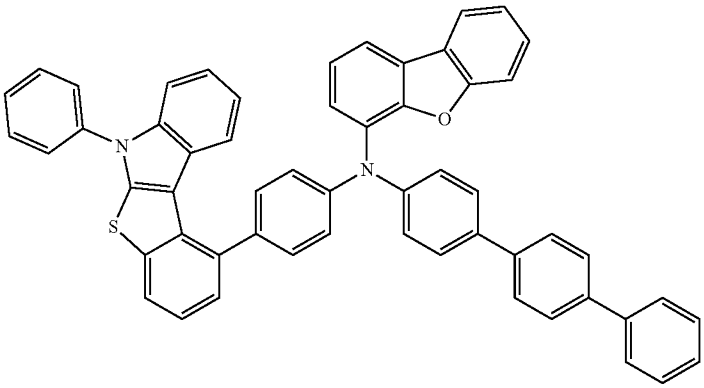
C89
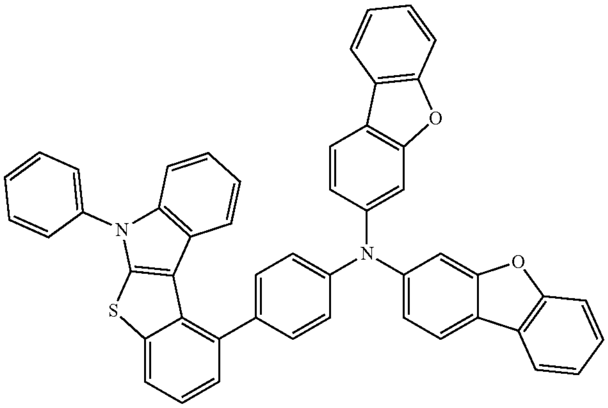
C90
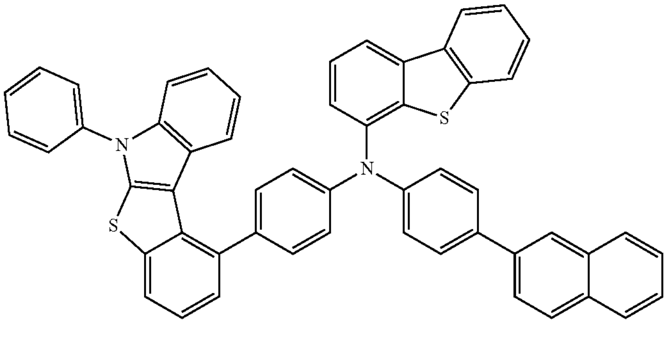

-continued
C91
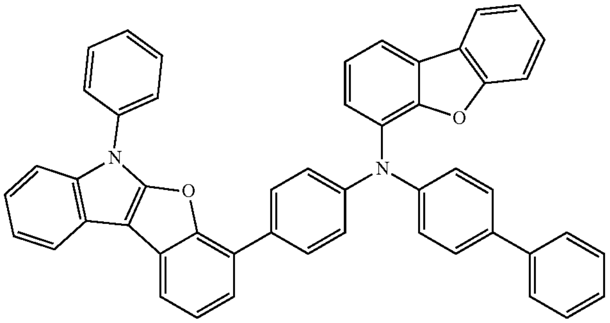
C92
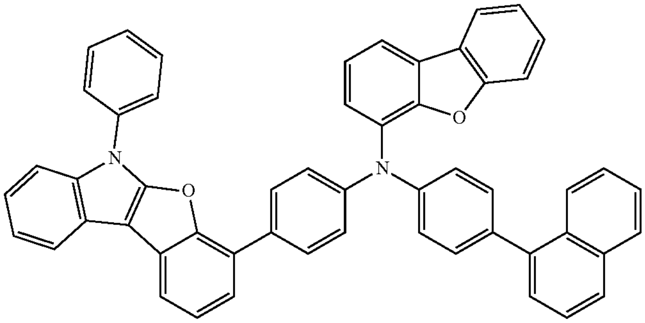
C93
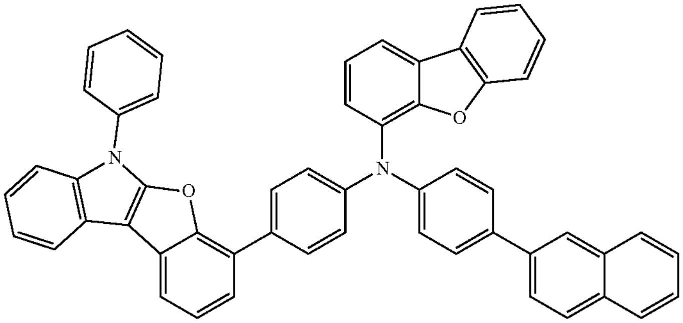
C94
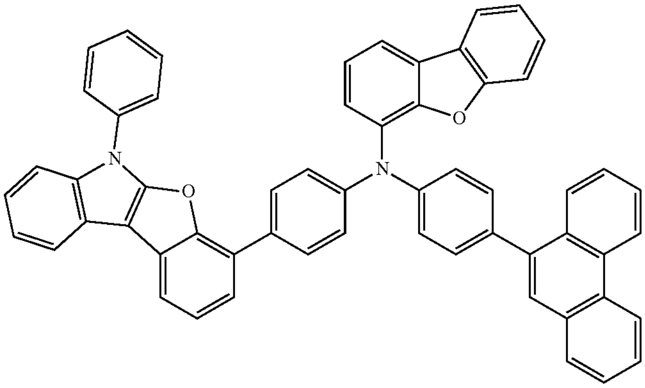

-continued
C95
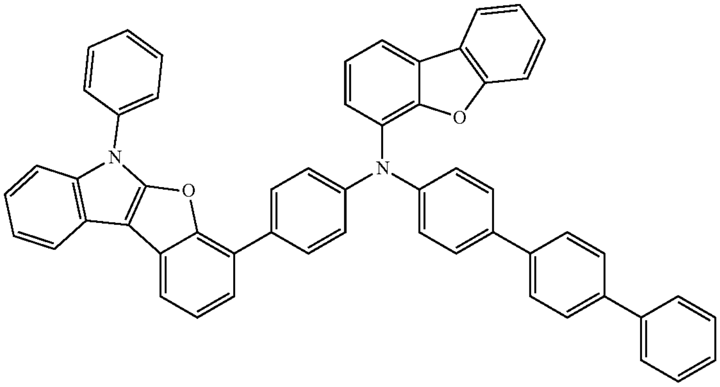
C96
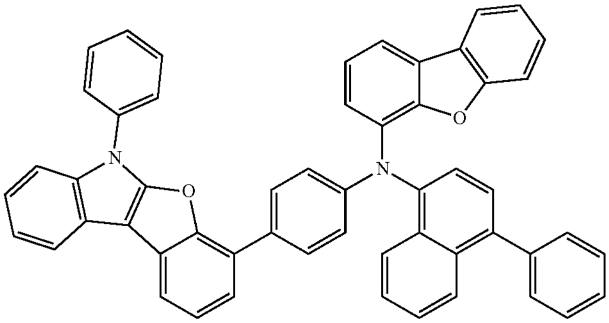
C97
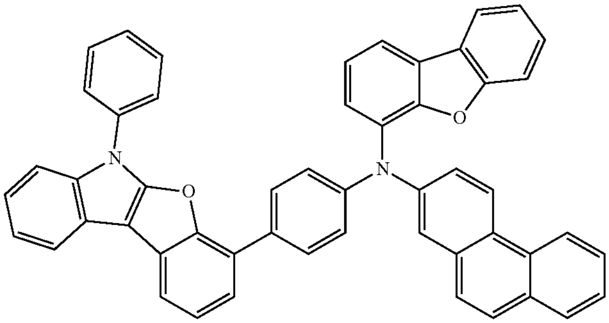
C98
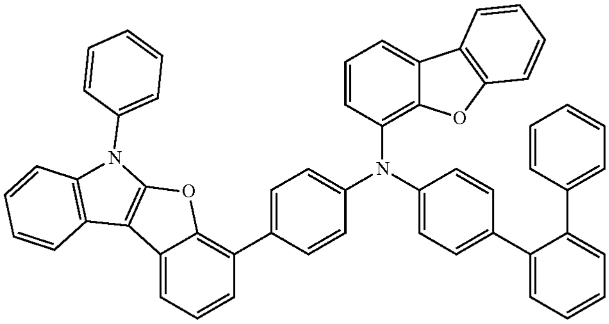

-continued
C99
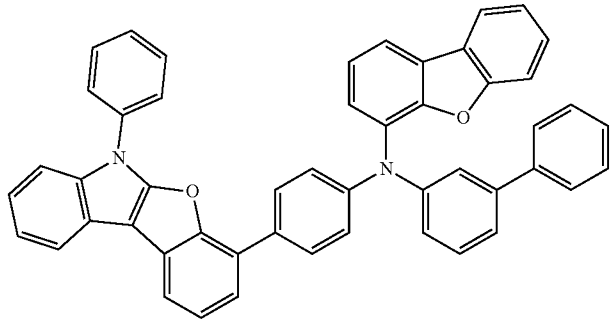
C100
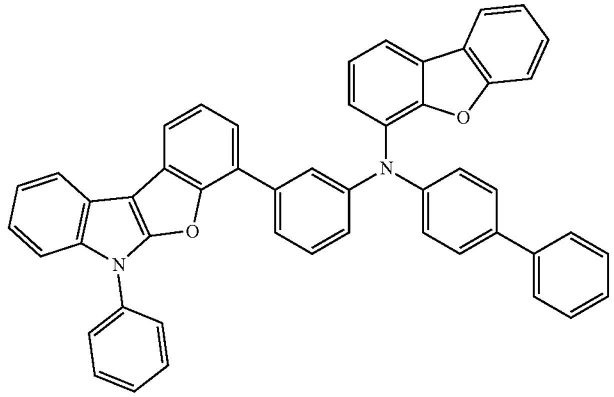
C101
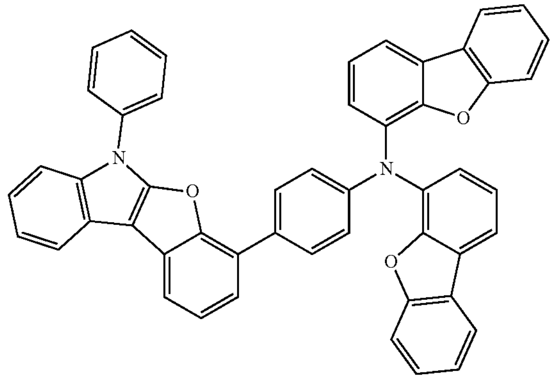
C102
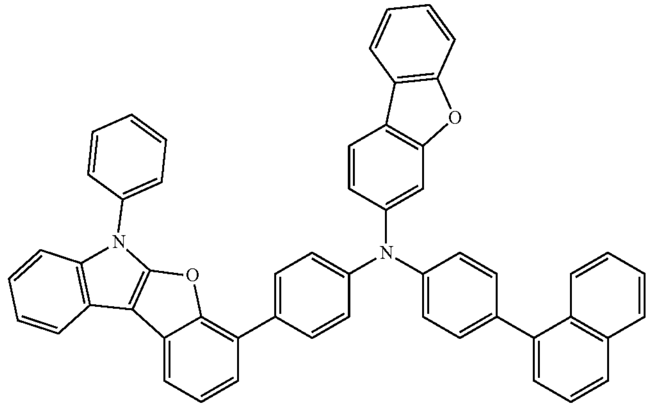

-continued
C103
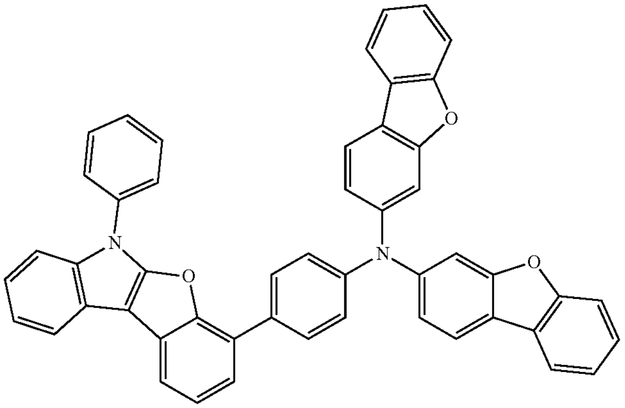
C104
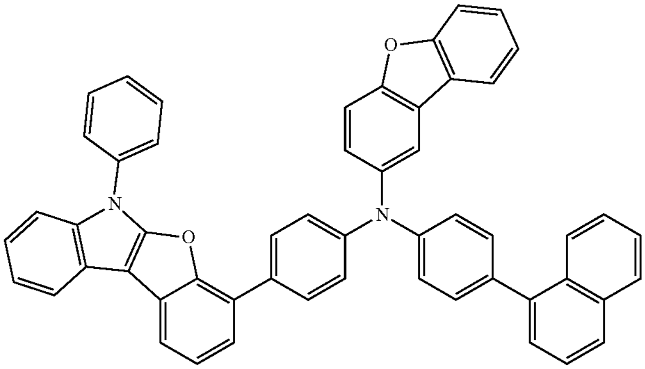
C105
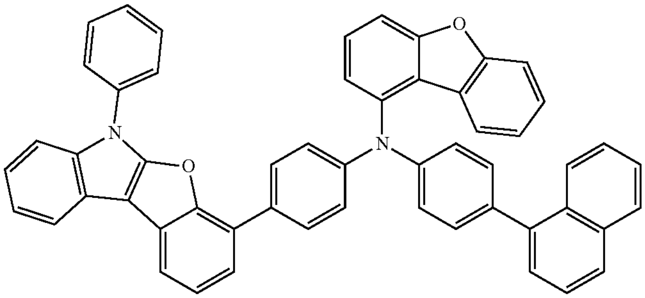
C106
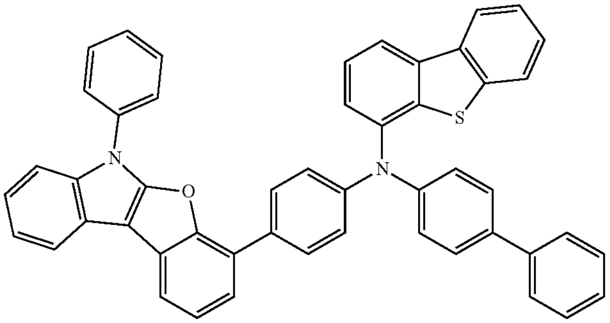

-continued
C107
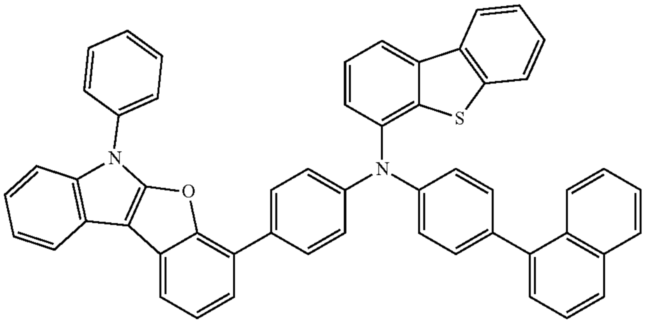
C108
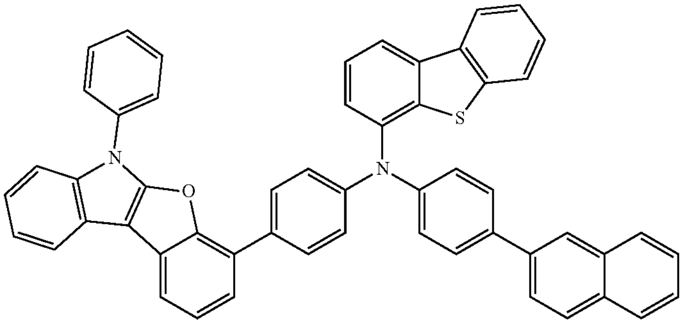
C109
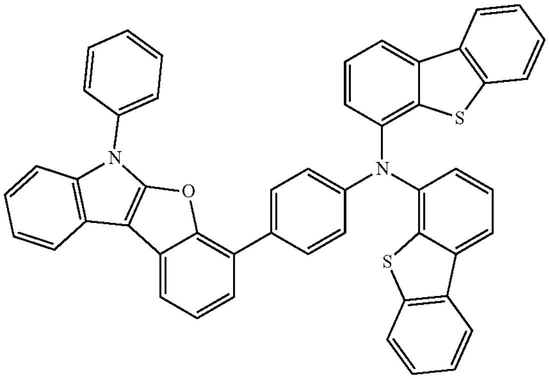
C110
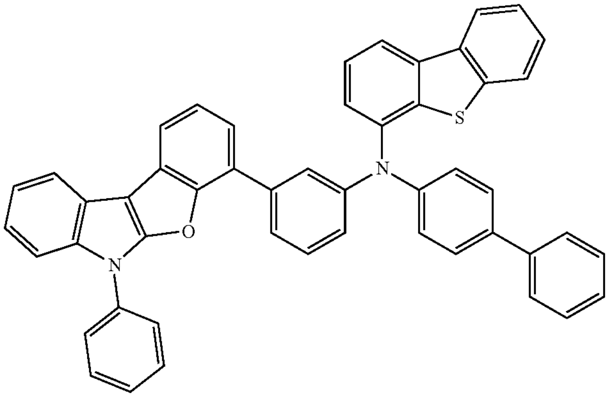

-continued
C111
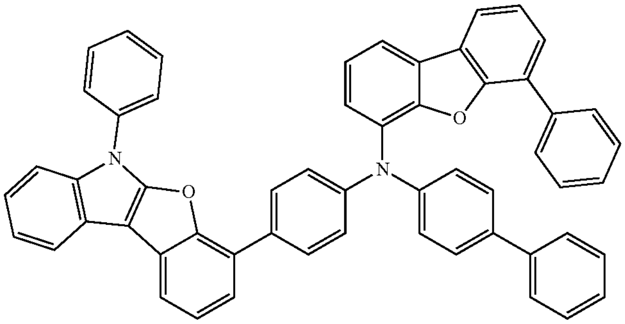
C112
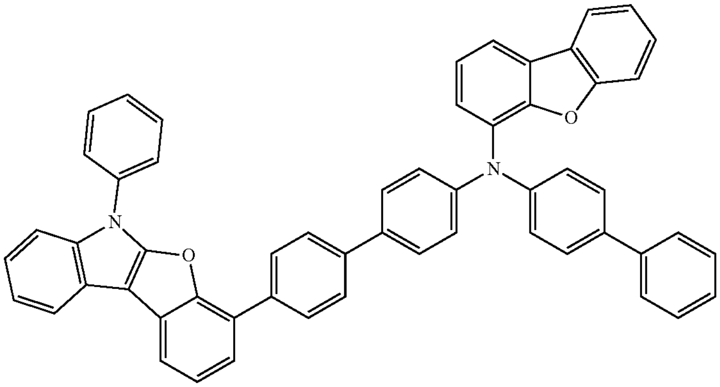
C113
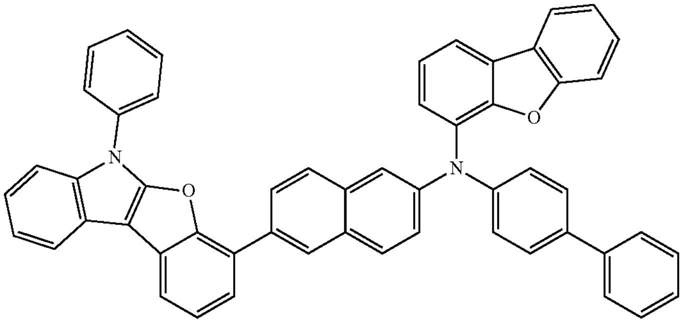
C114
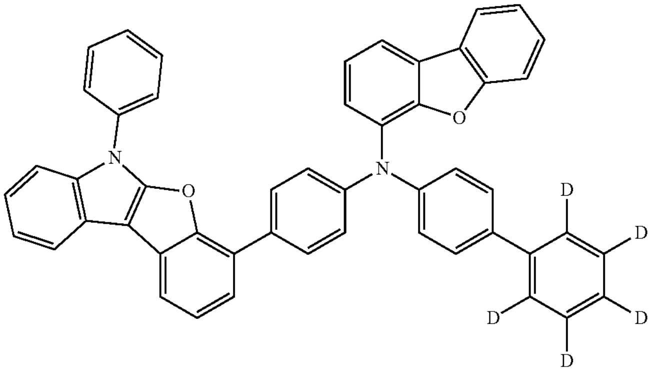

-continued
C115
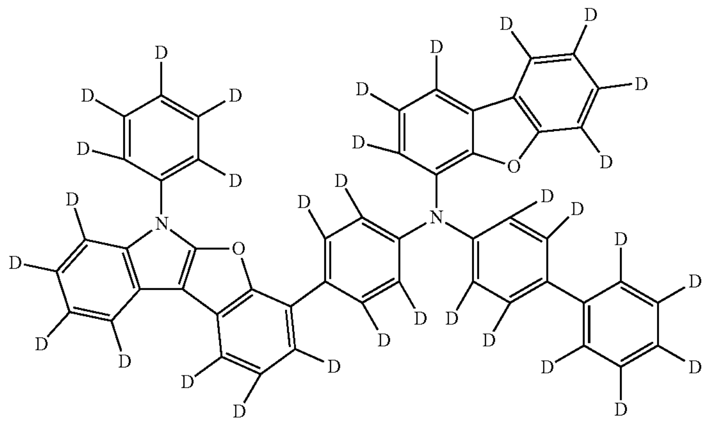
C116
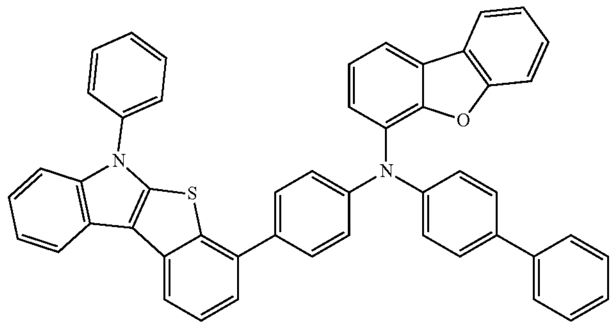
C117
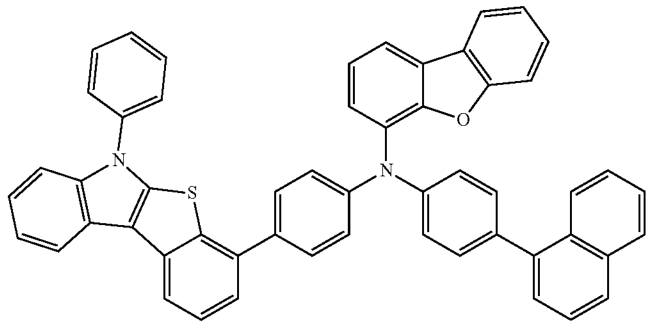
C118
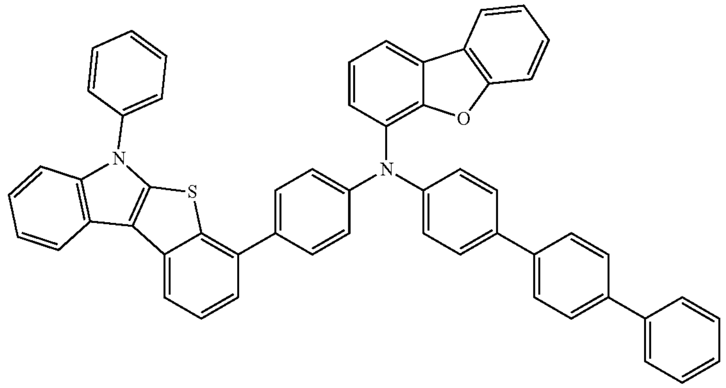

-continued
C119
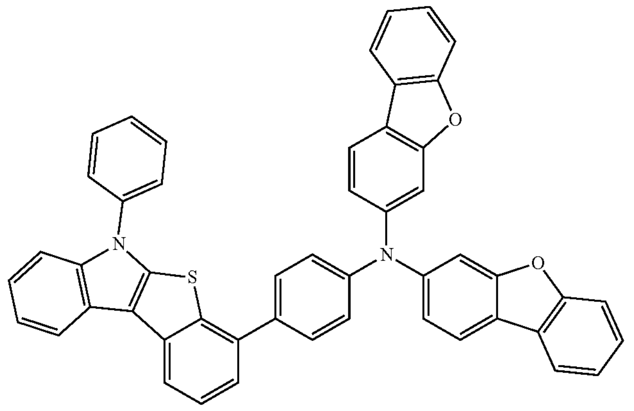
C120
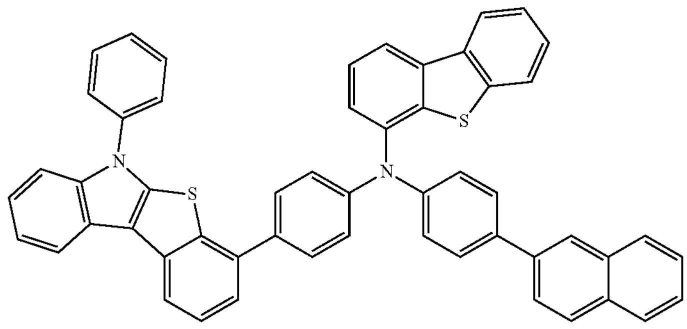
C121
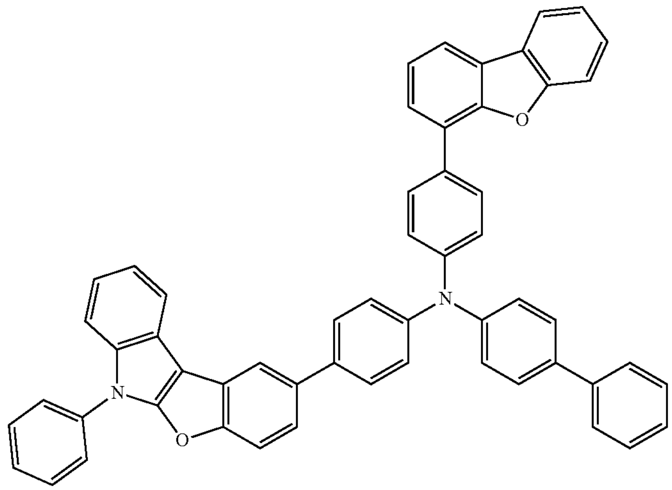

-continued
C122
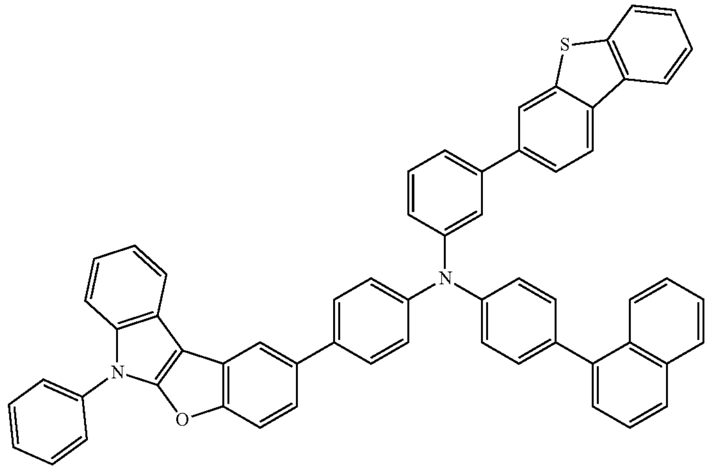
C123
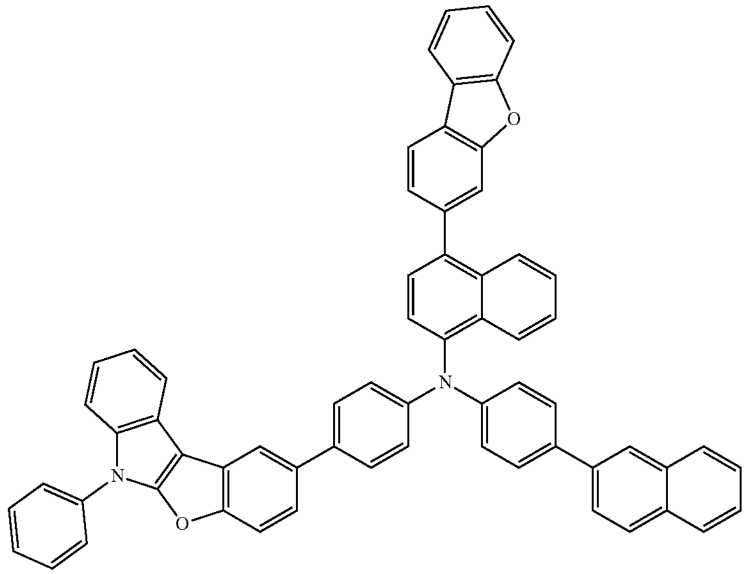

-continued
C124
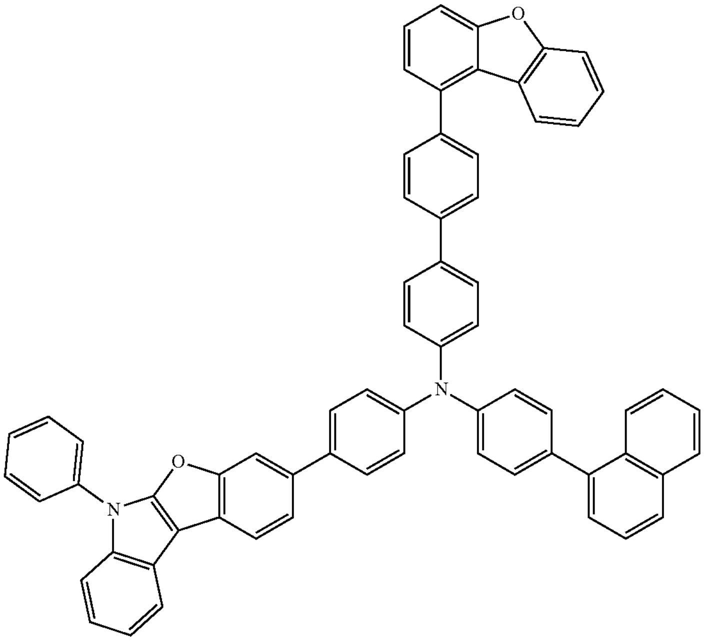
C125
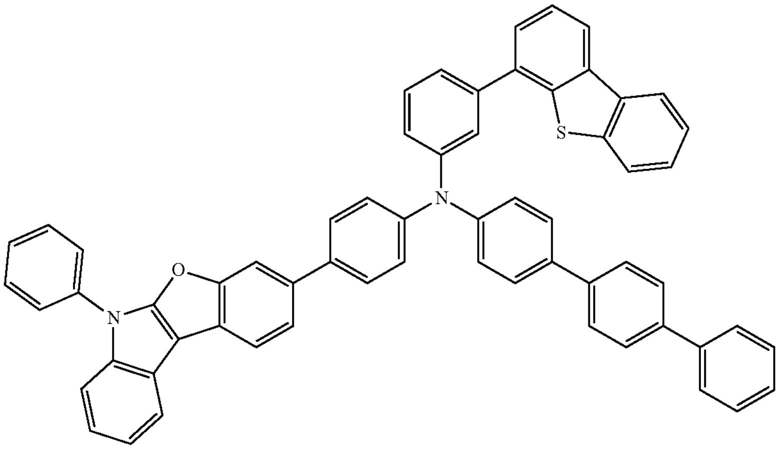
C126
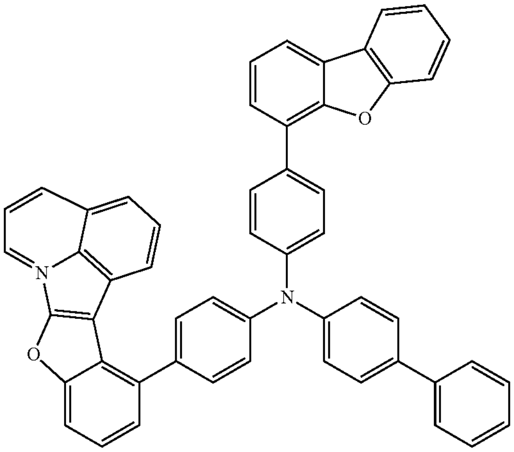

-continued
C127
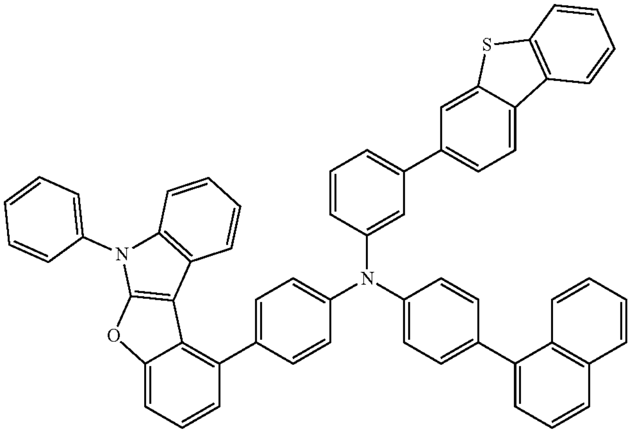
C128
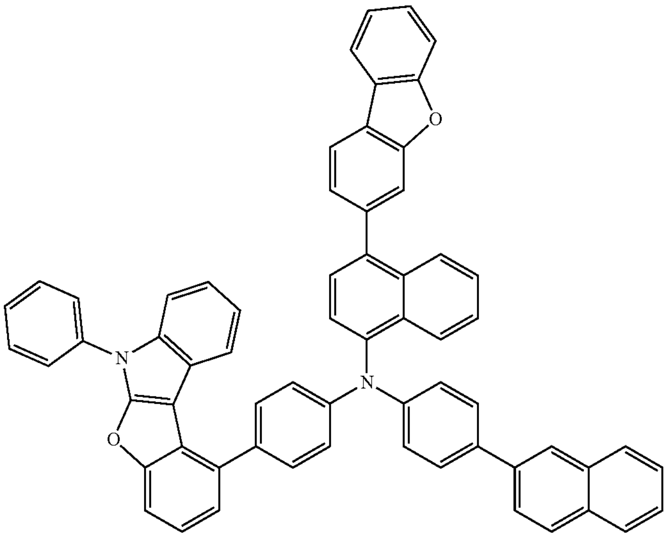
C129
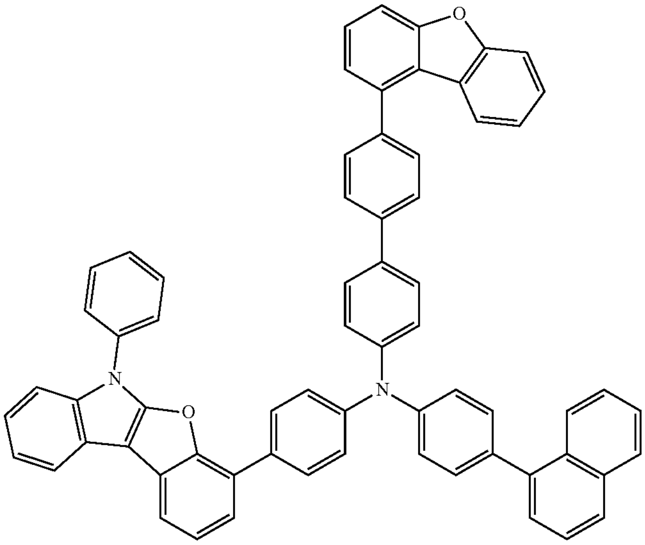

-continued
C130
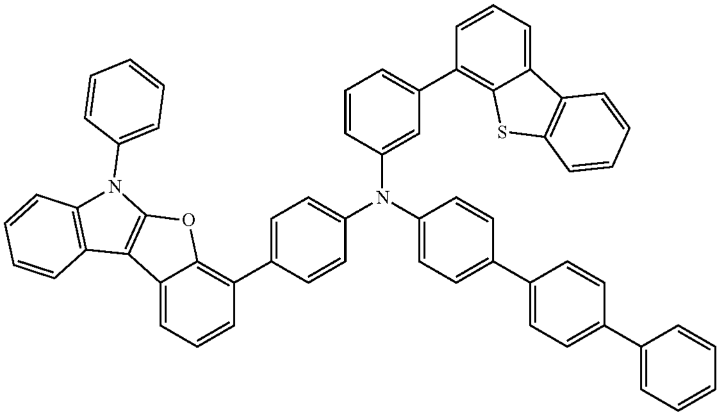
C131
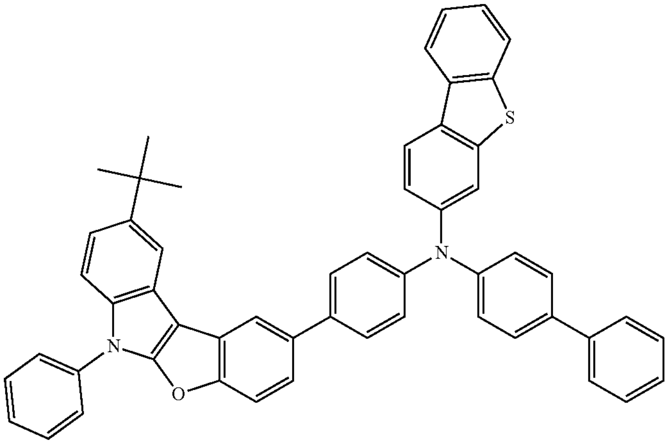
C132
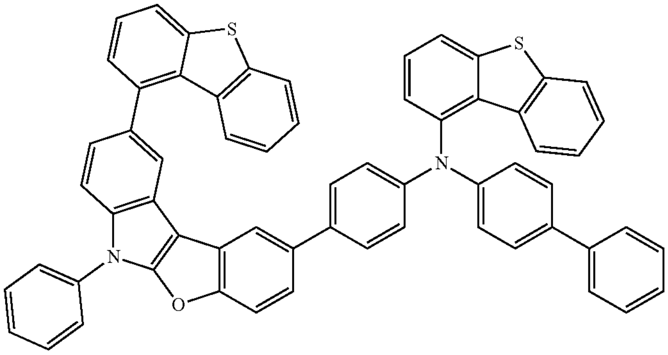
C133
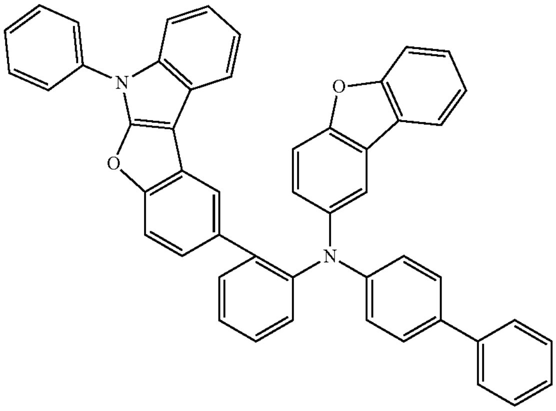

-continued
C134
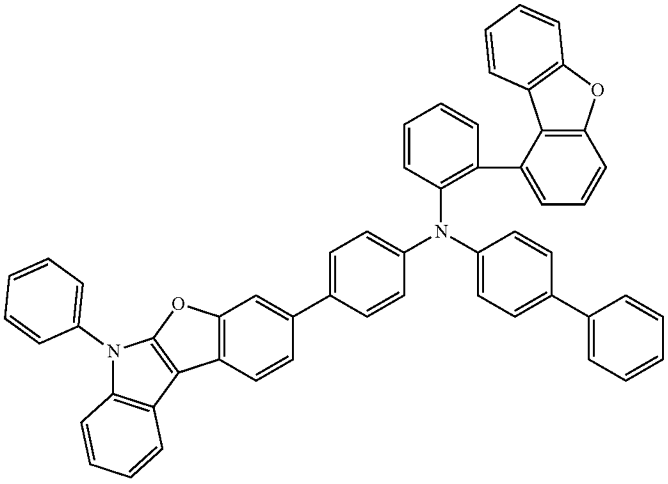
C135
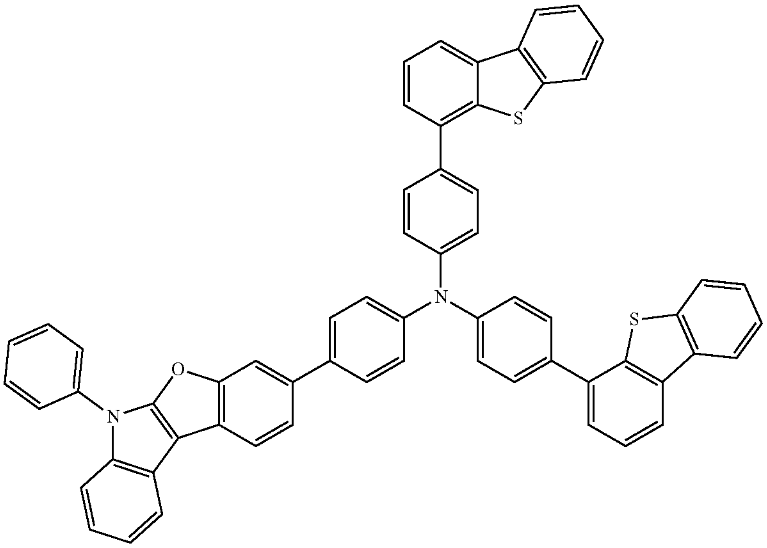
C136
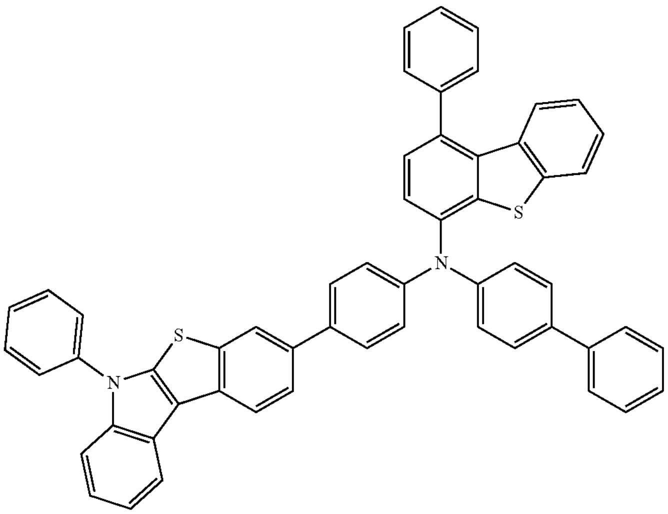

-continued
C137
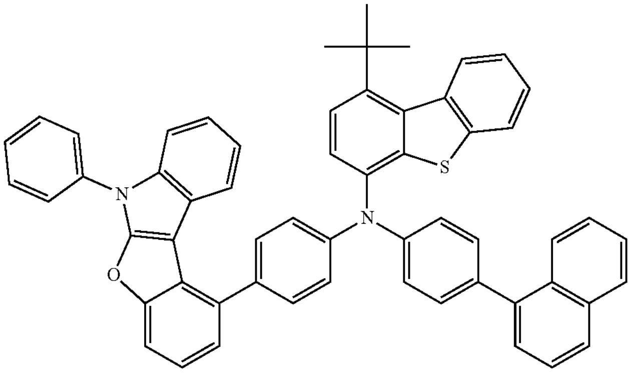
C138
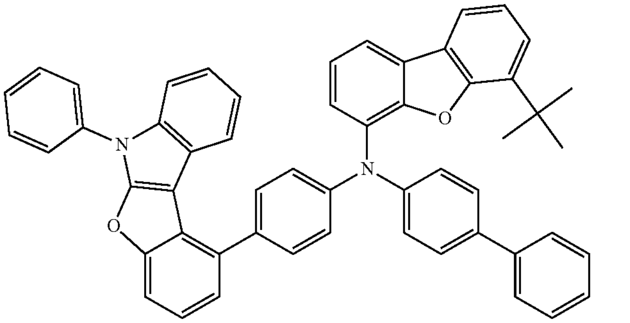
C139
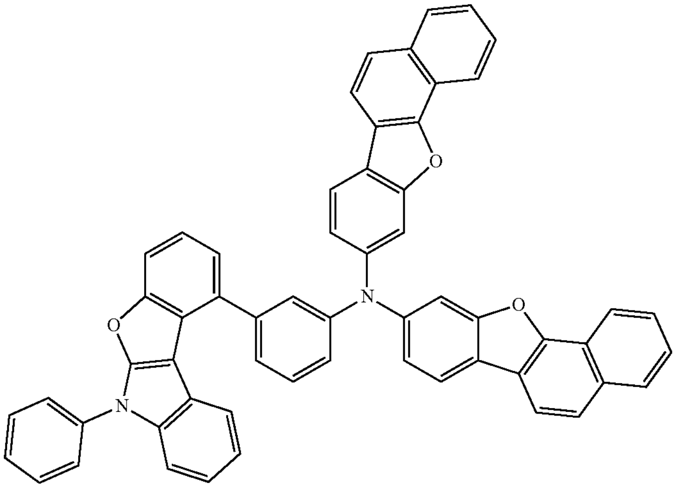

-continued

C140

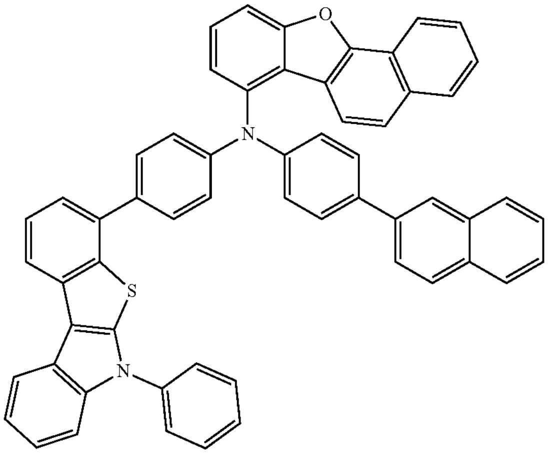

.

15. A monoamine compound represented by Formula 1:

[Formula 1]

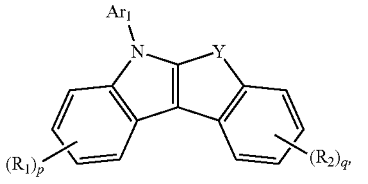

and wherein in Formula 1,

Y is O or S, p and q are each independently an integer of 0 to 4, $Ar_1$ is a substituted or unsubstituted aryl group of 6 to 30 carbon atoms for forming a ring, a substituted or unsubstituted heteroaryl group of 2 to 30 carbon atoms for forming a ring, or represented by Formula 2, $R_1$ is a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or represented by Formula 2, $R_2$ is a hydrogen atom, a deuterium atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or represented by Formula 2, where only one of $Ar_1$, $R_1$, and $R_2$ is represented by Formula 2:

[Formula 2]

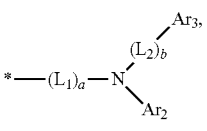

and wherein in Formula 2, $Ar_2$ is a substituted or unsubstituted aryl group of 6 to 30 carbon atoms for forming a ring or a substituted or unsubstituted heteroaryl group of 2 to 30 carbon atoms for forming a ring, $Ar_3$ is a substituted or unsubstituted heteroaryl group of 2 to 30 carbon atoms for forming a ring, $L_1$, and $L_2$ are each independently a direct linkage, a substituted or unsubstituted arylene group of 6 to 30 carbon atoms for forming a ring or a substituted or unsubstituted heteroarylene group of 2 to 30 carbon atoms for forming a ring, and a, and b are each independently an integer of 0 to 3, and wherein when $R_2$ is a substituted aryl group of 6 to 30 carbon atoms for forming a ring, a substituent of the substituted aryl group is selected from the group consisting of a deuterium atom, a halogen atom, a cyano group, a nitro group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group.

16. The monoamine compound of claim 15, wherein $Ar_3$ is represented by Formula 3:

[Formula 3]

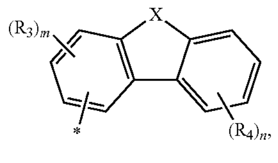

and wherein in Formula 3,

X is O or S, $R_3$ and $R_4$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, a substituted or unsubstituted heteroaryl group of 2 to 30 carbon atoms for forming a ring, or combined with an adjacent group to form a ring, m is an integer of 0 to 3, and n is an integer of 0 to 4.

17. The monoamine compound of claim 16, wherein Formula 1 is represented by any one of Formula 4 to Formula 6:

[Formula 4]

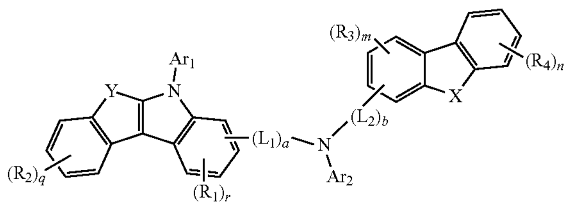

[Formula 5]

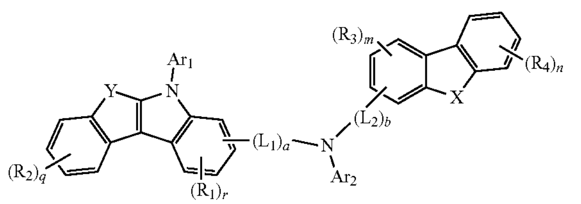

[Formula 6]

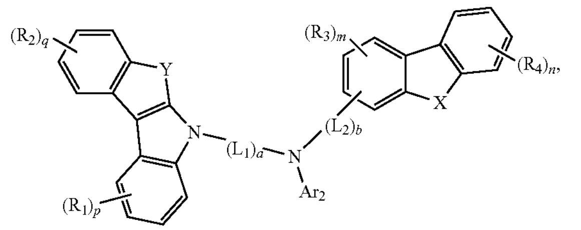

and wherein in Formula 4 to Formula 6, $Ar_1$ is a substituted or unsubstituted aryl group of 6 to 30 carbon atoms for forming a ring, or a substituted or unsubstituted heteroaryl group of 2 to 30 carbon atoms for forming a ring, $R_1$ is a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, $R_2$ is a hydrogen atom, a deuterium atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, r and s are each independently an integer of 0 to 3, X, Y, $Ar_2$, $L_1$, $L_2$, a, b, $R_3$, $R_4$, m, n, p and q are each independently the same as defined in Formula 1 to Formula 3, and wherein when $R_2$ is a substituted aryl group of 6 to 30 carbon atoms for forming a ring, a substituent of the substituted aryl group is selected from the group consisting of a deuterium atom, a halogen atom, a cyano group, a nitro group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group.

18. The monoamine compound of claim 16, wherein Formula 4 is represented by any one of Formula 4-1 to Formula 4-4:

[Formula 4-1]

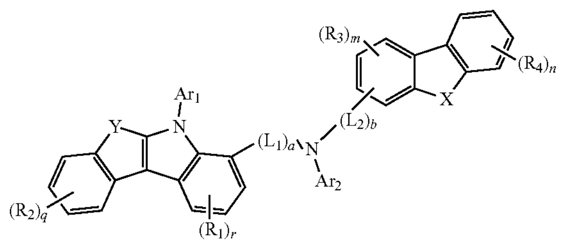

[Formula 4-2]

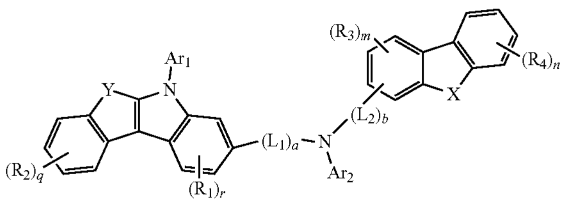

[Formula 4-3]

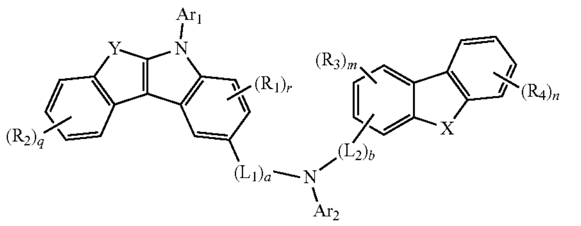

[Formula 4-4]

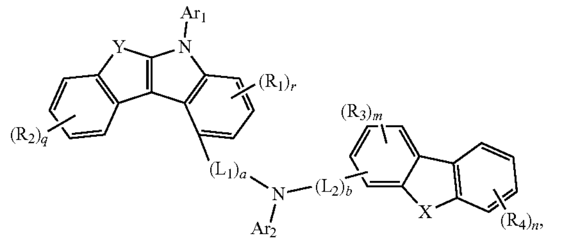

and wherein in Formula 4-1 to Formula 4-4,

X, Y, $Ar_1$, $Ar_2$, $L_1$, $L_2$, $R_1$ to $R_4$, a, b, m, n, q and r are each independently the same as defined in Formula 4.

19. The monoamine compound of claim 16, wherein Formula 5 is represented by any one of Formula 5-1 to Formula 5-4:

[Formula 5-1]

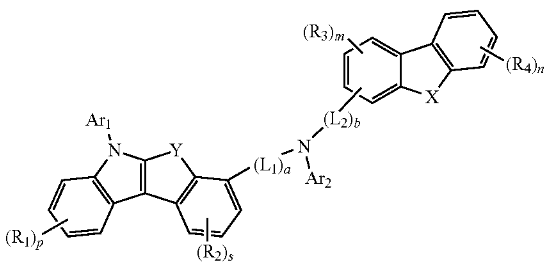

[Formula 5-2]

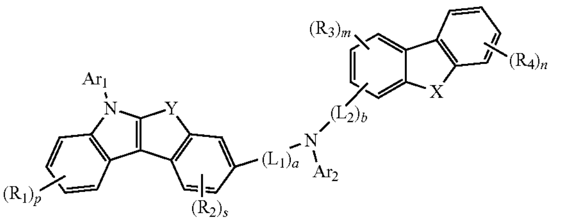

[Formula 5-3]

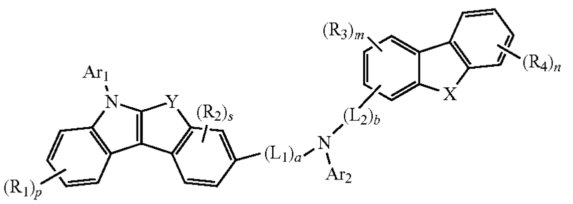

[Formula 5-4]

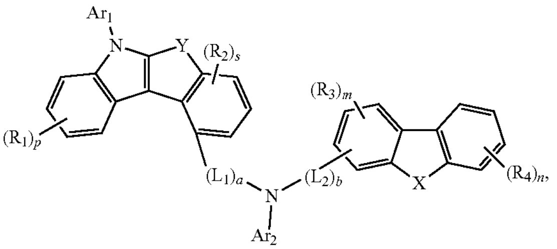

and wherein in Formula 5-1 to Formula 5-4,

X, Y, $Ar_1$, $Ar_2$, $L_1$, $L_2$, $R_1$ to $R_4$, a, b, m, n, p and s are each independently the same as defined in Formula 5.

20. The monoamine compound of claim 15, wherein $L_1$ is represented by any one of L-1 to L-4:

L-1

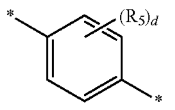

L-2

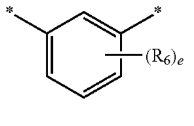

L-3

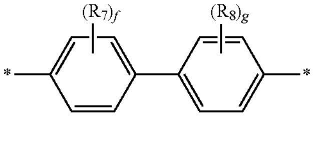

-continued

L-4

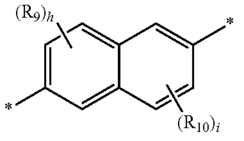

, wherein in L-1 to L-4, $R_5$ to $R_{10}$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, d to g are each independently an integer of 0 to 4, and h and i are each independently an integer of 0 to 3.

21. The monoamine compound of claim 15, wherein the monoamine compound represented by Formula 1 is a compound represented in Compound Group 1:

[Compound Group 1]

A1

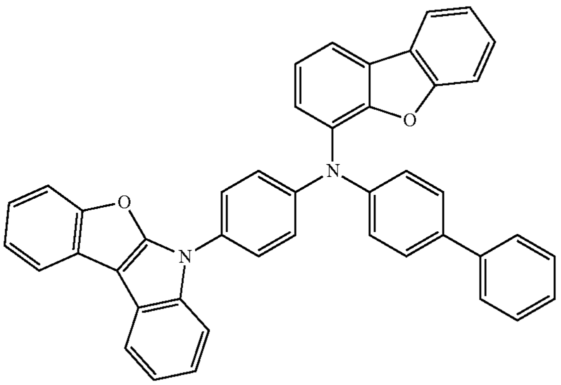

A2

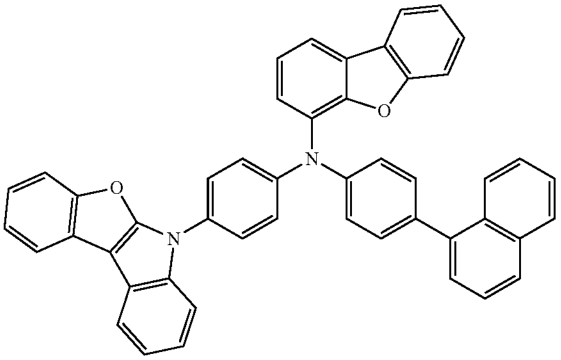

-continued
A3
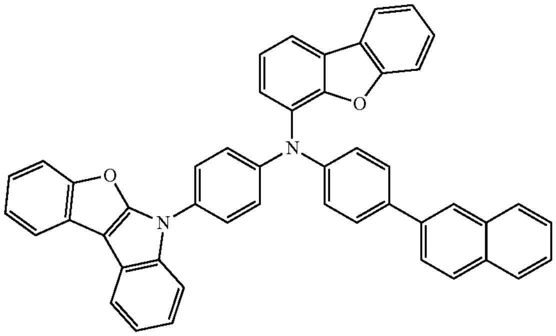
A4
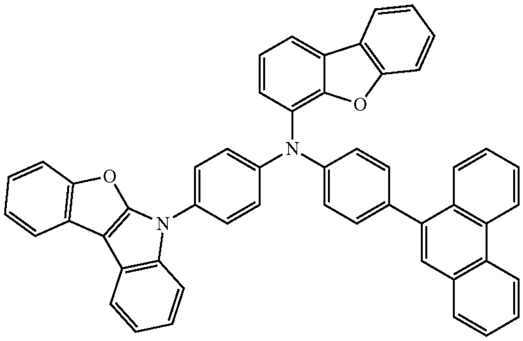
A5
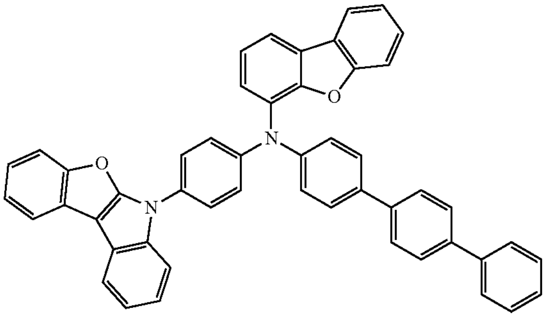
A6
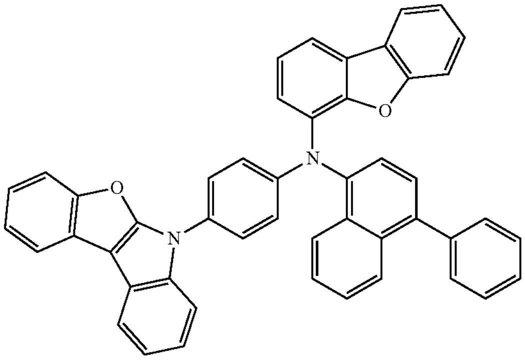
-continued
A7
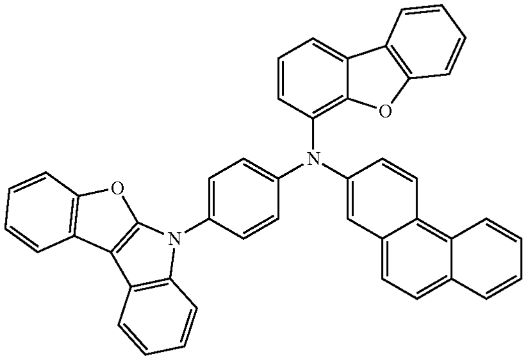
A8
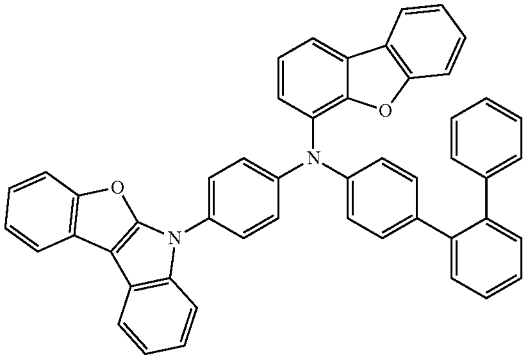
A9
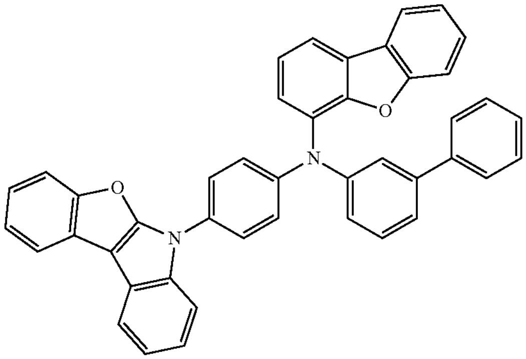
A10
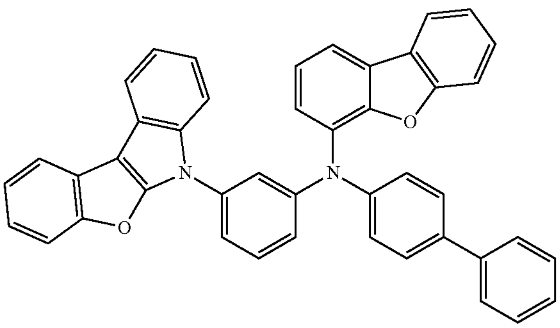

-continued
A11
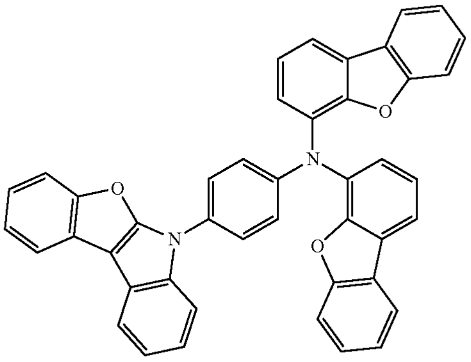
A12
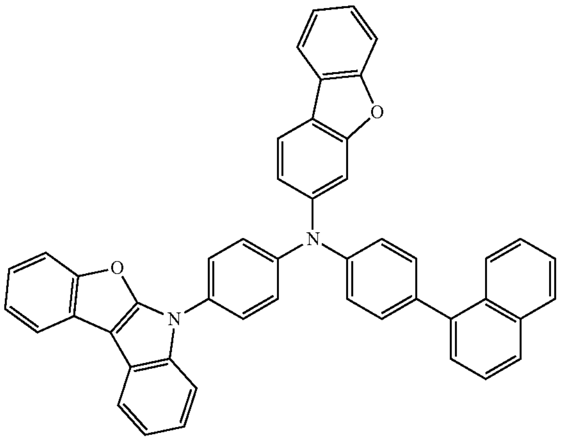
A13
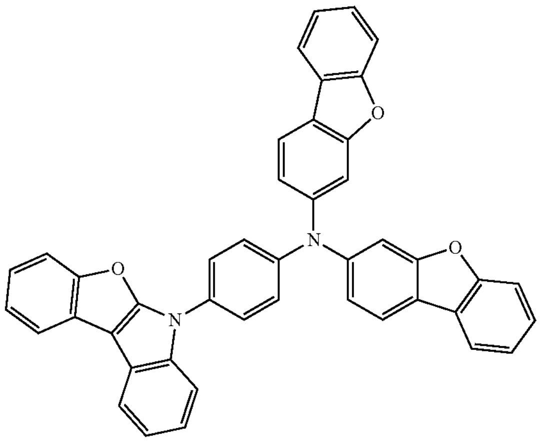
-continued
A14
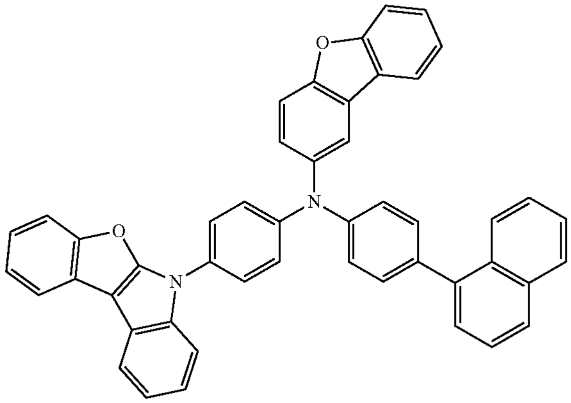
A15
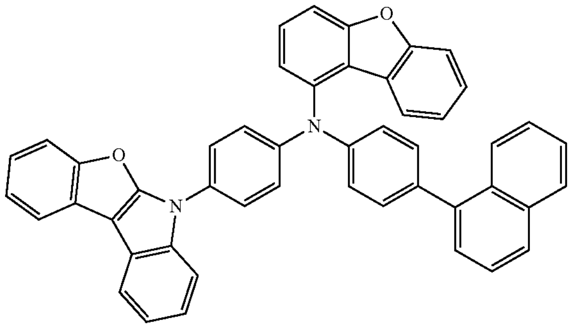
A16
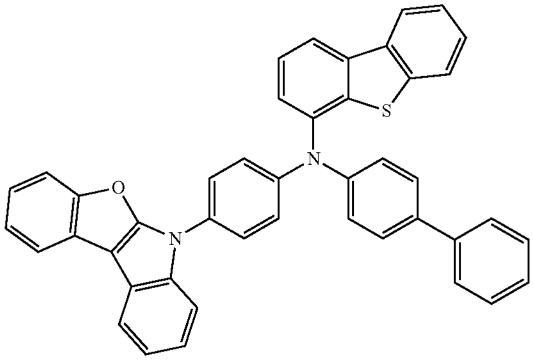
A17
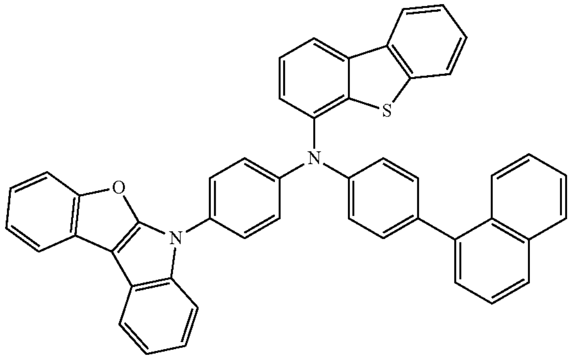

-continued
A18
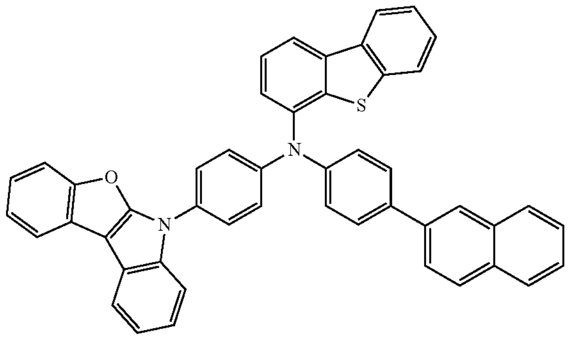
A19
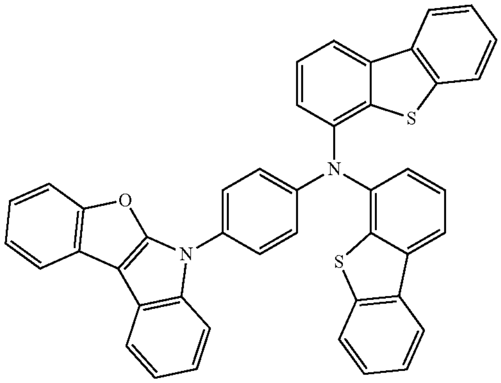
A20
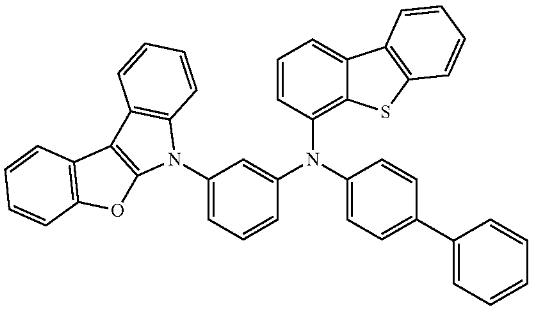
A21
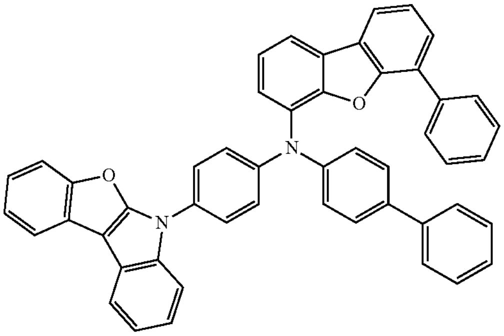
-continued
A22
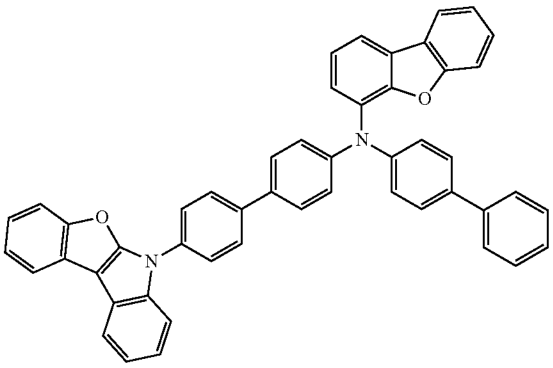
A23
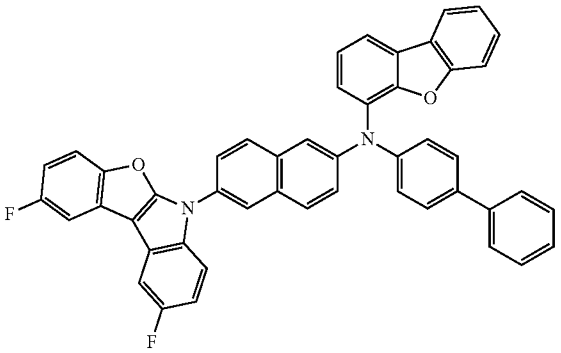
A24
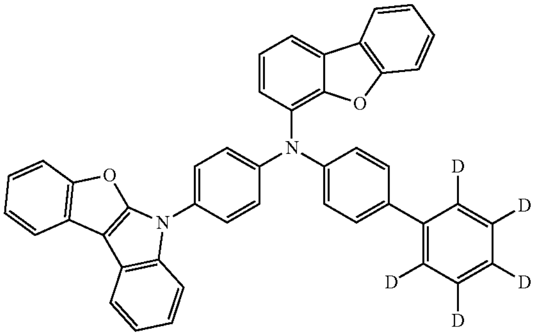
A25
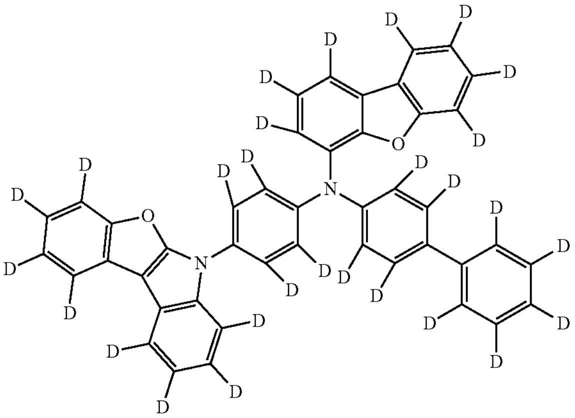

A26
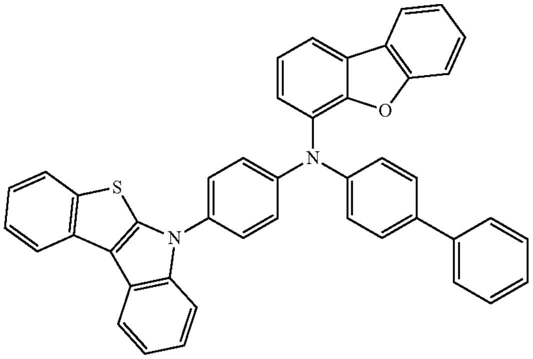
A27
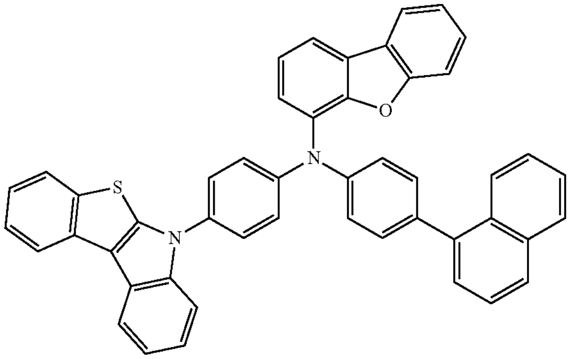
A28
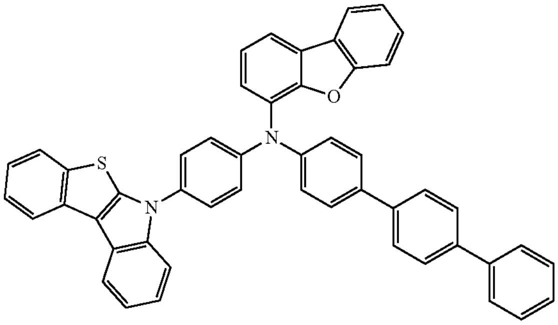
A29
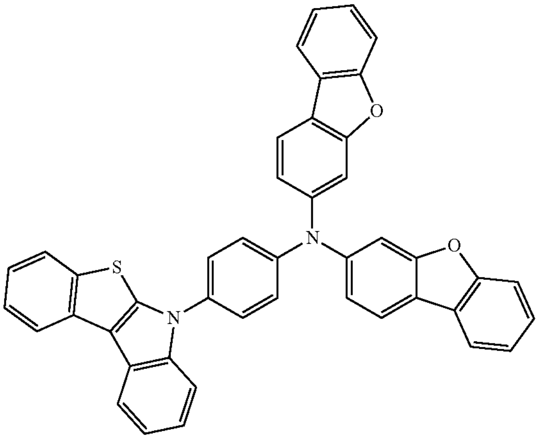
A30
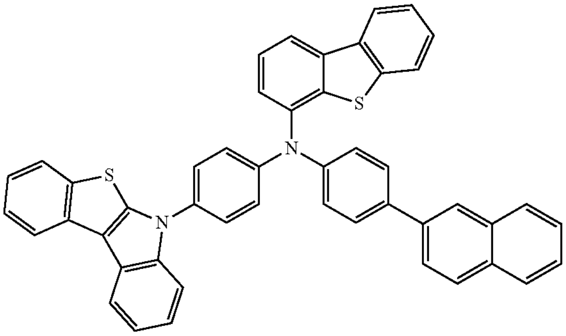
A31
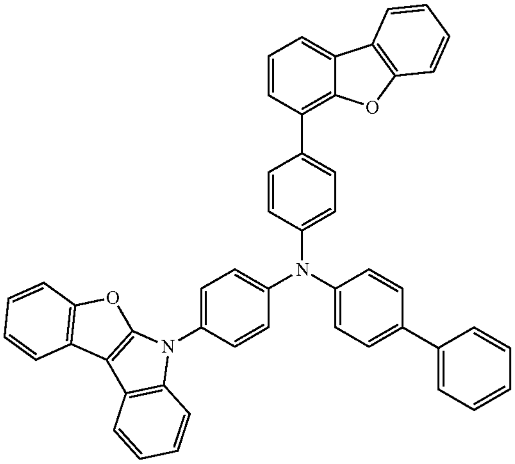
A32
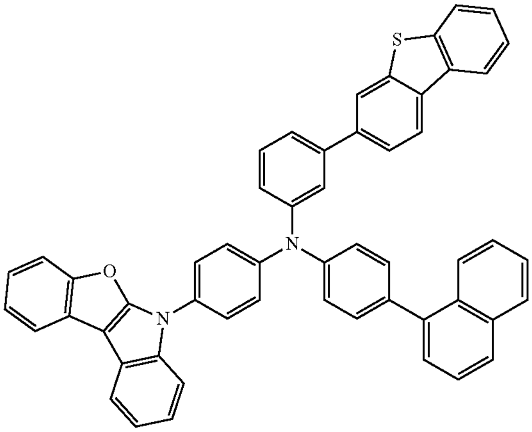

-continued
A33
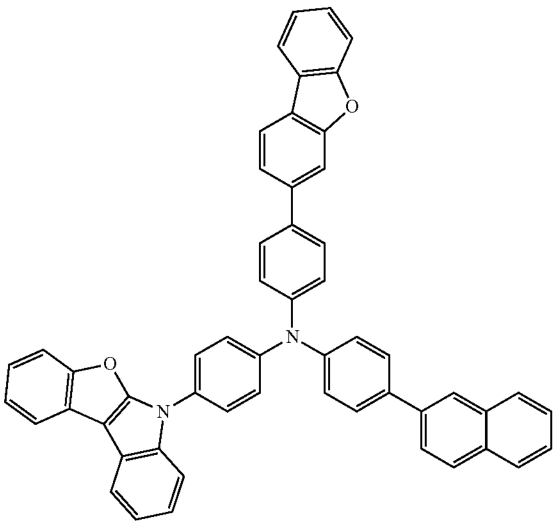
A34
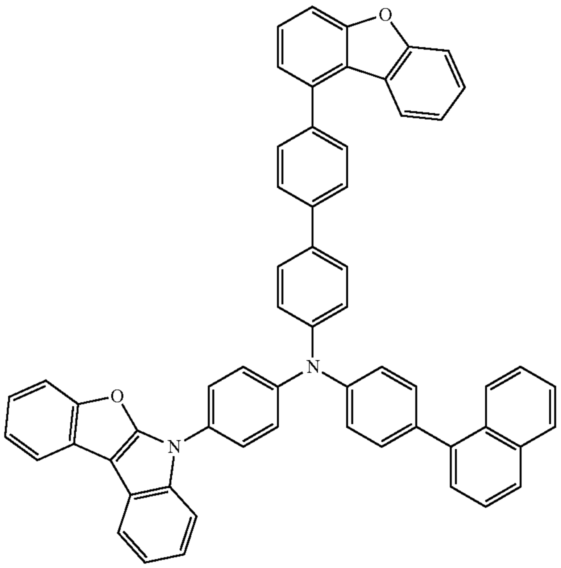
A35
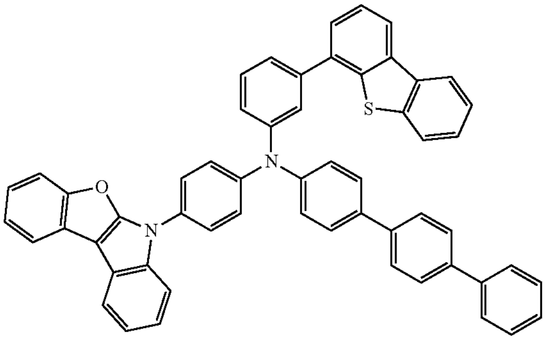
-continued
A36
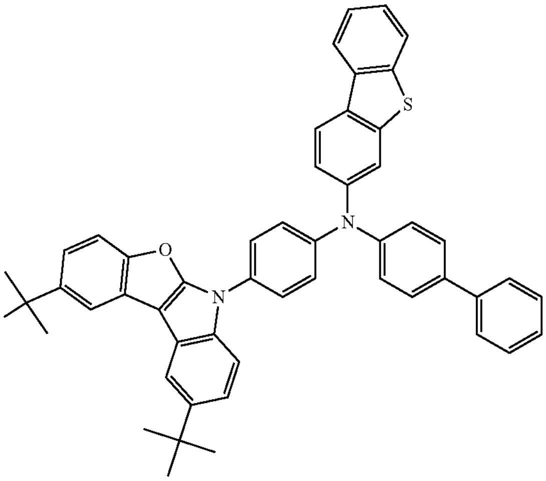
A37
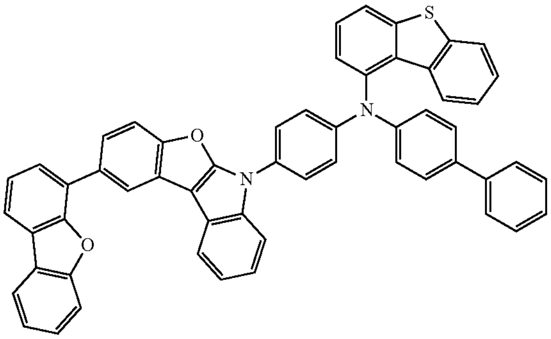
A38
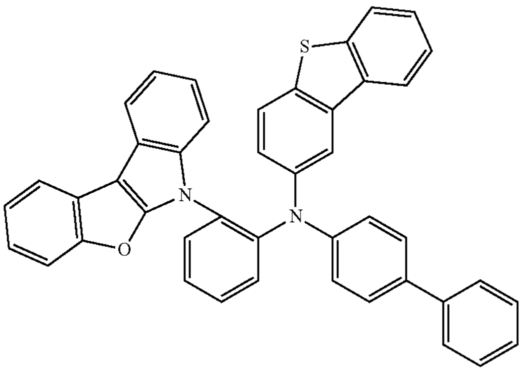

-continued
A39
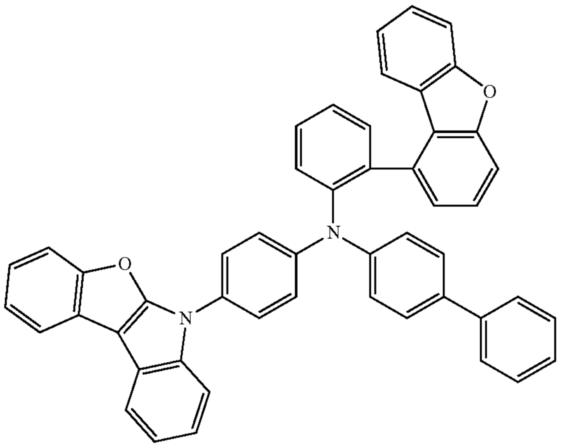
A40
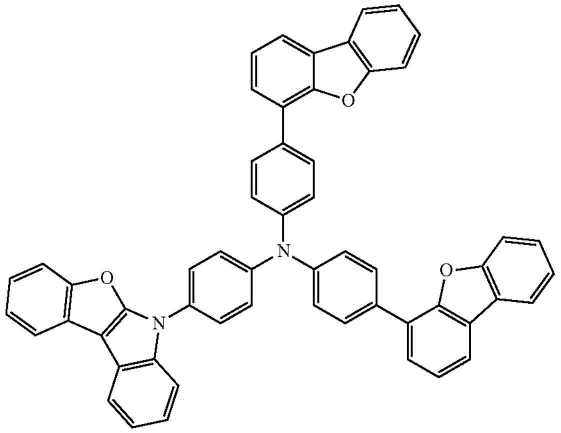
A41
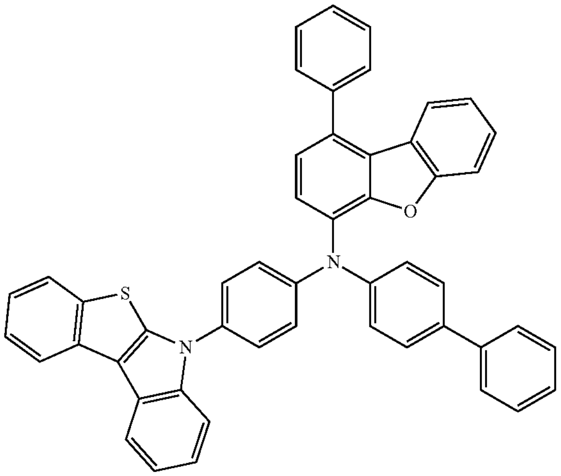
-continued
A42
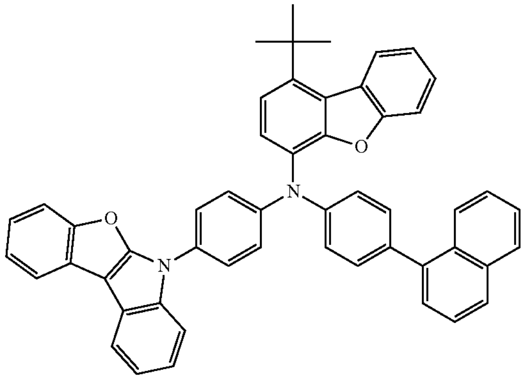
A43
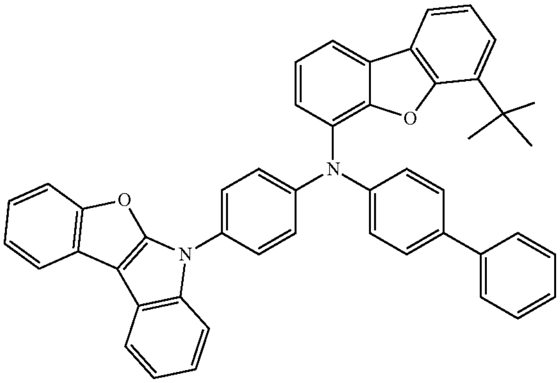
A44
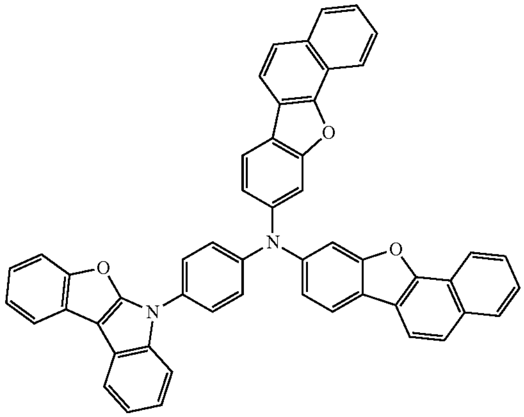
A45
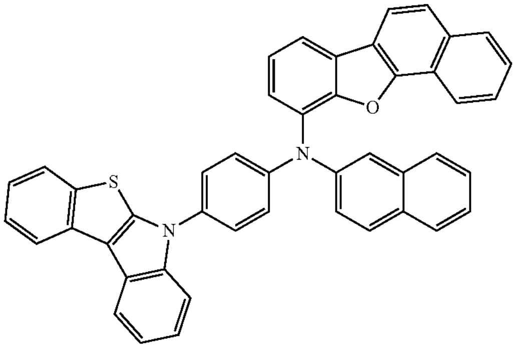
.

22. The monoamine compound of claim 15, wherein the monoamine compound represented by Formula 1 is a compound represented in Compound Group 2:
[Compound Group 2]
B1
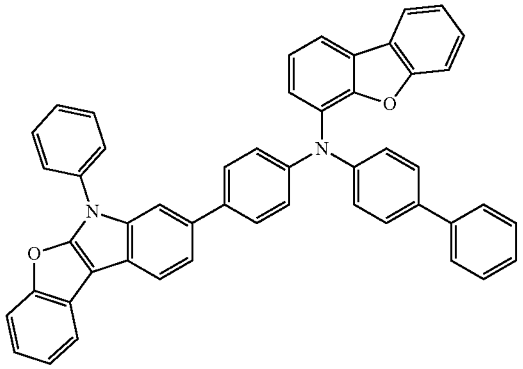
B2
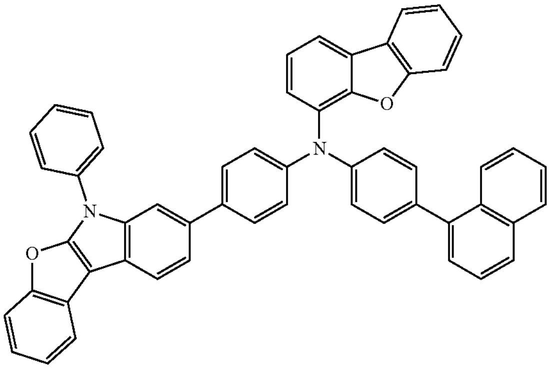
B3
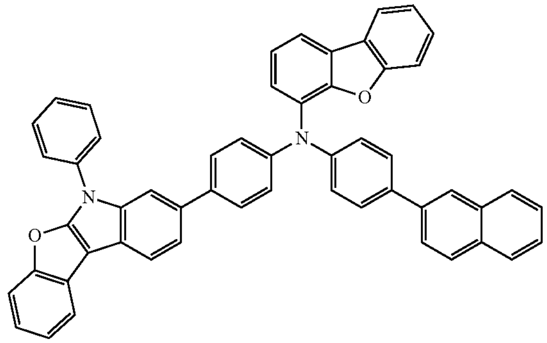
B4
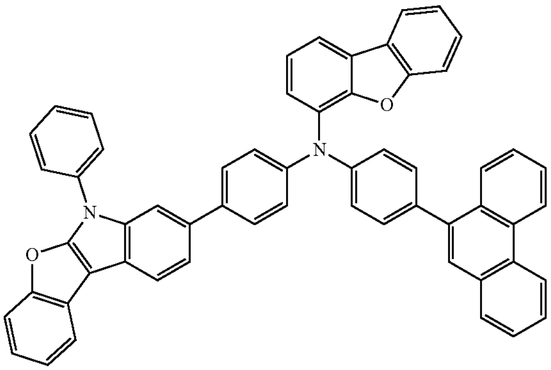
-continued
B5
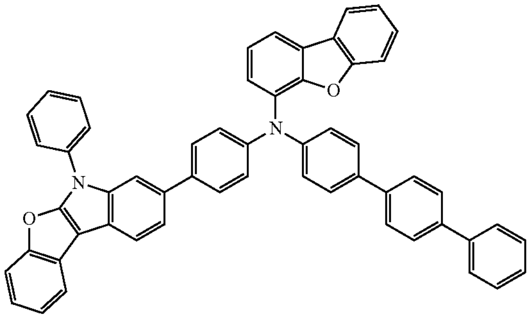
B6
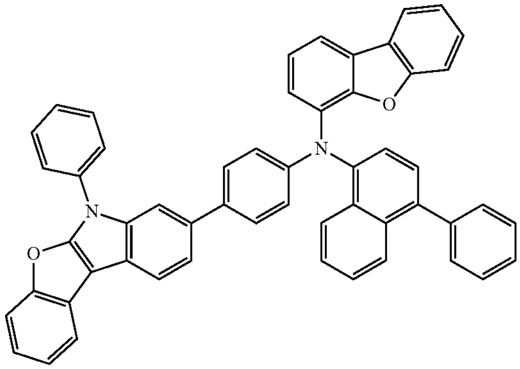
B7
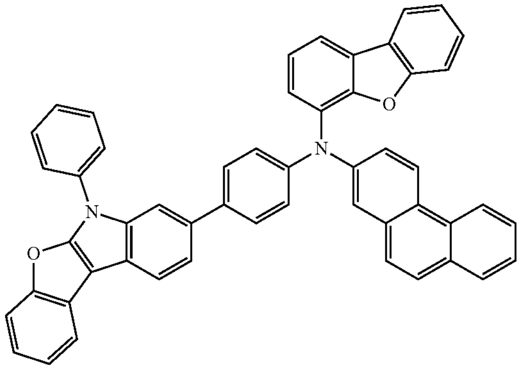
B8
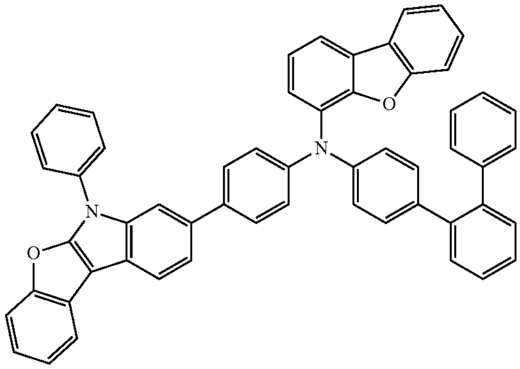

-continued
B9
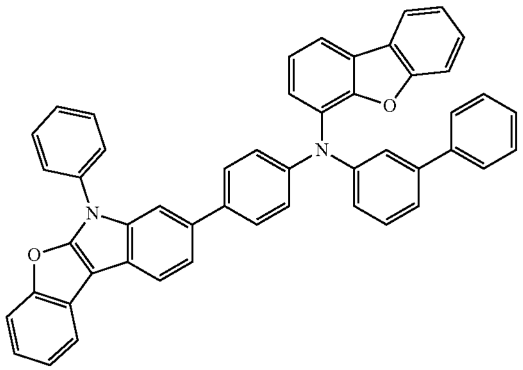
B10
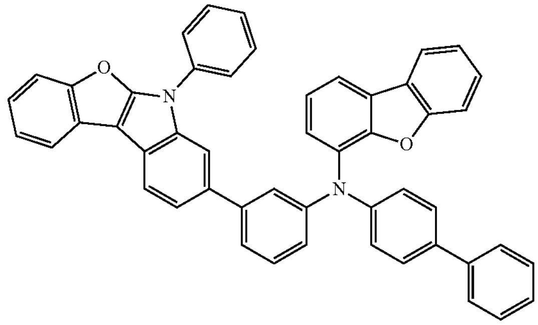
B11
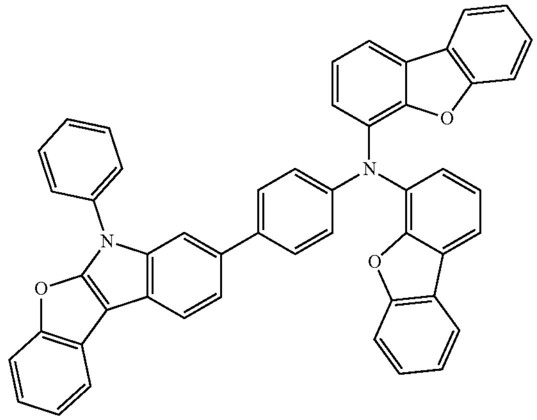
B12
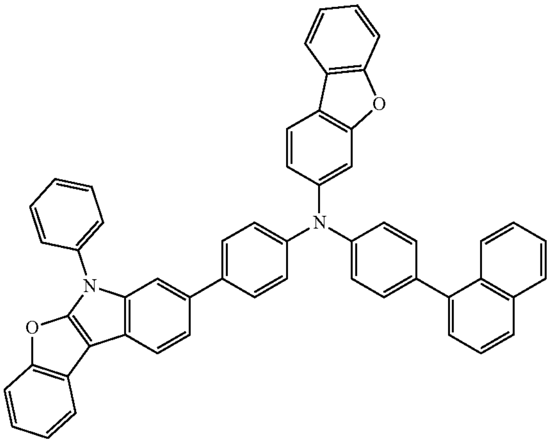
-continued
B13
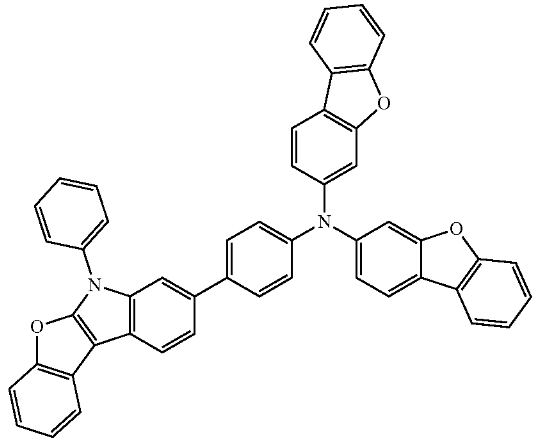
B14
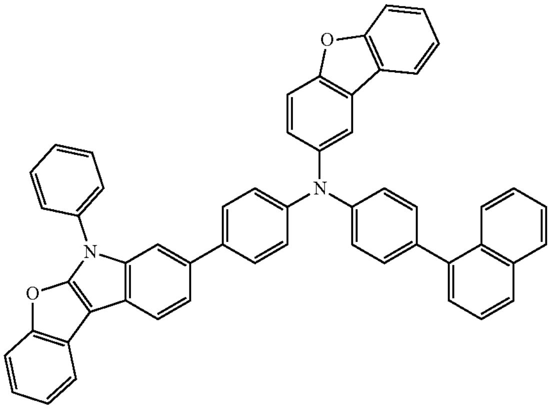
B15
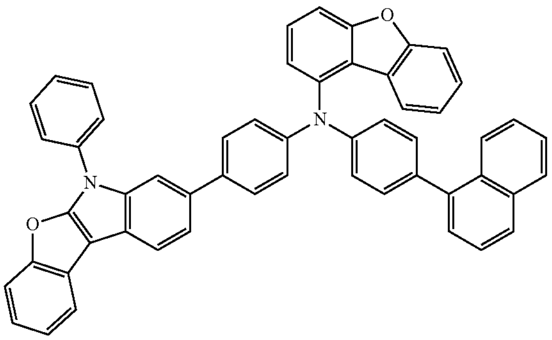
B16
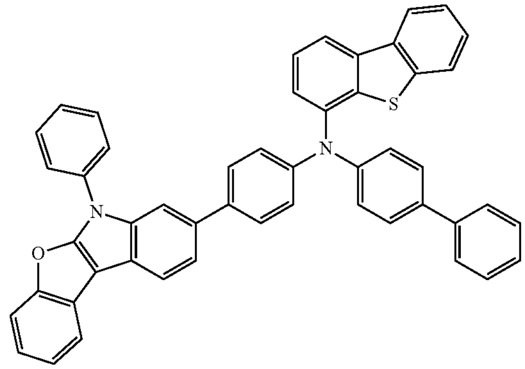

B17
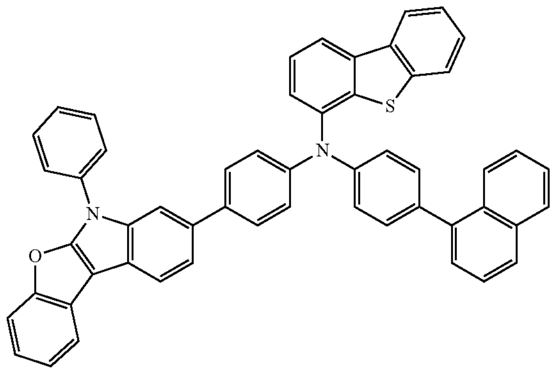
B18
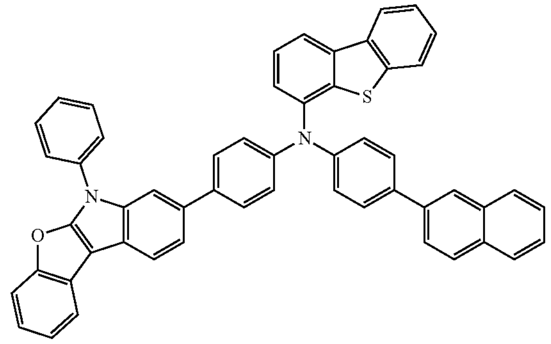
B19
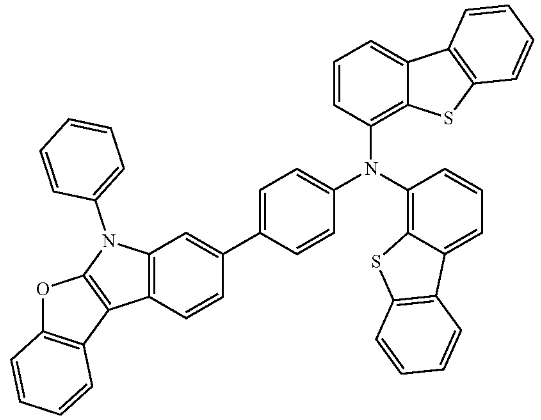
B20
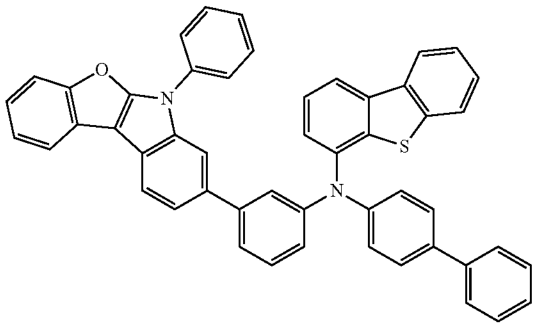
B21
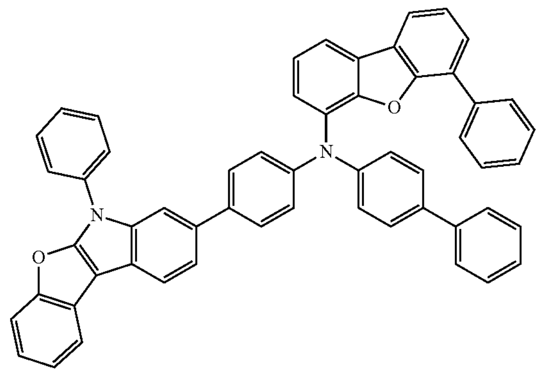
B22
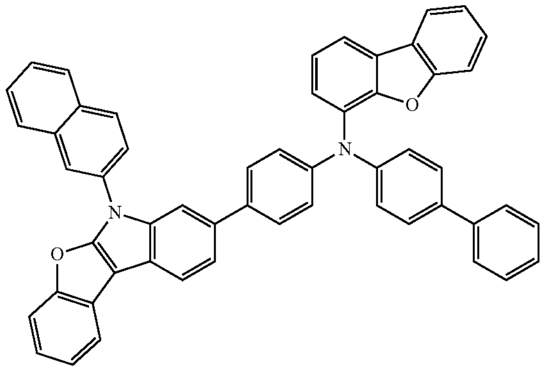
B23
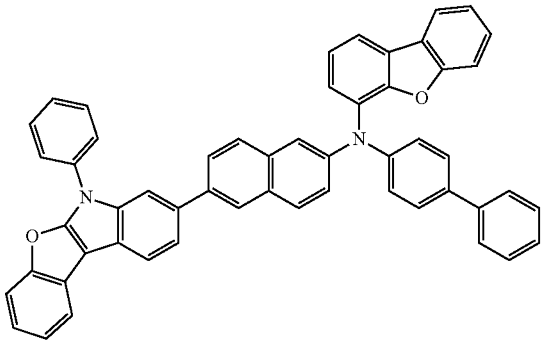
B24
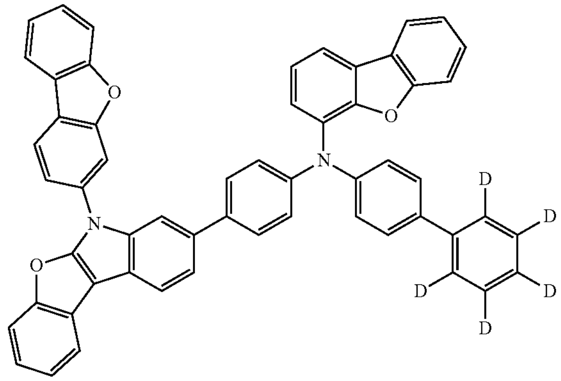

-continued
B25
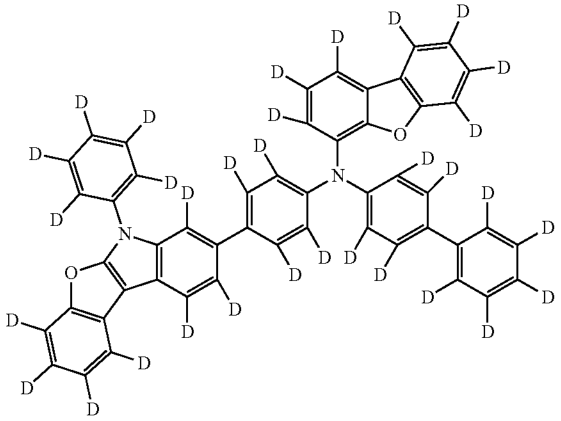
B26
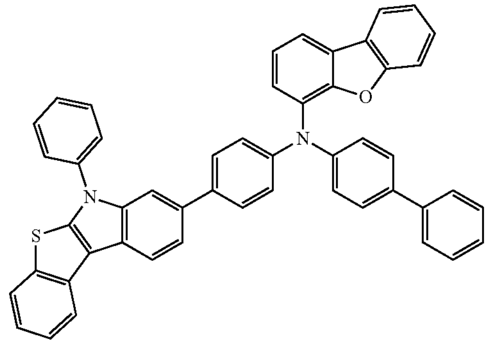
B27
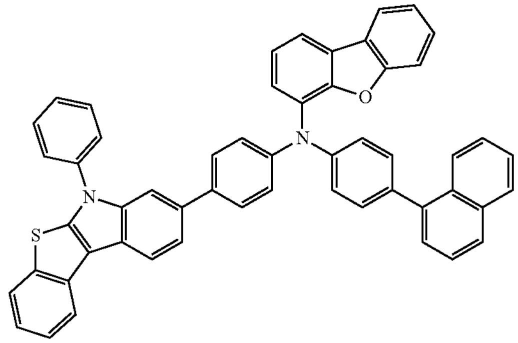
B28
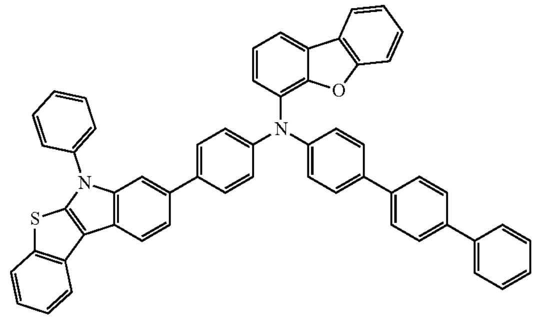
-continued
B29
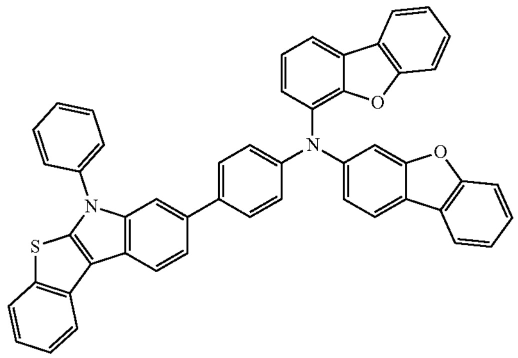
B30
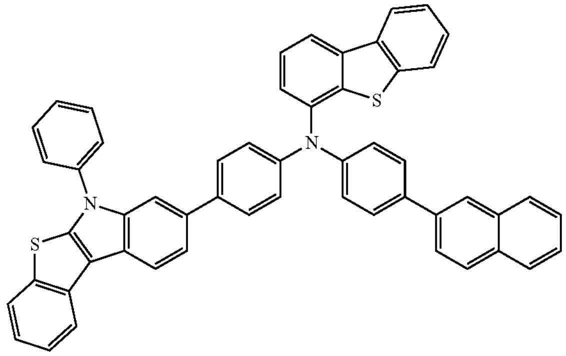
B31
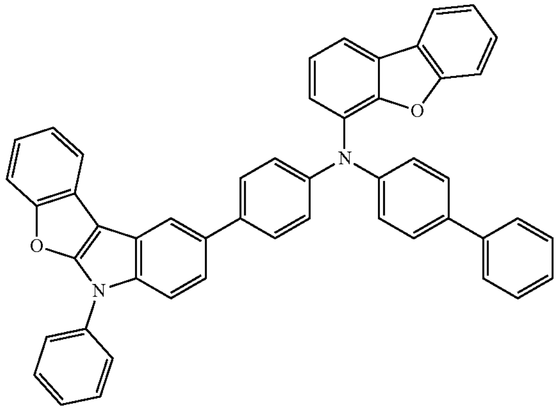
B32
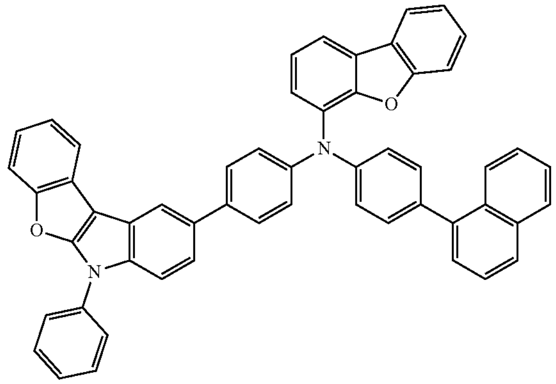

-continued
B33
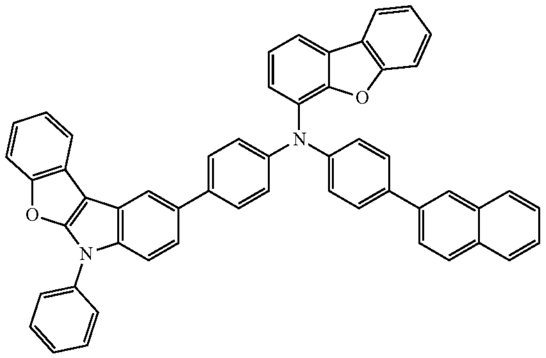
B34
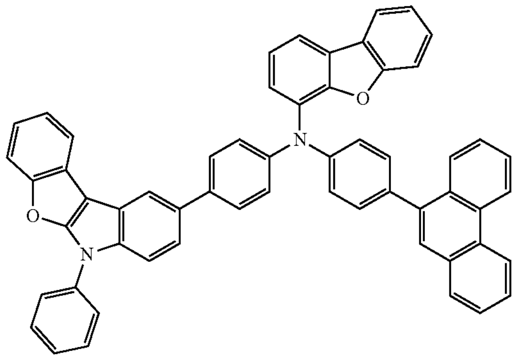
B35
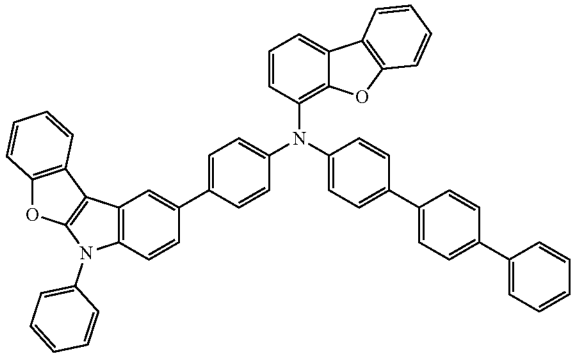
B36
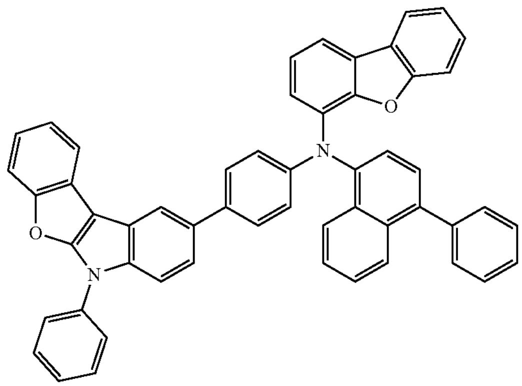
-continued
B37
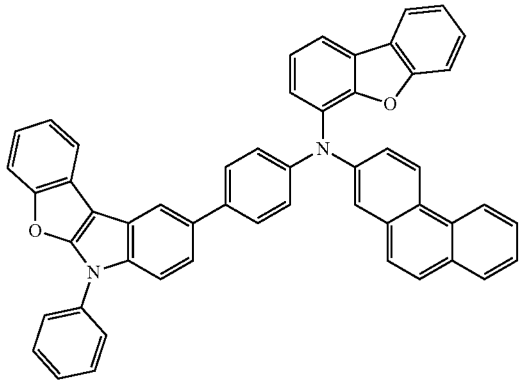
B38
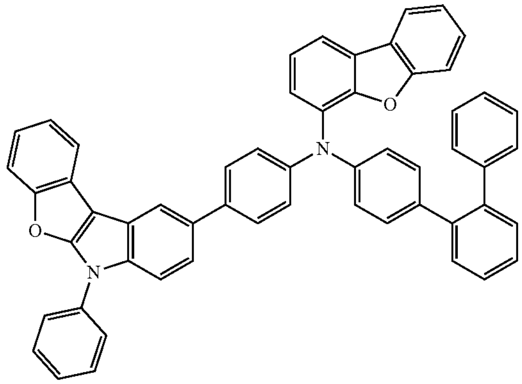
B39
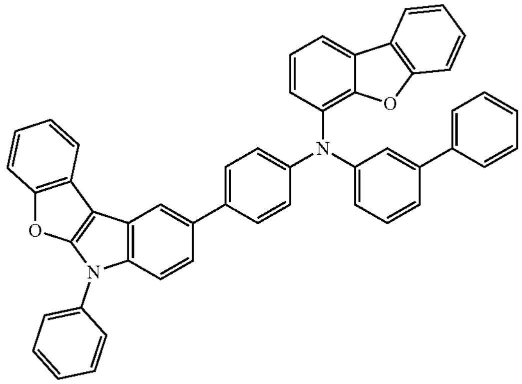
B40
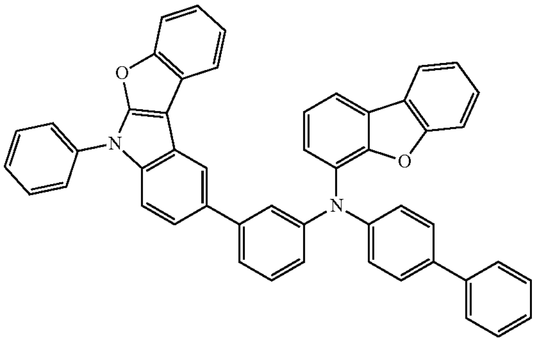

-continued
B41
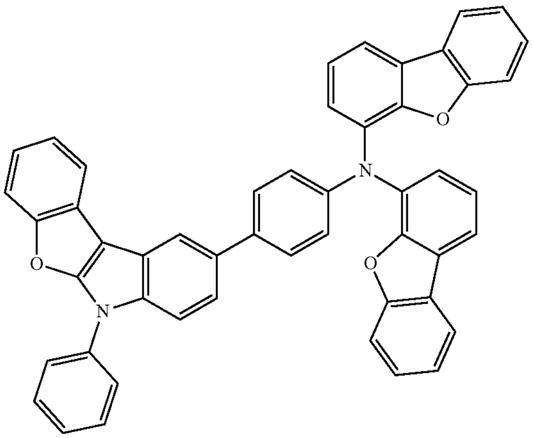
B42
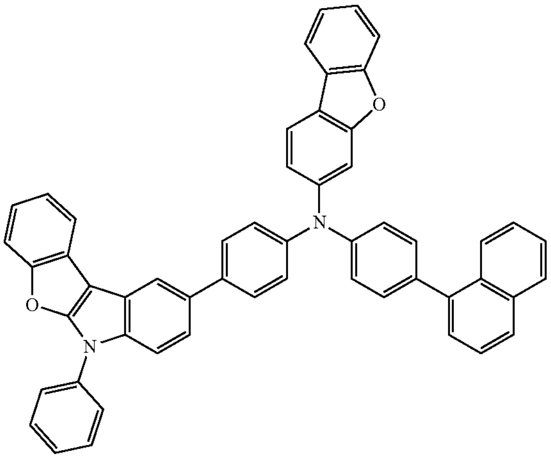
B43
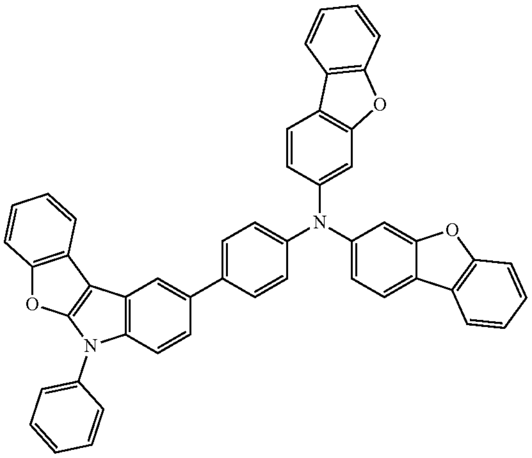
-continued
B44
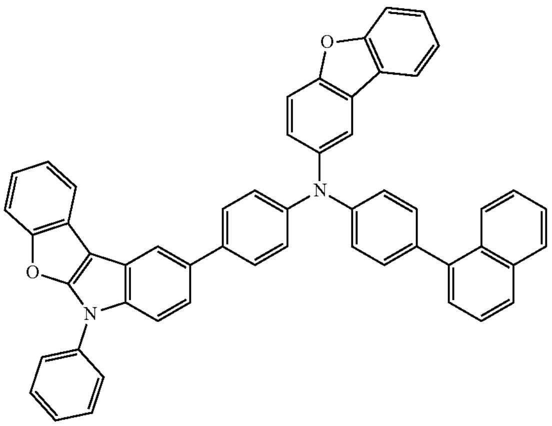
B45
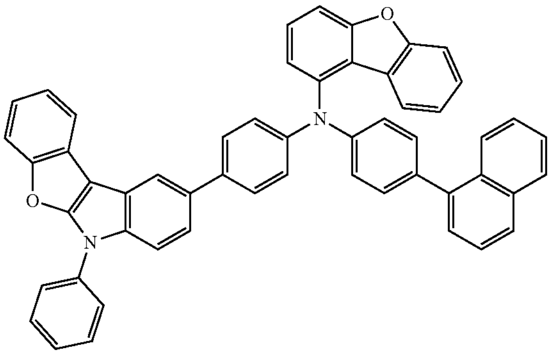
B46
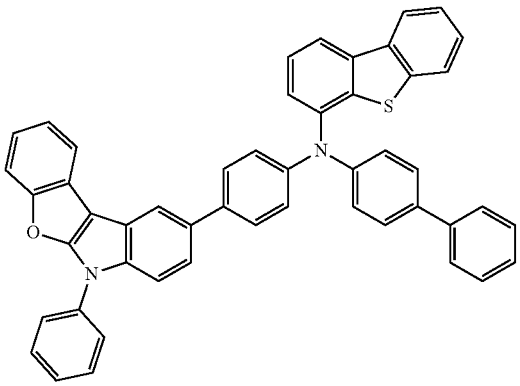
B47
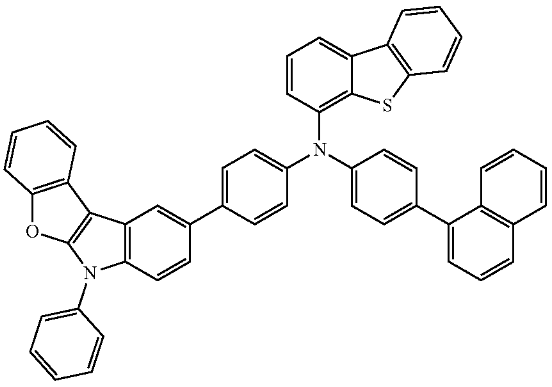

B48
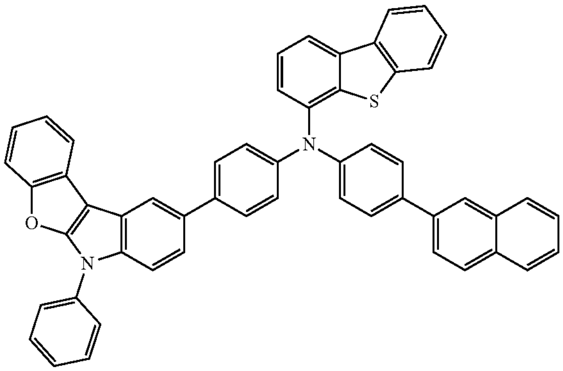
B49
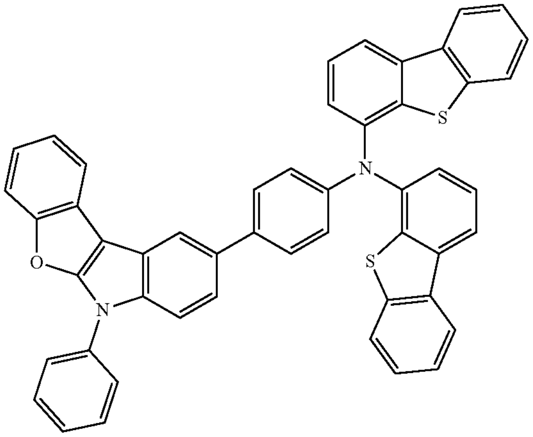
B50
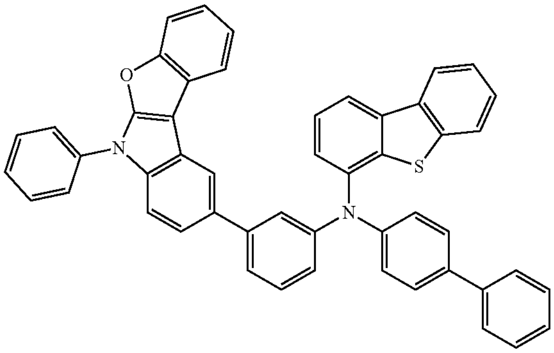
B51
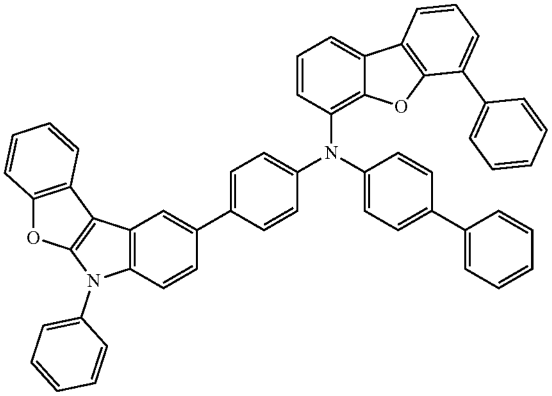
B52
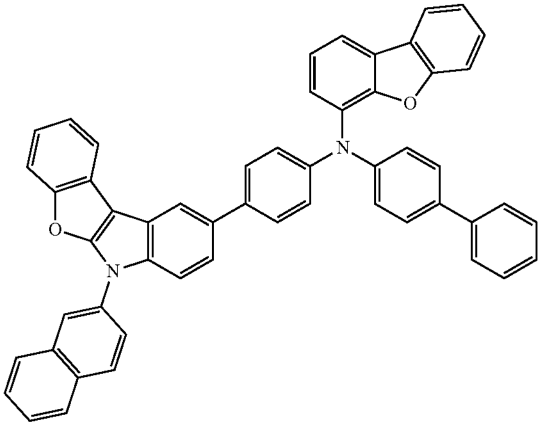
B53
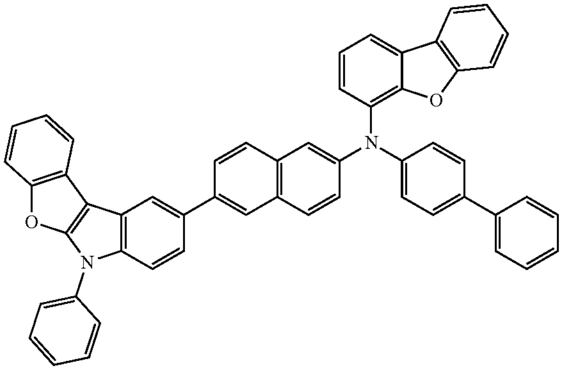
B54
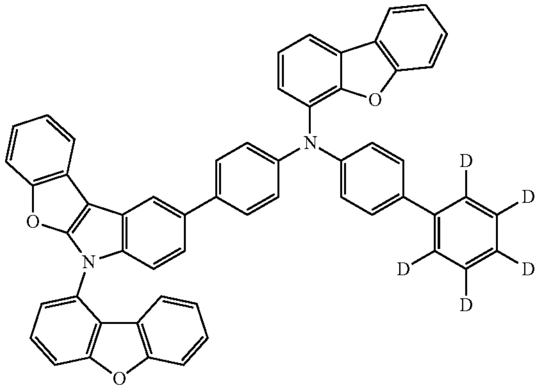

-continued
B55
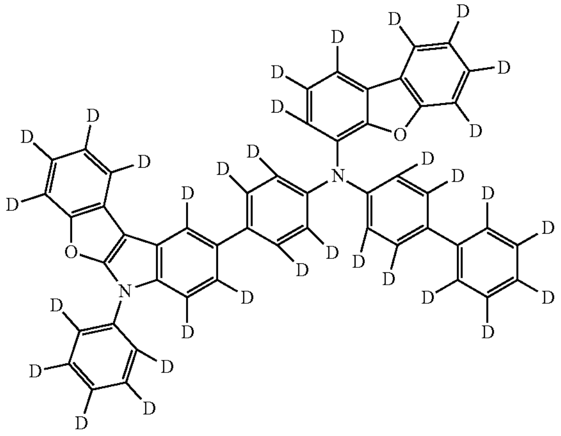
B56
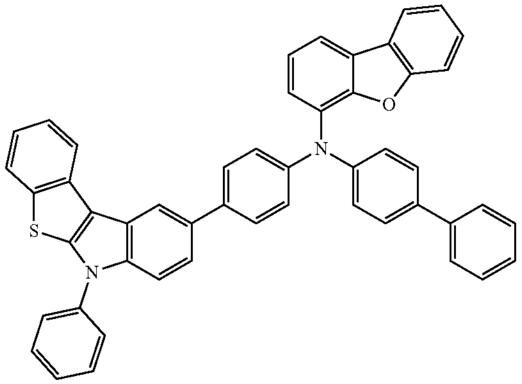
B57
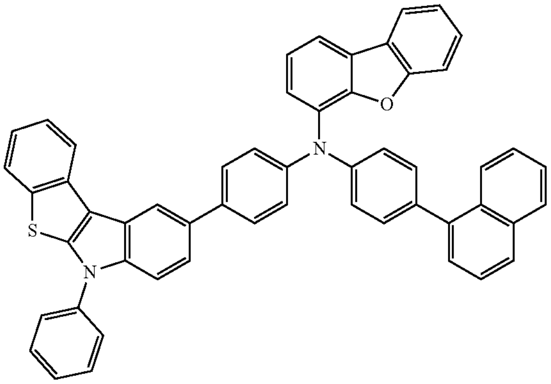
B58
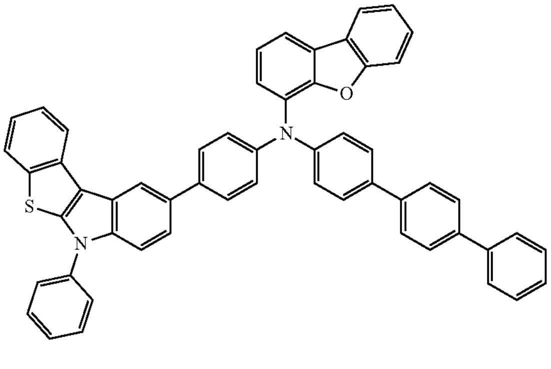
-continued
B59
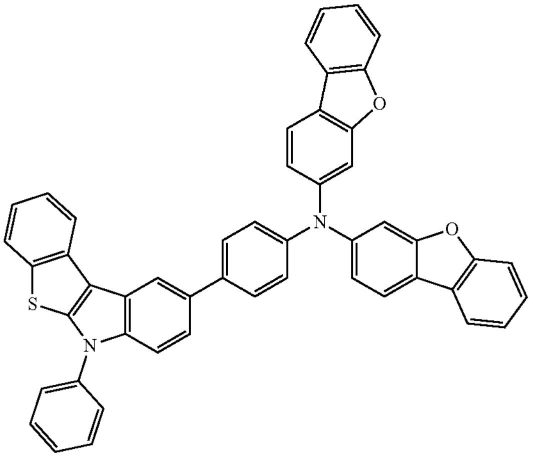
B60
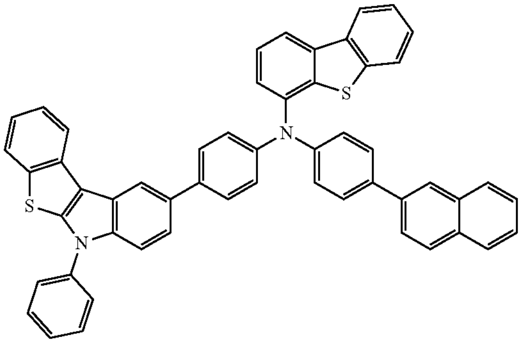
B61
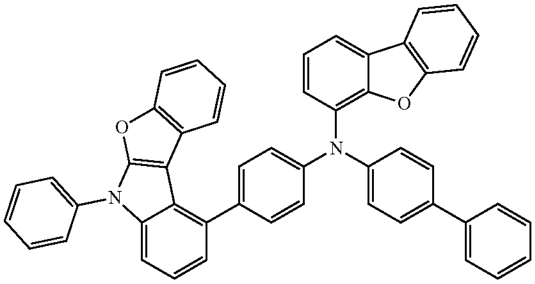
B62
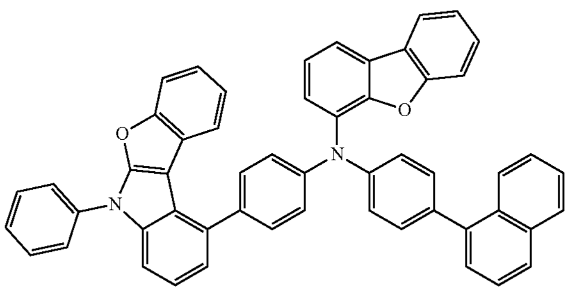

-continued
B63
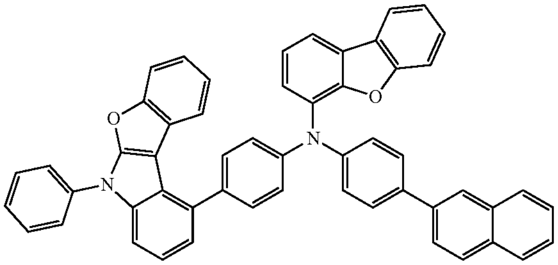
B64
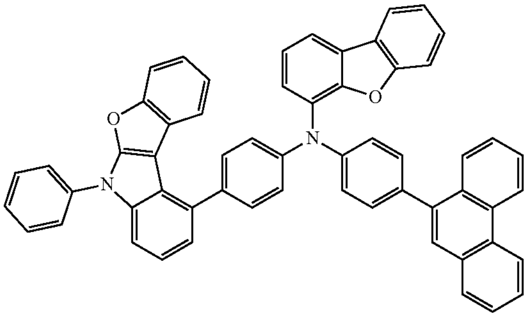
B65
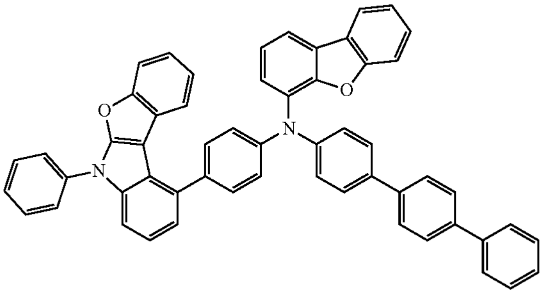
B66
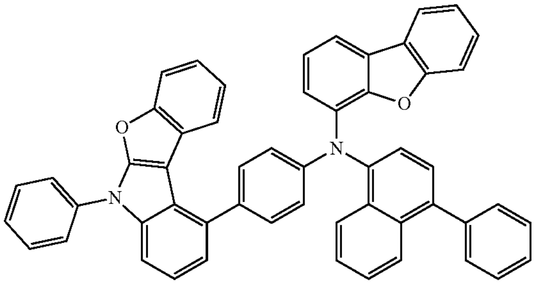
B67
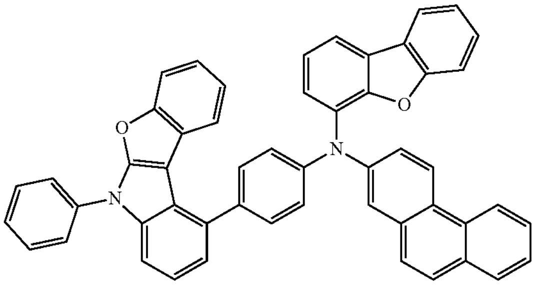
-continued
B68
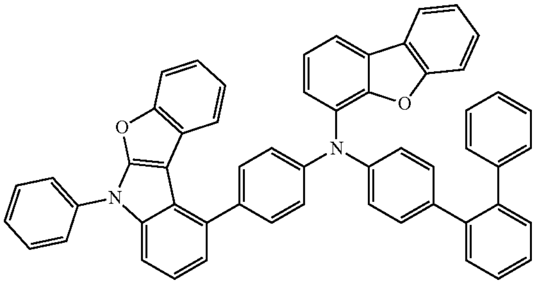
B69
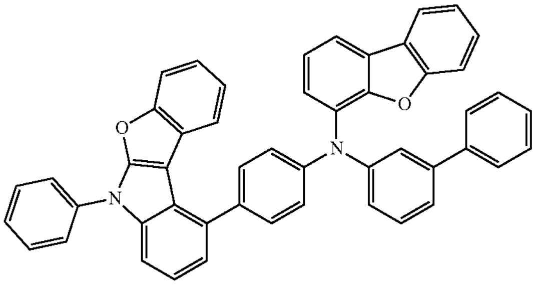
B70
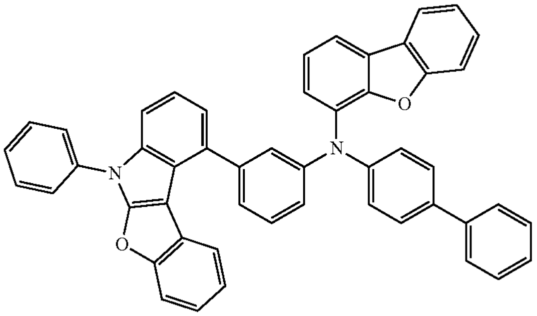
B71
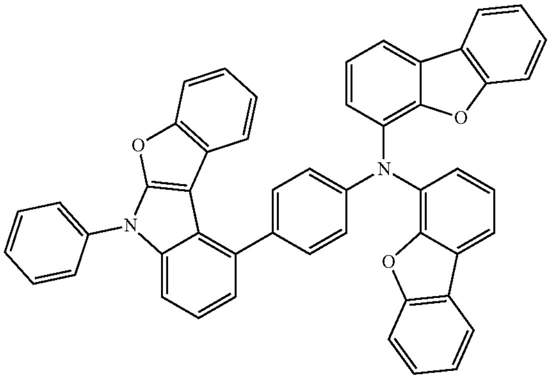

-continued
B72
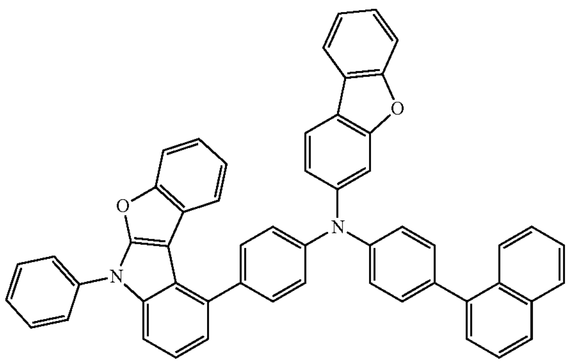
B73
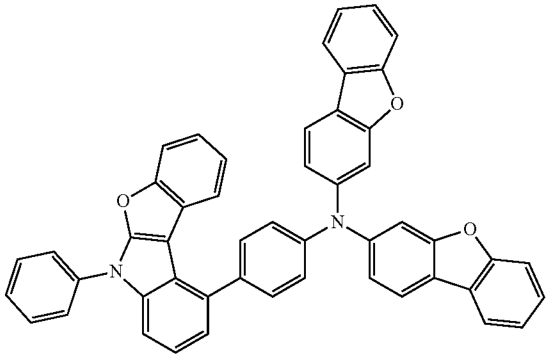
B74
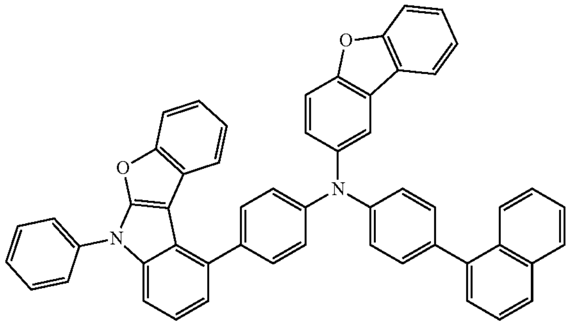
B75
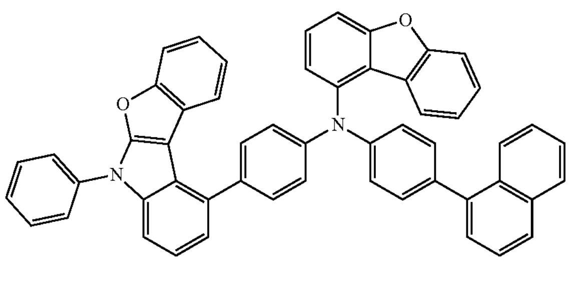
-continued
B76
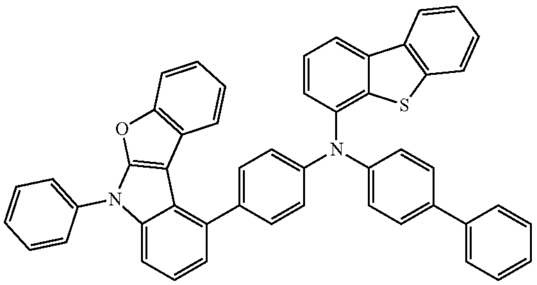
B77
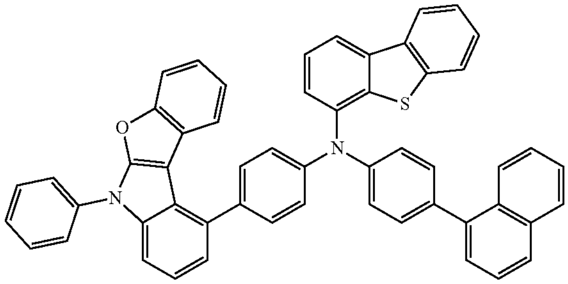
B78
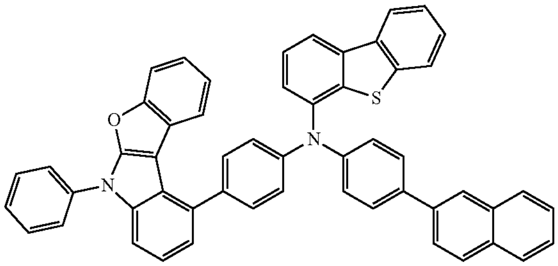
B79
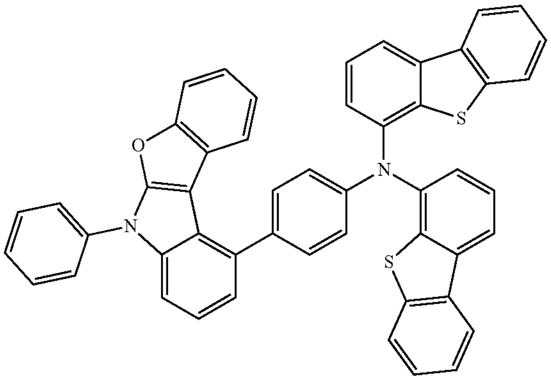
B80
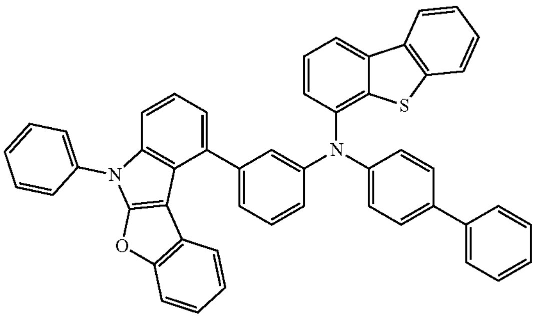

-continued
B81
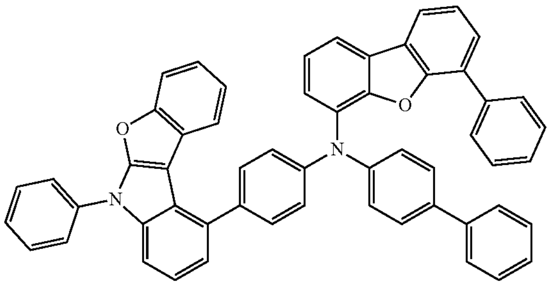
B82
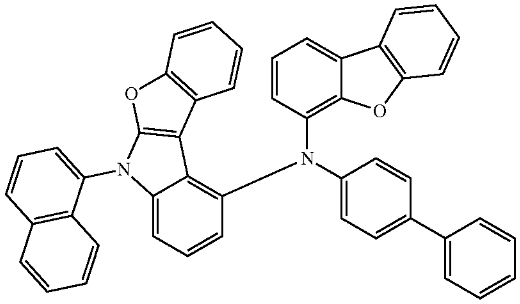
B83
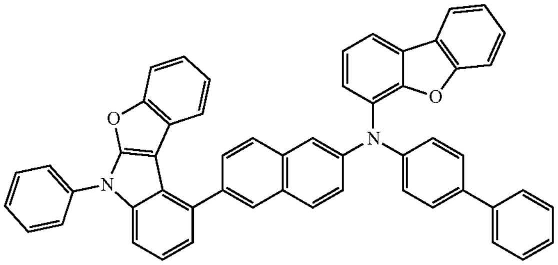
B84
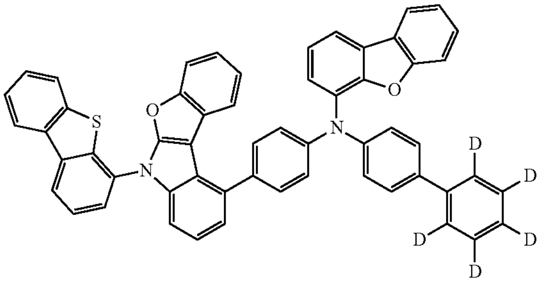
B85
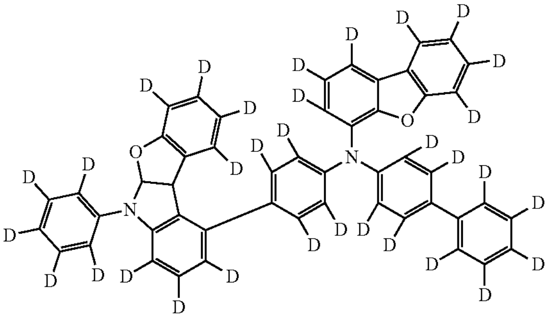
-continued
B86
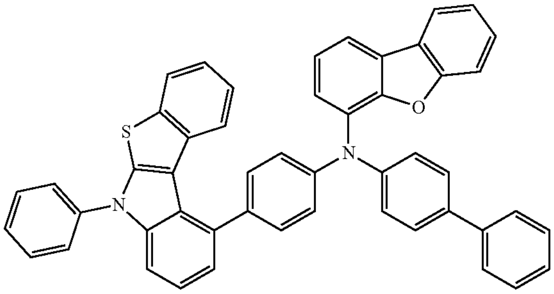
B87
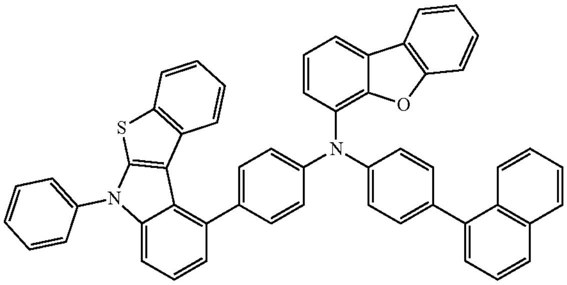
B88
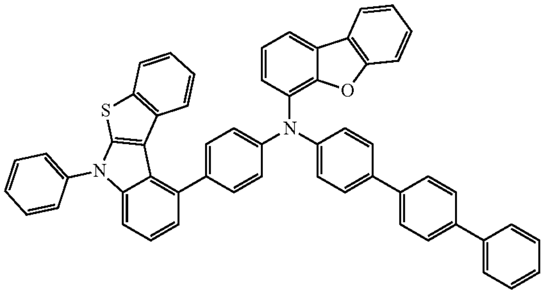
B89
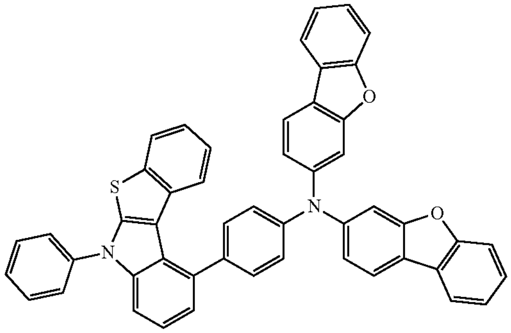
B90
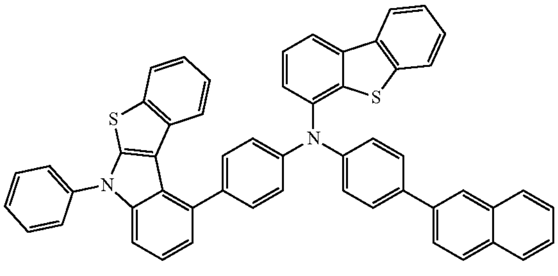

-continued
B91
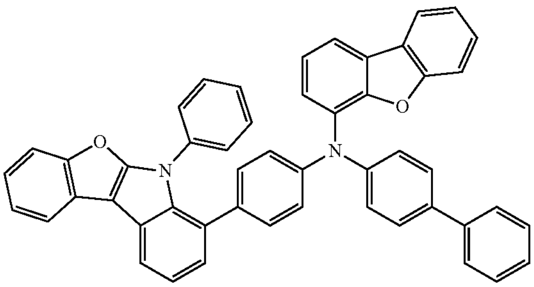
B92
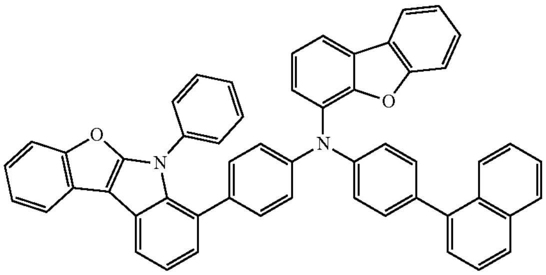
B93
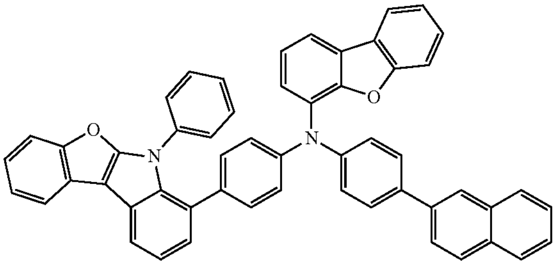
B94
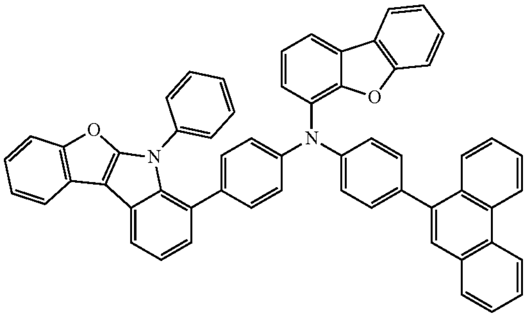
B95
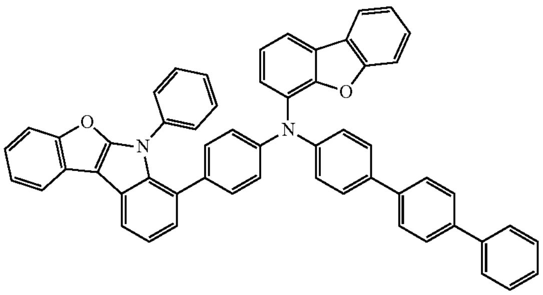
-continued
B96
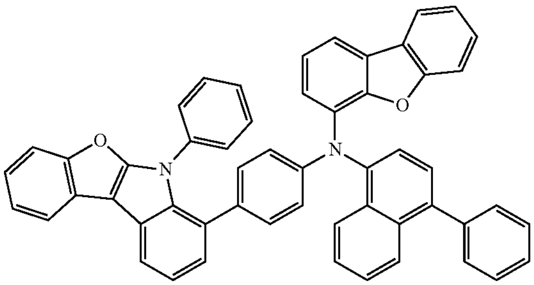
B97
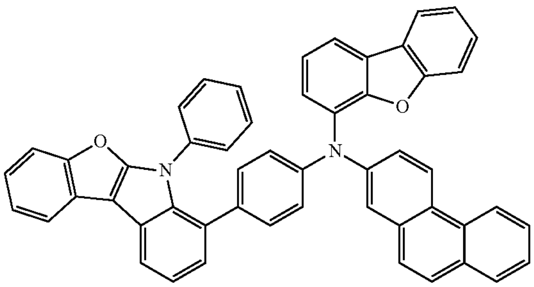
B98
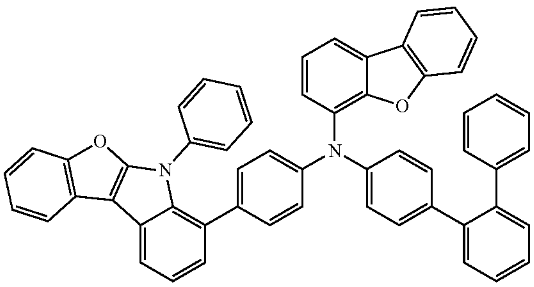
B99
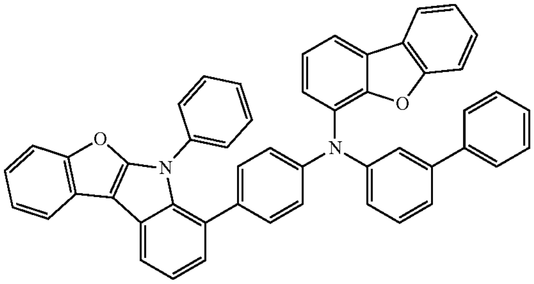
B100
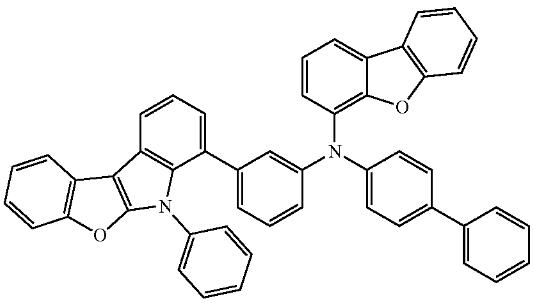

-continued
B101
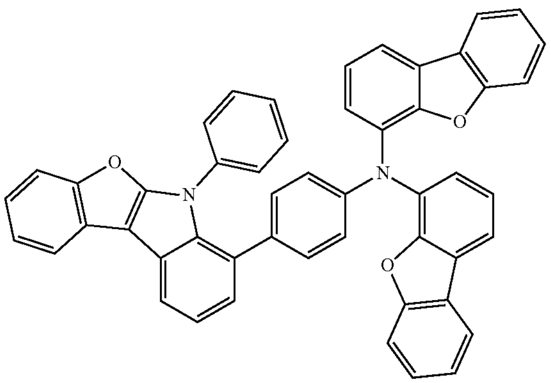
B102
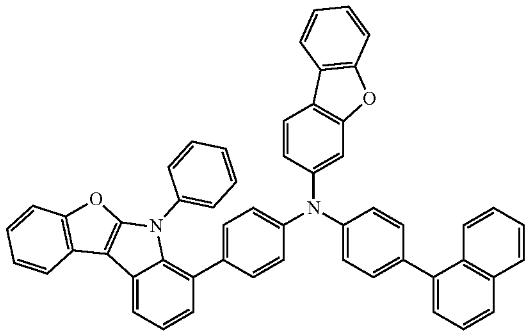
B103
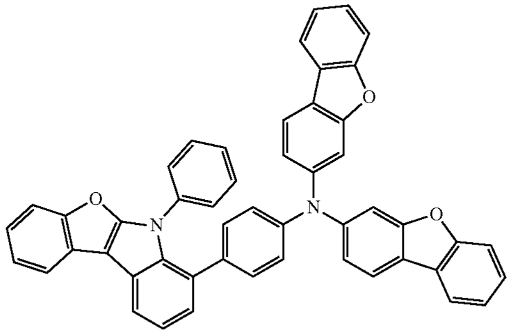
B104
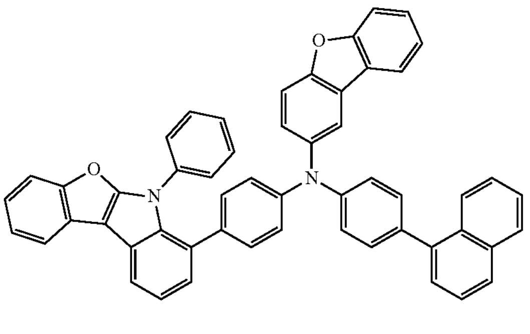
-continued
B105
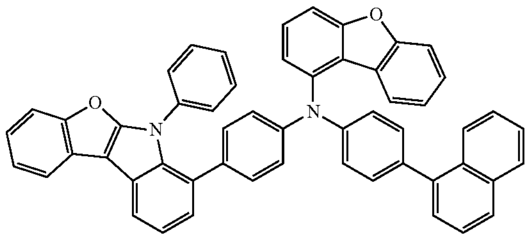
B106
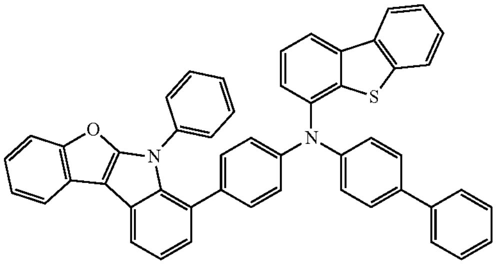
B107
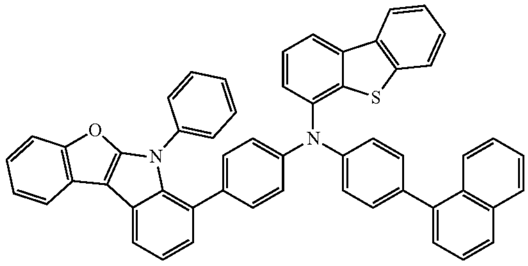
B108
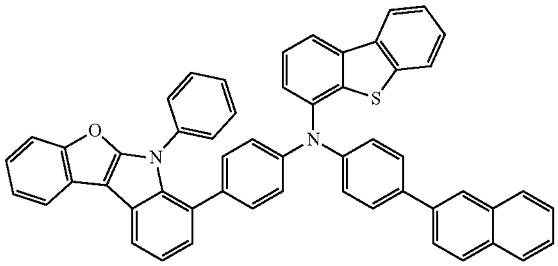
B109
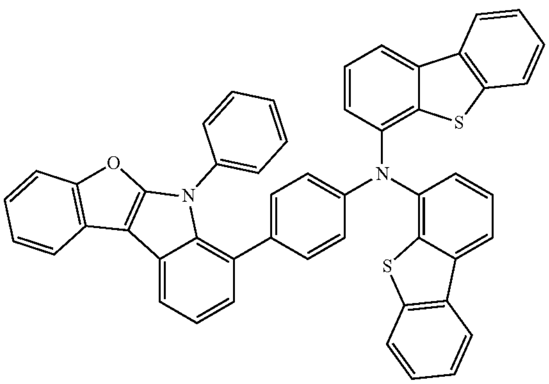

-continued
B110
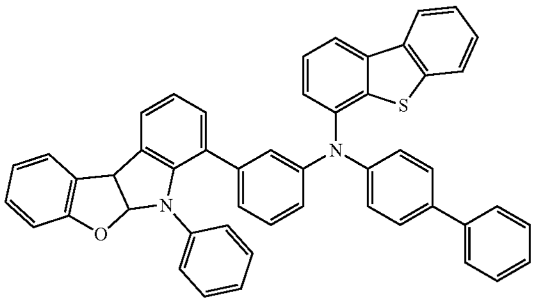
B111
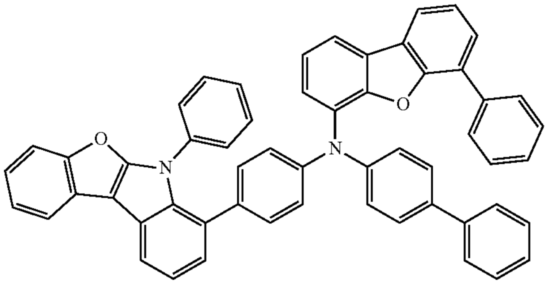
B112
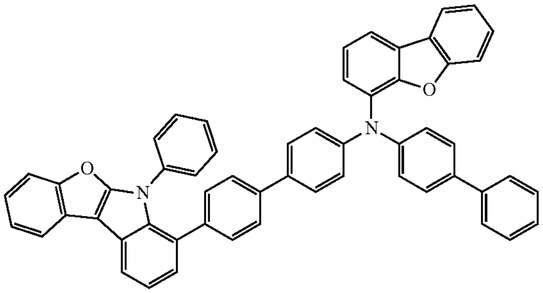
B113
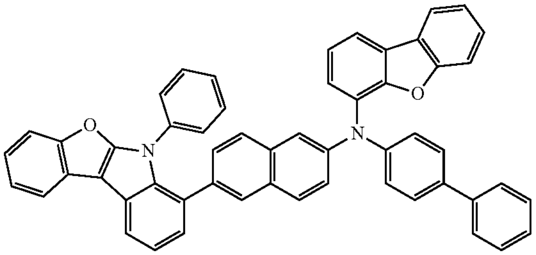
B114
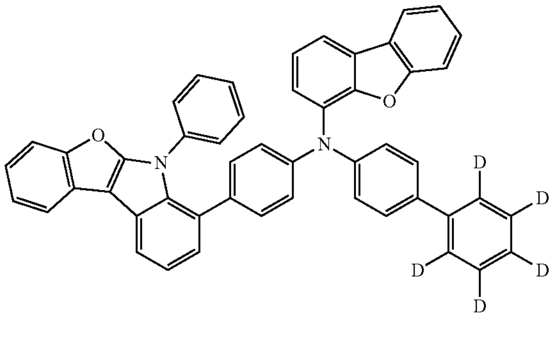
-continued
B115
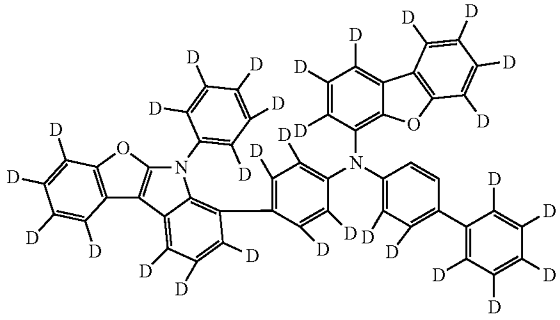
B116
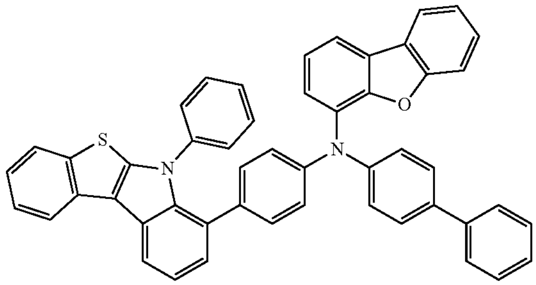
B117
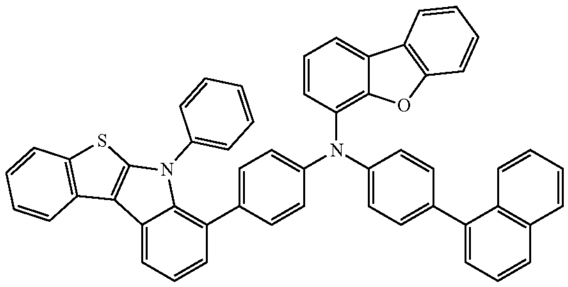
B118
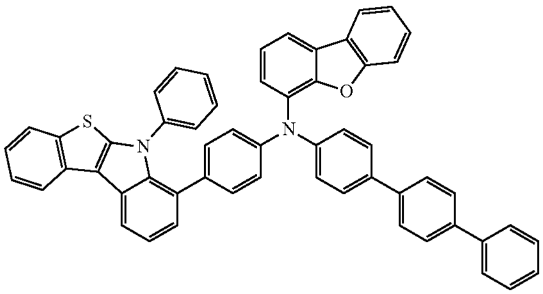

-continued
B119
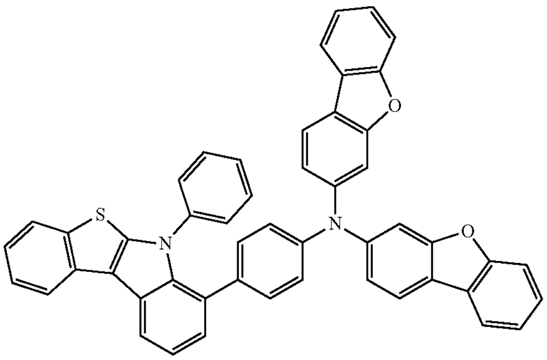
B120
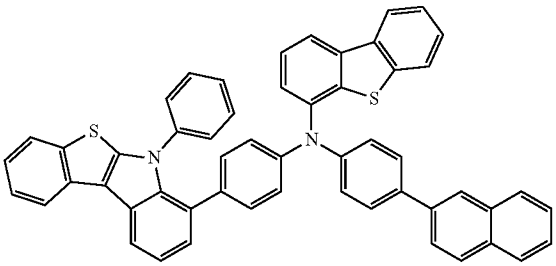
B121
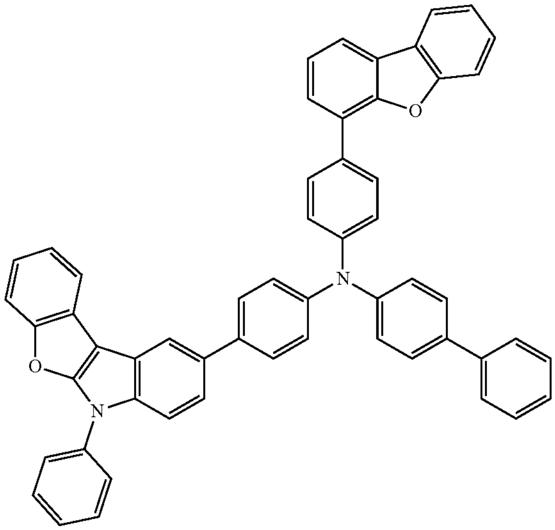
-continued
B122
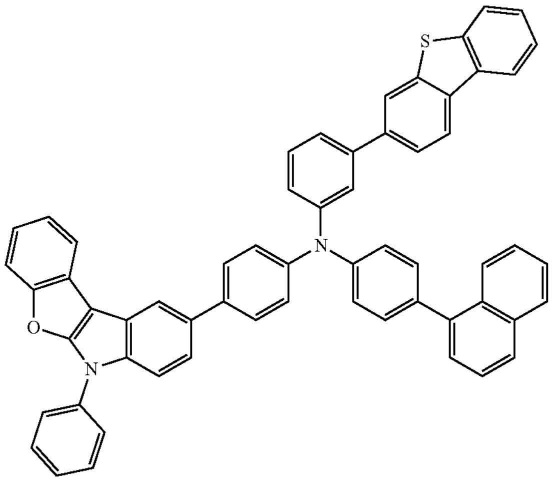
B123
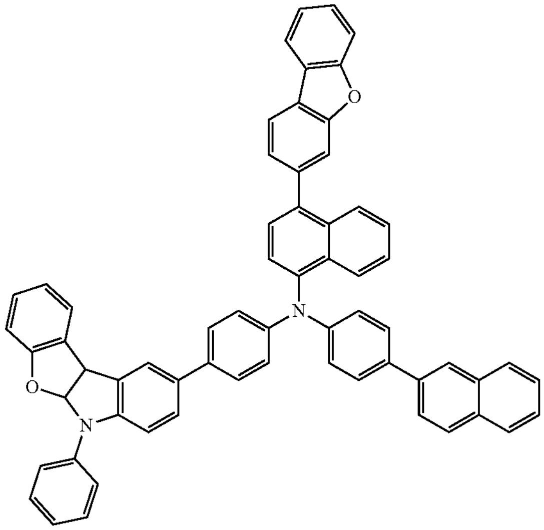
B124
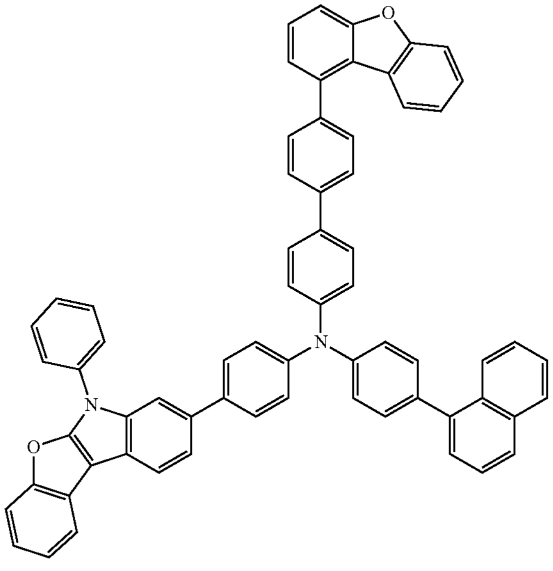

-continued
B125
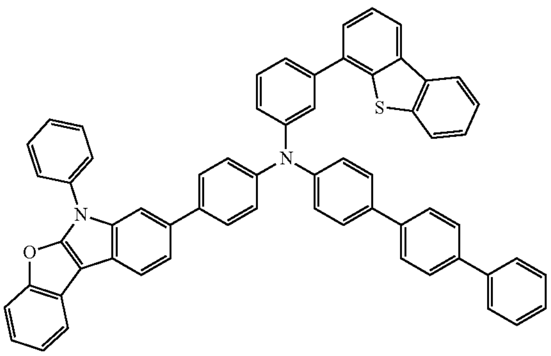
B126
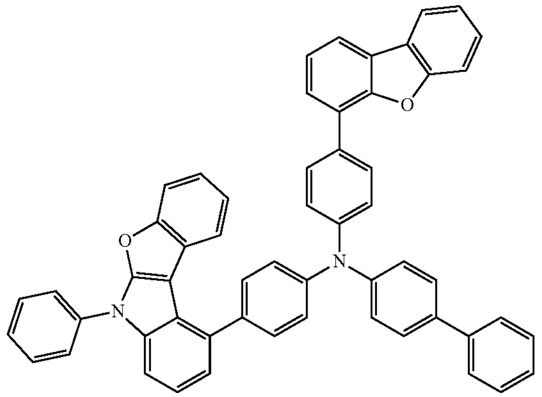
B127
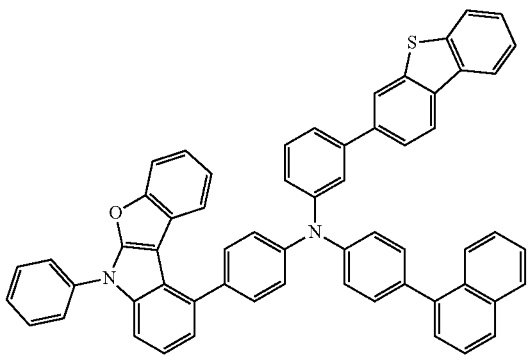
B128
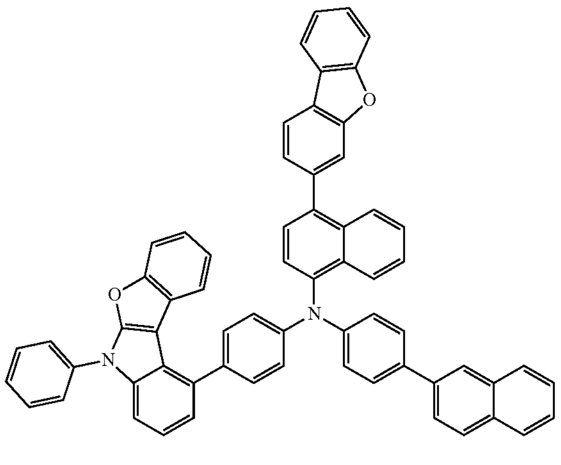
-continued
B129
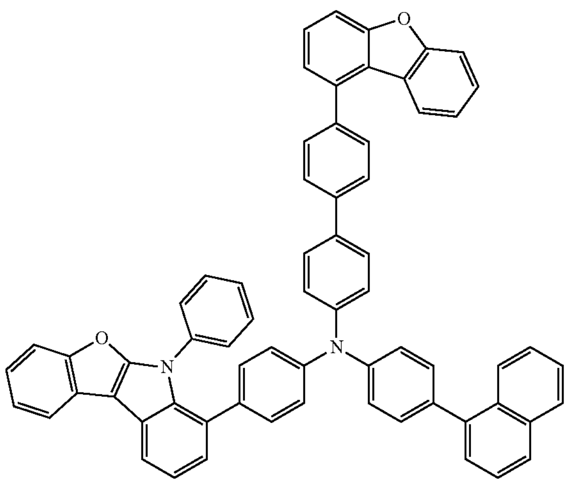
B130
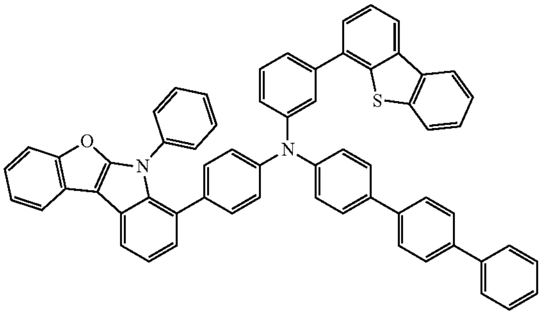
B131
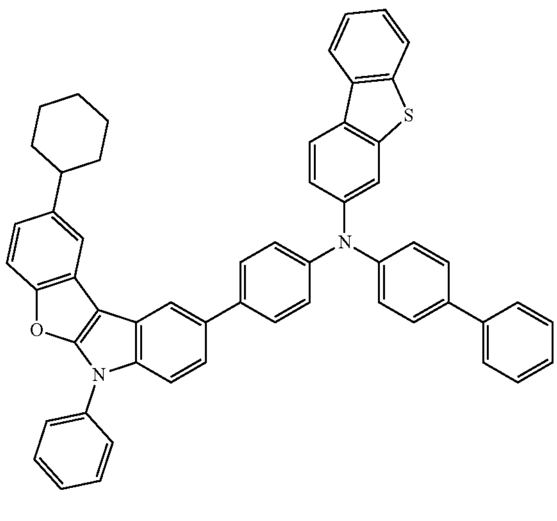

-continued
B132
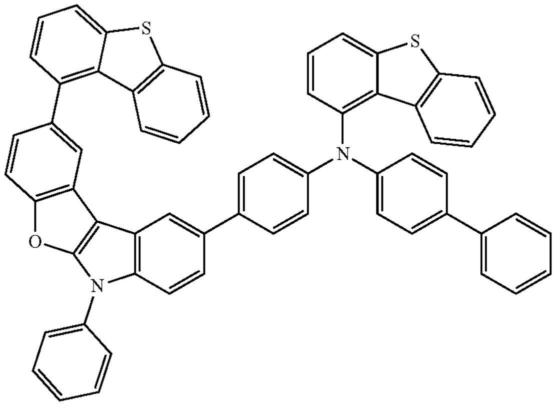
B133
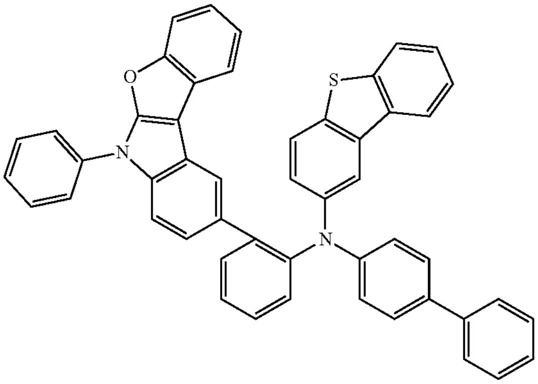
B134
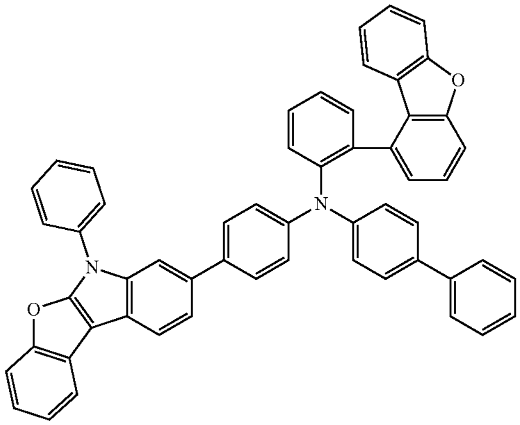
-continued
B135
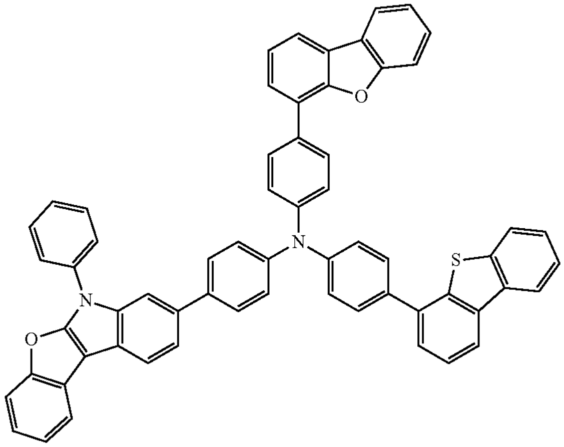
B136
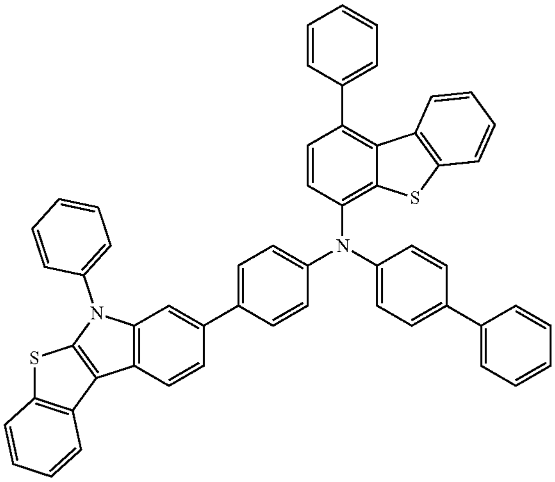
B137
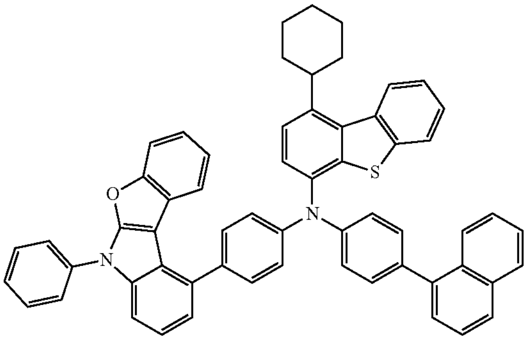
B138
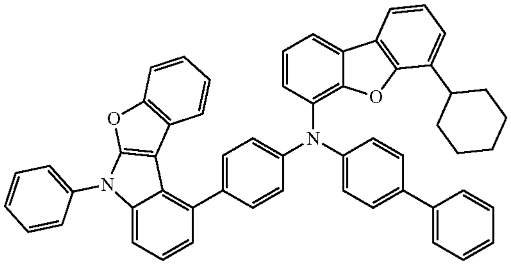

-continued
B139
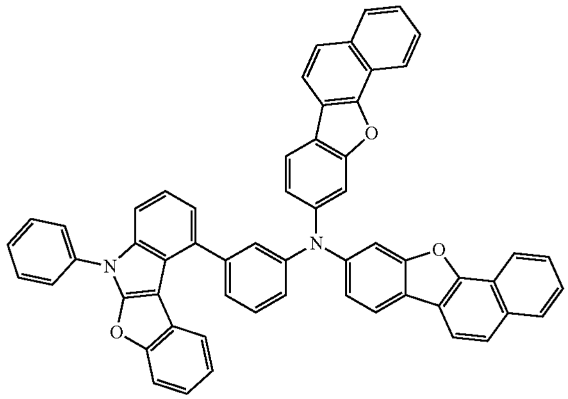
B140
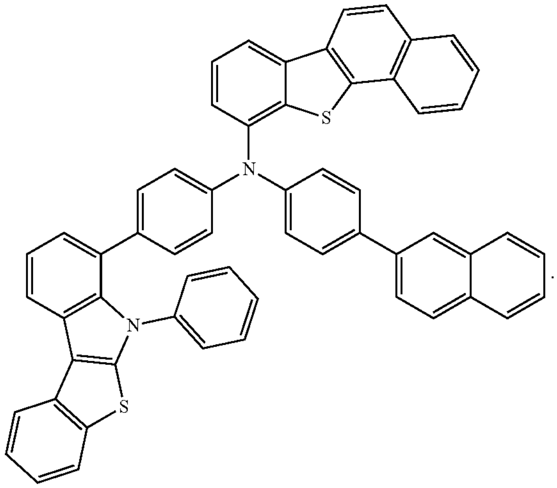
23. The monoamine compound of claim 15, wherein the monoamine compound represented by Formula 1 is a compound represented in Compound Group 3:
[Compound Group 3]
C1
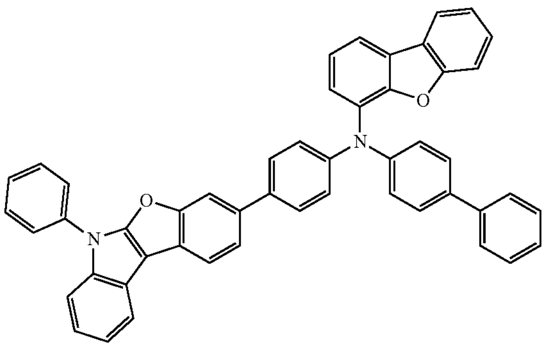
-continued
C2
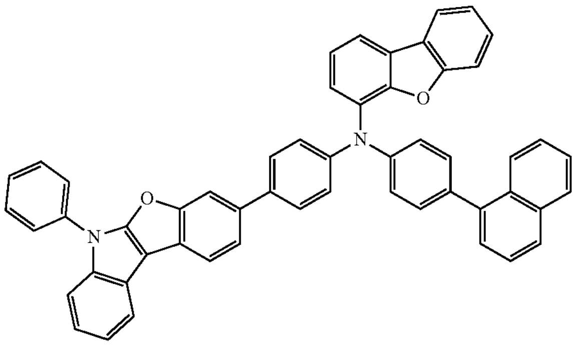
C3
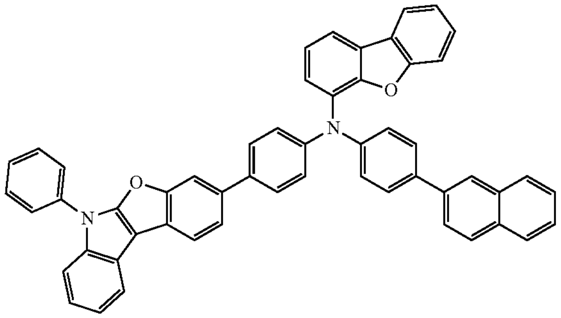
C4
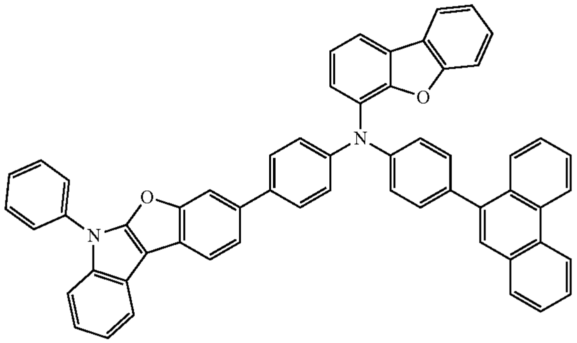
C5
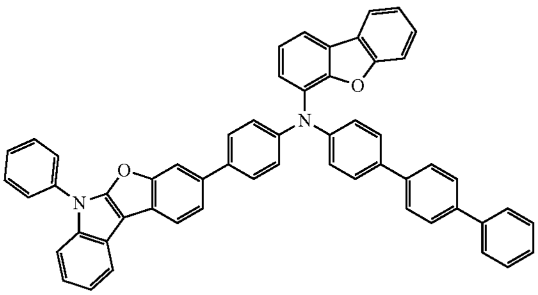

-continued
C6
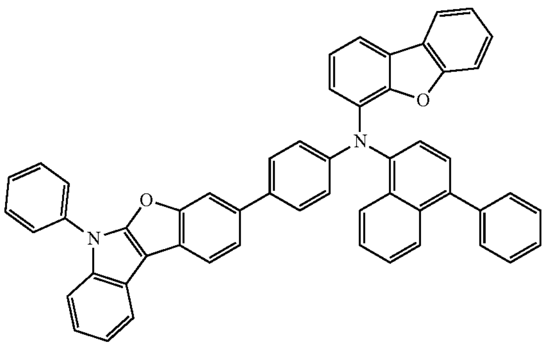
C7
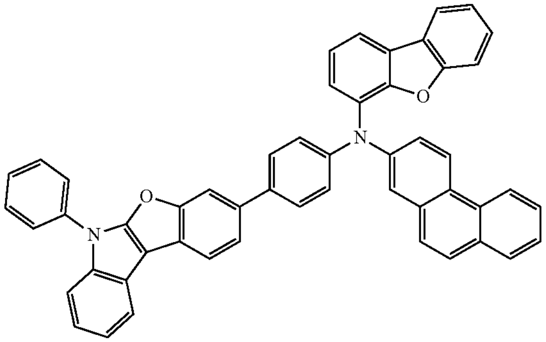
C8
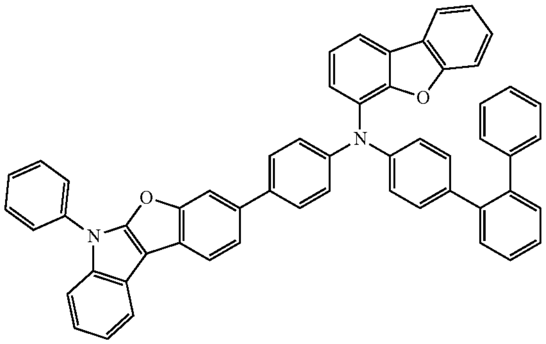
C9
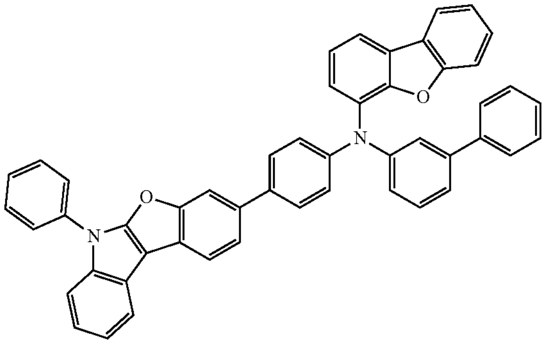
-continued
C10
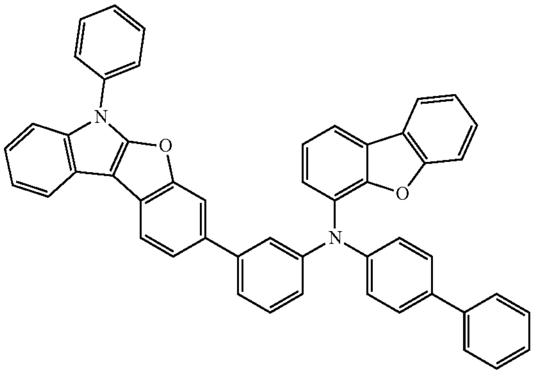
C11
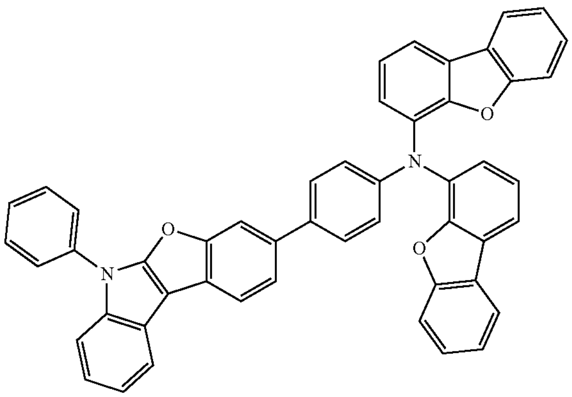
C12
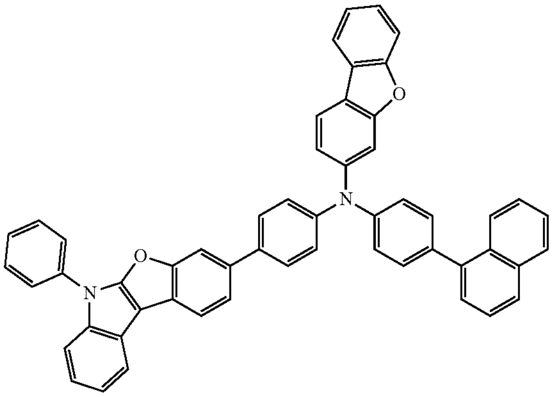

-continued
C13
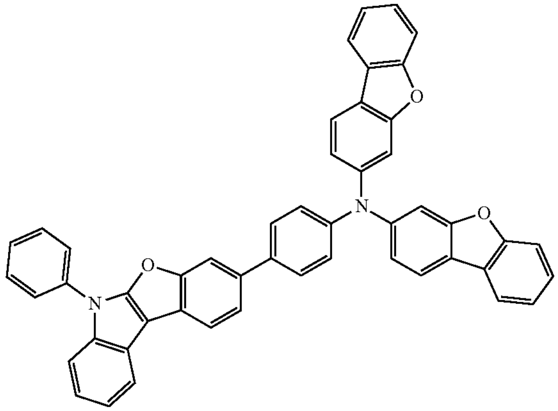
C14
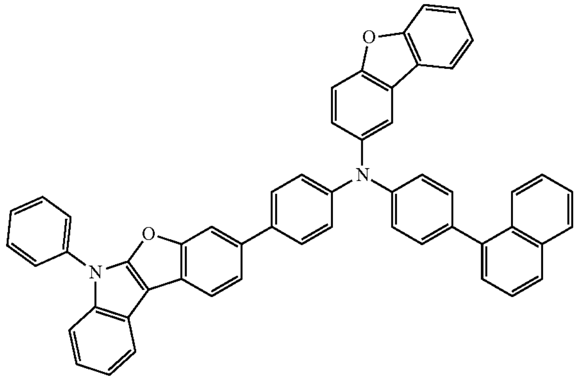
C15
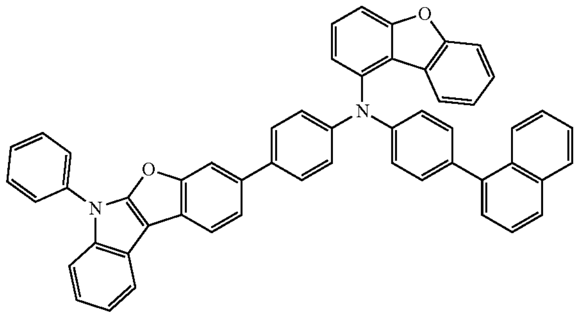
C16
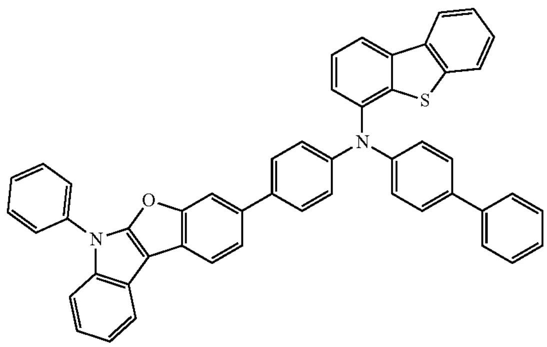
-continued
C17+
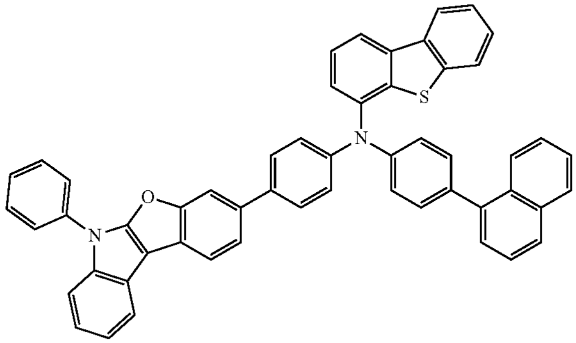
C18
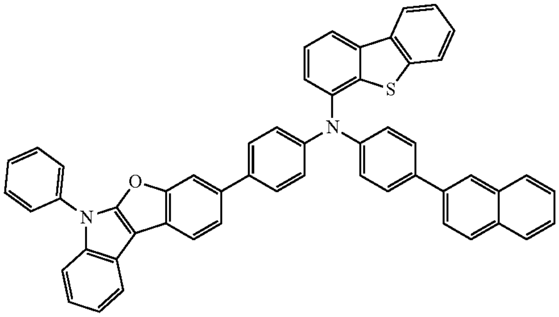
C19
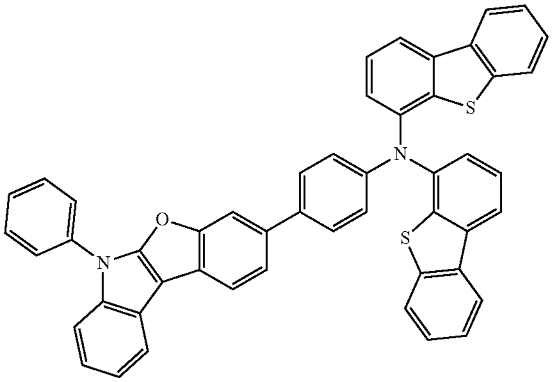
C20
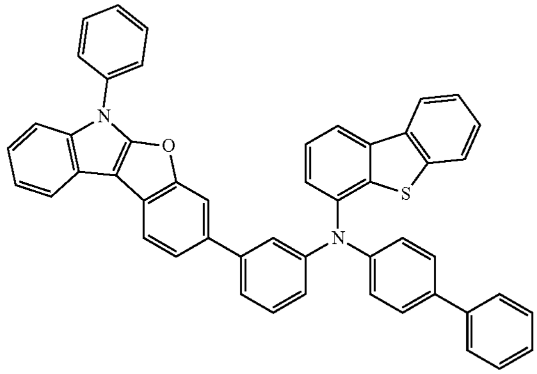

-continued
C21
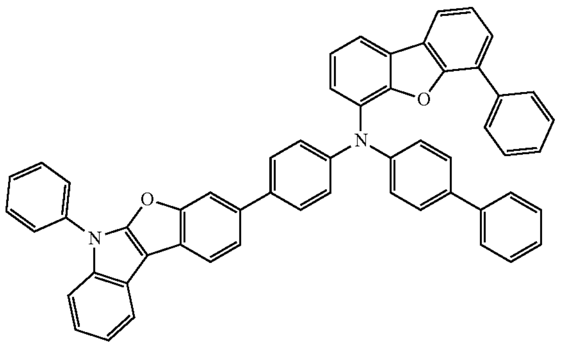
C22
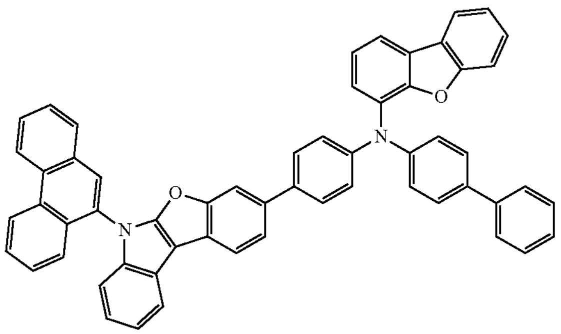
C23
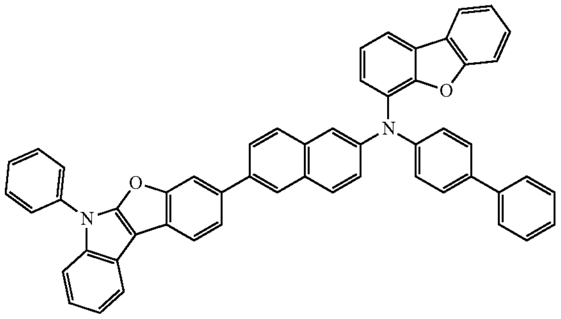
C24
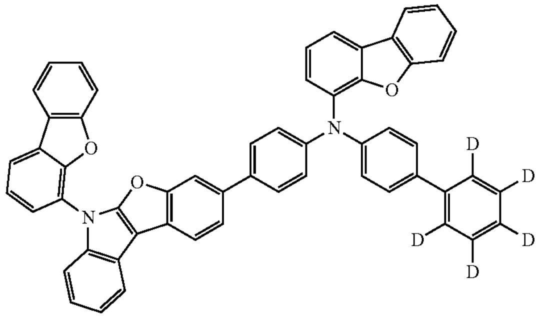
-continued
C25
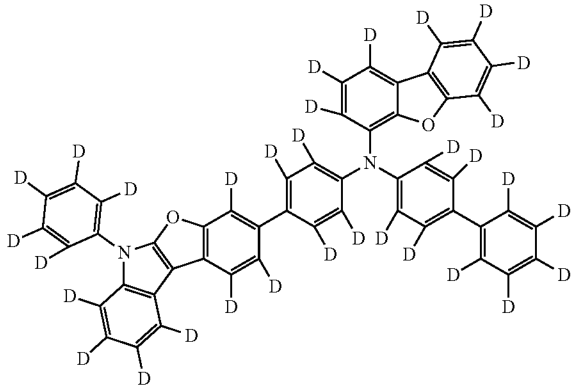
C26
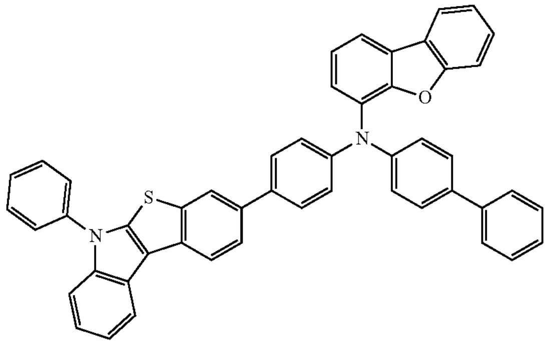
C27
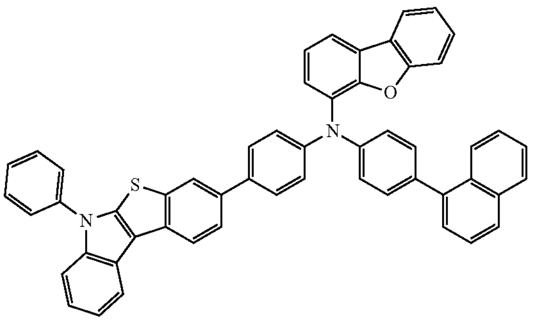
C28
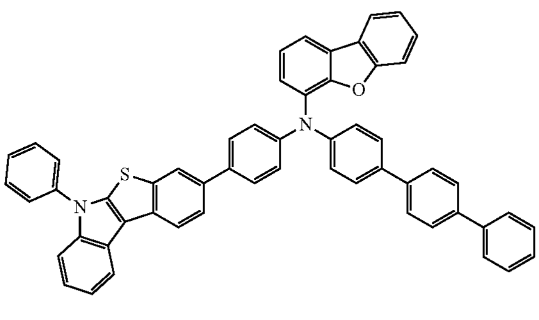

-continued
C29
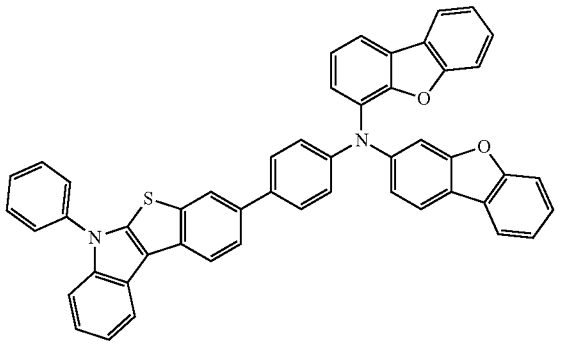
C30
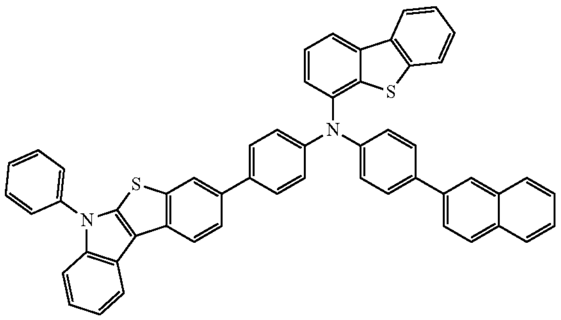
C31
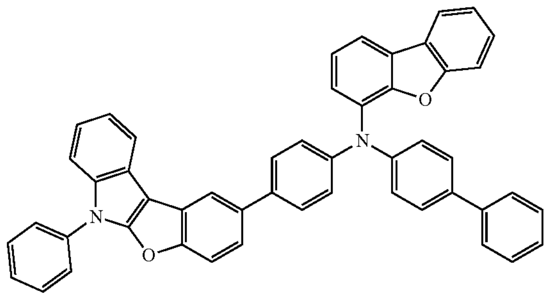
C32
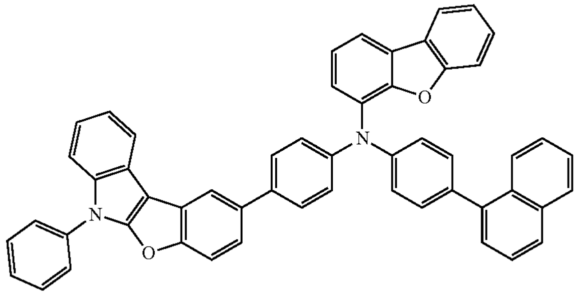
C33
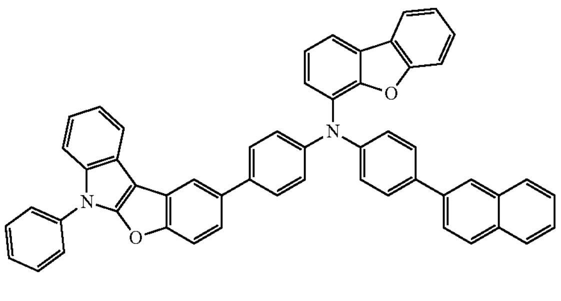
-continued
C34
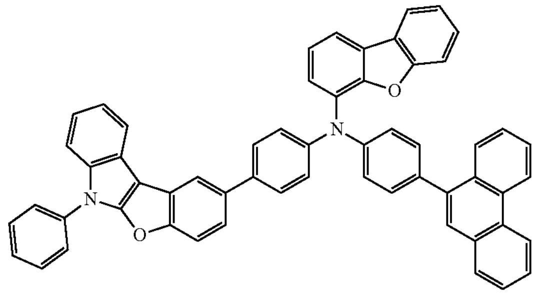
C35
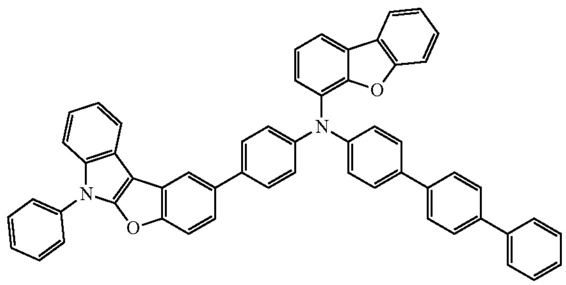
C36
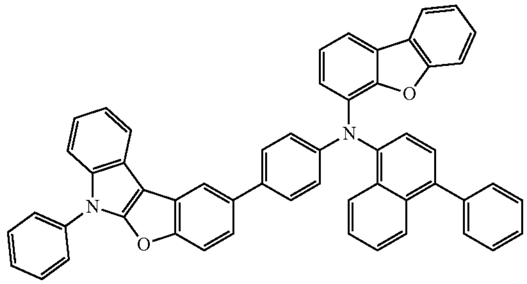
C37
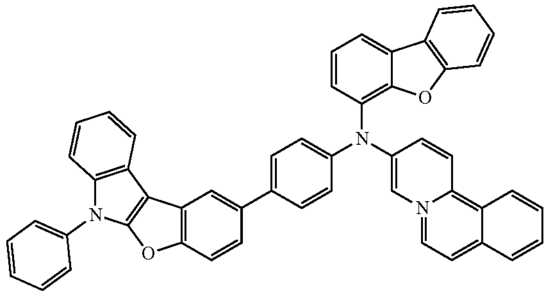
C38
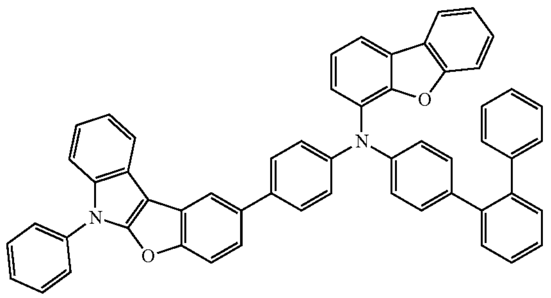

-continued
C39
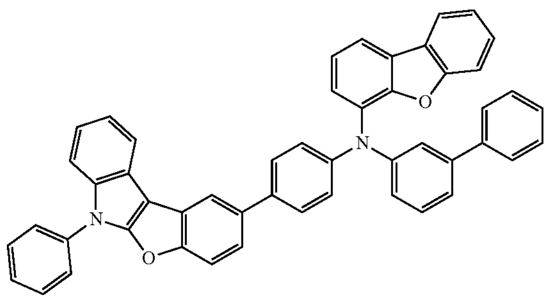
C40
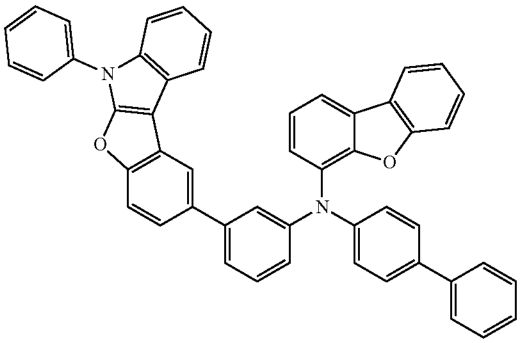
C41
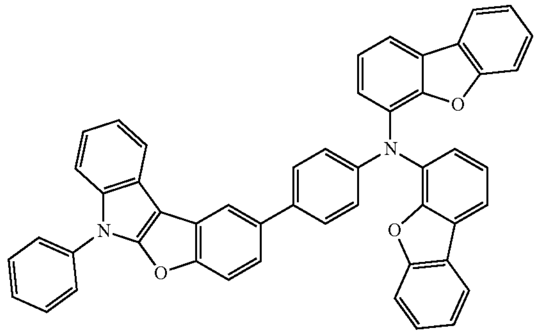
C42
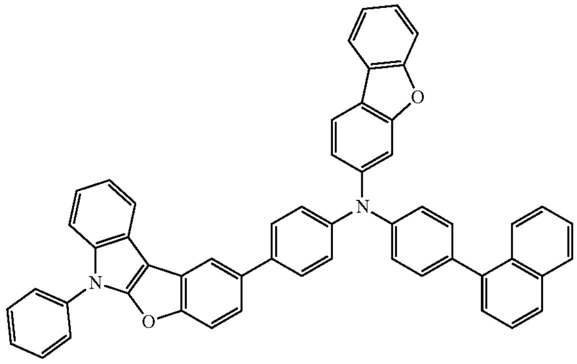
-continued
C43
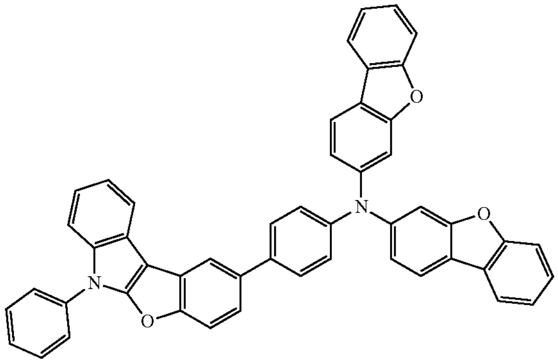
C44
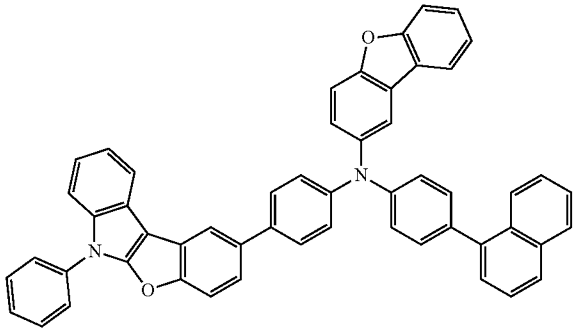
C45
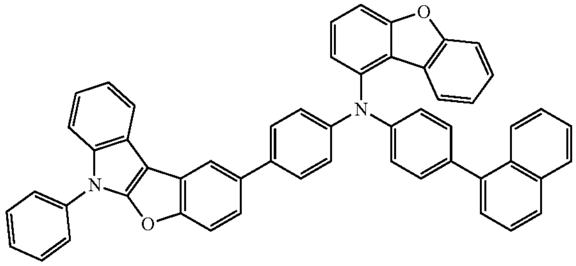
C46
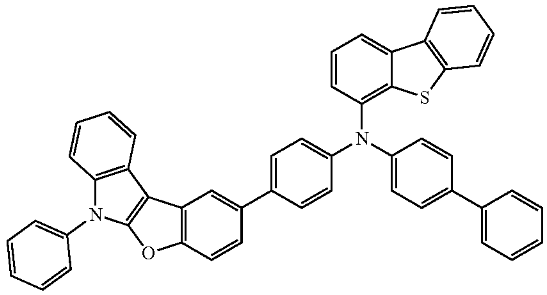

-continued
C47
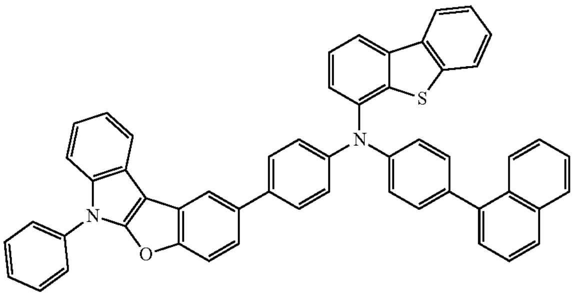
C48
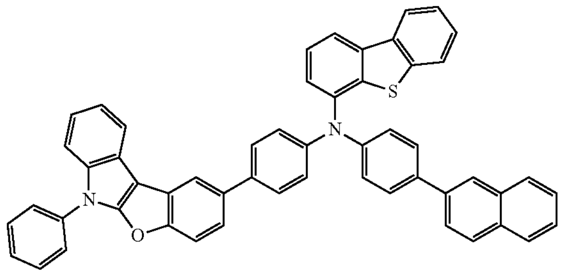
C49
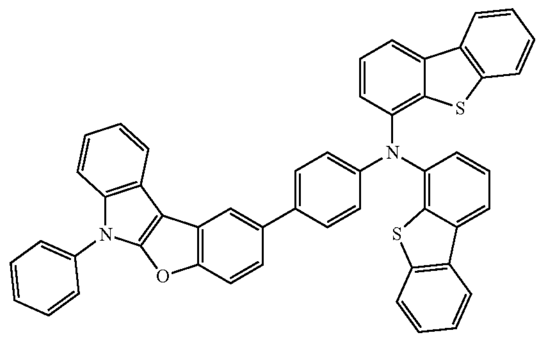
C50
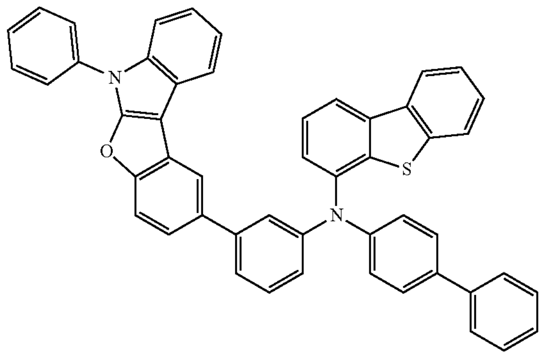
-continued
C51
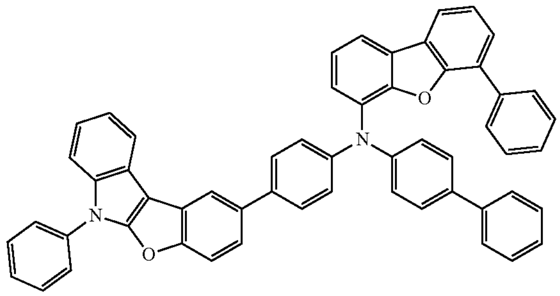
C52
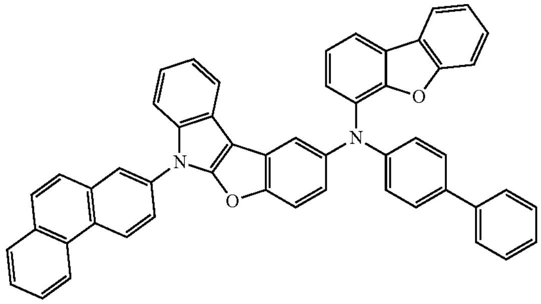
C53
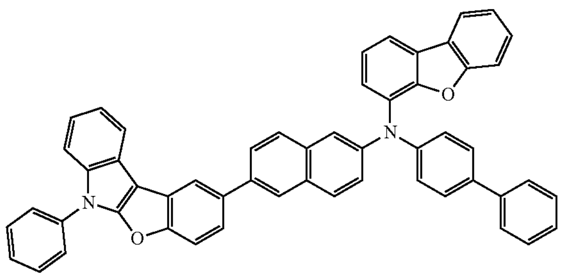
C54
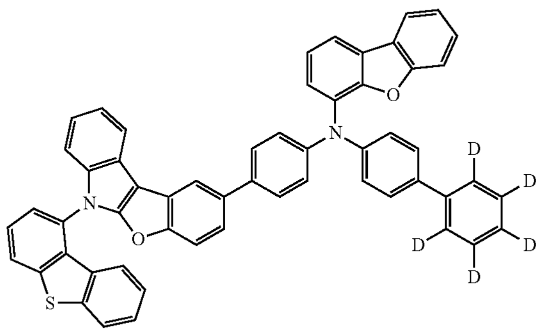

-continued
C55
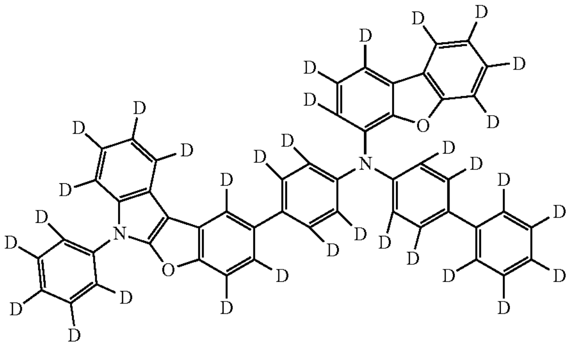
C56
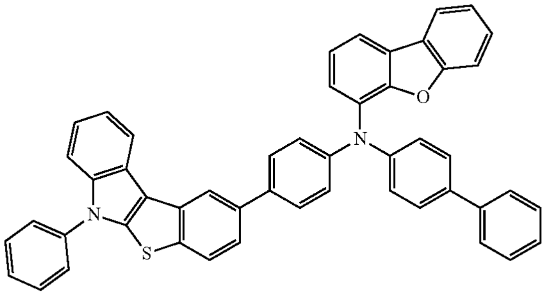
C57
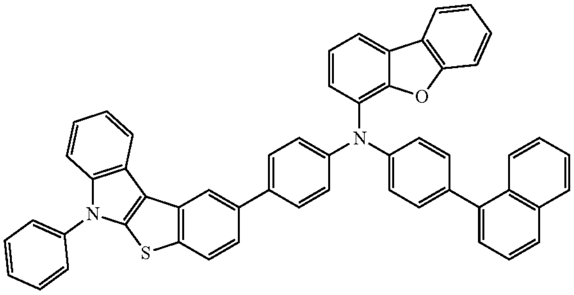
C58
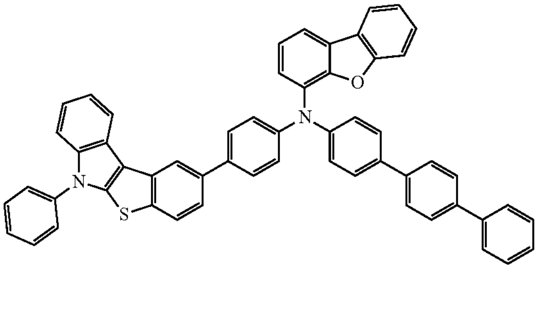
-continued
C59
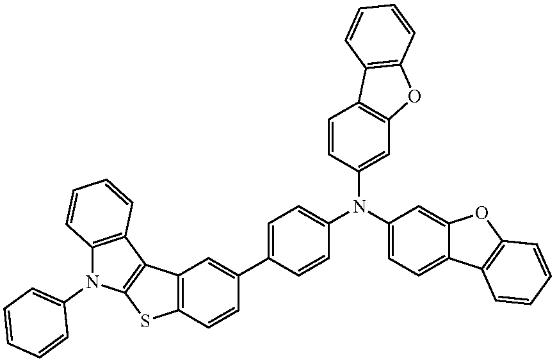
C60
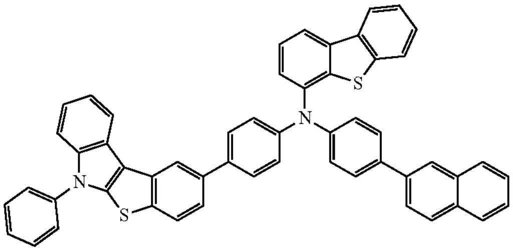
C61
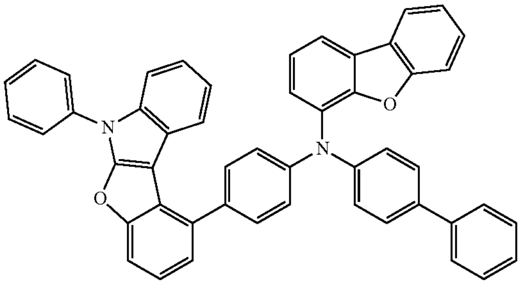
C62
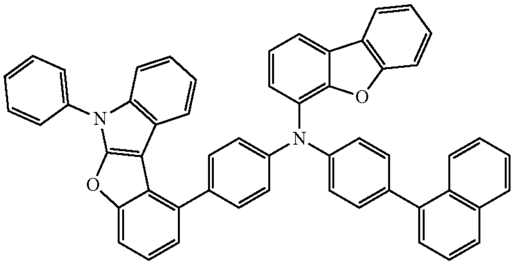
C63
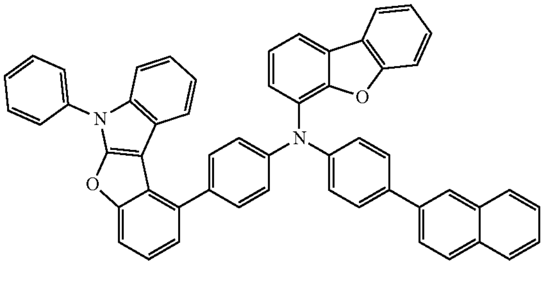

-continued
C64
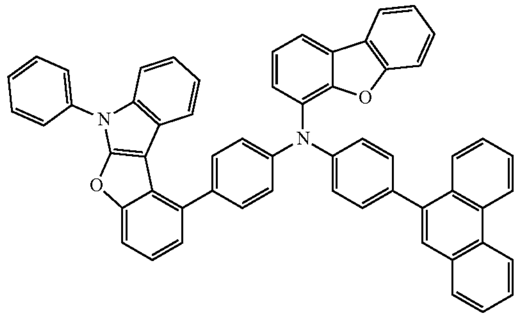
C65
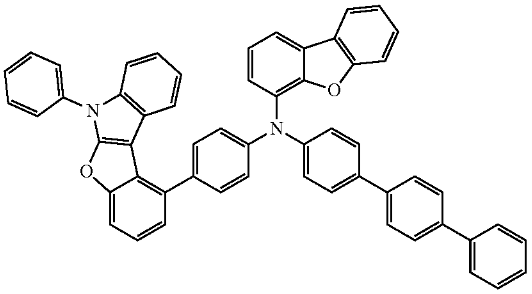
C66
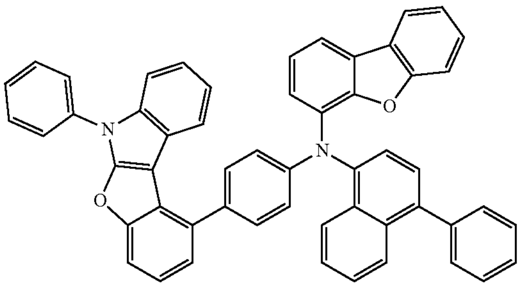
C67
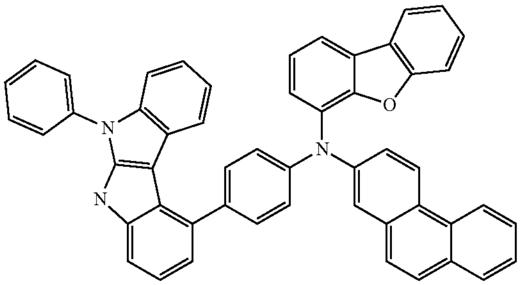
C68
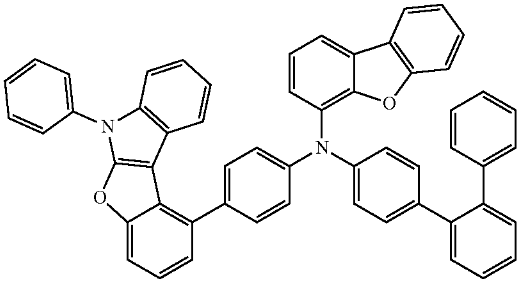
-continued
C69
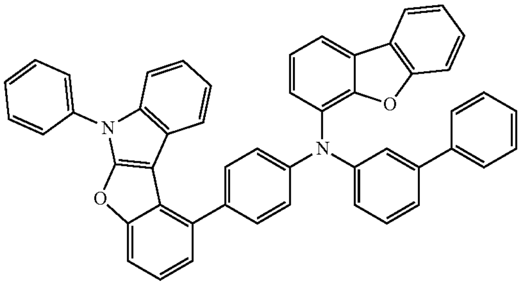
C70
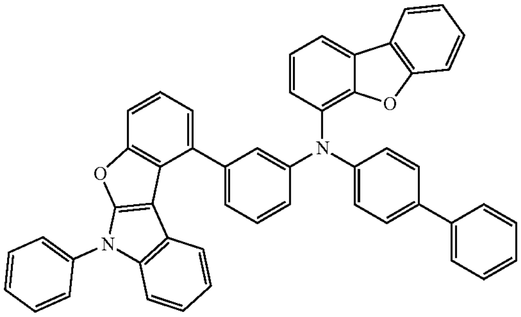
C71
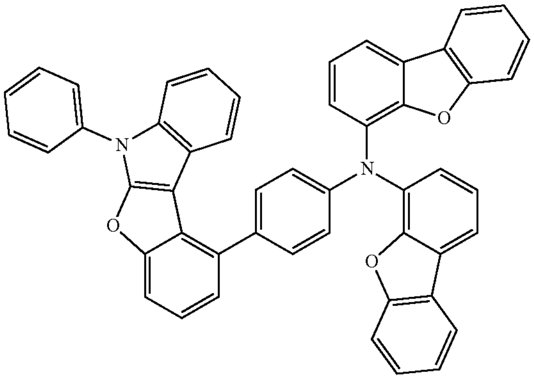
C72
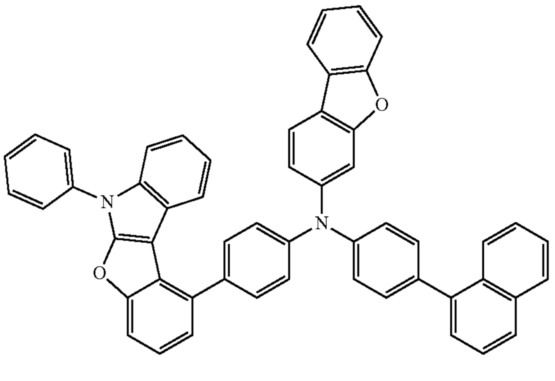

-continued
C73
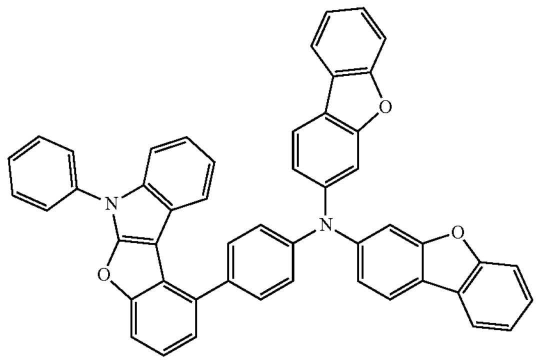
C74
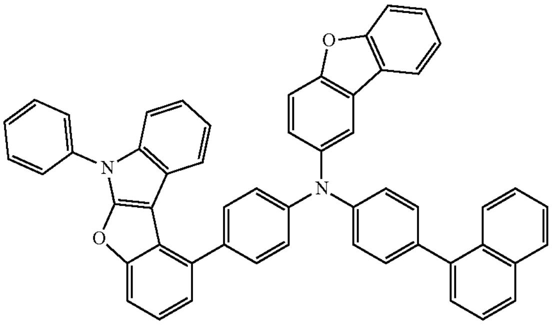
C75
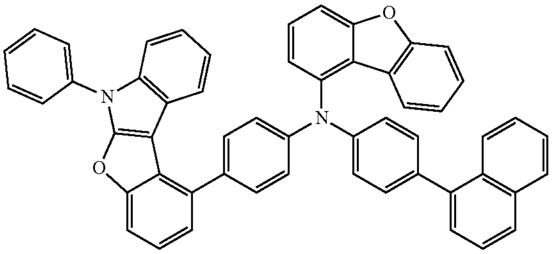
C76
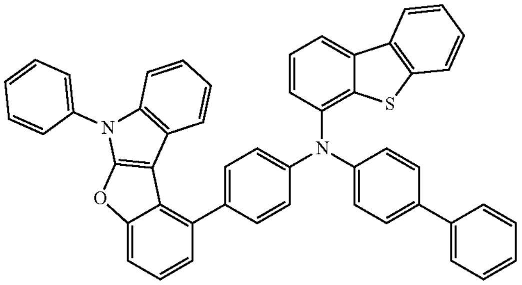
C77
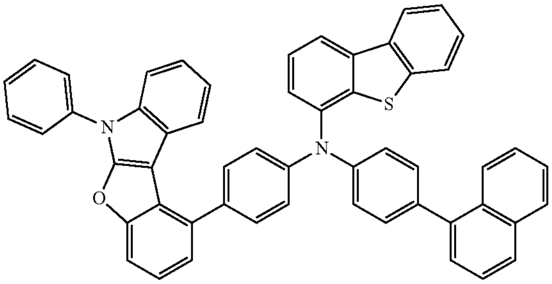
-continued
C78
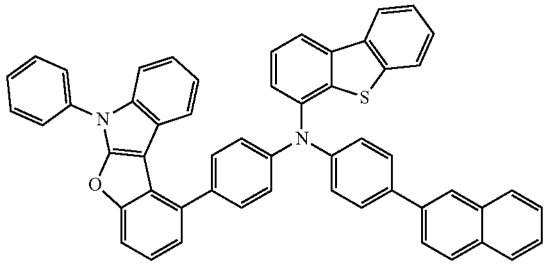
C79
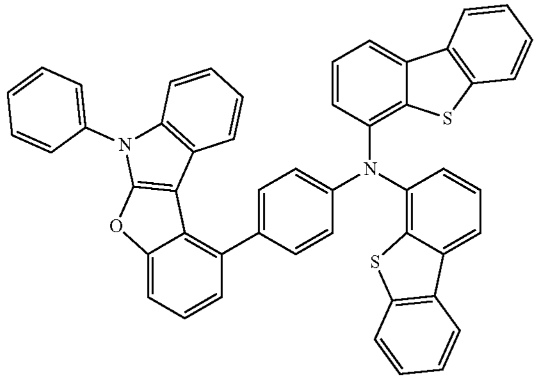
C80
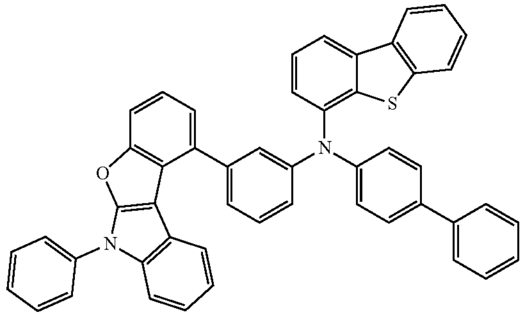
C81
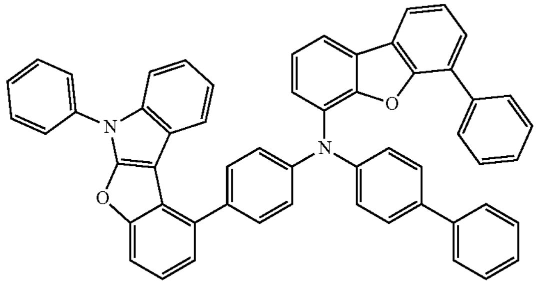

-continued
C82
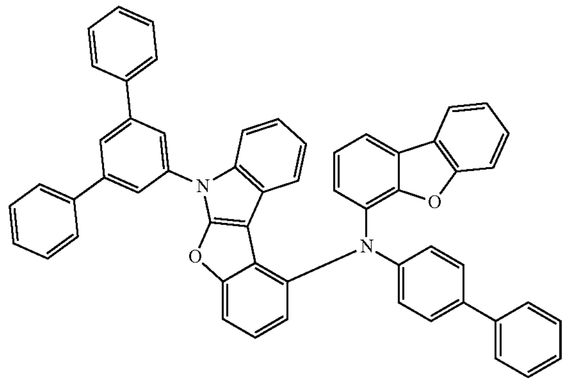
C83
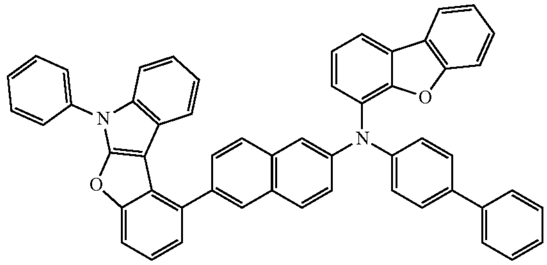
C84
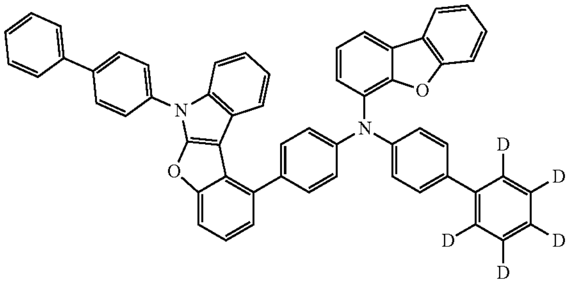
C85
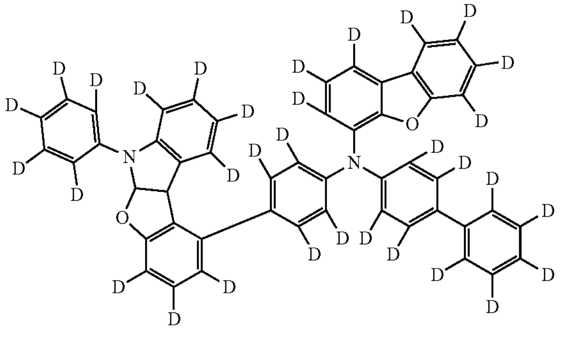
-continued
C86
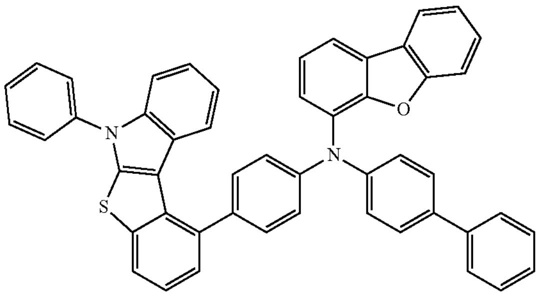
C87
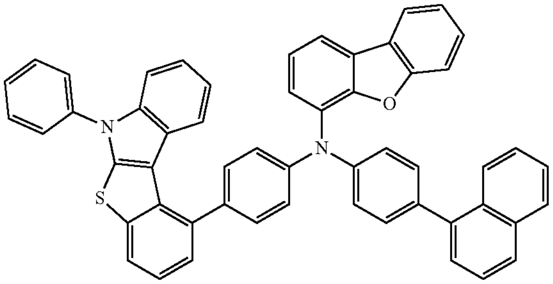
C88
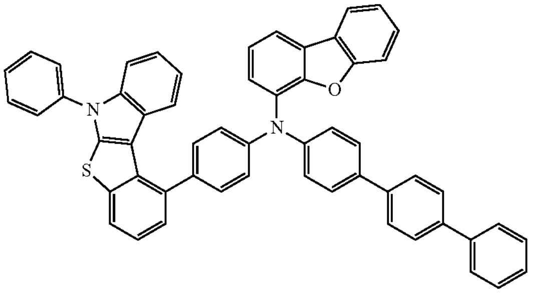
C89
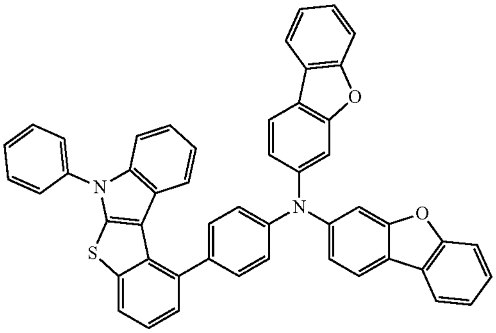
C90
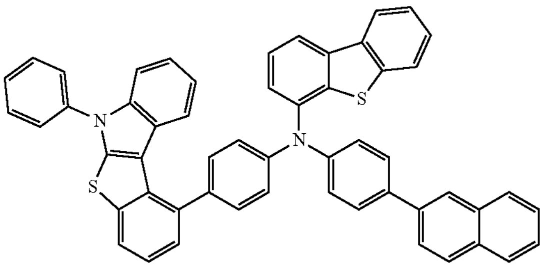

-continued
C91
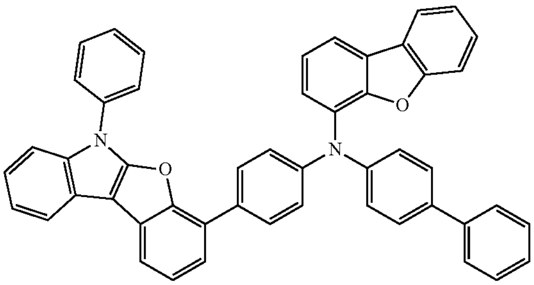
C92
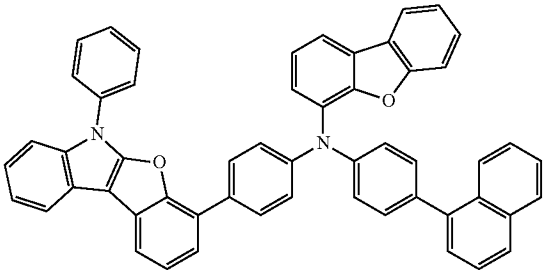
C93
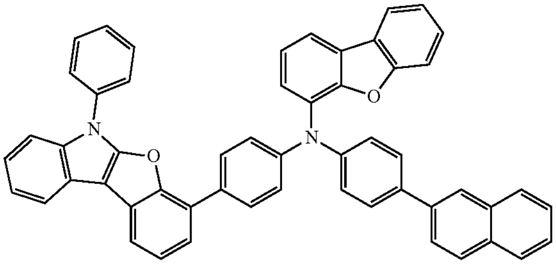
C94
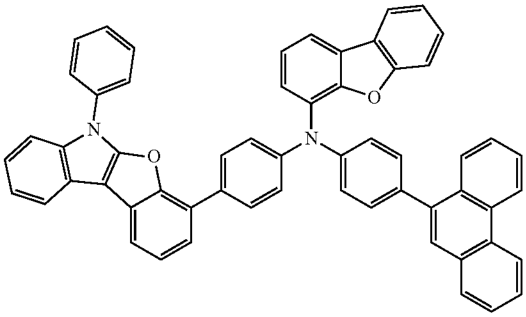
C95
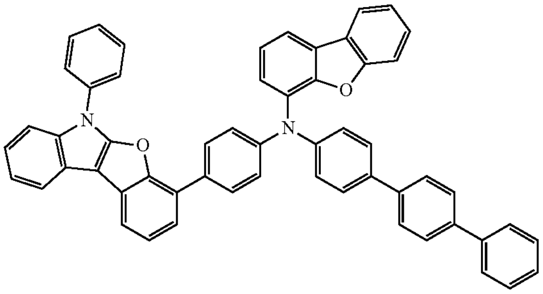
-continued
C96
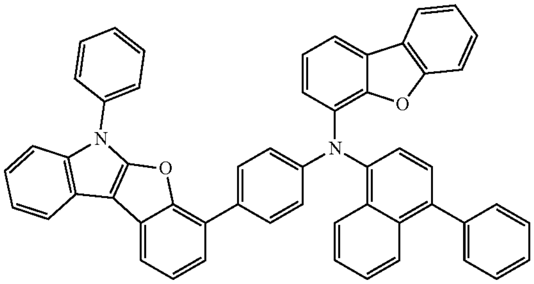
C97
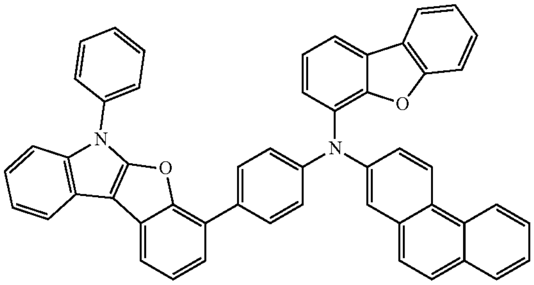
C98
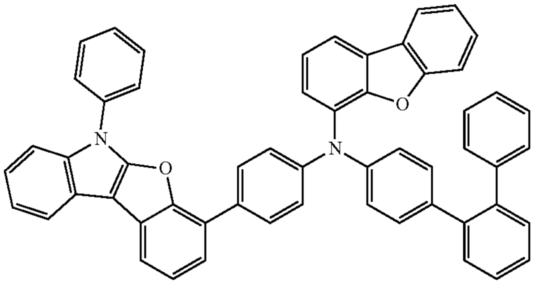
C99
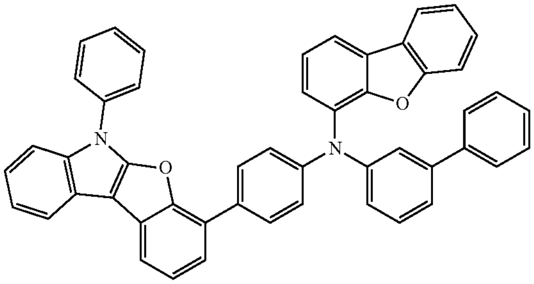
C100
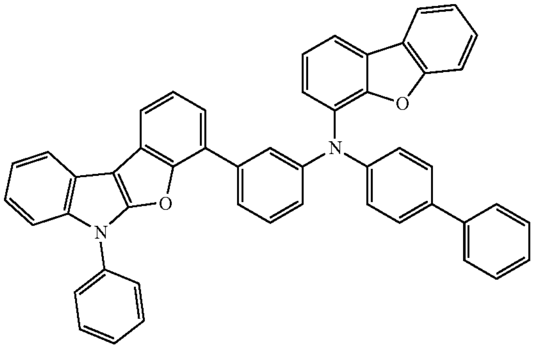

-continued
C101
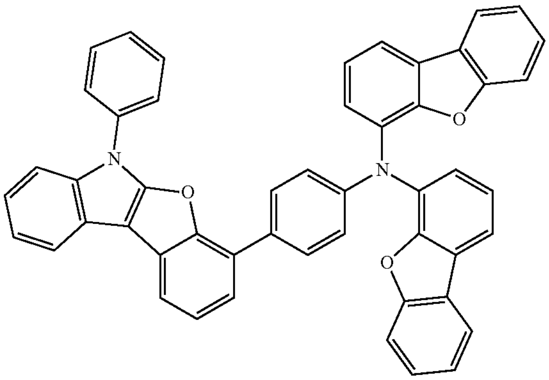
C102
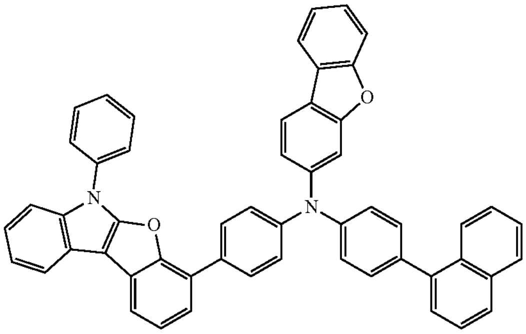
C103
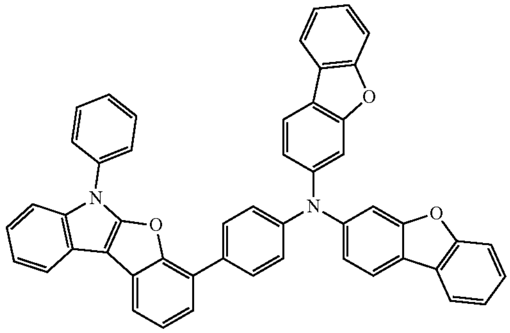
C104
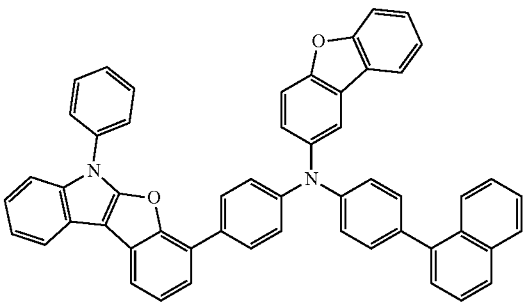
-continued
C105
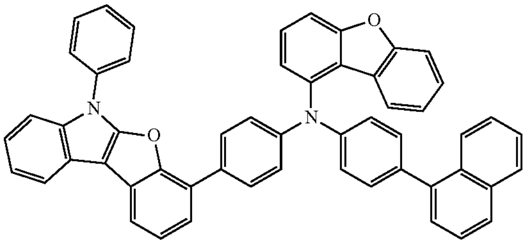
C106
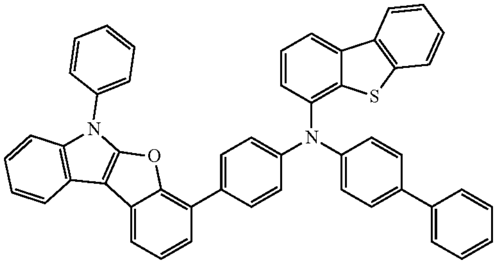
C107
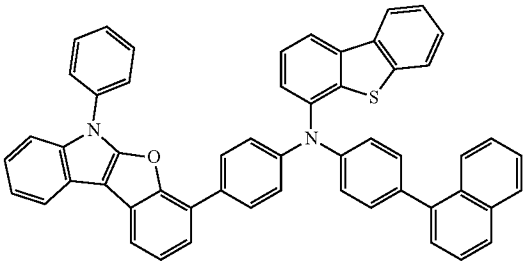
C108
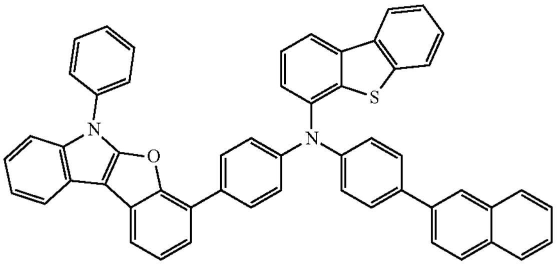
C109
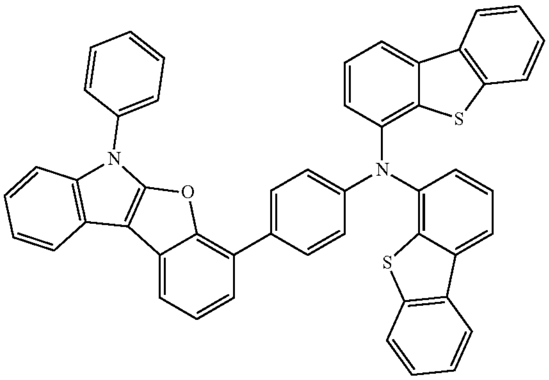

-continued
C110
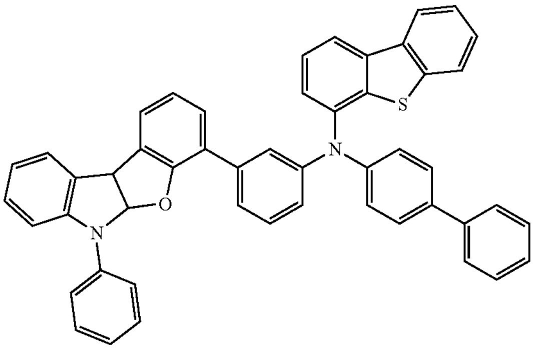
C111
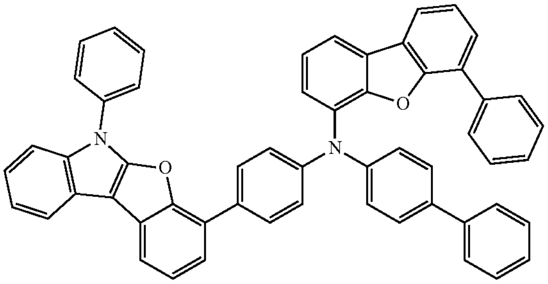
C112
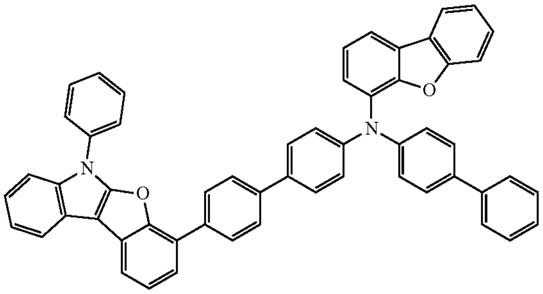
C113
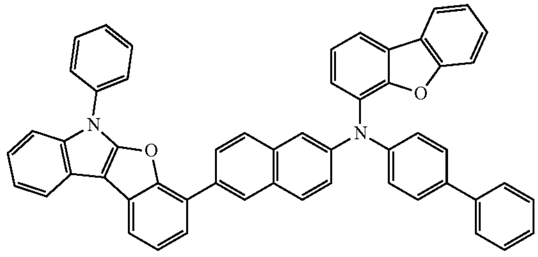
C114
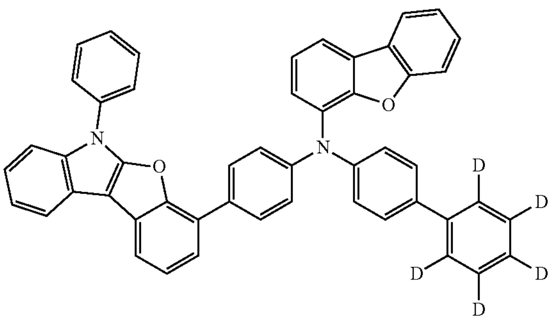
-continued
C115
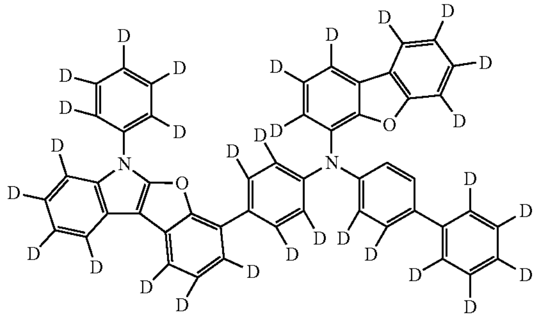
C116
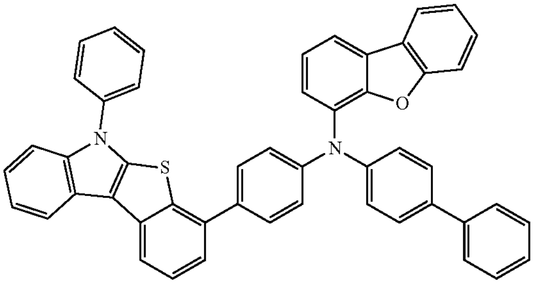
C117
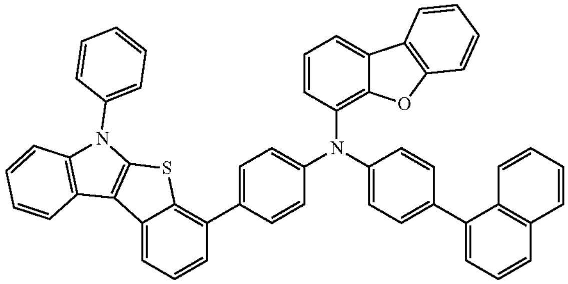
C118
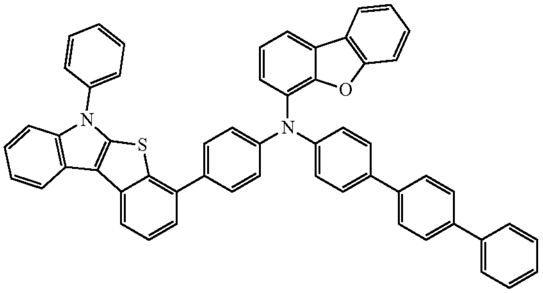

-continued
C119
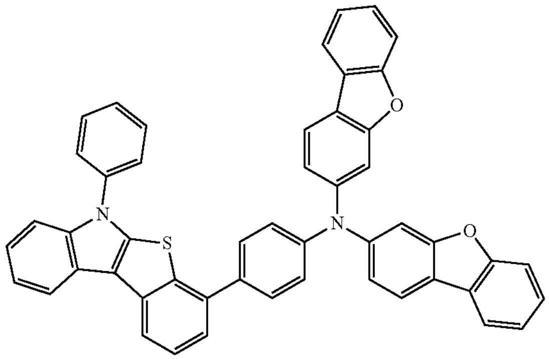
C120
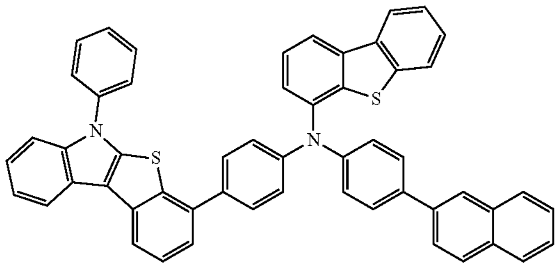
C121
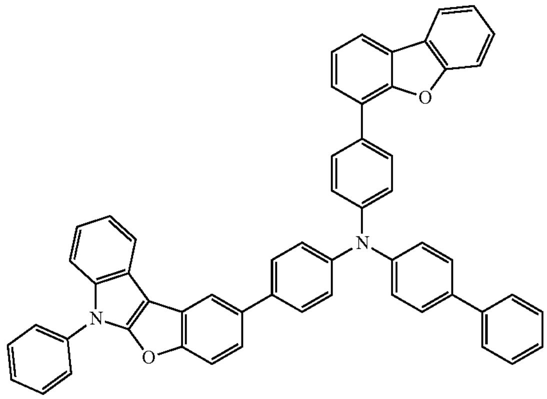
C122
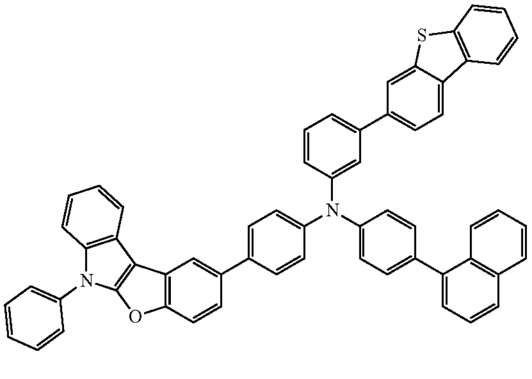
-continued
C123
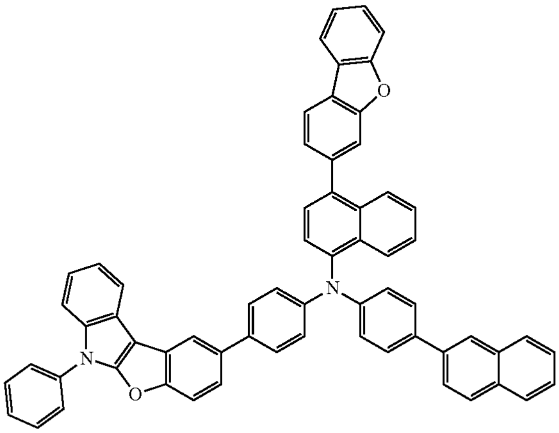
C124
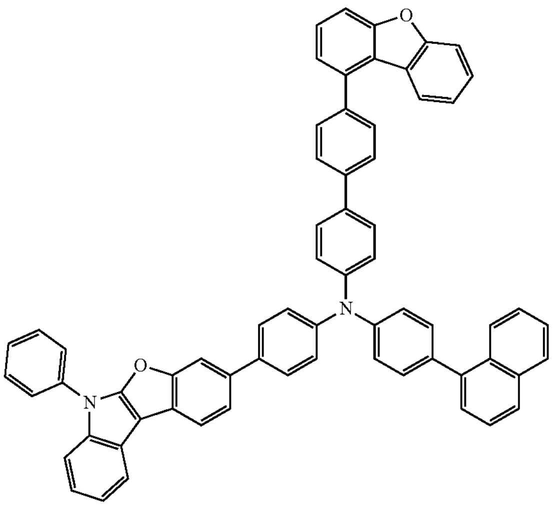
C125
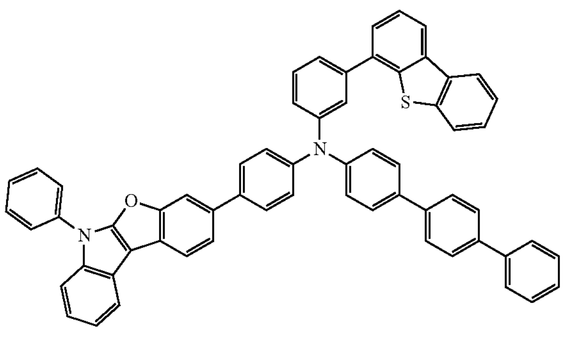

-continued
C126
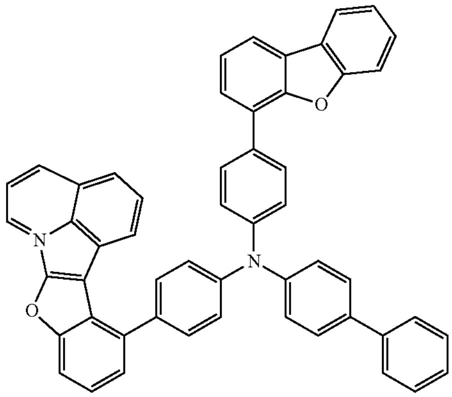
C127
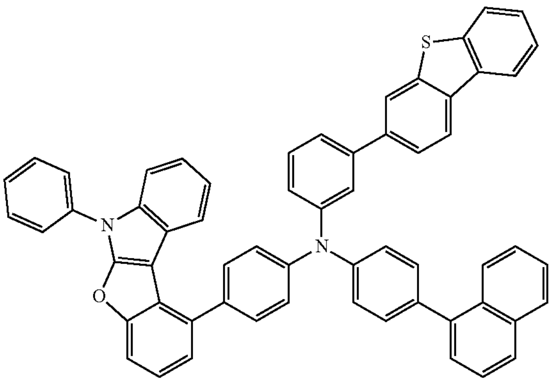
C128
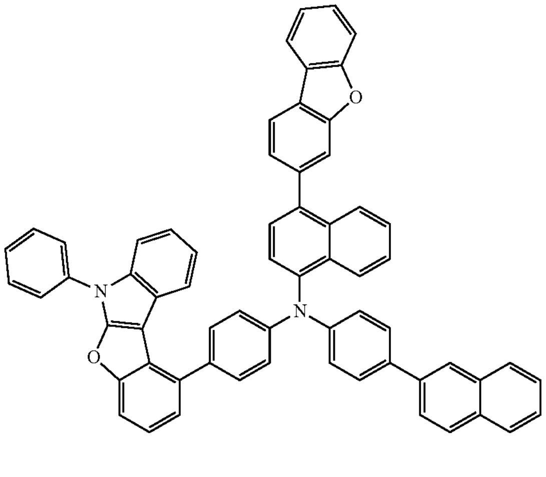
-continued
C129
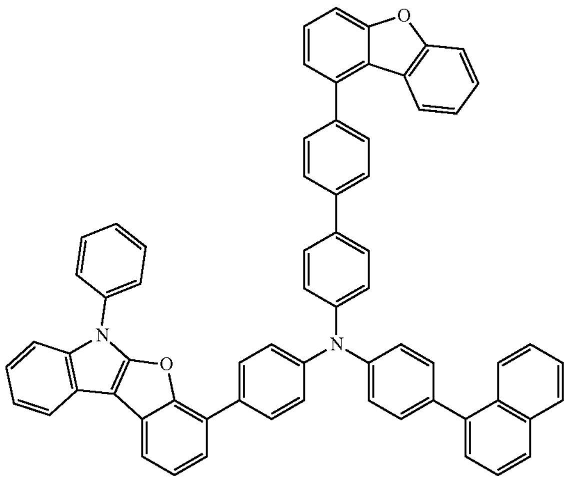
C130
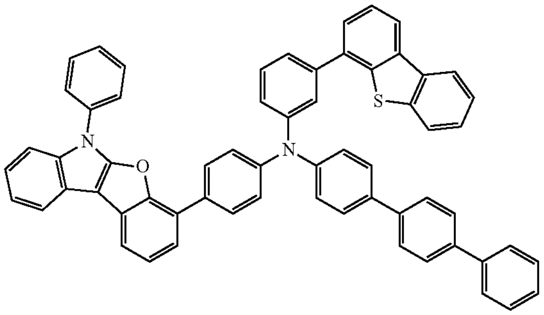
C131
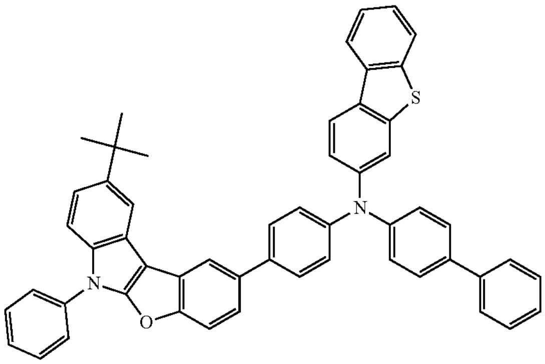
C132
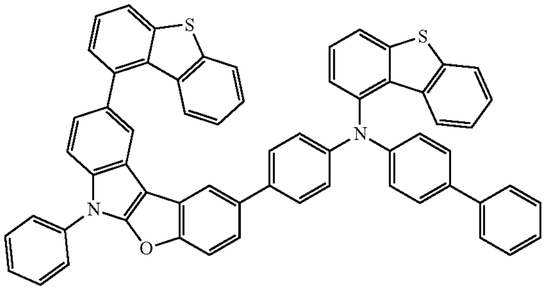

-continued
C133
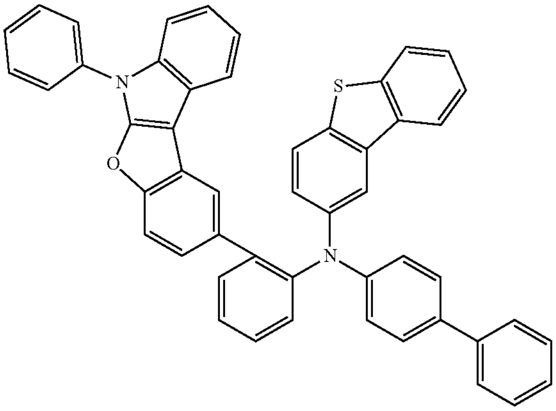
C134
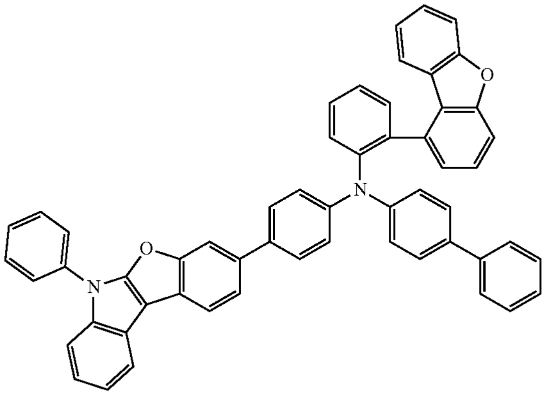
C135
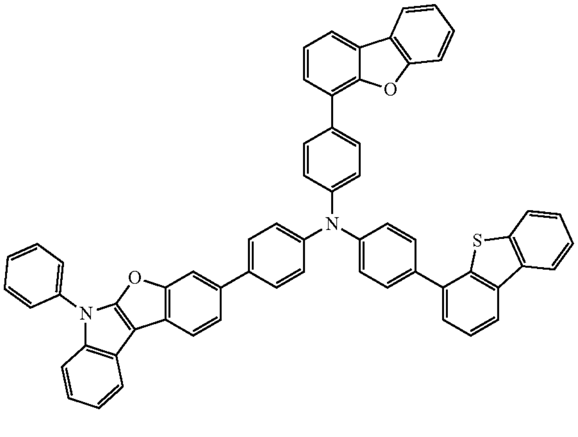
-continued
C136
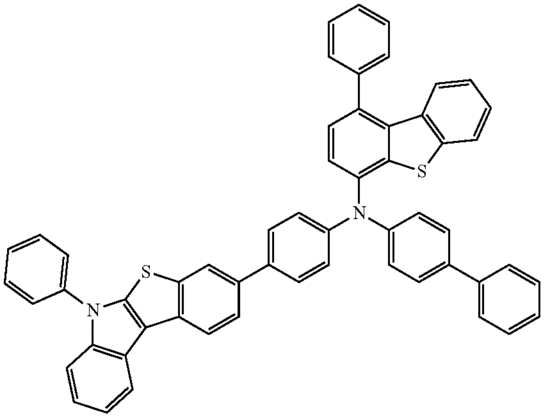
C137
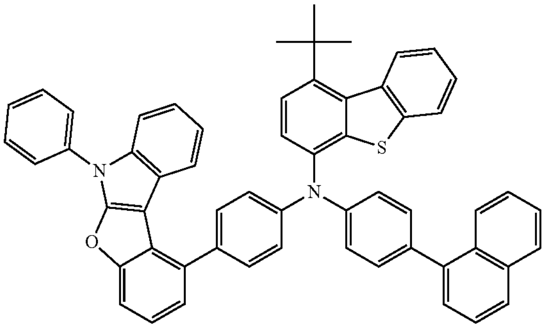
C138
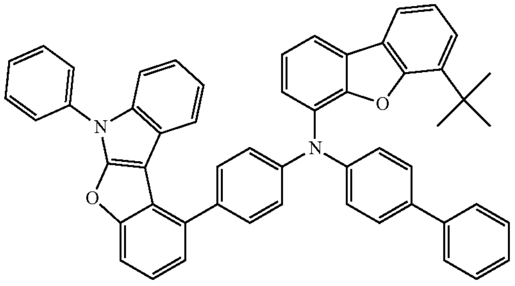
C139
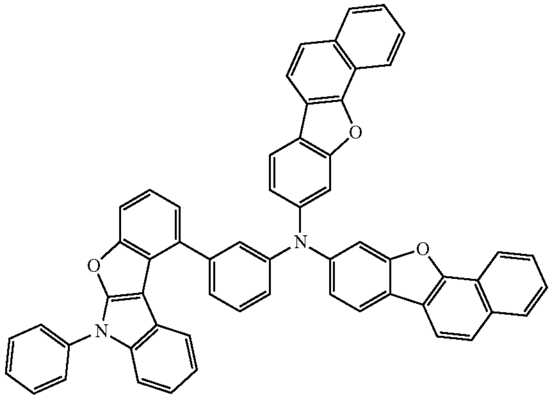

-continued
C140
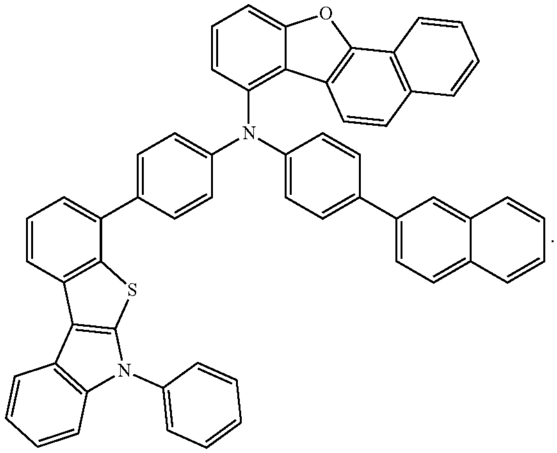
.
* * * * *